United States Patent
Worrell et al.

(10) Patent No.: US 10,258,363 B2
(45) Date of Patent: Apr. 16, 2019

(54) METHOD OF OPERATING AN ARTICULATING ULTRASONIC SURGICAL INSTRUMENT

(71) Applicant: Ethicon Endo-Surgery, Inc., Cincinnati, OH (US)

(72) Inventors: Barry C. Worrell, Centerville, OH (US); Benjamin J. Danziger, Cincinnati, OH (US); Benjamin D. Dickerson, Cincinnati, OH (US); Brian D. Black, Loveland, OH (US); Cara L. Shapiro, Milford, OH (US); Charles J. Scheib, Loveland, OH (US); Craig N. Faller, Batavia, OH (US); Daniel J. Mumaw, Liberty Township, OH (US); David J. Cagle, Cincinnati, OH (US); David T. Martin, Milford, OH (US); David A. Monroe, Milford, OH (US); Disha V. Labhasetwar, Cincinnati, OH (US); Foster B. Stulen, Mason, OH (US); Frederick L. Estera, Cincinnati, OH (US); Geoffrey S. Strobl, Williamsburg, OH (US); Gregory W. Johnson, Milford, OH (US); Jacob S. Gee, Cincinnati, OH (US); Jason R. Sullivan, Morrow, OH (US); Jeffrey D. Messerly, Cincinnati, OH (US); Jeffrey S. Swayze, West Chester, OH (US); John A. Hibner, Mason, OH (US); John B. Schulte, West Chester, OH (US); Joseph E. Hollo, Liberty Township, OH (US); Kristen G. Denzinger, Cincinnati, OH (US); Kristen L. Pirozzi, Cincinnati, OH (US); Matthew C. Miller, Cincinnati, OH (US); Michael R. Lamping, Cincinnati, OH (US); Richard W. Timm, Cincinnati, OH (US); Rudolph H. Nobis, Mason, OH (US); Ryan M. Asher, Cincinnati, OH (US); Stephen M. Leuck, Cincinnati, OH (US); Tylor C. Muhlenkamp, Cincinnati, OH (US); William B. Weisenburgh, II, Maineville, OH (US); William A. Olson, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 391 days.

(21) Appl. No.: 14/688,684

(22) Filed: Apr. 16, 2015

(65) Prior Publication Data
US 2015/0320437 A1   Nov. 12, 2015

Related U.S. Application Data

(60) Provisional application No. 62/176,880, filed on Apr. 22, 2014.

(51) Int. Cl.
*A61B 17/32* (2006.01)
*A61N 7/00* (2006.01)
(Continued)

(52) U.S. Cl.
CPC .............. *A61B 17/320092* (2013.01); *A61B 17/320068* (2013.01); *A61B 18/1445* (2013.01);
(Continued)

(58) Field of Classification Search
CPC ......... A61B 17/28; A61B 17/29; A61B 17/32; A61B 17/320016; A61B 17/32002;
(Continued)

(56) References Cited

U.S. PATENT DOCUMENTS

| 2,906,143 A | 9/1959 | Walton |
|---|---|---|
| 5,322,055 A | 6/1994 | Davison et al. |

(Continued)

FOREIGN PATENT DOCUMENTS

| EP | 2668911 A2 | 12/2013 |
|---|---|---|
| WO | WO 2012/088167 A2 | 12/2013 |

OTHER PUBLICATIONS

U.S. Appl. No. 14/258,179, filed Apr. 22, 2014.
(Continued)

*Primary Examiner* — Todd Scherbel
(74) *Attorney, Agent, or Firm* — Frost Brown Todd LLC

(57) ABSTRACT

An apparatus comprises a body assembly, a shaft, an acoustic waveguide, an articulation section, an end effector, and an articulation drive assembly. The shaft extends distally from the body assembly and defines a longitudinal axis. The acoustic waveguide comprises a flexible portion. The articulation section is coupled with the shaft. A portion of the
(Continued)

articulation section encompasses the flexible portion of the waveguide. The articulation section comprises a plurality of body portions aligned along the longitudinal axis and a flexible locking member. The flexible locking member is operable to secure the body portions in relation to each other and in relation to the shaft. The end effector comprises an ultrasonic blade in acoustic communication with the waveguide. The articulation drive assembly is operable to drive articulation of the articulation section to thereby deflect the end effector from the longitudinal axis.

19 Claims, 345 Drawing Sheets

(51) Int. Cl.
| | |
|---|---|
| *A61B 18/14* | (2006.01) |
| *A61B 18/00* | (2006.01) |
| *A61B 17/00* | (2006.01) |
| *A61B 17/22* | (2006.01) |
| *A61B 17/29* | (2006.01) |
| *A61B 90/00* | (2016.01) |

(52) U.S. Cl.
CPC .......... *A61N 7/00* (2013.01); *A61B 2017/003* (2013.01); *A61B 2017/00309* (2013.01); *A61B 2017/00314* (2013.01); *A61B 2017/00327* (2013.01); *A61B 2017/00398* (2013.01); *A61B 2017/22018* (2013.01); *A61B 2017/2927* (2013.01); *A61B 2017/320088* (2013.01); *A61B 2018/0063* (2013.01); *A61B 2018/00589* (2013.01); *A61B 2018/00595* (2013.01); *A61B 2018/00601* (2013.01); *A61B 2018/00607* (2013.01); *A61B 2018/00619* (2013.01); *A61B 2018/00642* (2013.01); *A61B 2018/00791* (2013.01); *A61B 2018/00875* (2013.01); *A61B 2018/00892* (2013.01); *A61B 2090/0811* (2016.02)

(58) Field of Classification Search
CPC .... A61B 17/320068; A61B 17/320092; A61B 2017/003; A61B 2017/00305; A61B 2017/00318; A61B 2017/00323; A61B 2017/2908; A61B 2017/2927; A61B 2017/320069; A61B 2017/320071
See application file for complete search history.

(56) References Cited

U.S. PATENT DOCUMENTS

| | | | |
|---|---|---|---|
| 5,873,873 A | 2/1999 | Smith et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,500,176 B1 | 12/2002 | Truckai et al. | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,135,030 B2 | 11/2006 | Schwemberger et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,888,809 B2 | 11/2014 | Davison et al. | |
| 8,939,974 B2 | 1/2015 | Boudreaux et al. | |
| 8,986,302 B2 | 3/2015 | Aldridge et al. | |
| 9,089,327 B2 | 7/2015 | Worrell et al. | |
| 9,161,803 B2 | 10/2015 | Yates et al. | |
| 2003/0191494 A1 | 10/2003 | Gray et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0069940 A1 | 3/2010 | Miller et al. | |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 | 1/2013 | Worrell et al. | |
| 2013/0030428 A1* | 1/2013 | Worrell ............... | A61B 5/0205 606/33 |
| 2013/0289592 A1 | 10/2013 | Stulen et al. | |
| 2014/0005677 A1 | 1/2014 | Shelton et al. | |
| 2014/0005701 A1 | 1/2014 | Olson et al. | |
| 2014/0005703 A1 | 1/2014 | Stulen et al. | |
| 2014/0114334 A1 | 4/2014 | Olson et al. | |
| 2015/0080924 A1 | 3/2015 | Stulen et al. | |
| 2015/0245850 A1 | 9/2015 | Hibner et al. | |
| 2016/0302812 A1 | 10/2016 | Monroe et al. | |
| 2016/0302817 A1 | 10/2016 | Worrell et al. | |
| 2016/0302818 A1 | 10/2016 | Weisenburgh et al. | |
| 2016/0302819 A1 | 10/2016 | Stulen et al. | |
| 2016/0302820 A1 | 10/2016 | Hibner et al. | |
| 2016/0302840 A1 | 10/2016 | Scheib et al. | |
| 2016/0303403 A1 | 10/2016 | Shapiro et al. | |

OTHER PUBLICATIONS

U.S. Appl. No. 14/688,692, filed Apr. 16, 2015.
U.S. Appl. No. 61/410,603, filed Nov. 5, 2010.
U.S. Appl. No. 62/176,880, filed Apr. 22, 2014.
International Search Report and Written Opinion dated Jun. 5, 5015 re Application No. PCT/US2015/026322.
U.S. Appl. No. 14/688,692.

* cited by examiner

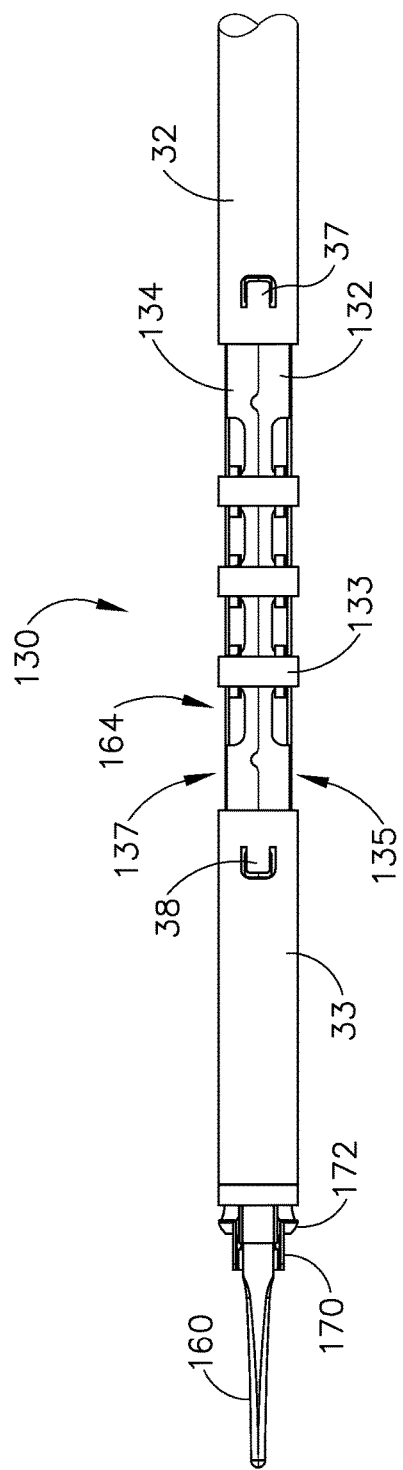

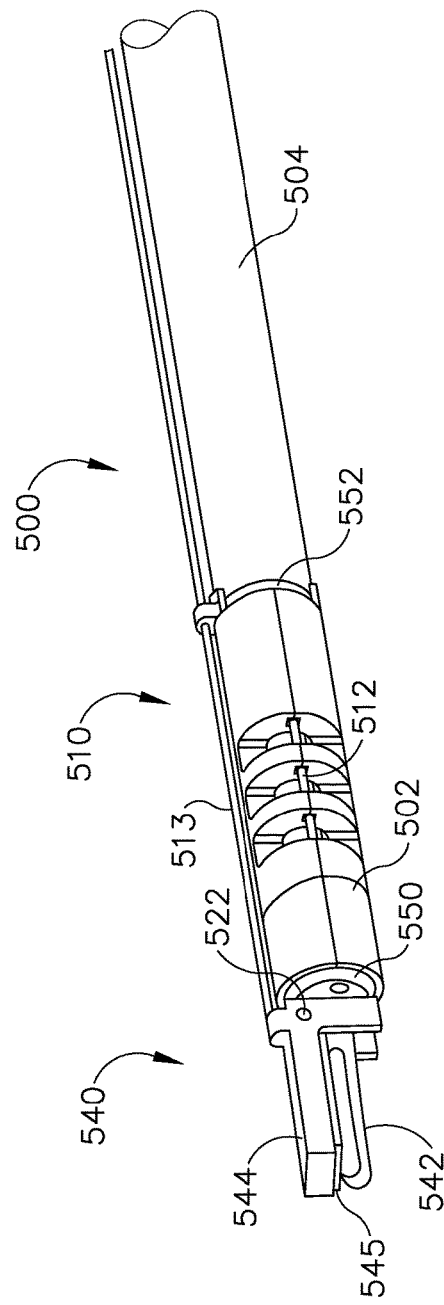

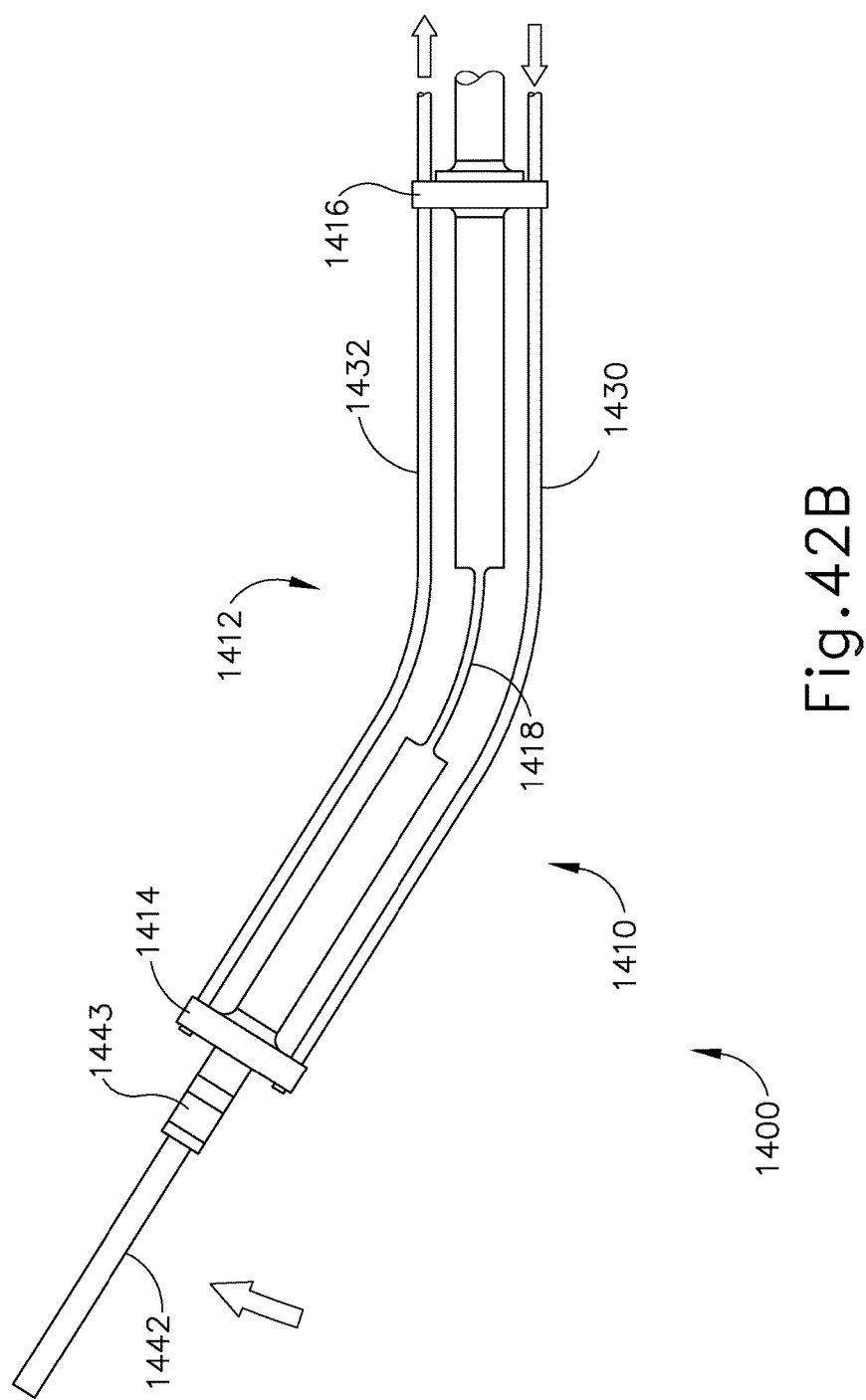

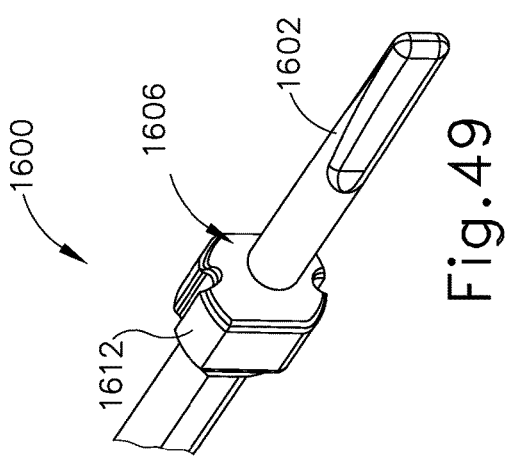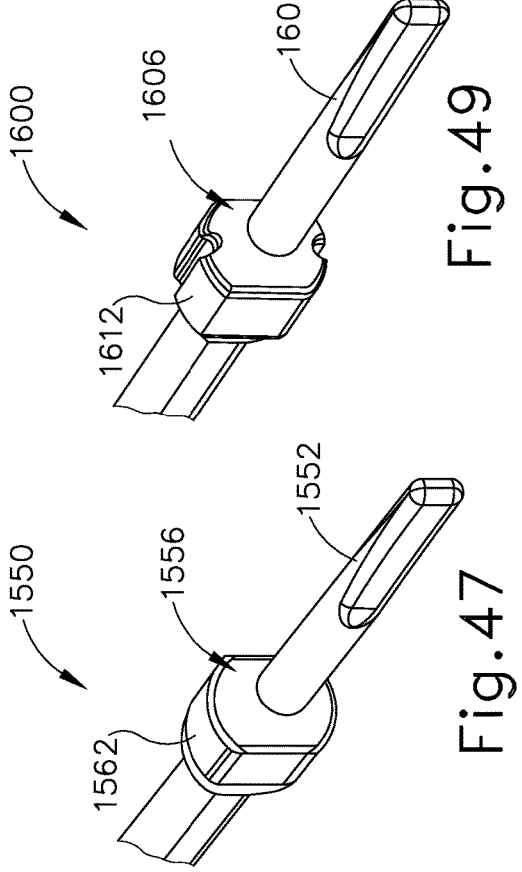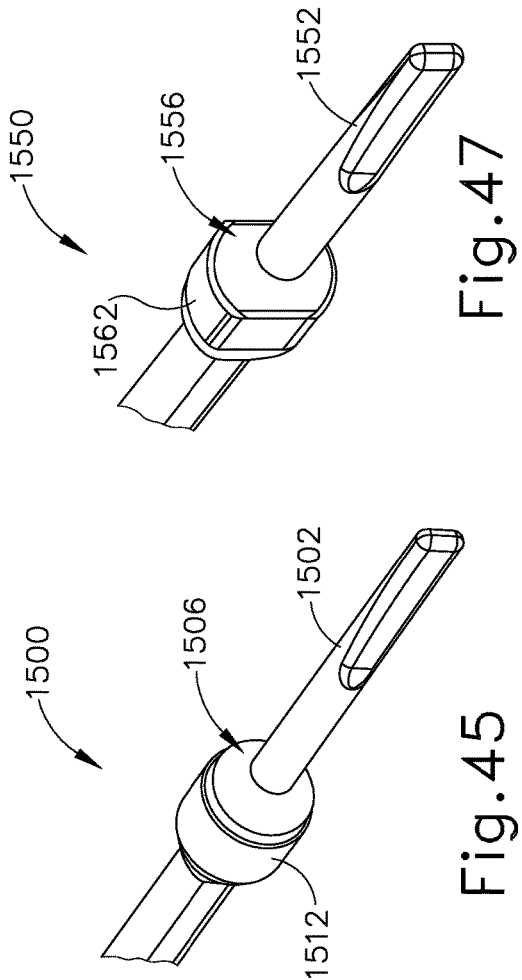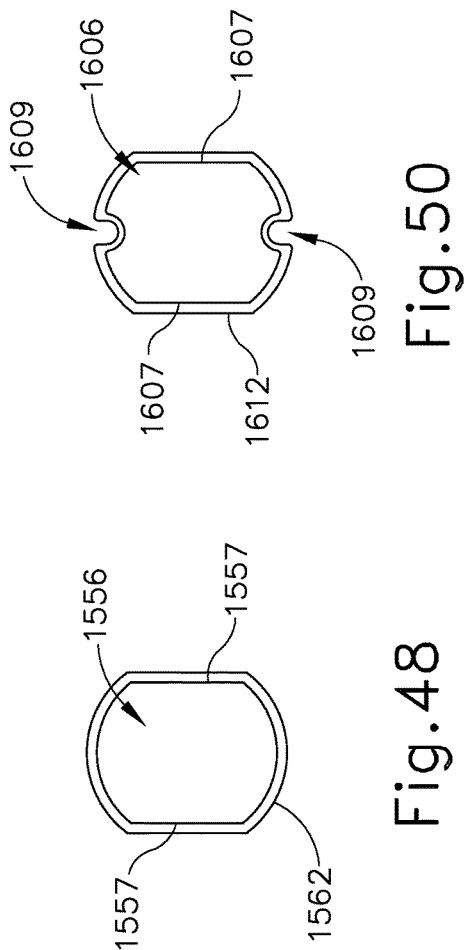

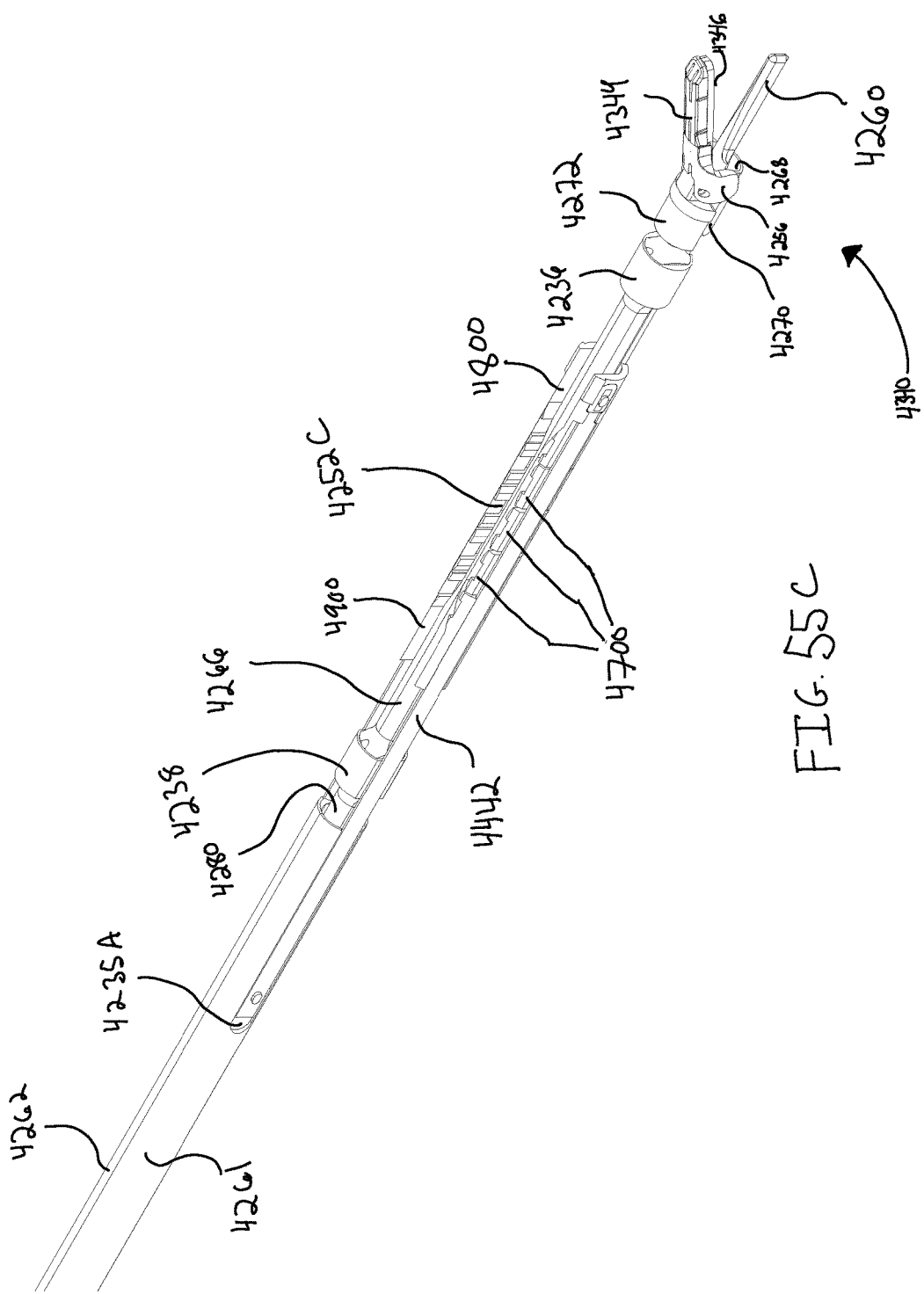

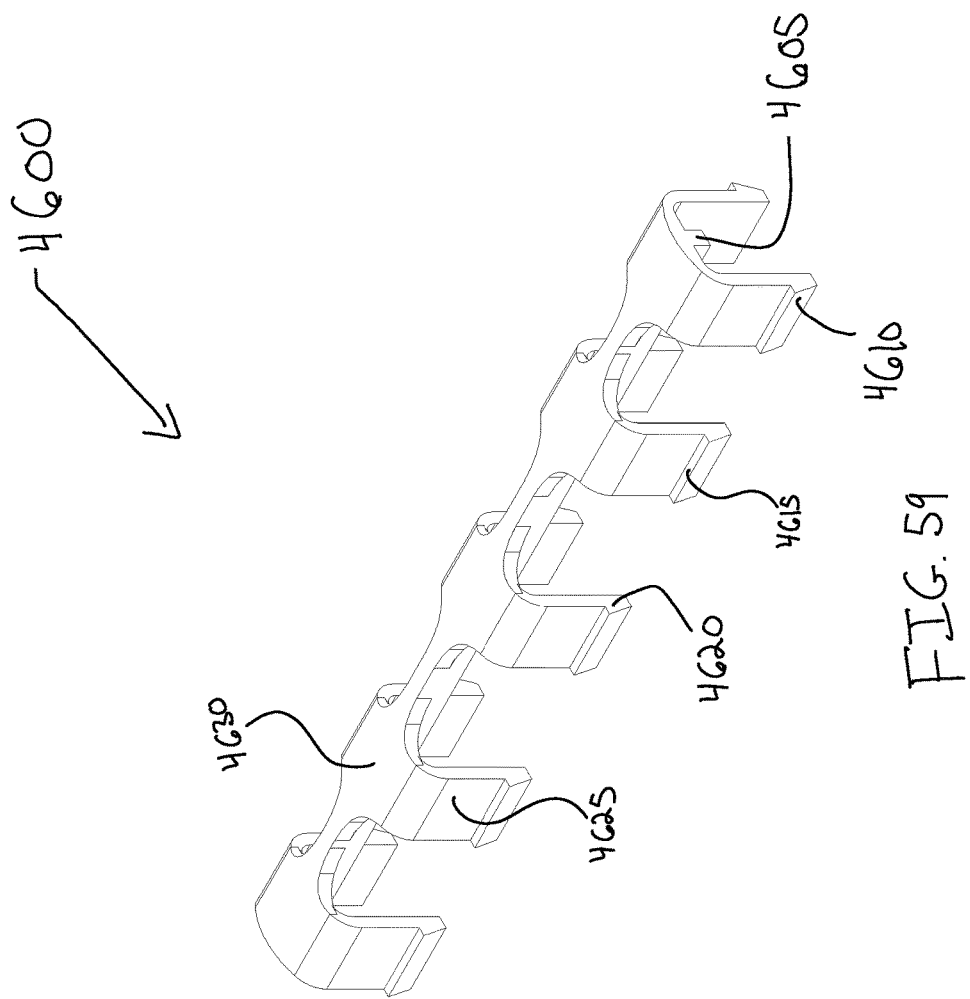

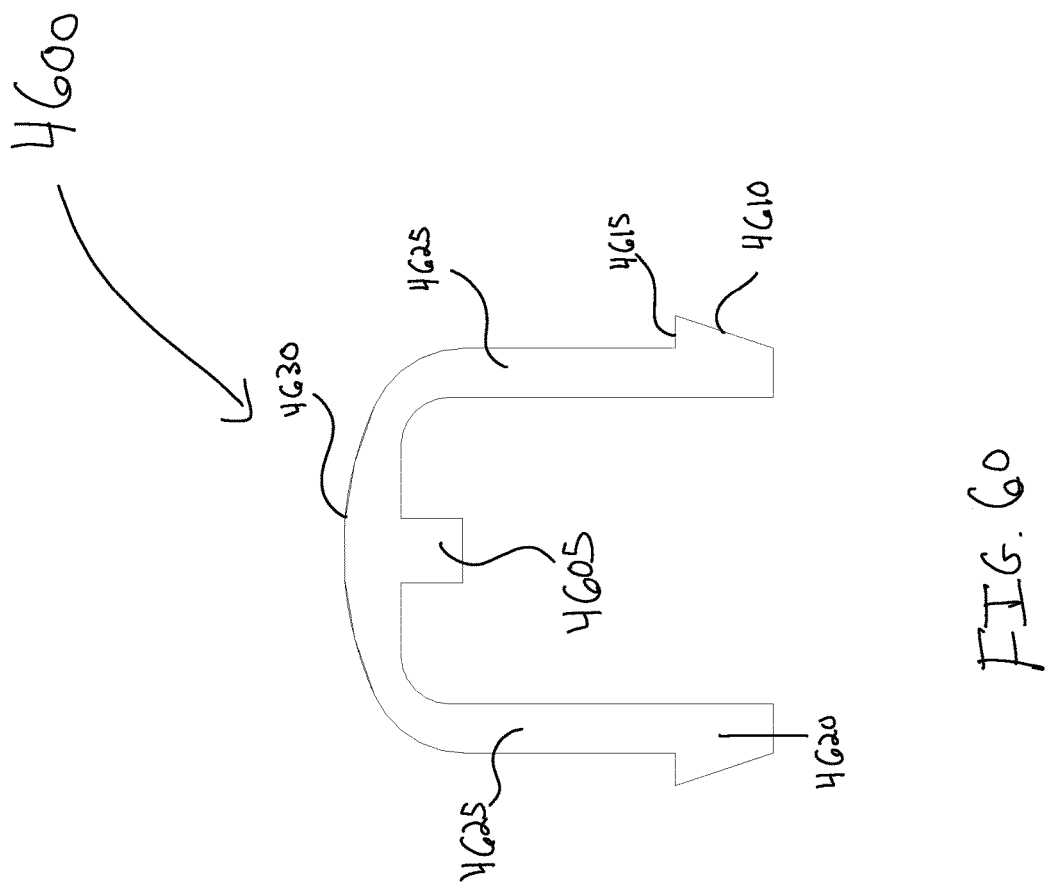

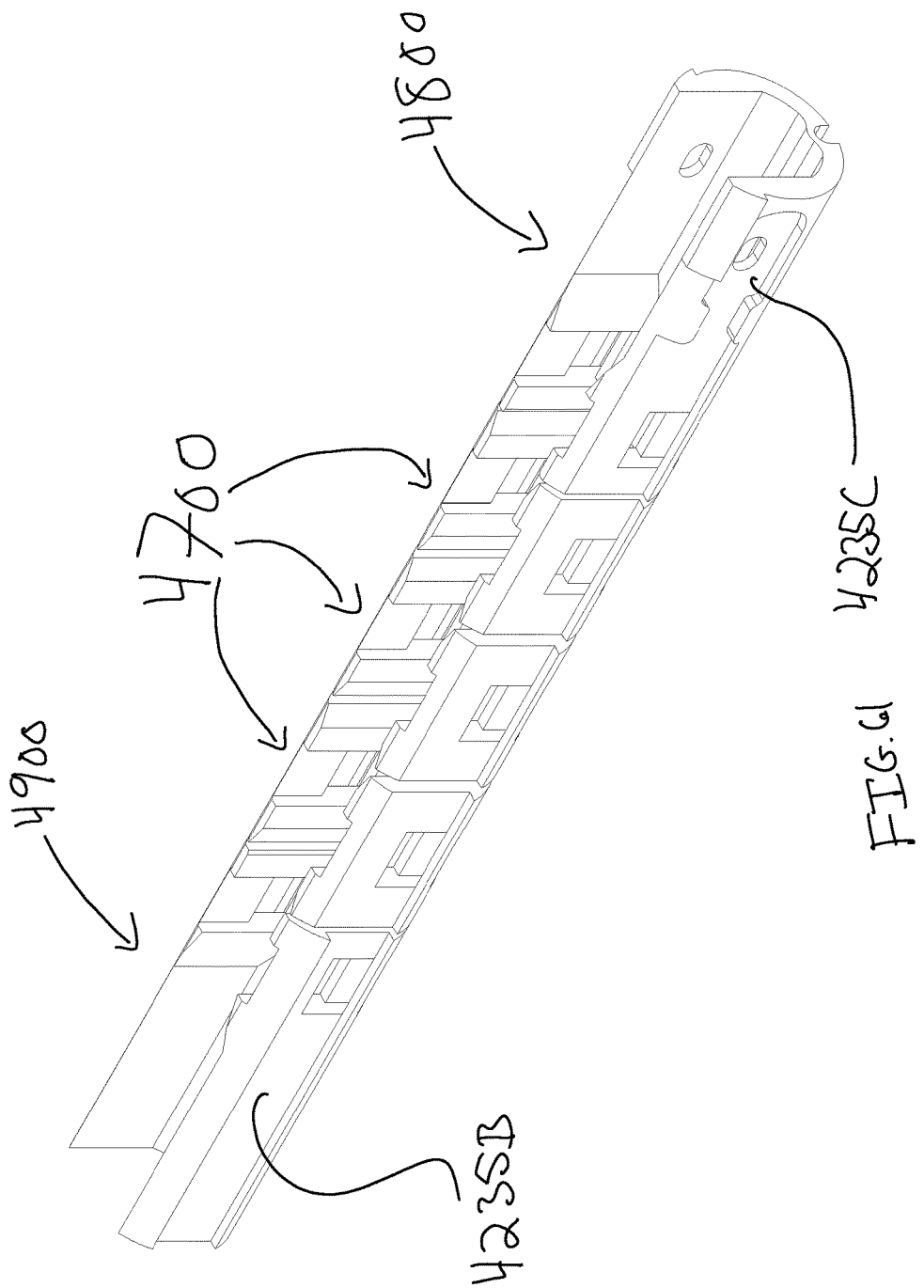

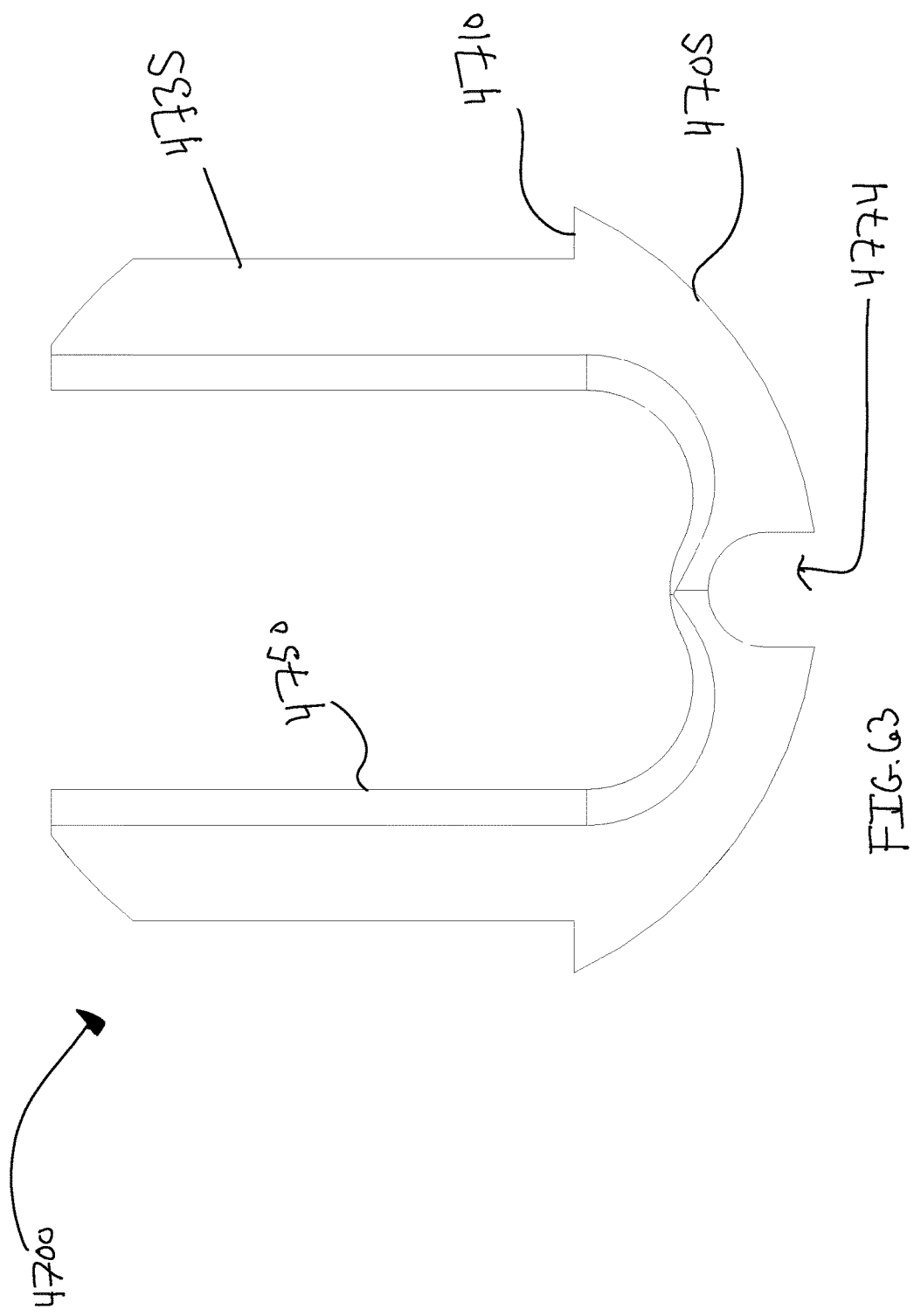

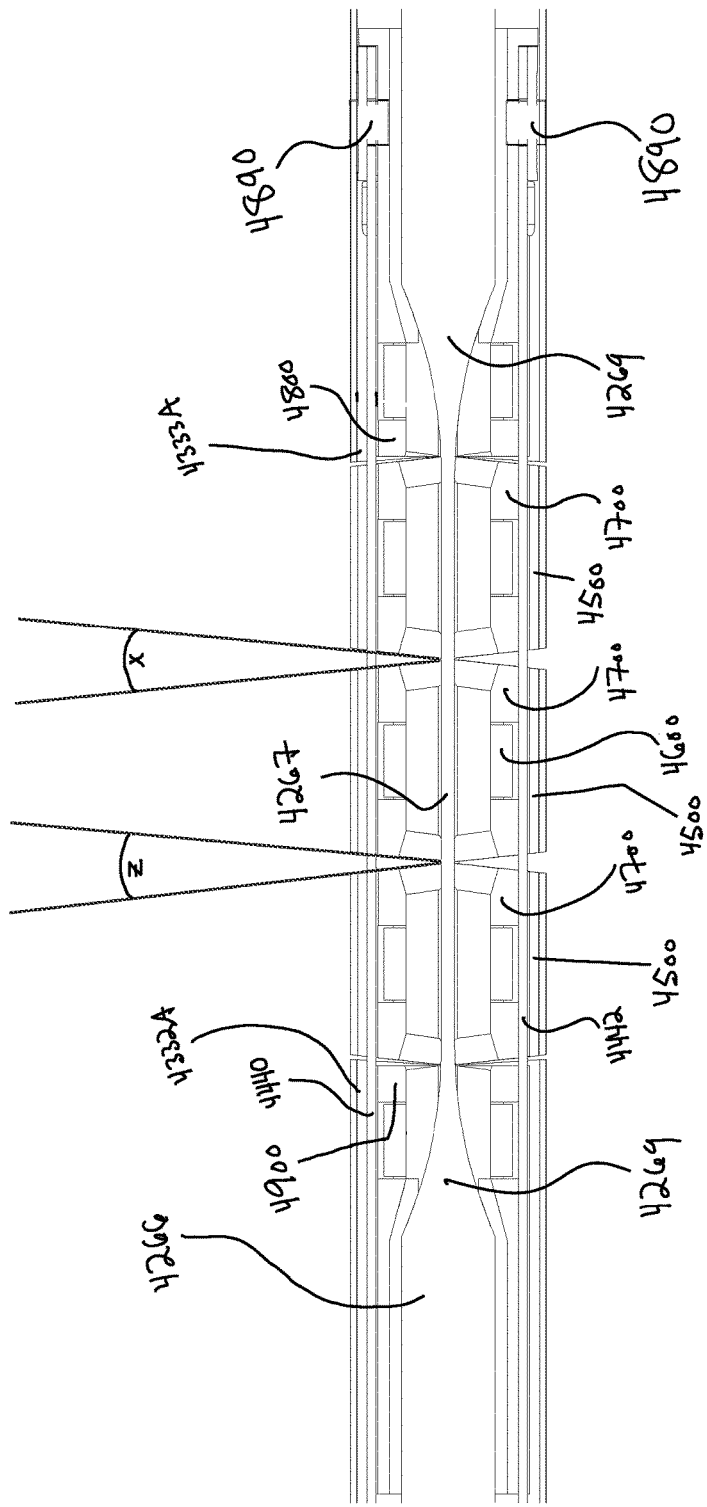

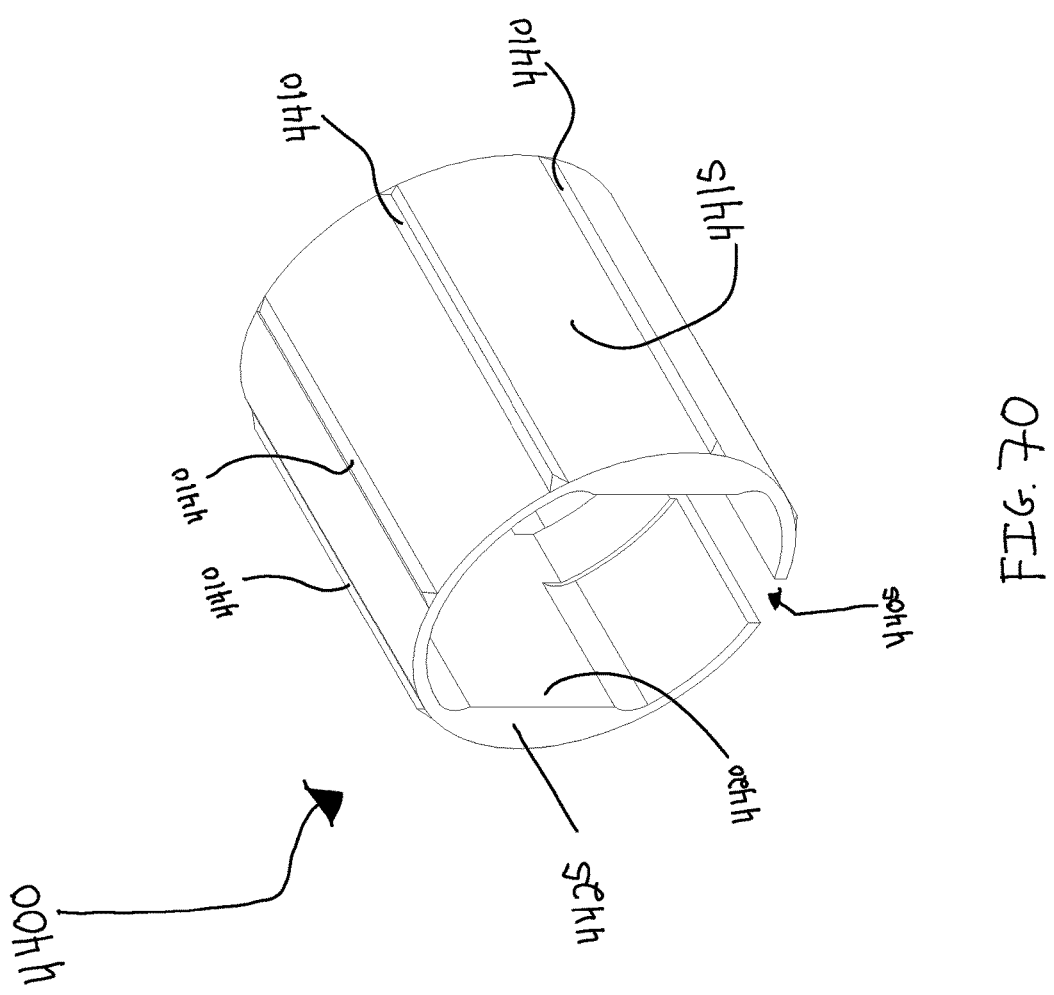

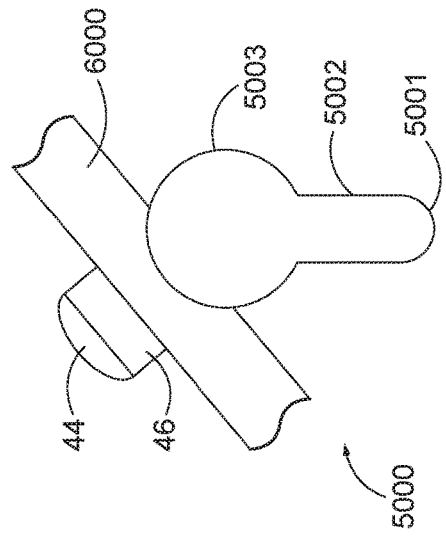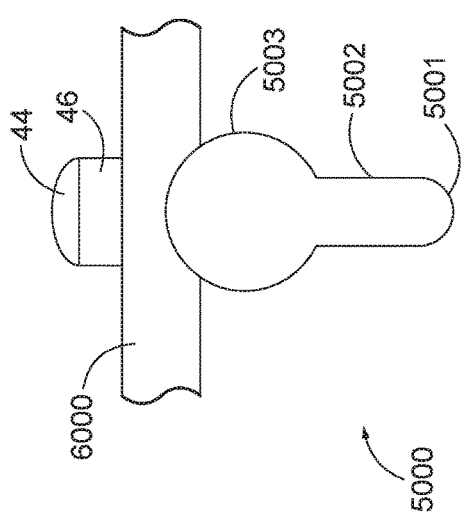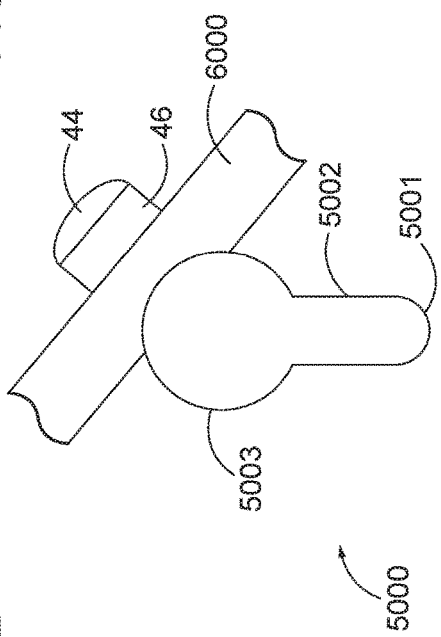

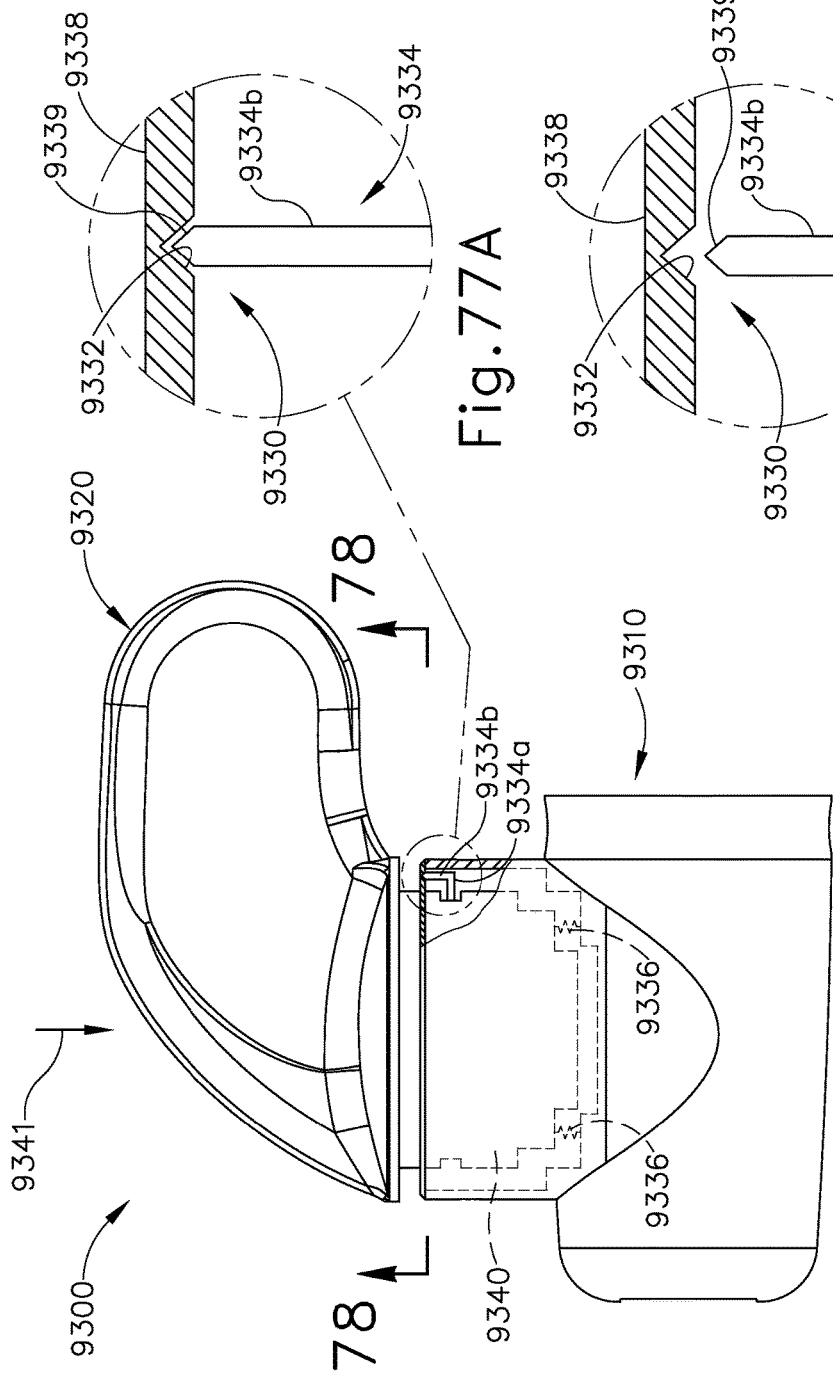
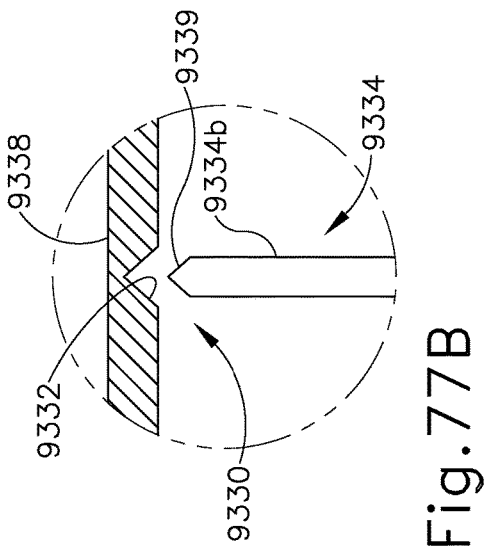
Fig.77A
Fig.77B
Fig.77

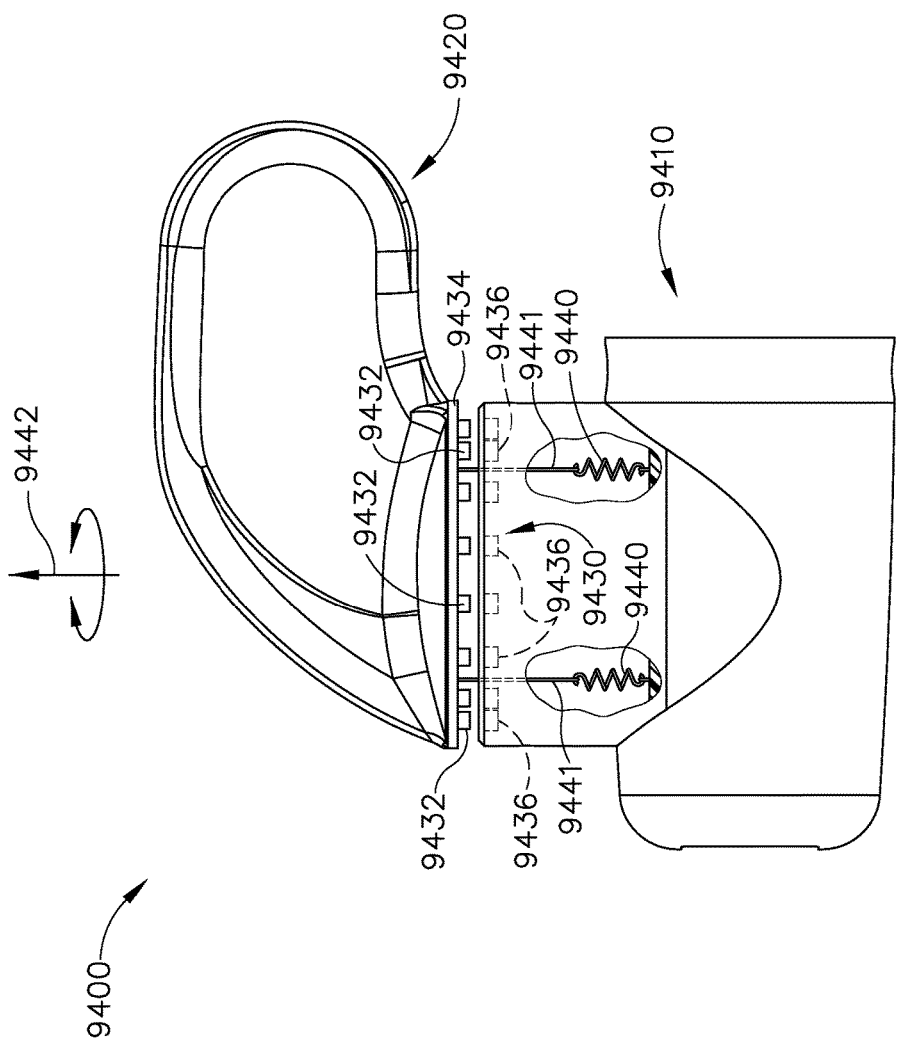

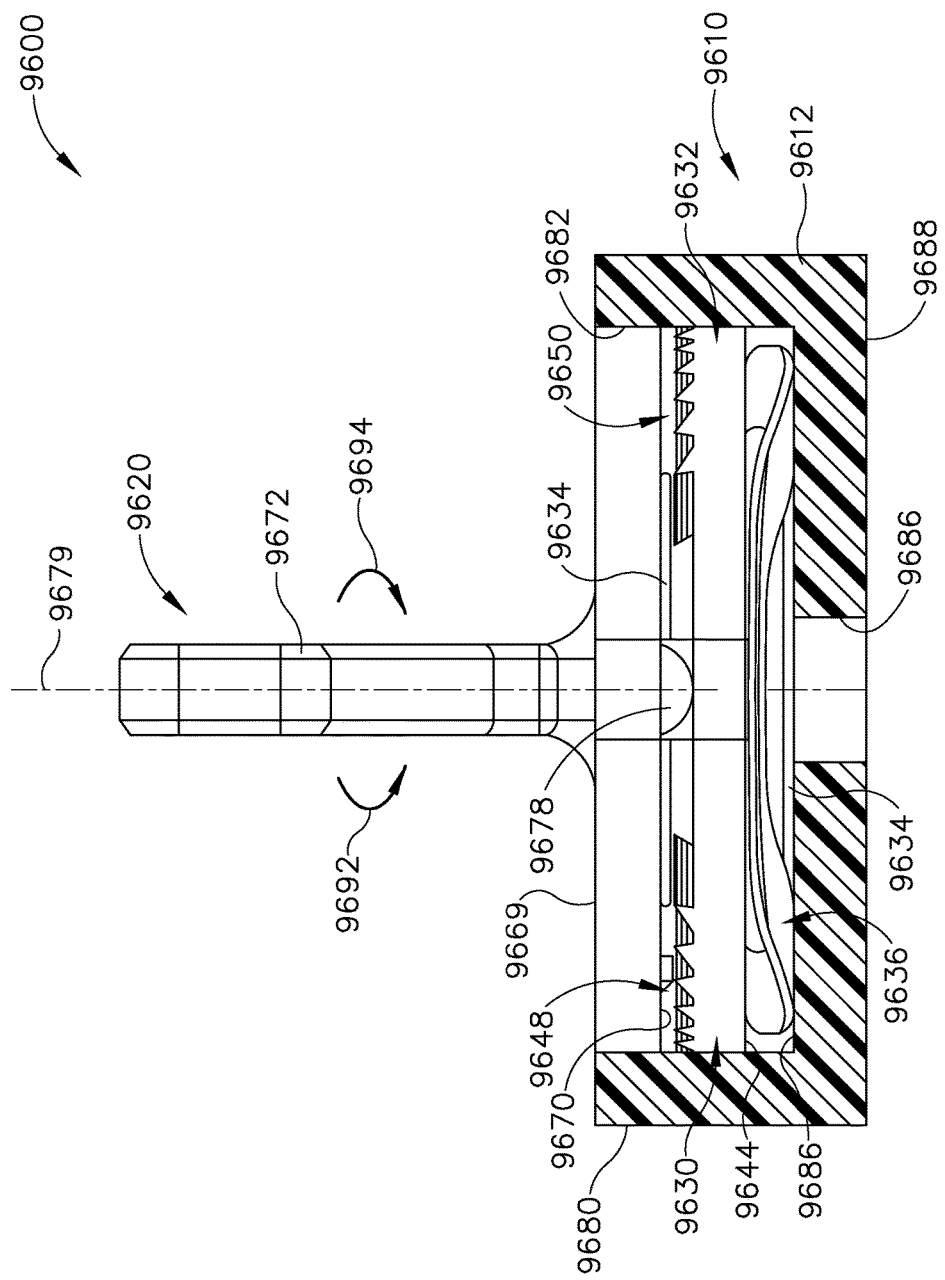

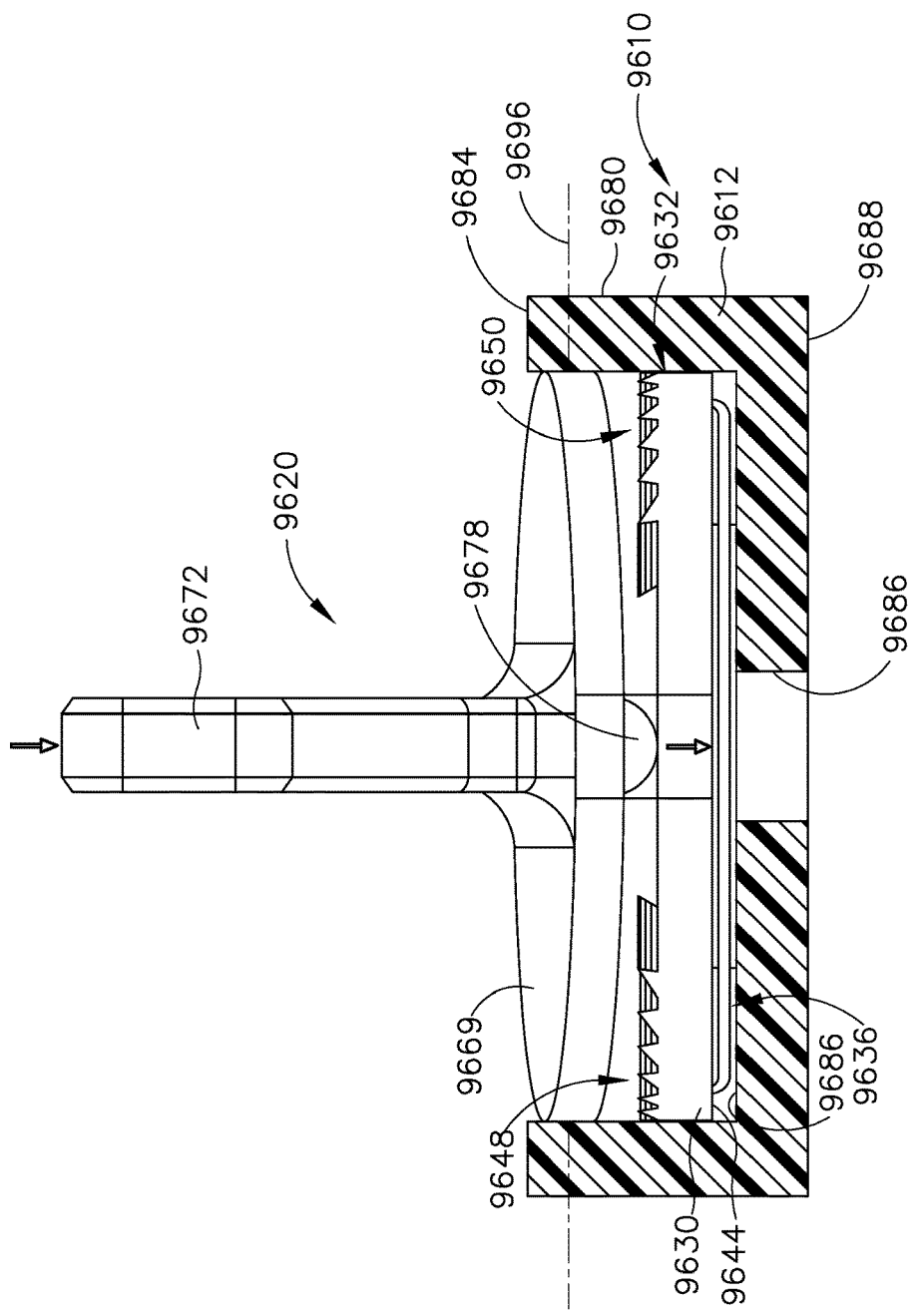

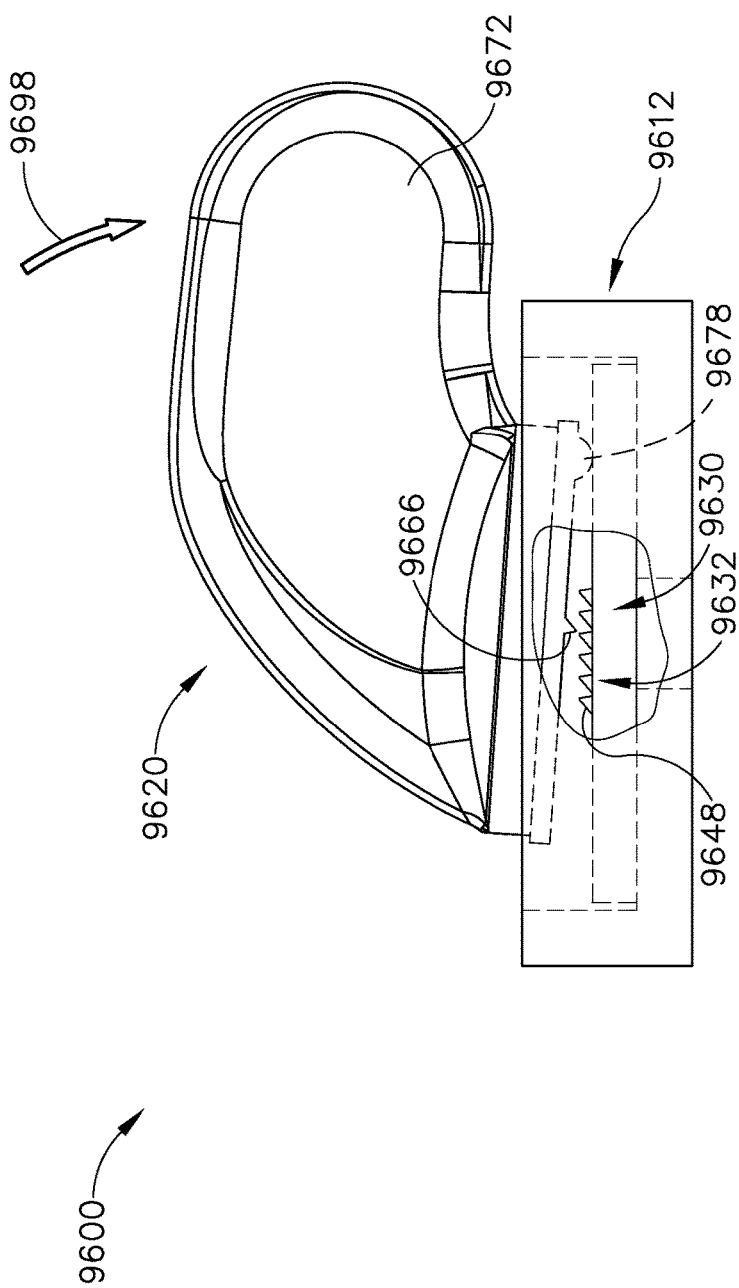

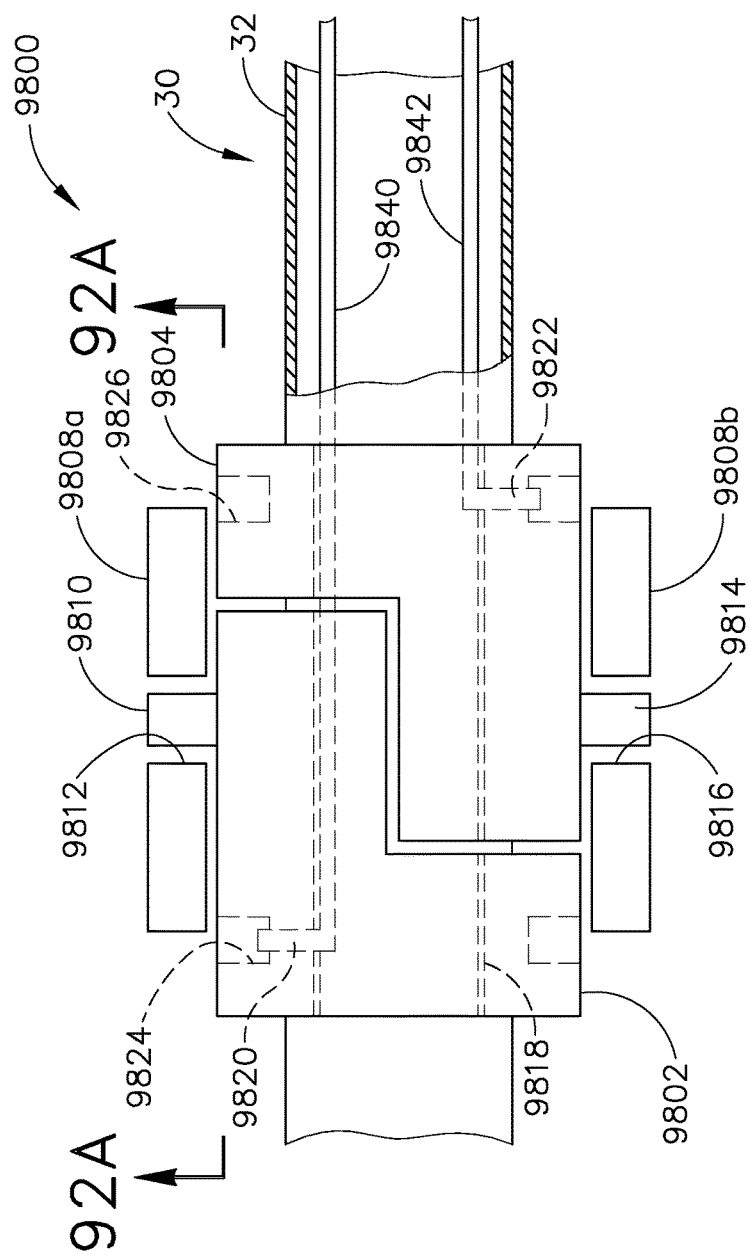

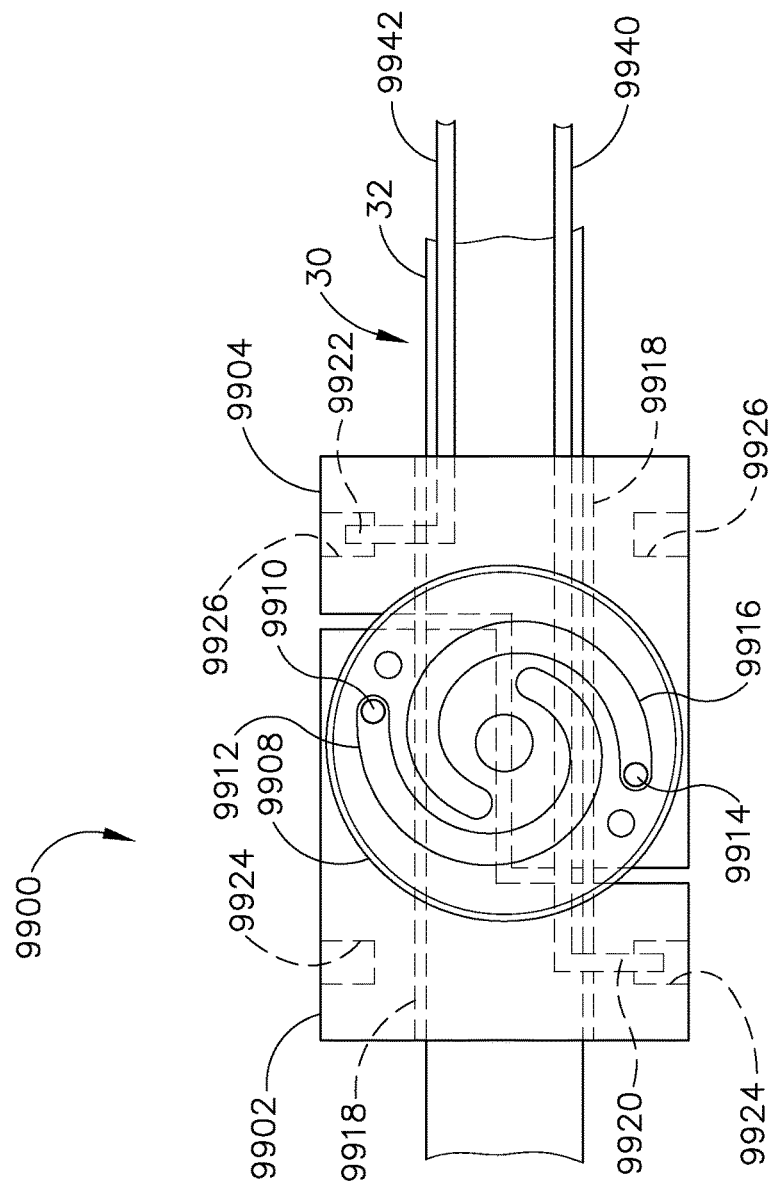

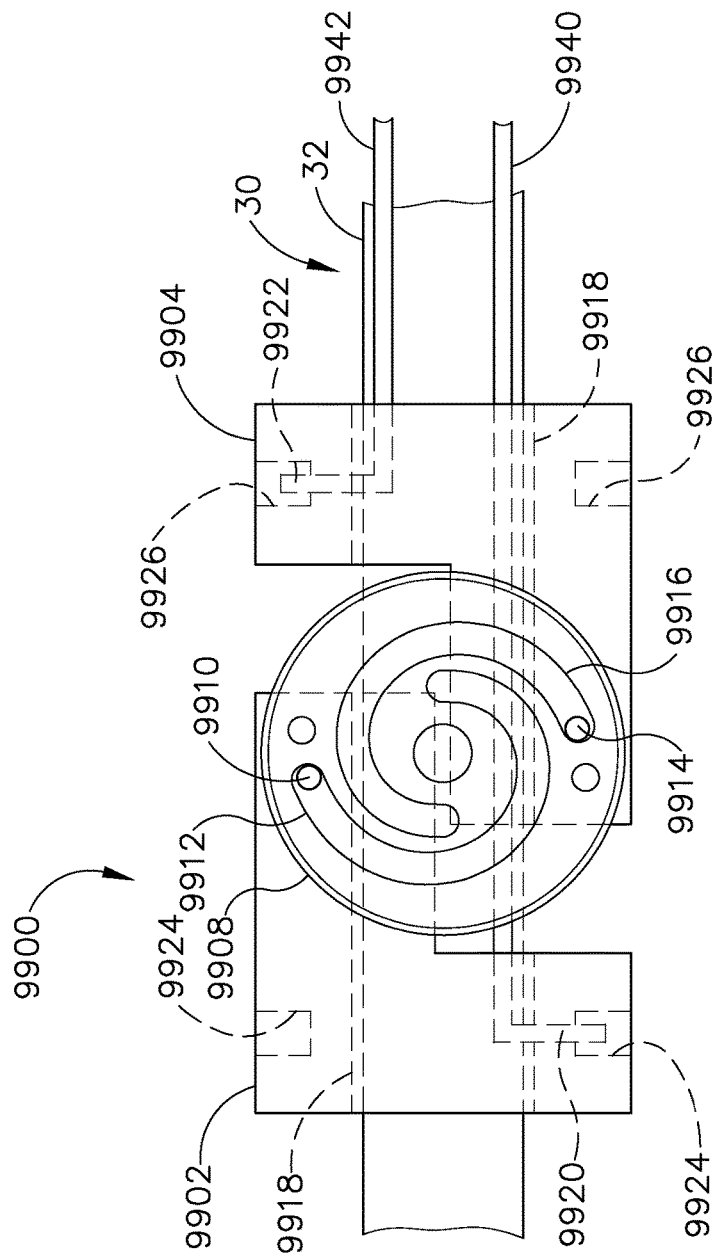

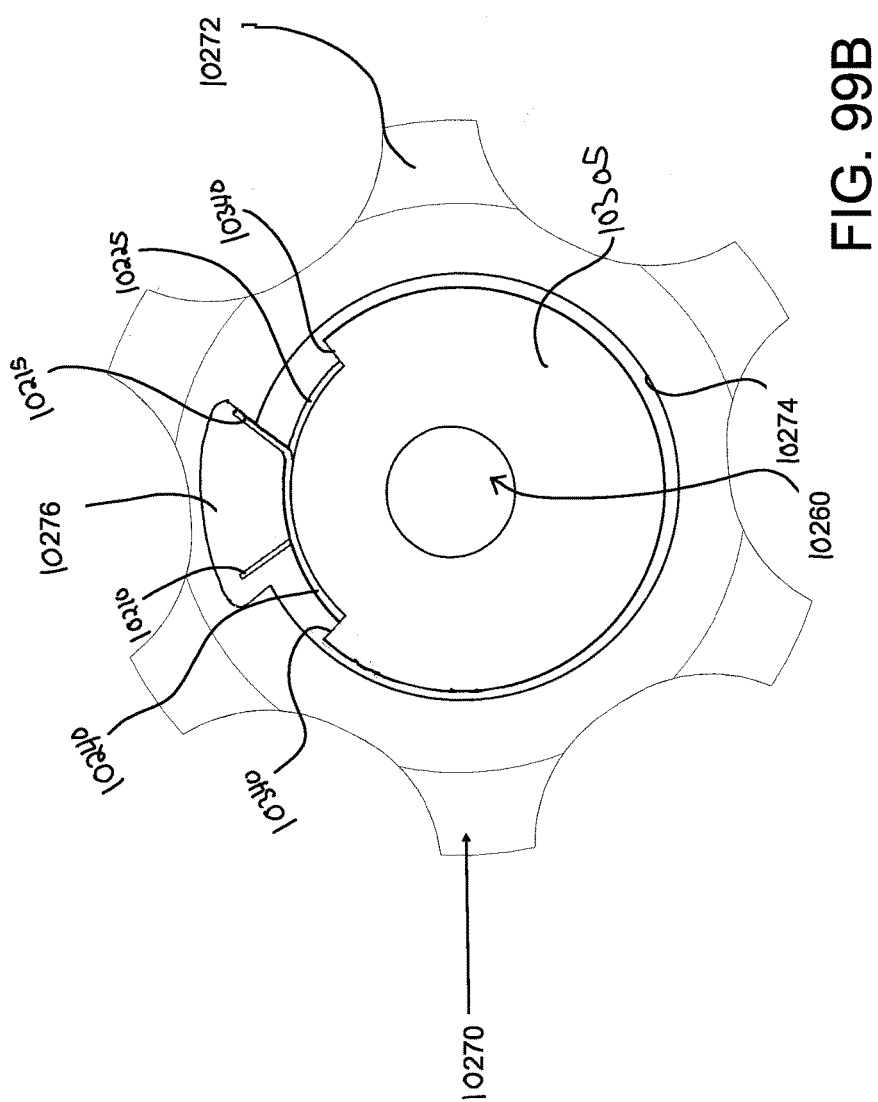

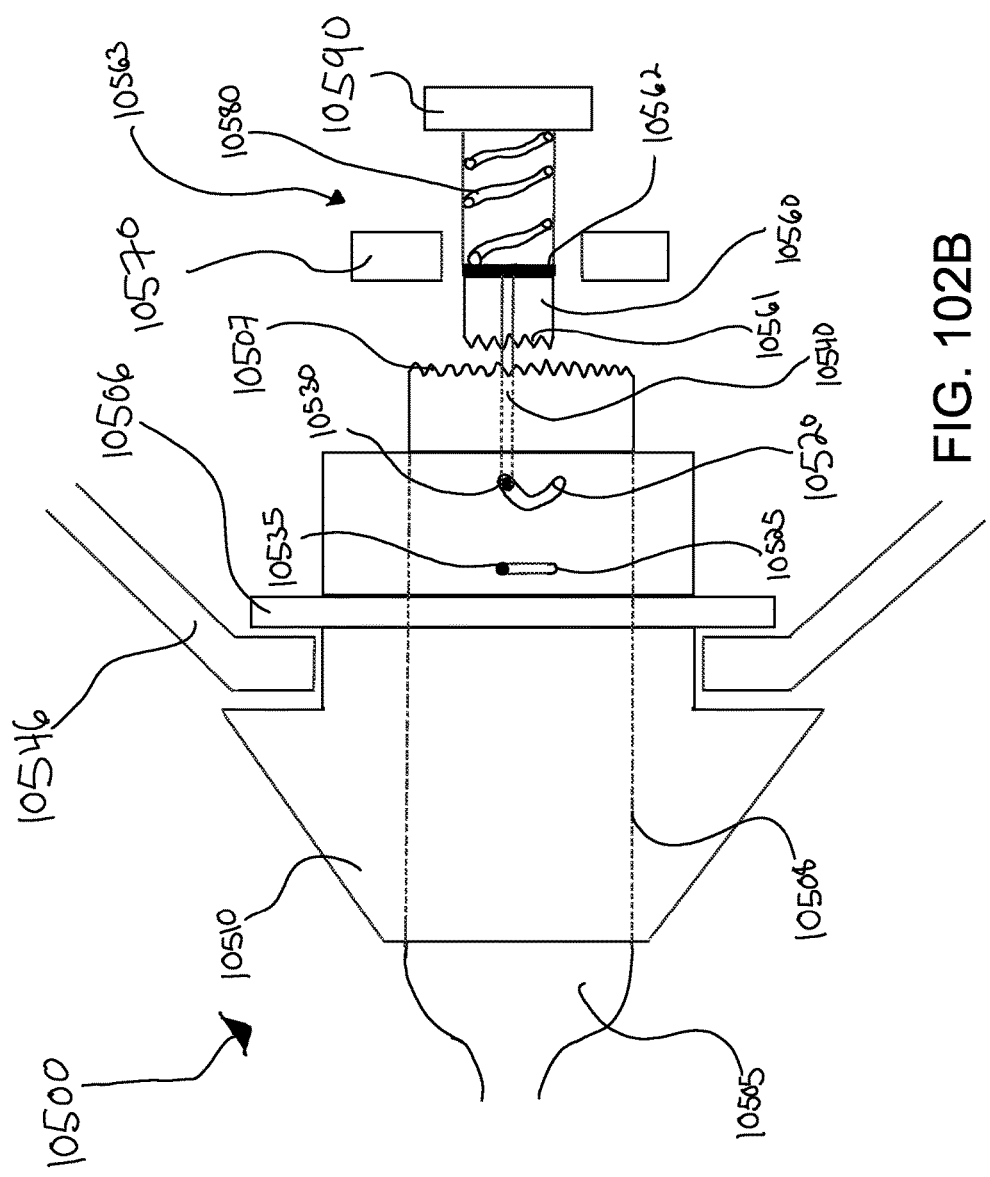

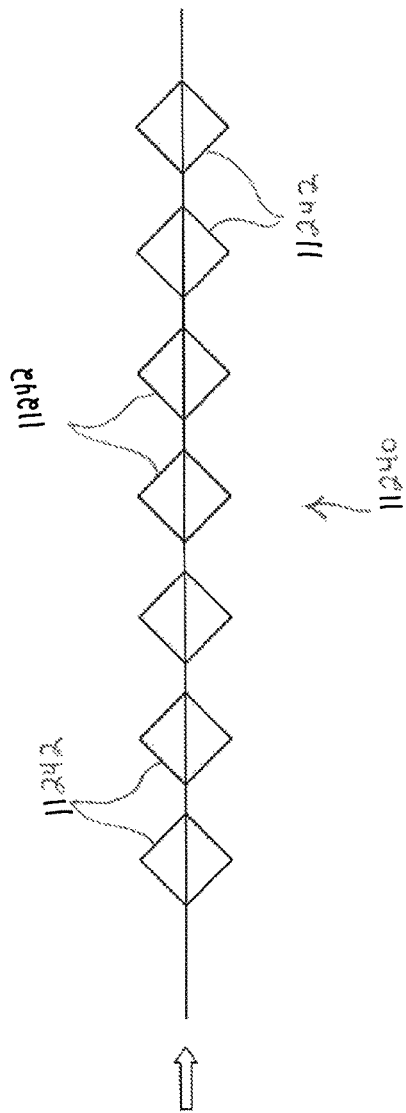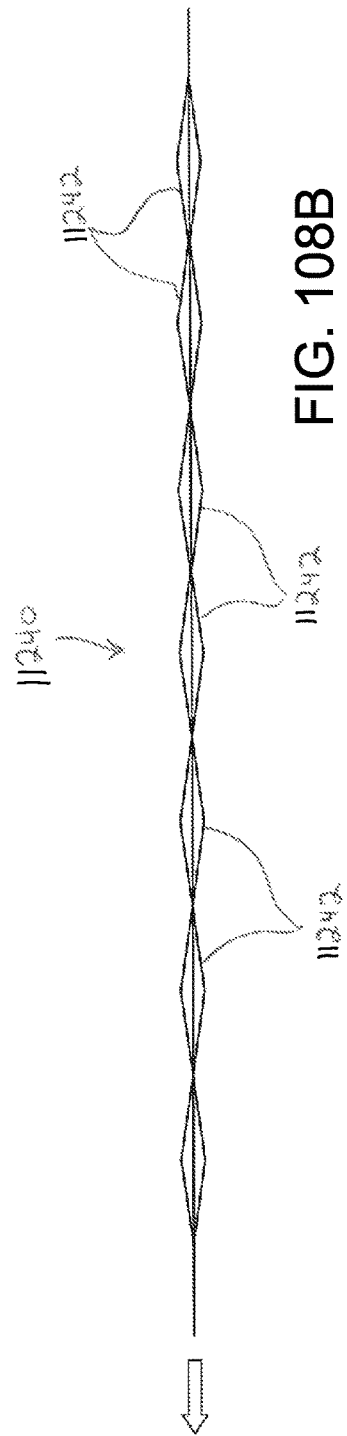

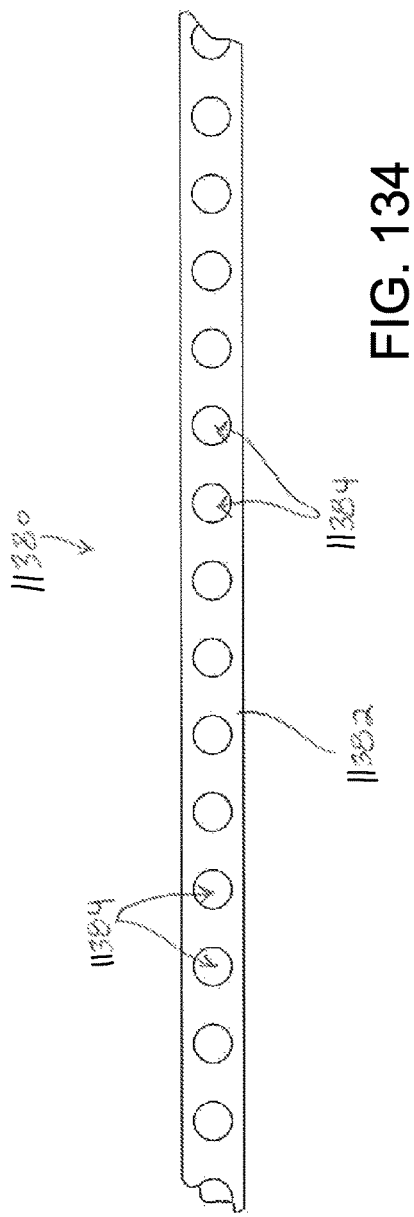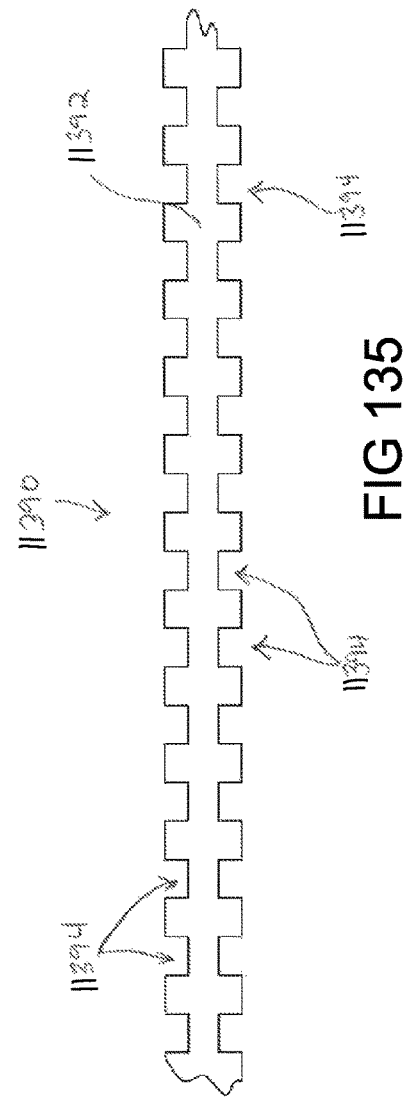

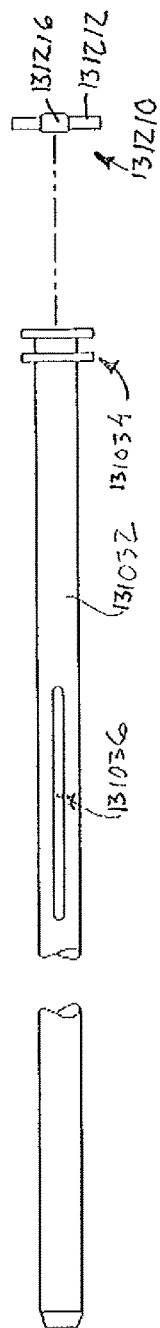
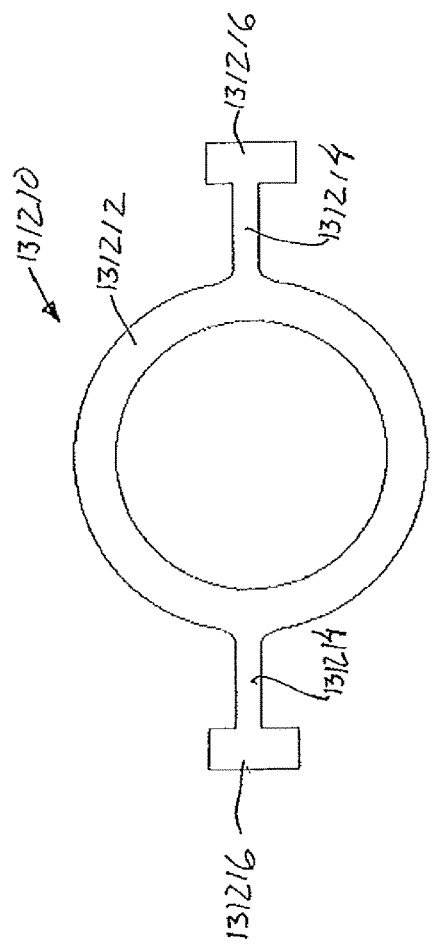
Fig. 184
Fig. 185

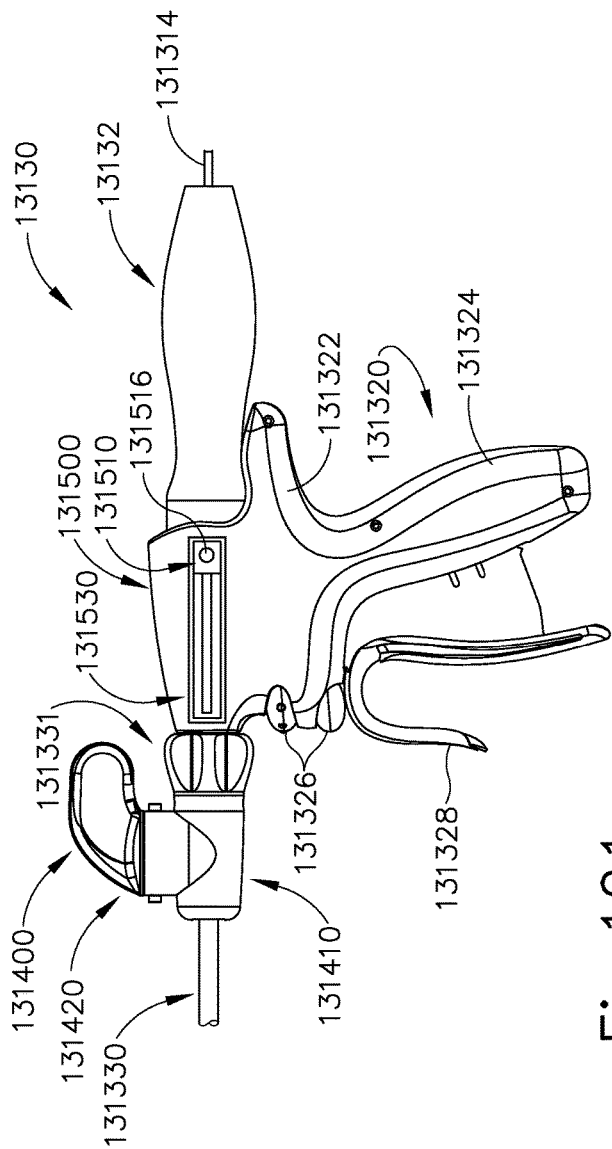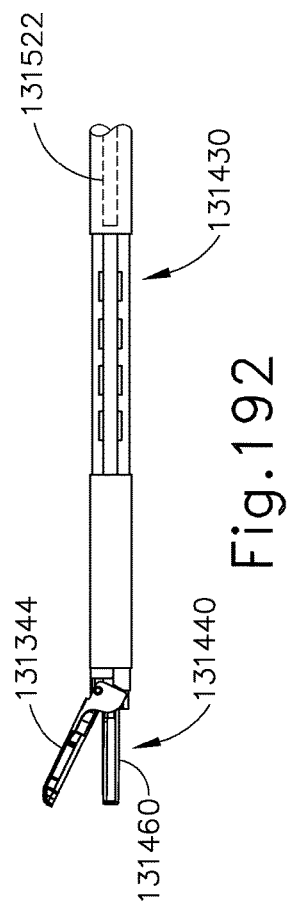
Fig.191
Fig.192

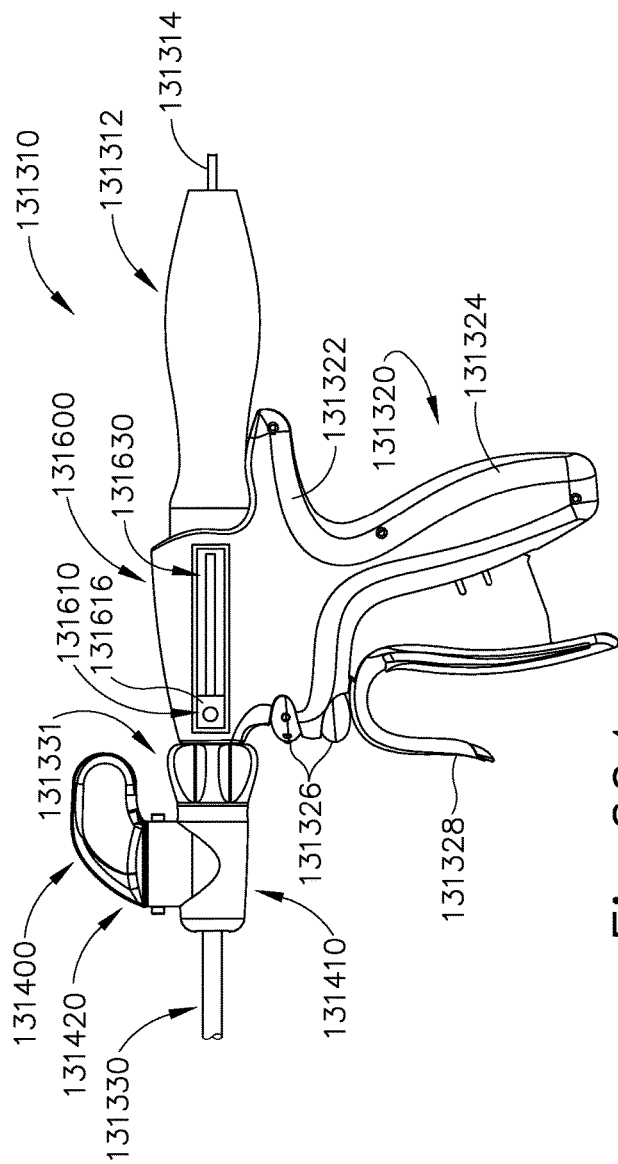
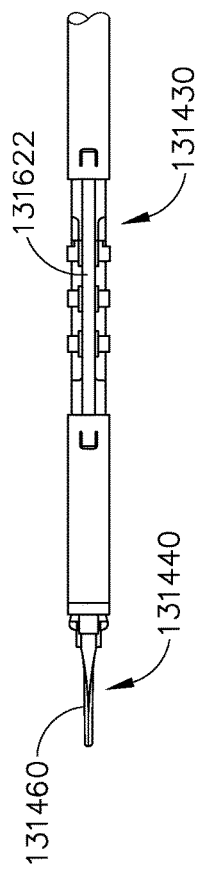
Fig. 204
Fig. 205

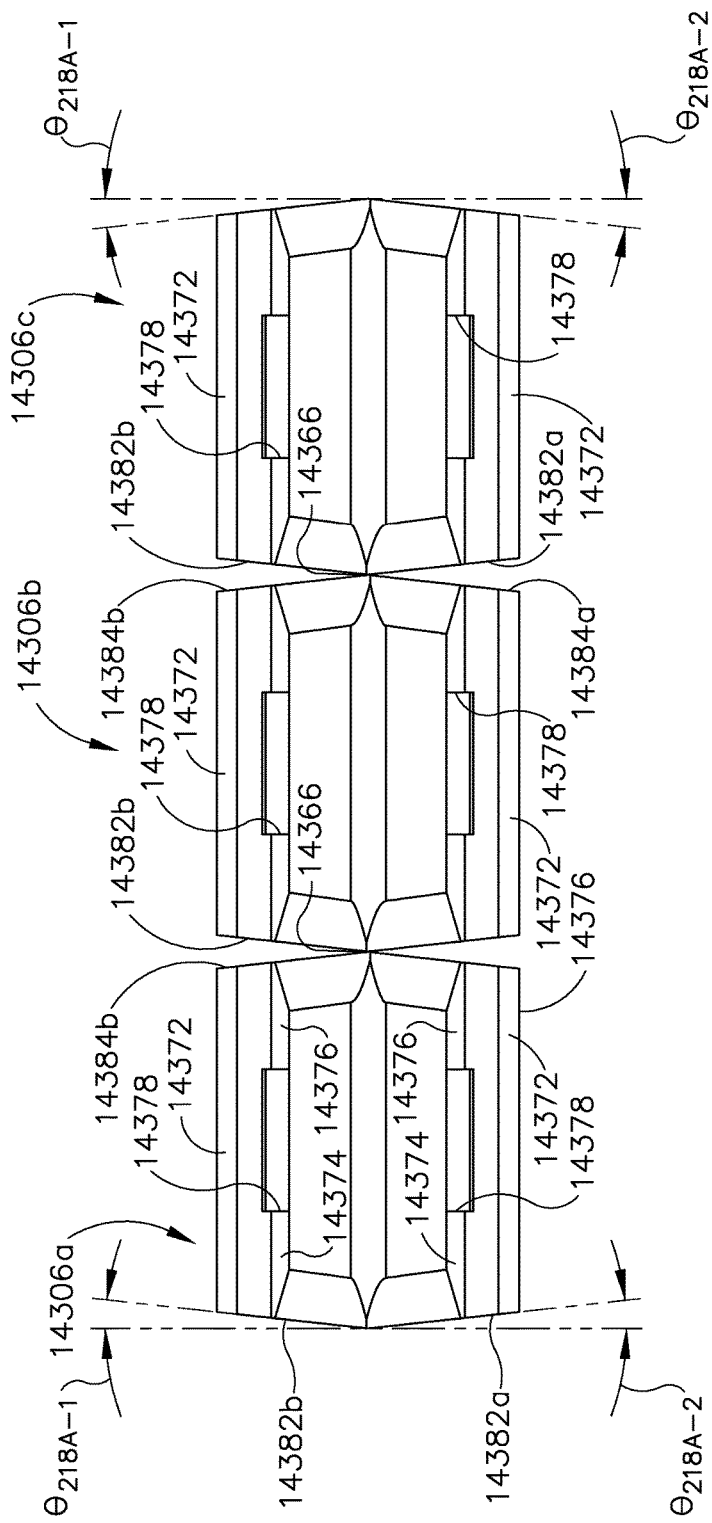

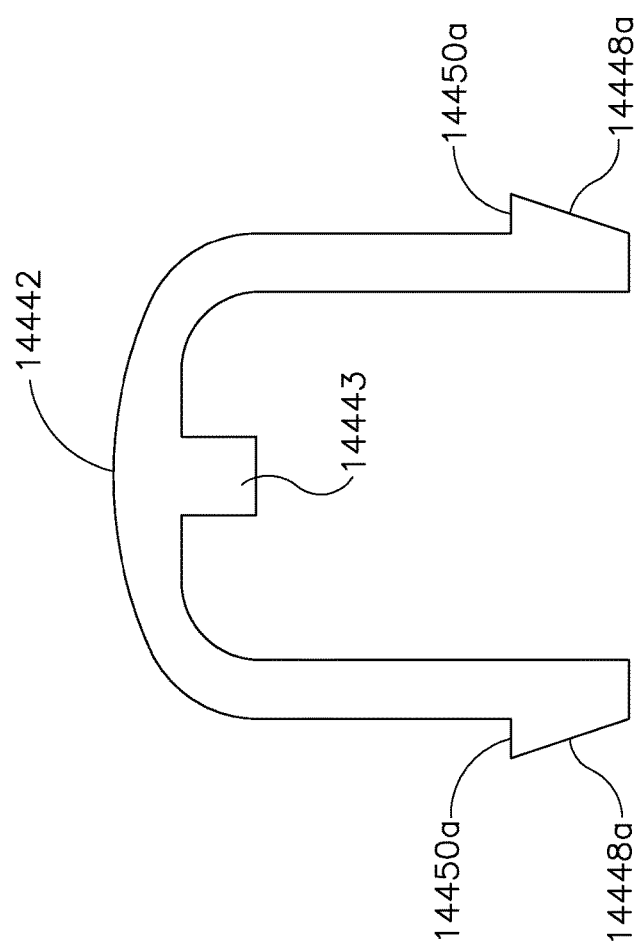

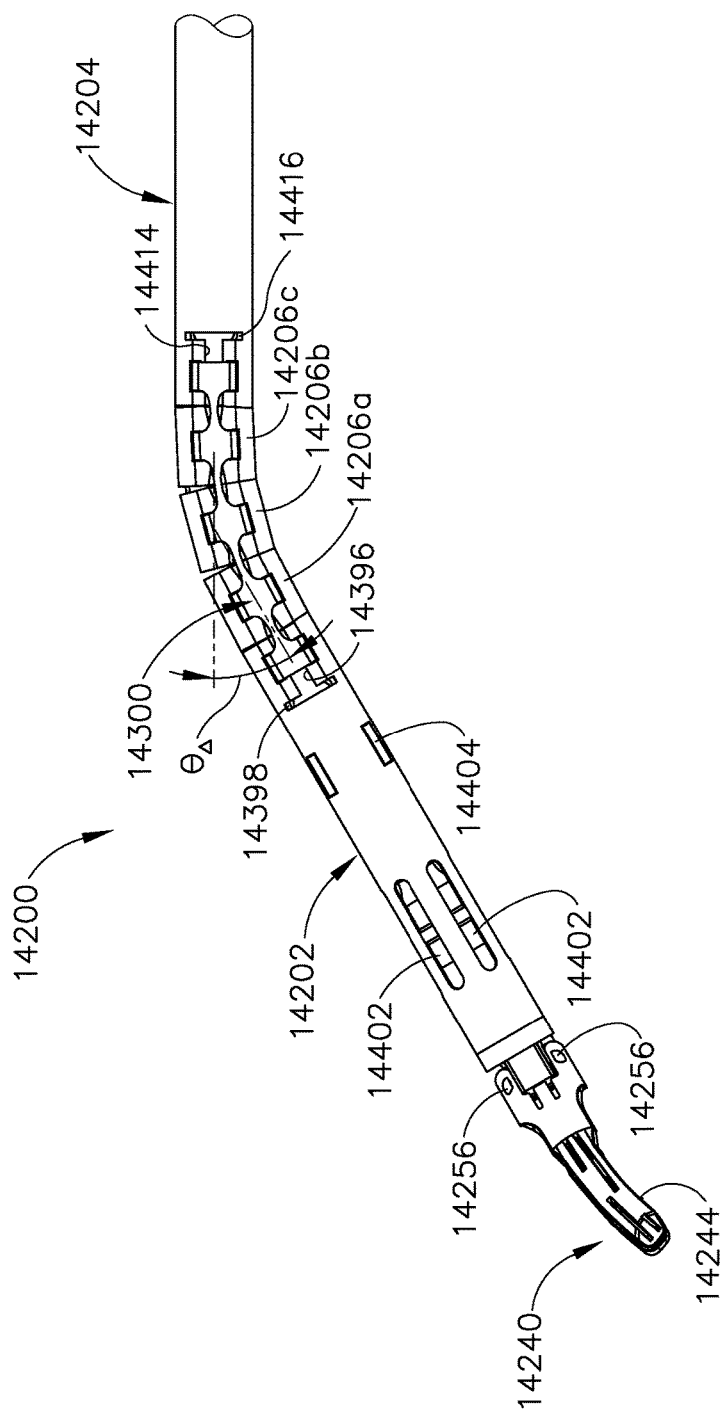

METHOD OF OPERATING AN ARTICULATING ULTRASONIC SURGICAL INSTRUMENT

PRIORITY

This application claims priority to U.S. Provisional Pat. App. No. 62/176,880, entitled "Ultrasonic Surgical Device with Articulating End Effector," filed Apr. 22, 2014, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, now abandoned, entitled "Tissue Pad for Use with an Ultrasonic Surgical Instrument," published Apr. 13, 2006, the disclosure of which is incorporated by reference herein; U.S. Pub. No. 2007/0191713, now abandoned, entitled "Ultrasonic Device for Cutting and Coagulating," published Aug. 16, 2007, the disclosure of which is incorporated by reference herein; U.S. Pub. No. 2007/0282333, now abandoned, entitled "Ultrasonic Waveguide and Blade," published Dec. 6, 2007, the disclosure of which is incorporated by reference herein; U.S. Pub. No. 2008/0200940, now abandoned, entitled "Ultrasonic Device for Cutting and Coagulating," published Aug. 21, 2008, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pat. No. 8,461,744, entitled "Rotating Transducer Mount for Ultrasonic Surgical Instruments," published Jan. 20, 2011, the disclosure of which is incorporated by reference herein; and U.S. Pat. No. 8,591,536, entitled "Ultrasonic Surgical Instrument Blades," published Feb. 2, 2012, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015 the disclosure of which is incorporated by reference herein; U.S. Pub. No. 2015/0080924, entitled ""Articulation Features for Ultrasonic Surgical Instrument," published Mar. 19, 2015, issued as U.S. Pat. No. 9,936,949 on Nov. 15, 2018, the disclosure of which is incorporated by reference herein; and U.S. patent application Ser. No. 14/258,179, entitled Ultrasonic Surgical Device with Articulating End Effector," filed Apr. 22, 2014, disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5 depicts a top plan view of the shaft assembly and end effector of FIG. 2;

FIG. 17A depicts a perspective view of yet another exemplary alternative end effector and the distal portion of a shaft assembly and end effector, configured for incorporation in the instrument of FIG. 1, with a clamp arm of the end effector in a closed position;

FIG. 42B depicts a top plan view of the shaft assembly of FIG. 41 in an articulated configuration;

FIG. 45 depicts a detailed perspective view of the flange of FIG. 44;

FIG. 46 depicts a cross-sectional end view of the flange of FIG. 44;

FIG. 47 depicts a detailed perspective view of an exemplary alternative flange;

FIG. 48 depicts a cross-sectional end view of the flange of FIG. 47;

FIG. 49 depicts a detailed perspective view of another exemplary alternative flange;

FIG. 50 depicts a cross-sectional end view of the flange of FIG. 49;

FIG. 55C depicts a perspective view of the articulation section of the shaft assembly and the end effector of FIG. 55A with certain elements omitted to show greater detail;

FIG. 59 depicts a perspective view of a flexible locking feature of the articulation section of FIG. 55A;

FIG. 61 depicts a perspective view of body portions of the articulation section of FIG. 55A longitudinally aligned with one another;

FIG. 62 depicts a perspective view of the intermediate body portion of FIG. 55A;

FIG. 63 depicts a front elevational view of the intermediate body portion of FIG. 55A;

FIG. 69A depicts a cross sectional top view of the articulation section of the shaft assembly of the surgical instrument of FIG. 55A, with the articulation section in a non-articulated state;

FIG. 70 depicts a perspective view of an exemplary distal node bumper that may be incorporated into the shaft assembly of FIG. 2;

FIG. 72 depicts a front elevational view of tissue clamped between an exemplary keyhole blade and clamp arm assembly that may be incorporated into the end effector of FIG. 2, in an on-plane configuration;

FIG. 73 depicts a front elevational view of tissue clamped between the keyhole blade and clamp arm assembly of FIG. 71, in a first off-plane configuration;

FIG. 74 depicts a front elevational view of tissue clamped between the keyhole blade and clamp arm assembly of FIG. 71, in a second off-plane configuration;

FIG. 77 depicts a side elevational view of another exemplary alternative articulation control assembly that may be incorporated into the instrument of FIG. 1, with a locking feature in a locked configuration;

FIG. 77A depicts a detailed side elevational view of the locking feature of the articulation control assembly of FIG. 77 in the locked configuration;

FIG. 77B depicts a detailed side elevational view of the locking feature of the articulation control assembly of FIG. 77 in the unlocked configuration;

FIG. 79B depicts a side elevational view of the articulation control assembly of FIG. 79A, with the locking feature in an unlocked configuration;

FIG. 88A shows a rear elevational view of the articulation control assembly of FIG. 84, with a portion of the housing hidden to show details of the components, and with the knob in a home position;

FIG. 88B shows a rear elevational view of the articulation control assembly of FIG. 84, with a portion of the housing broken away to show details of the components, and with the knob tilted to the unlocking position;

FIG. 89 shows a side elevational view of the articulation control assembly of FIG. 84, with a portion of the housing being shown as transparent to show details of the components, and with the knob tilted to the unlocking position;

FIG. 91A depicts a top plan view of another exemplary alternative articulation control assembly that may be incorporated into the instrument of FIG. 1, with the articulation control assembly in a first configuration;

FIG. 93A depicts a side elevational view of another exemplary alternative articulation control assembly that may be incorporated into the instrument of FIG. 1, with the articulation control assembly in a first configuration;

FIG. 93B depicts a side elevational view of the articulation control assembly of FIG. 93A, with the articulation control assembly in a second configuration;

FIG. 94A depicts a partial cross-sectional view of the articulation control assembly of FIG. 93A, taken along line 94A-94A of FIG. 93A, with the articulation control assembly in the first configuration;

FIG. 94B depicts a partial cross-sectional view of the articulation control assembly of FIG. 93A, taken along line 94B-94B of FIG. 93B, with the articulation control assembly in the second configuration;

FIG. 95 depicts a side elevational view of an exemplary electrosurgical instrument;

FIG. 96 depicts a perspective view of a partially assembled rotation lock feature that may be incorporated into the instrument of FIG. 1 or the instrument of FIG. 95;

FIG. 97 depicts an enlarged perspective view of the partially assembled rotation lock feature of FIG. 96, with a housing half of the instrument handle assembly omitted;

FIG. 98 depicts a perspective view of the assembled rotation lock feature of FIG. 96, positioned on a shaft assembly;

FIG. 99A depicts a cross sectional front view of the assembled rotation lock feature of FIG. 96 in a first unengaged position;

FIG. 99B depicts a cross sectional front view of the assembled rotation lock feature of FIG. 96 in a second unengaged position;

FIG. 99C depicts a cross sectional front view of the assembled rotation lock feature of FIG. 96 in a first engaged position;

FIG. 99D depicts a cross sectional front view of the assembled rotation lock feature of FIG. 96 in a second engaged position and rotated 90 degrees;

Figure 1:
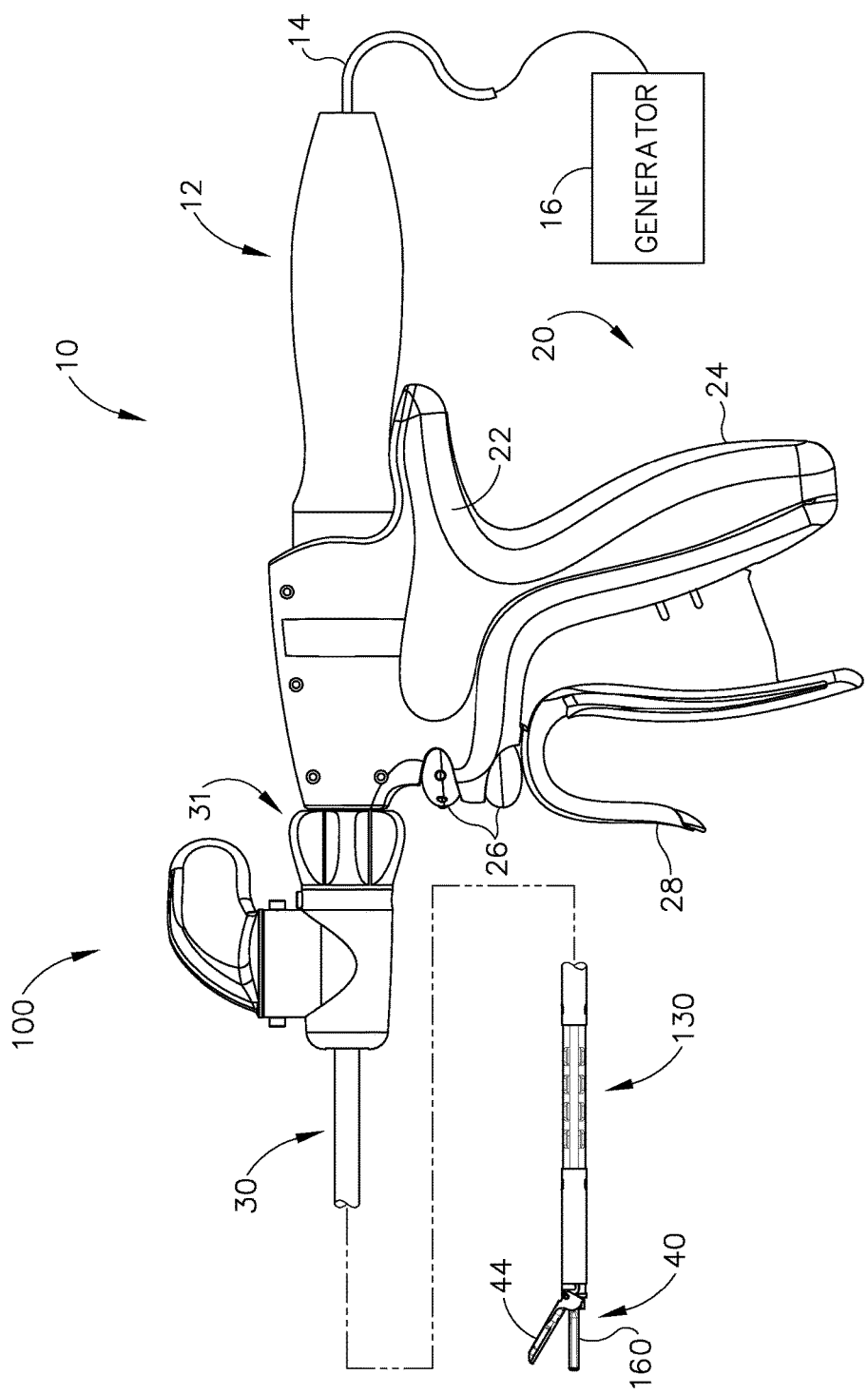
FIG. 1 depicts a side elevational view of an exemplary ultrasonic surgical instrument.
Figure 2:
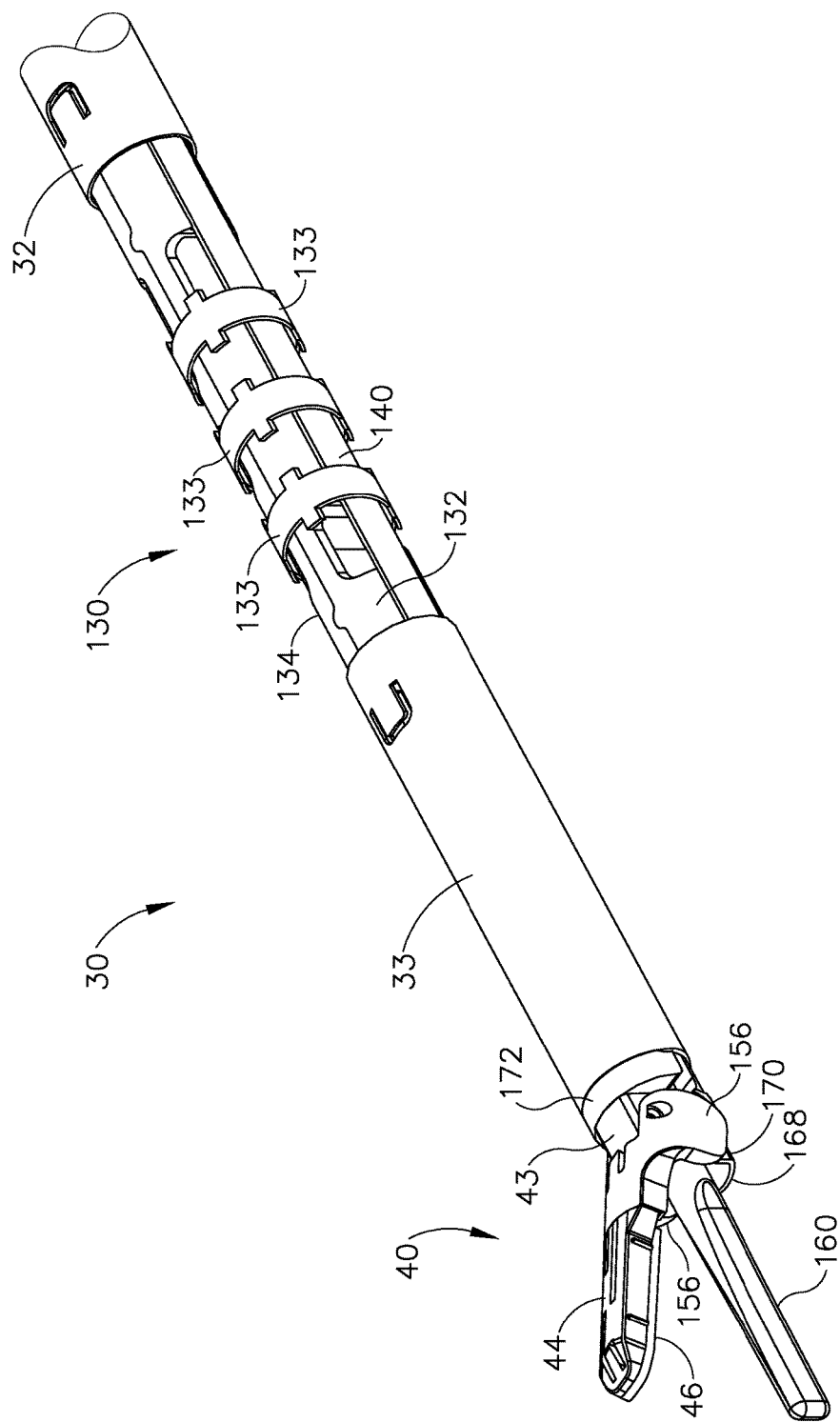
FIG. 2 depicts a perspective view of an articulation section of a shaft assembly and an end effector of the surgical instrument of FIG. 1.
Figure 9:
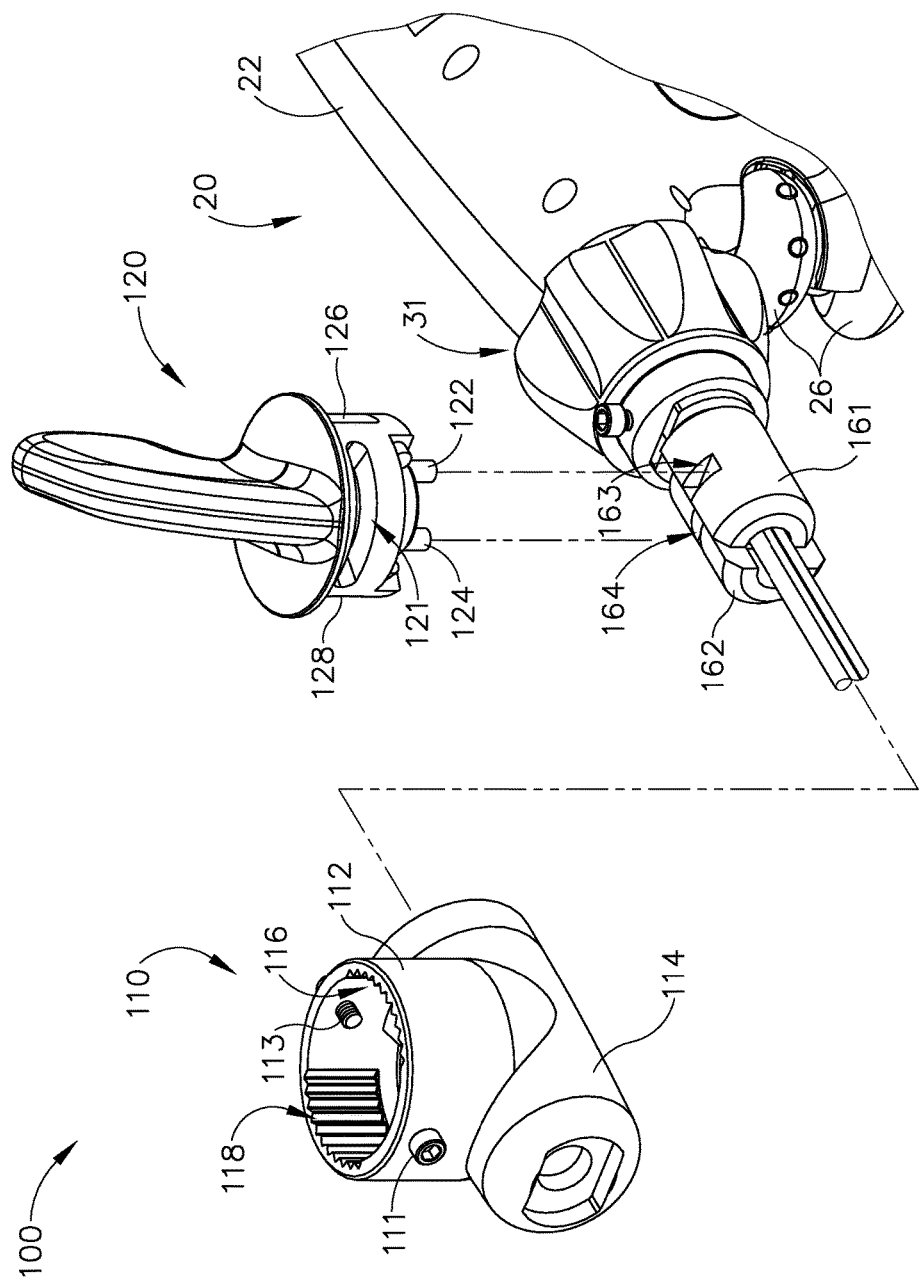
FIG. 9 depicts a partially exploded perspective view of an articulation control assembly of the instrument of FIG. 1.
Figure 30:
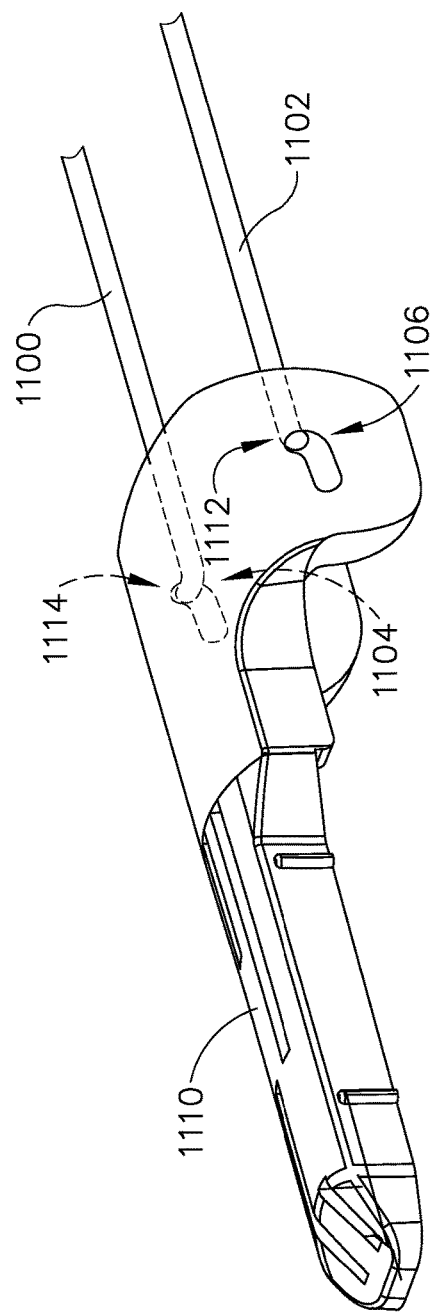
FIG. 30 depicts a perspective view of an exemplary alternative push/pull cable assembly configured for incorporation in any of the shaft assemblies and end effectors described herein.
Figure 34A:
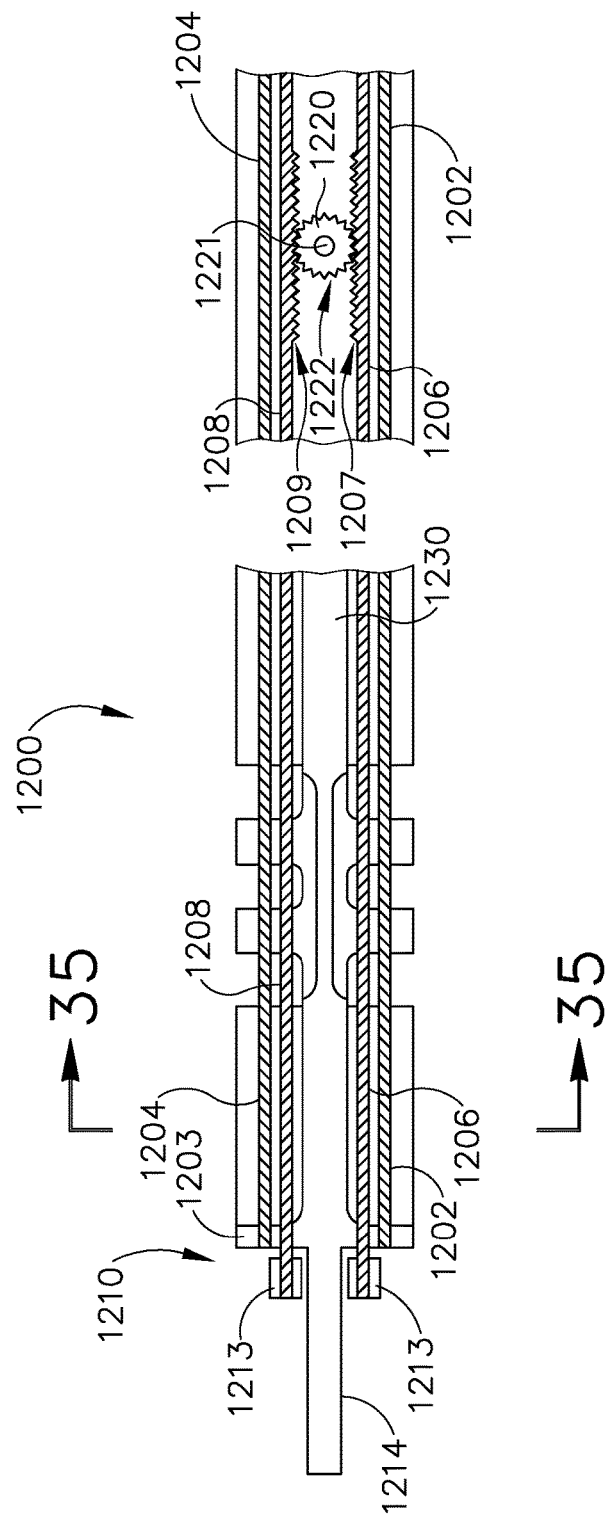
FIG. 34A depicts a cross-sectional top view of a distal portion of yet another exemplary alternative shaft assembly and end effector configured for incorporation in the instrument of FIG. 1, with the shaft assembly and end effector in a substantially straight configuration.
Figure 95:
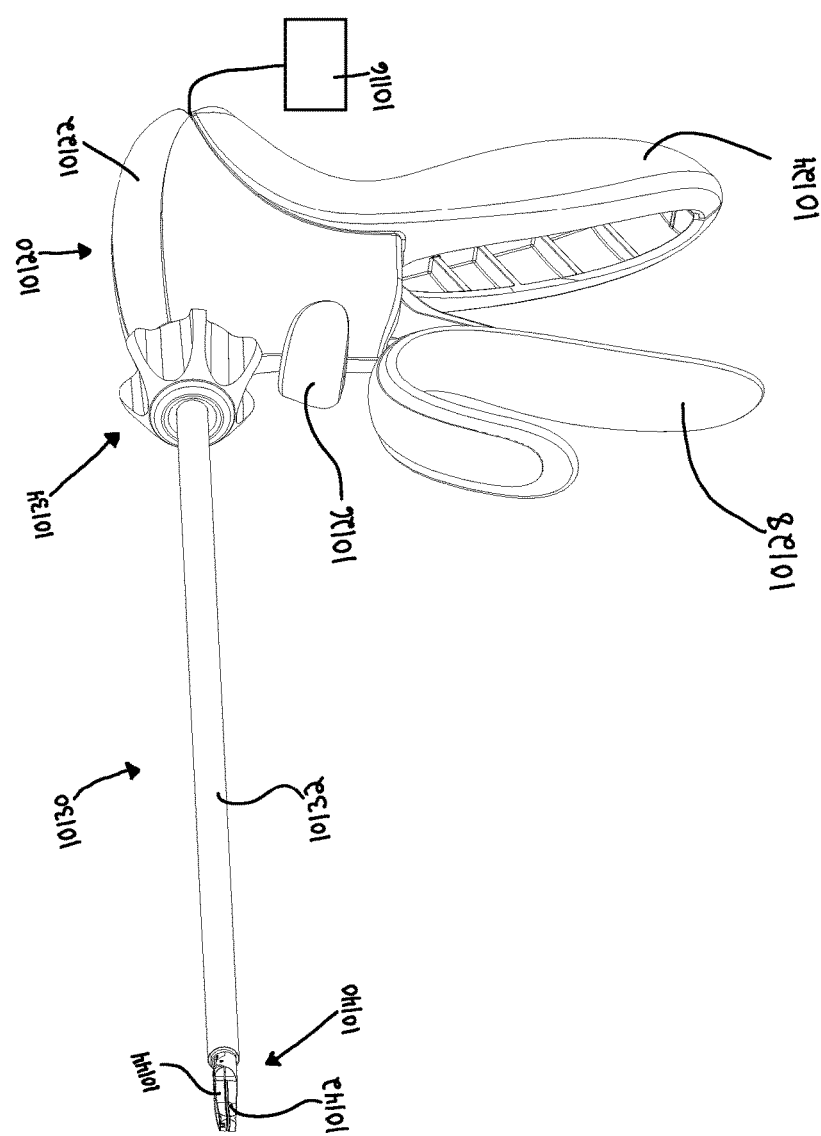
Figure 96:
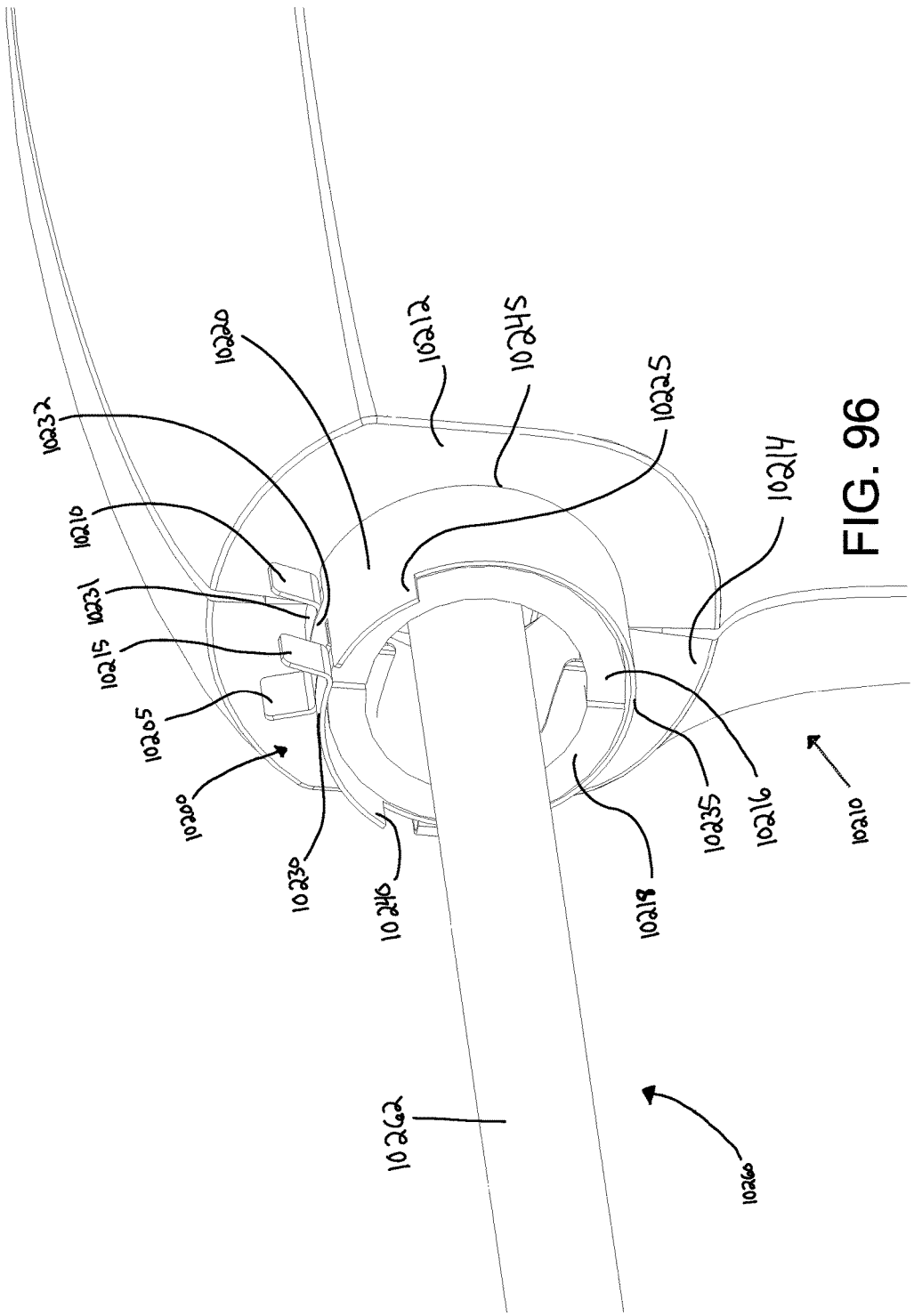
Figure 99A:
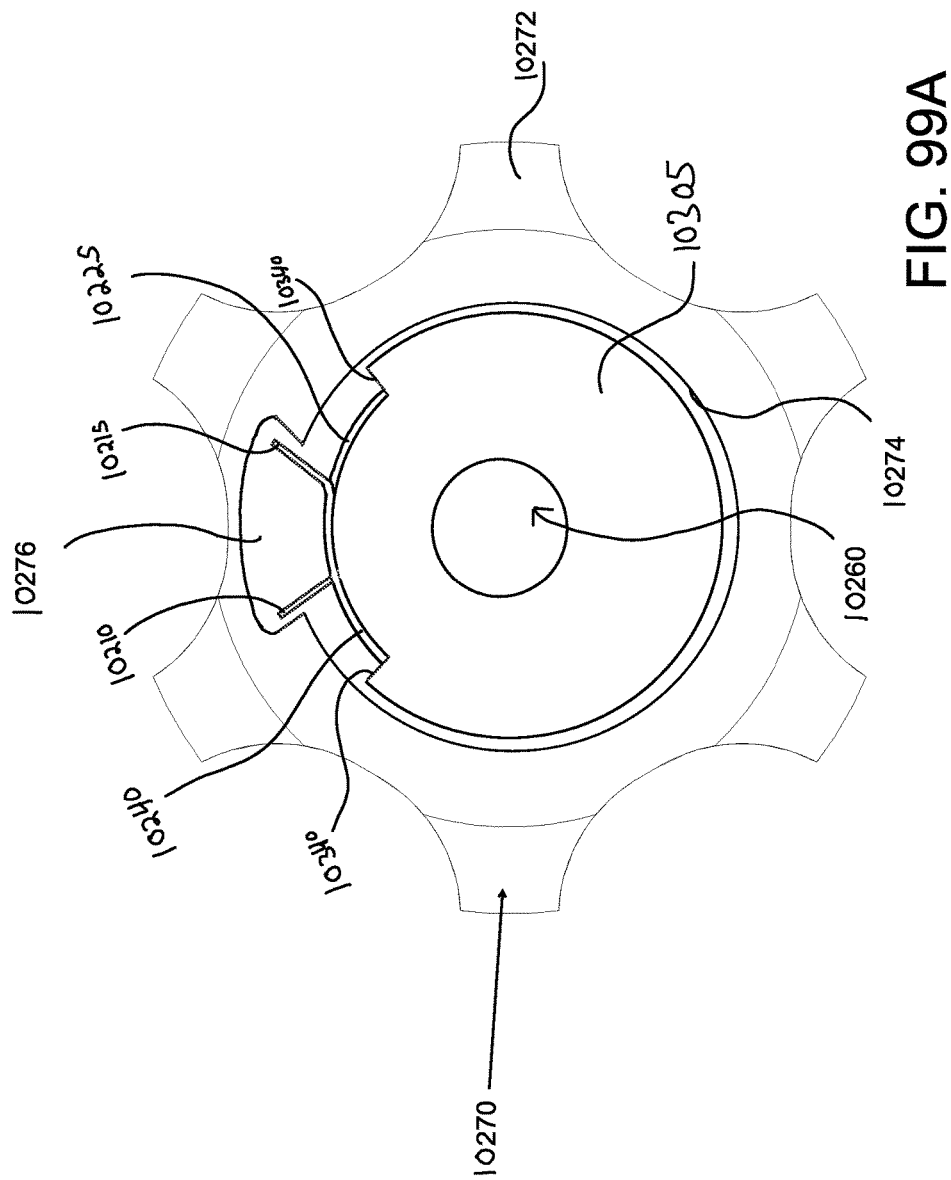
Figure 99C:
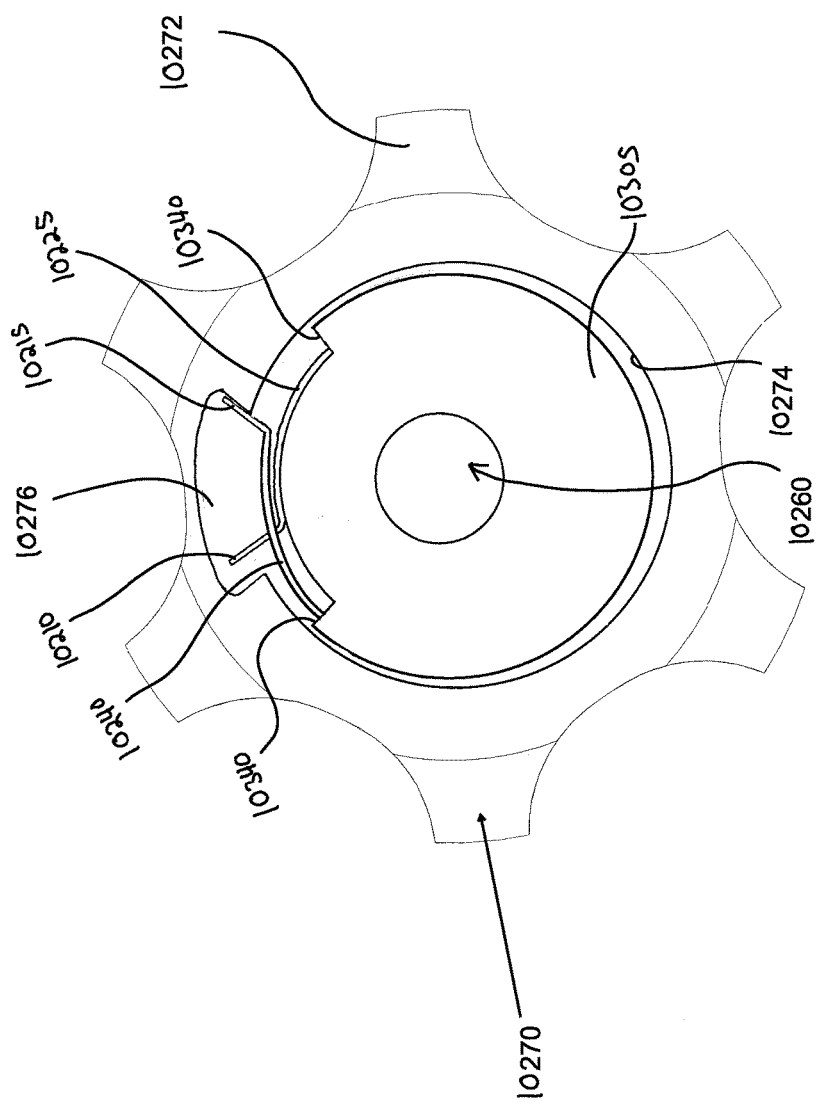
Figure 99D:
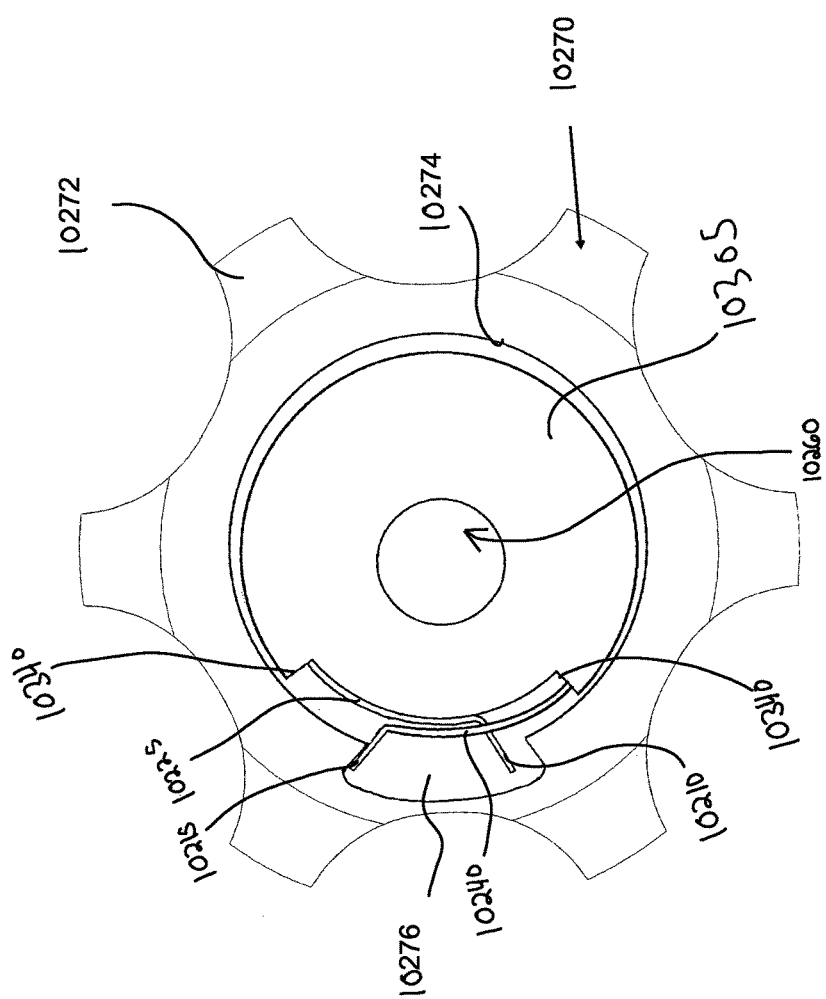
Figure 99E:
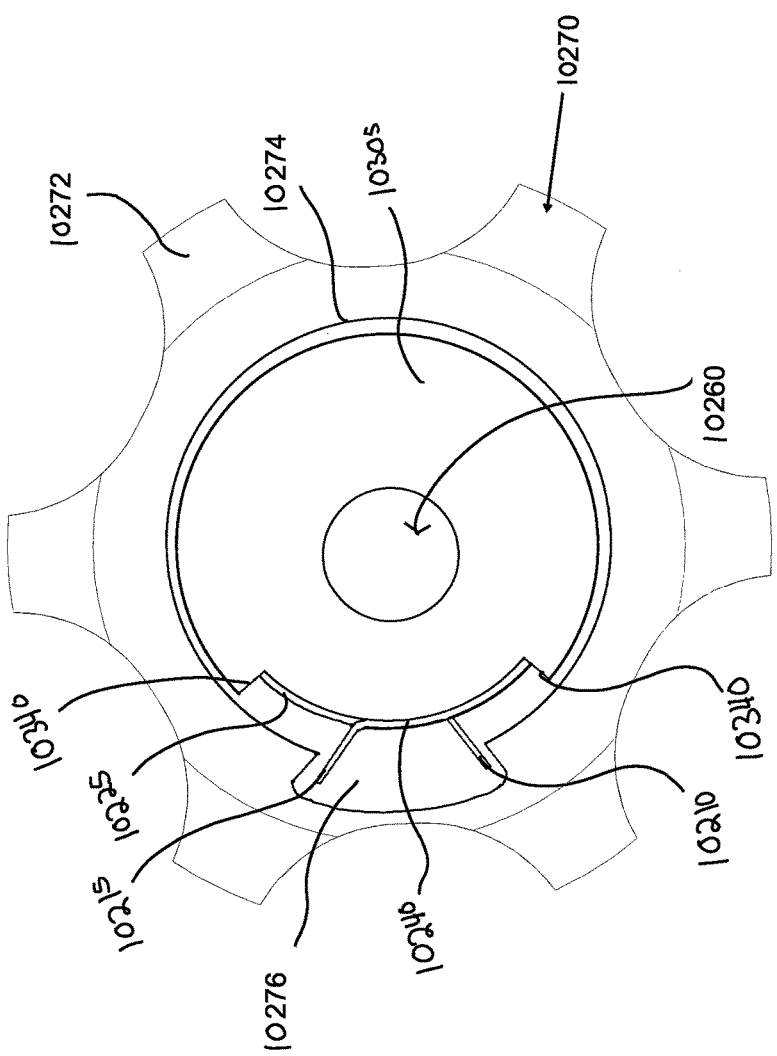
Figure 100A:
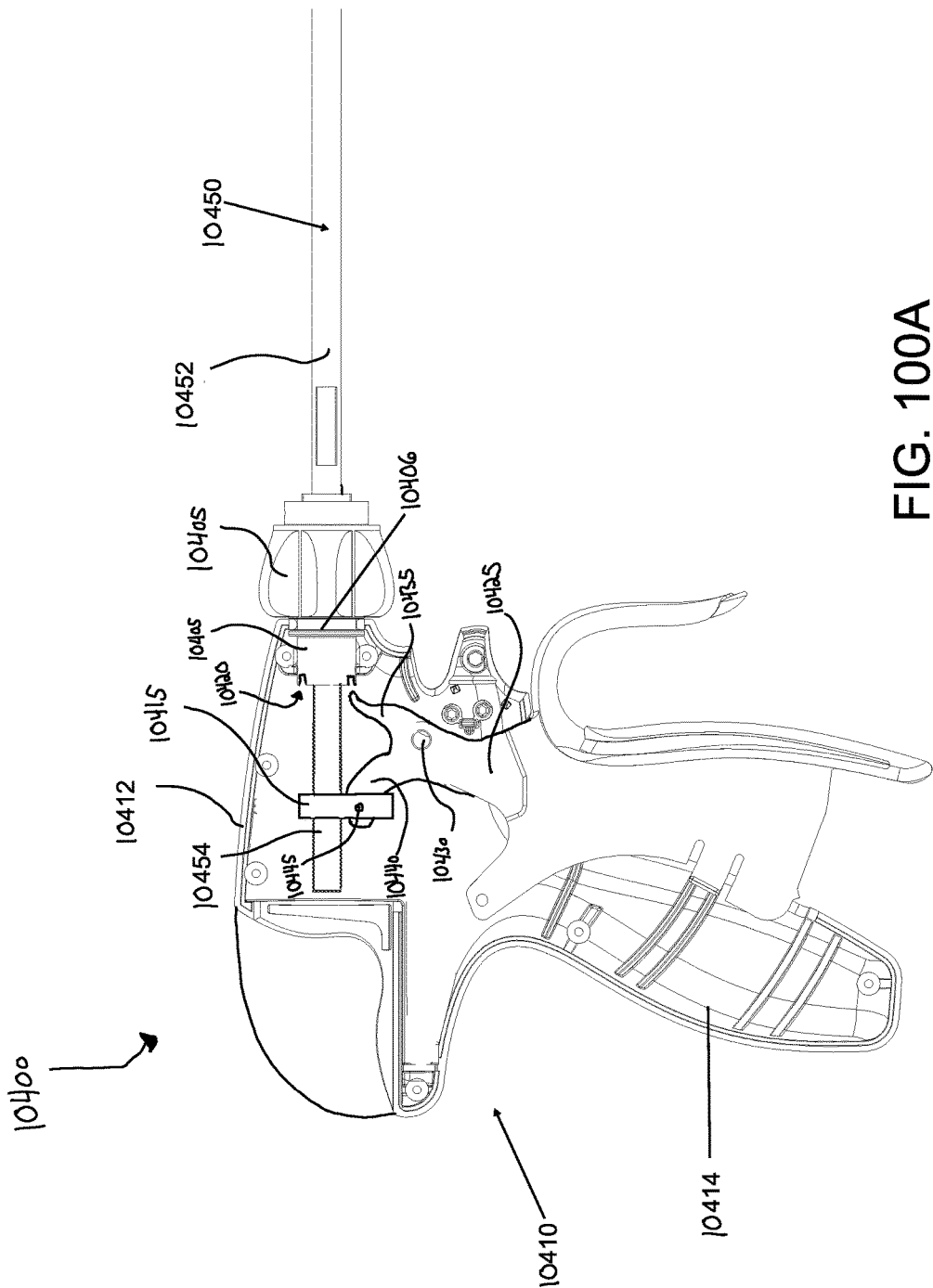
Figure 100B:
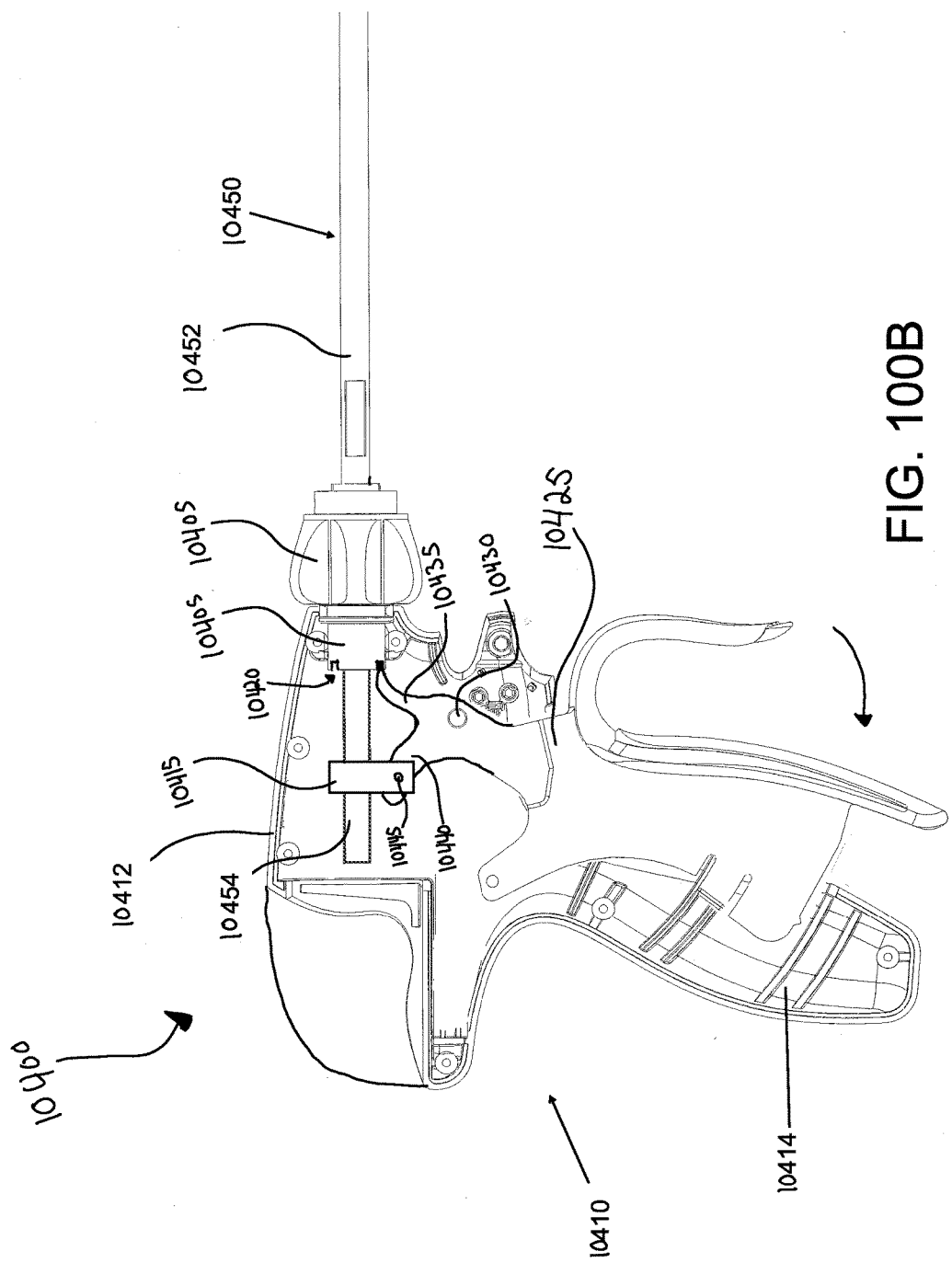
Figure 101A:
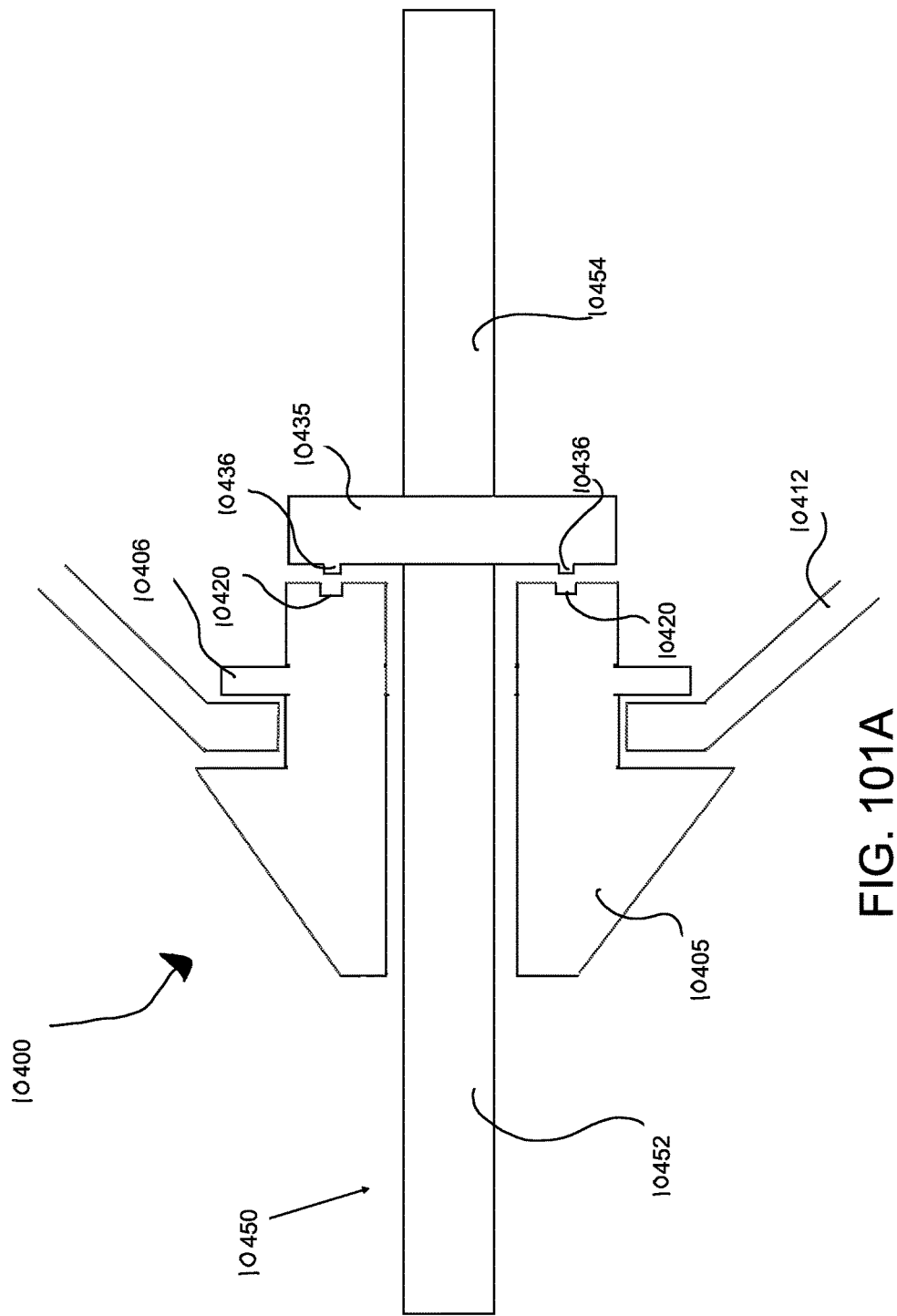
Figure 101B:
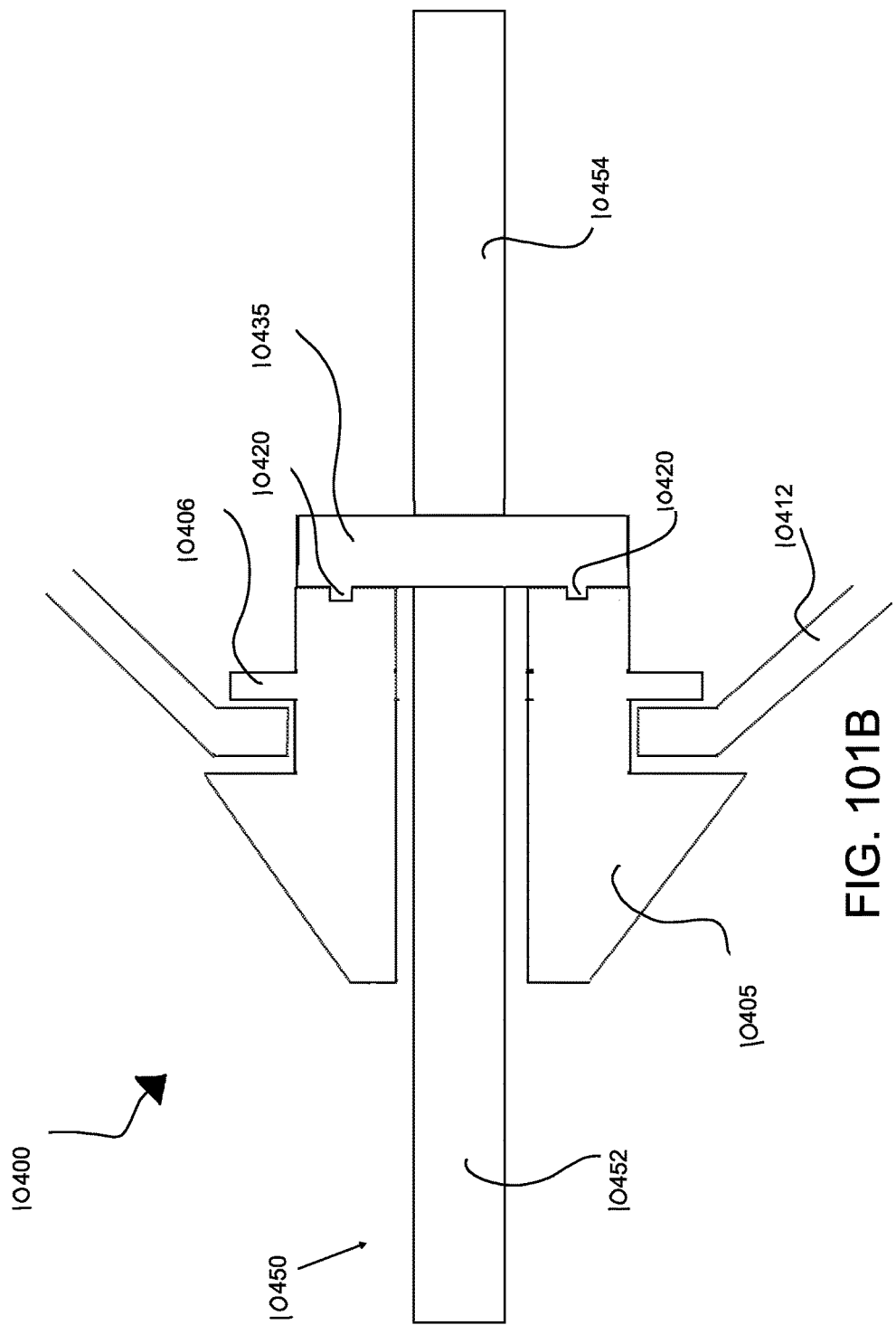
Figure 102A:
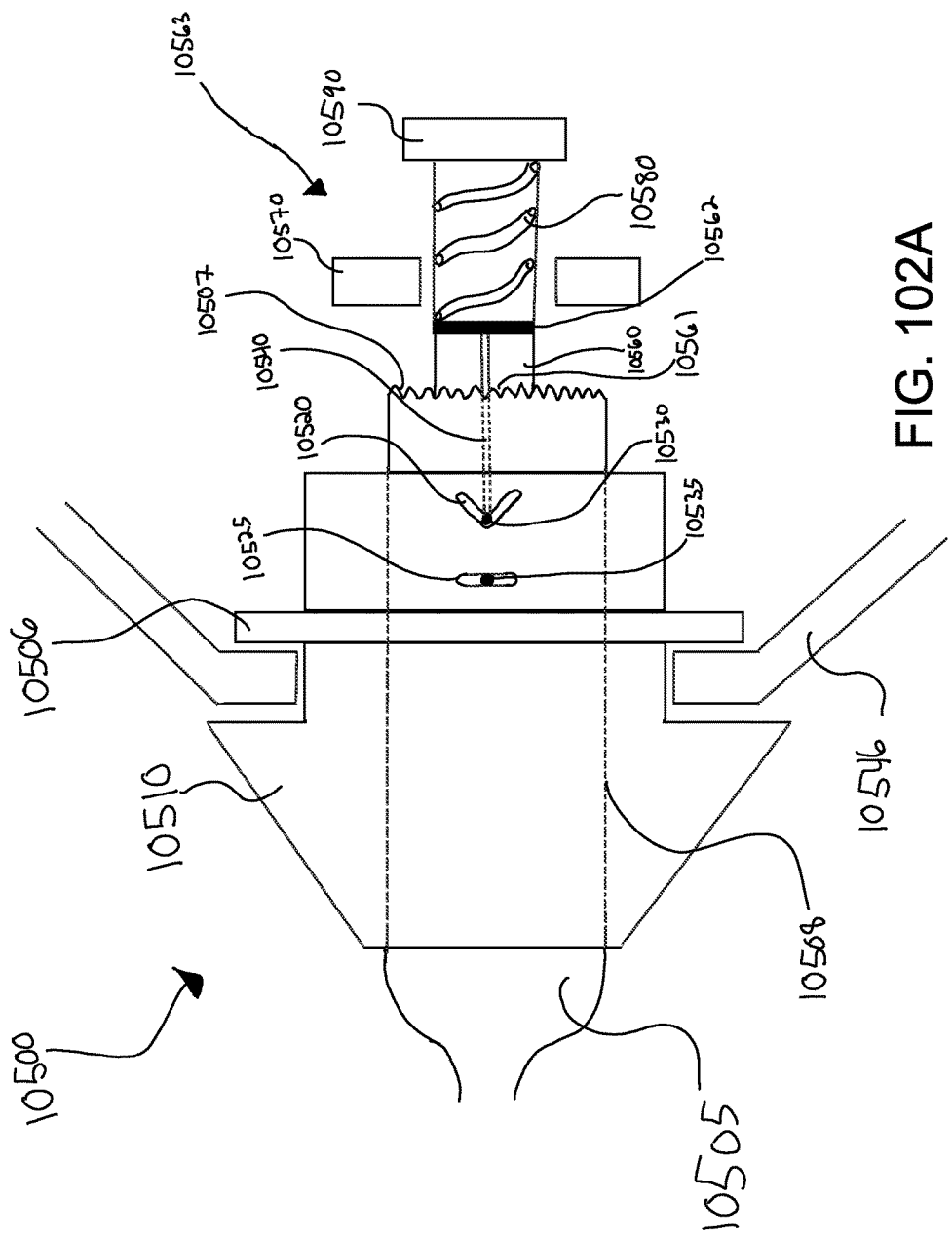
Figure 103A:
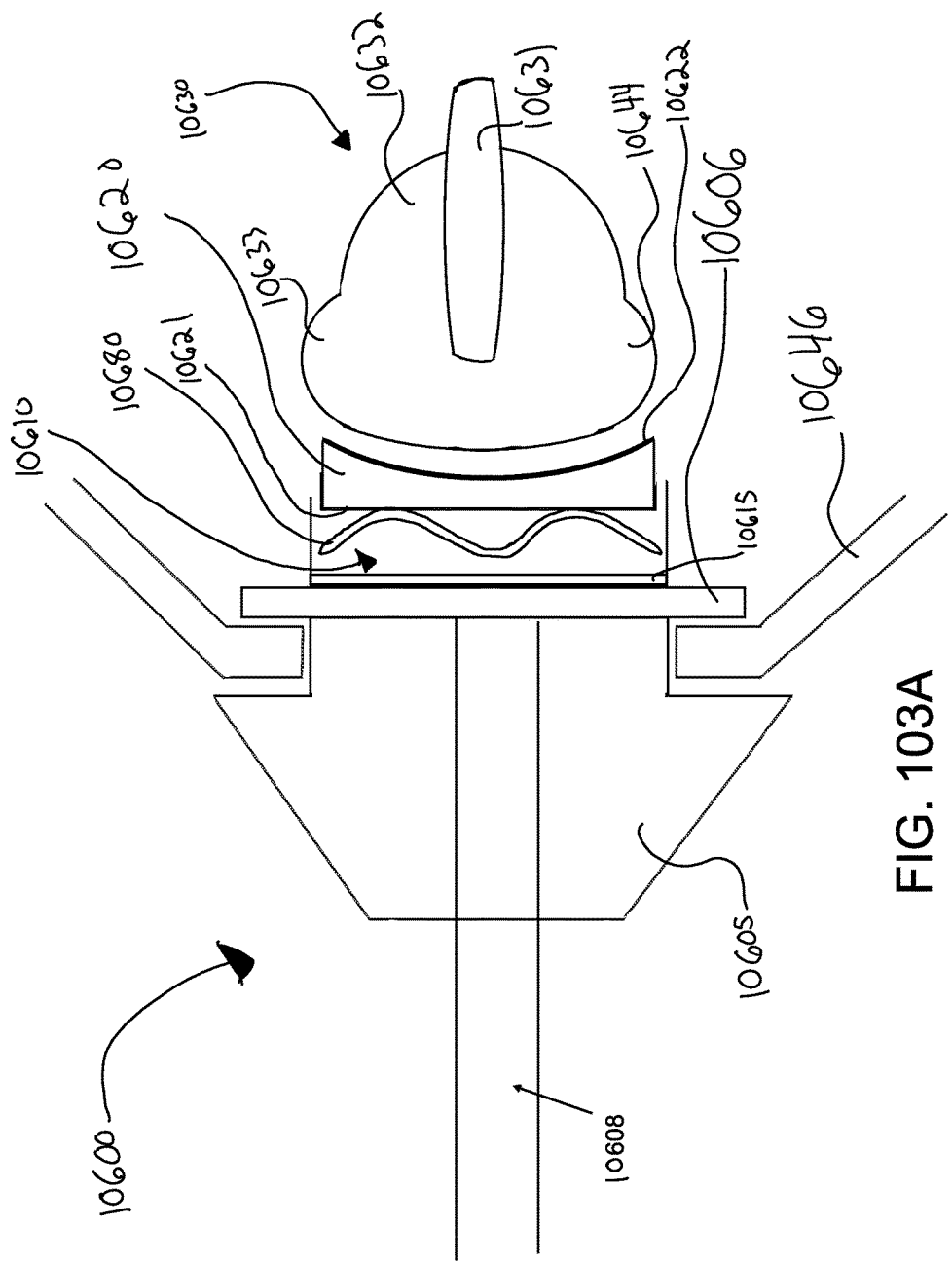
Figure 103B:
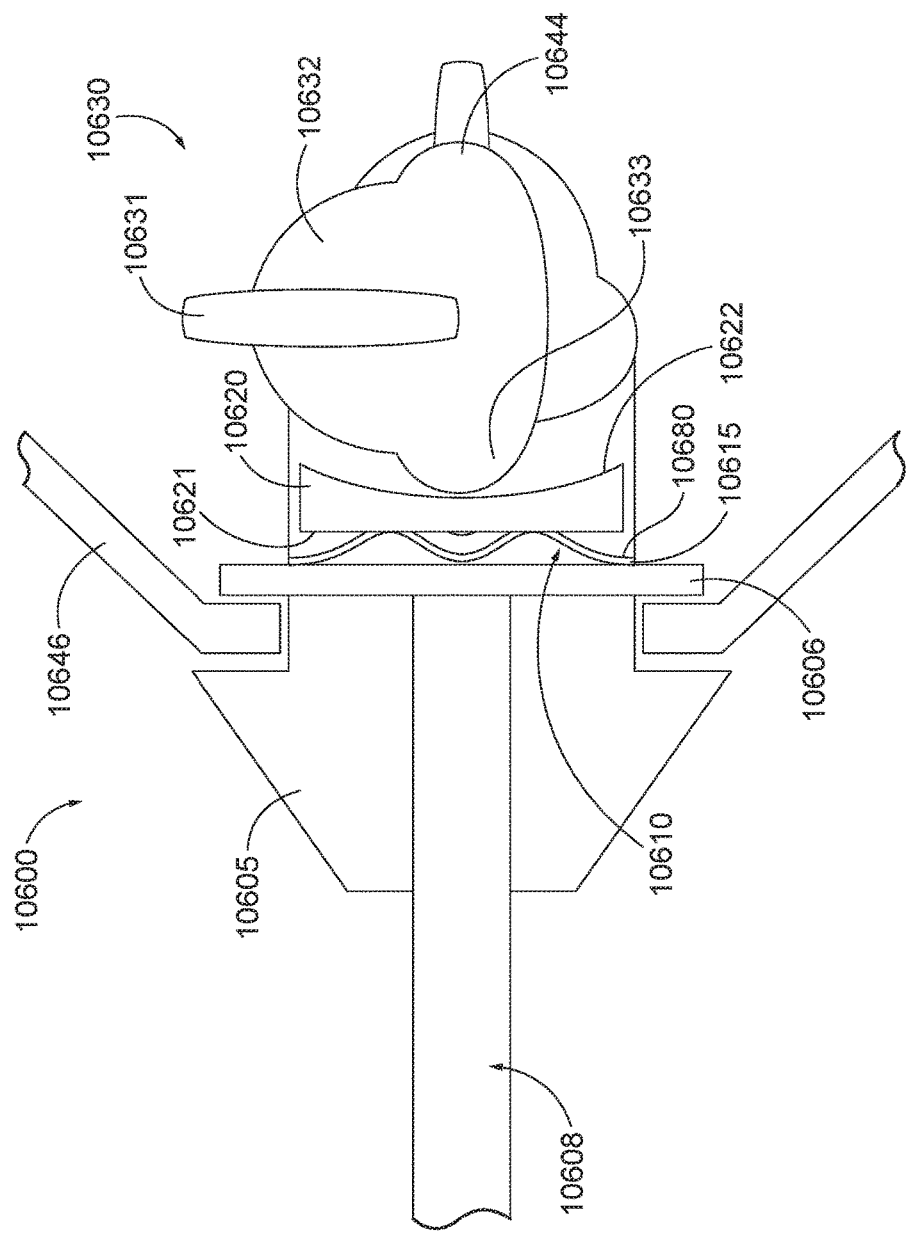
Figure 104A:
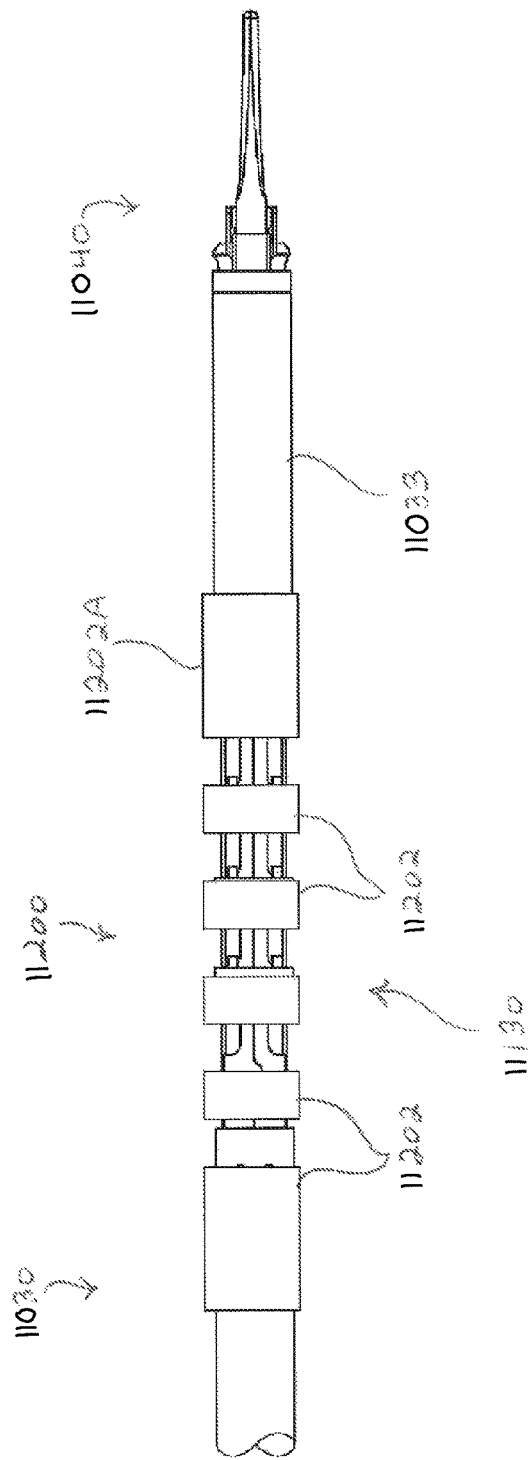
Figure 104B:
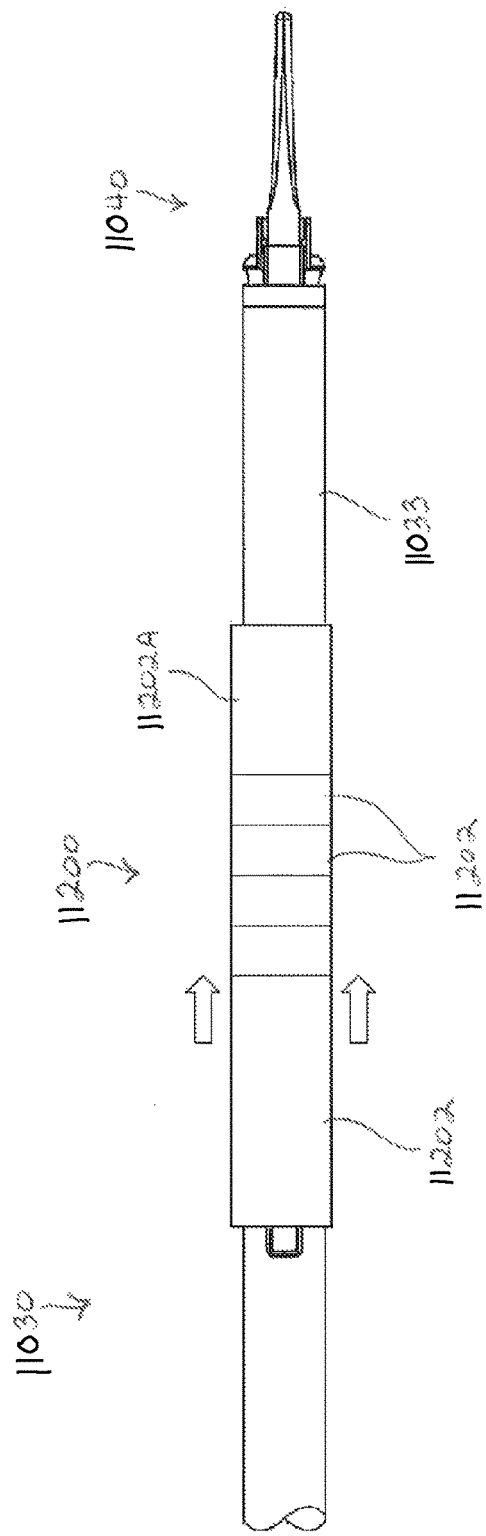
Figure 105:
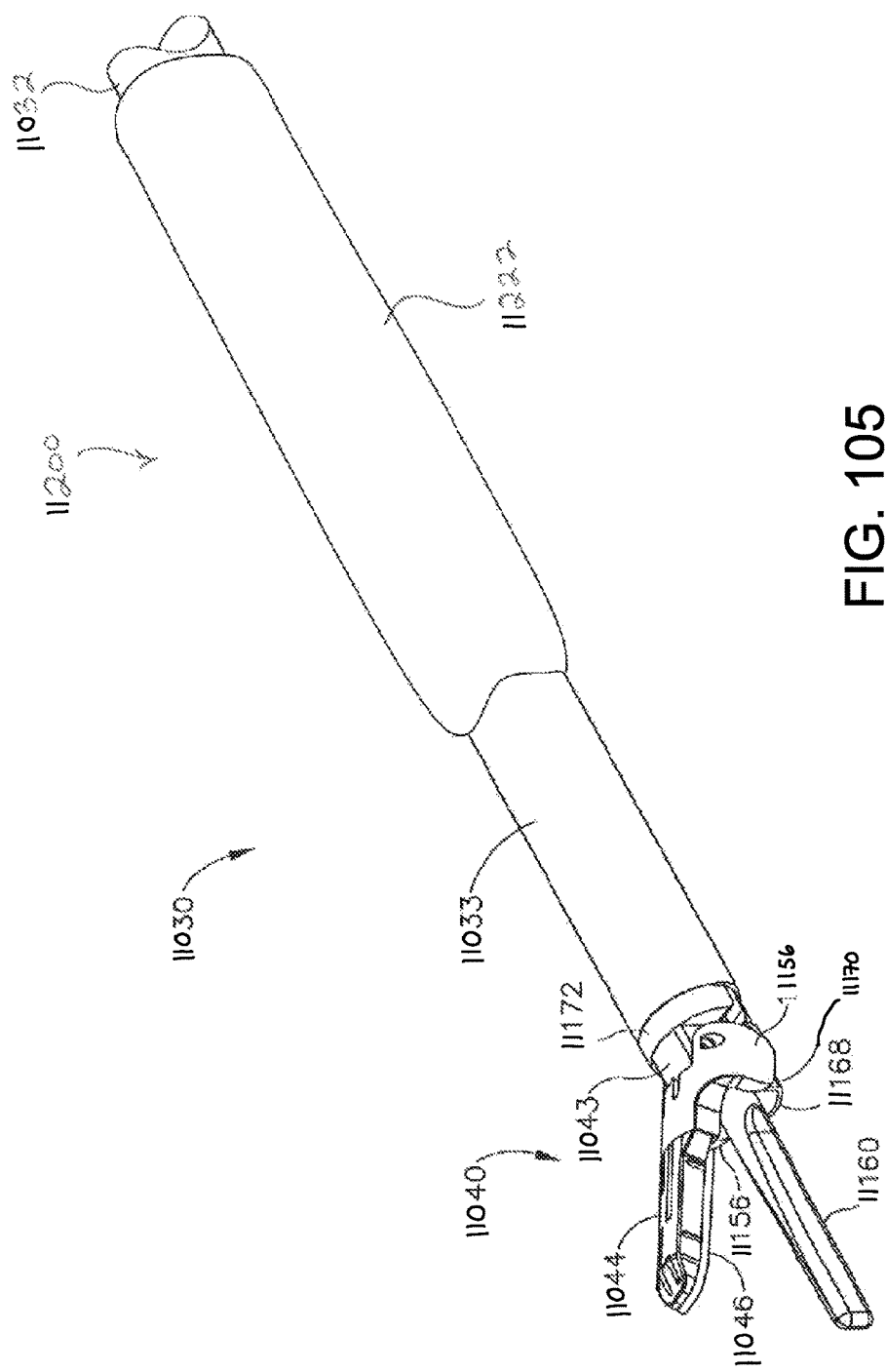
Figure 106A:
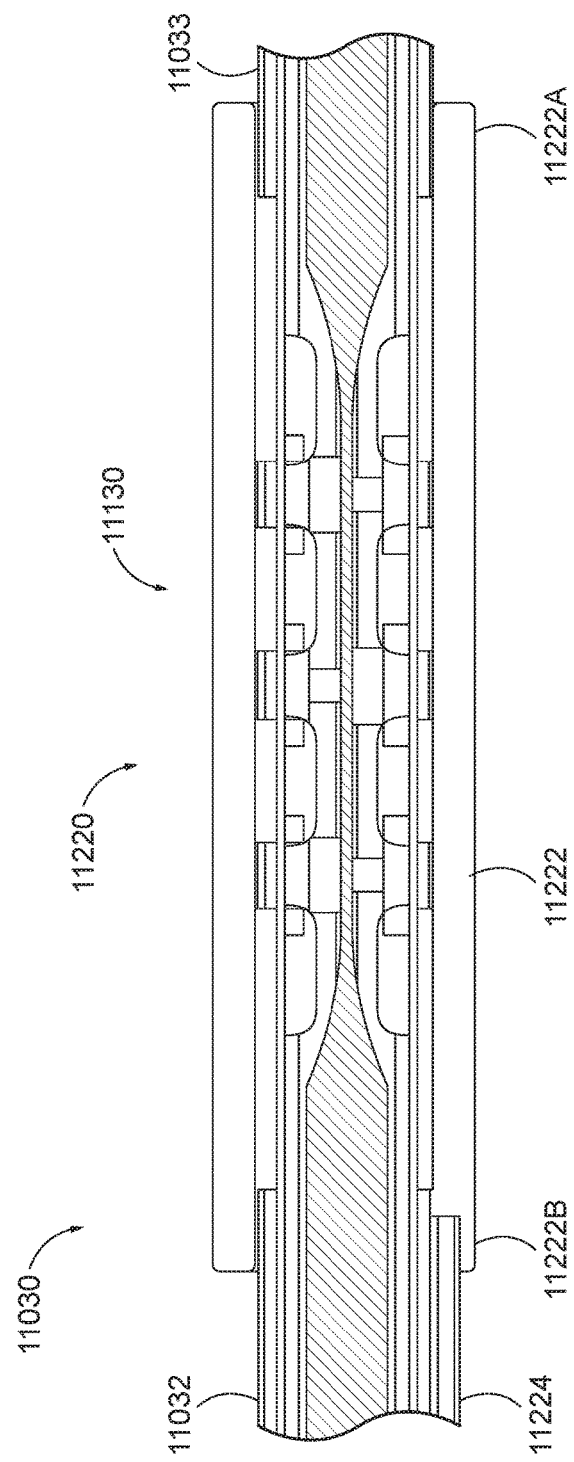
Figure 106B:
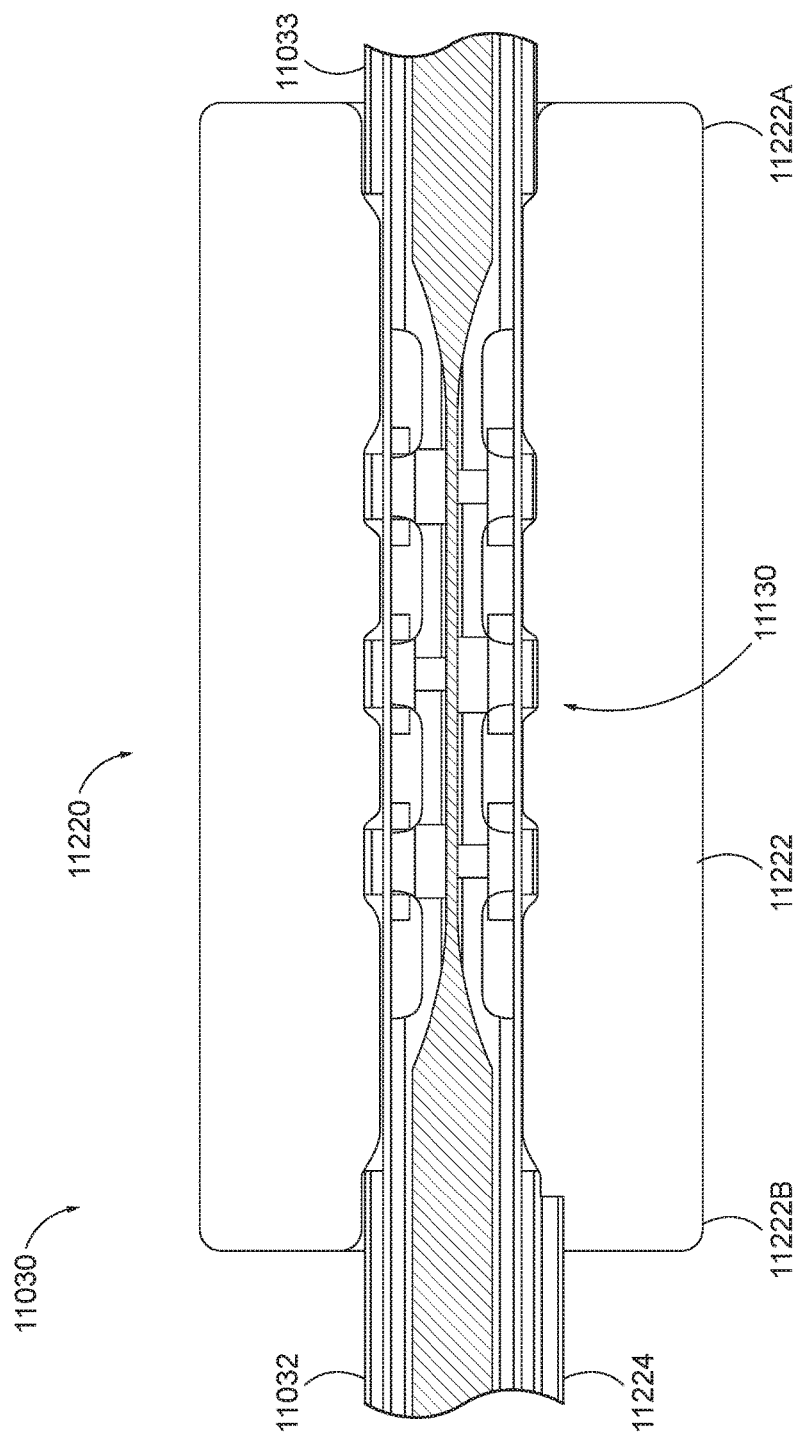
Figure 106C:
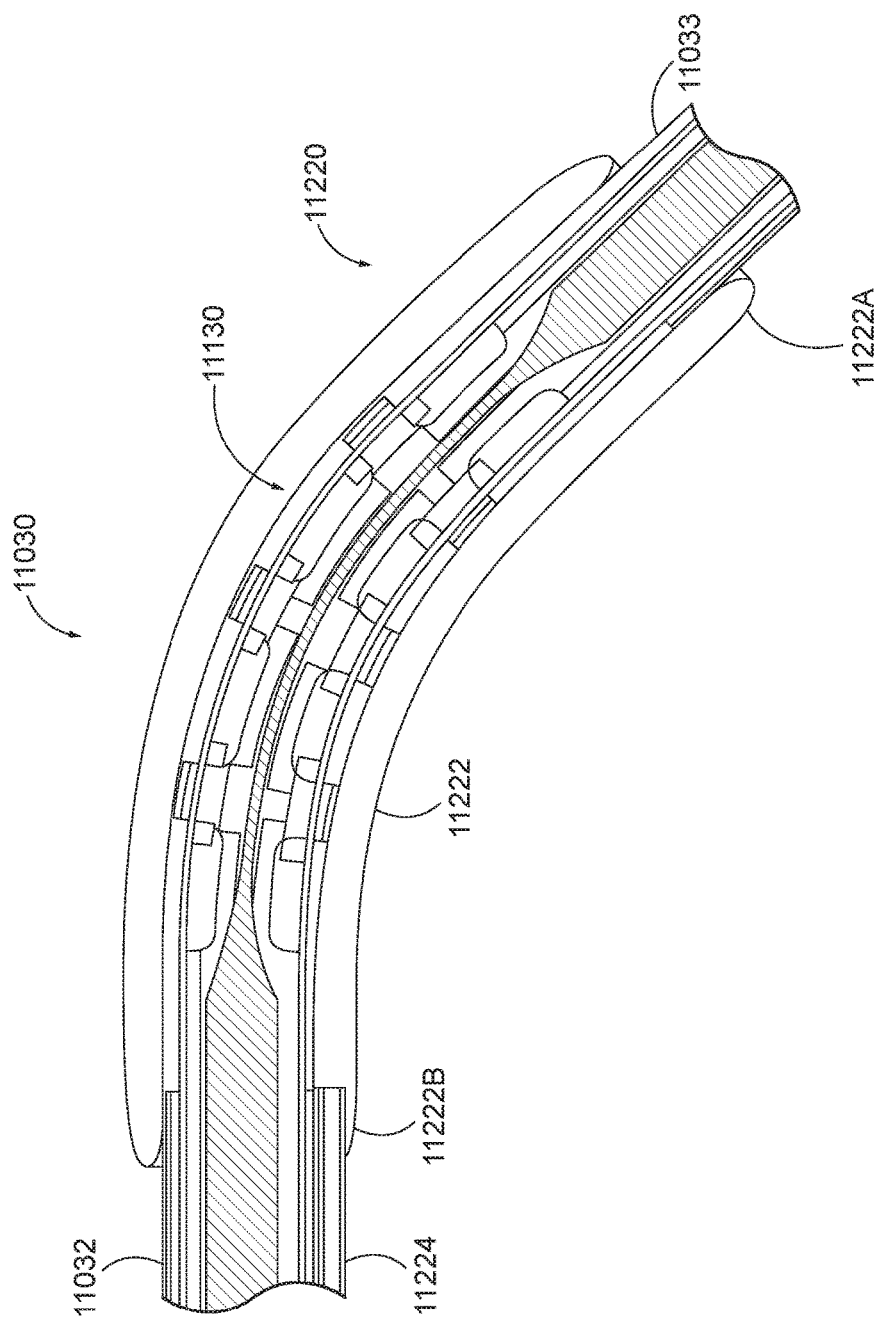
Figure 107:
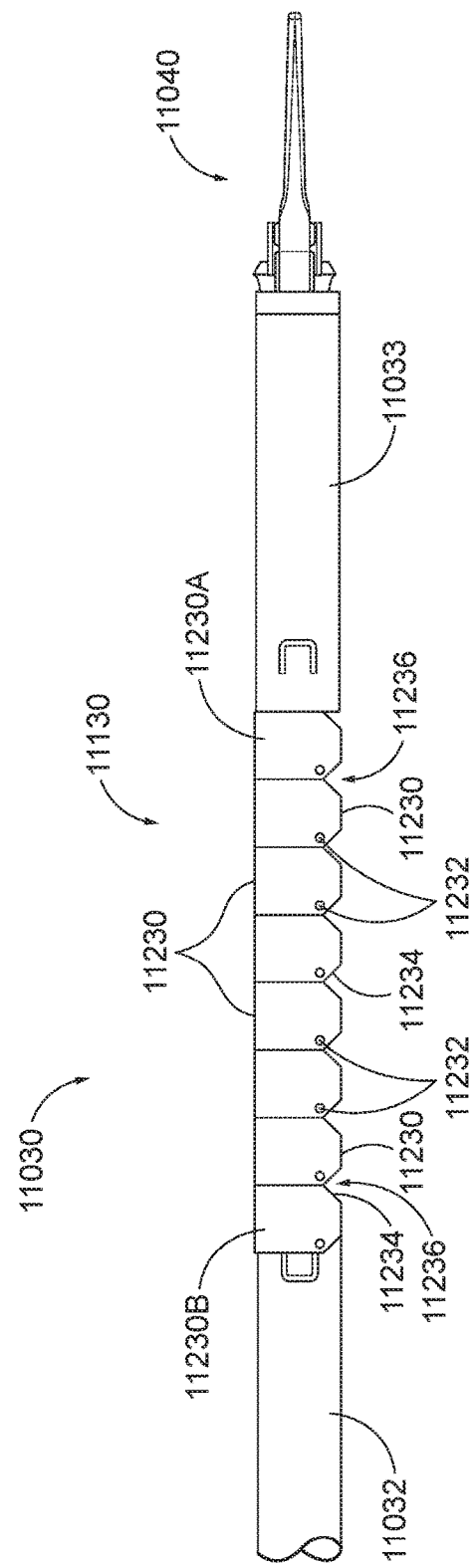
Figure 109:
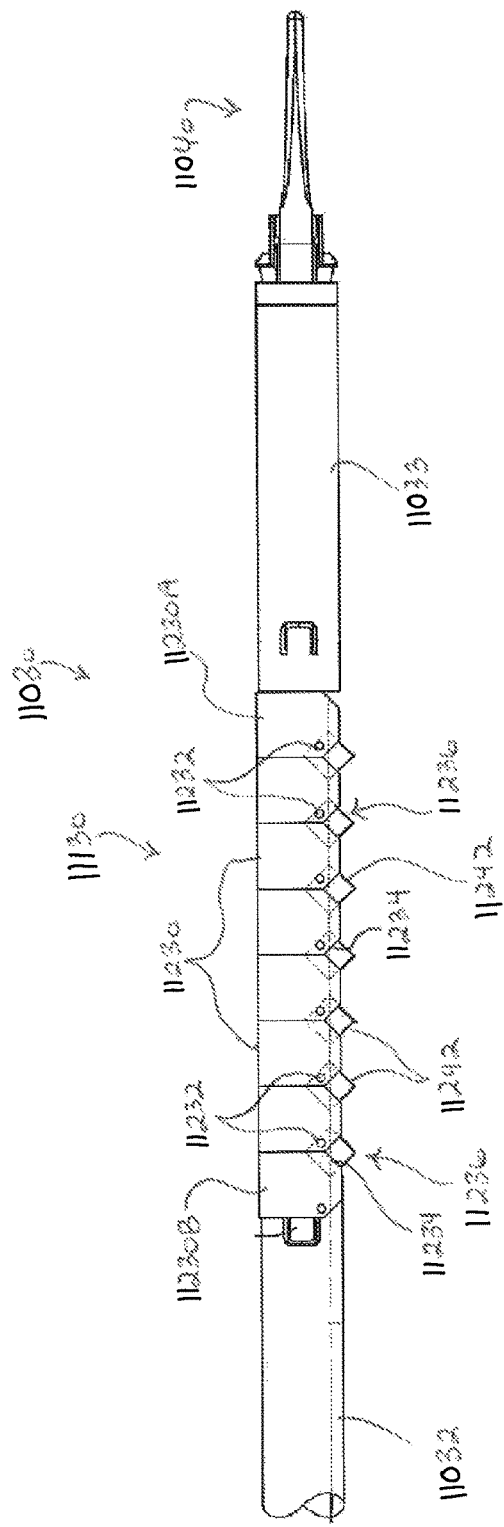
Figure 110A:
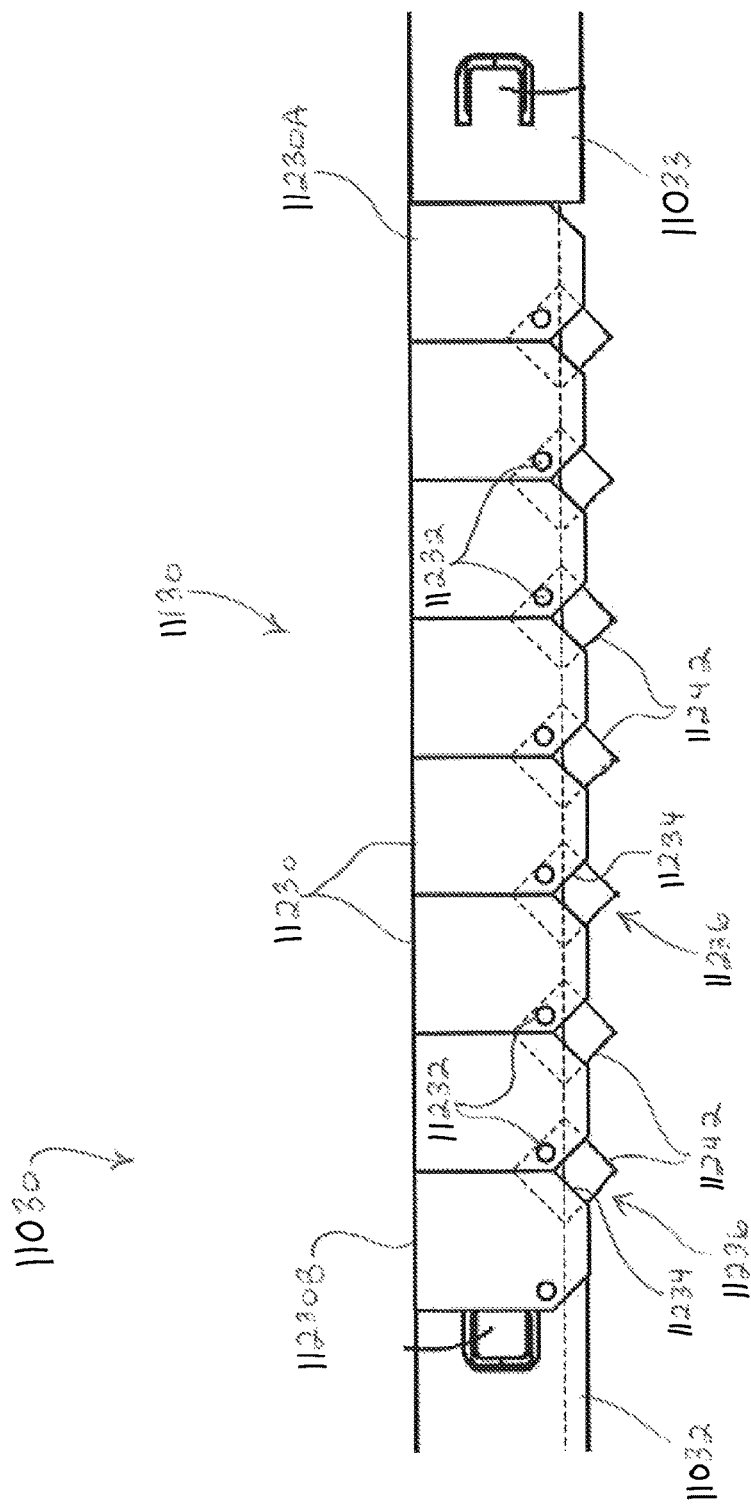
Figure 110B:
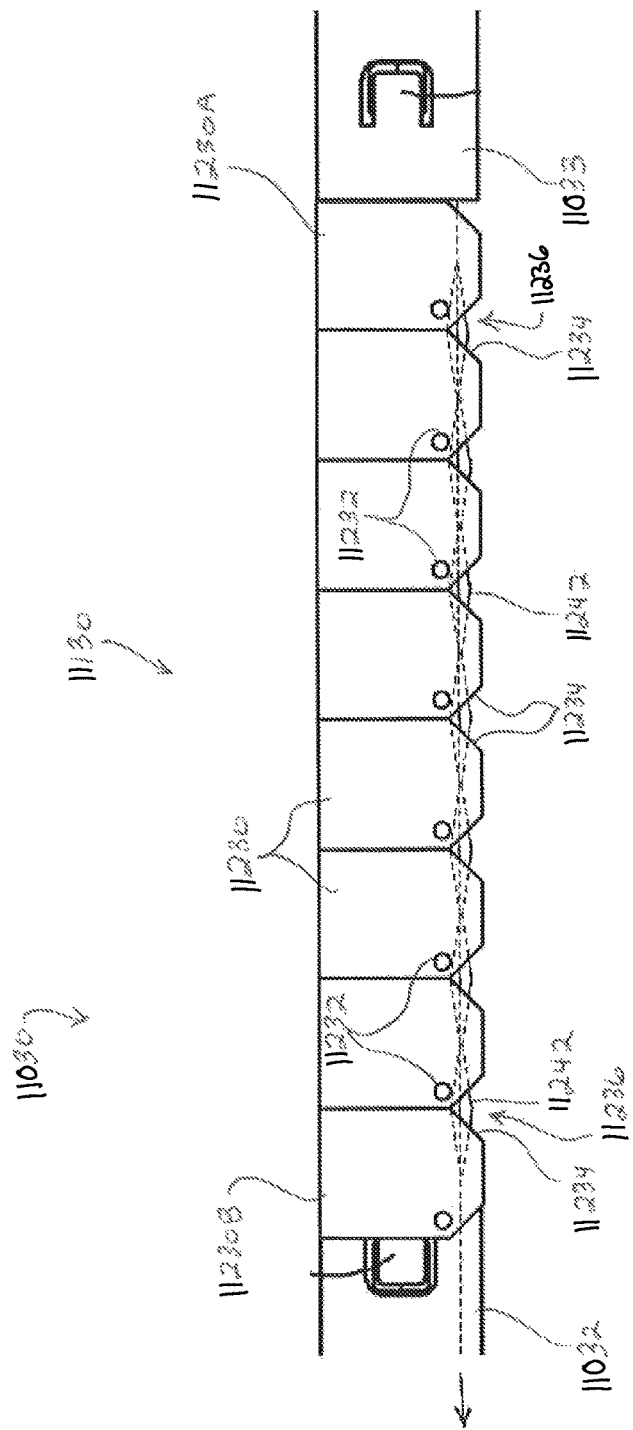
Figure 111A:
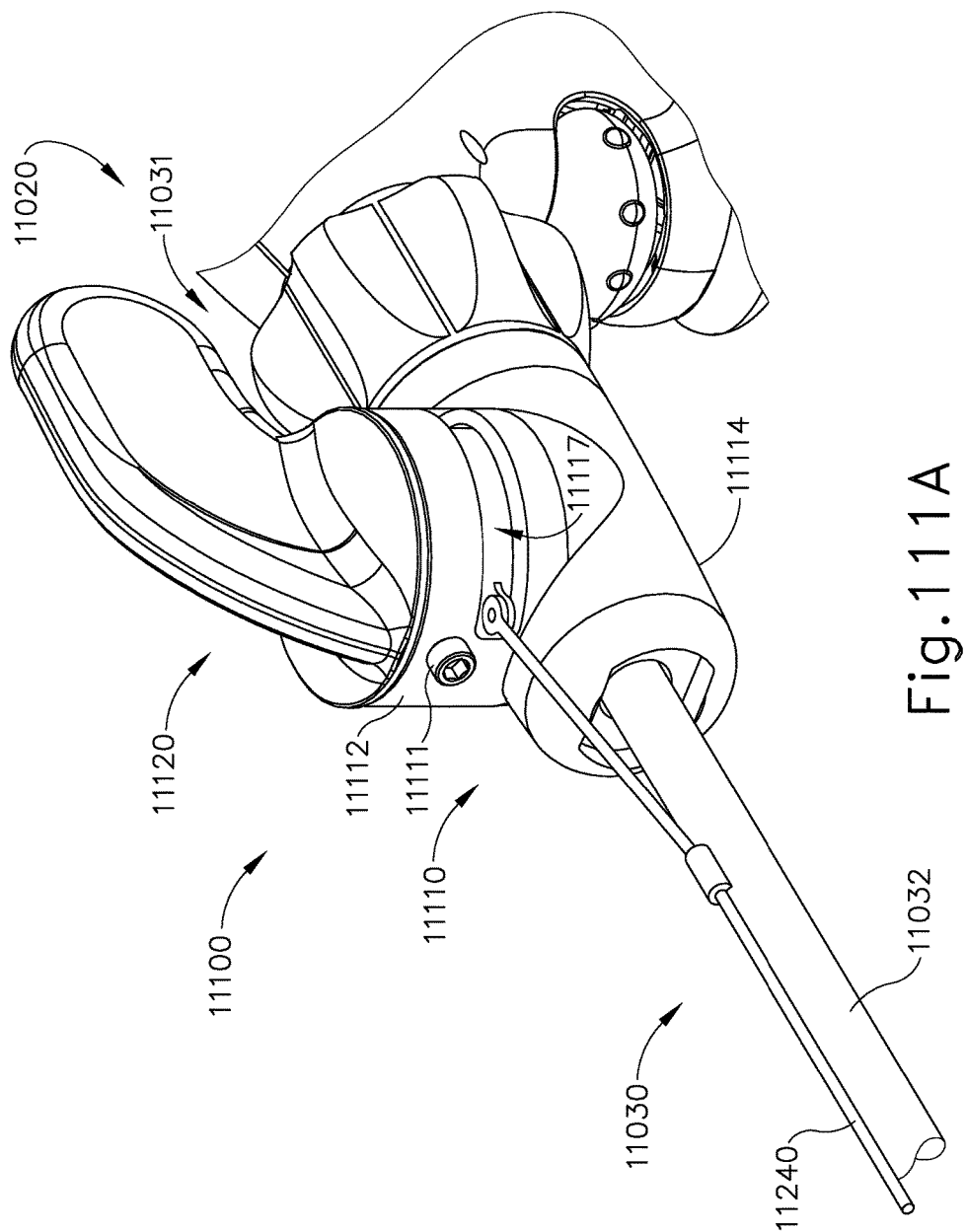
Figure 111B:
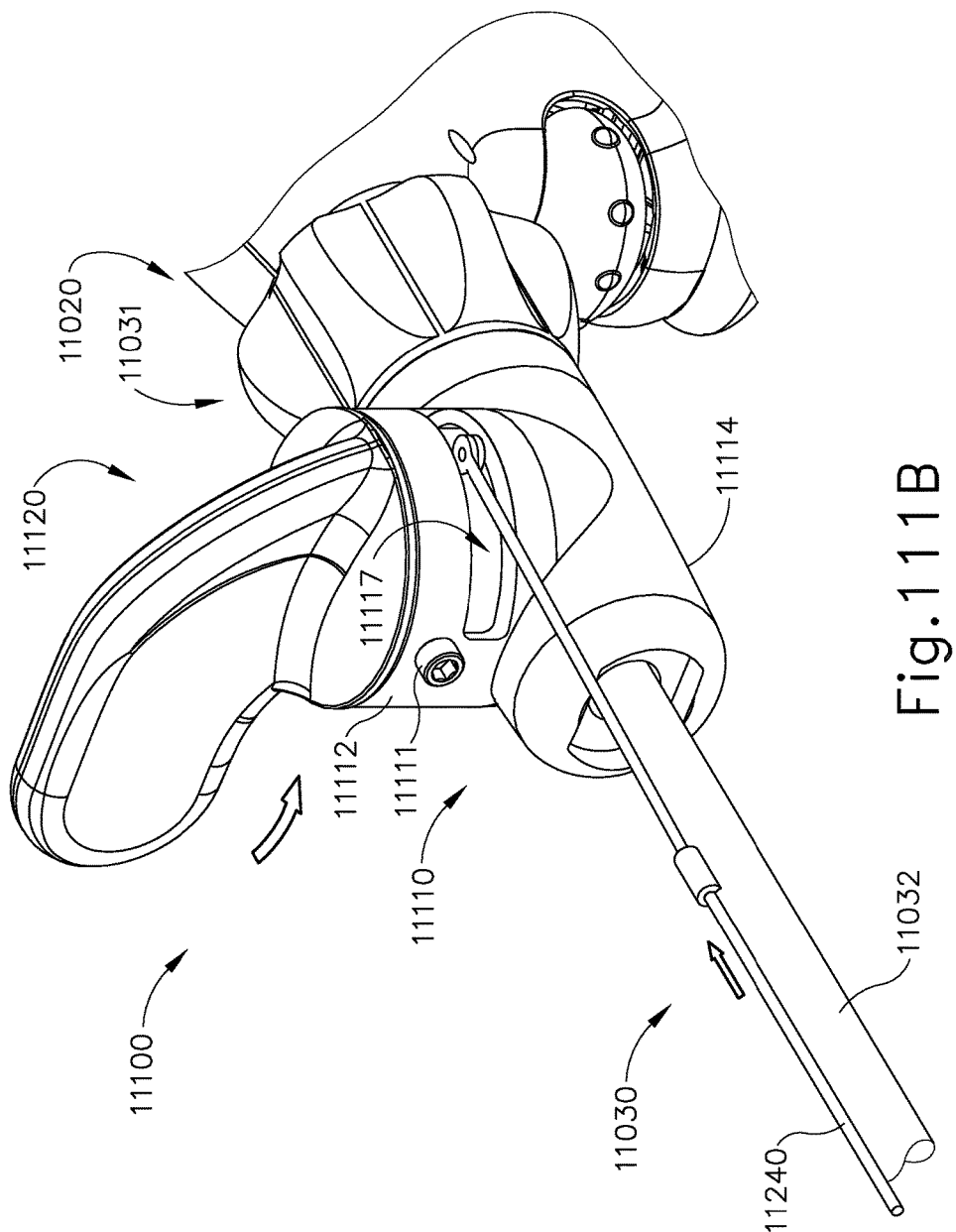
Figure 112:
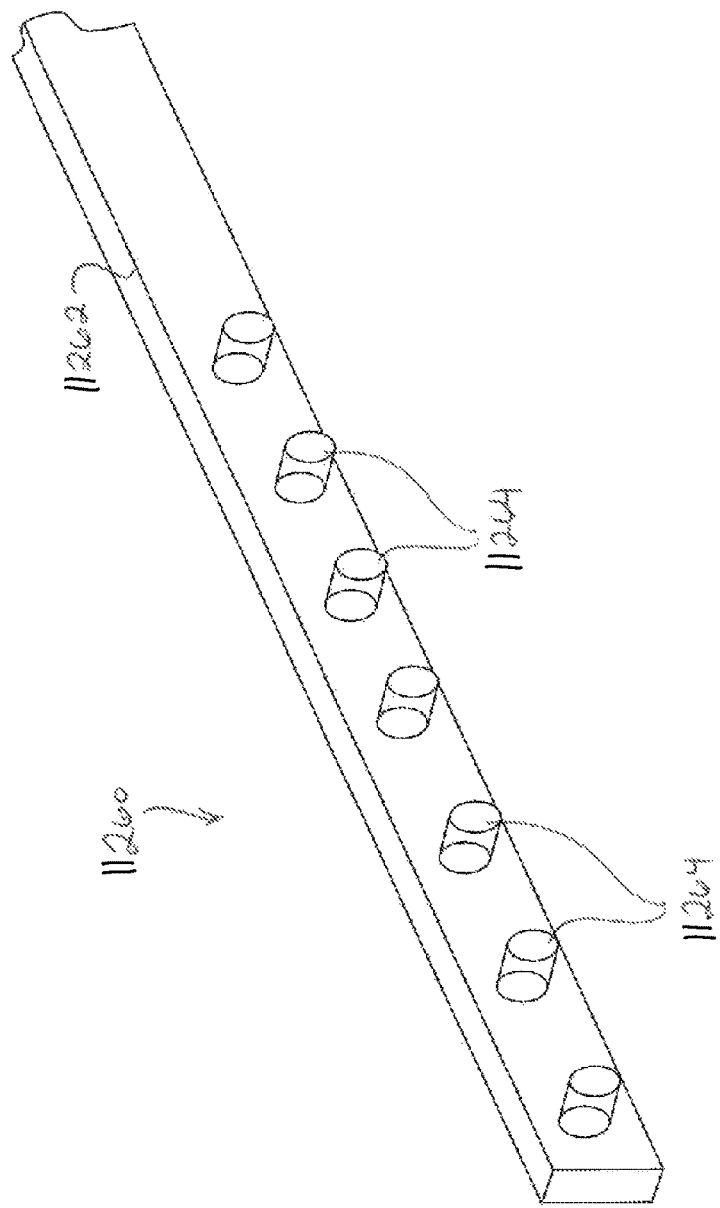
Figure 113:
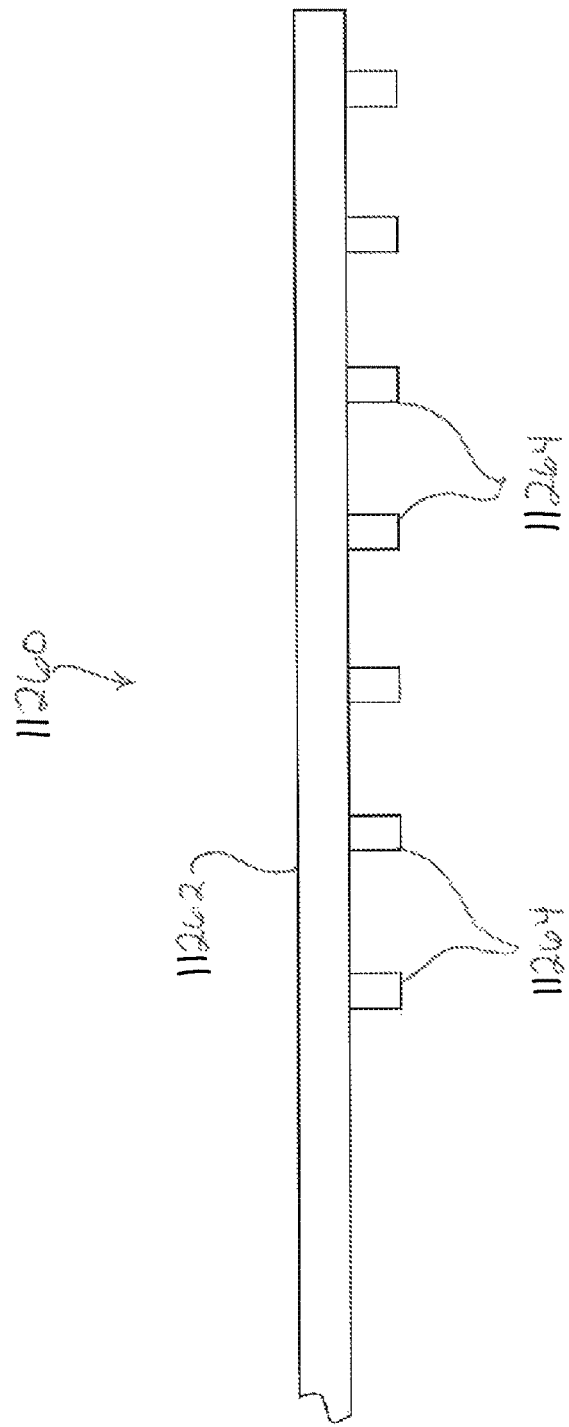
Figure 114A:
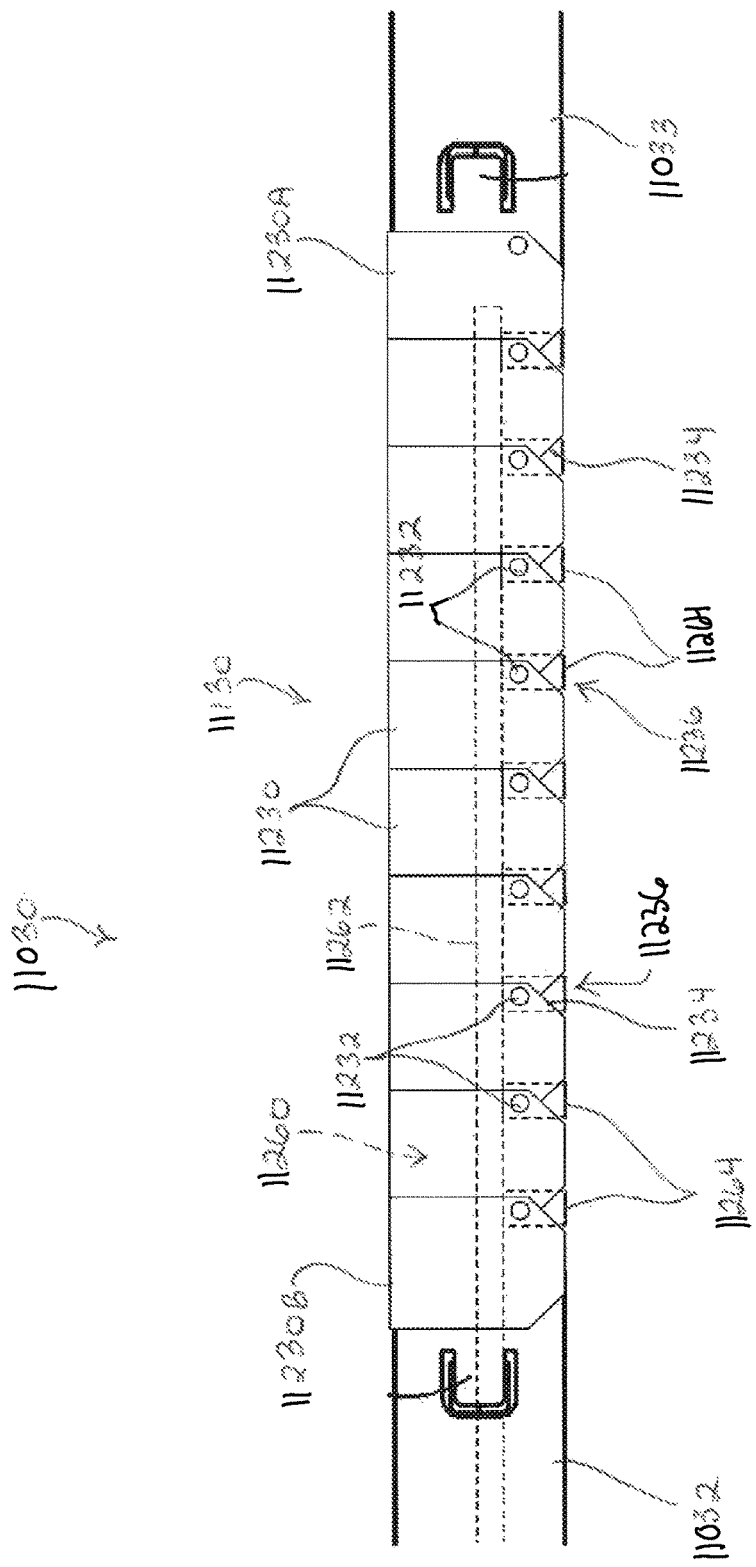
Figure 114B:
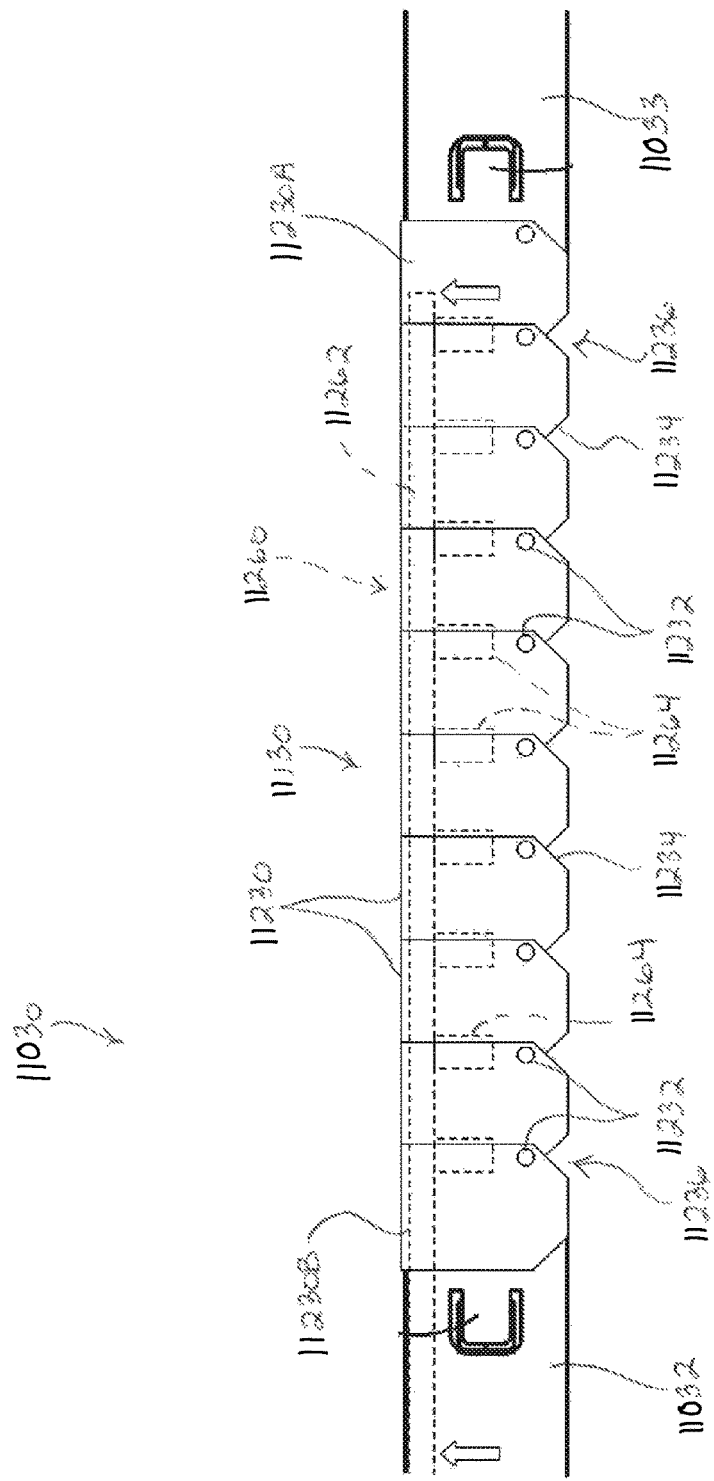
Figure 115:
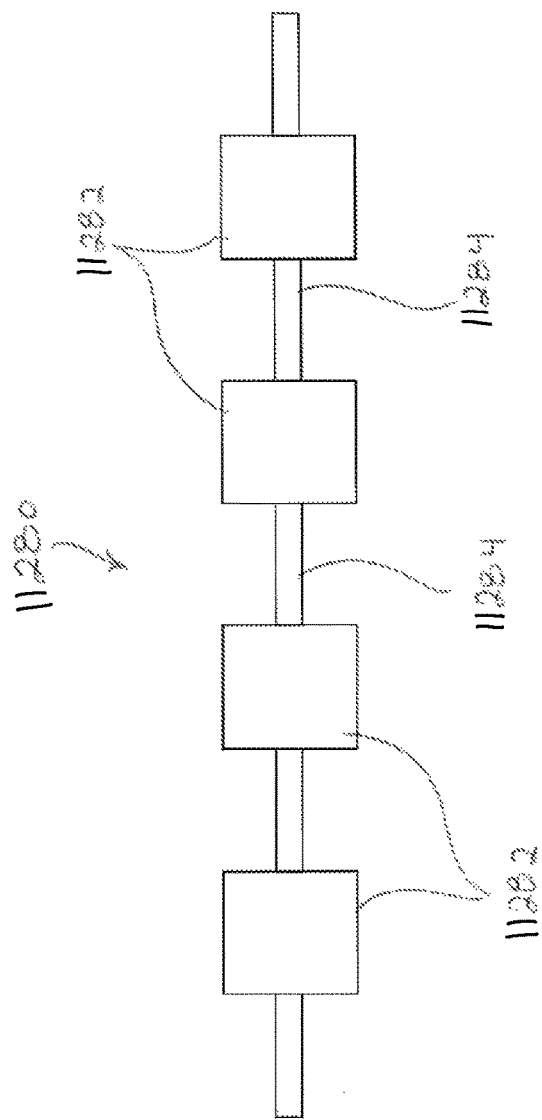
Figure 116A:
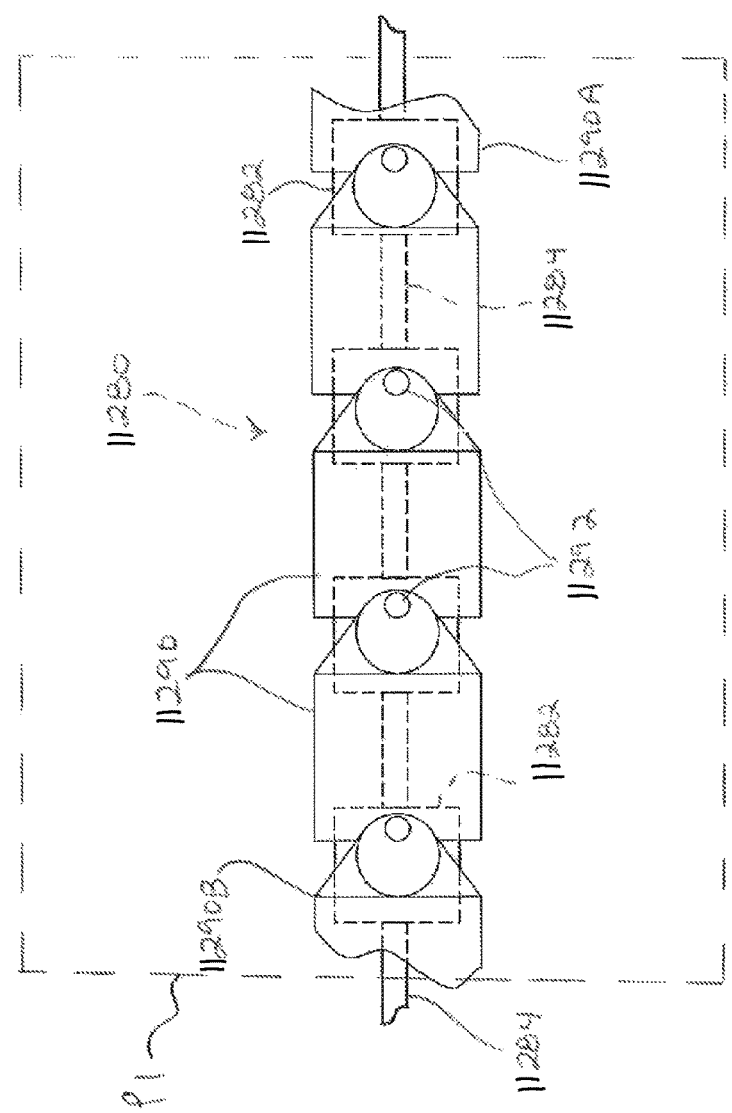
Figure 116B:
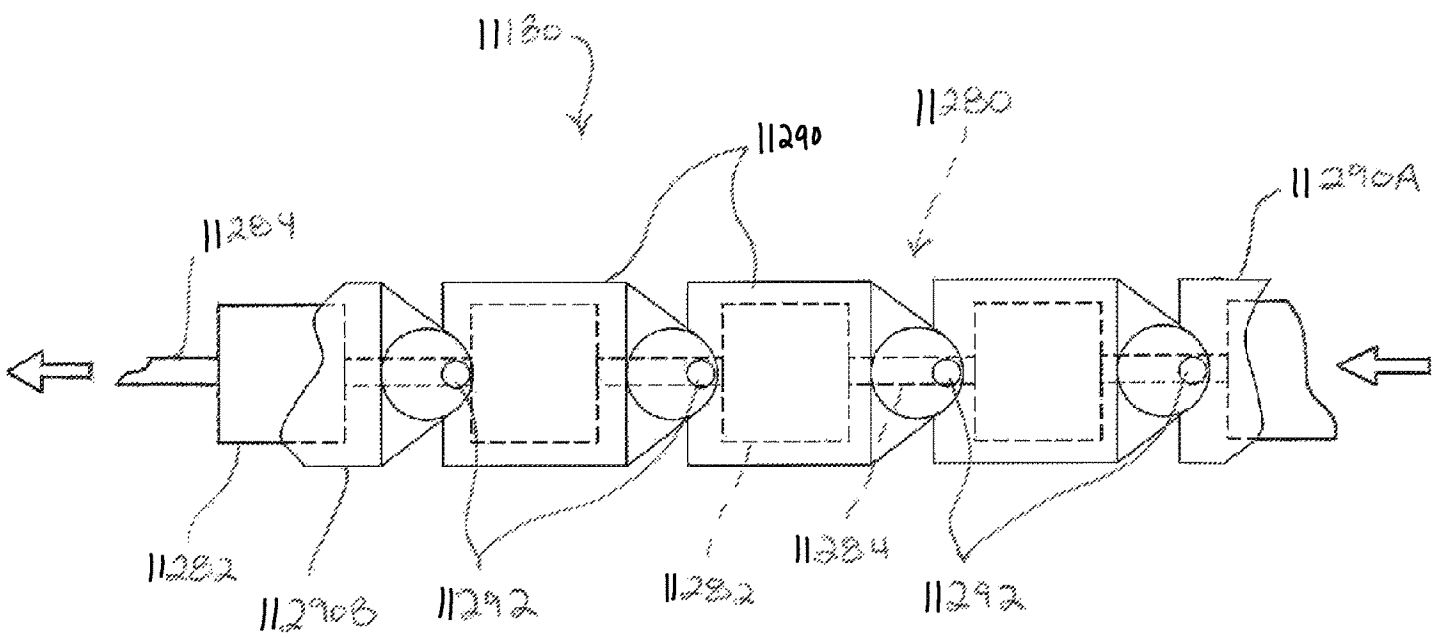
Figure 116C:
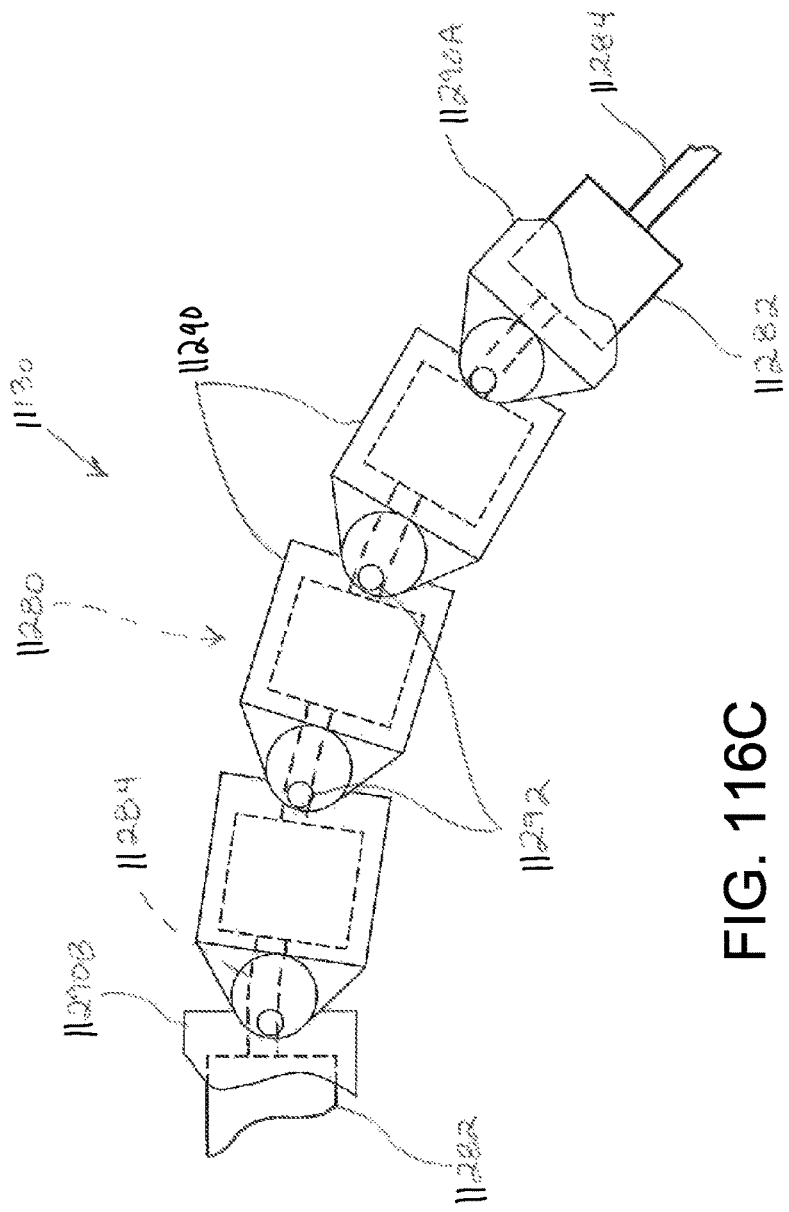
Figure 117:
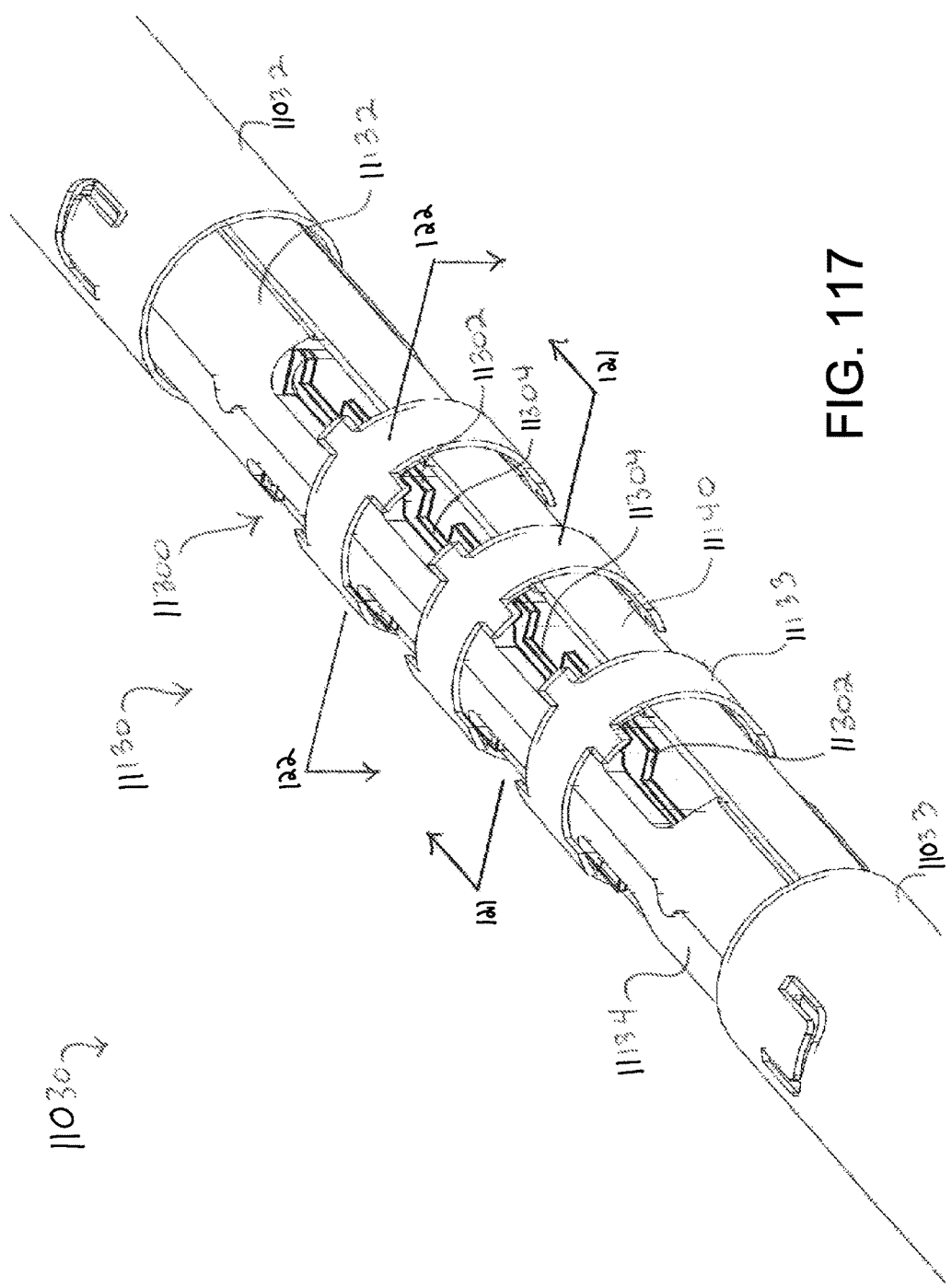
Figure 118:
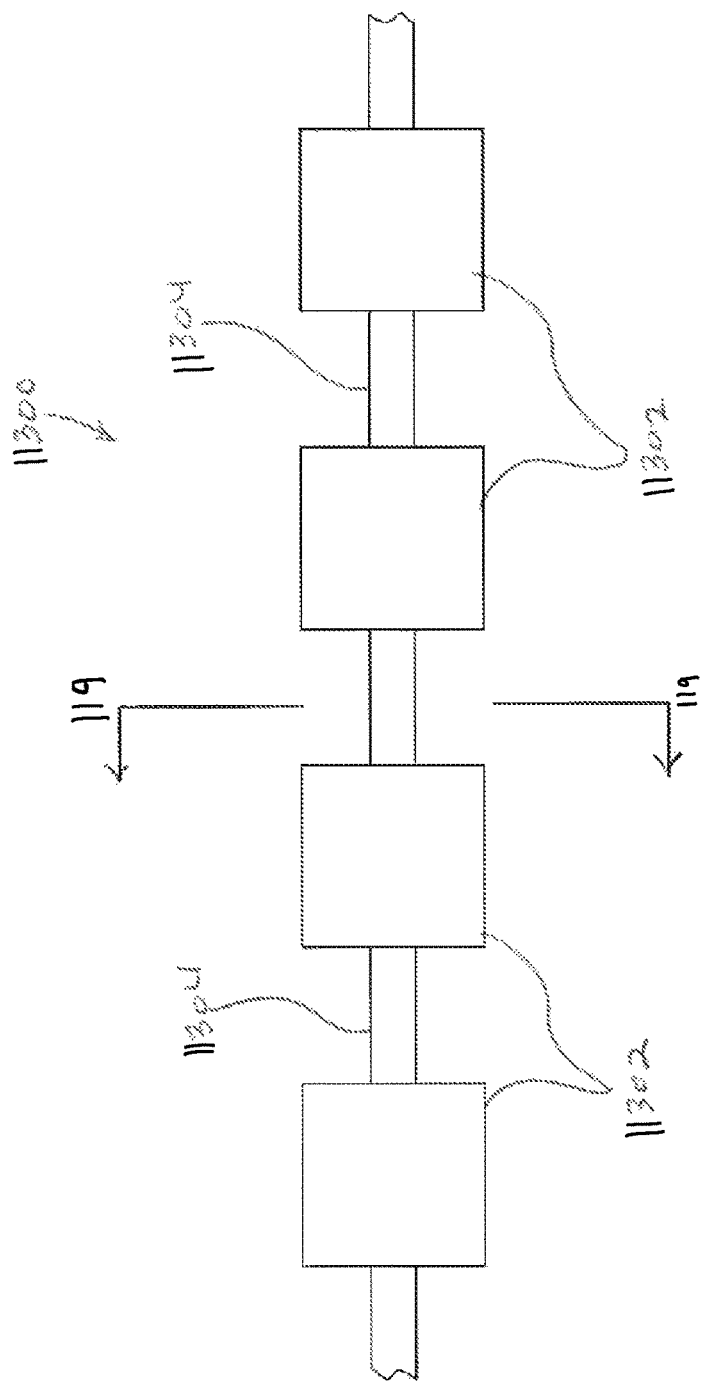
Figure 119:
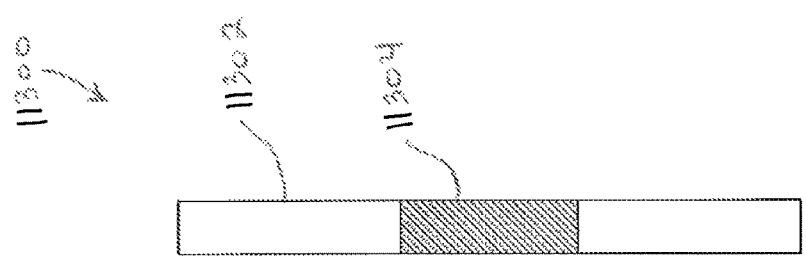
Figure 120:
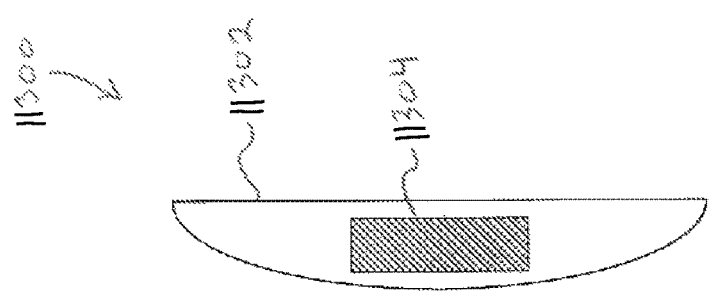
Figure 121:
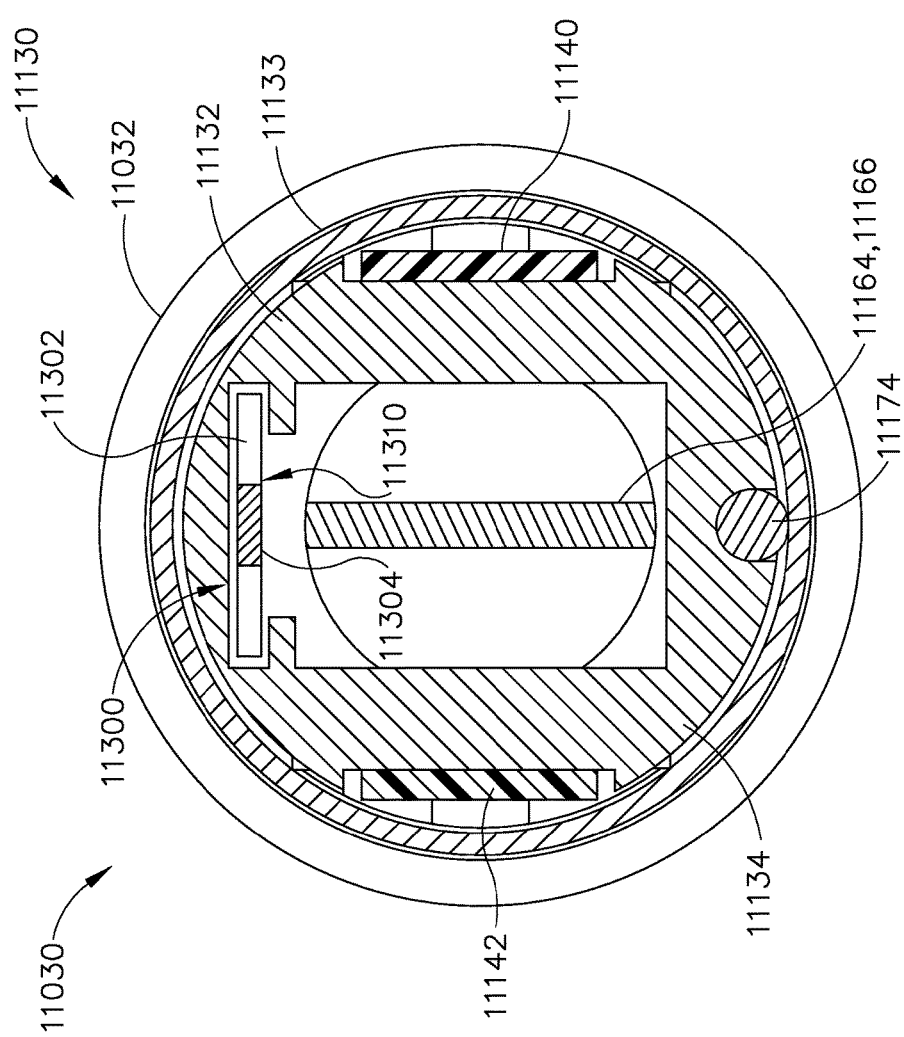
Figure 122A:
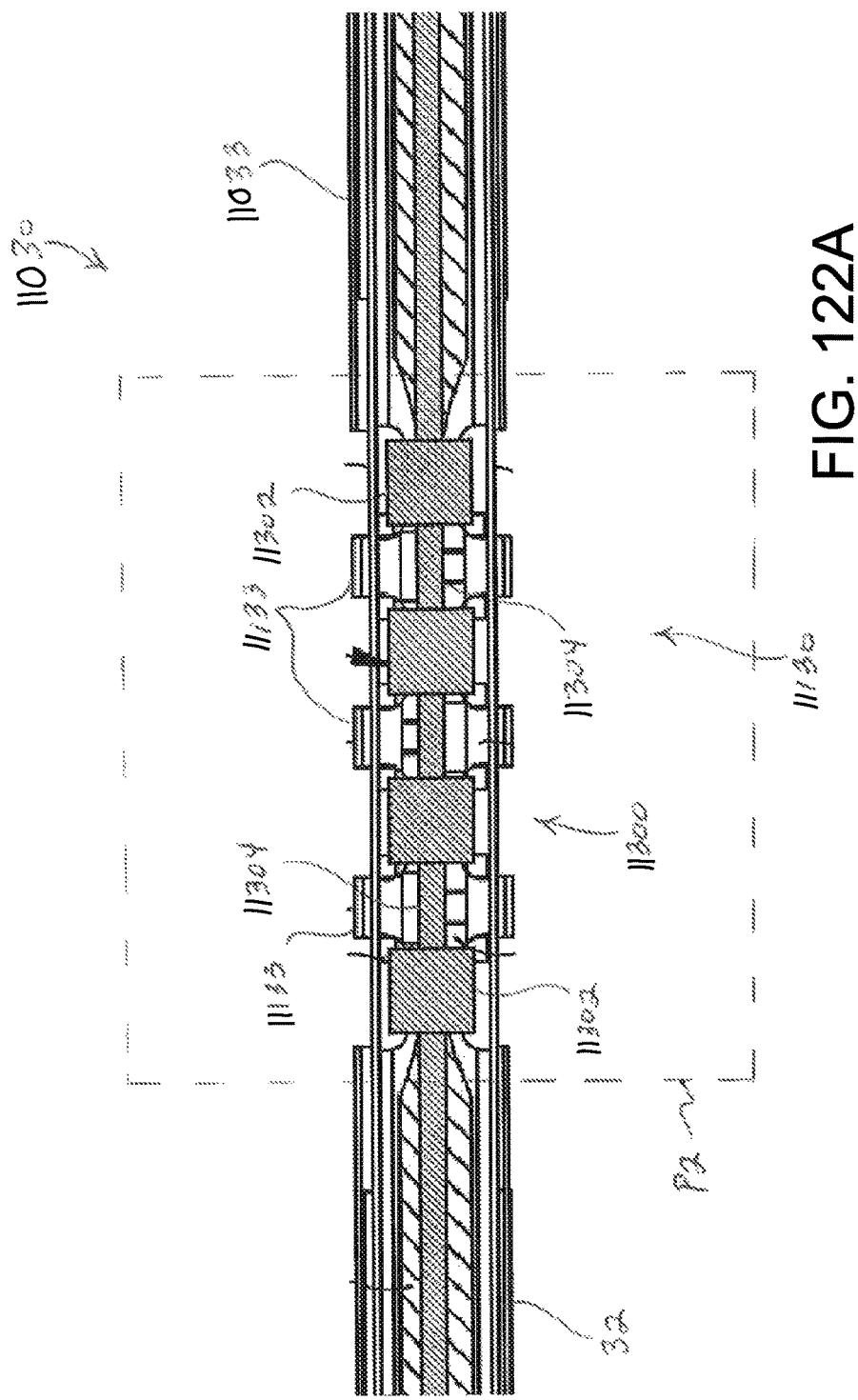
Figure 122B:
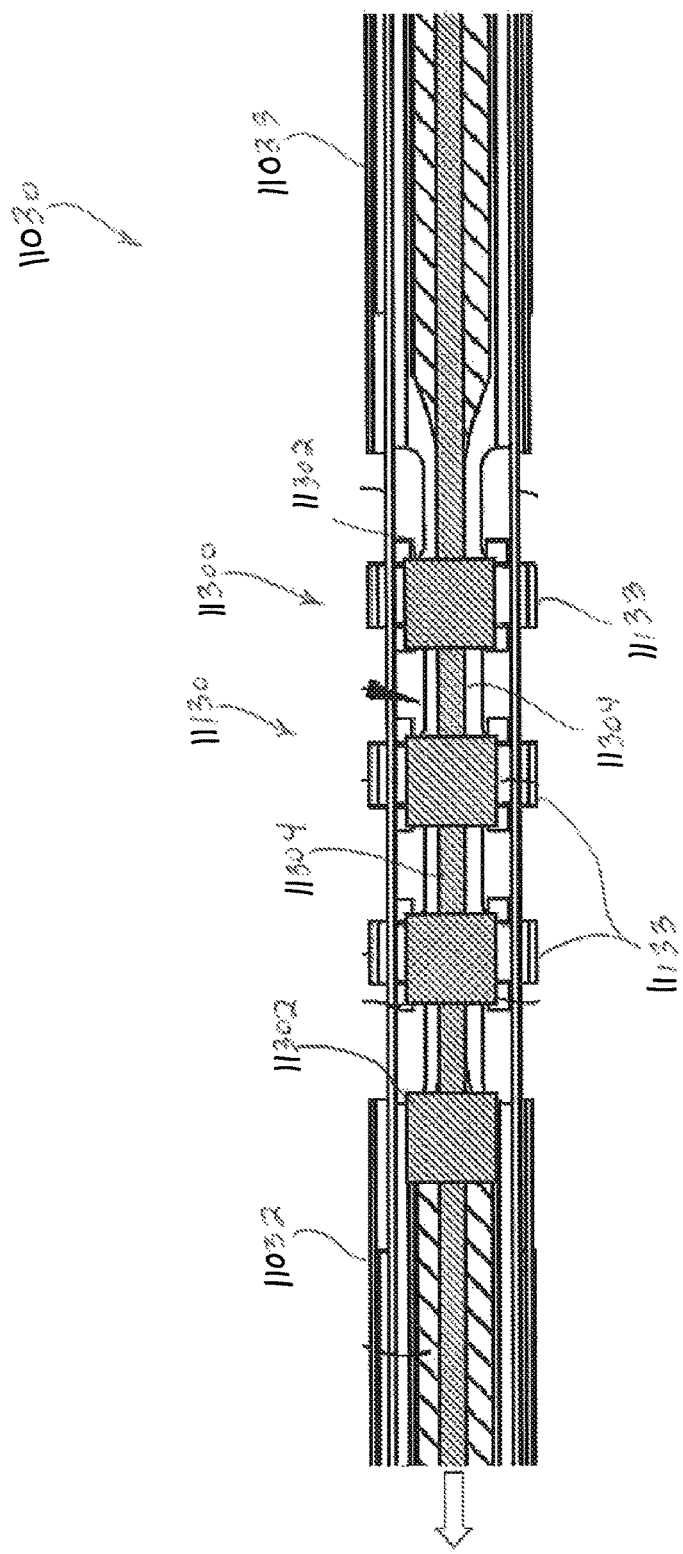
Figure 122C:
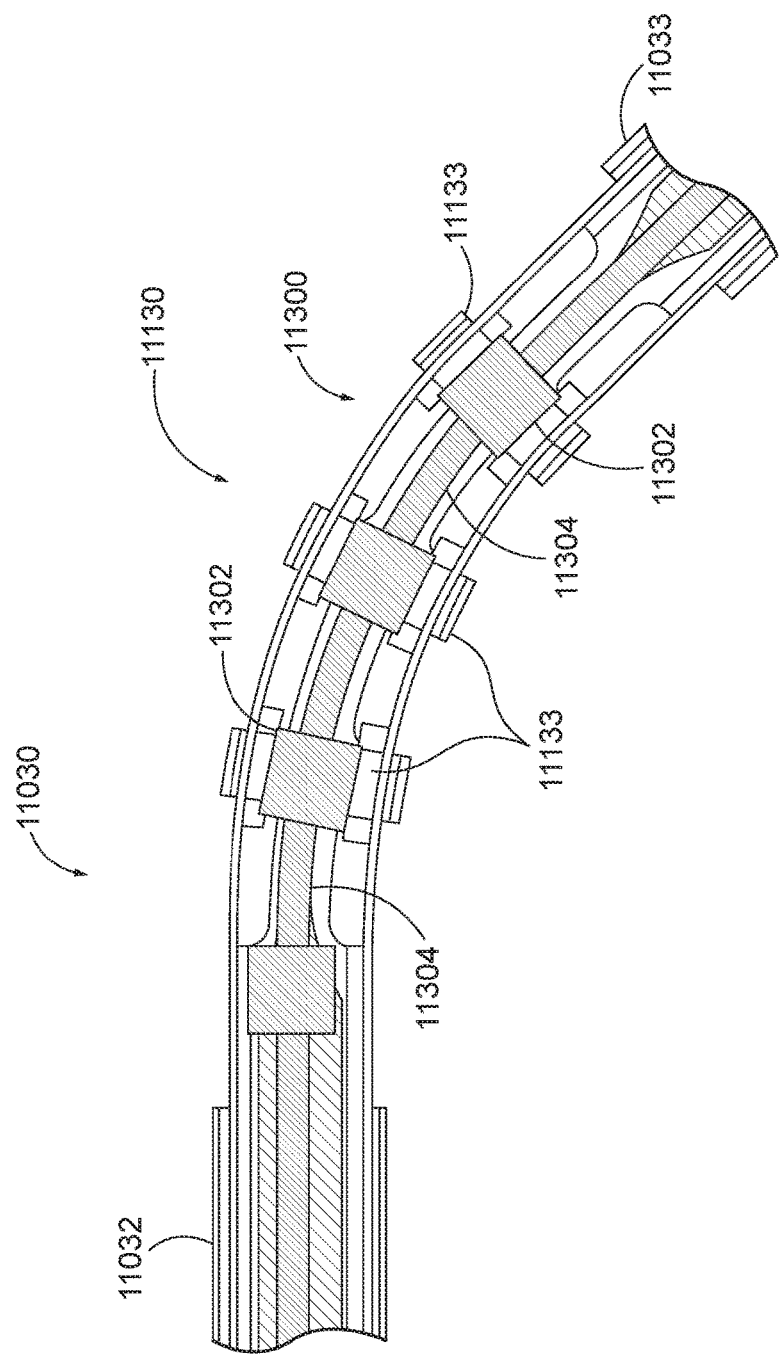
Figure 123:
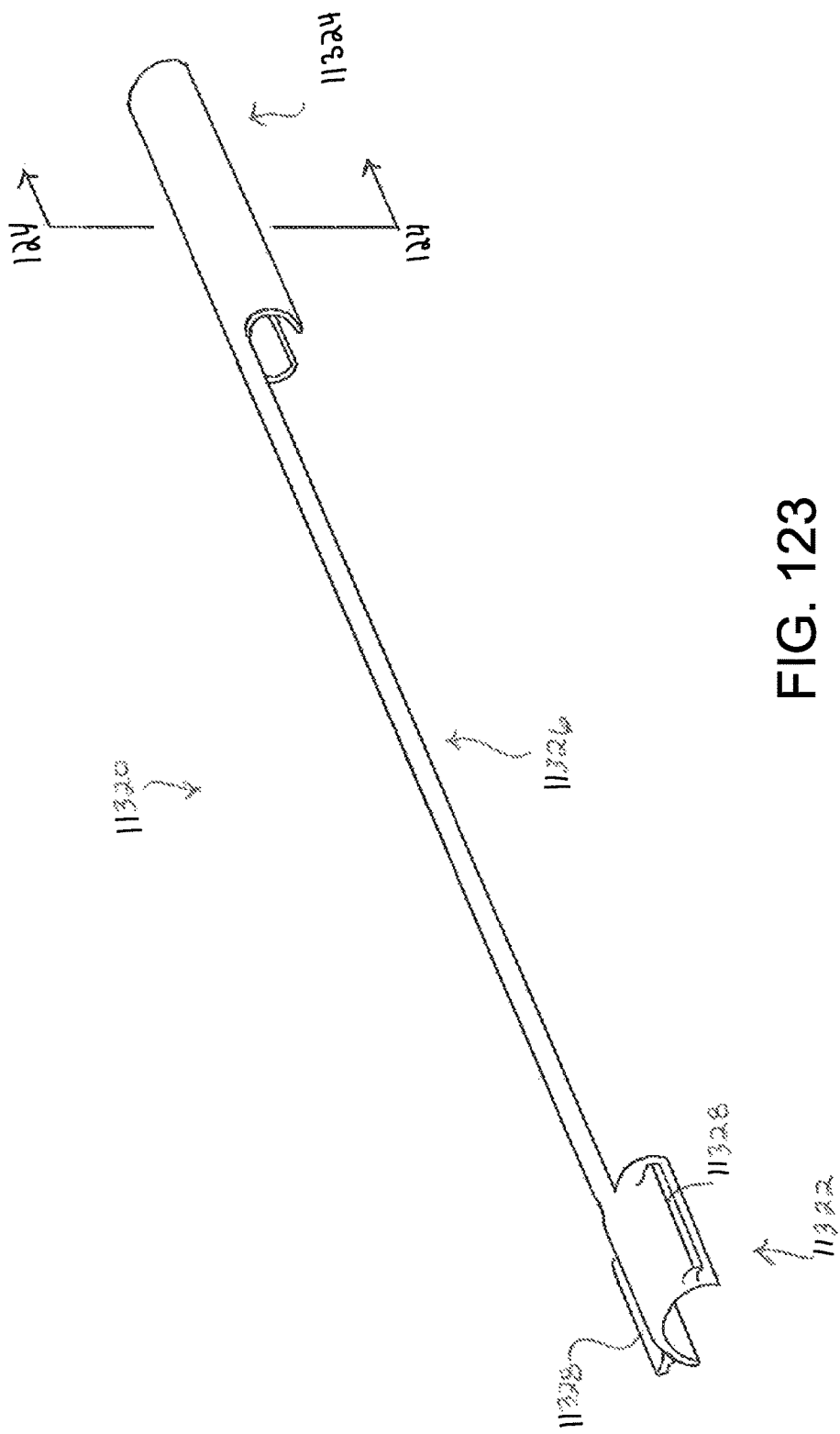
Figure 124:
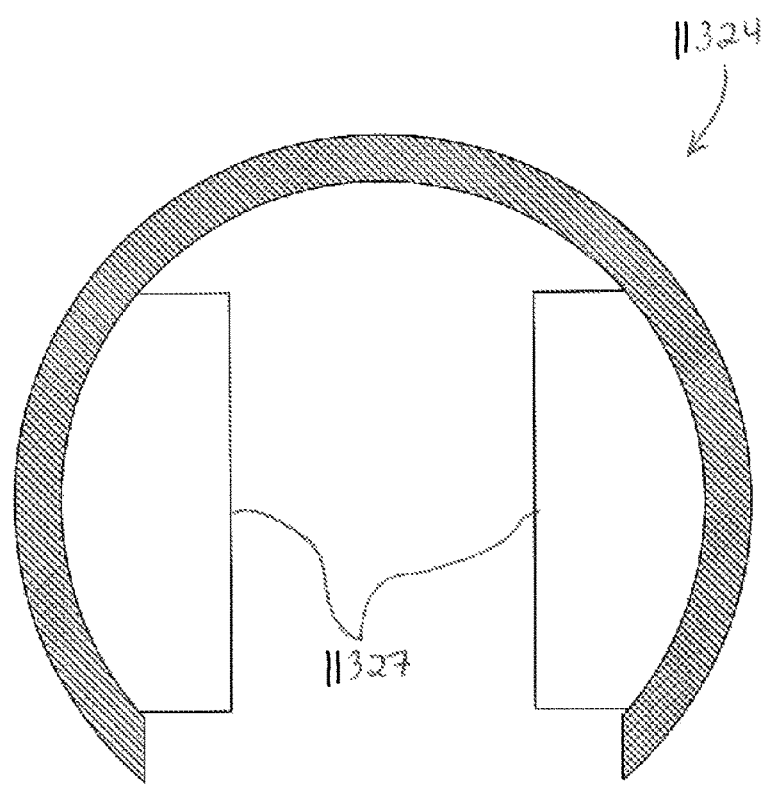
Figure 125A:
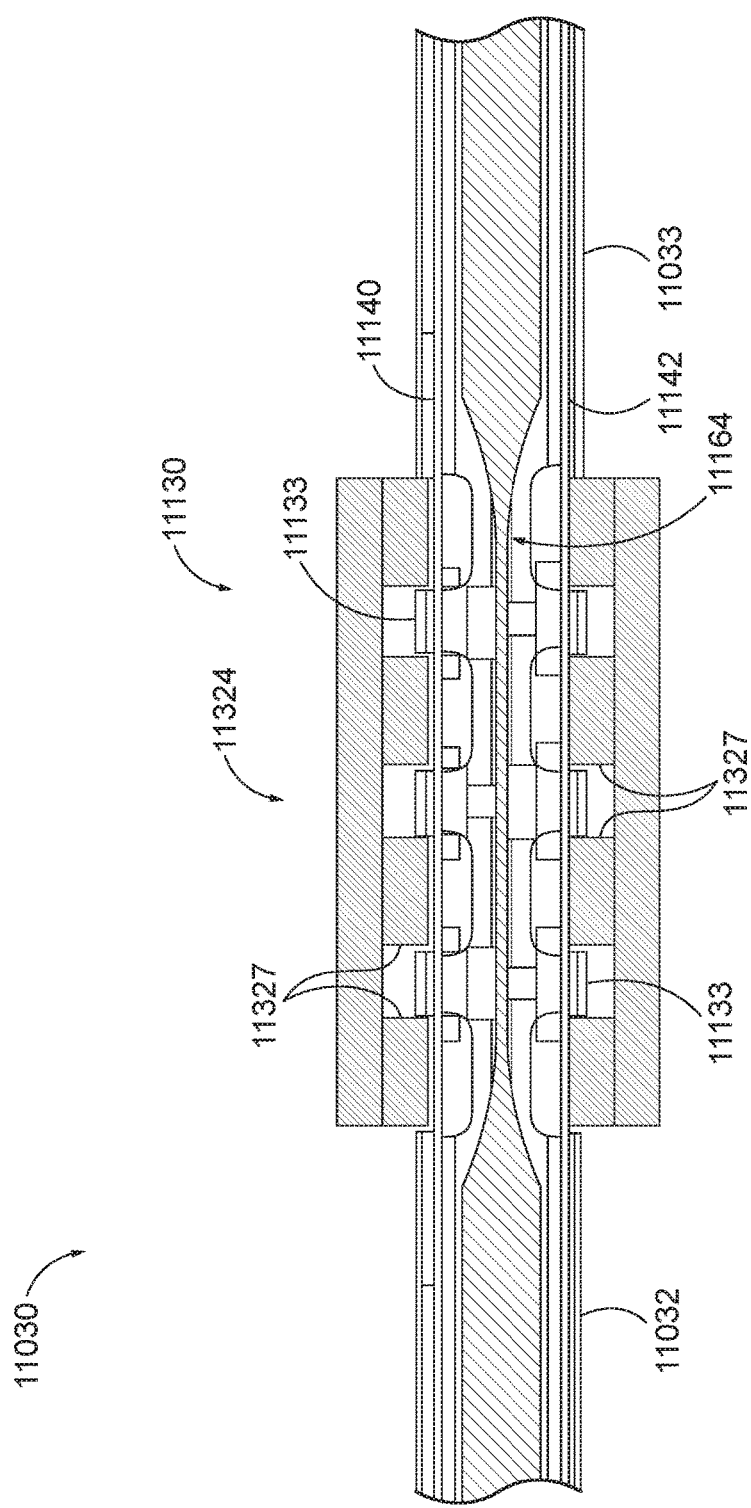
Figure 125B:
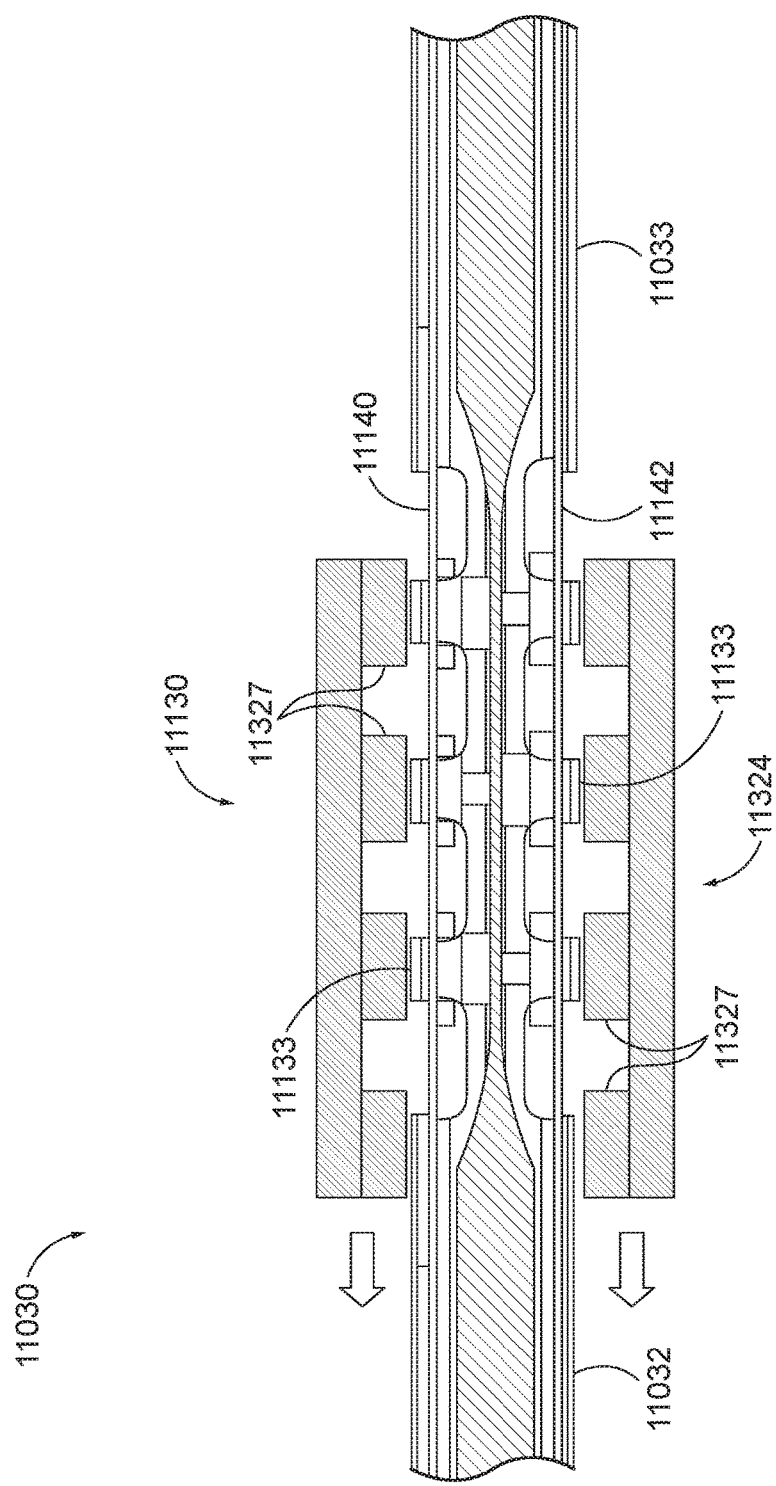
Figure 125C:
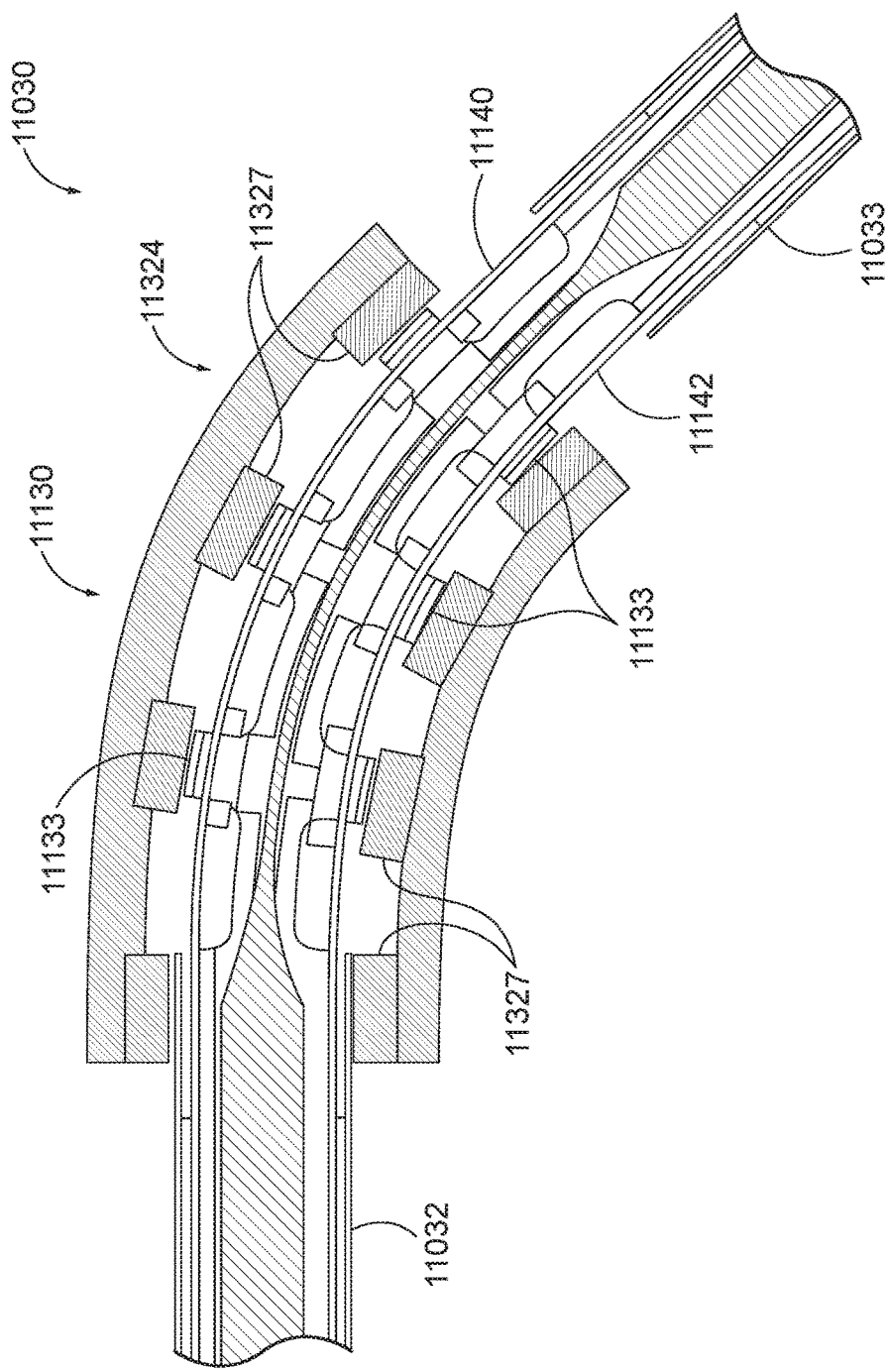
Figure 126:
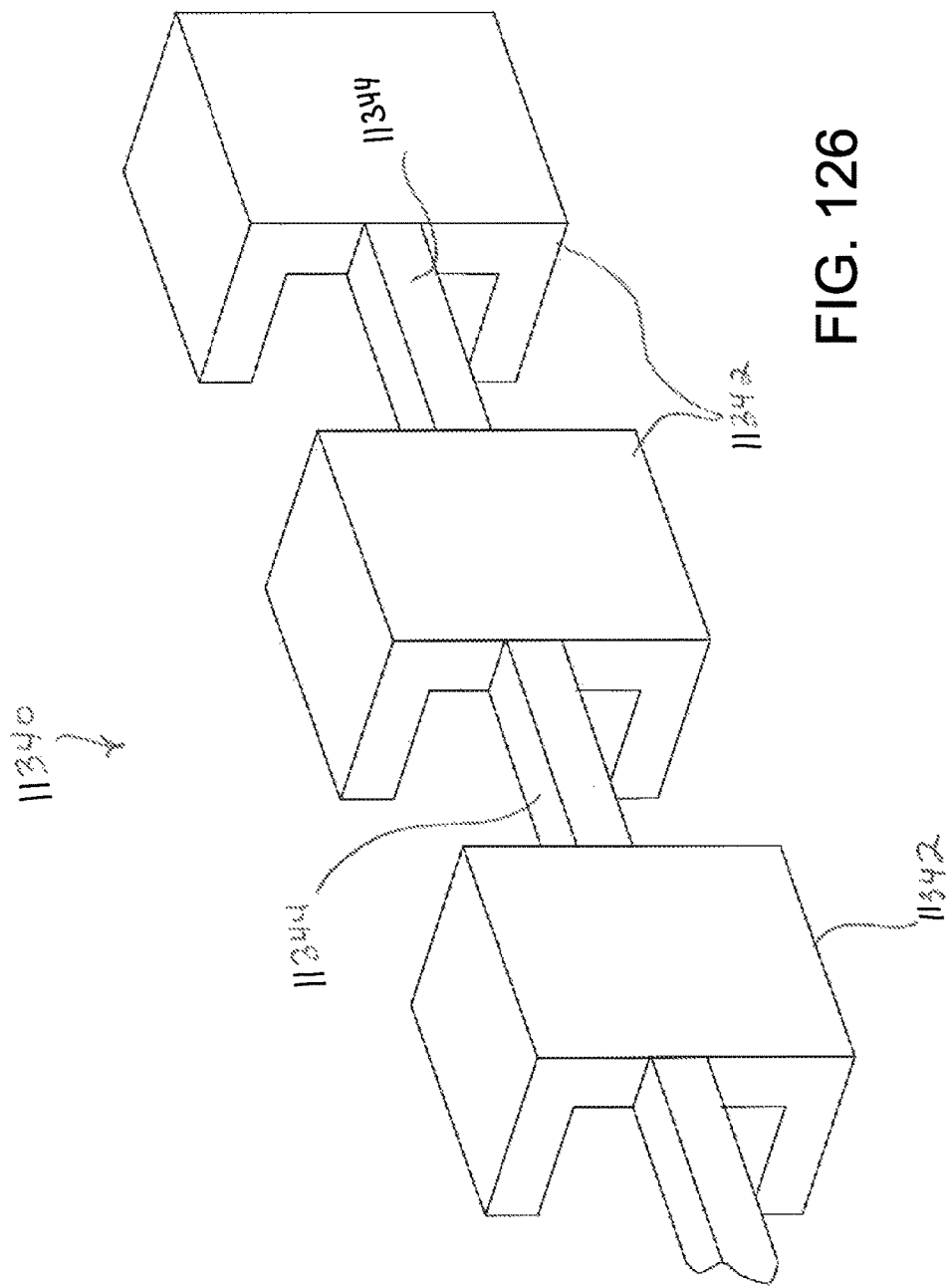
Figure 127:
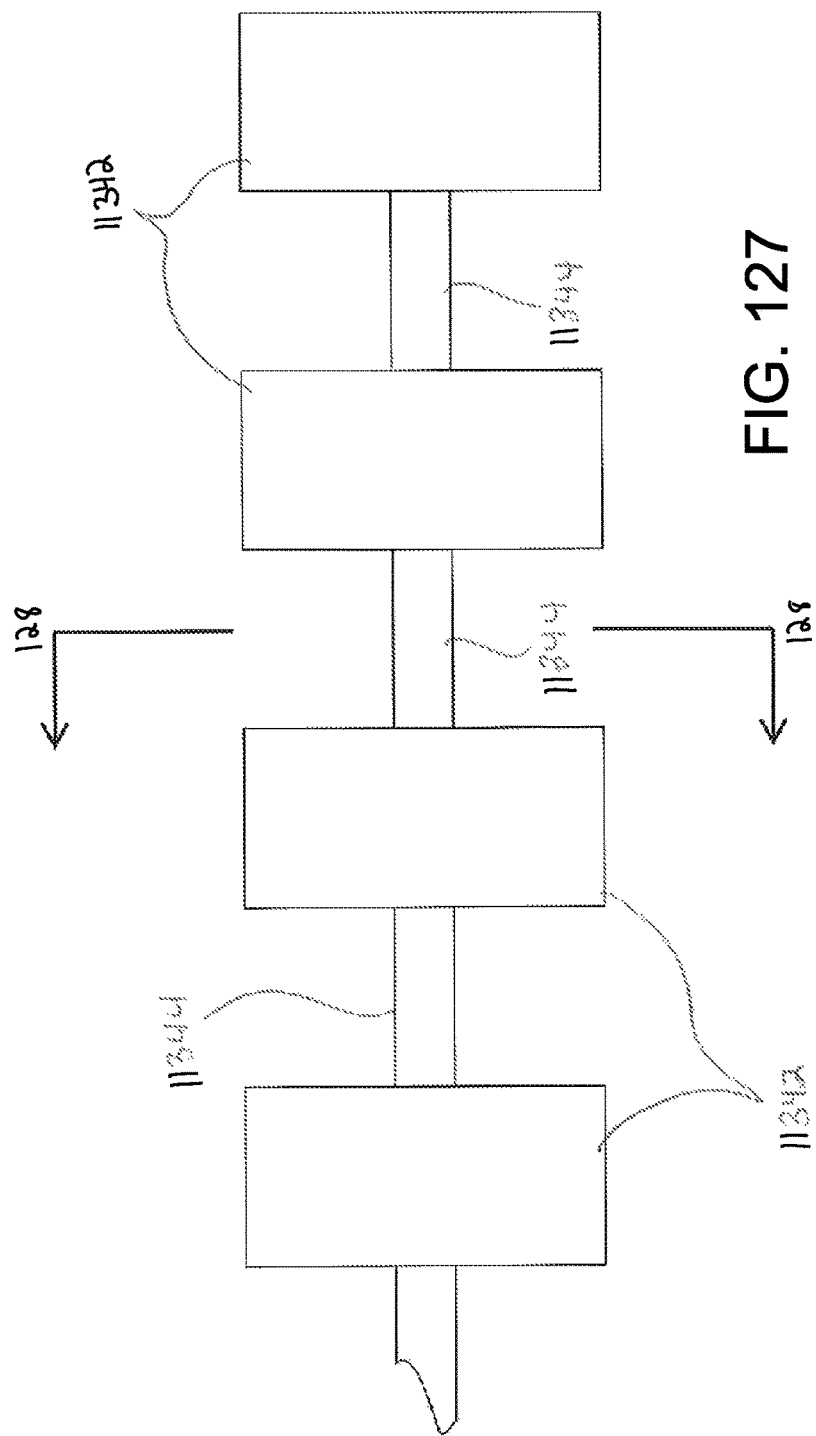
Figure 128:
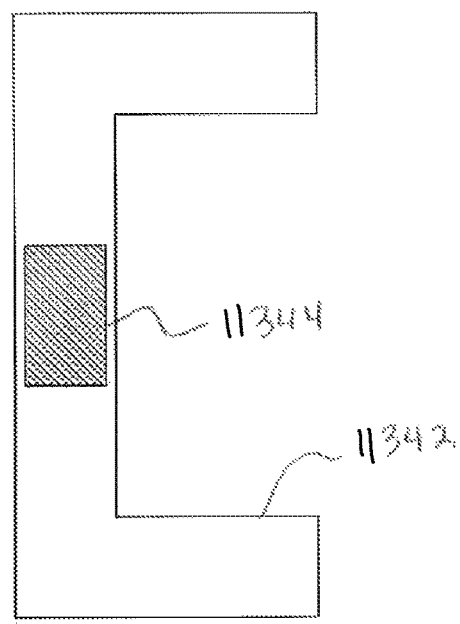
Figure 129A:
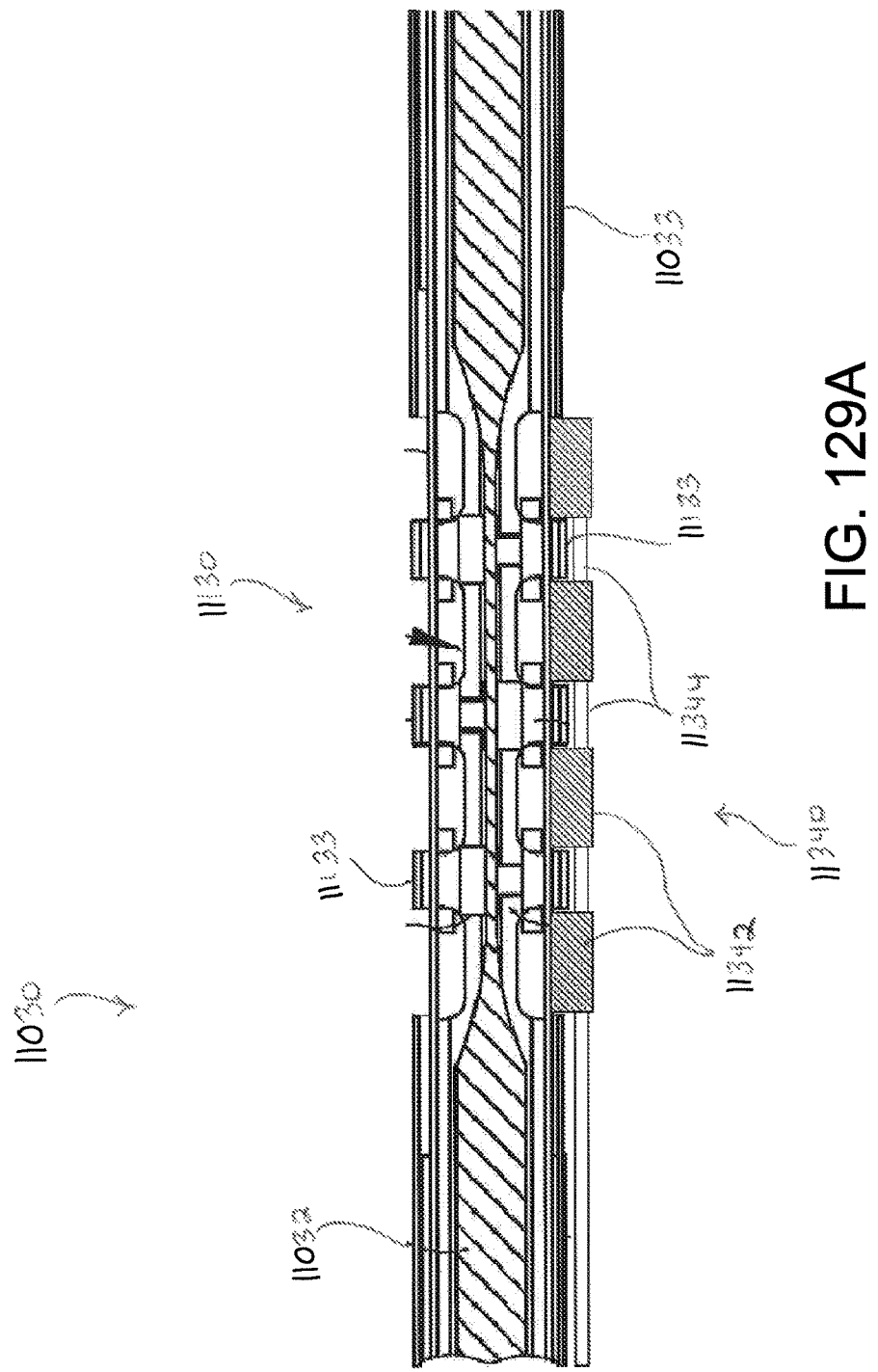
Figure 129B:
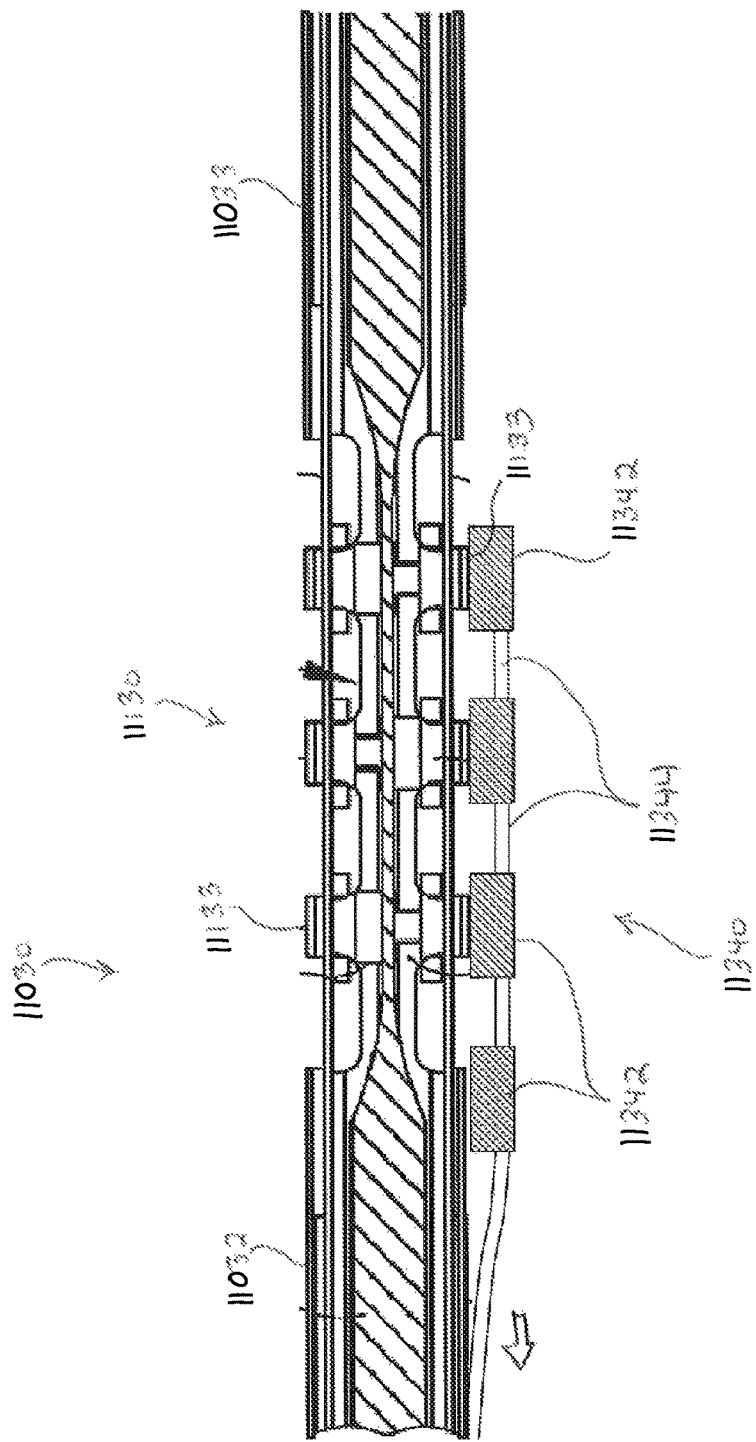
Figure 129C:
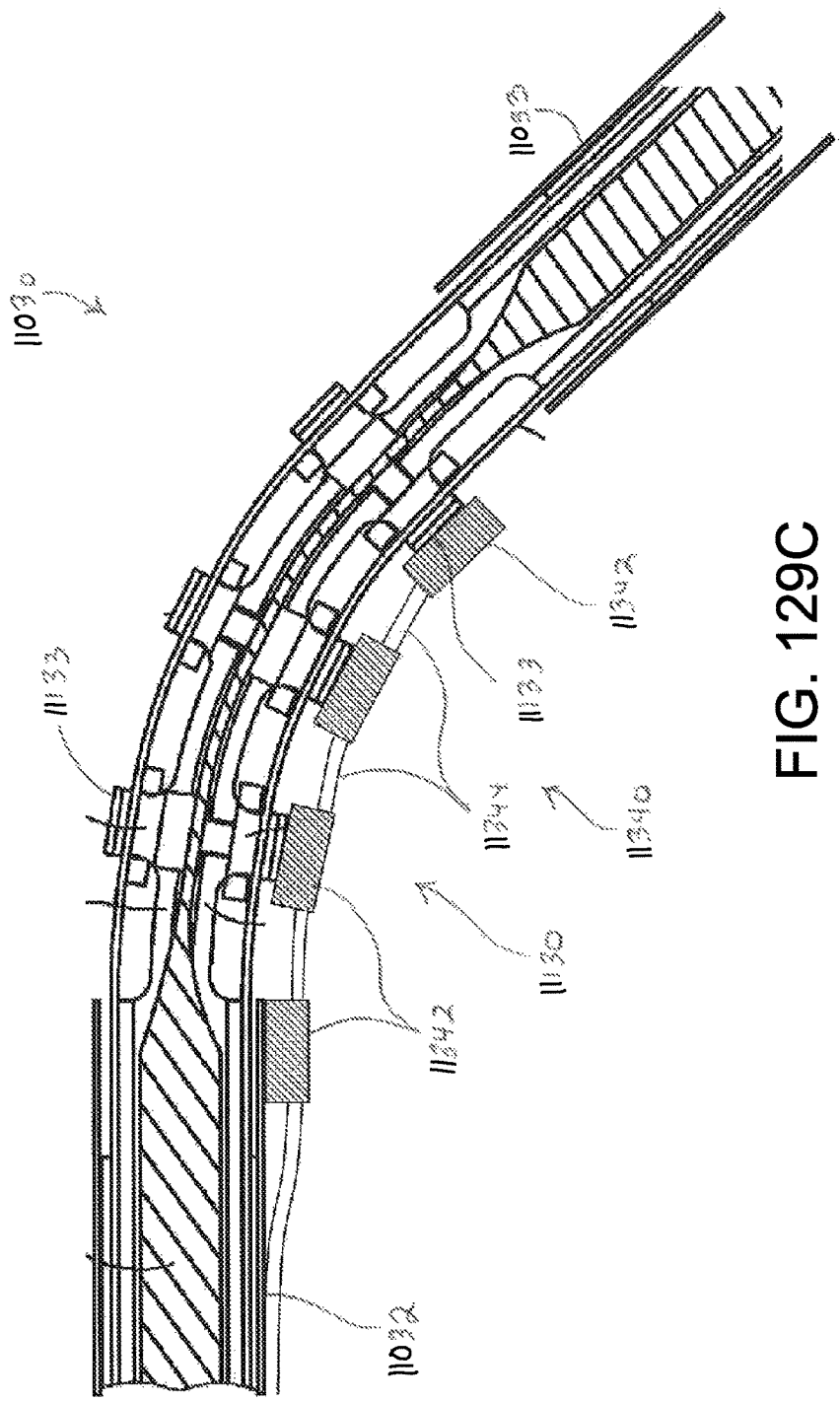
Figure 130A:
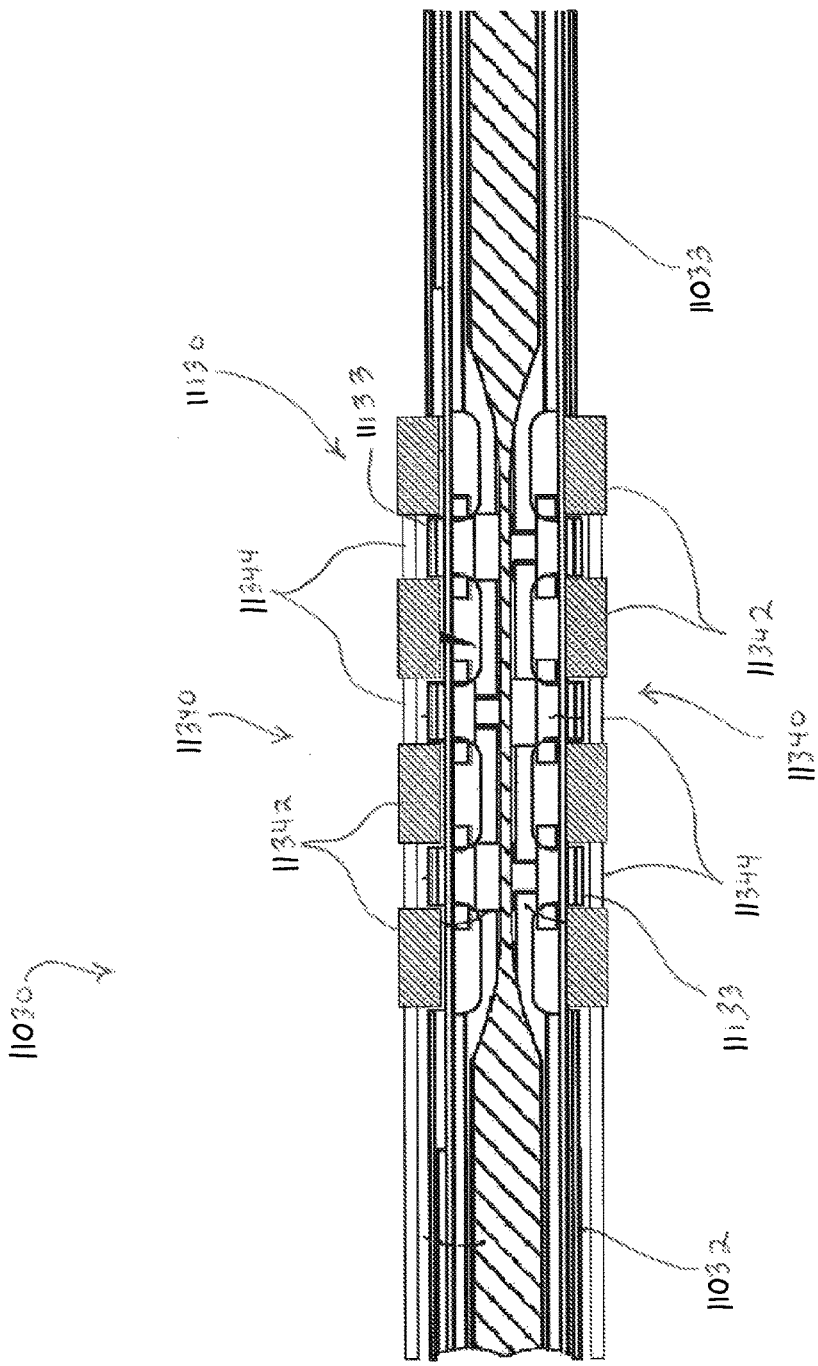
Figure 130B:
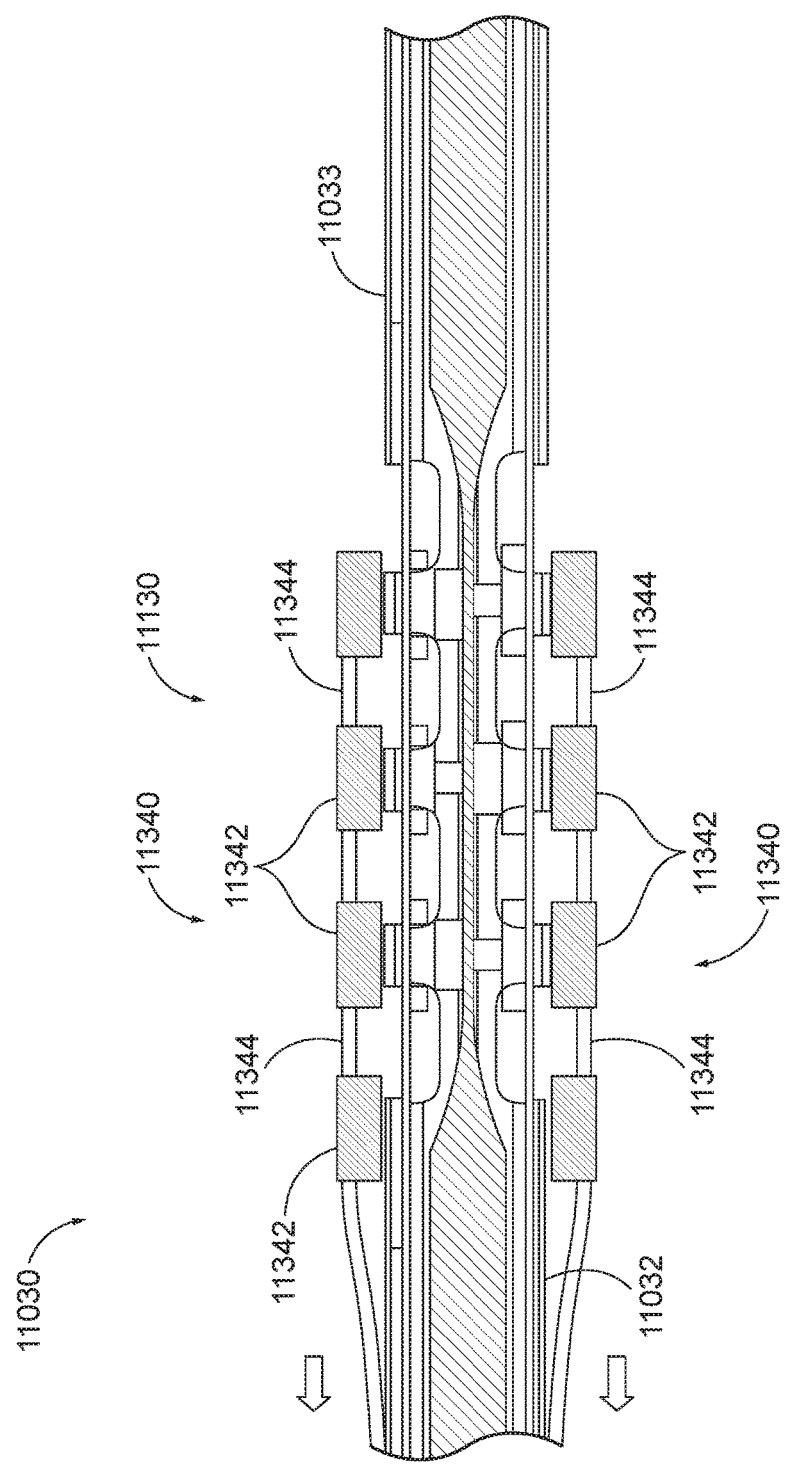
Figure 131:
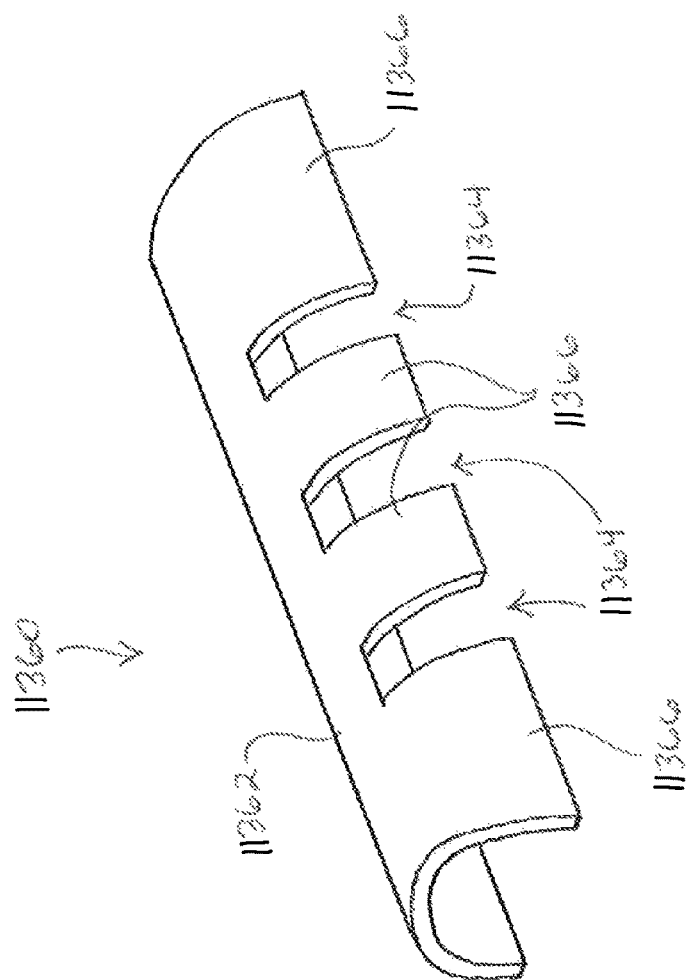
Figure 132A:
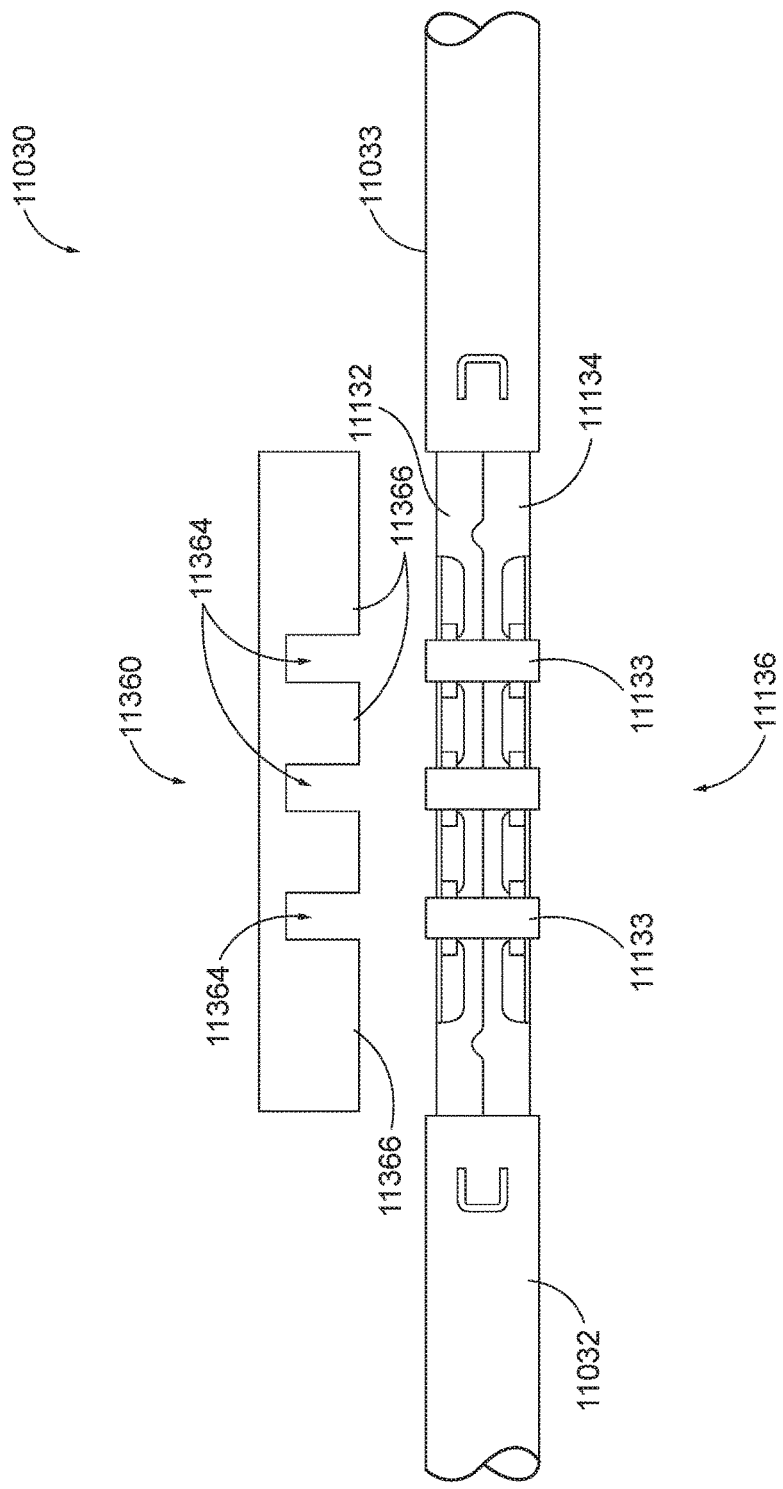
Figure 132B:
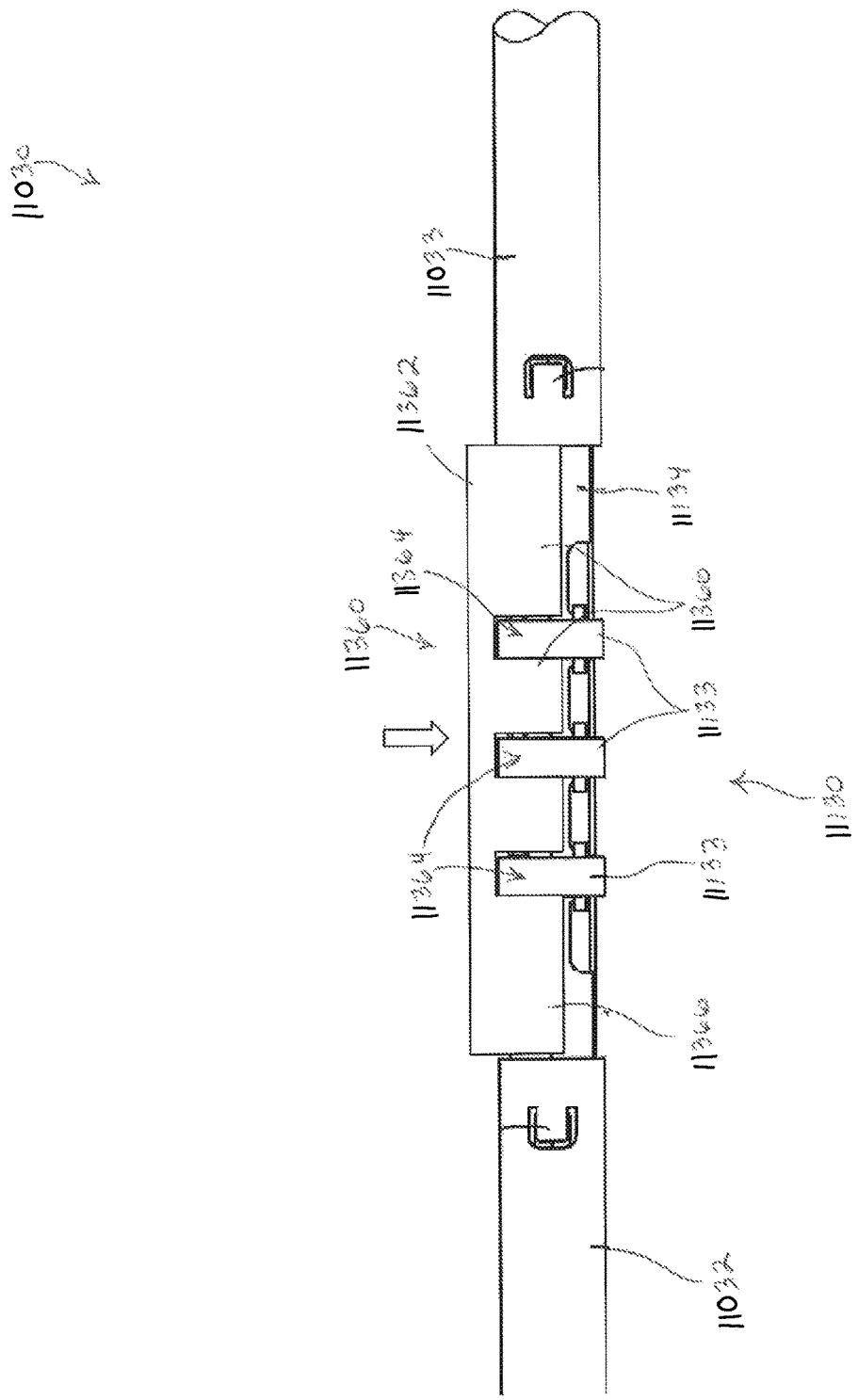
Figure 133A:
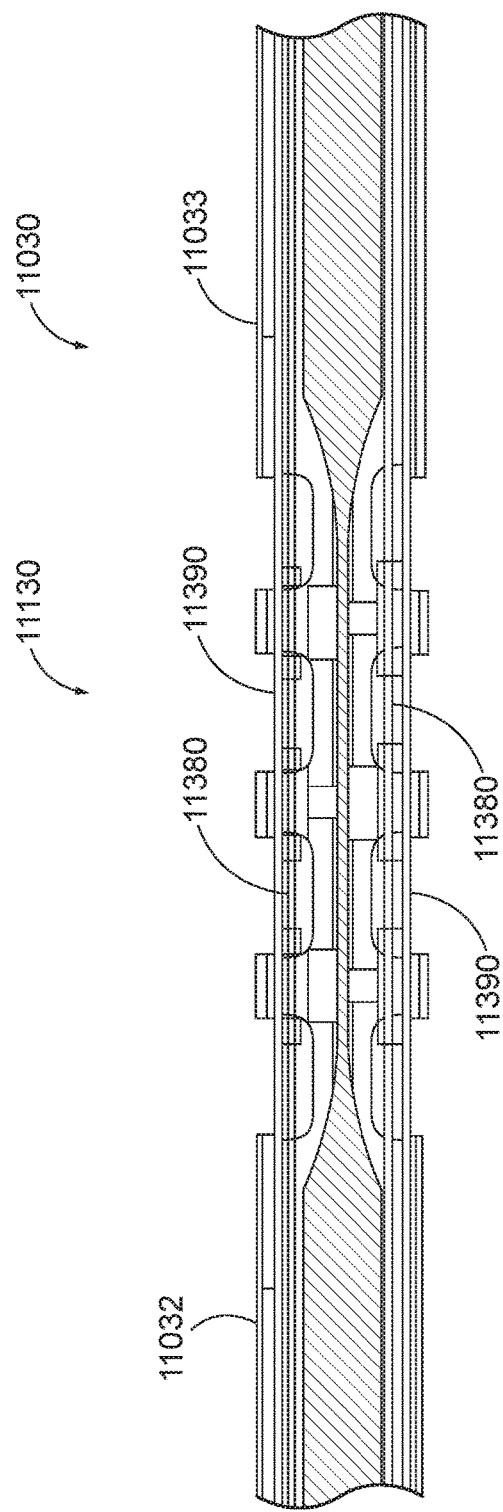
Figure 133B:
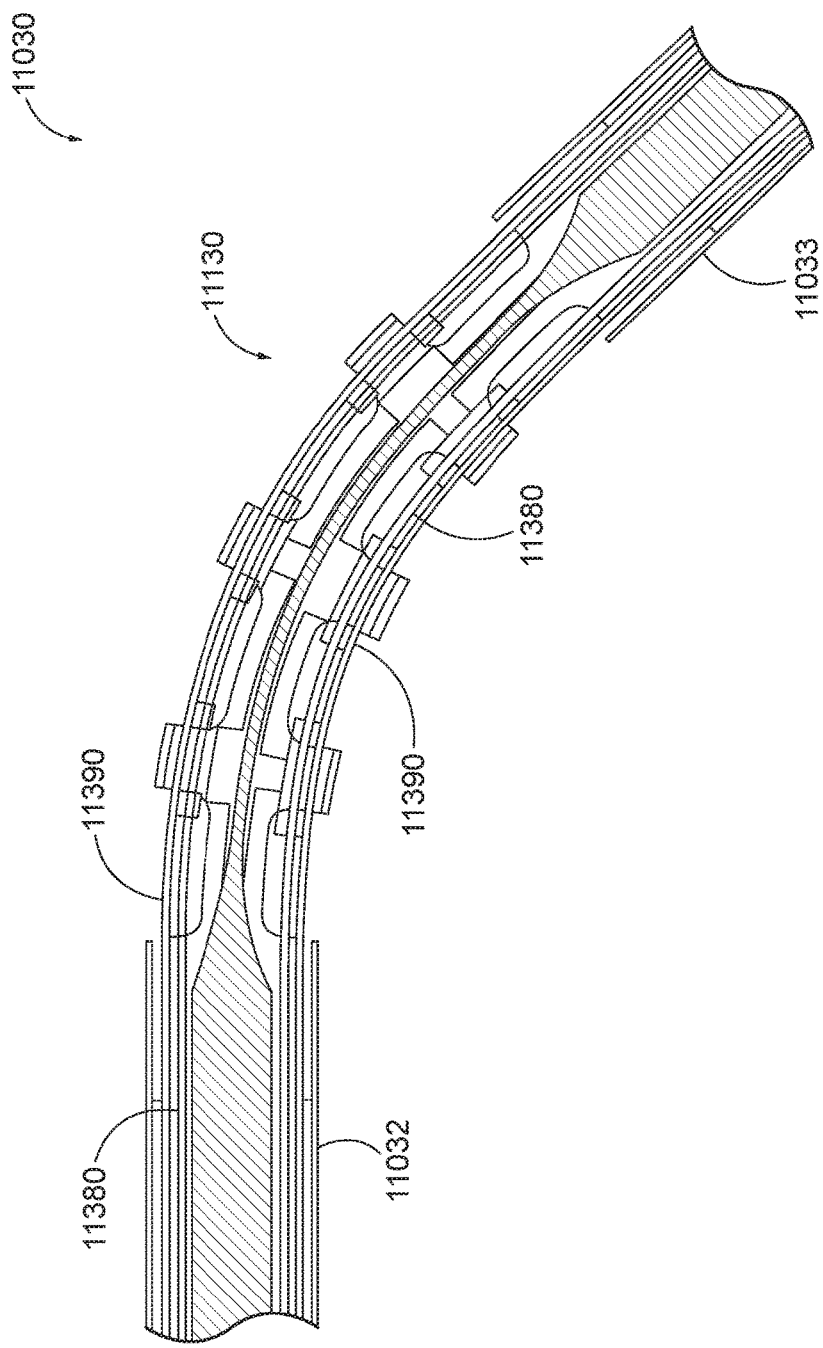
Figure 136A:
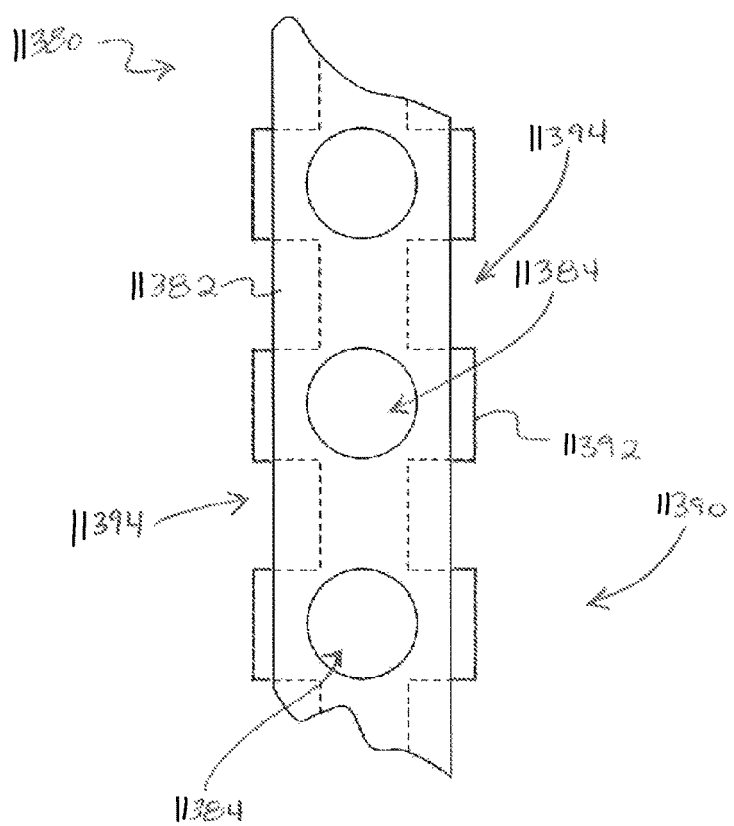
Figure 136B:
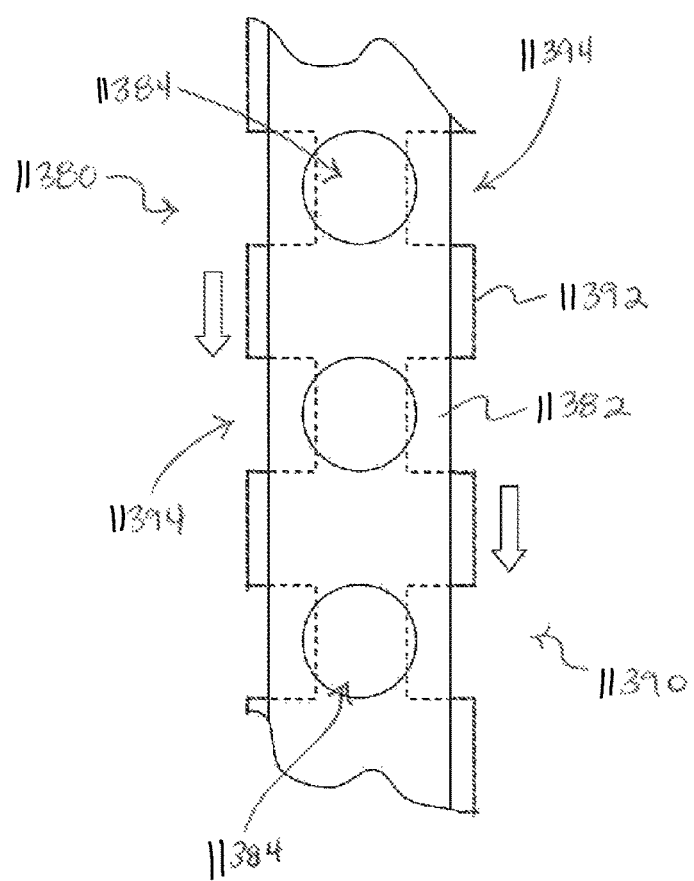
Figure 137:
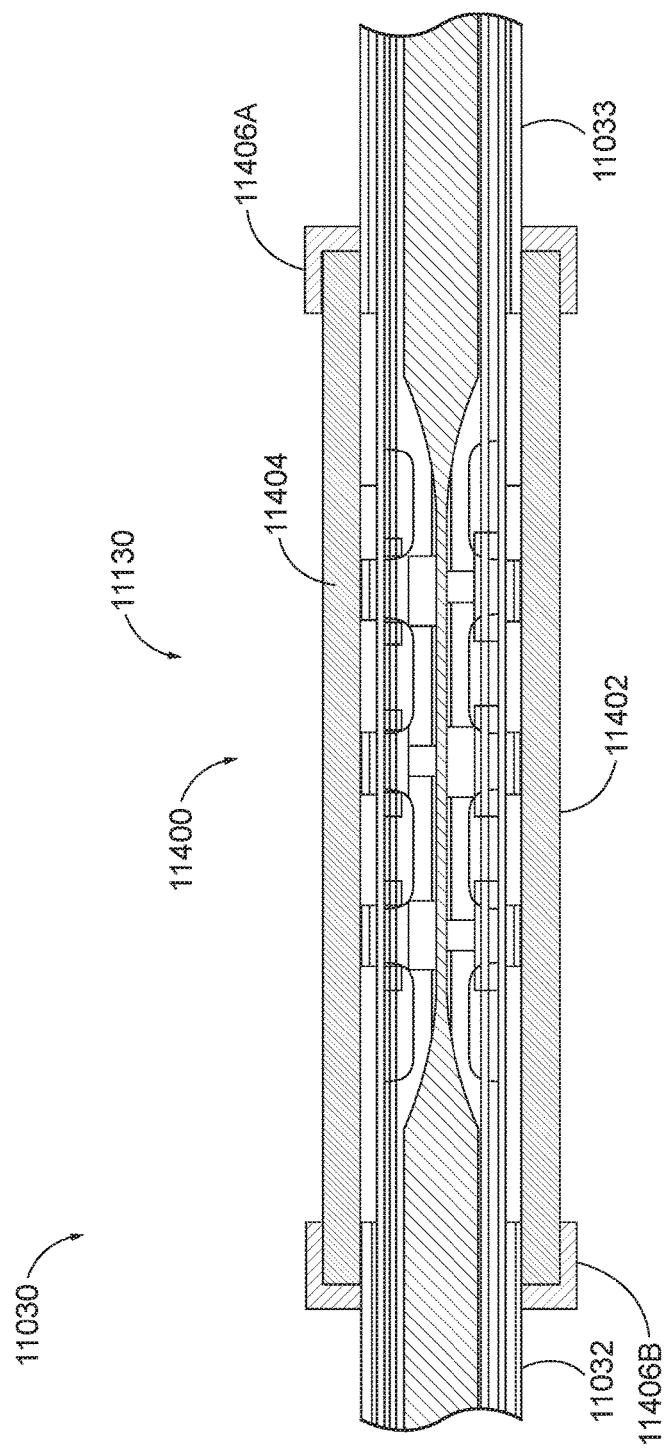
Figure 138:
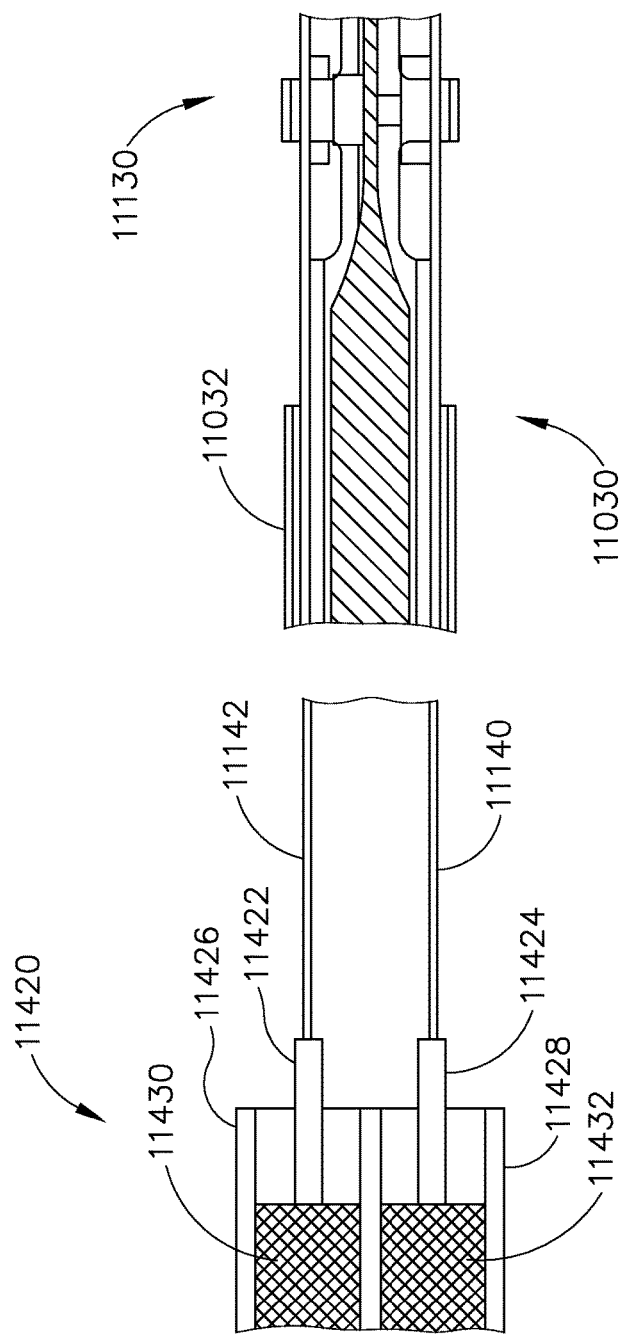
Figure 139:
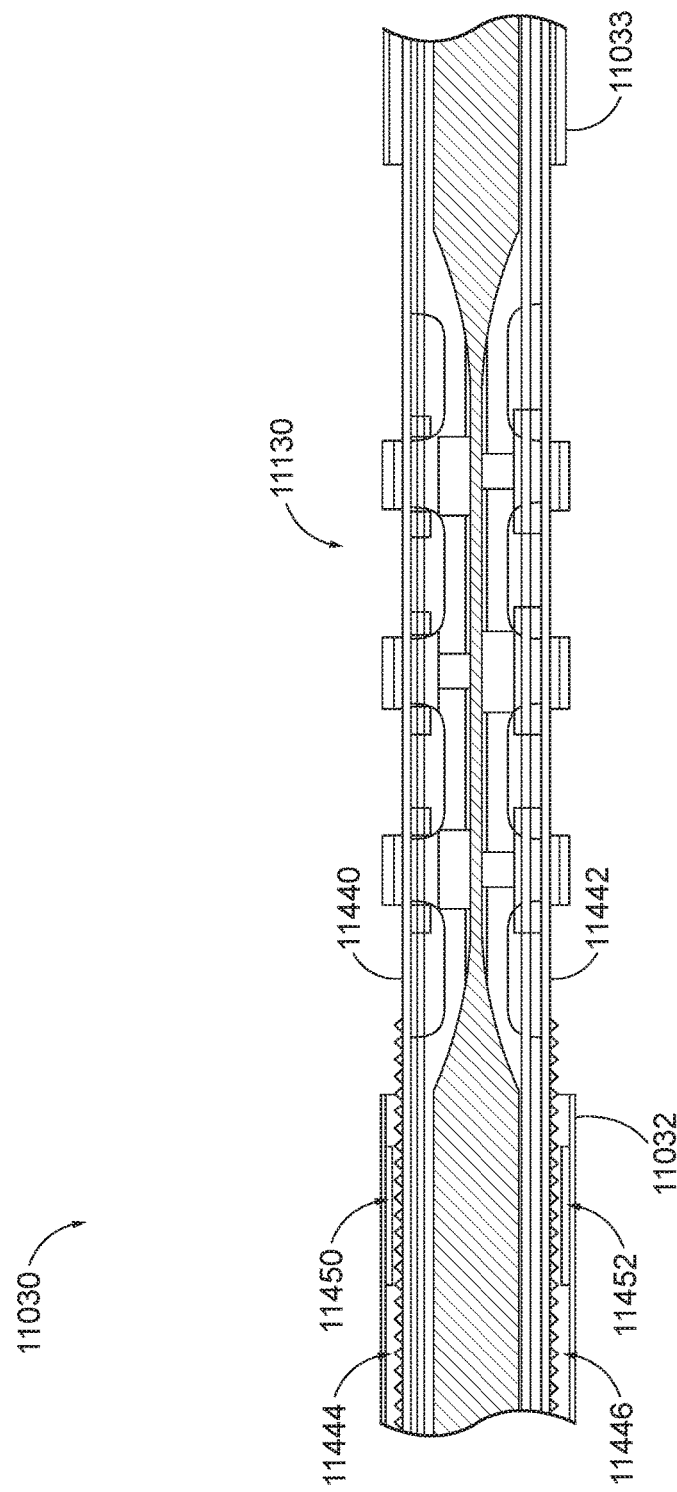
Figure 140A:
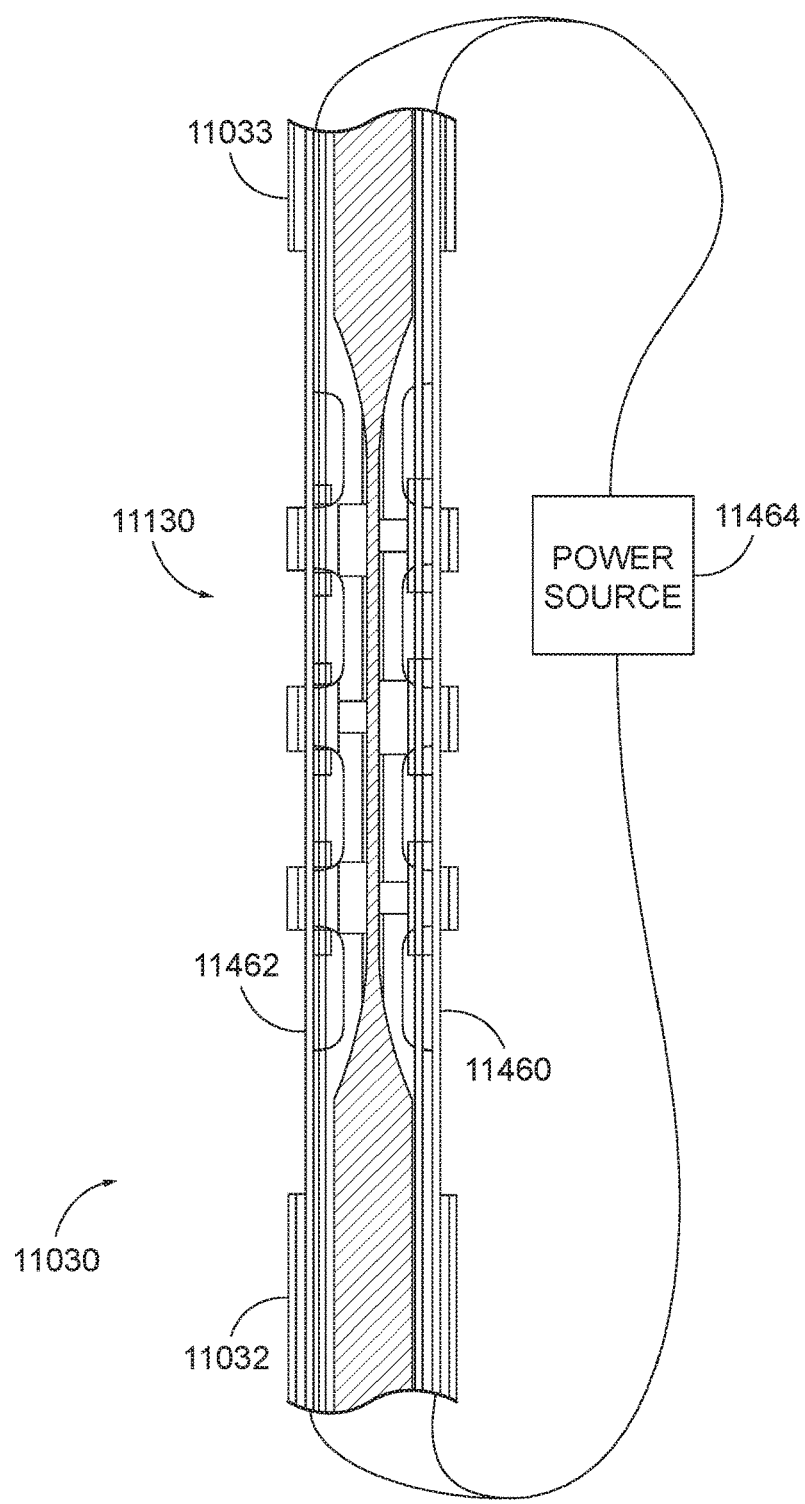
Figure 140B:
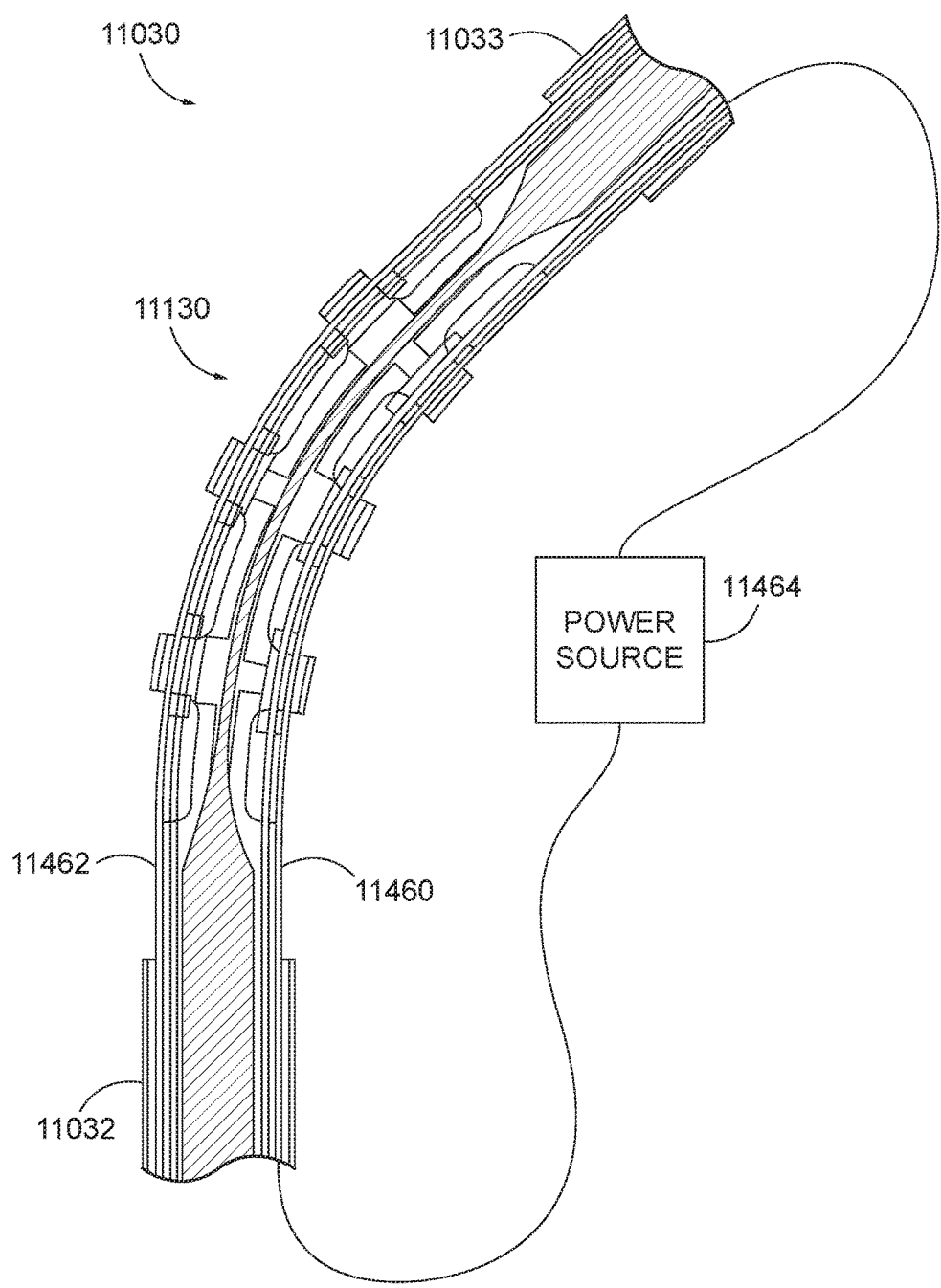
Figure 141:
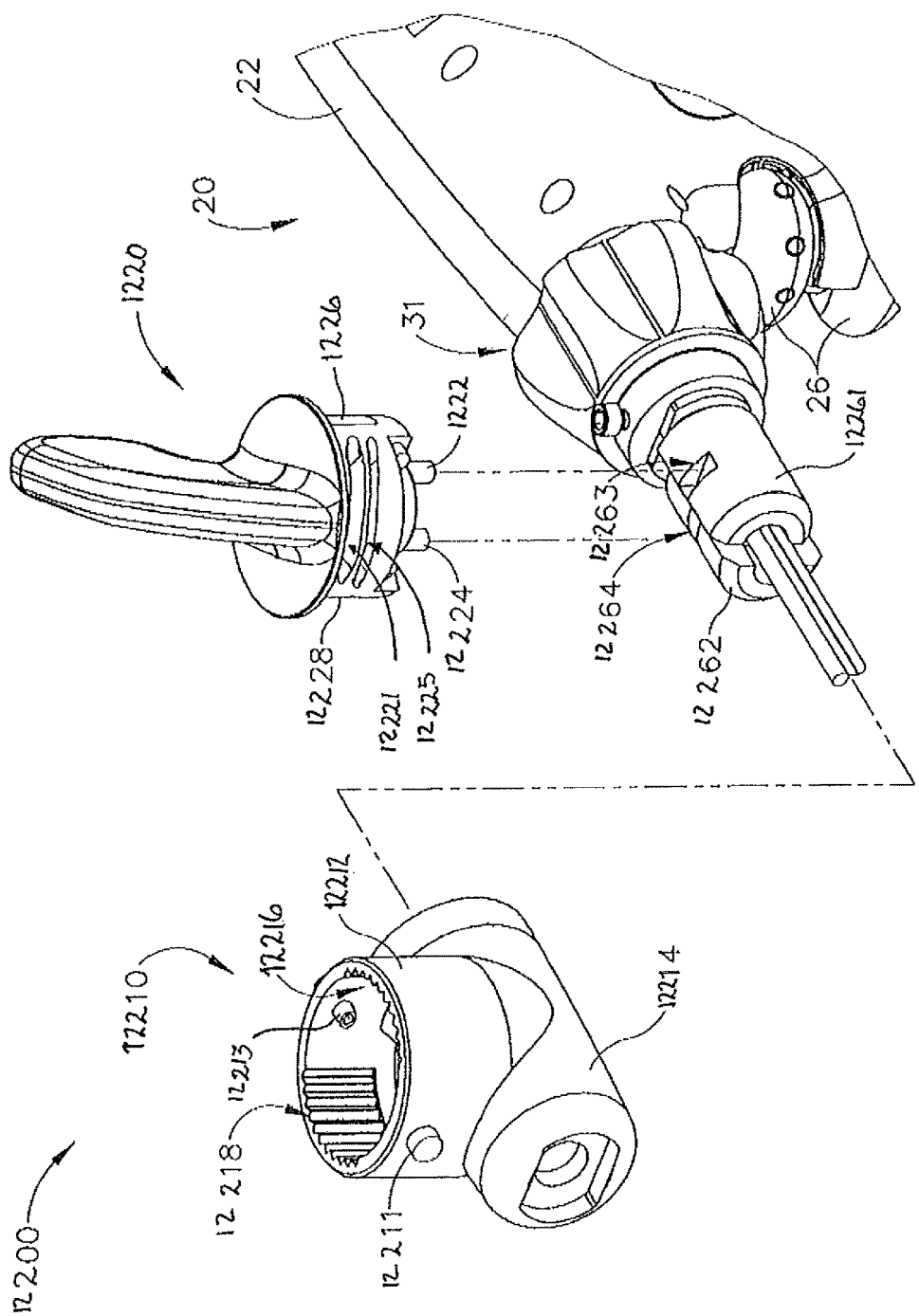
Figure 142:
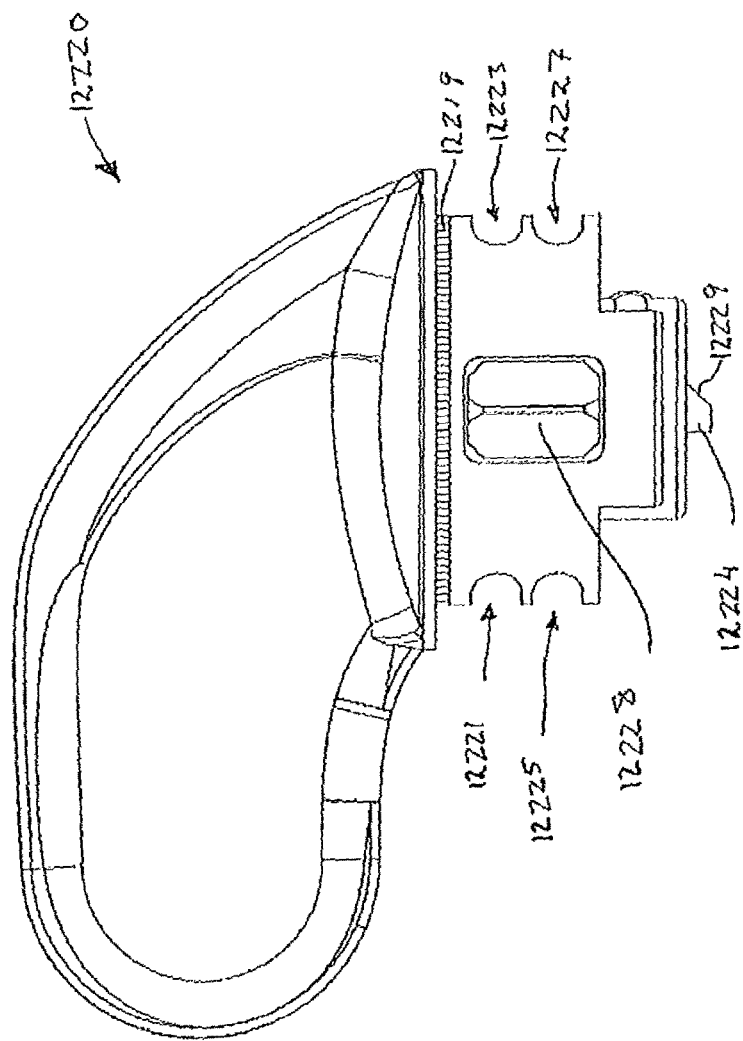
Figure 143:
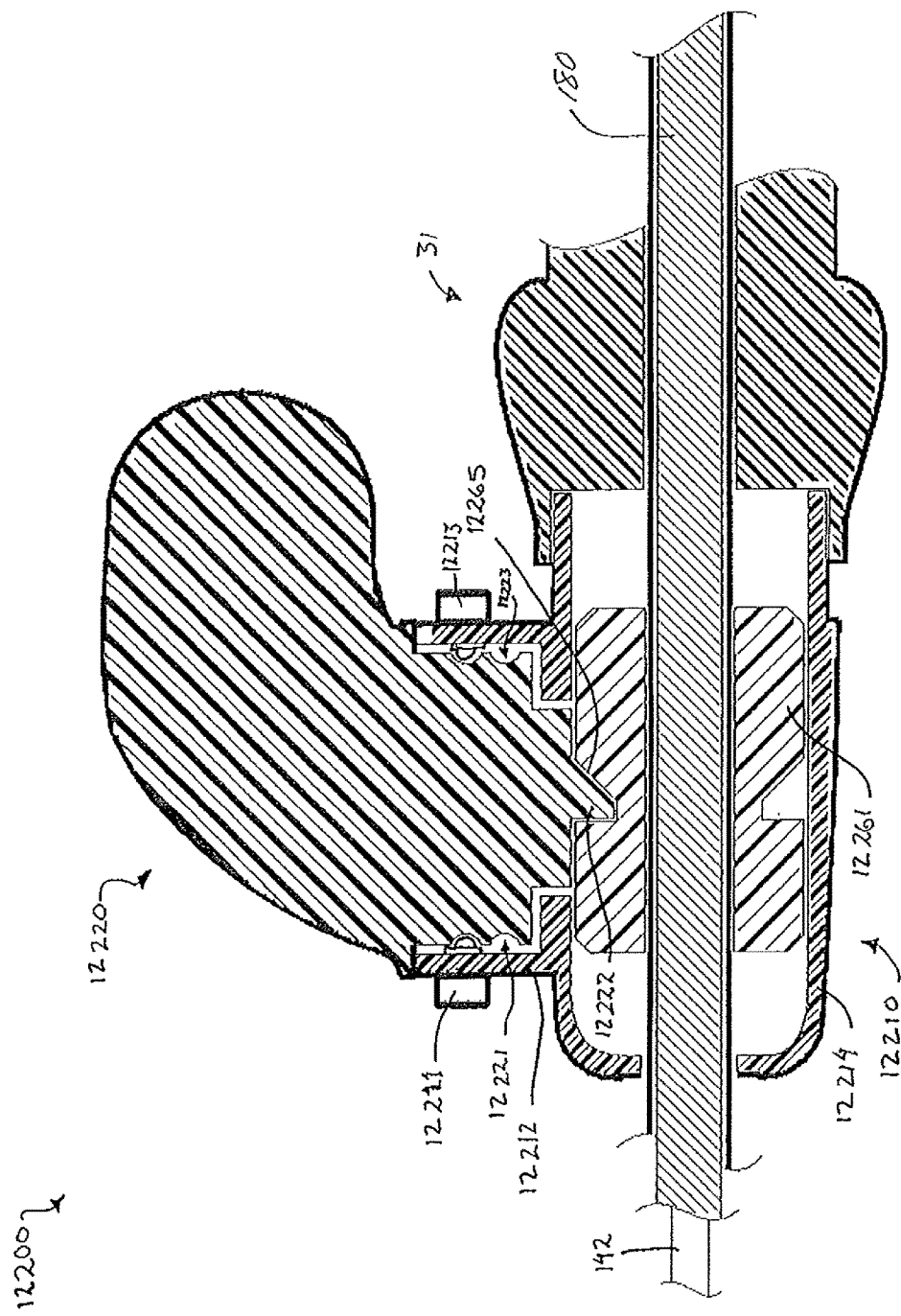
Figure 144:
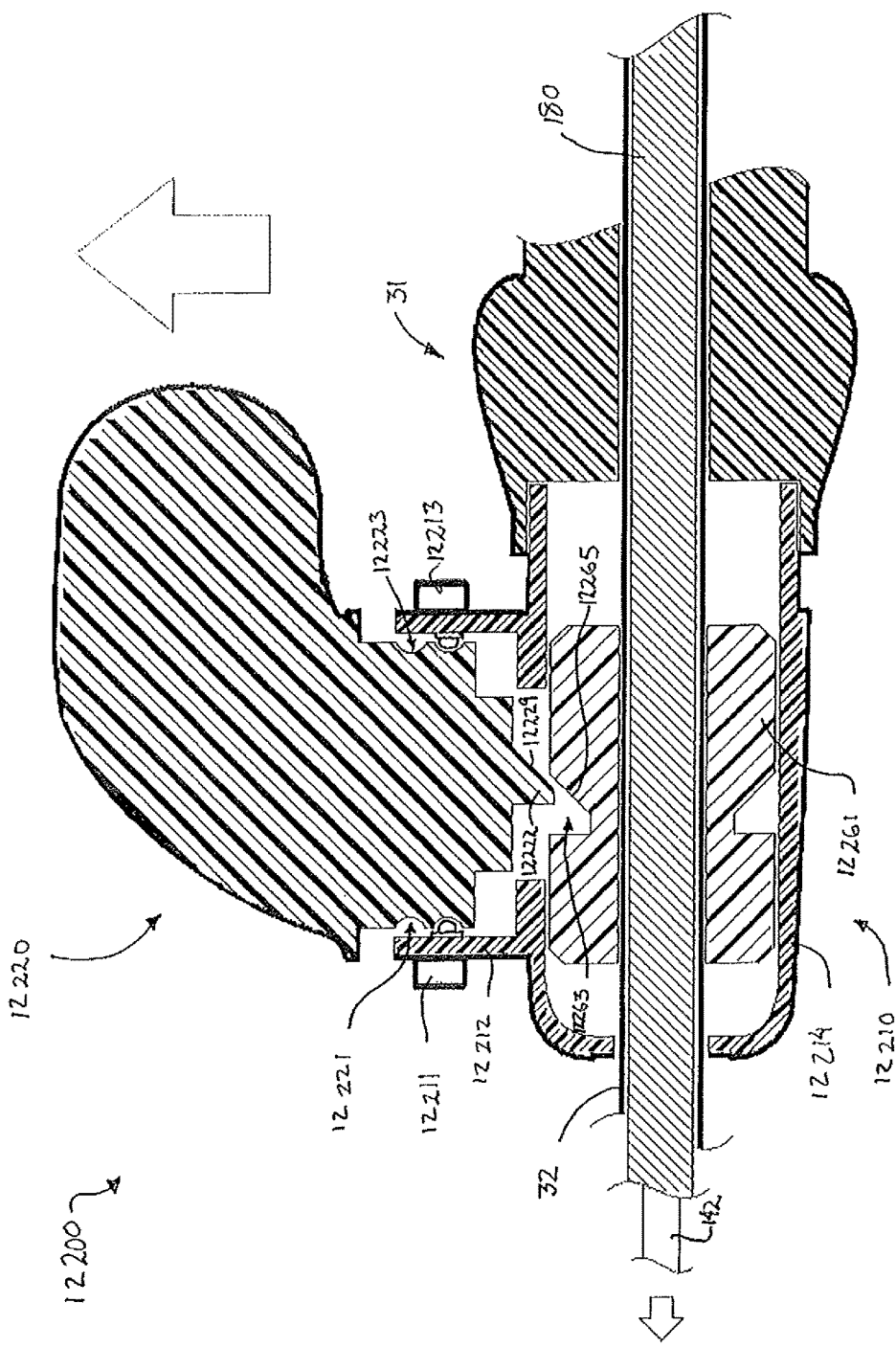
Figure 145:
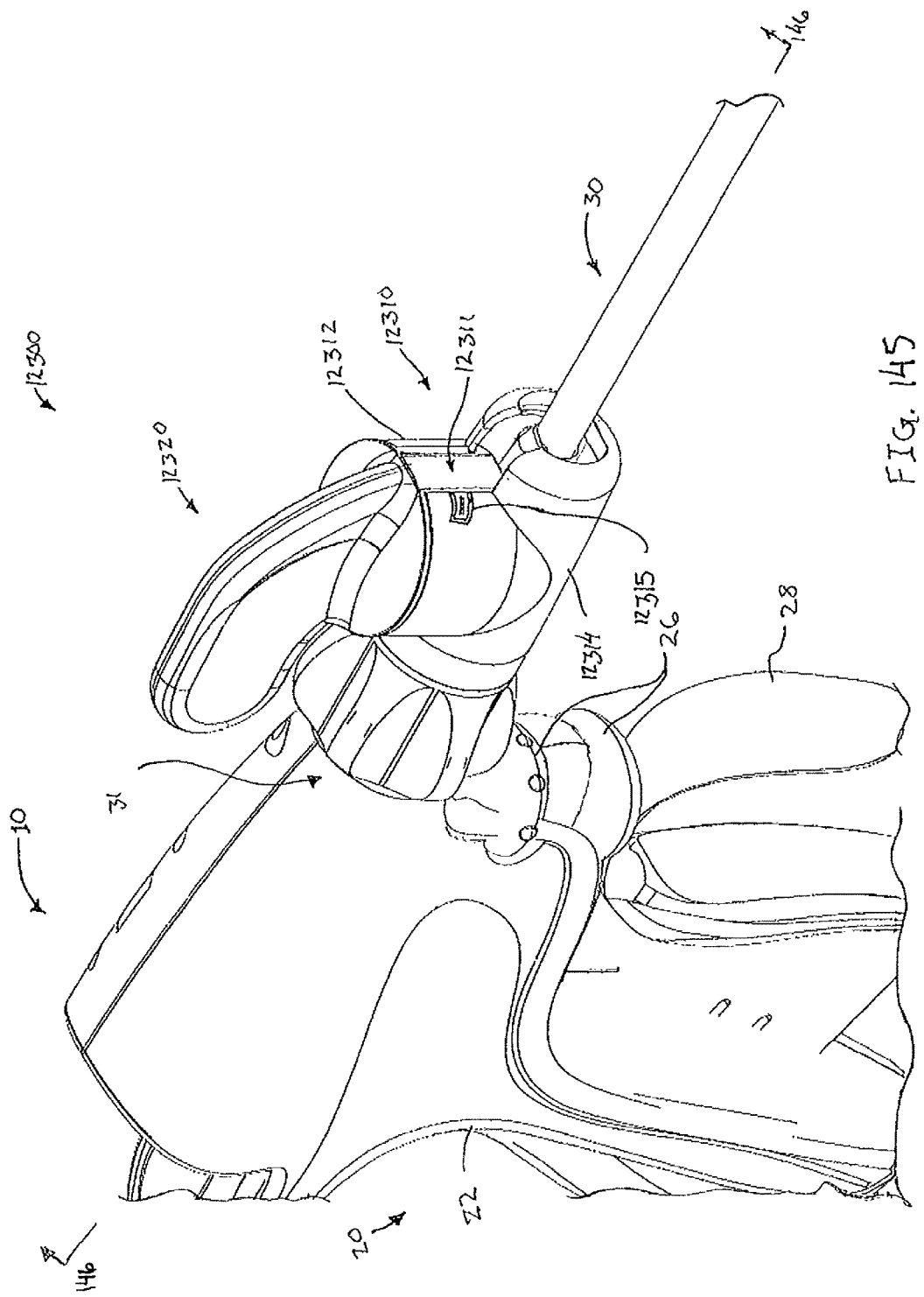
Figure 146:
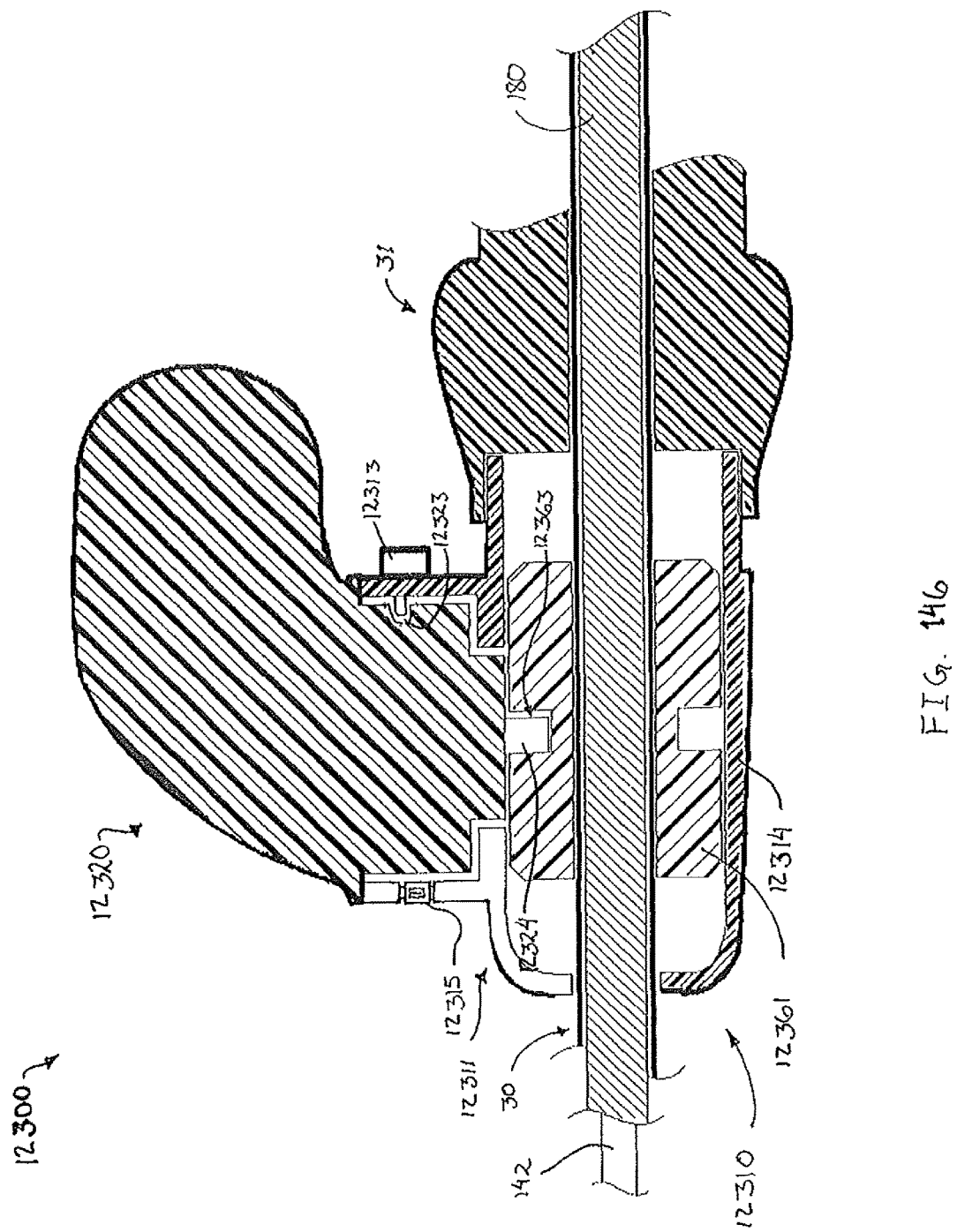
Figure 147:
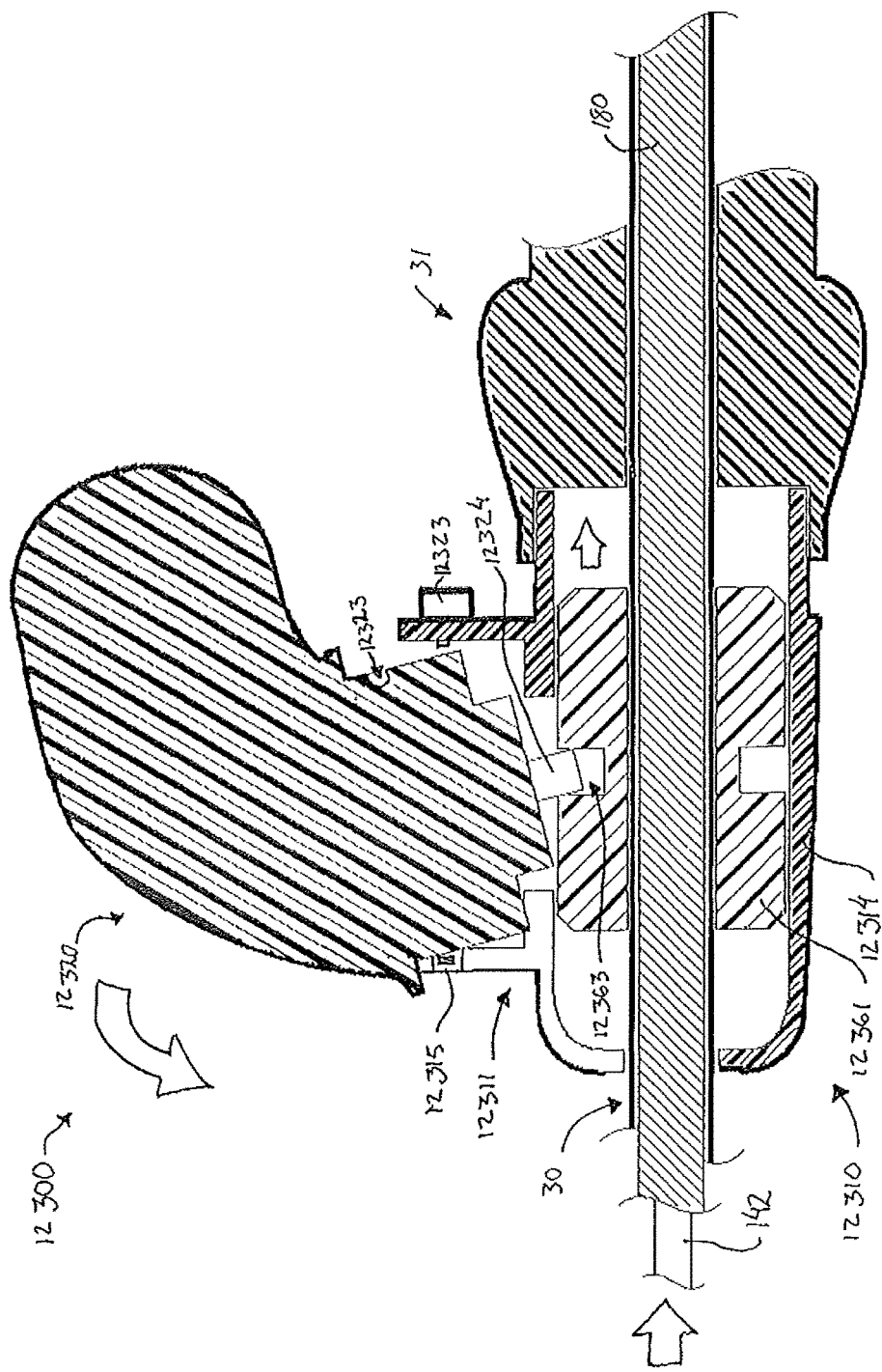
Figure 148:
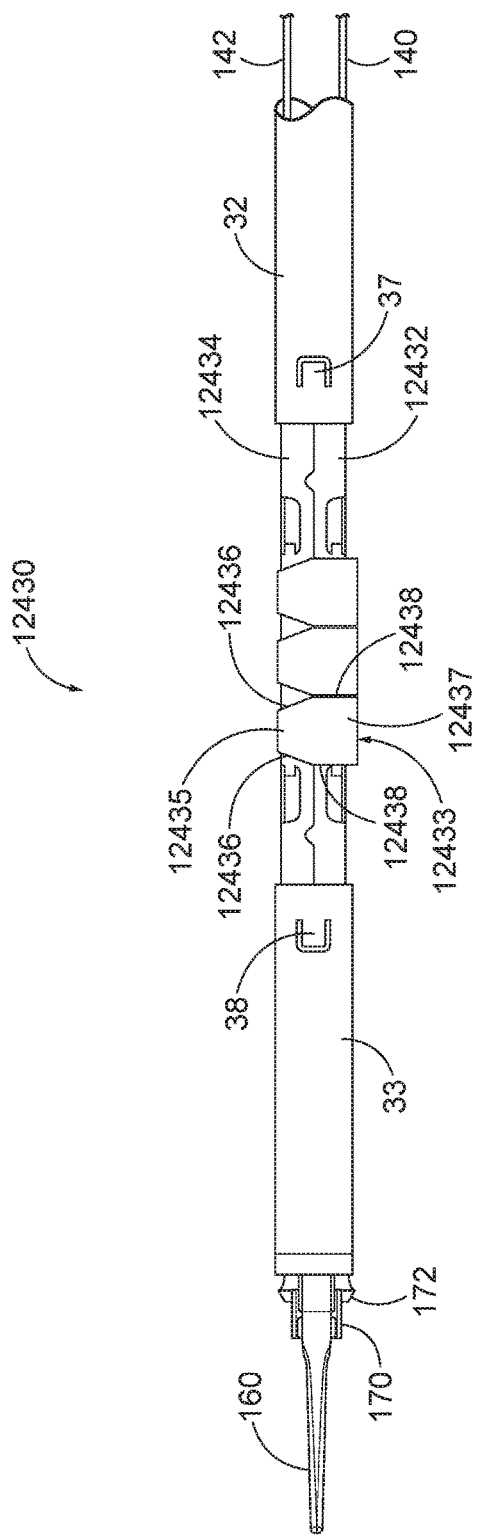
Figure 149:
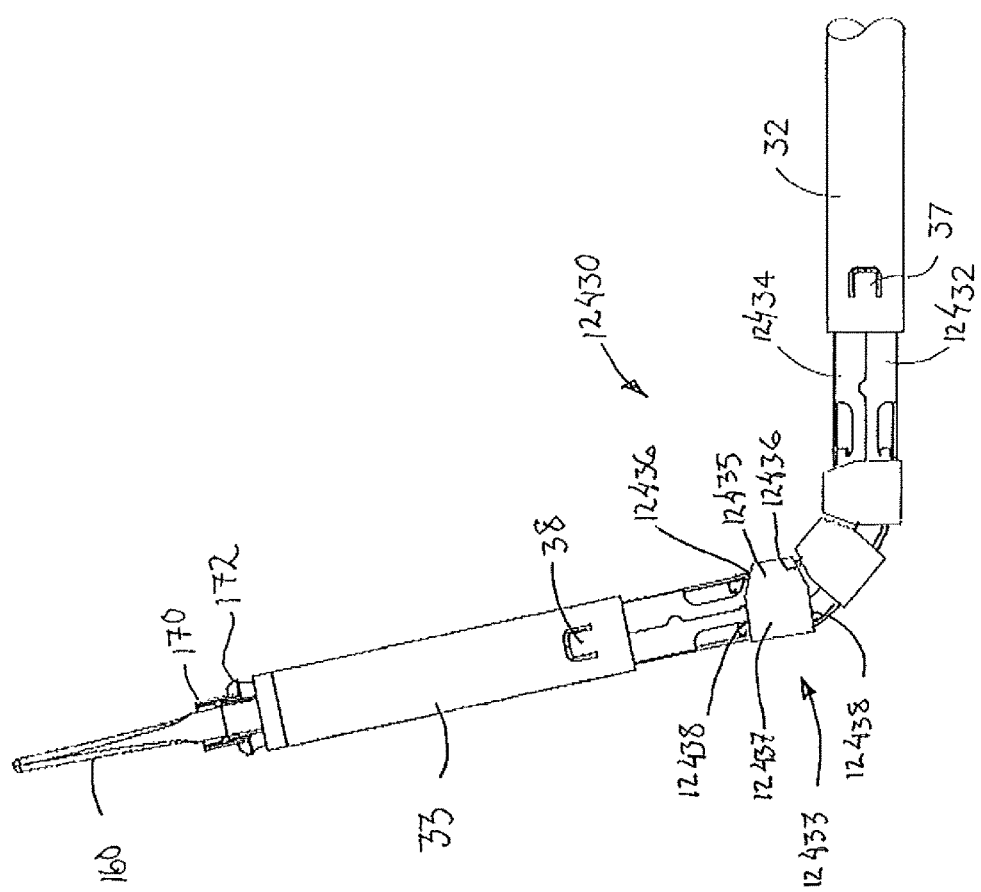
Figure 150:
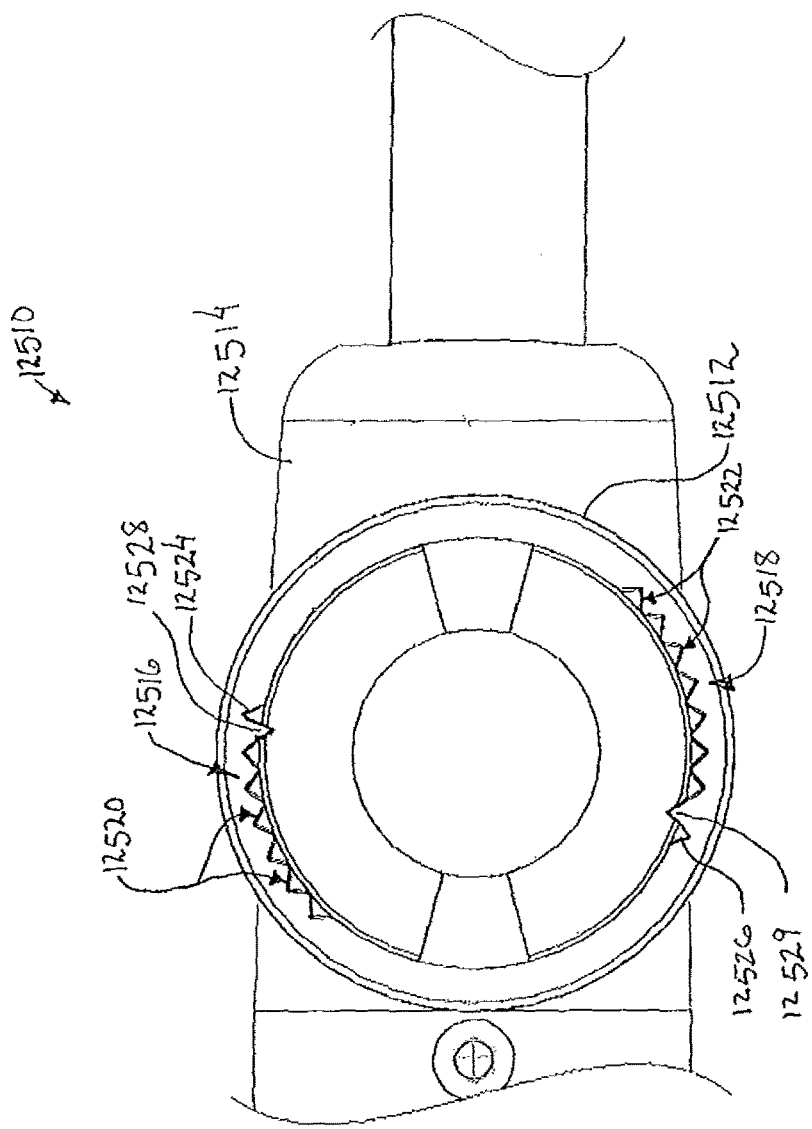
Figure 151:
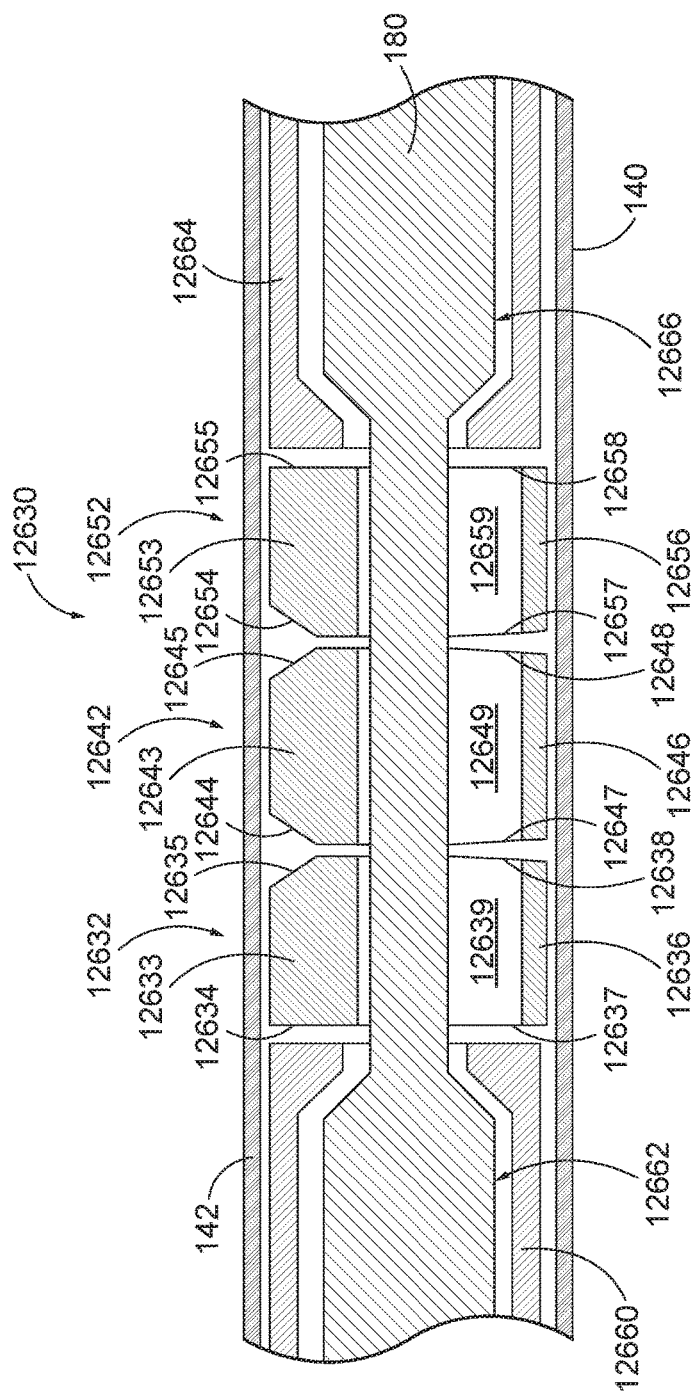
Figure 152:
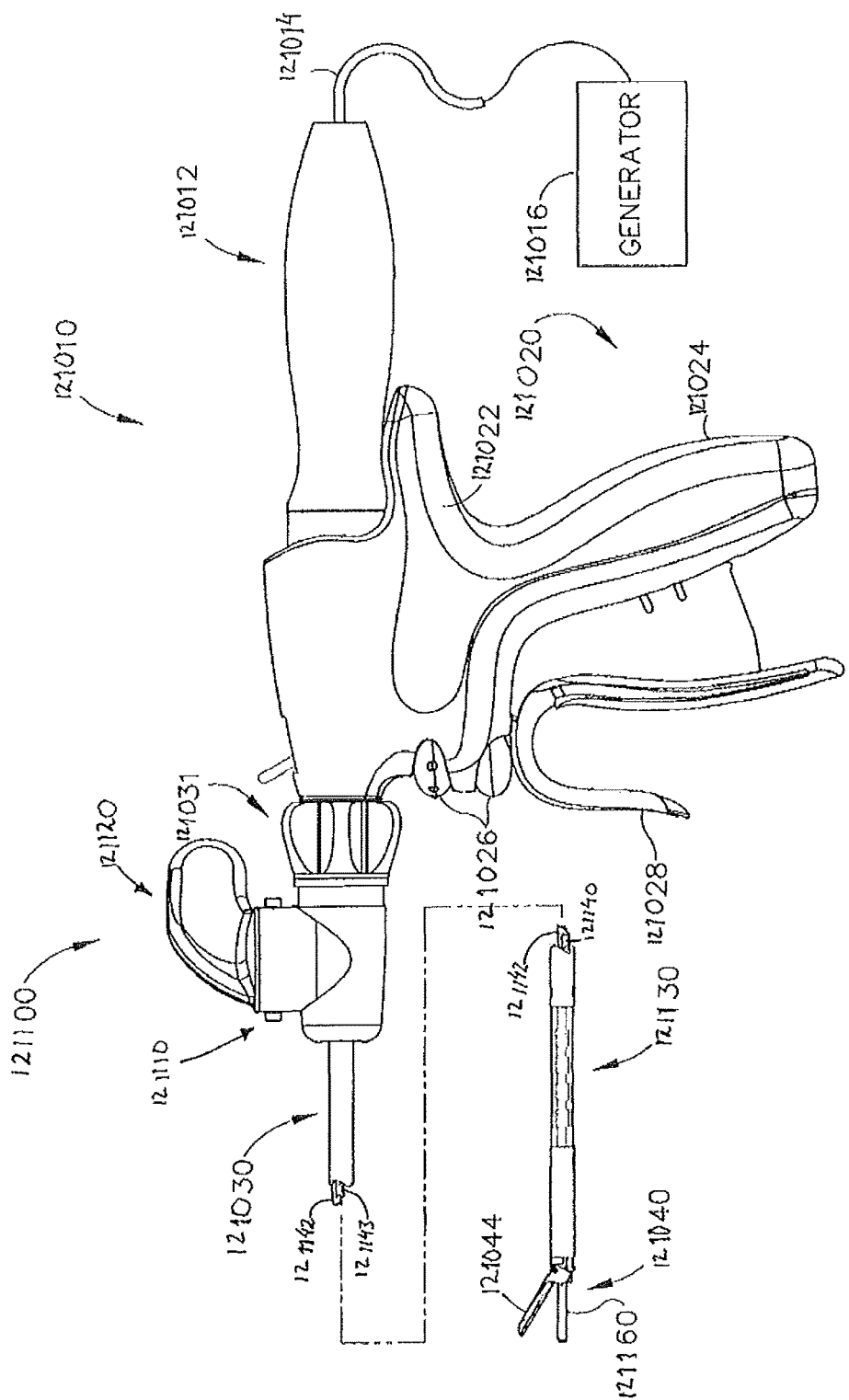
Figure 153:
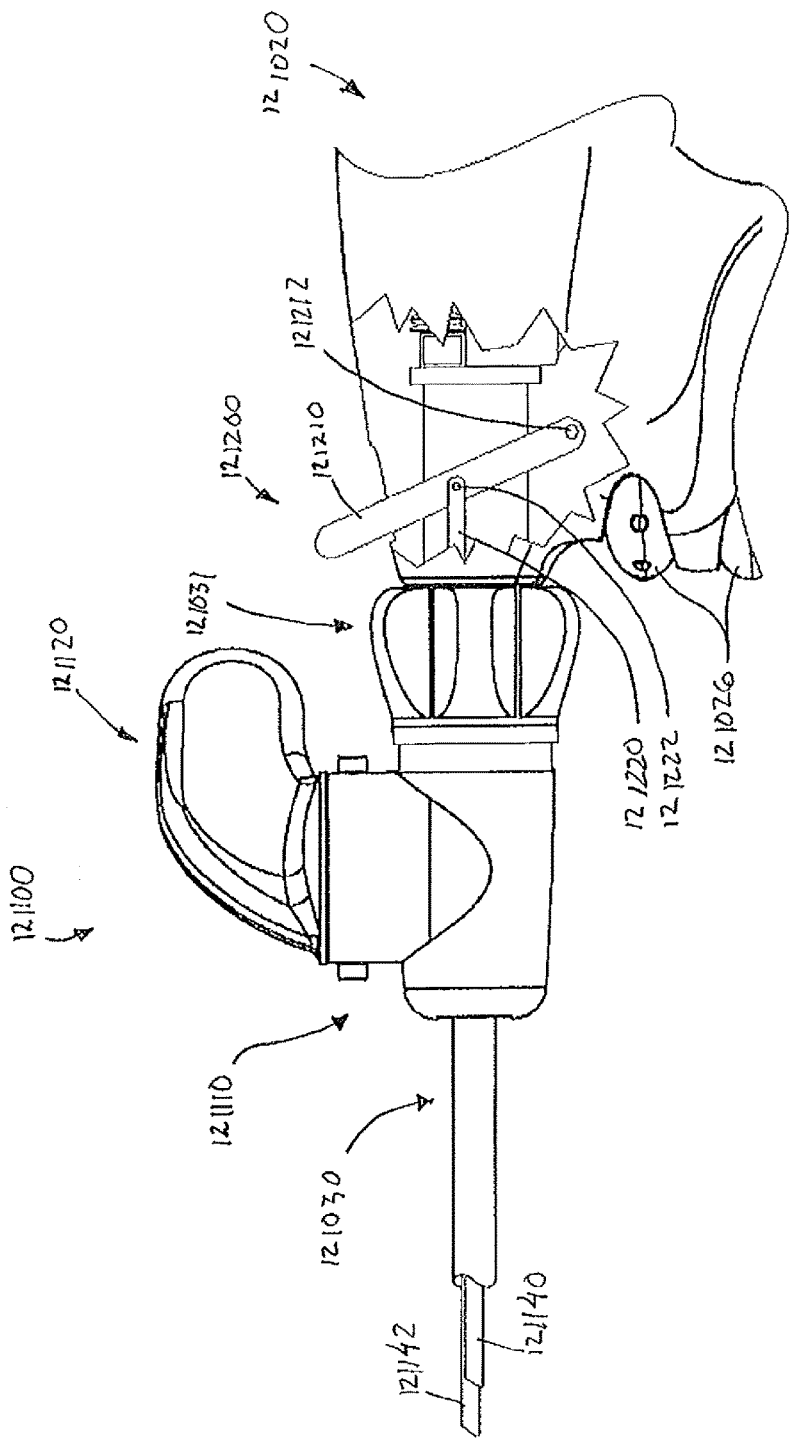
Figure 154:
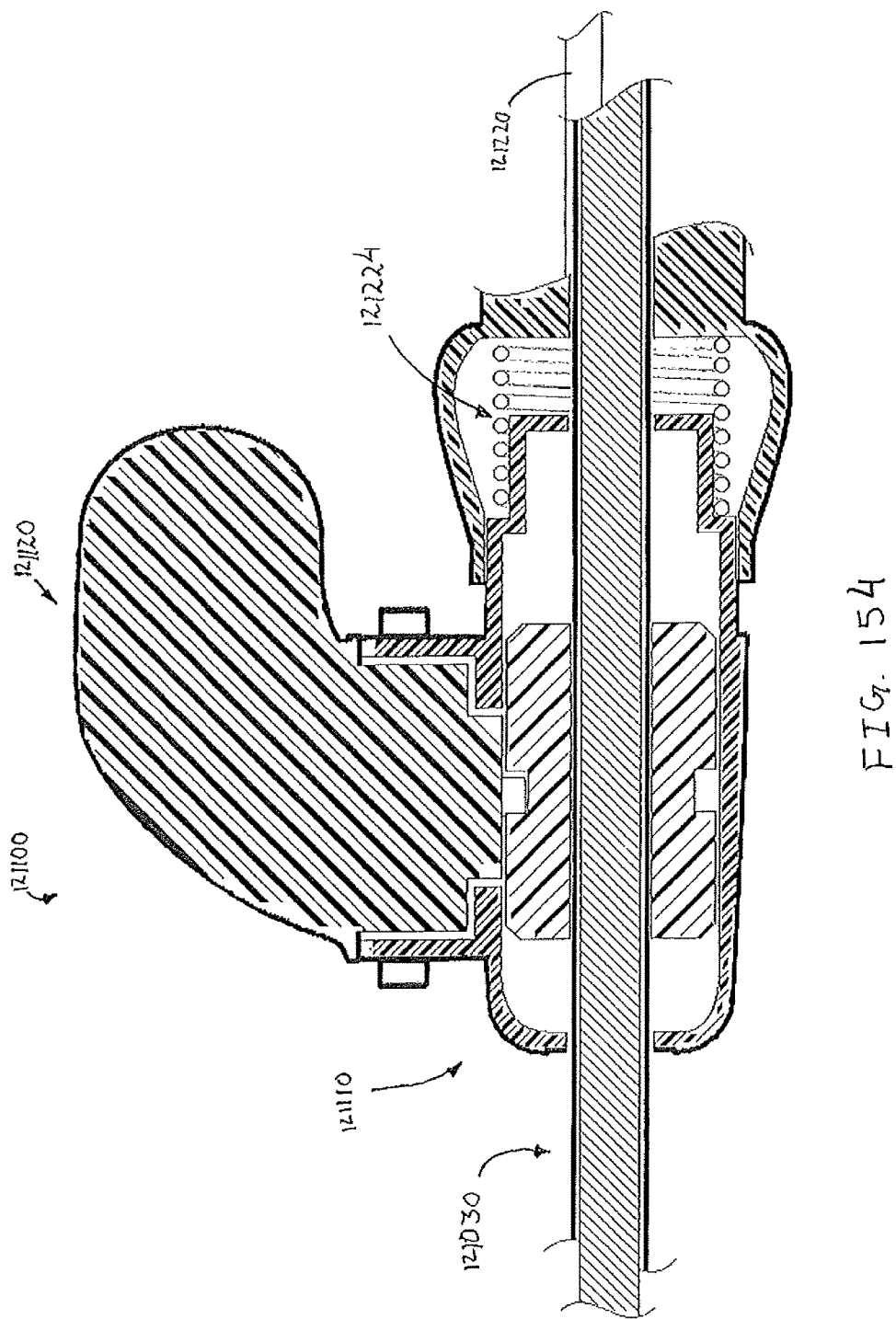
Figure 155:
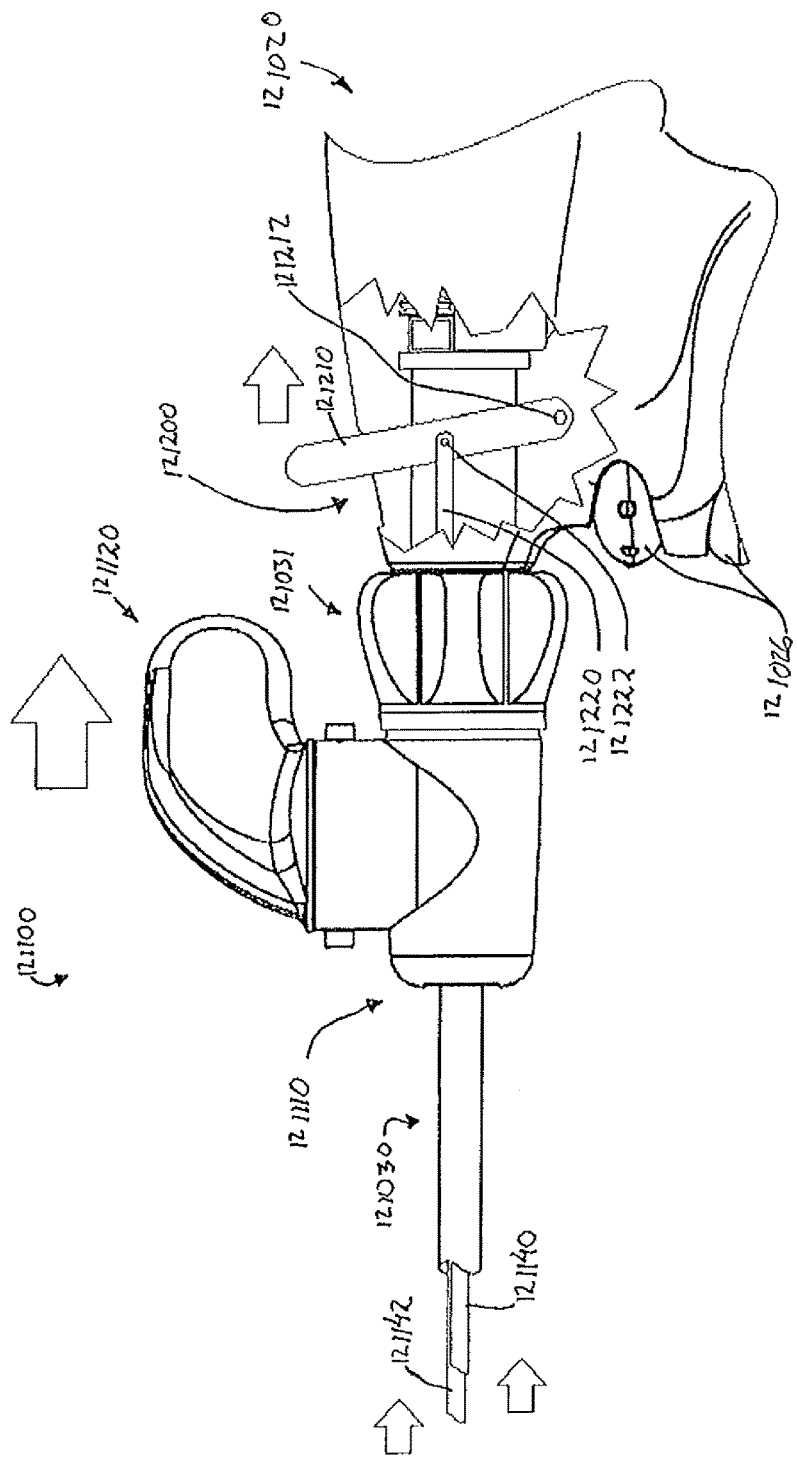
Figure 156:
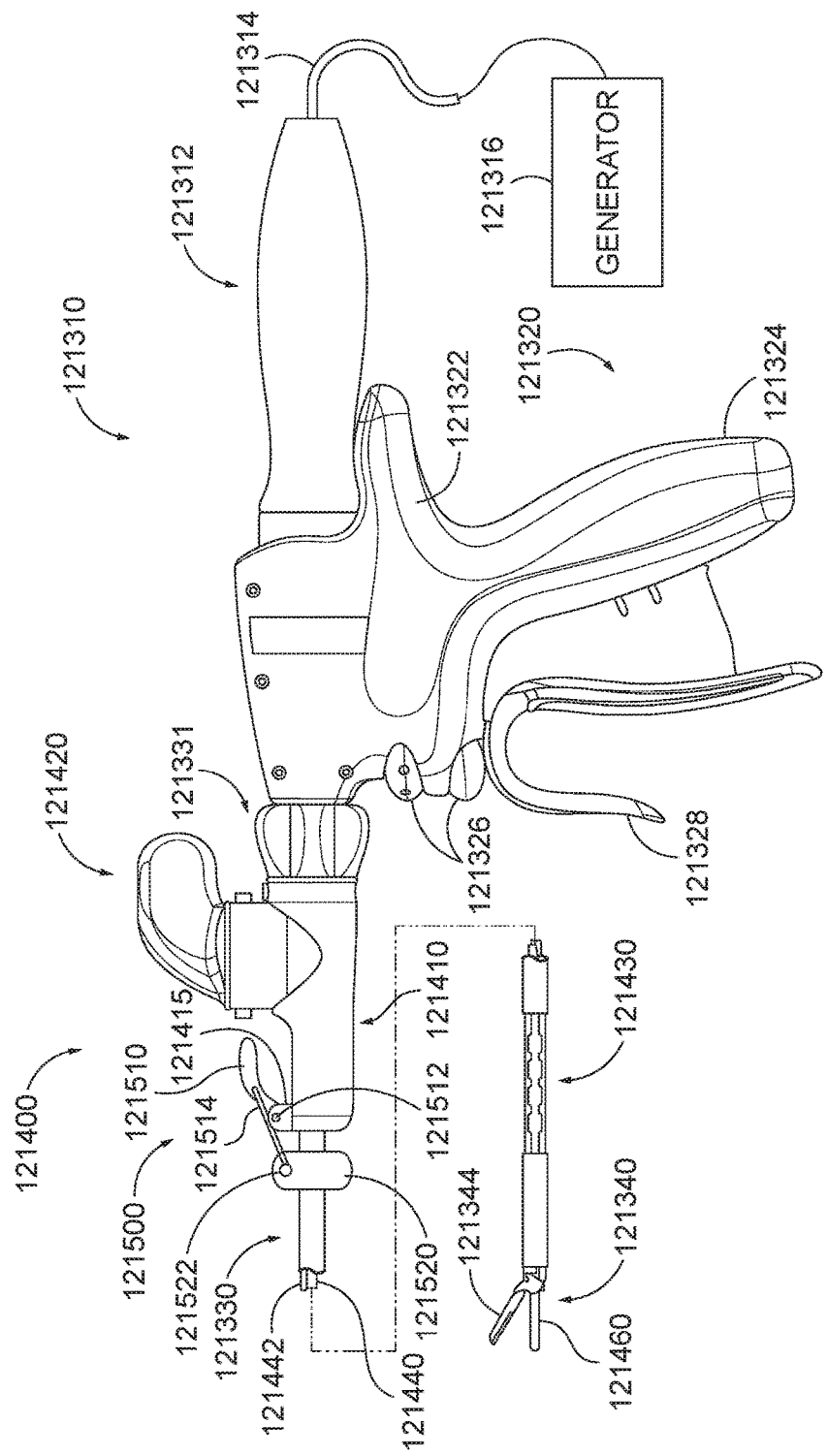
Figure 157:
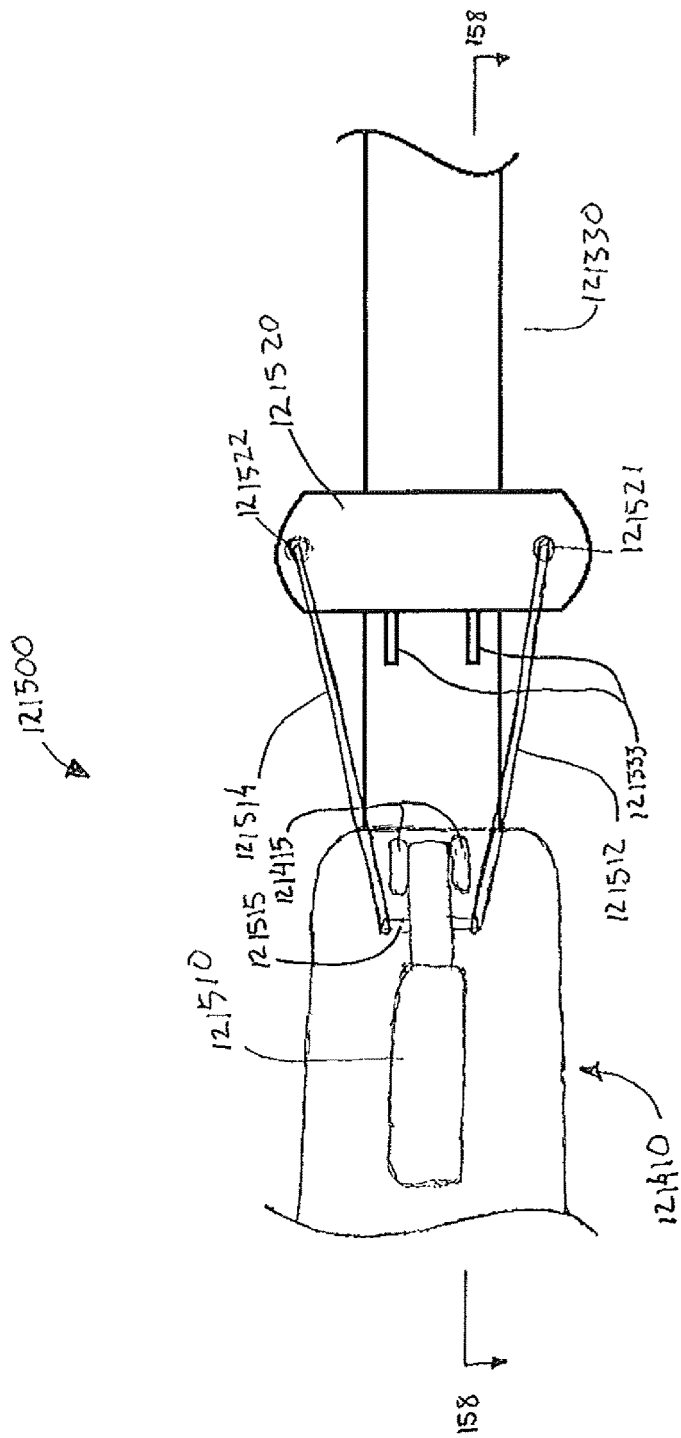
Figure 158:
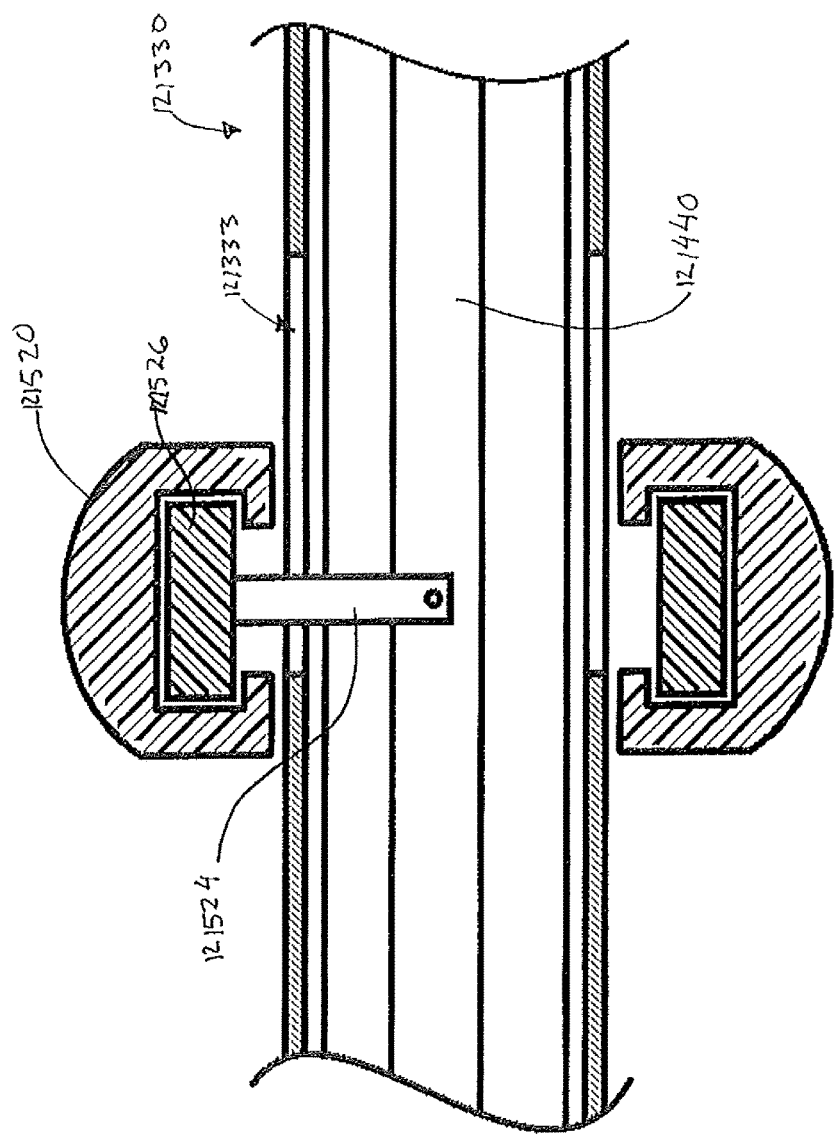
Figure 159:
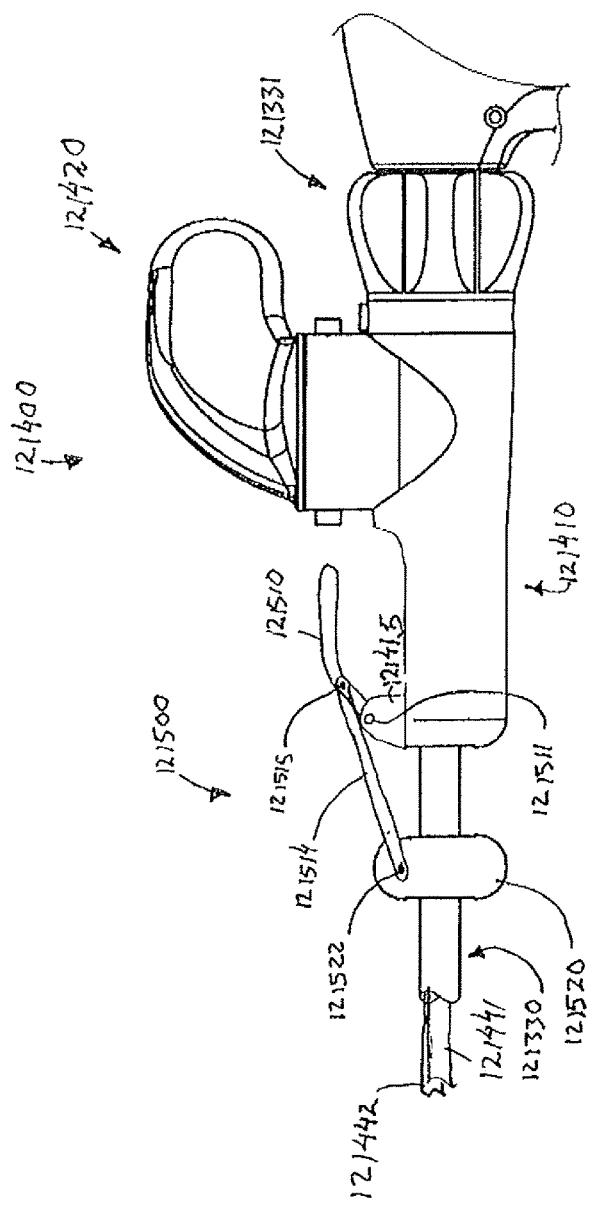
Figure 160:
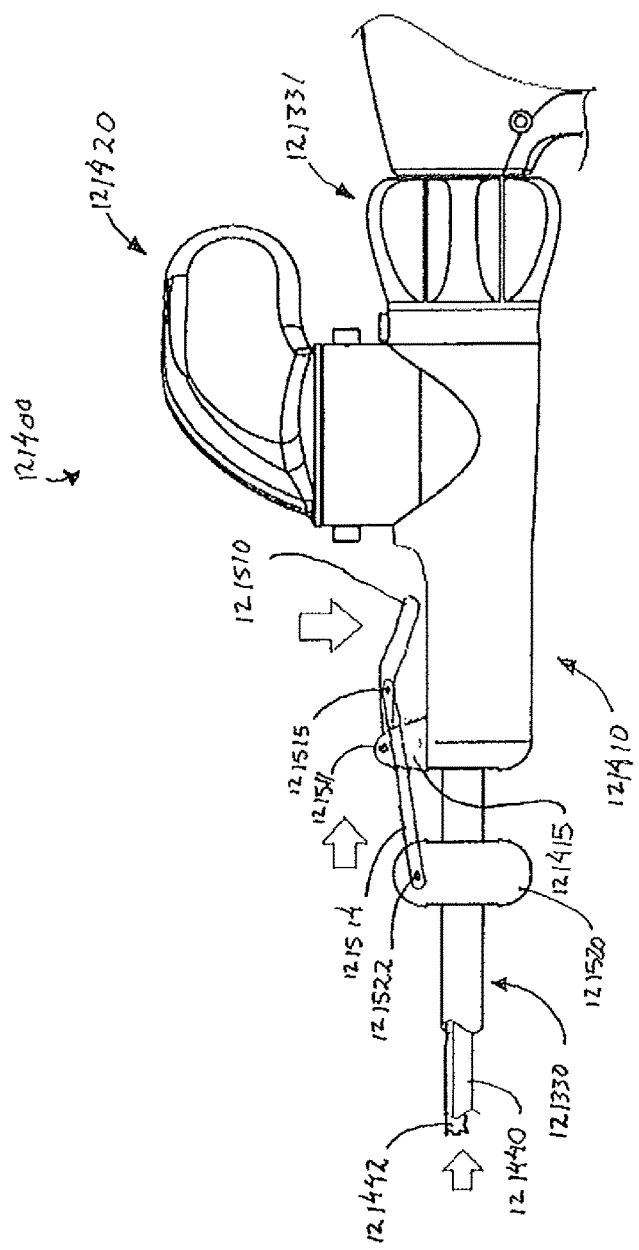
Figure 161:
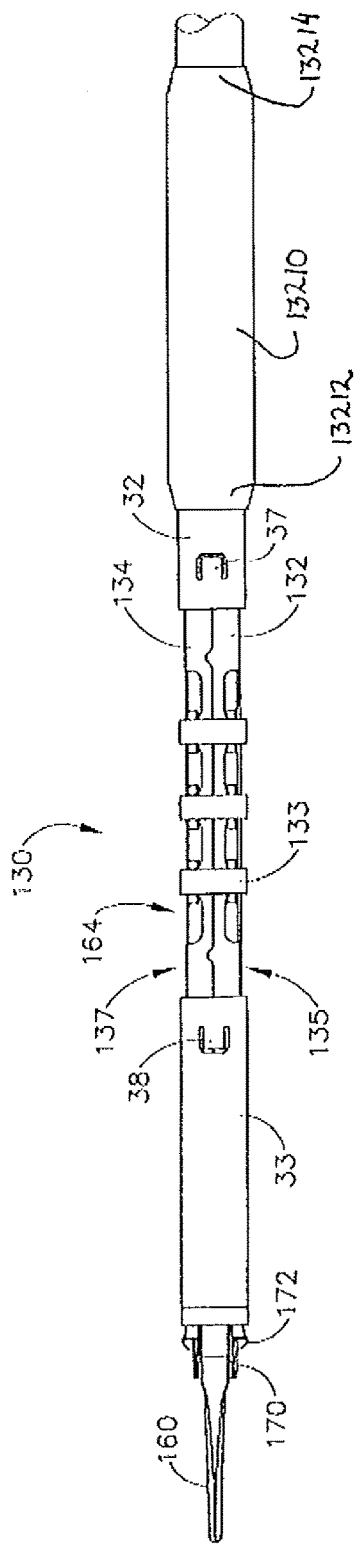
Figure 162:
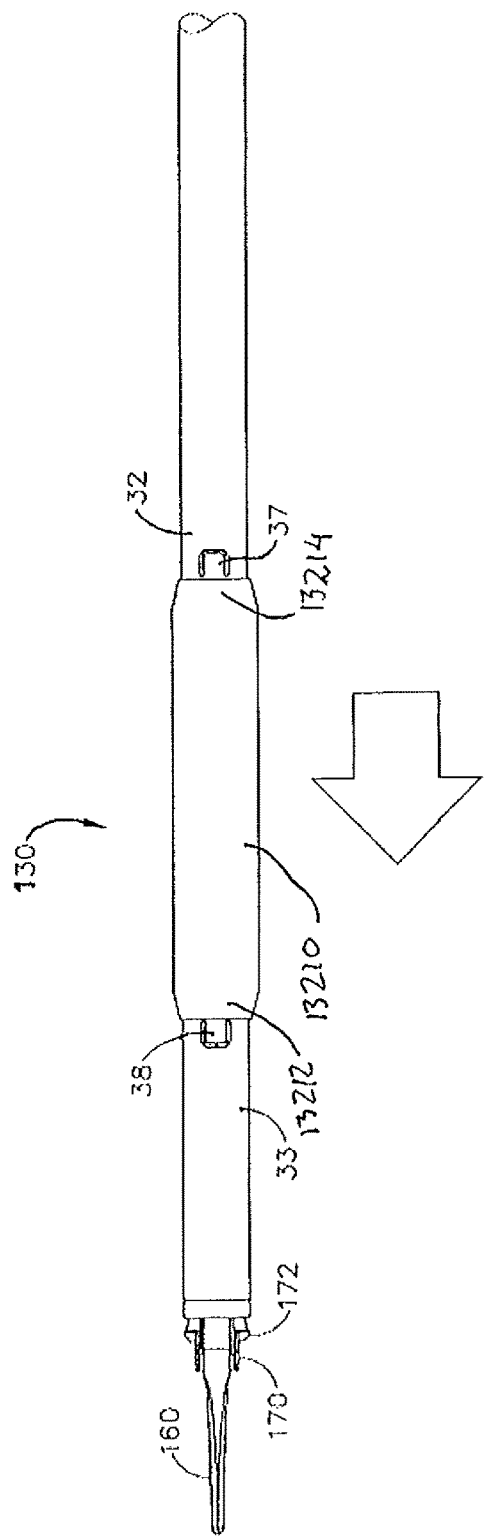
Figure 163:
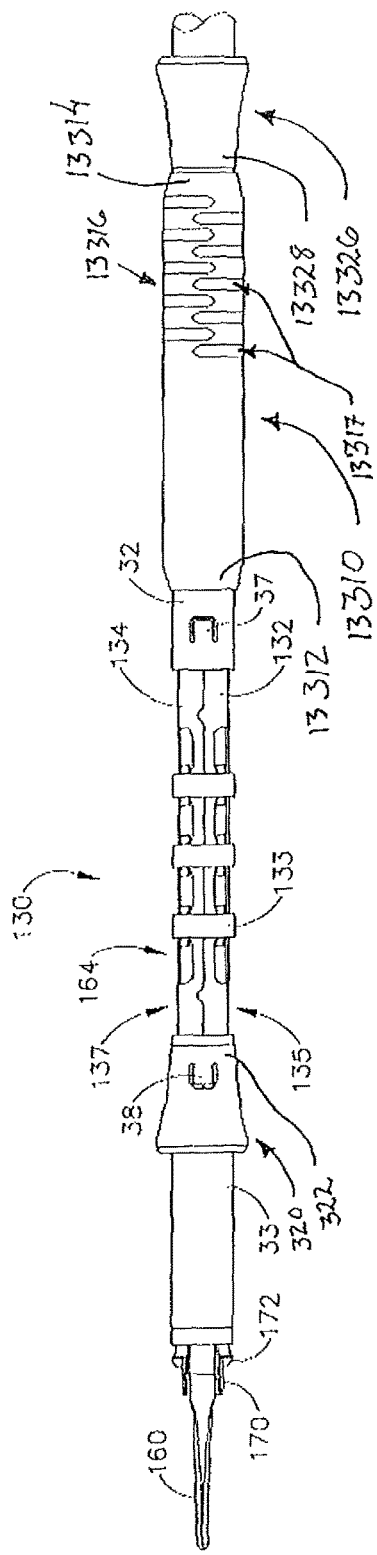
Figure 164:
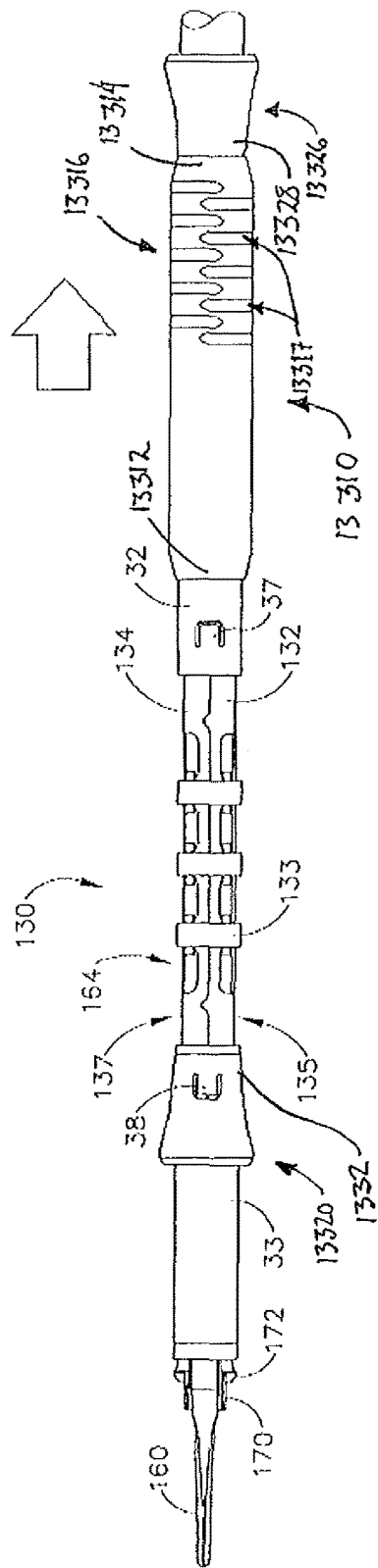
Figure 165:
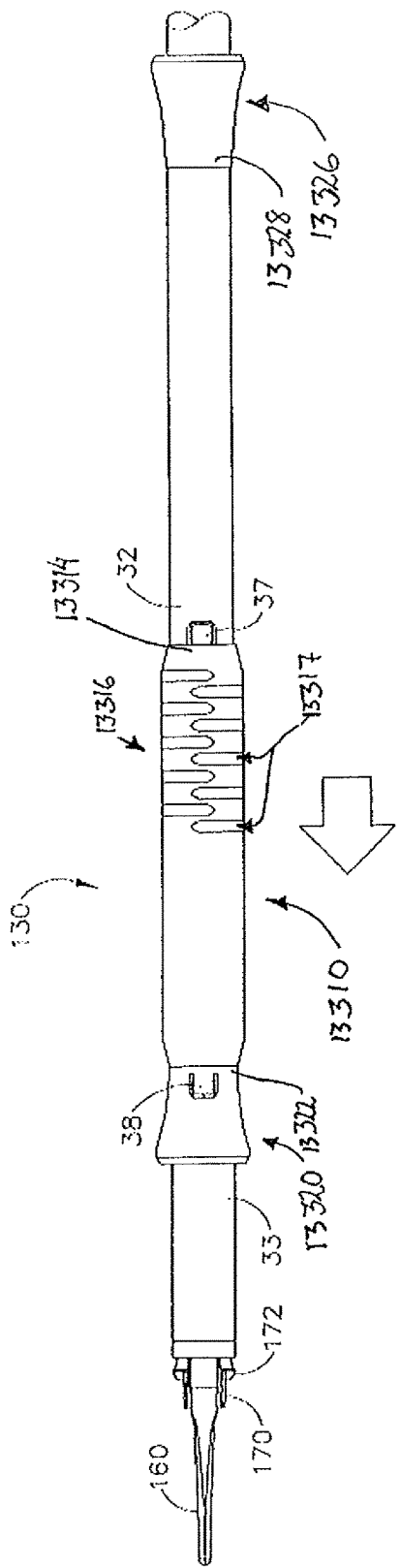
Figure 166:
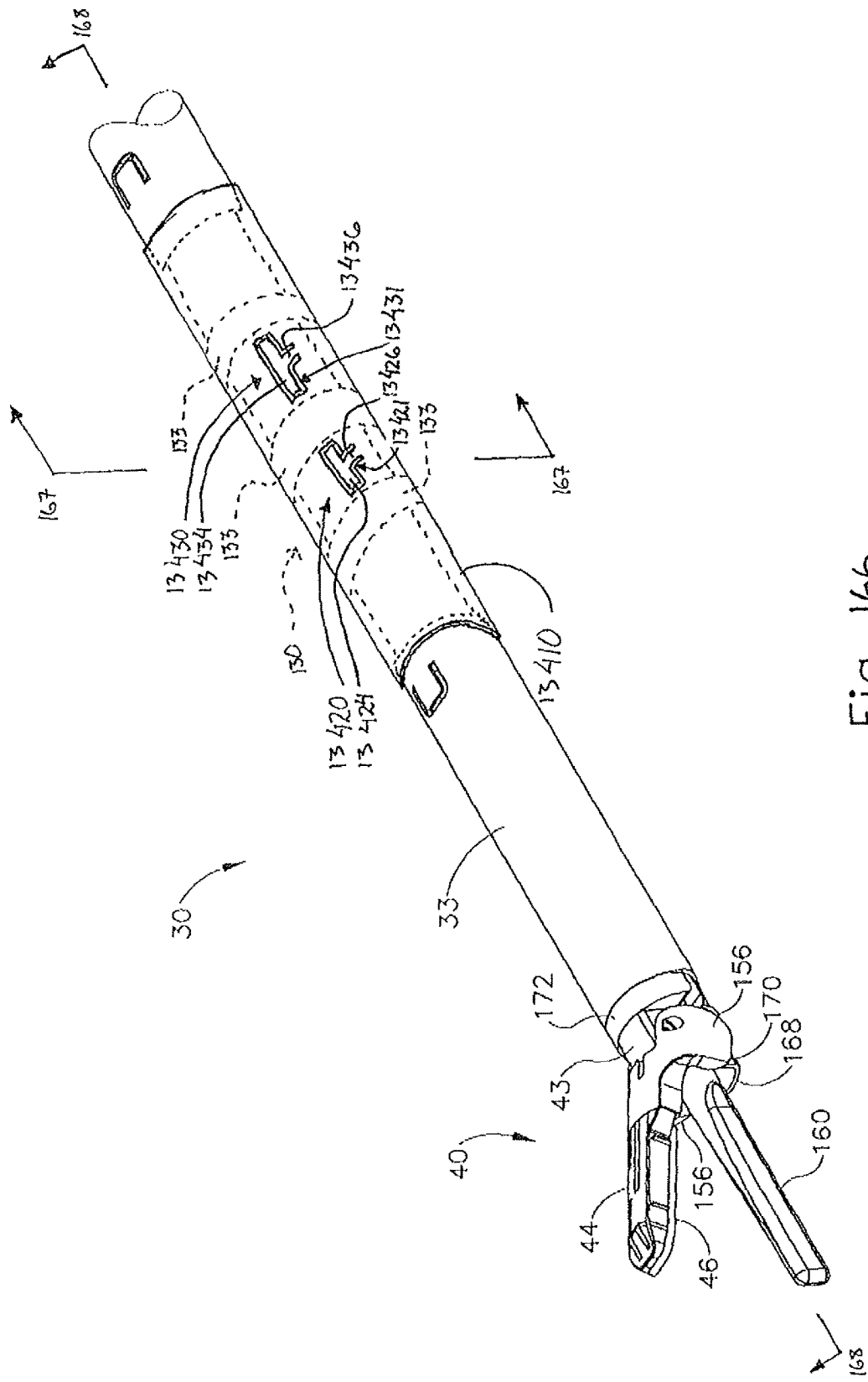
Figure 167:
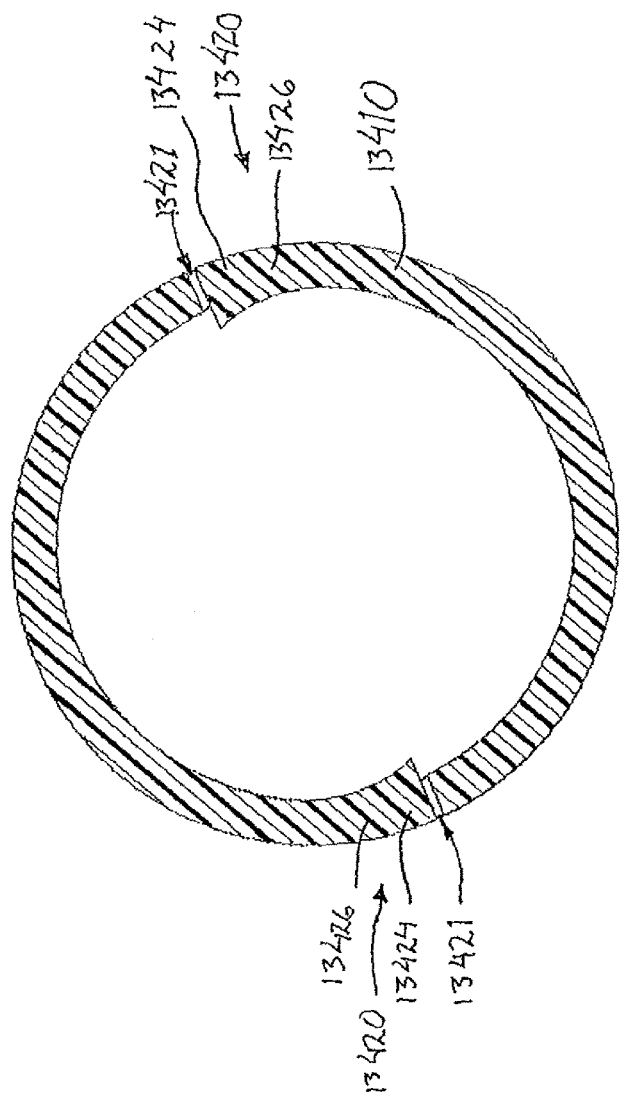
Figure 168:
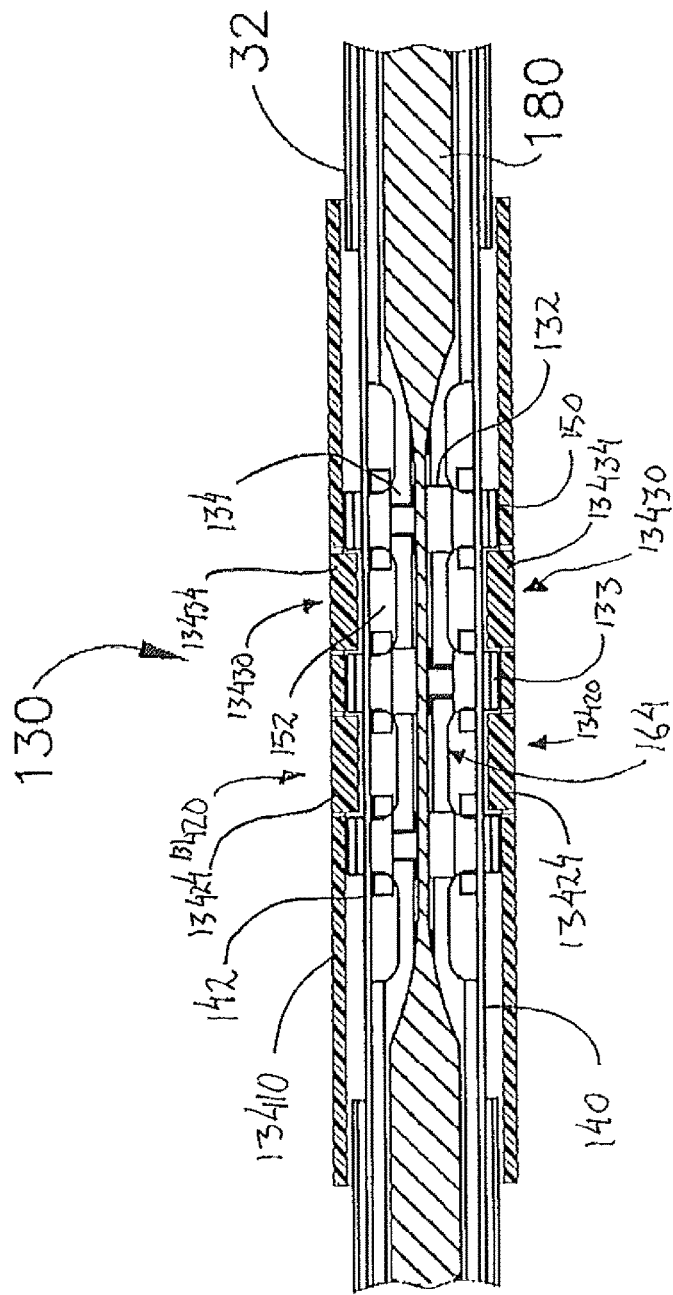
Figure 169:
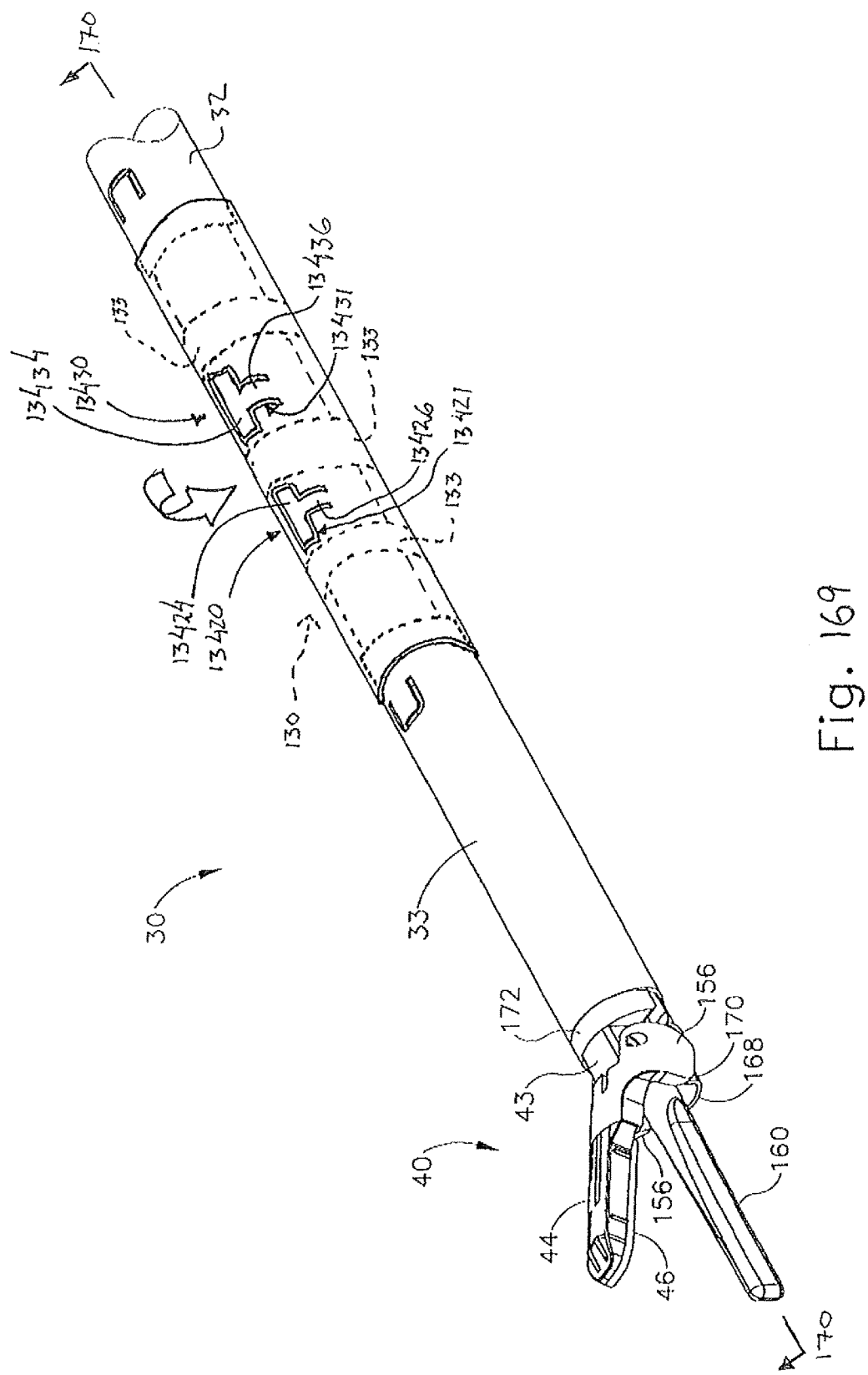
Figure 170:
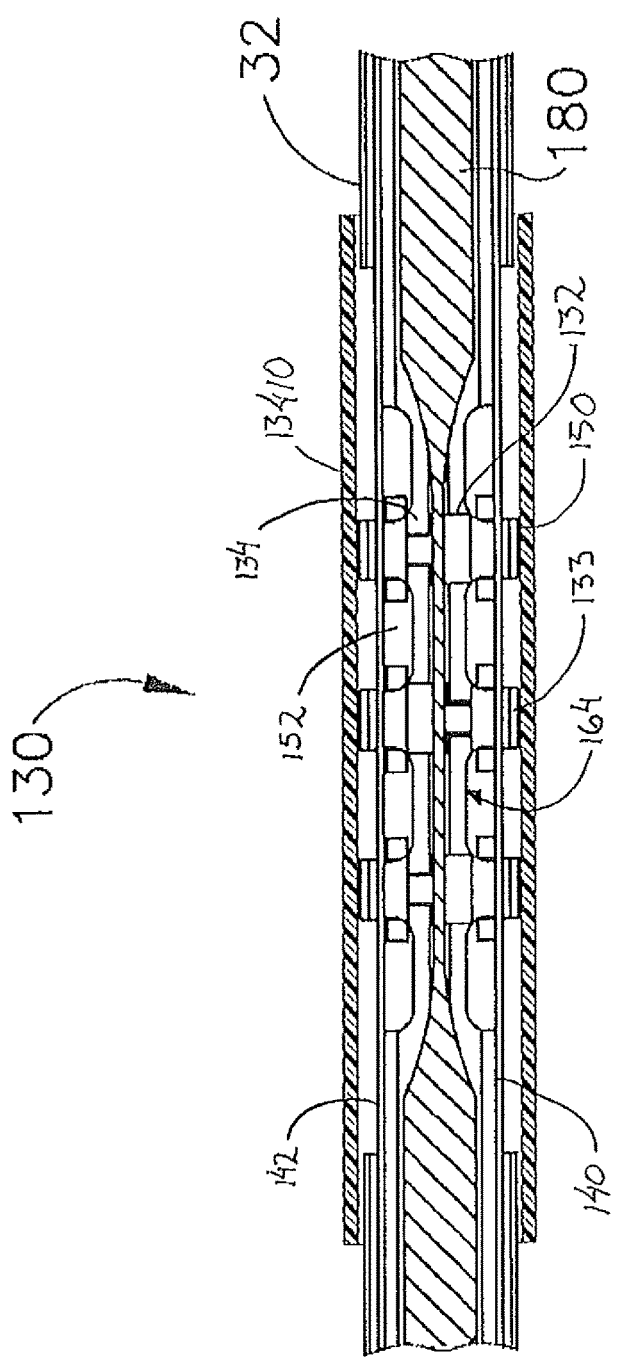
Figure 171:
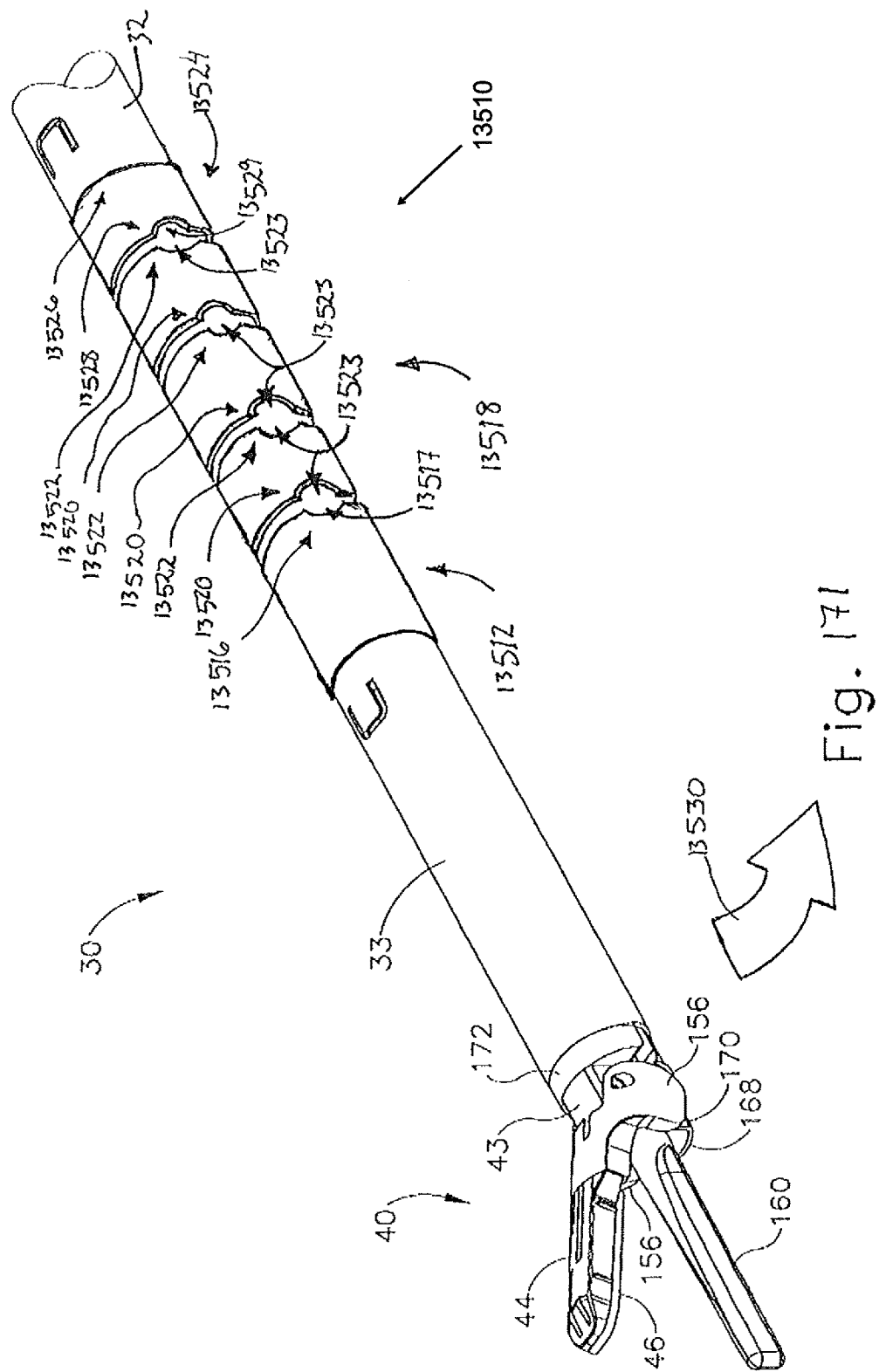
Figure 172:
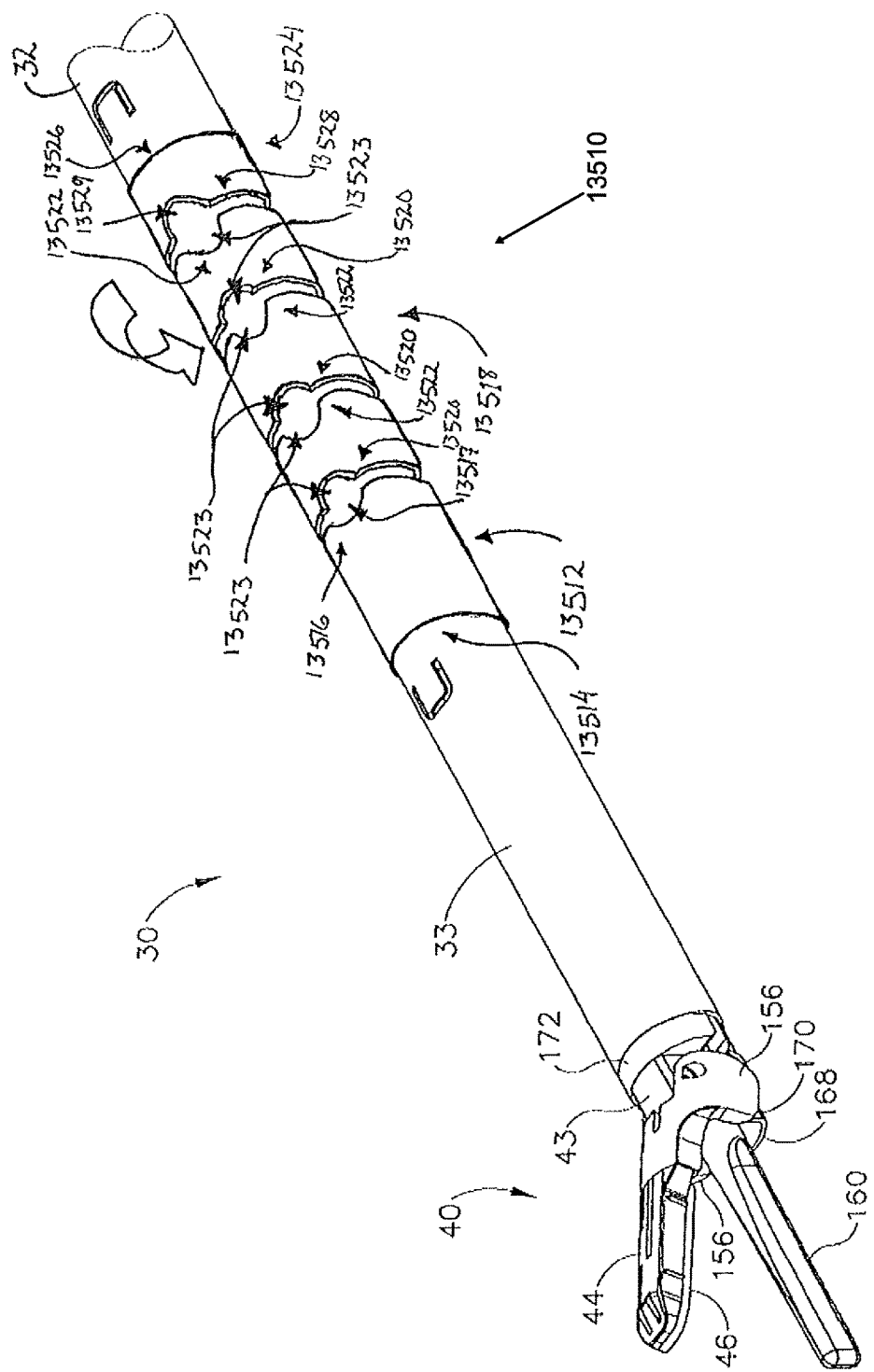
Figure 173:
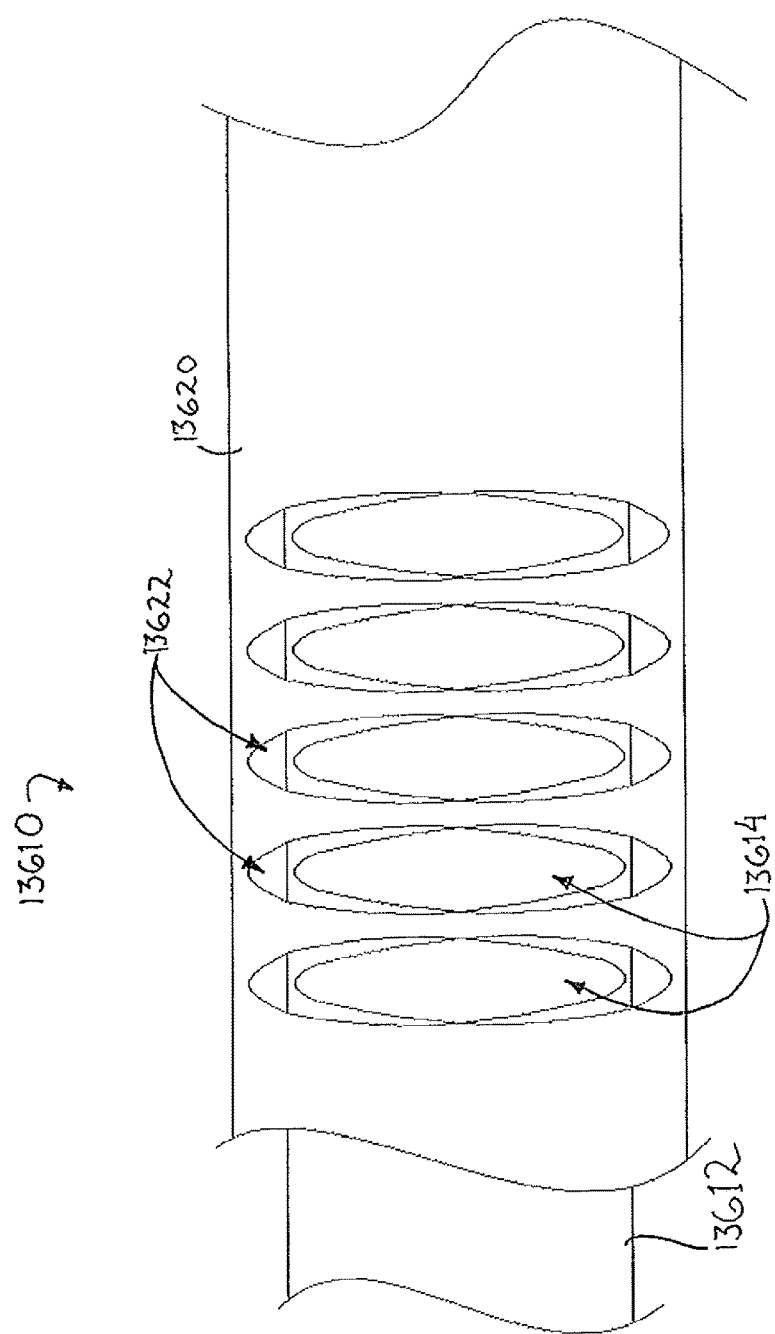
Figure 174:
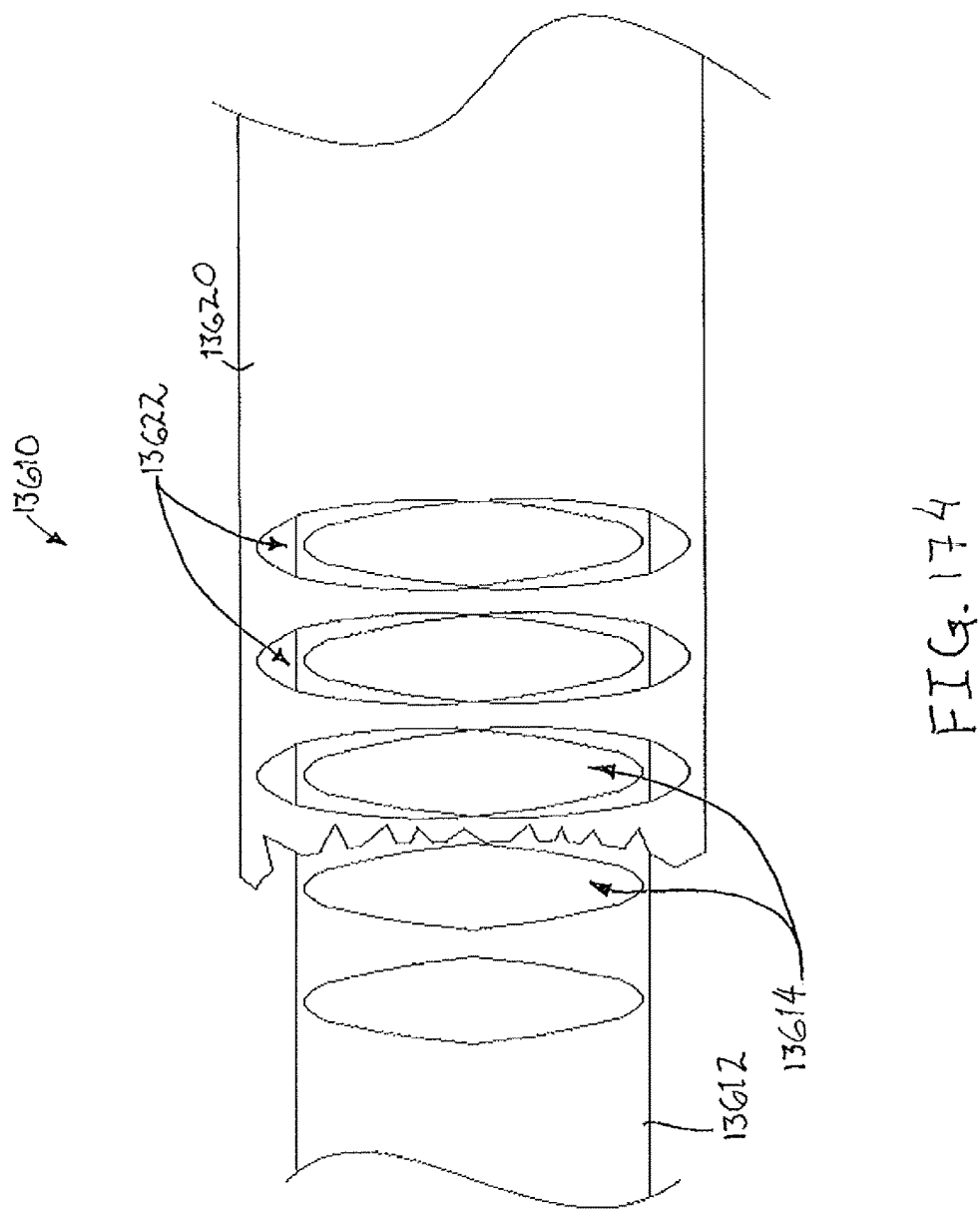
Figure 175:
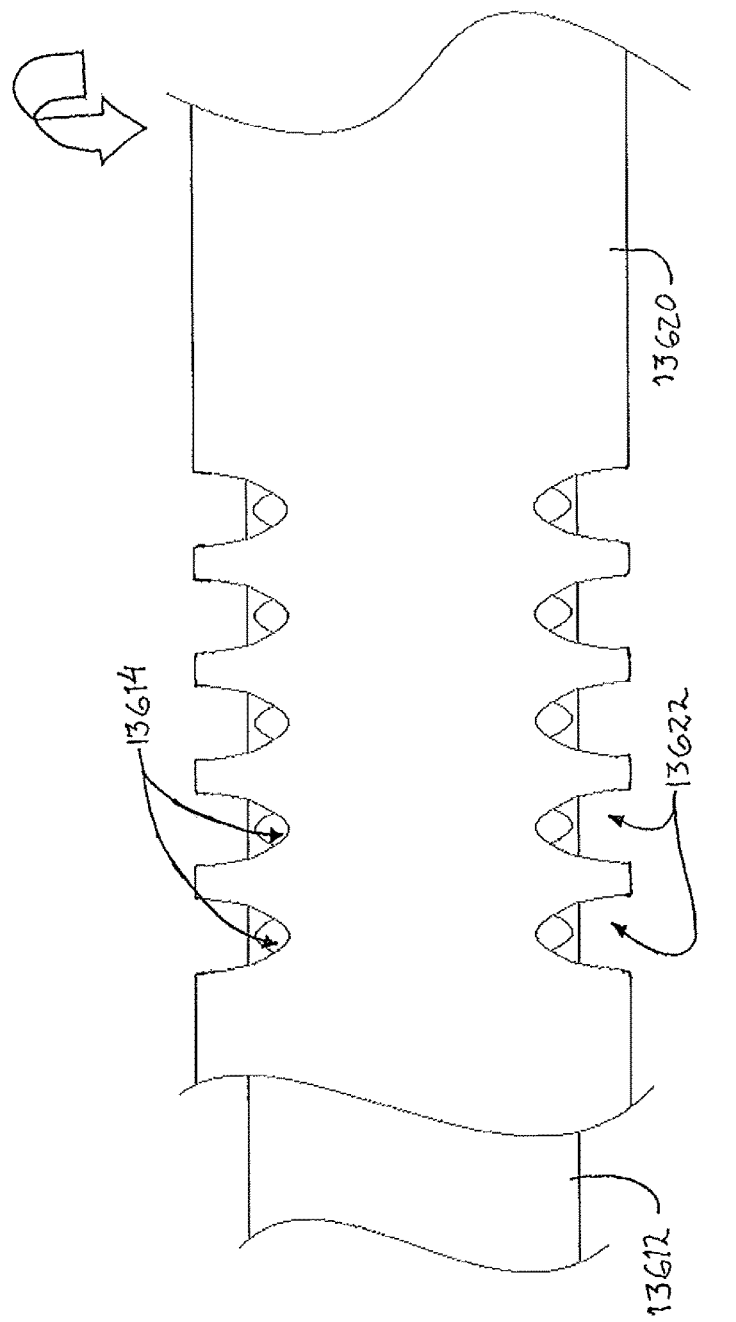
Figure 176:
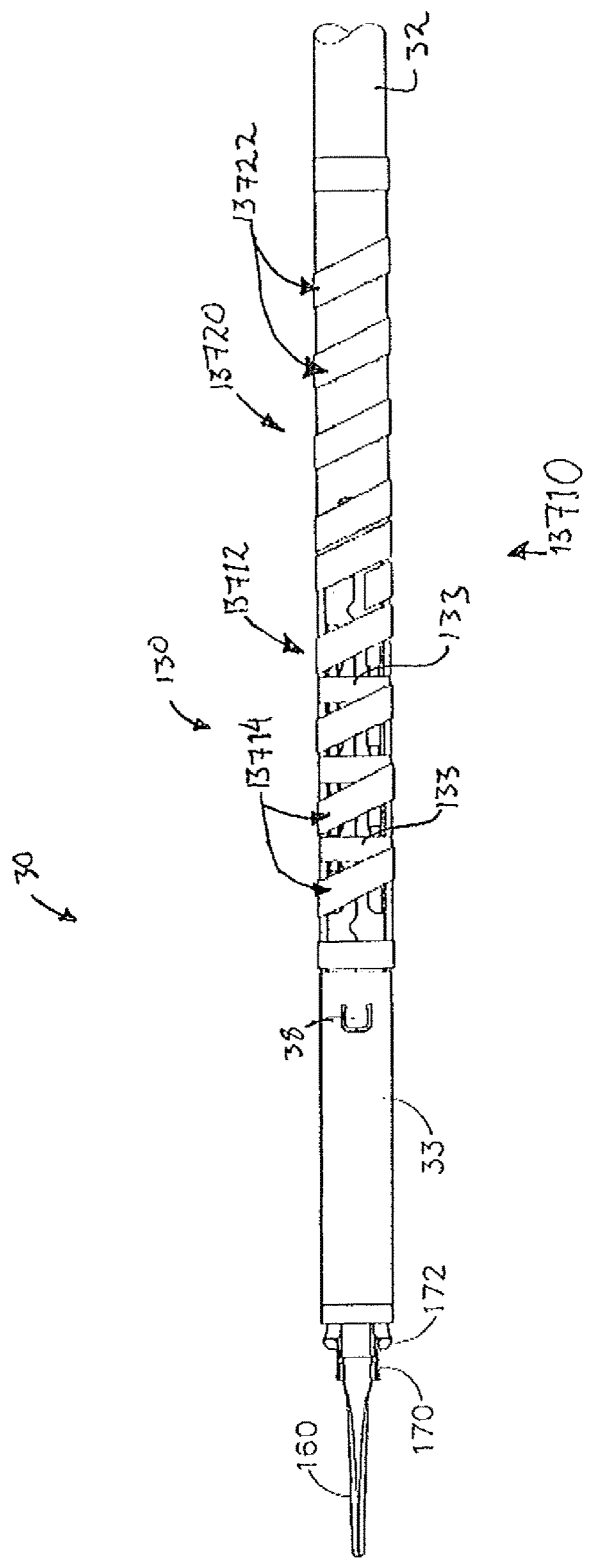
Figure 177:
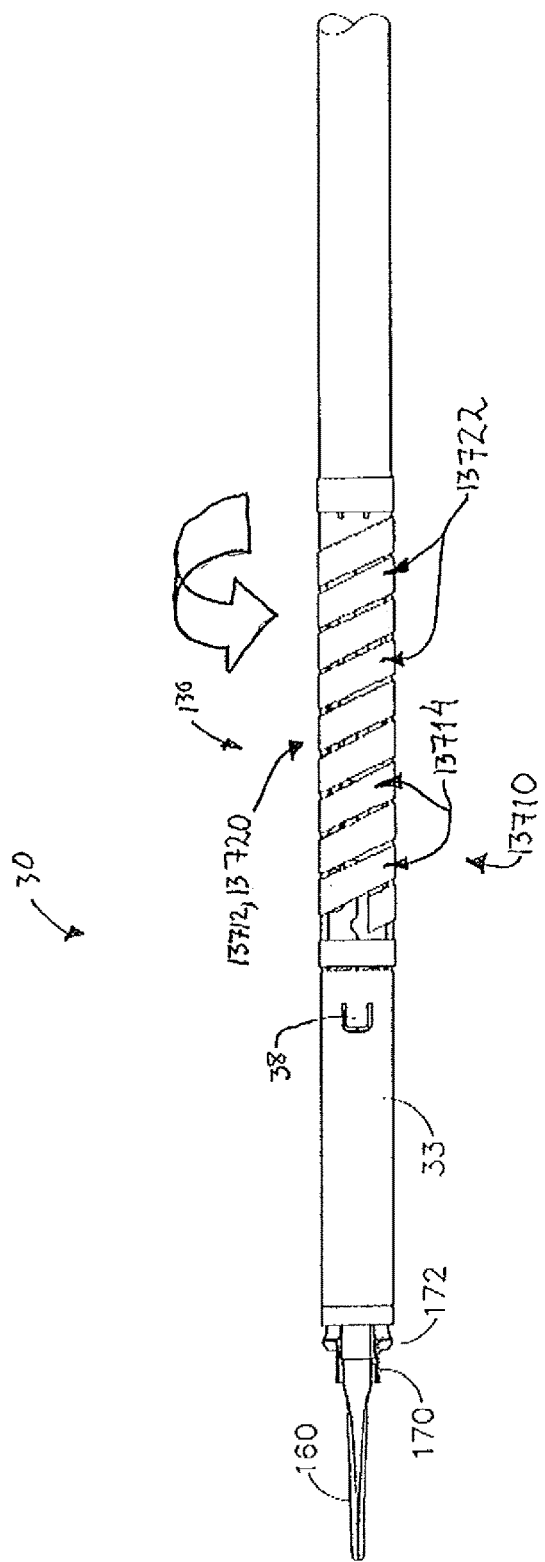
Figure 178:
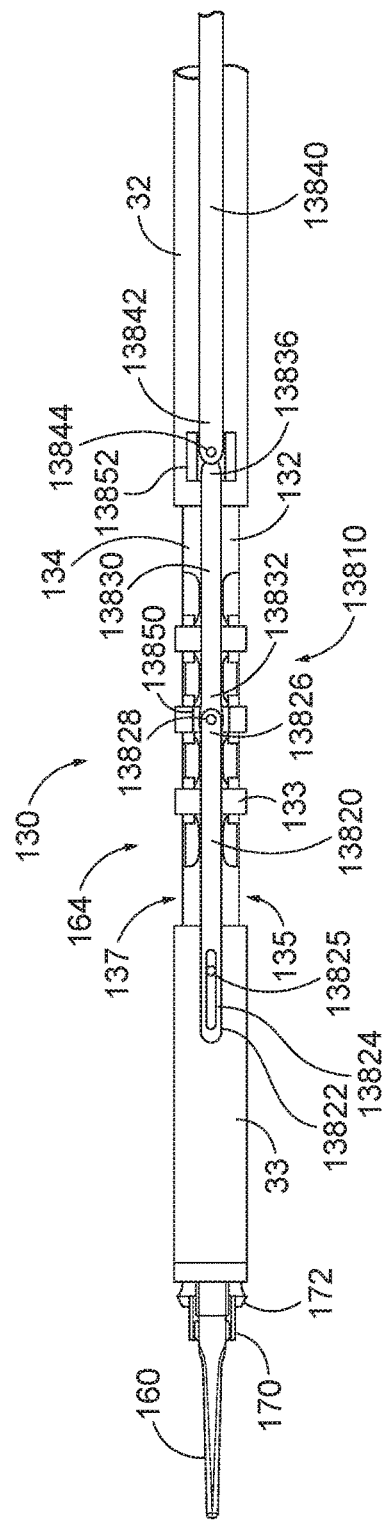
Figure 179:
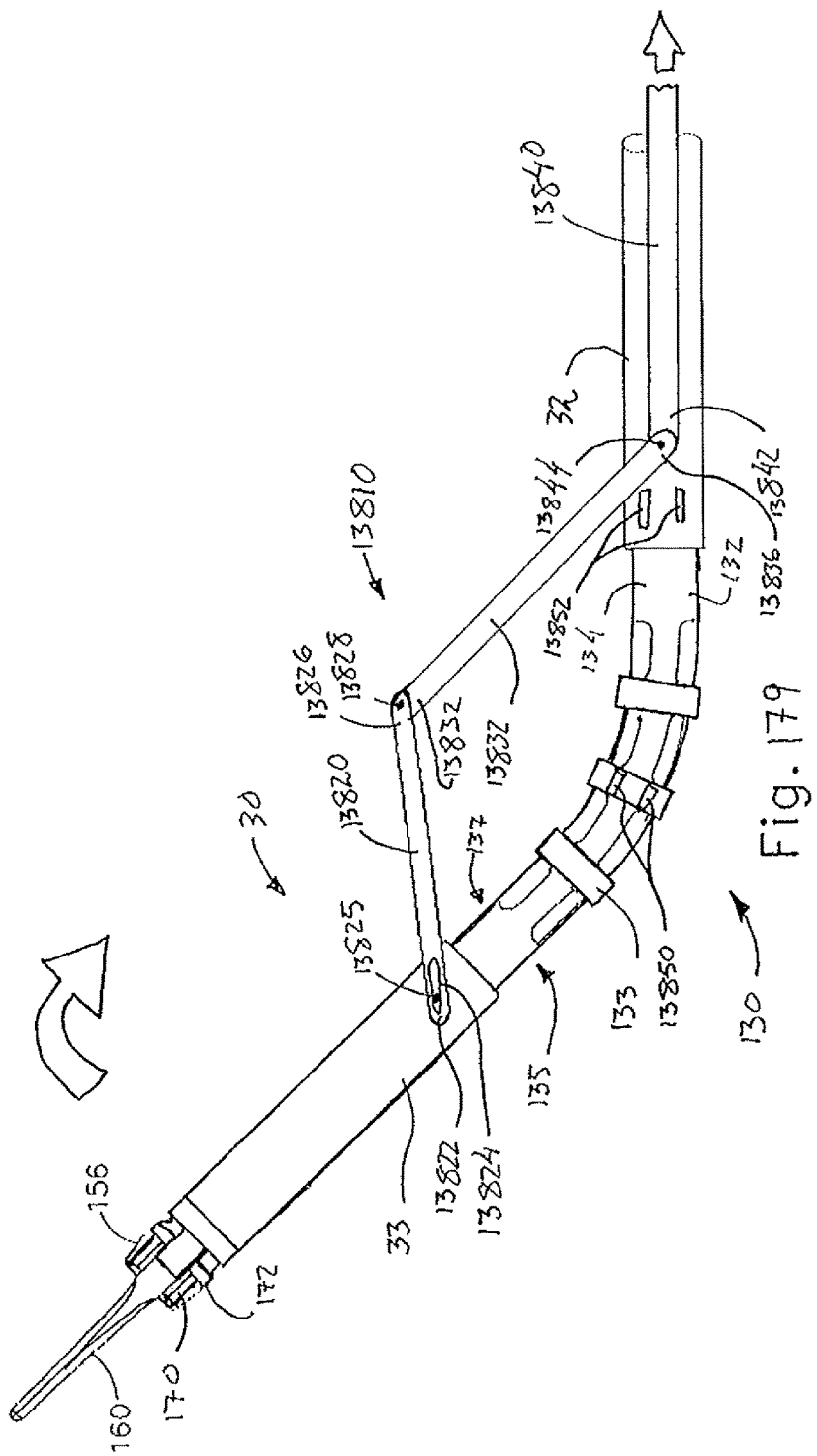
Figure 180:
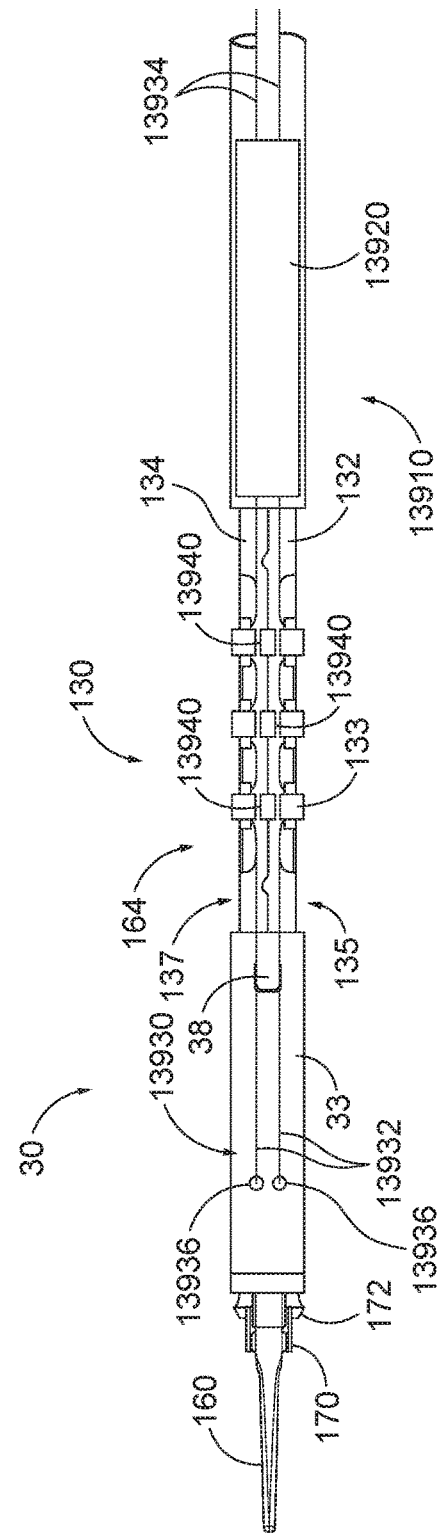
Figure 181:
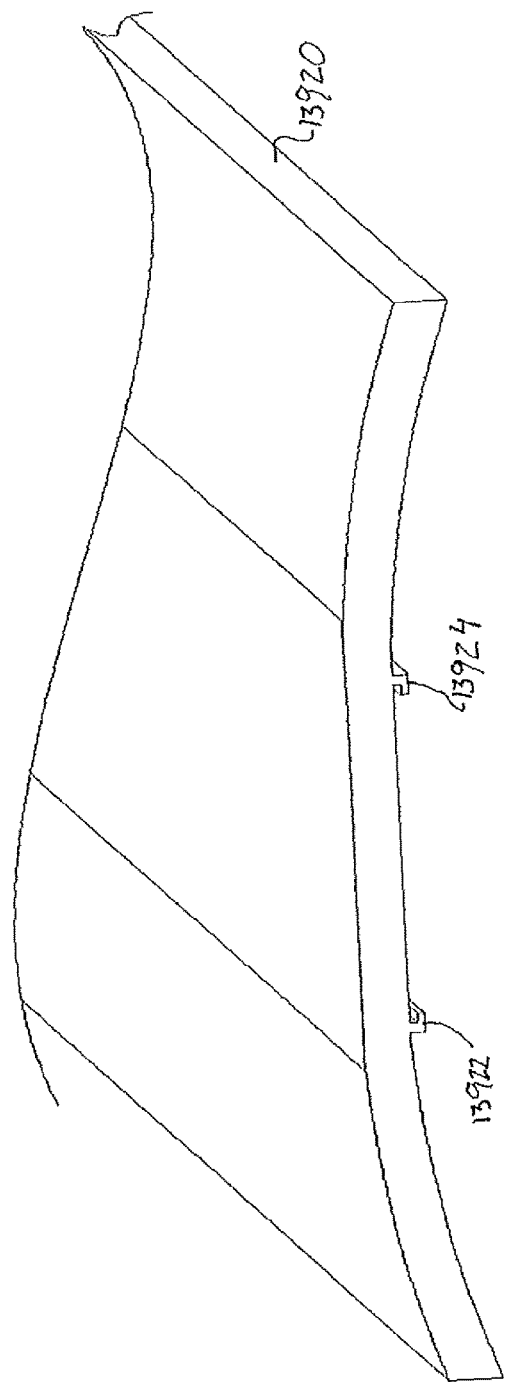
Figure 182:
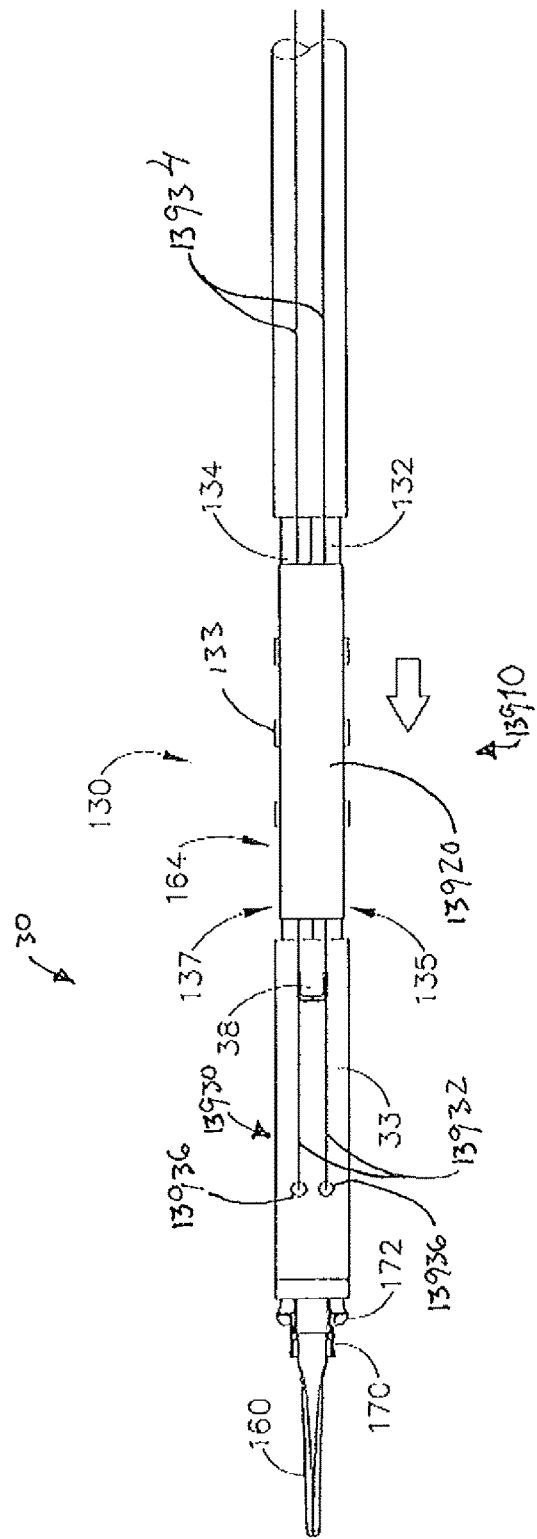
Figure 183:
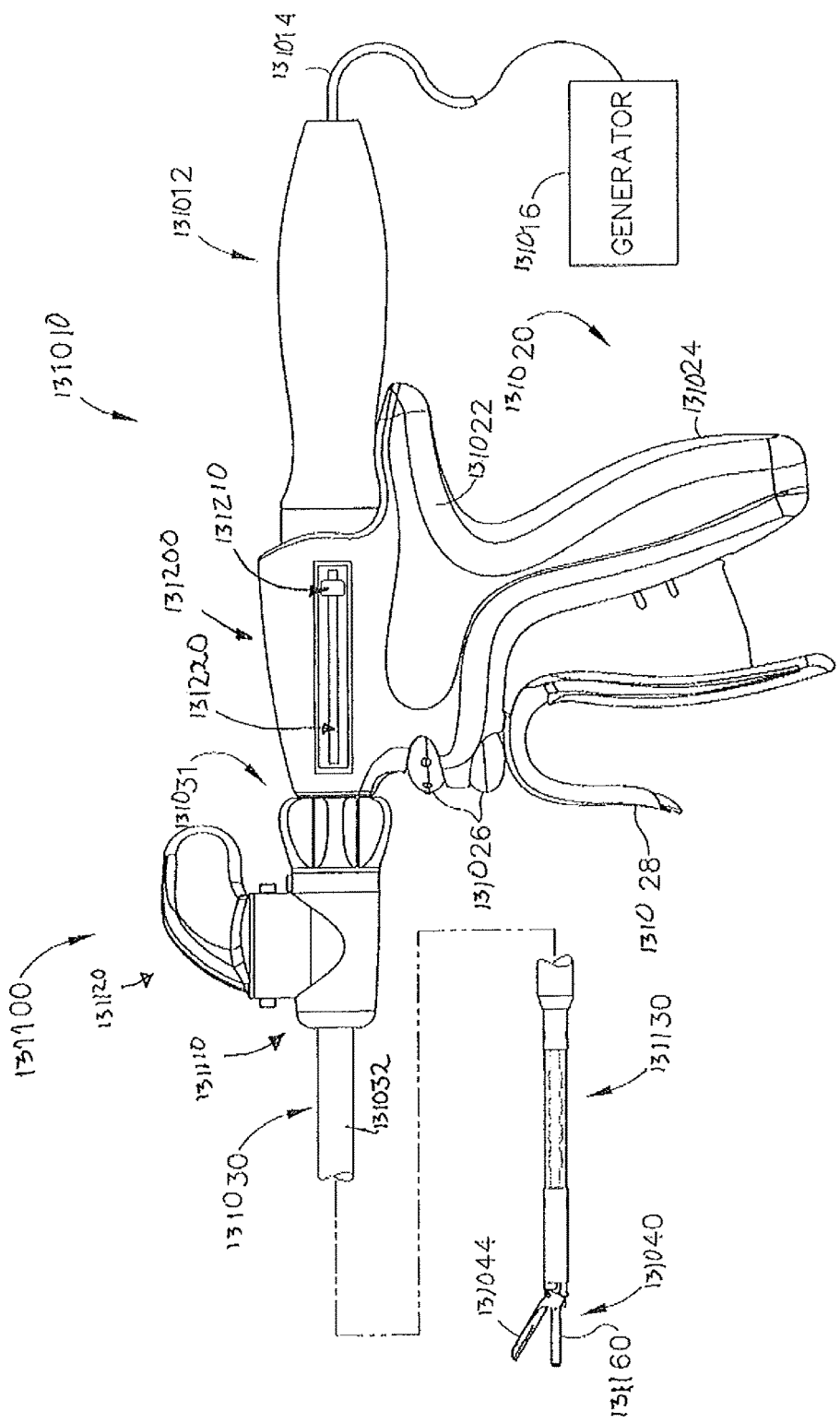
Figure 186:
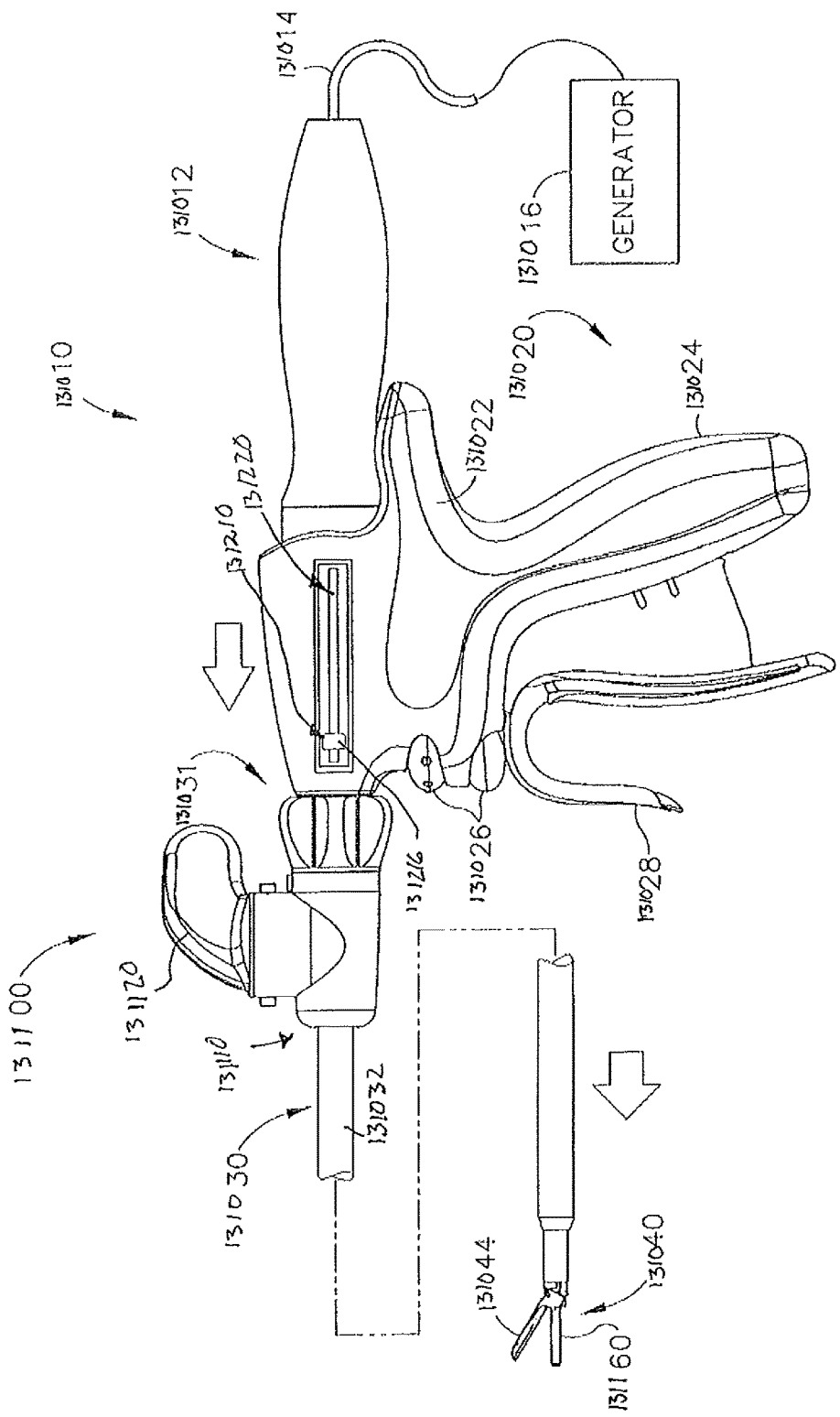
Figure 187:
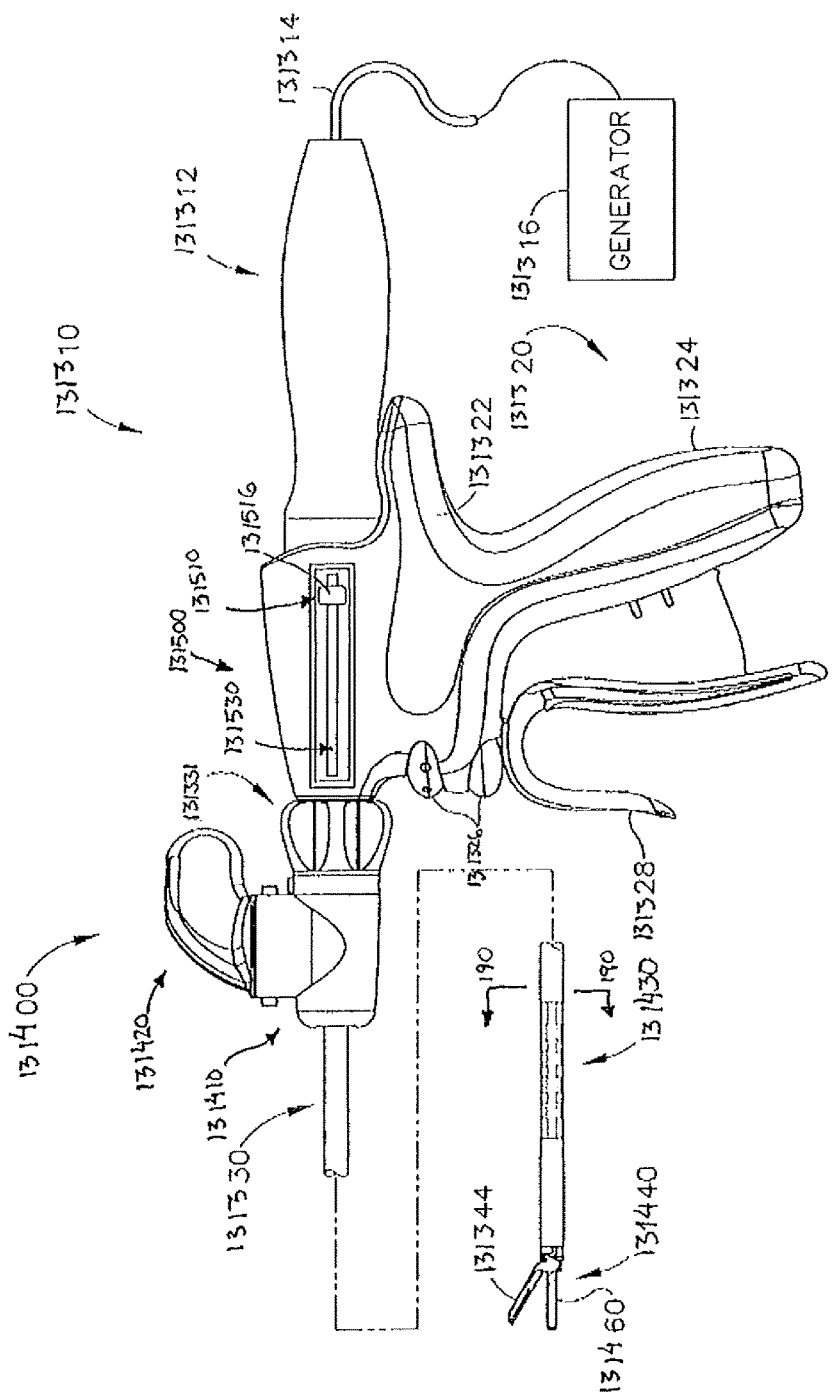
Figure 188:
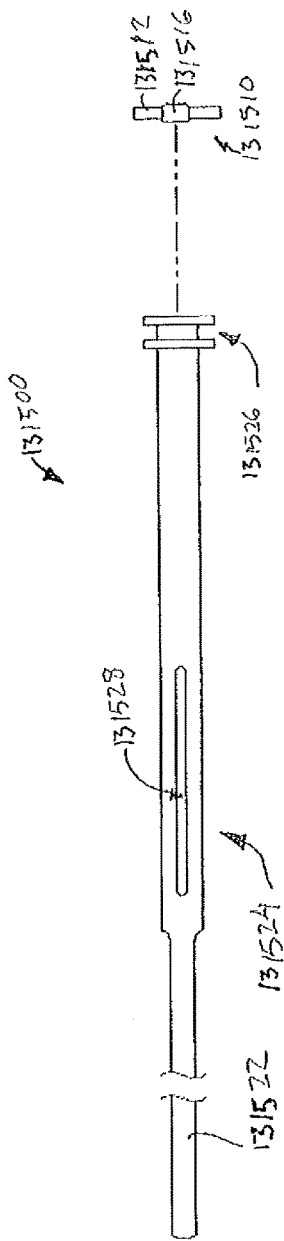
Figure 189:
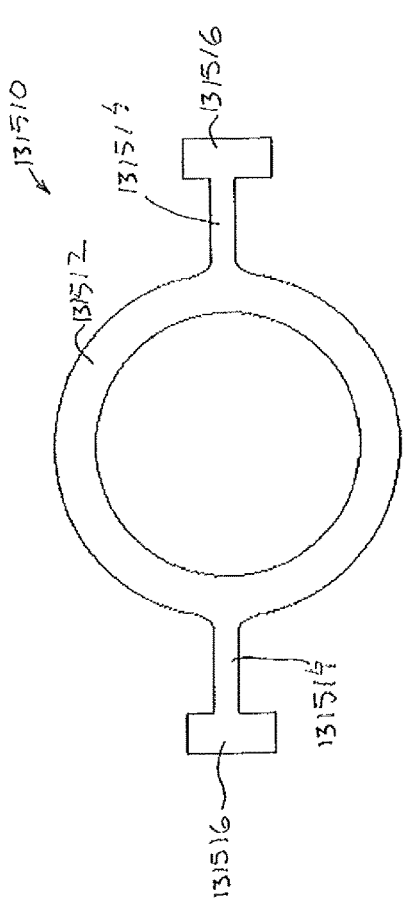
Figure 190:
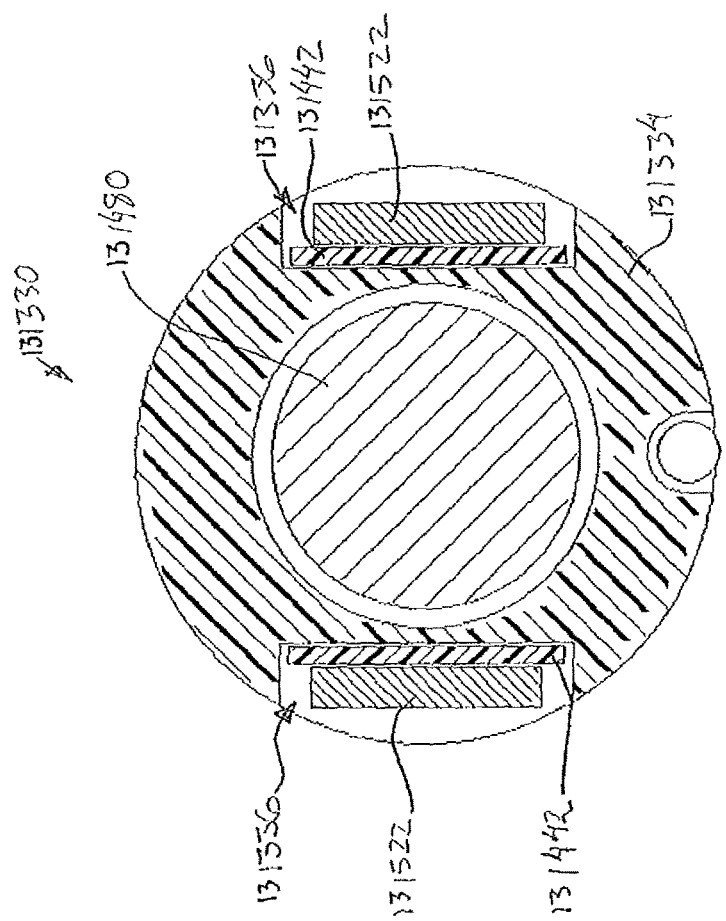
Figure 193:
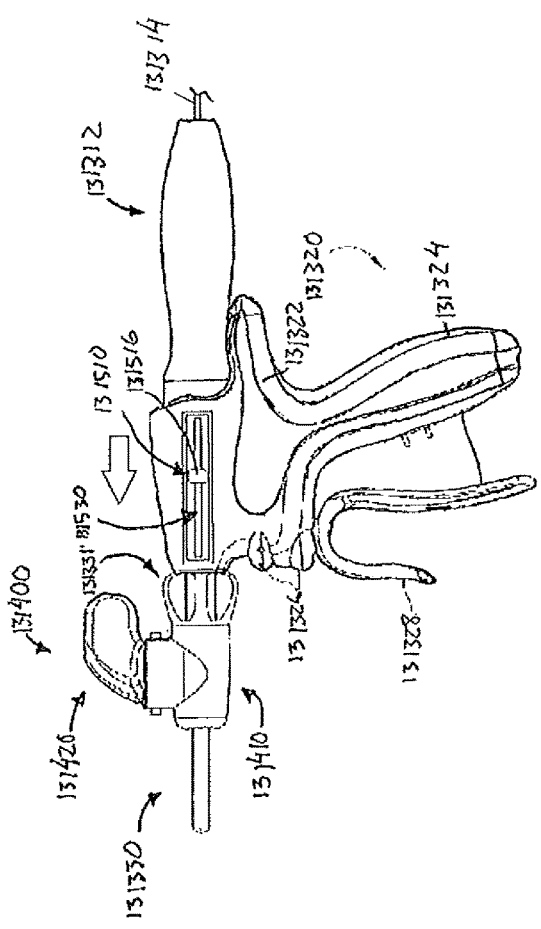
Figure 194:
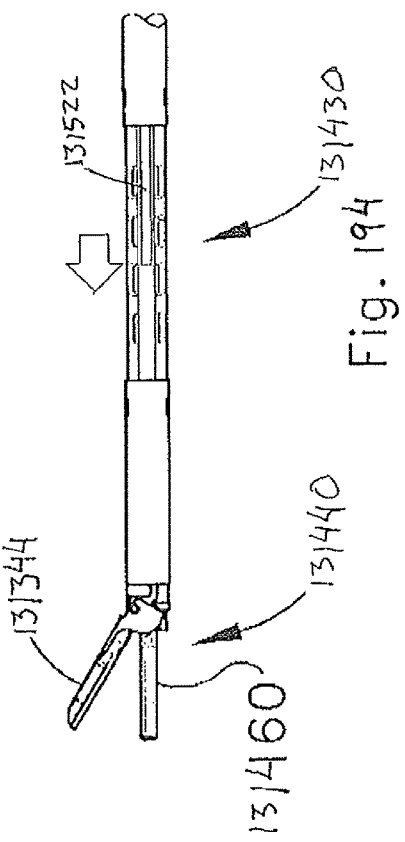
Figure 195:
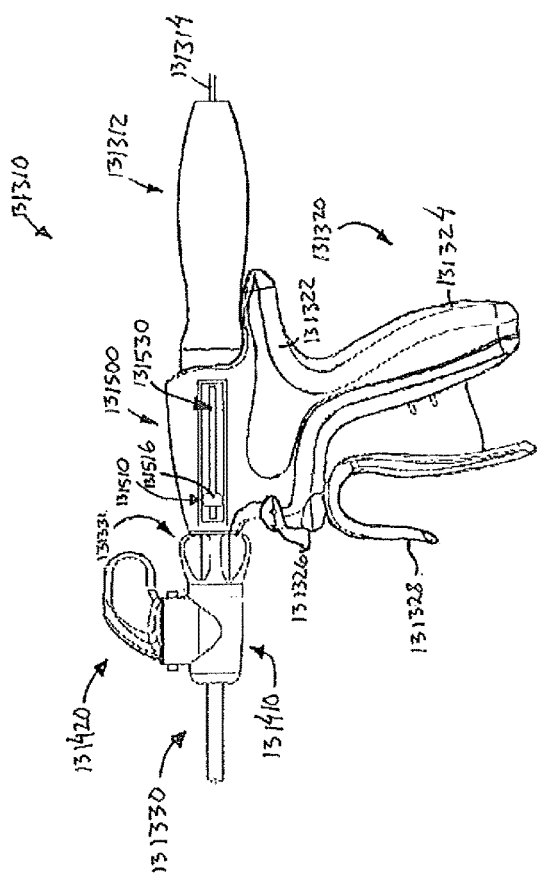
Figure 196:
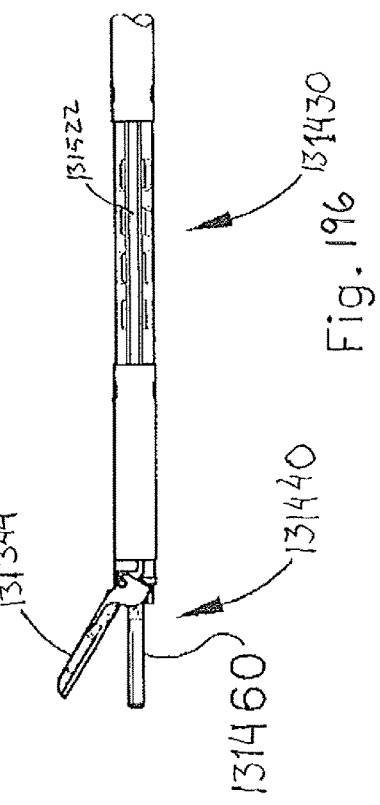
Figure 197:
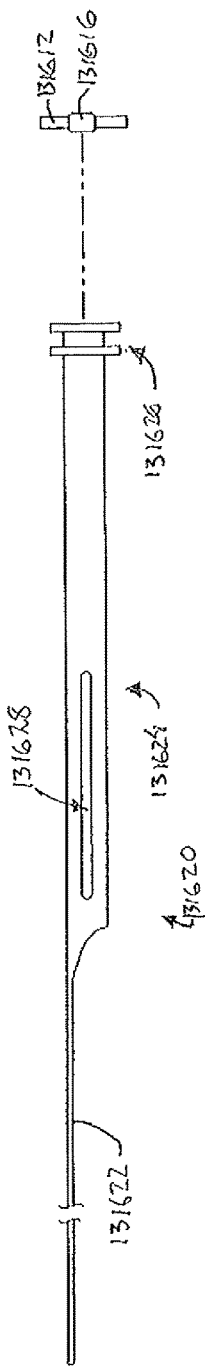
Figure 198:
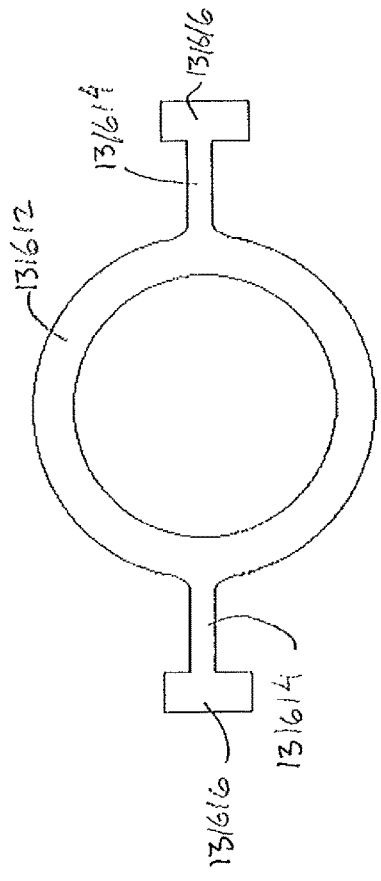
Figure 199:
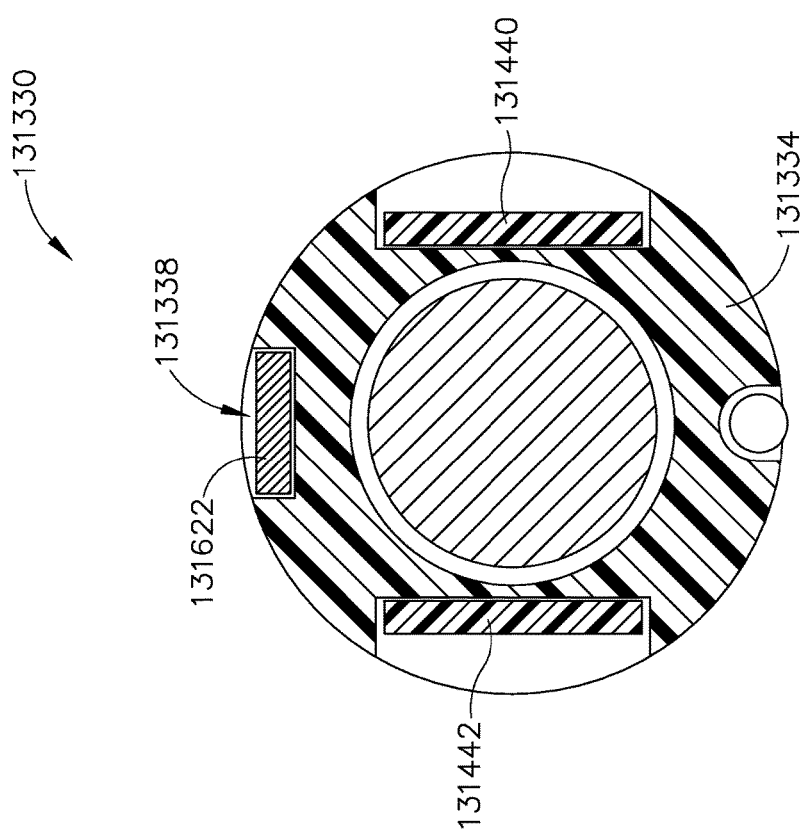
Figure 200:
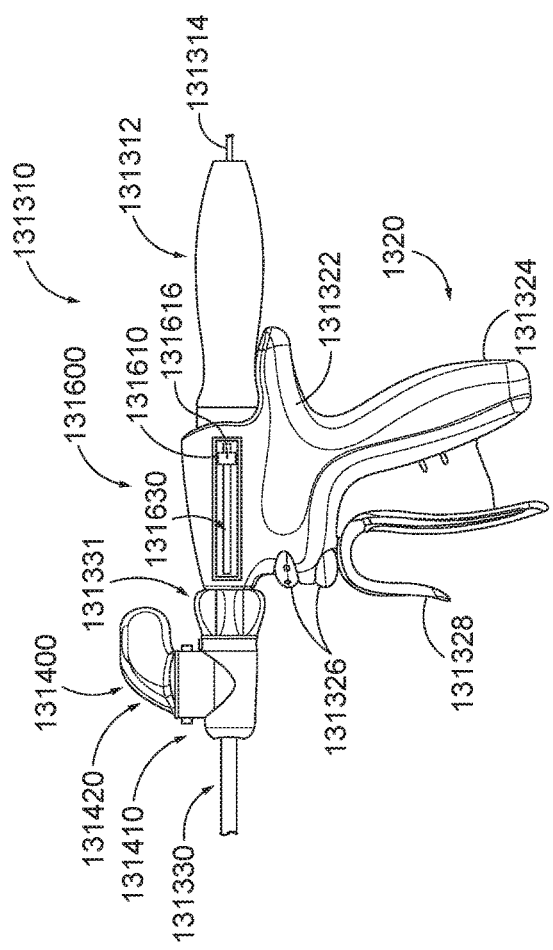
Figure 201:
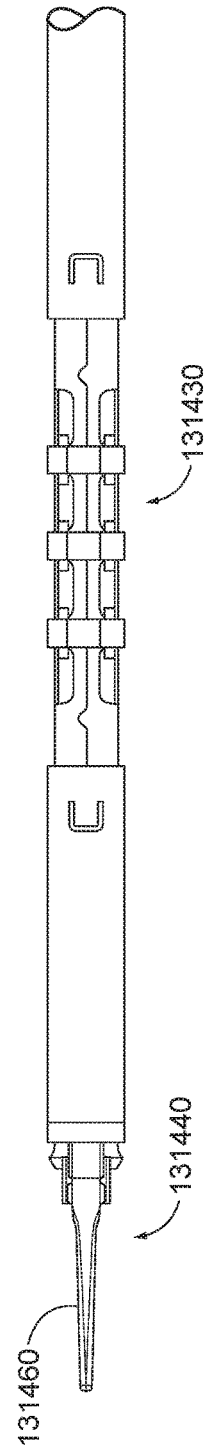
Figure 202:
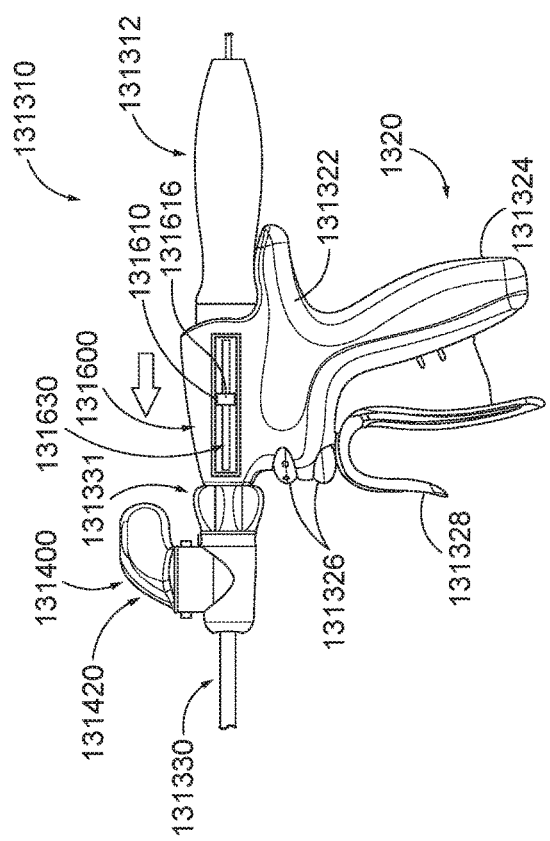
Figure 203:
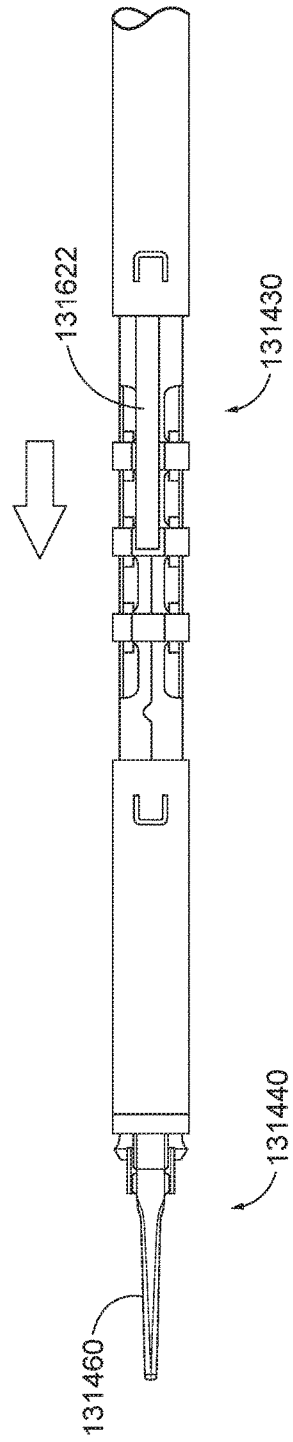
Figure 206:
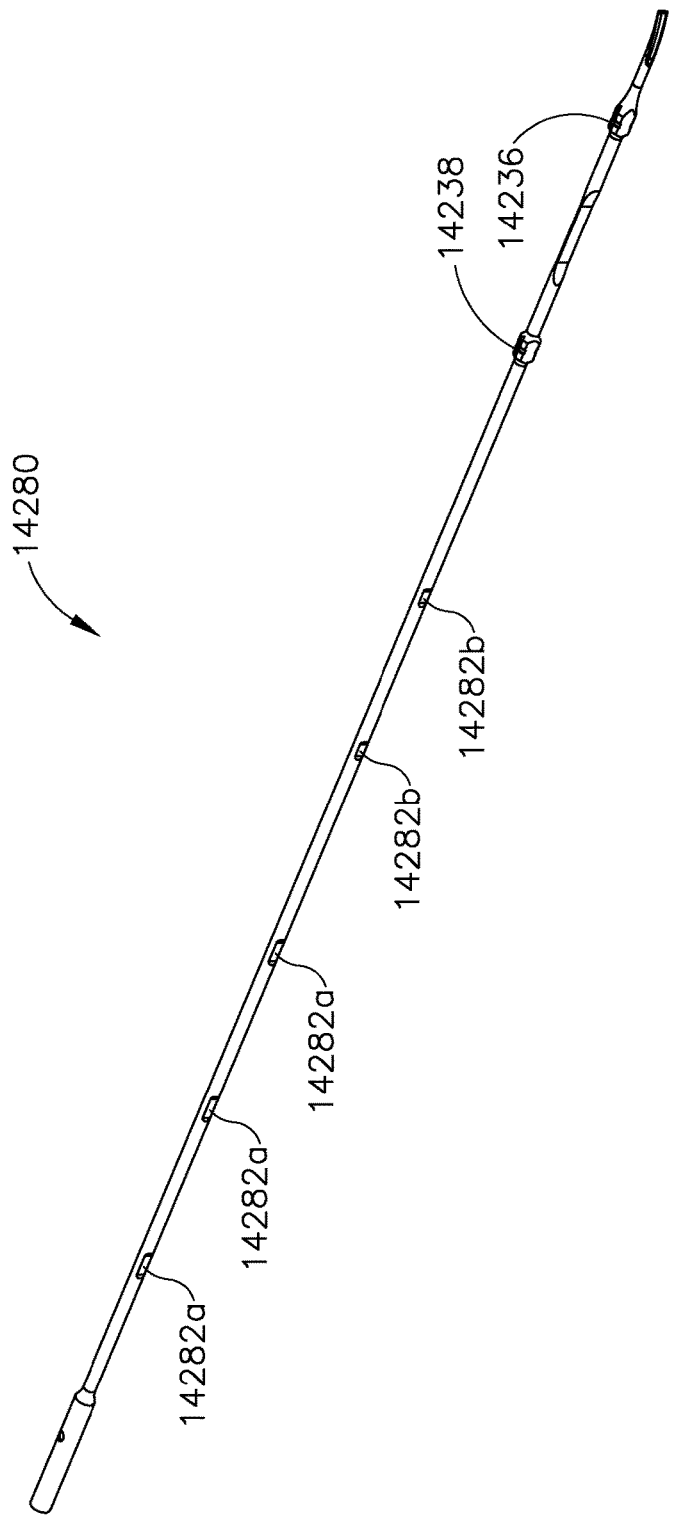
Figure 207:
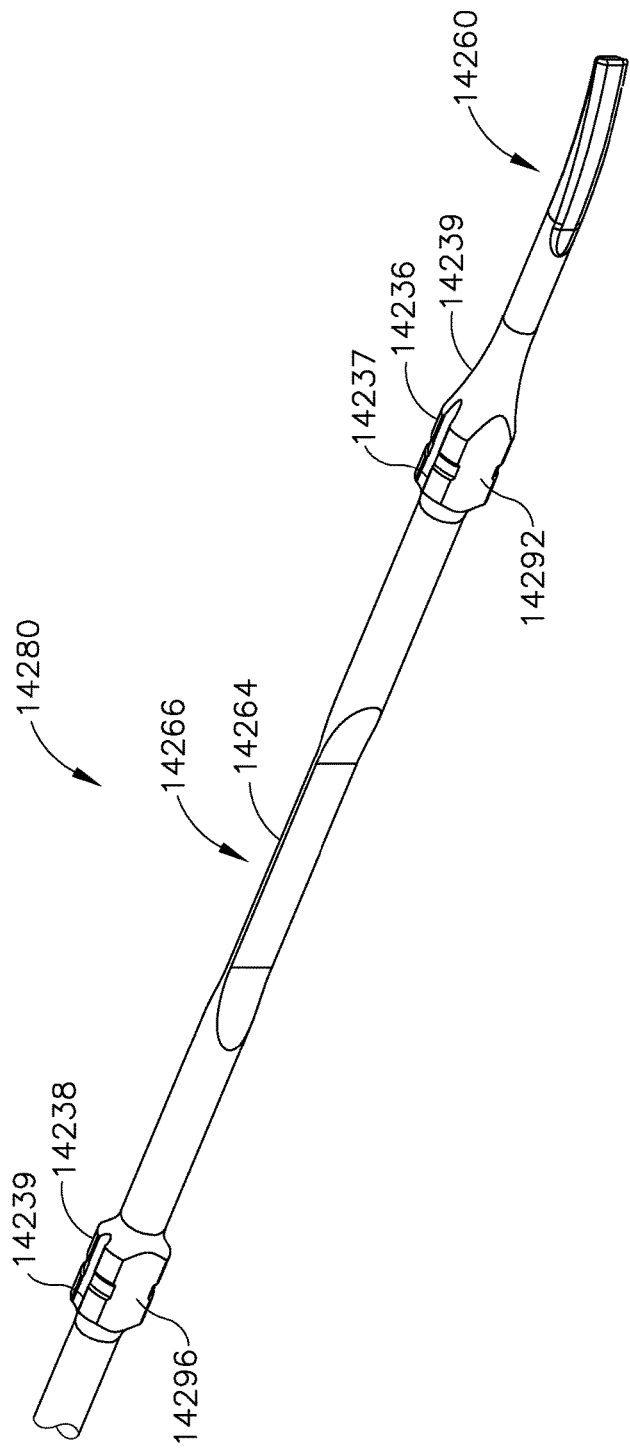
Figure 208:
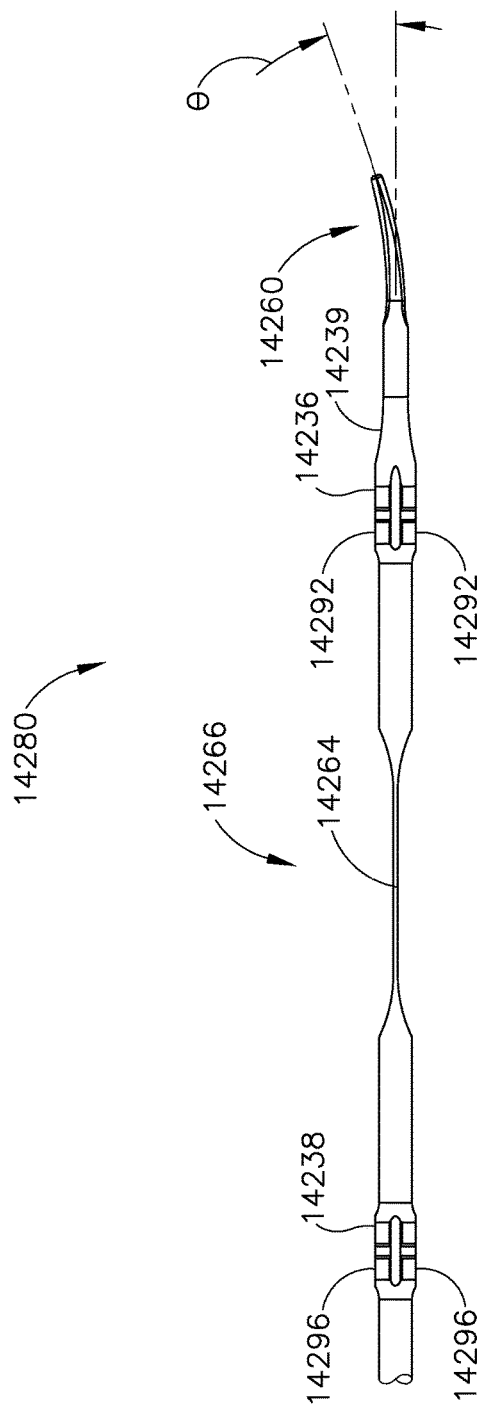
Figure 209:
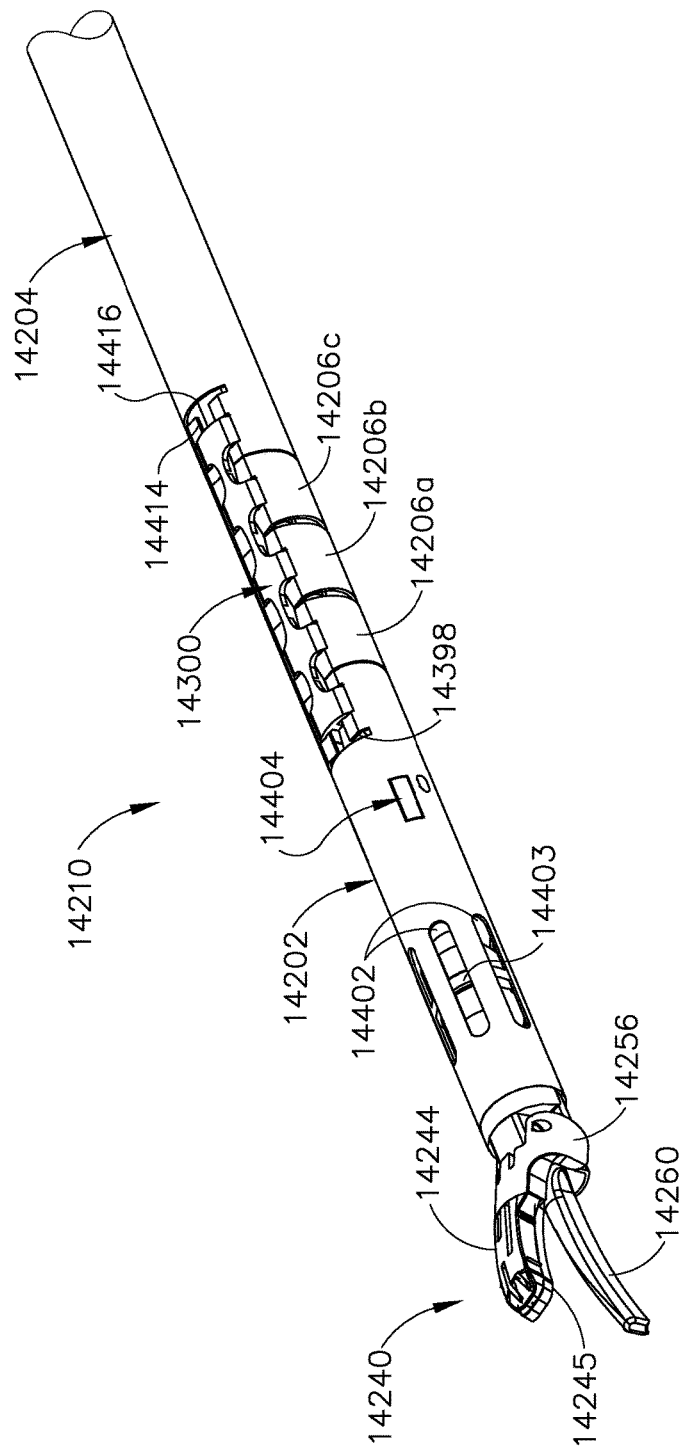
Figure 210:
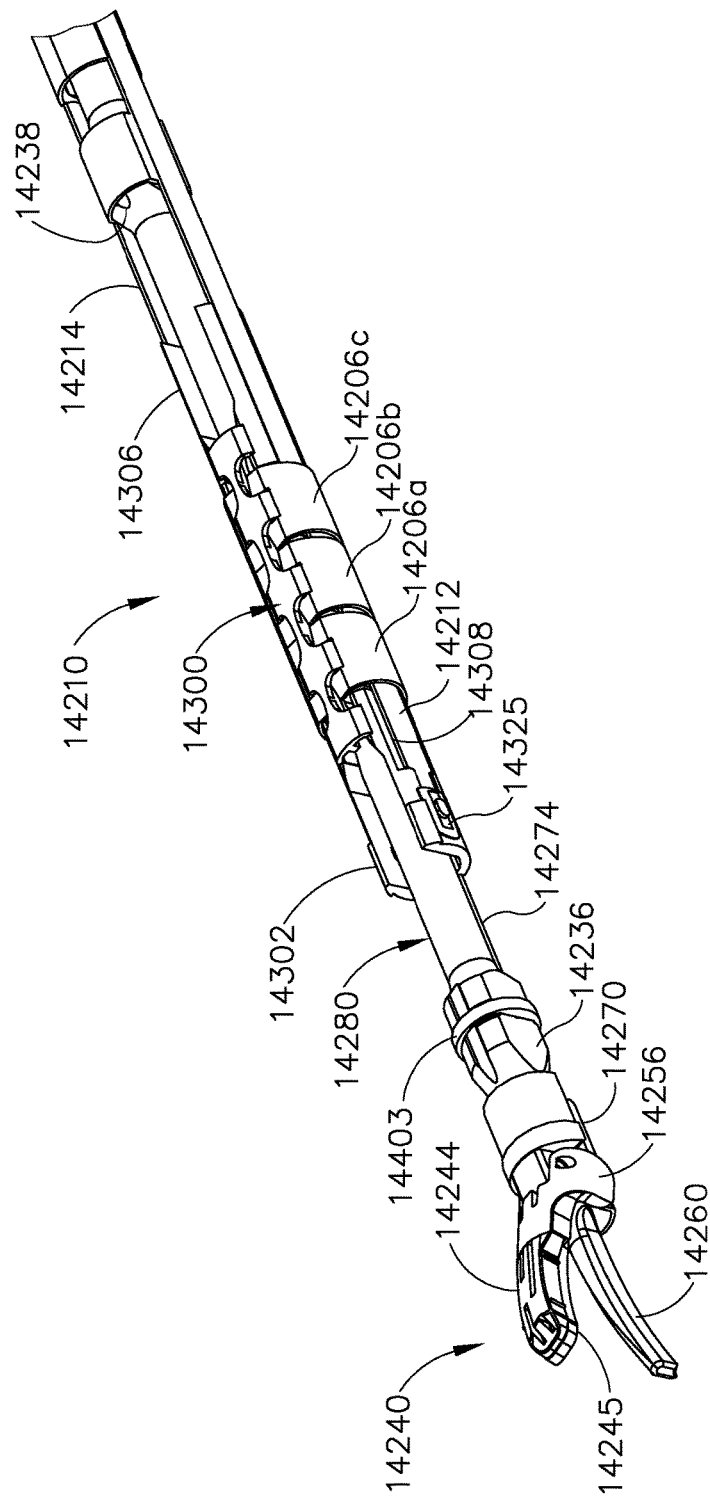
Figure 211:
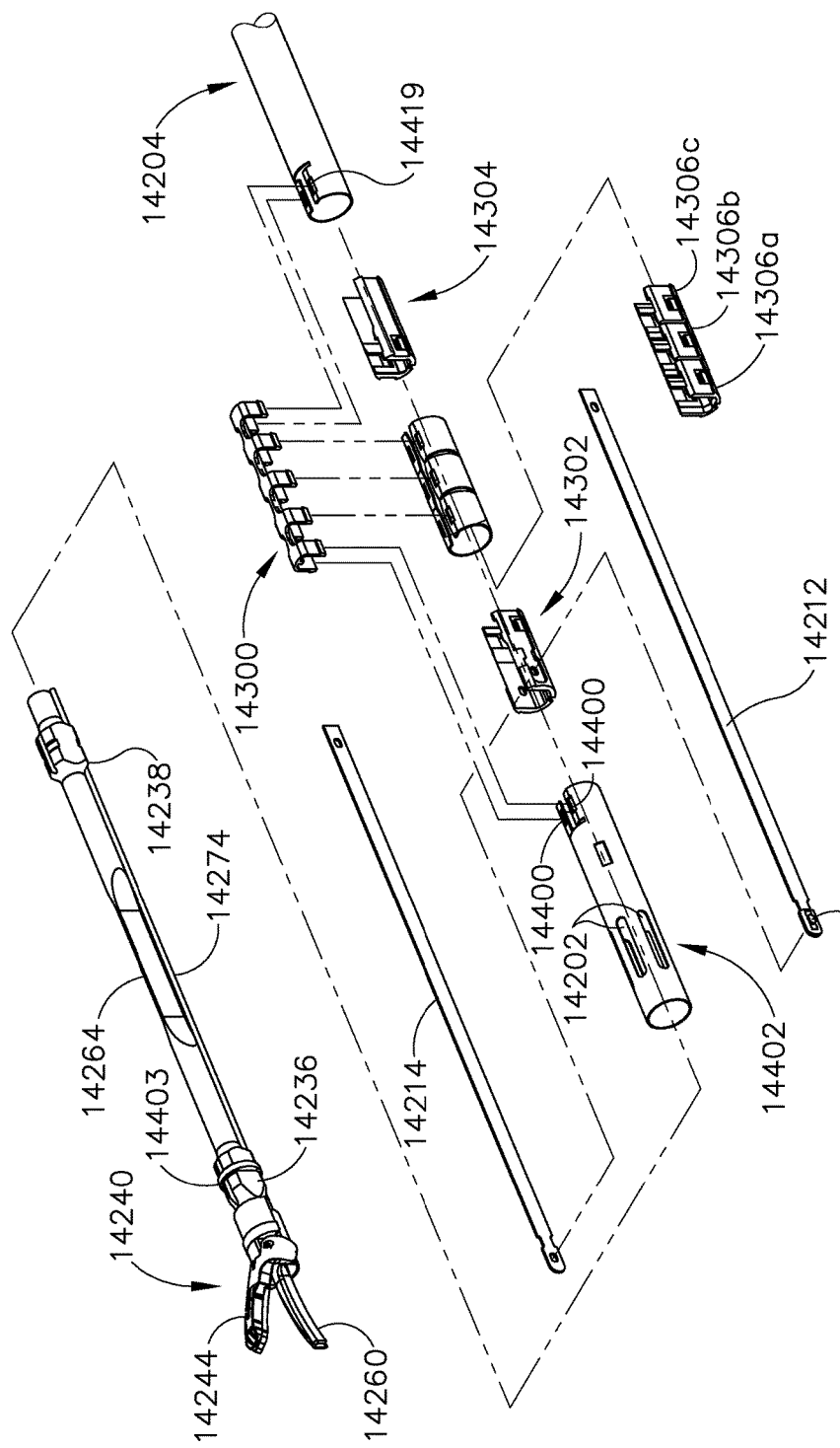
Figure 212:
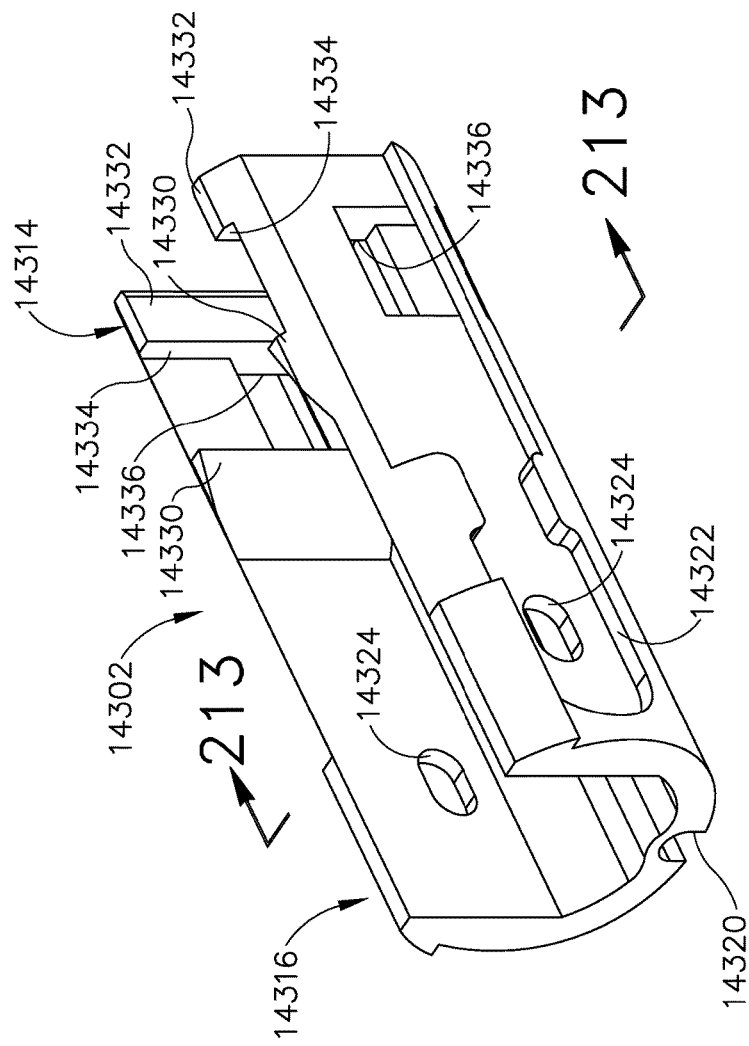
Figure 213:
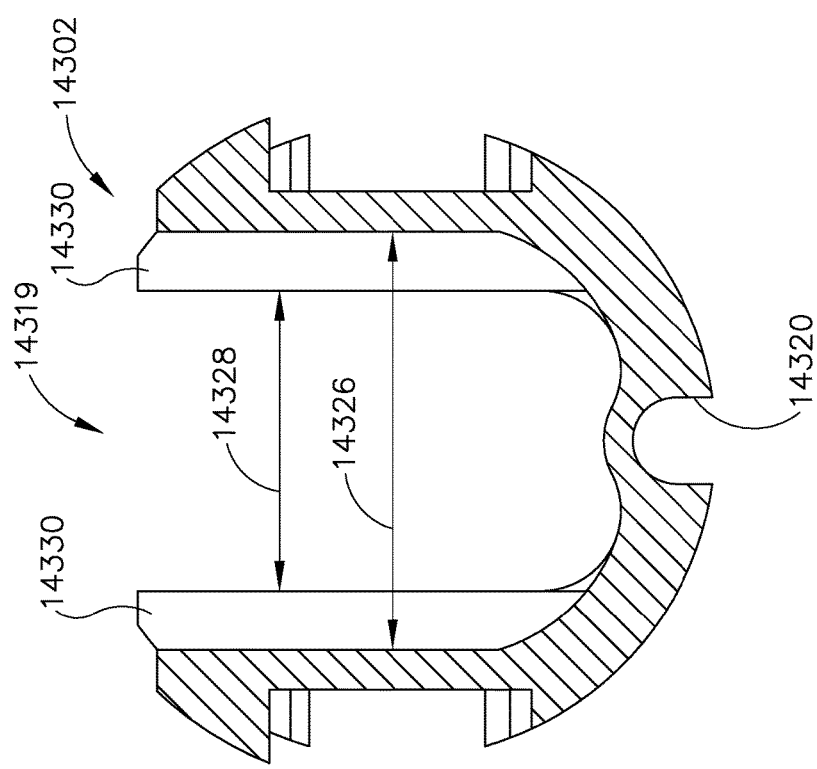
Figure 214:
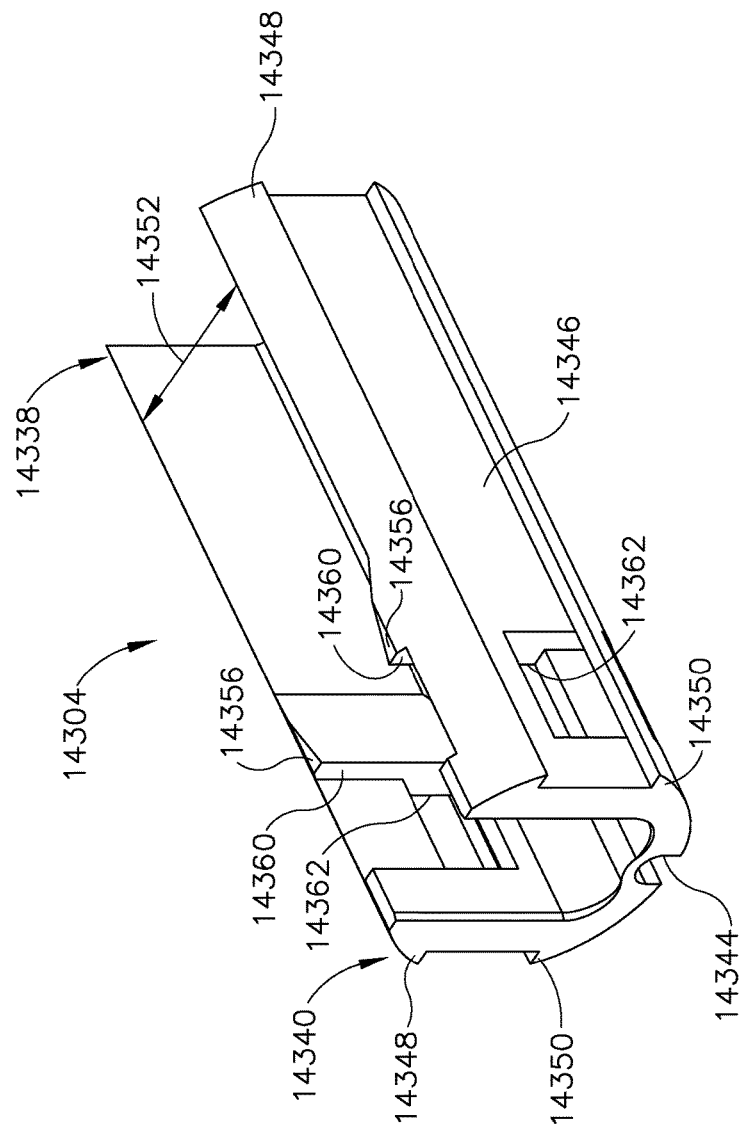
Figure 215:
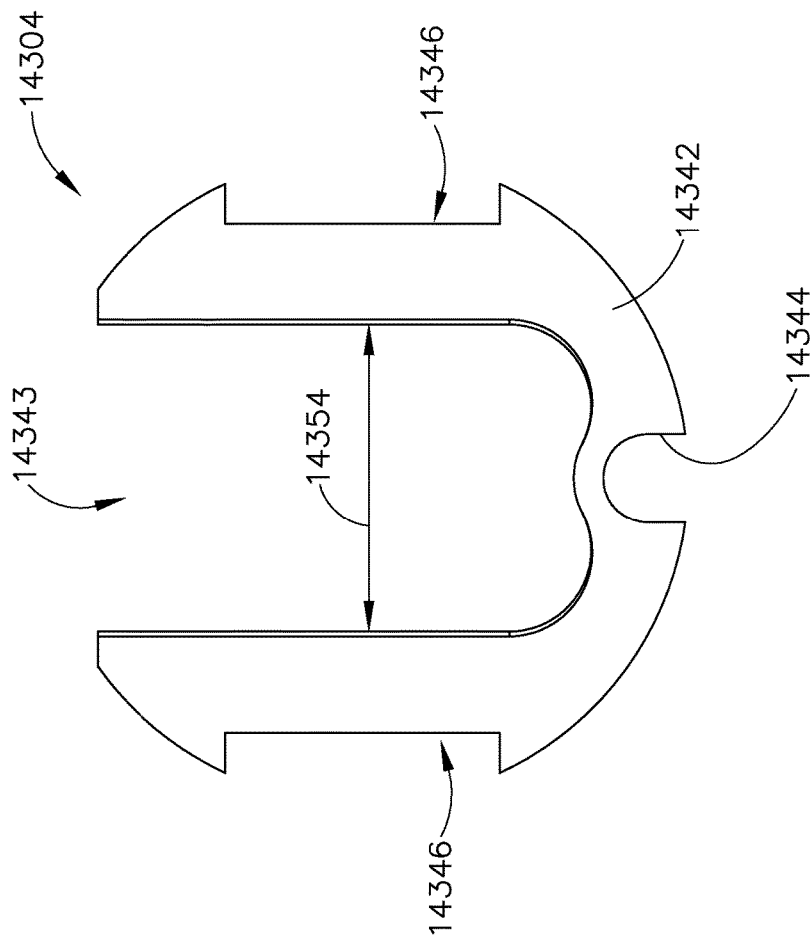
Figure 216:
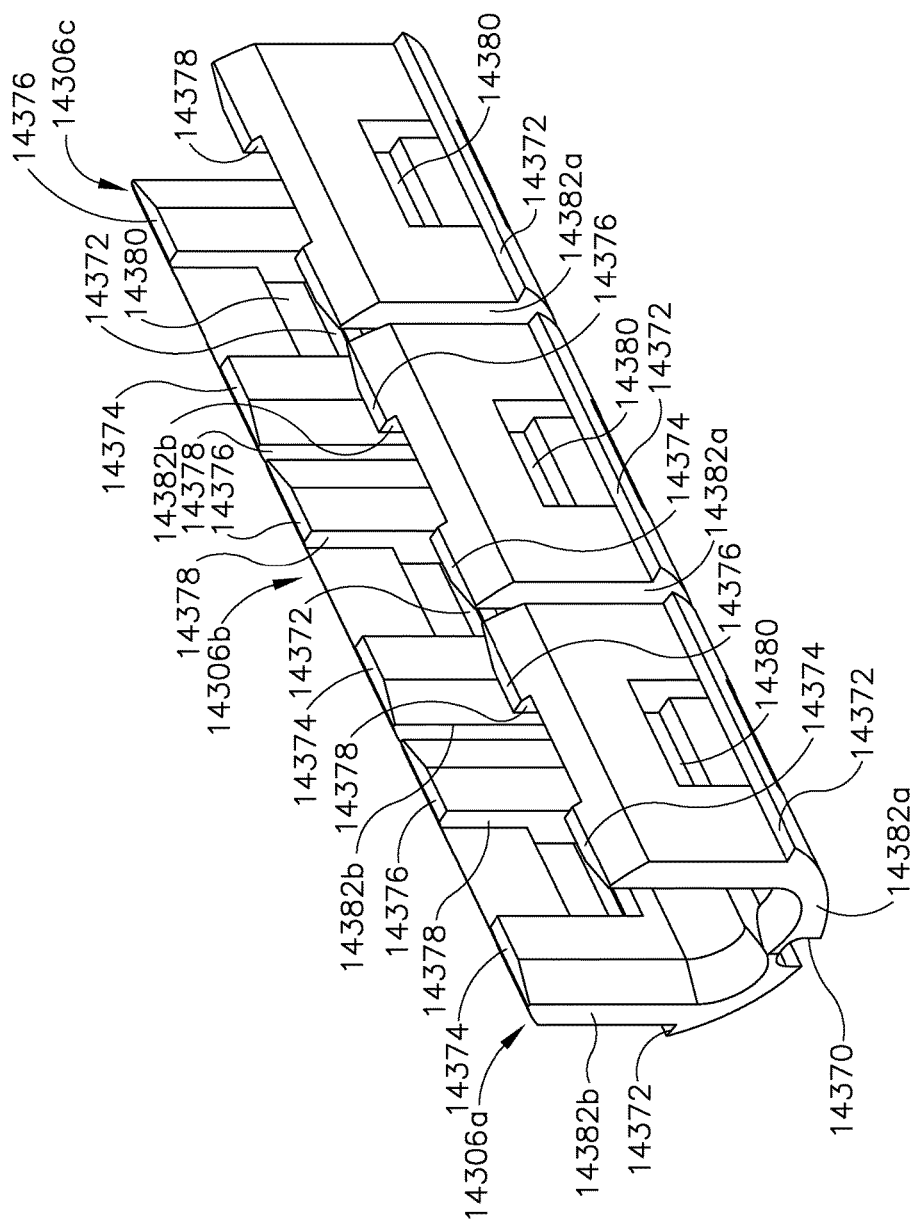
Figure 217:
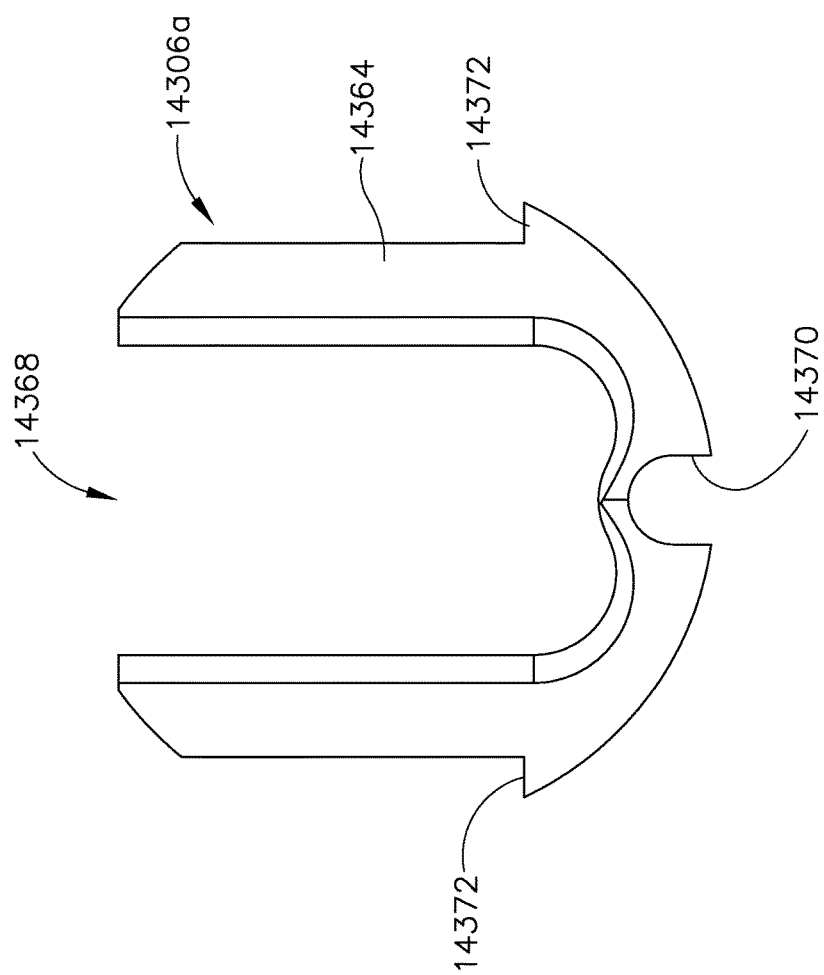
Figure 218B:
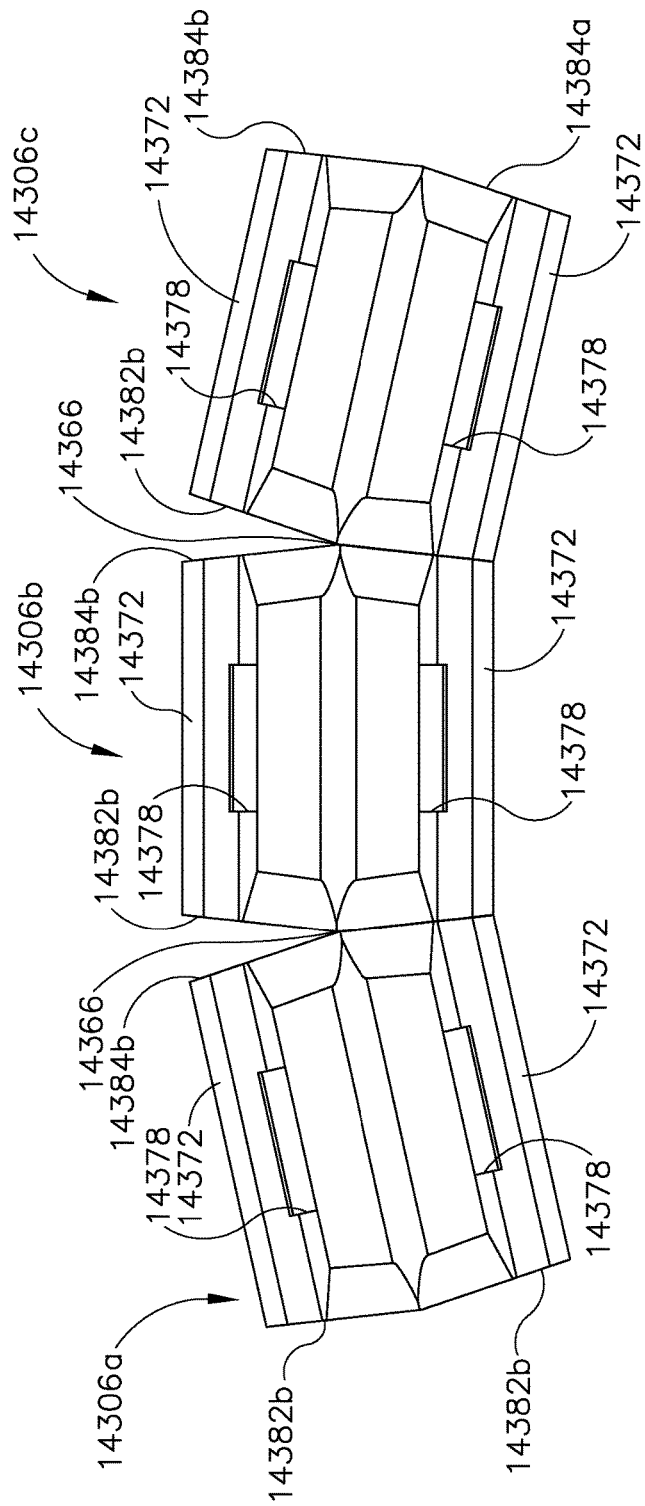
Figure 219:
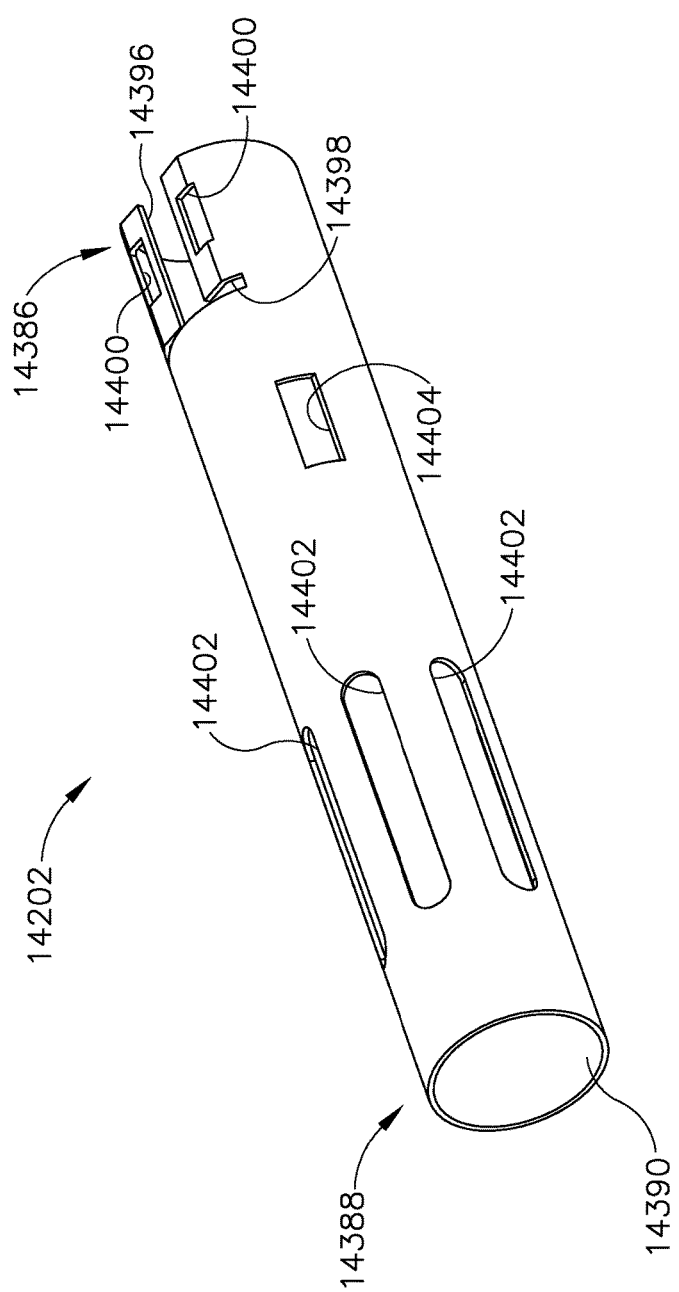
Figure 220:
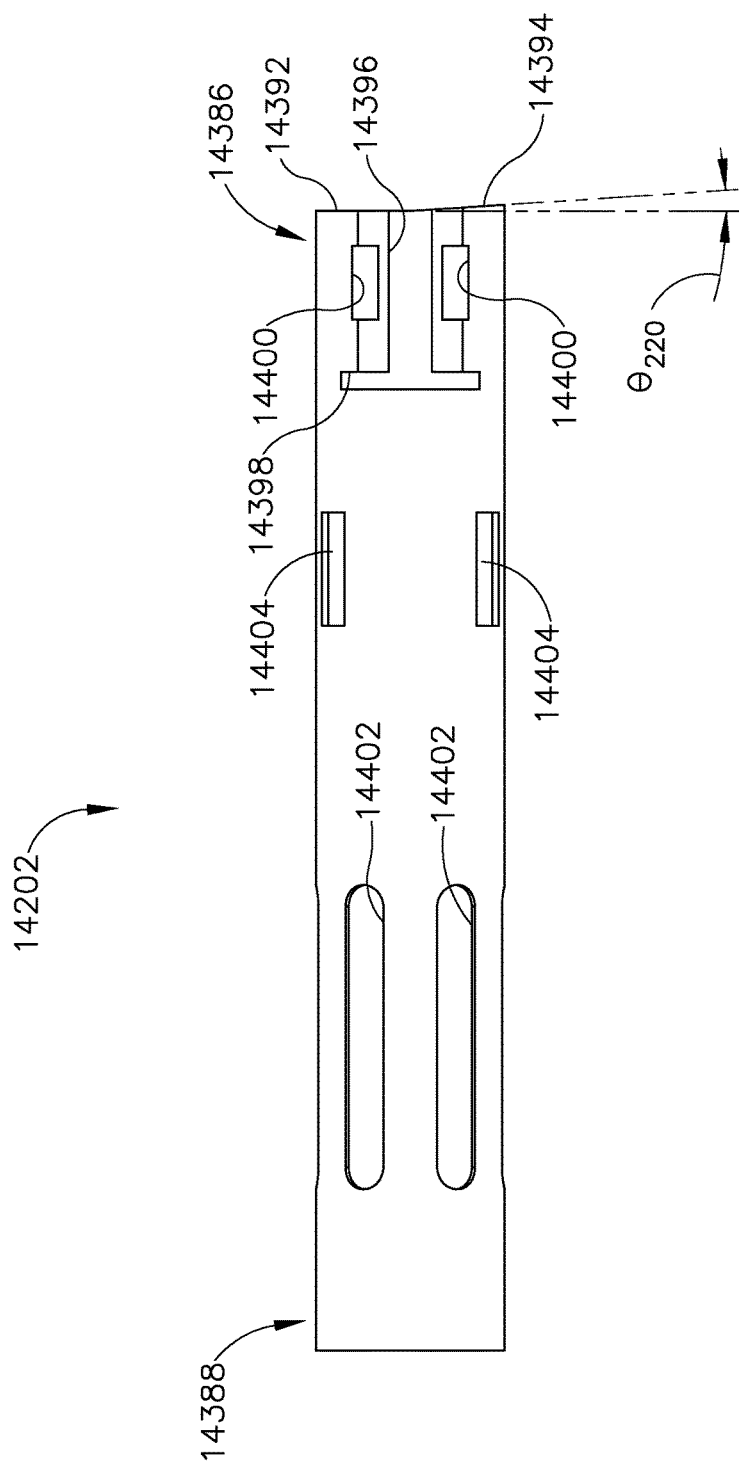
Figure 221:
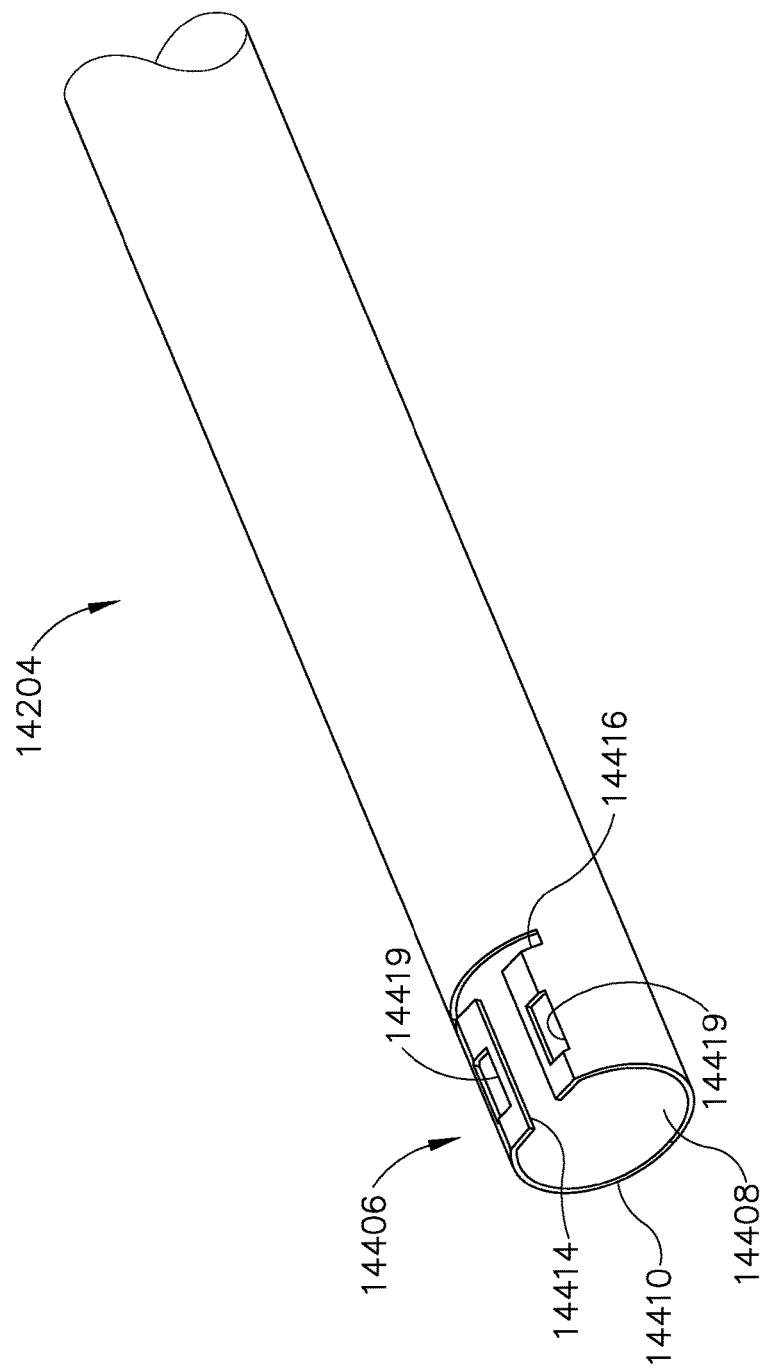
Figure 222:
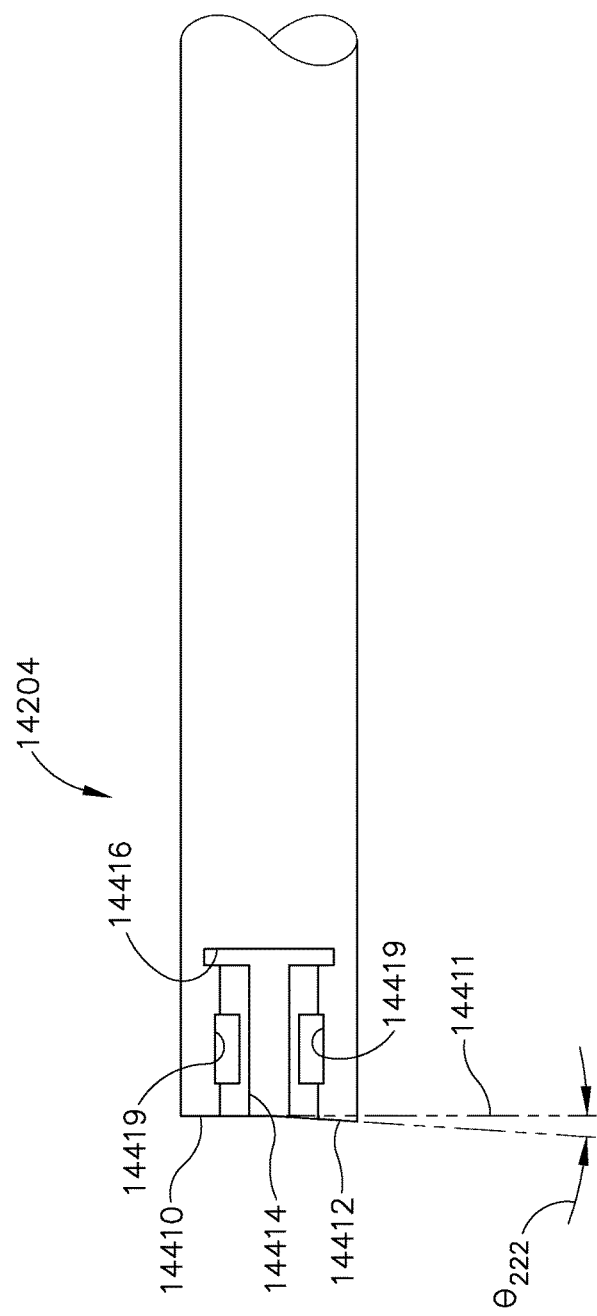
Figure 223:
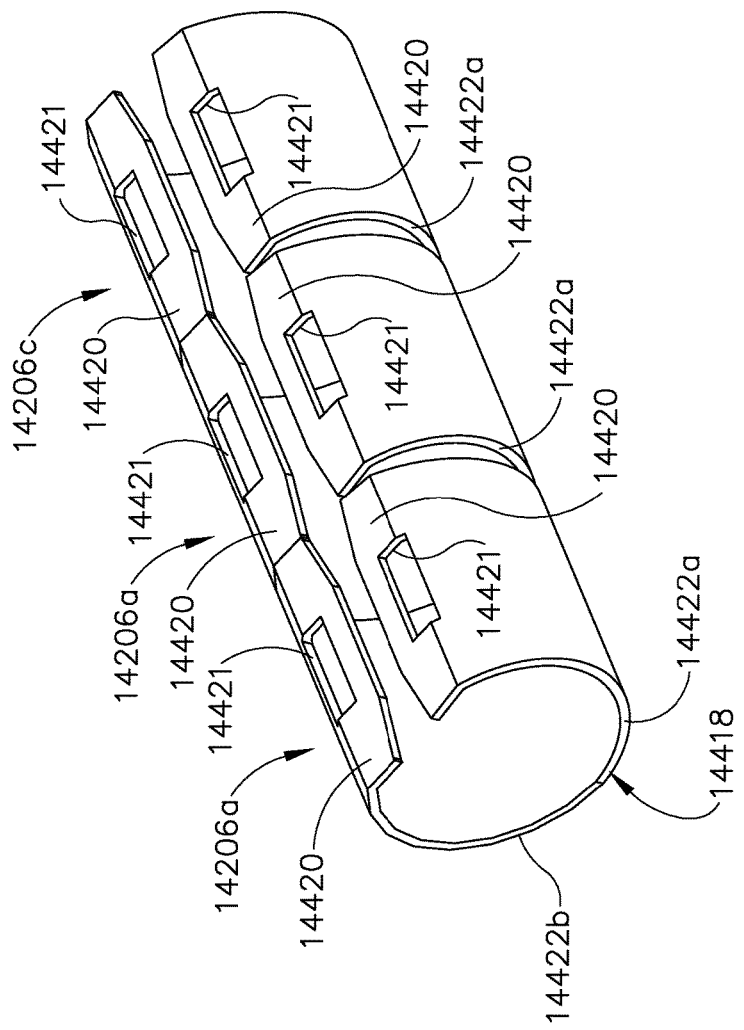
Figure 224A:
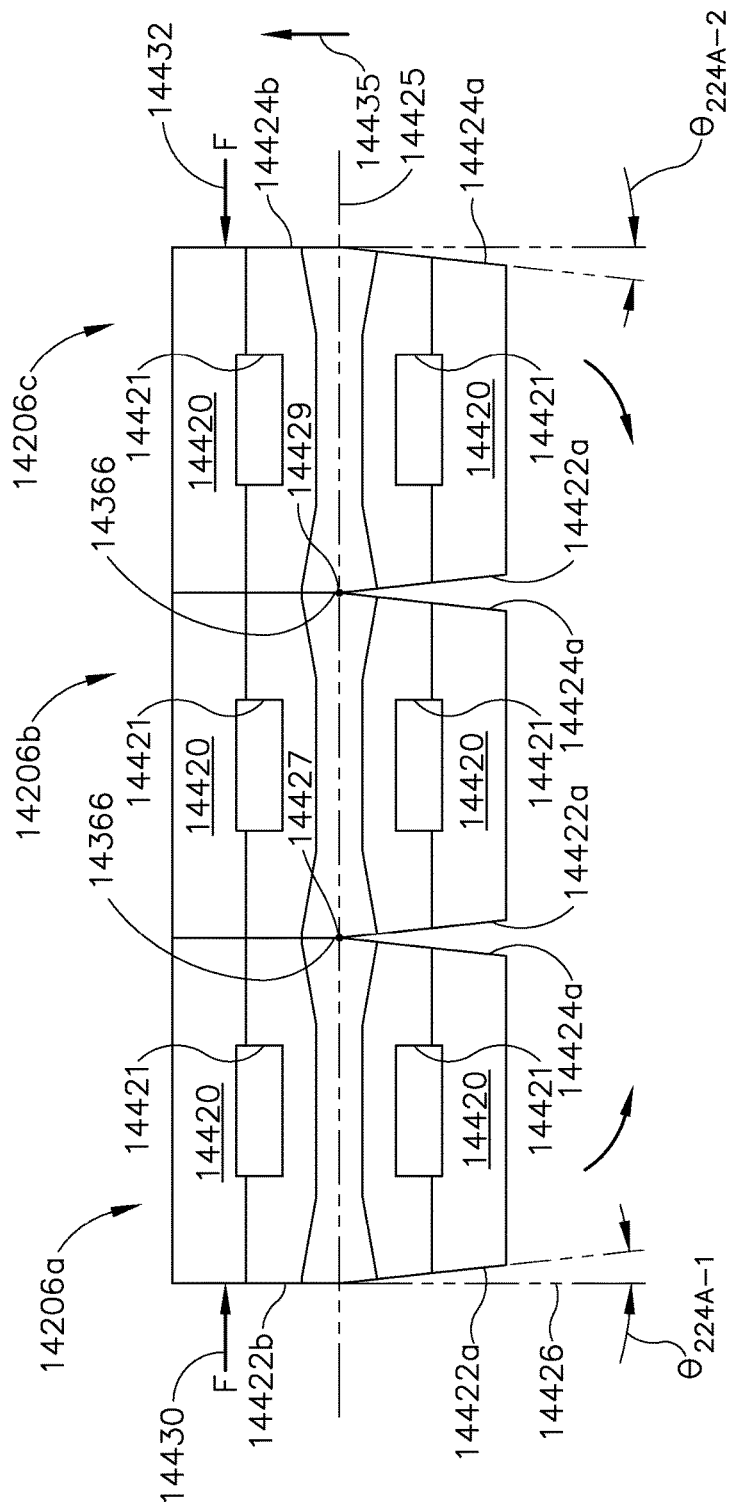
Figure 224B:
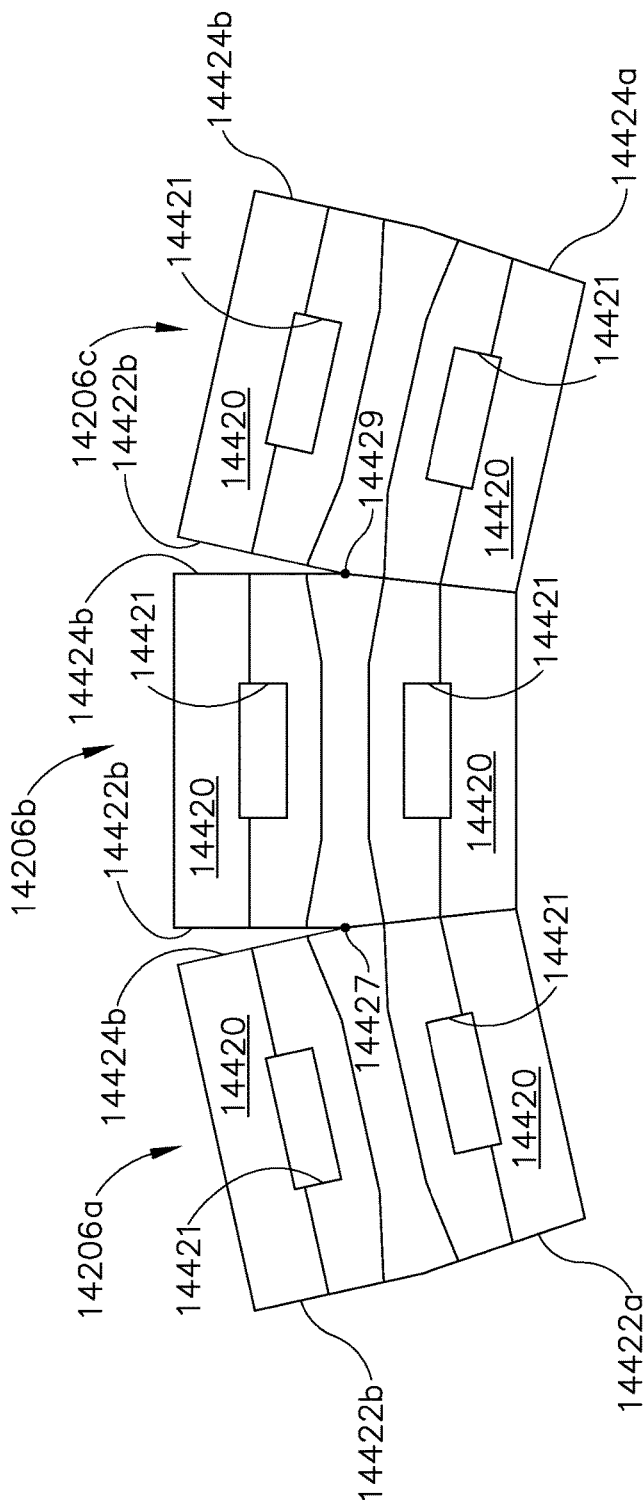
Figure 225:
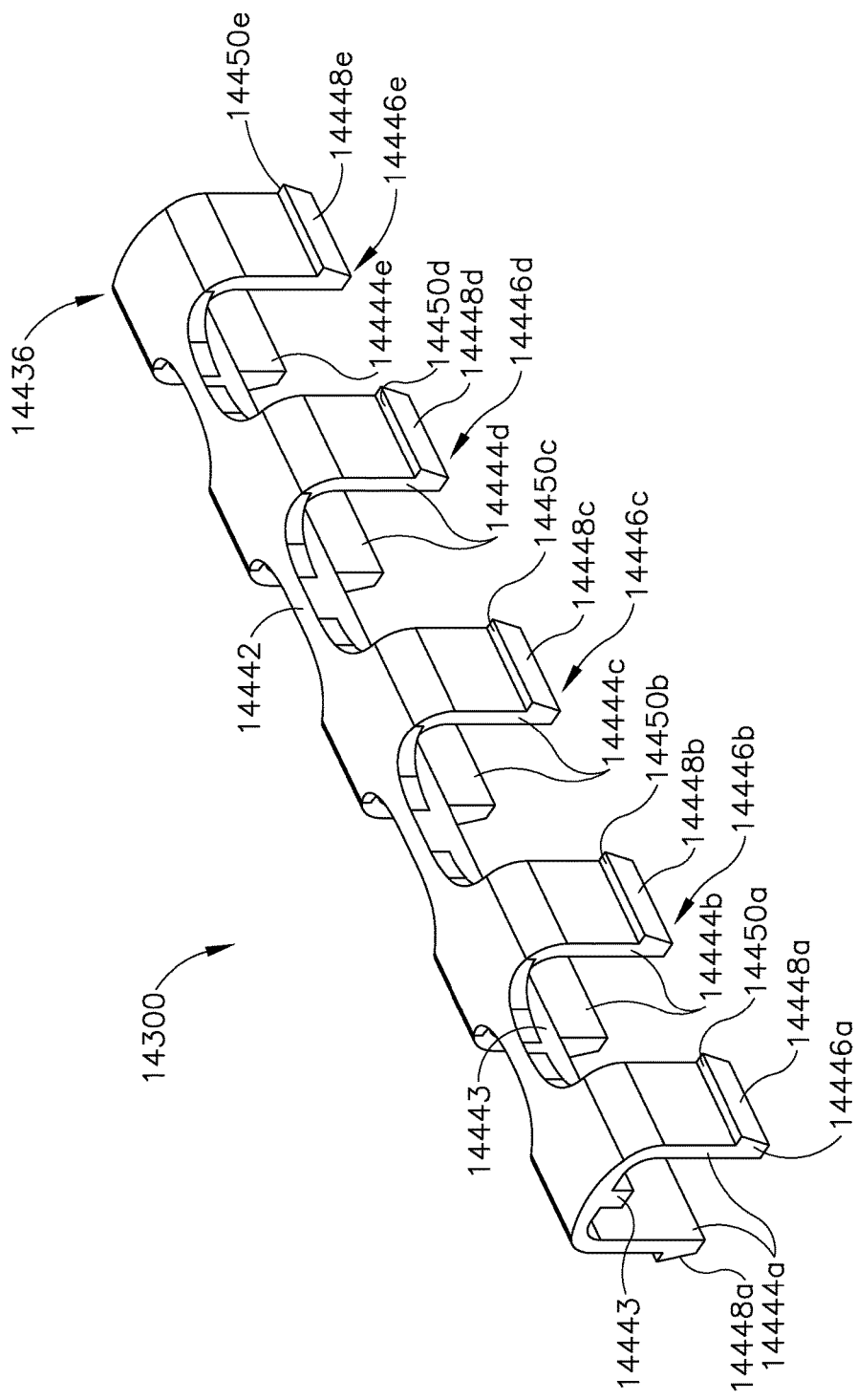
Figure 227A:
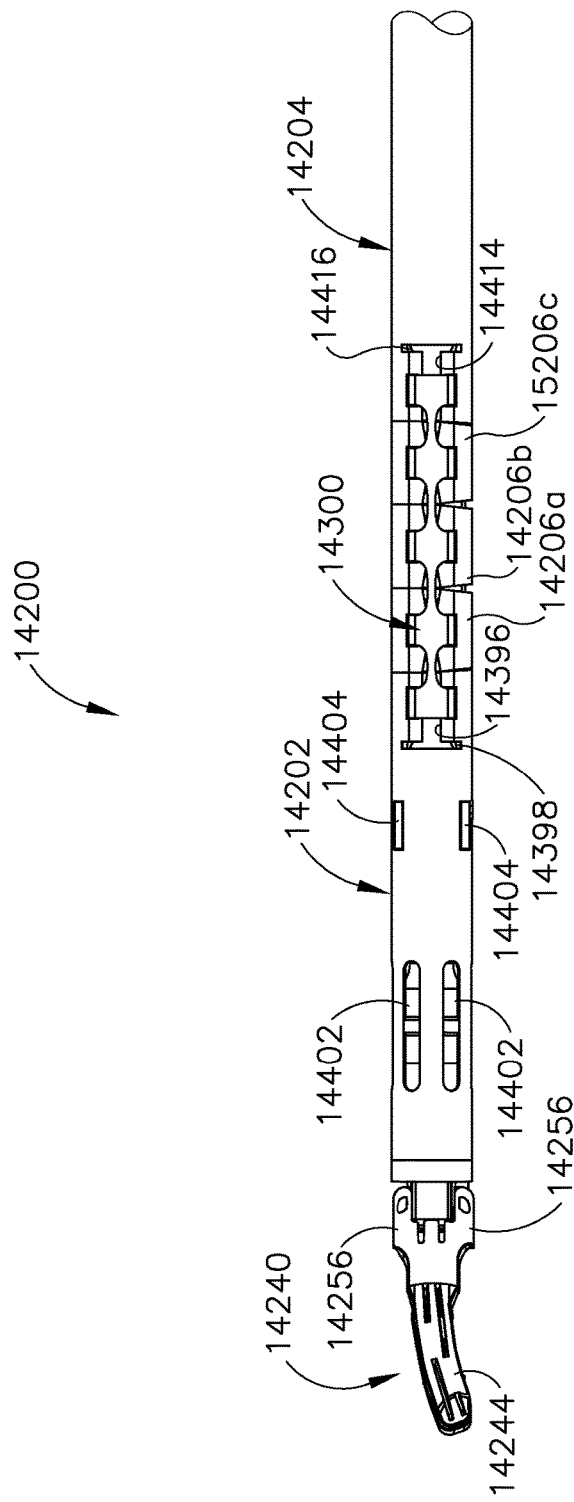
Figure 228A:
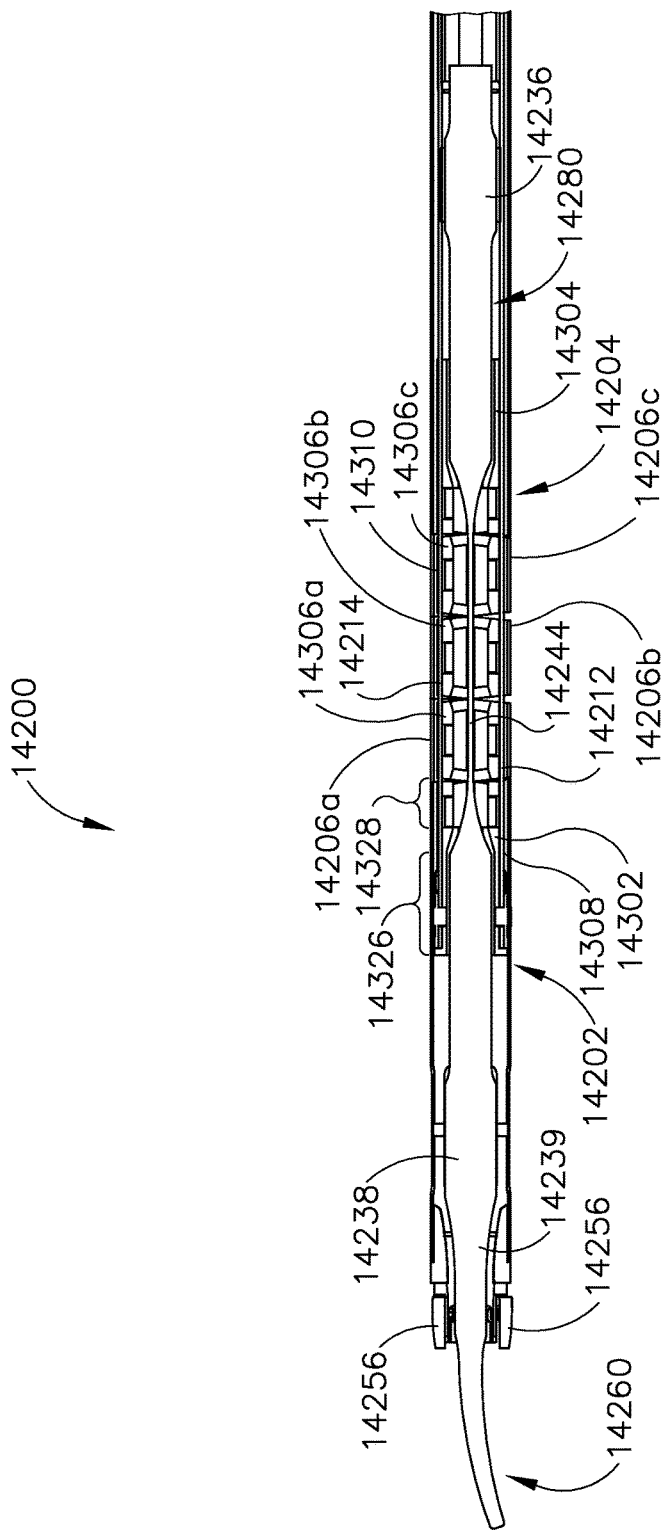
Figure 228B:
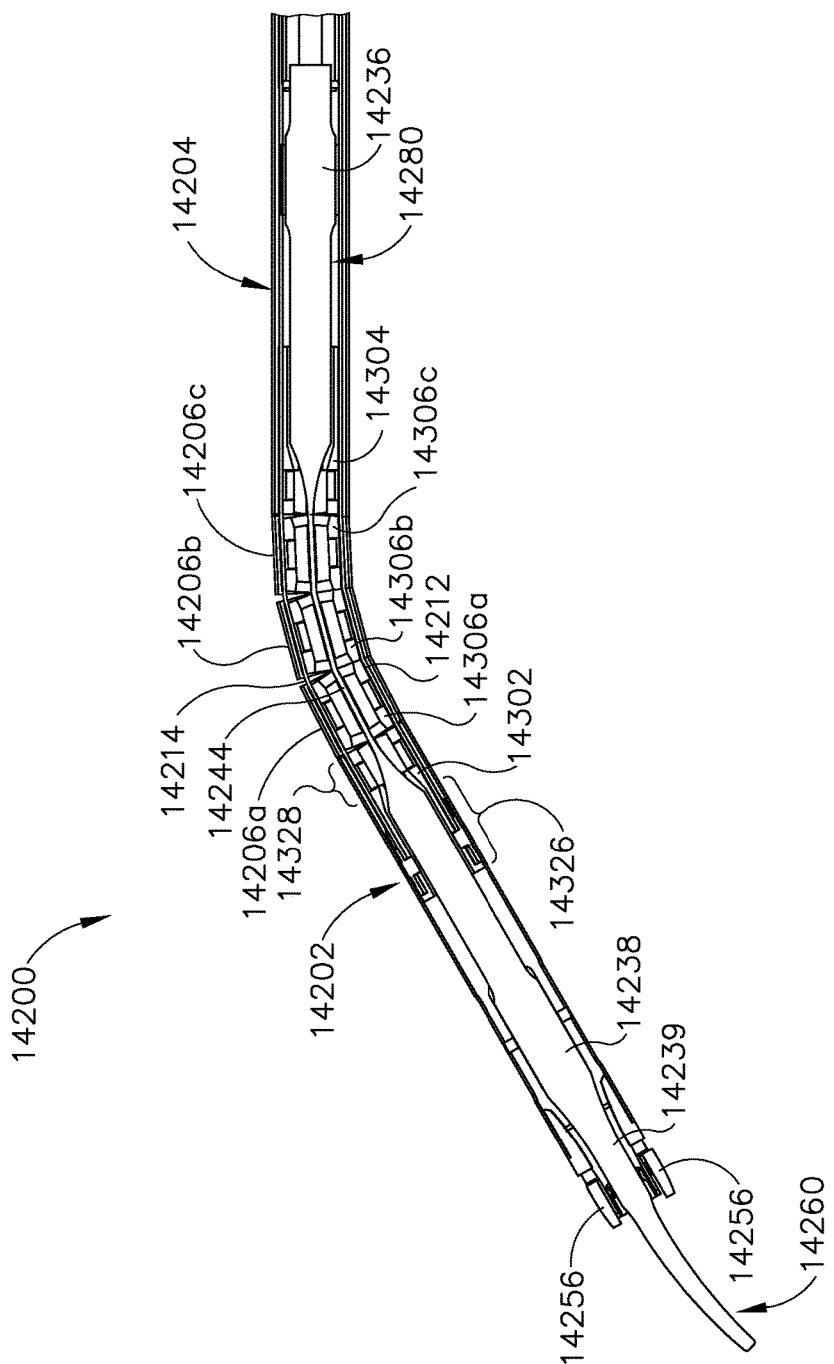
Figure 229:
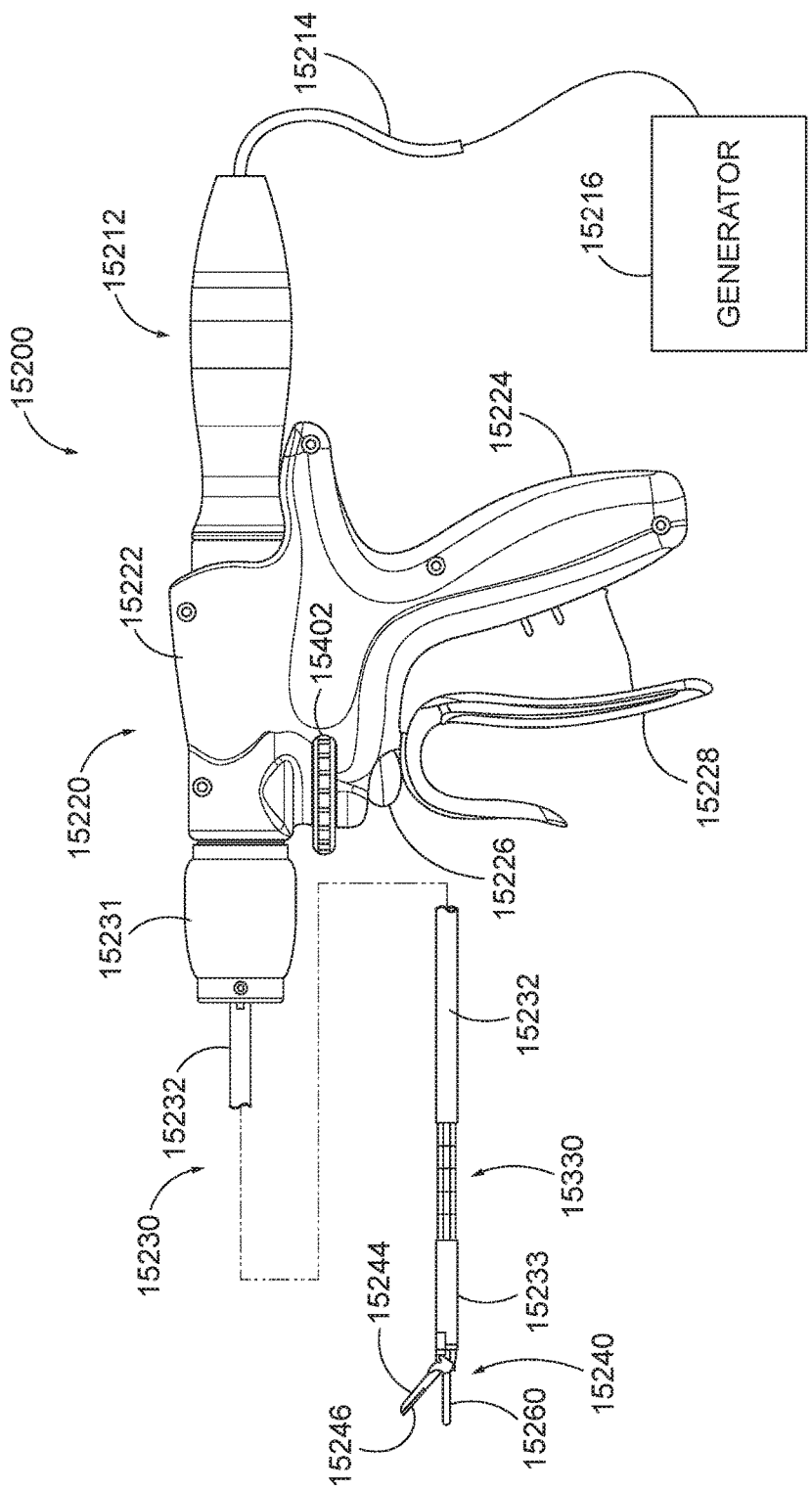
Figure 230:
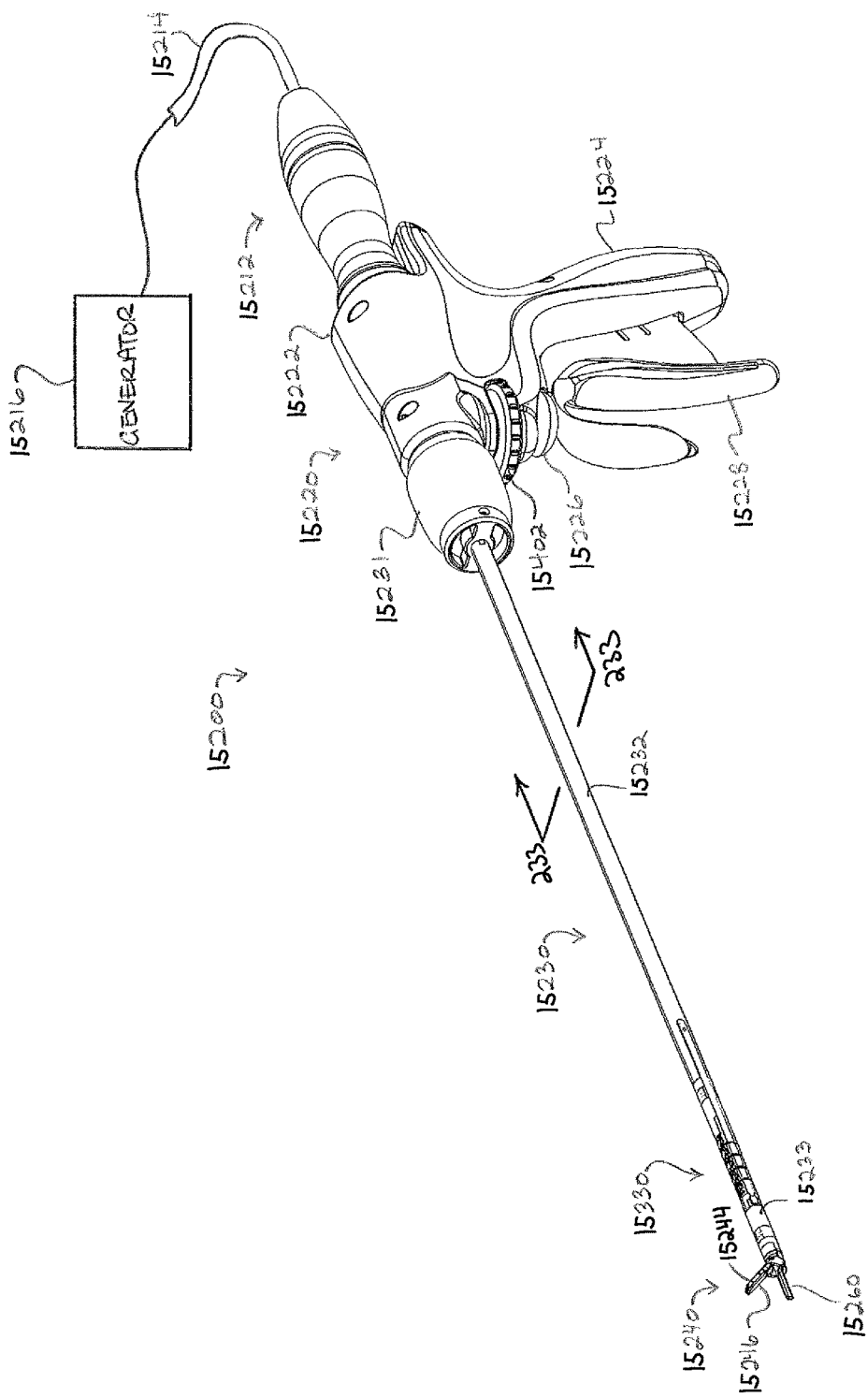
Figure 231:
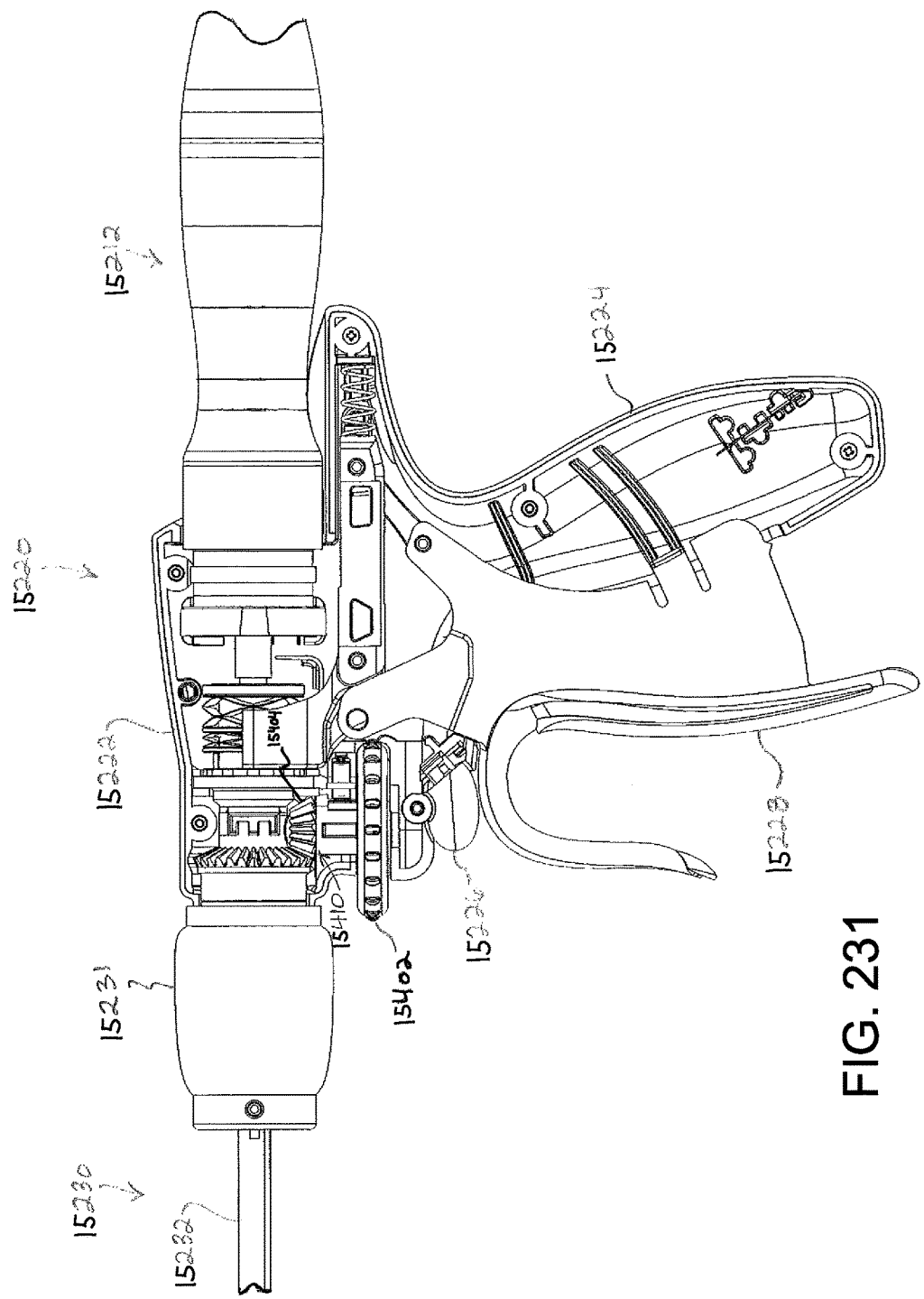
Figure 232:
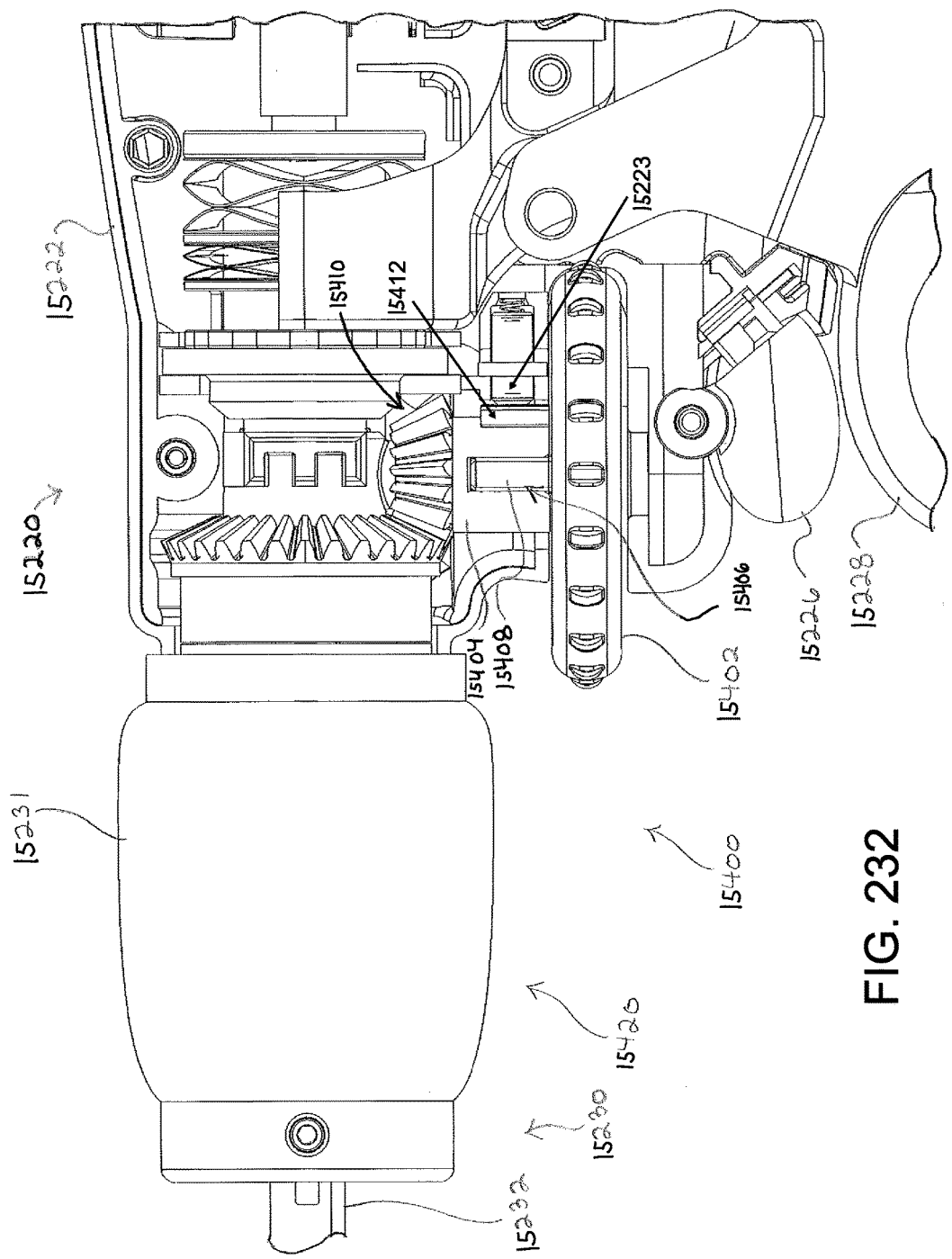
Figure 233:
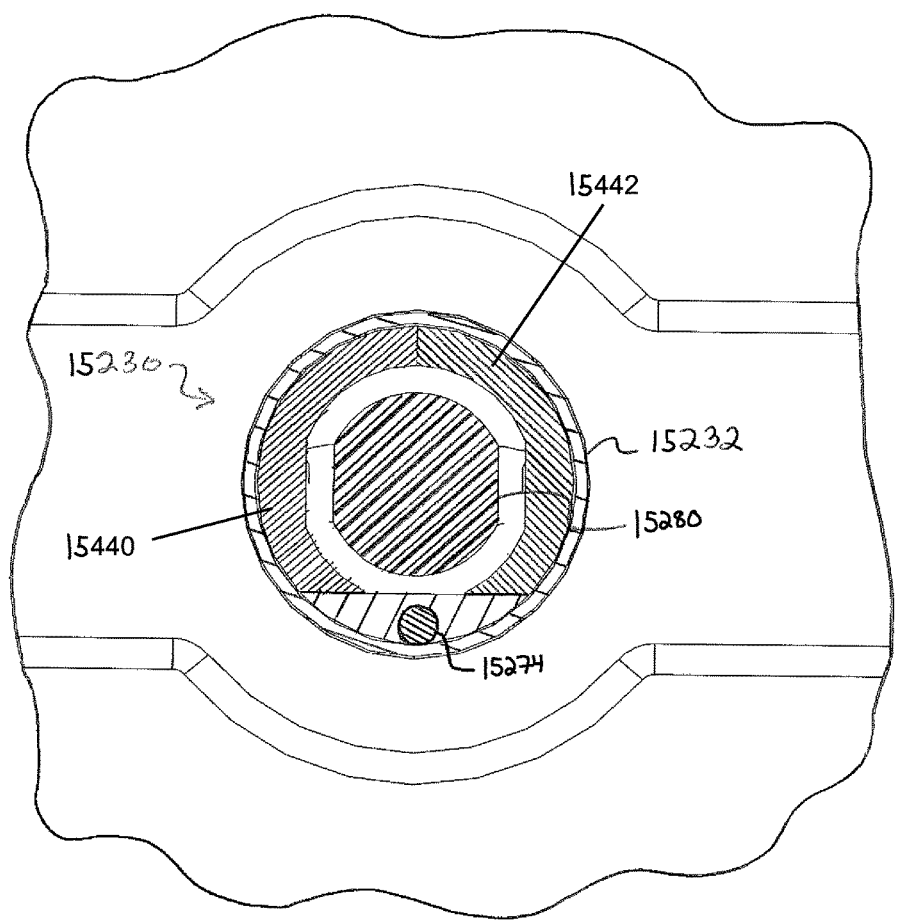
Figure 234:
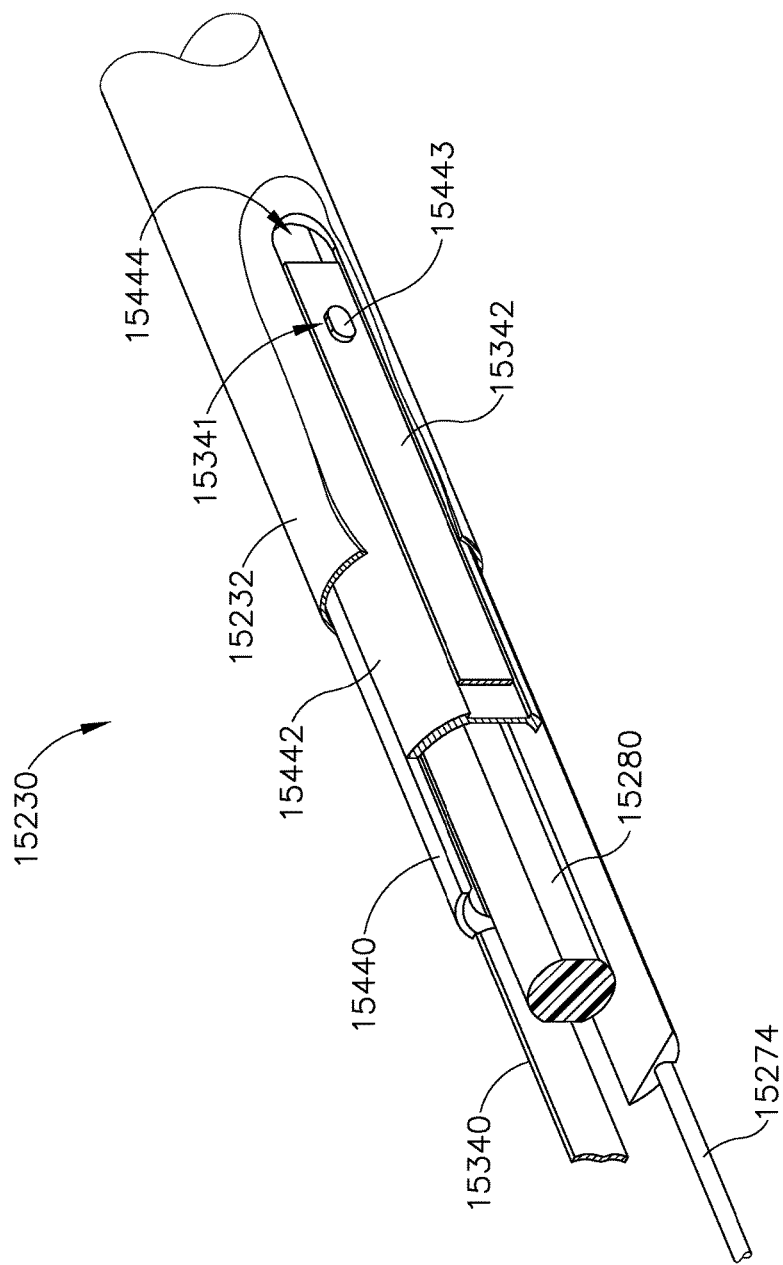
Figure 235:
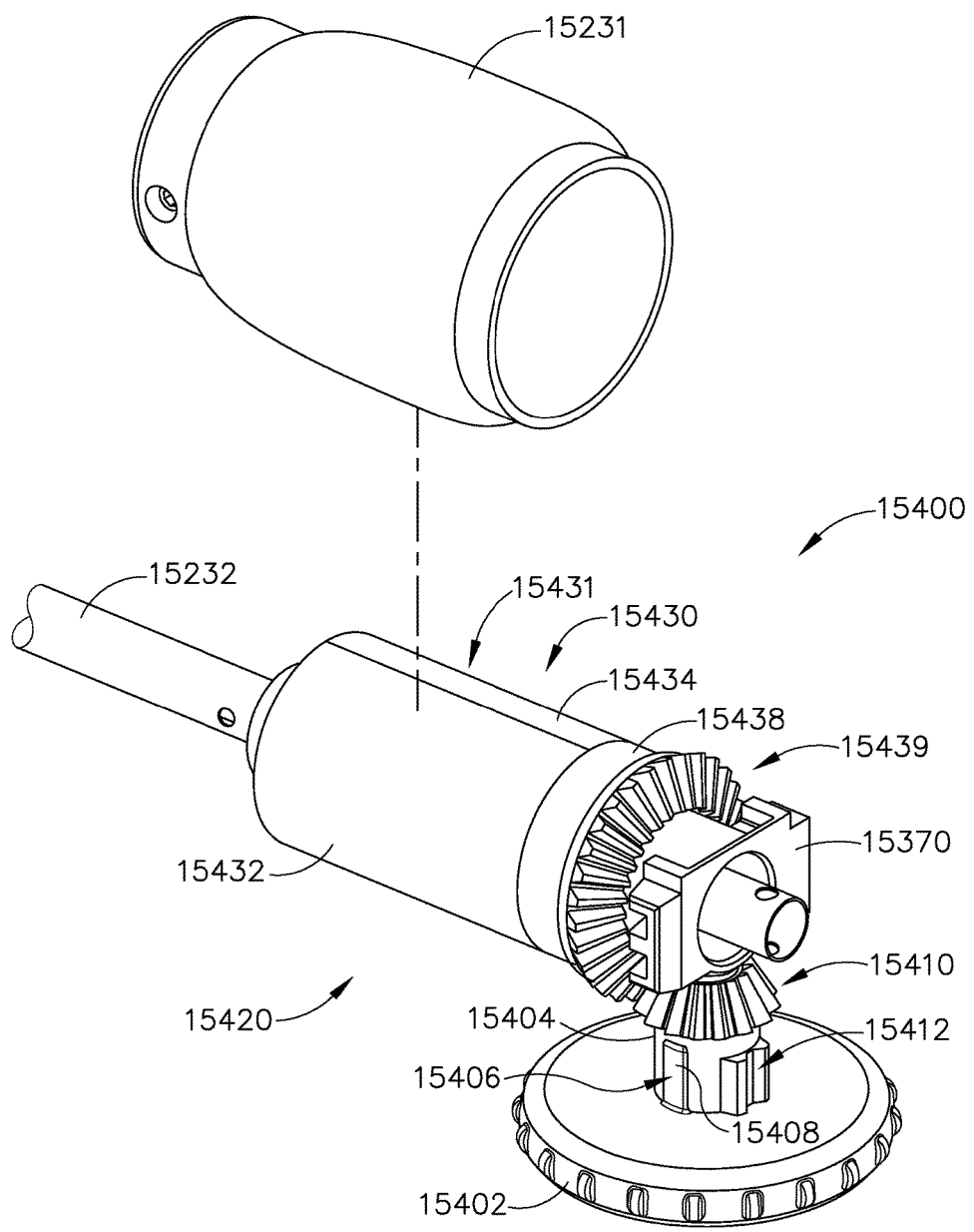
Figure 236:
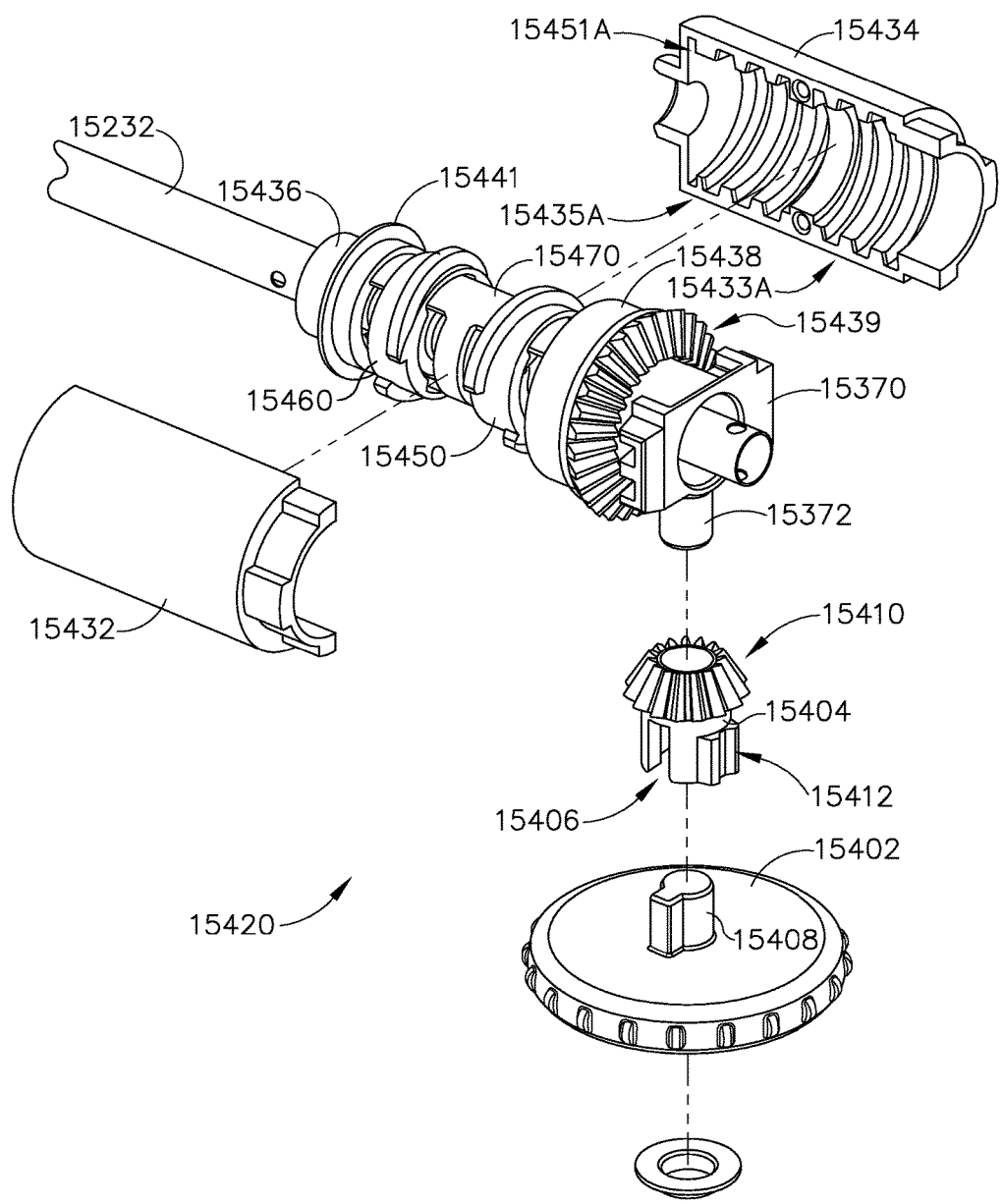
Figure 237:
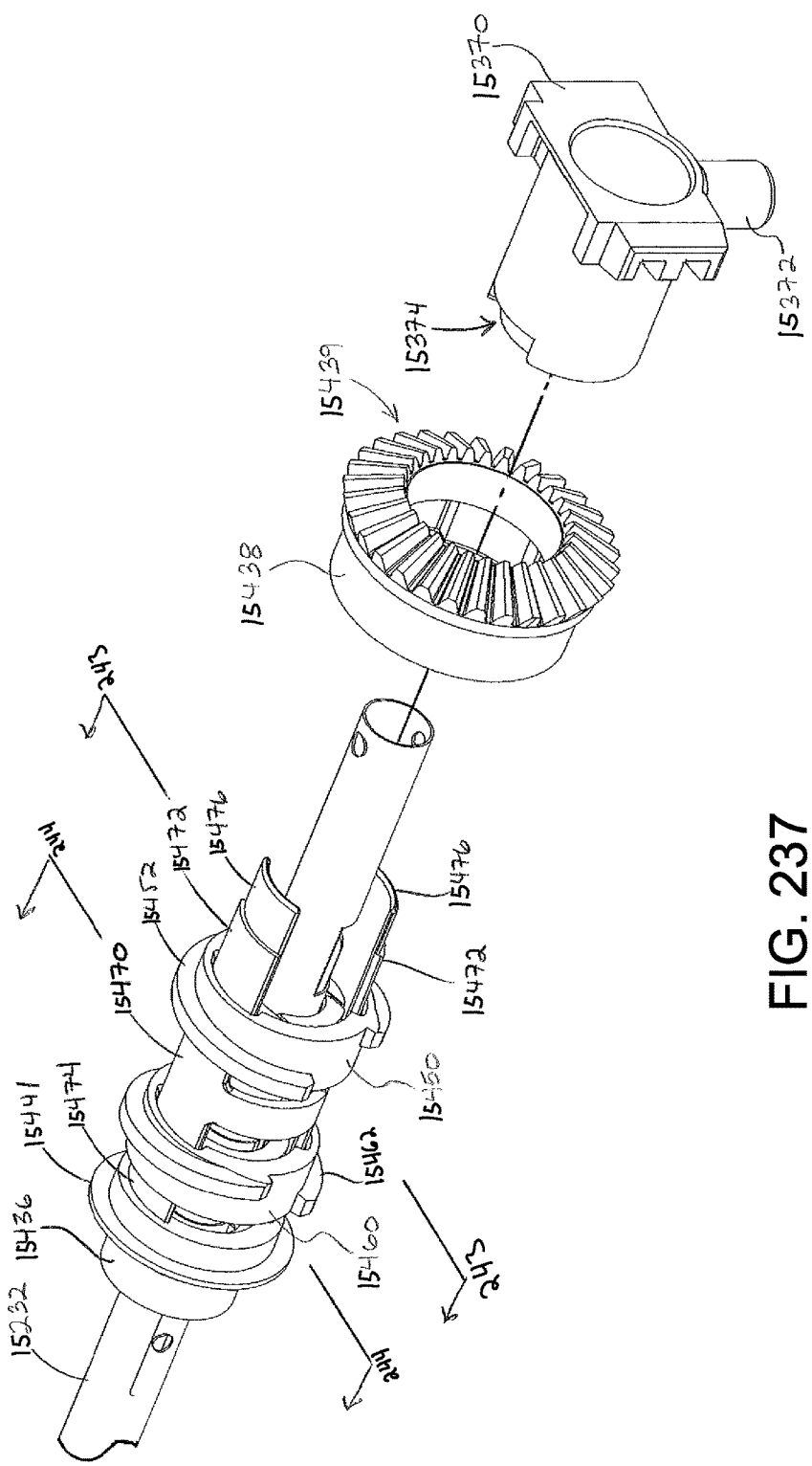
Figure 238:
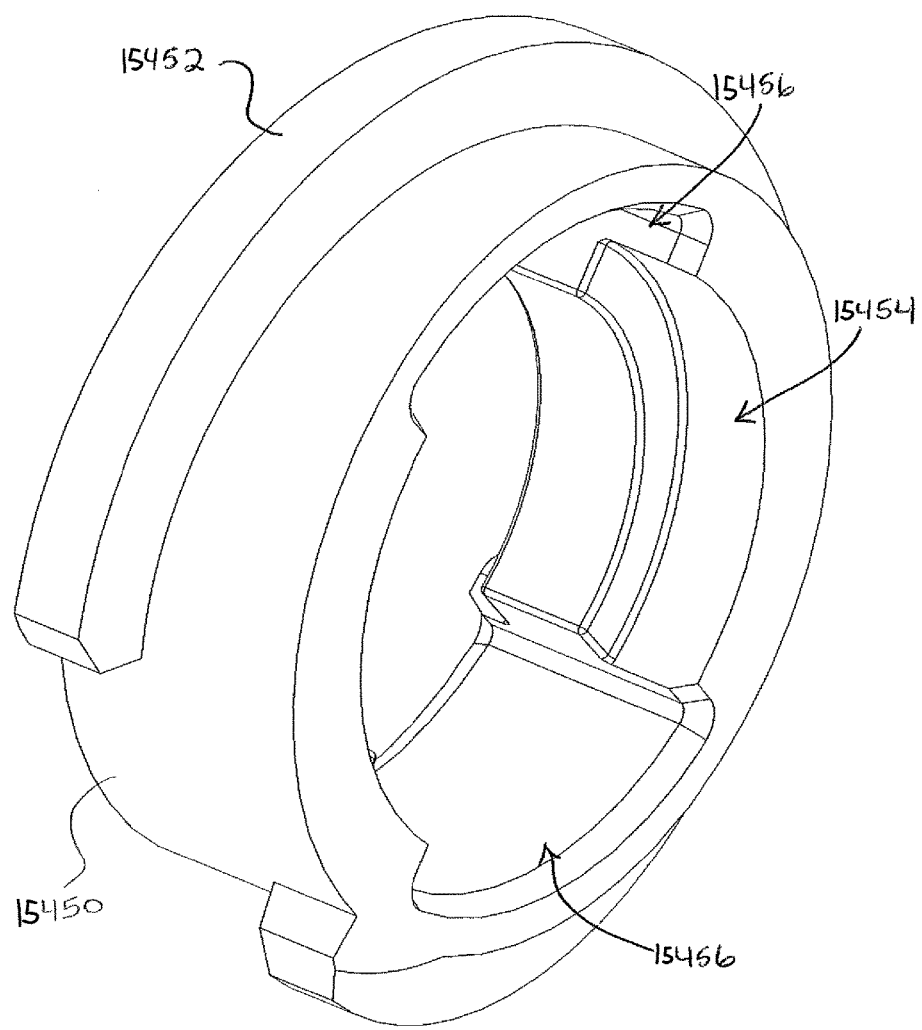
Figure 239:
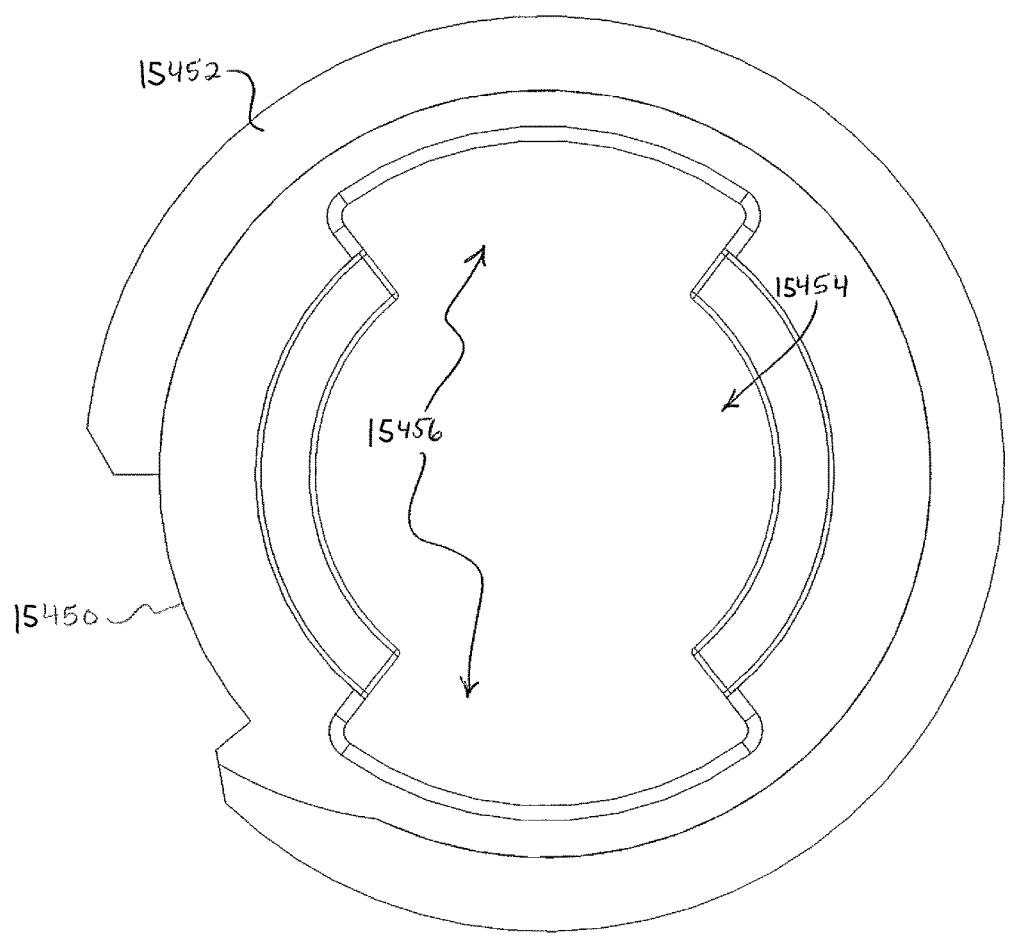
Figure 240:
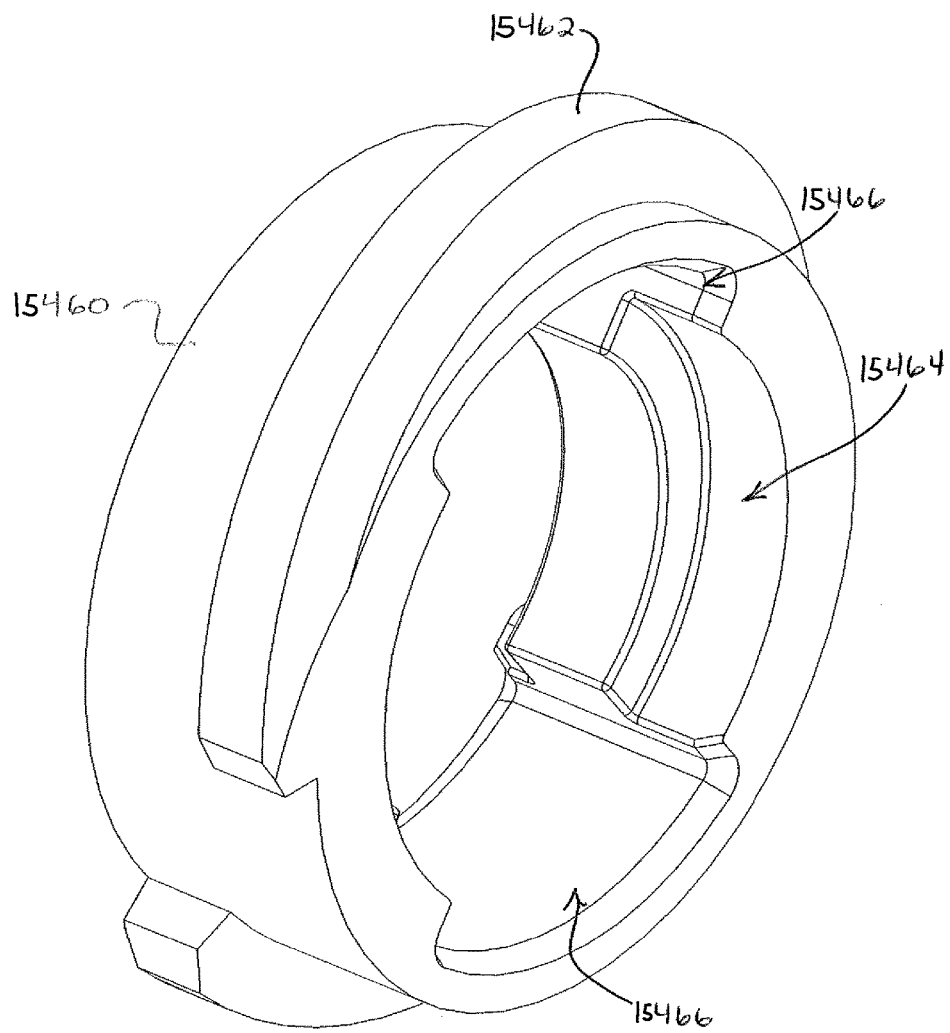
Figure 241:
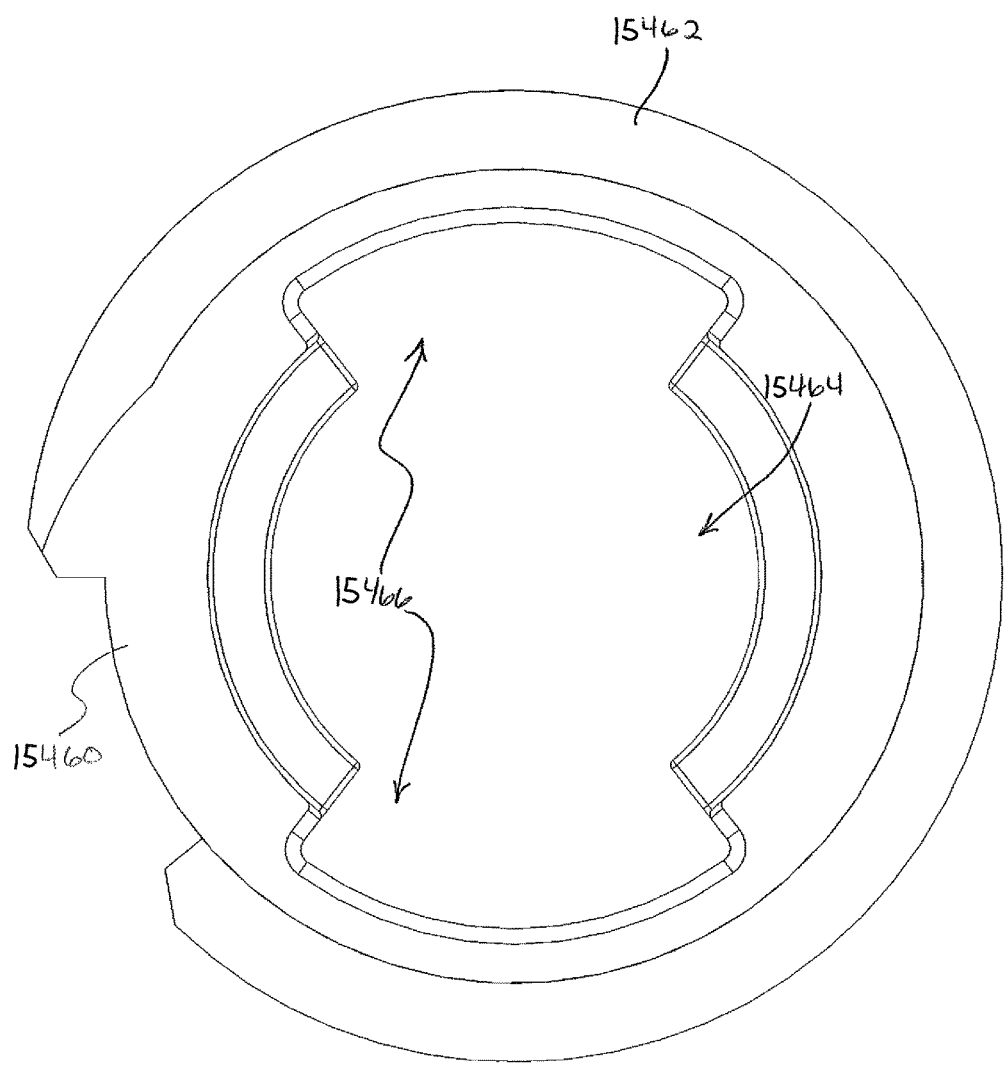
Figure 242A:
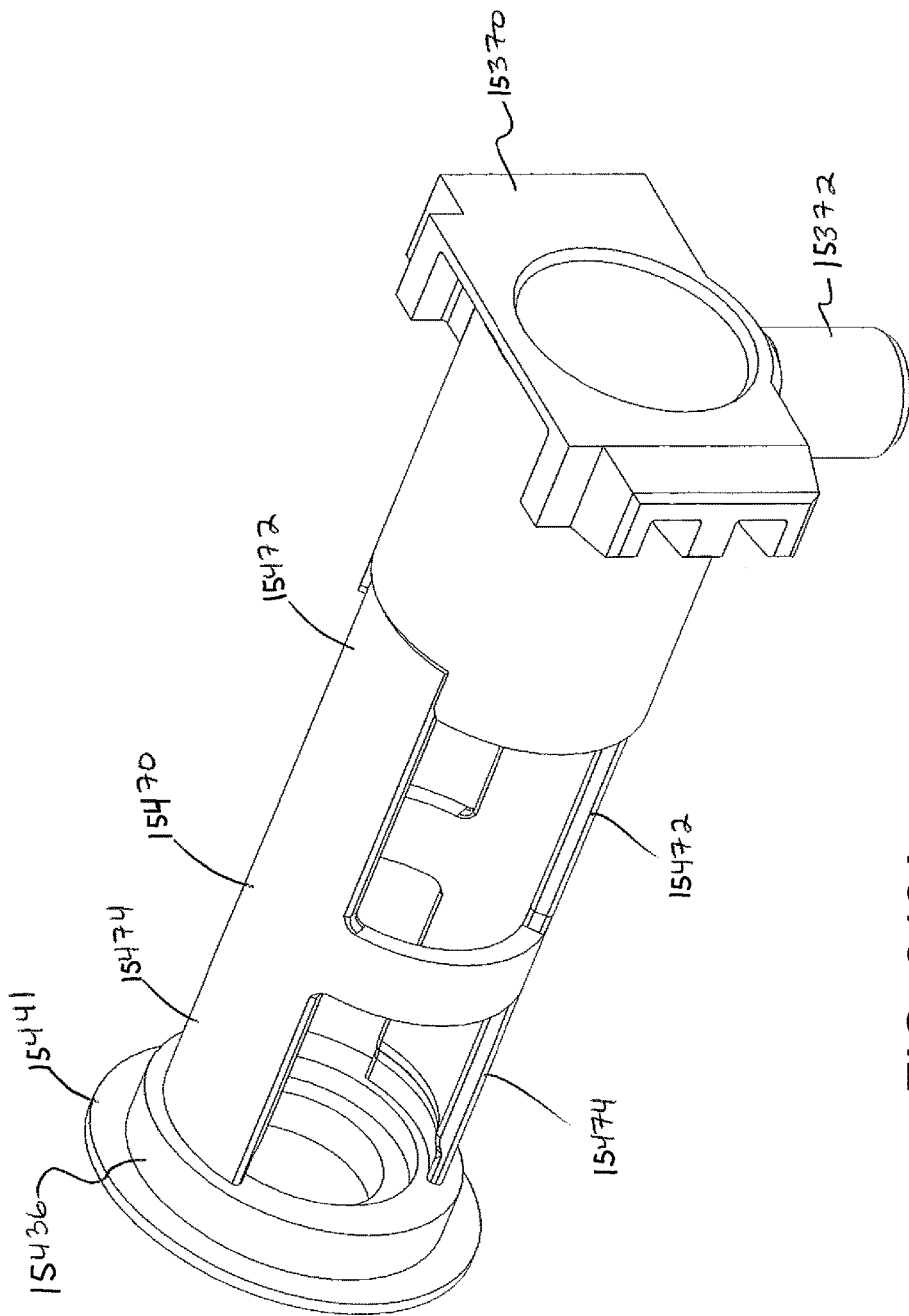
Figure 242B:
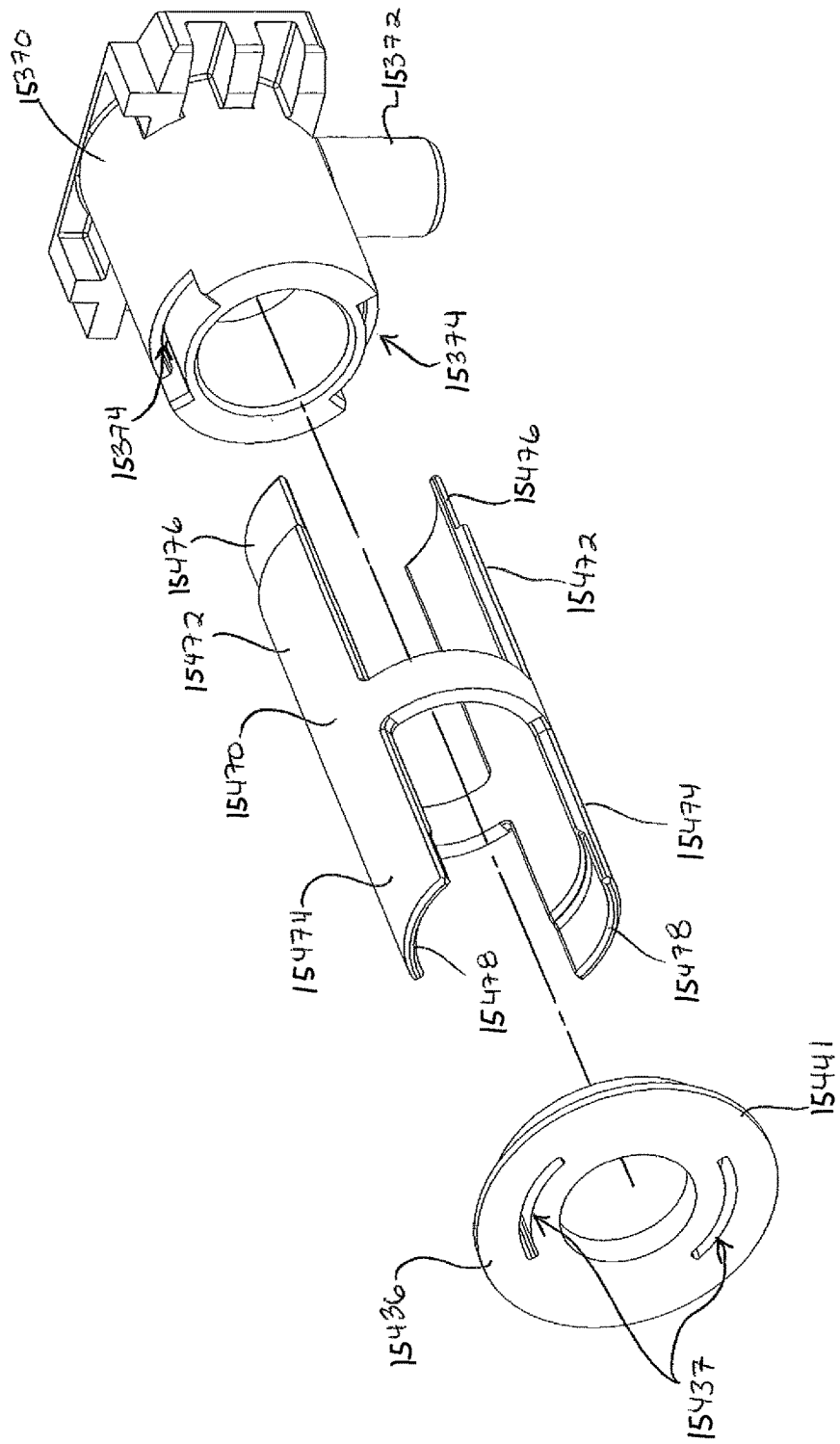
Figure 243:
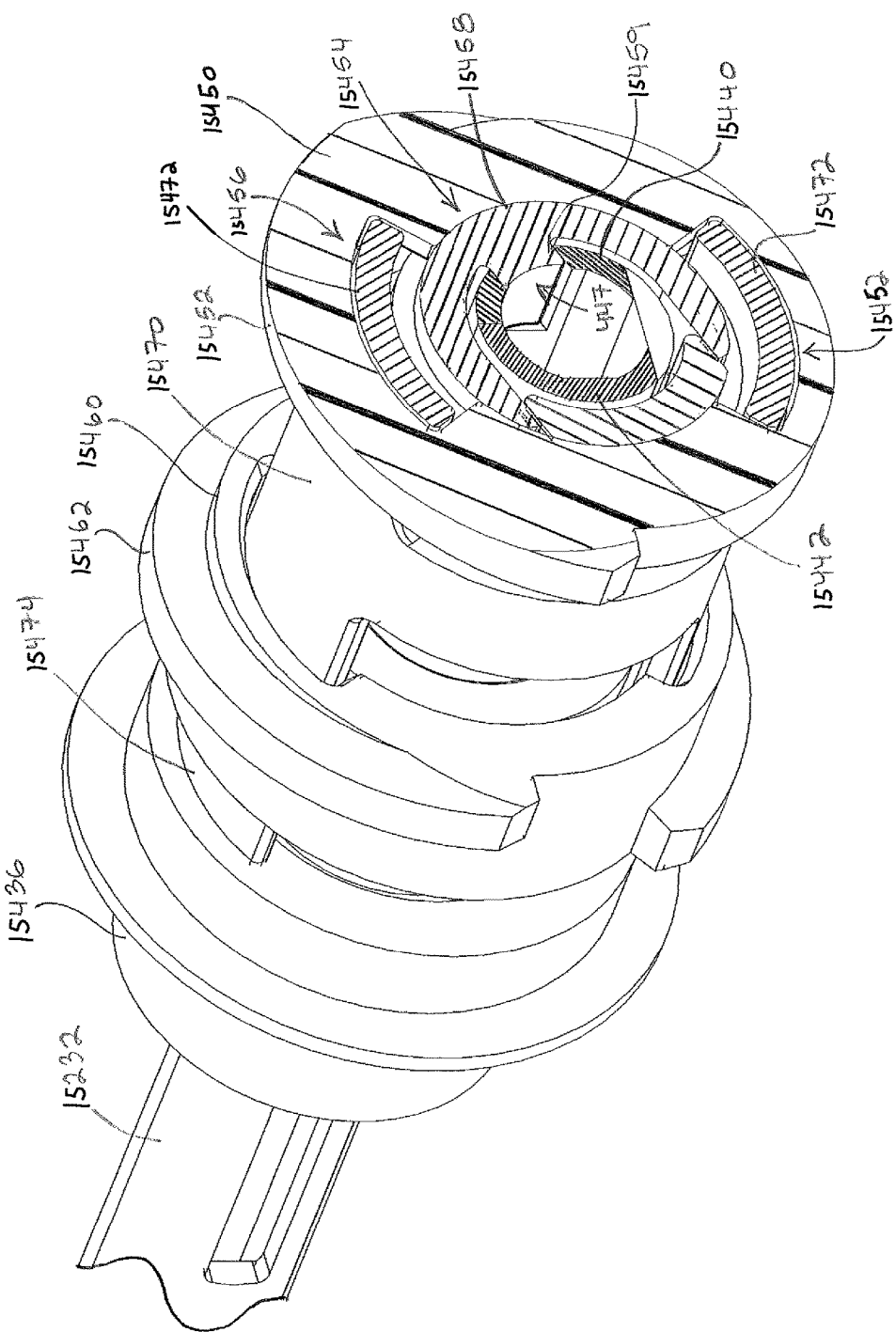
Figure 244:
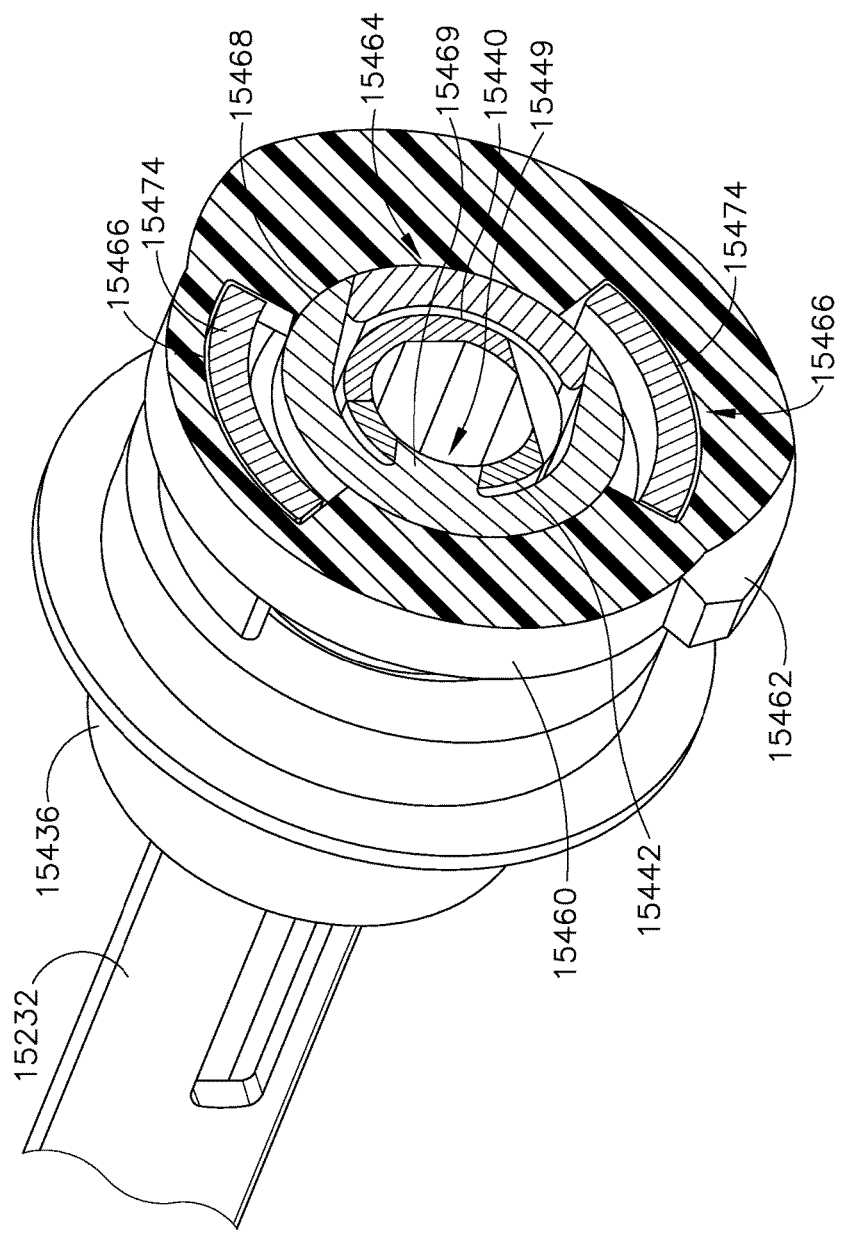
Figure 245A:
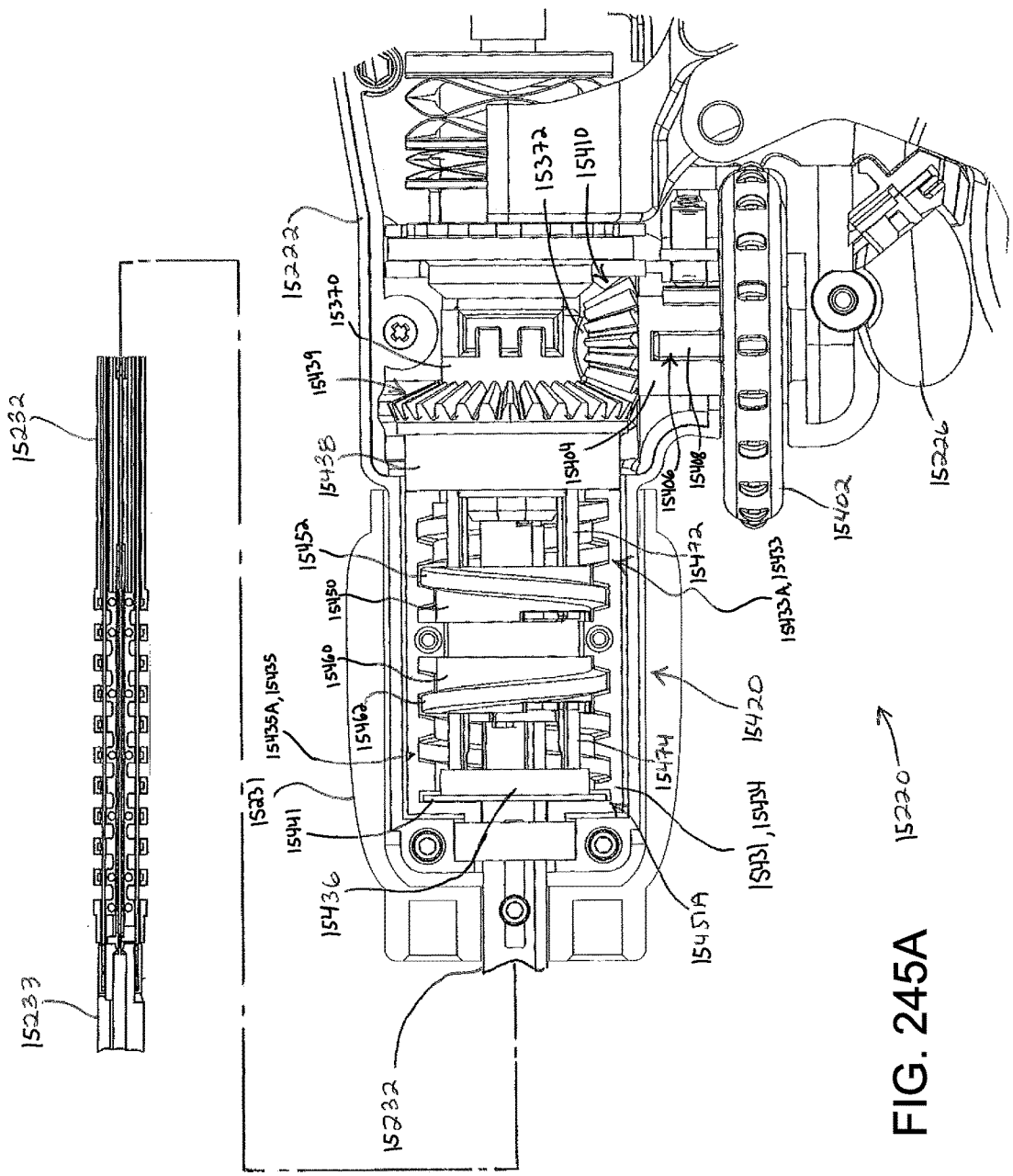
Figure 245B:
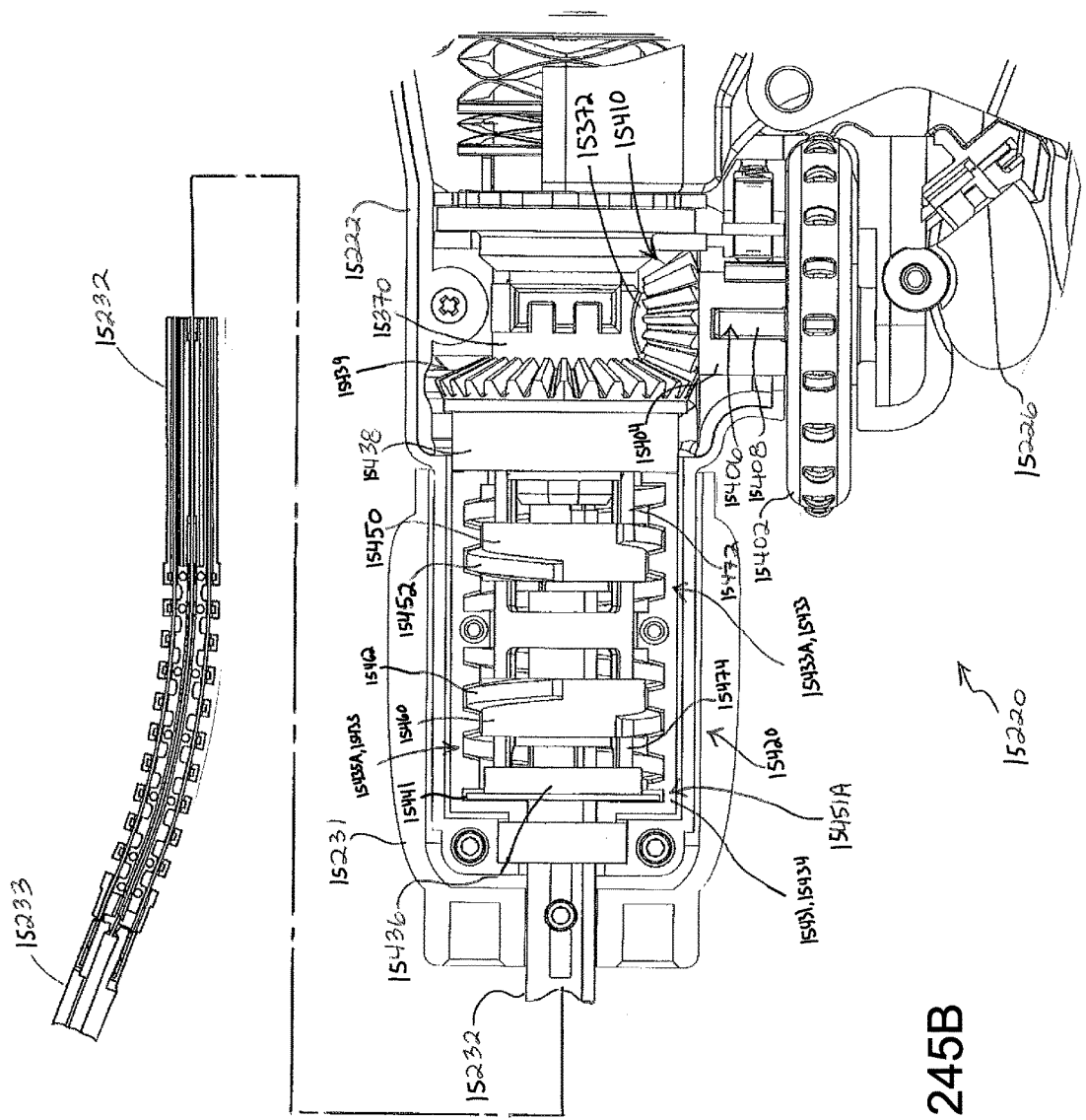
Figure 245C:
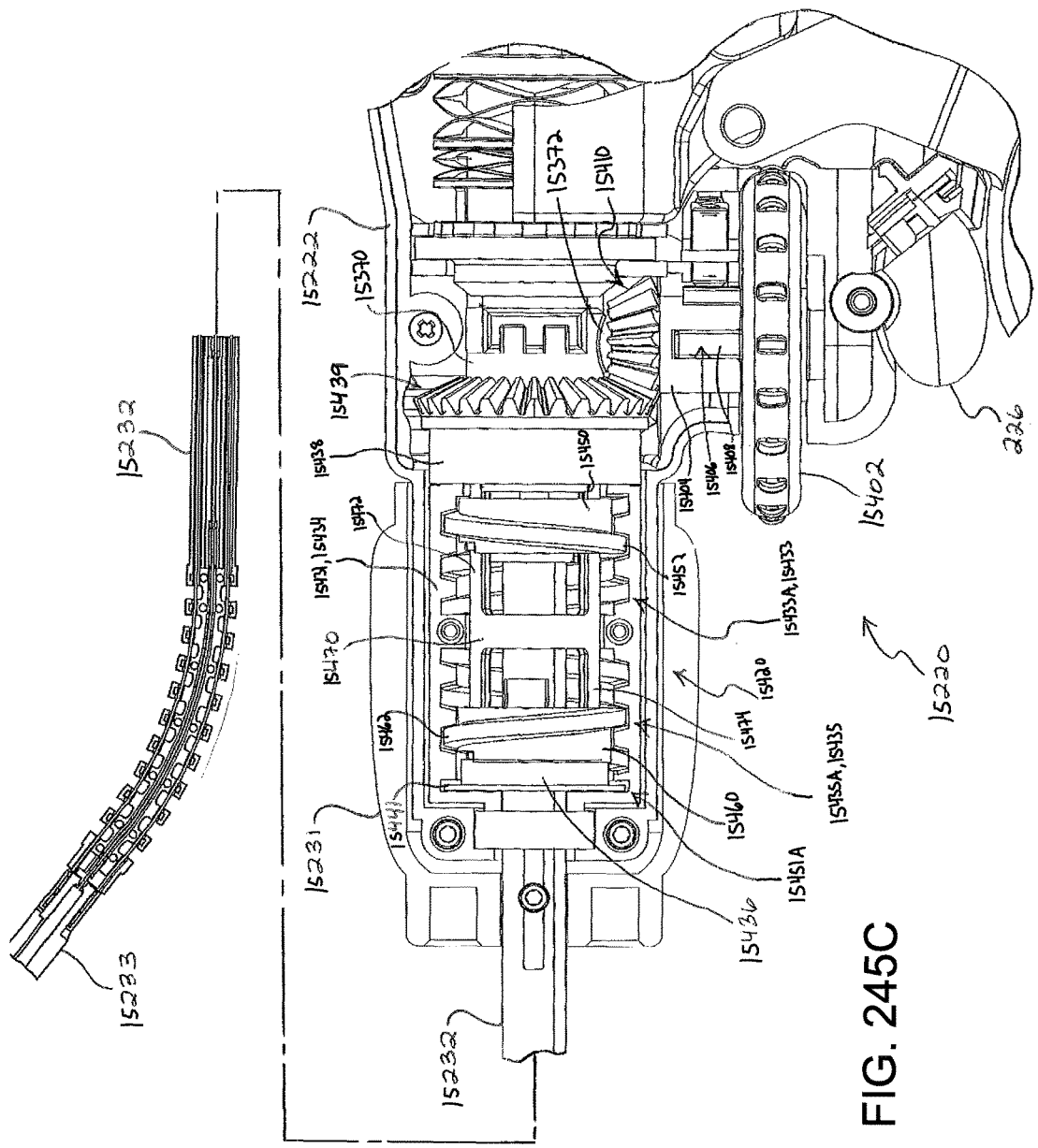
Figure 246:
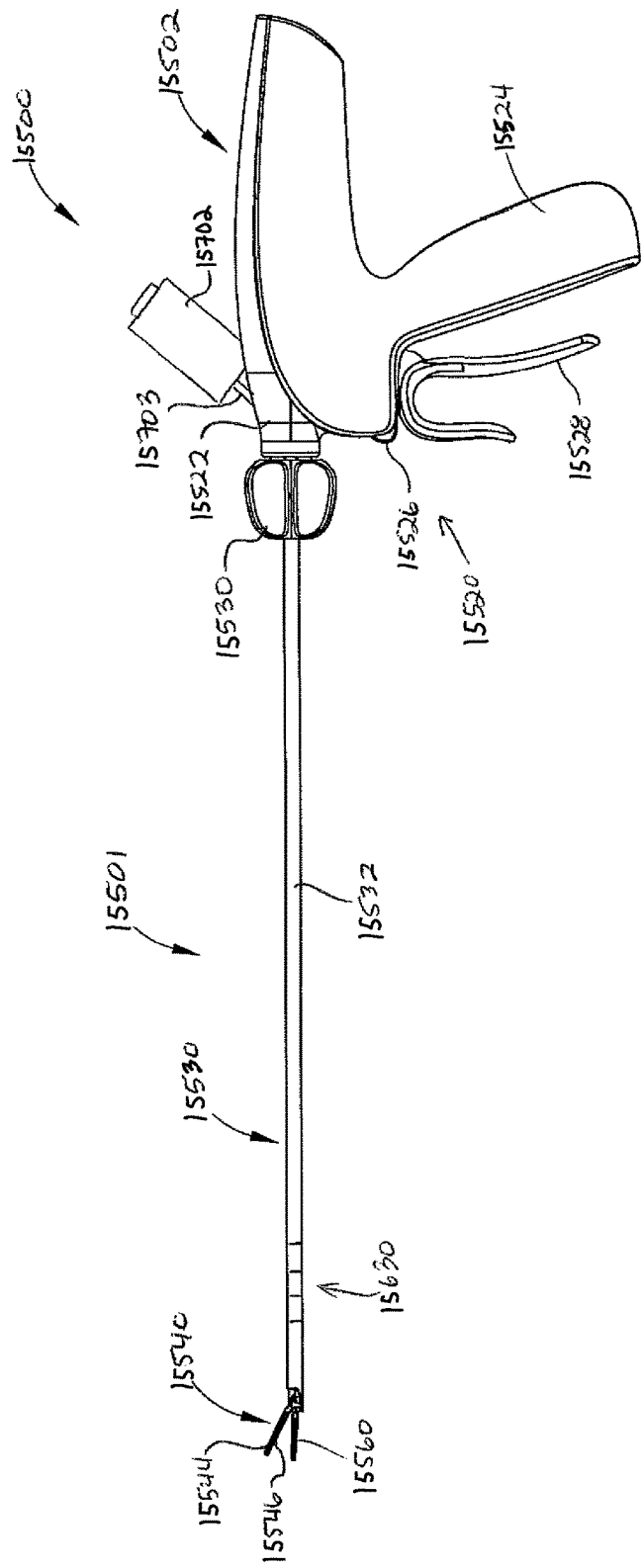
Figure 247:
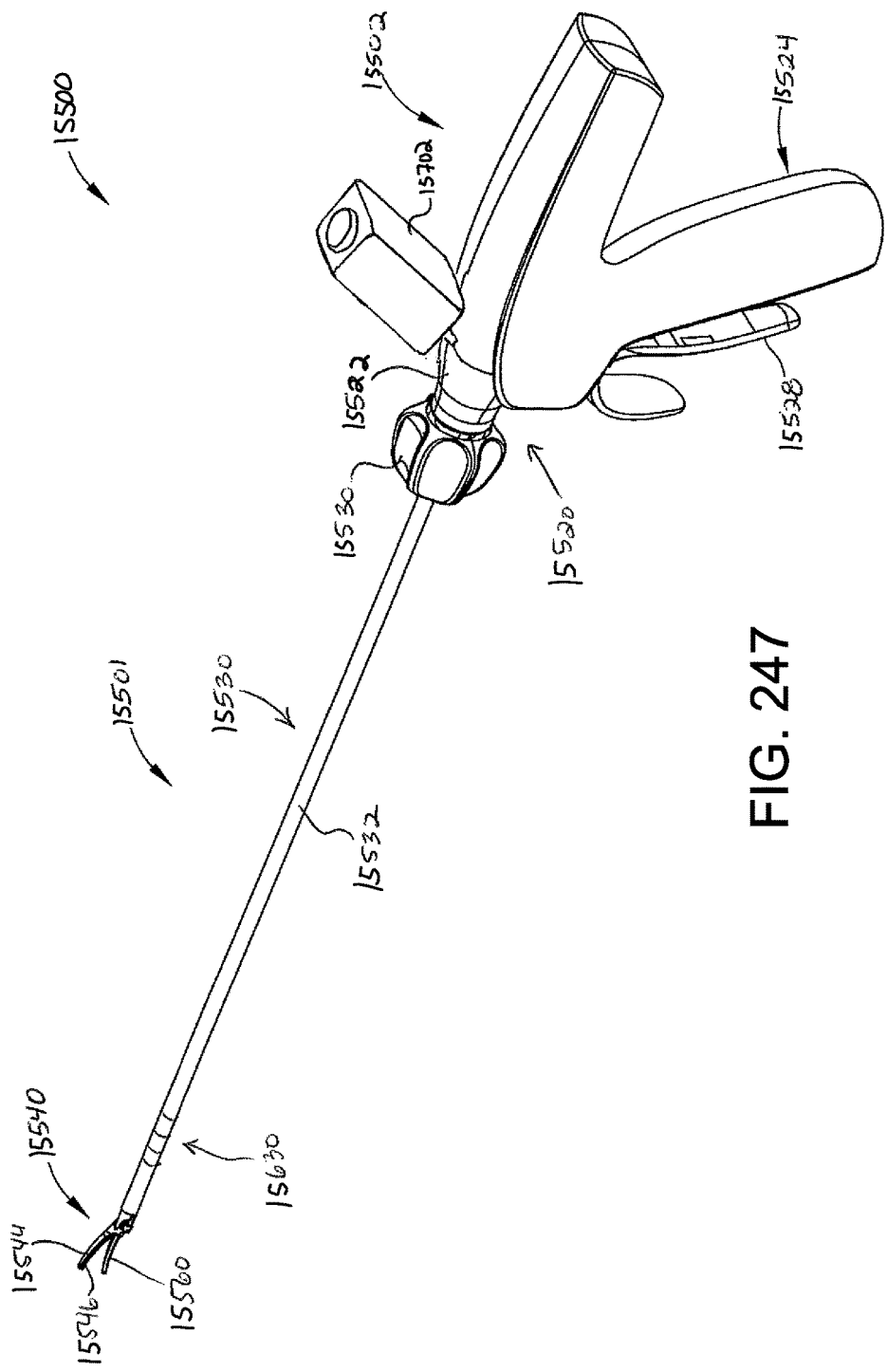
Figure 248:
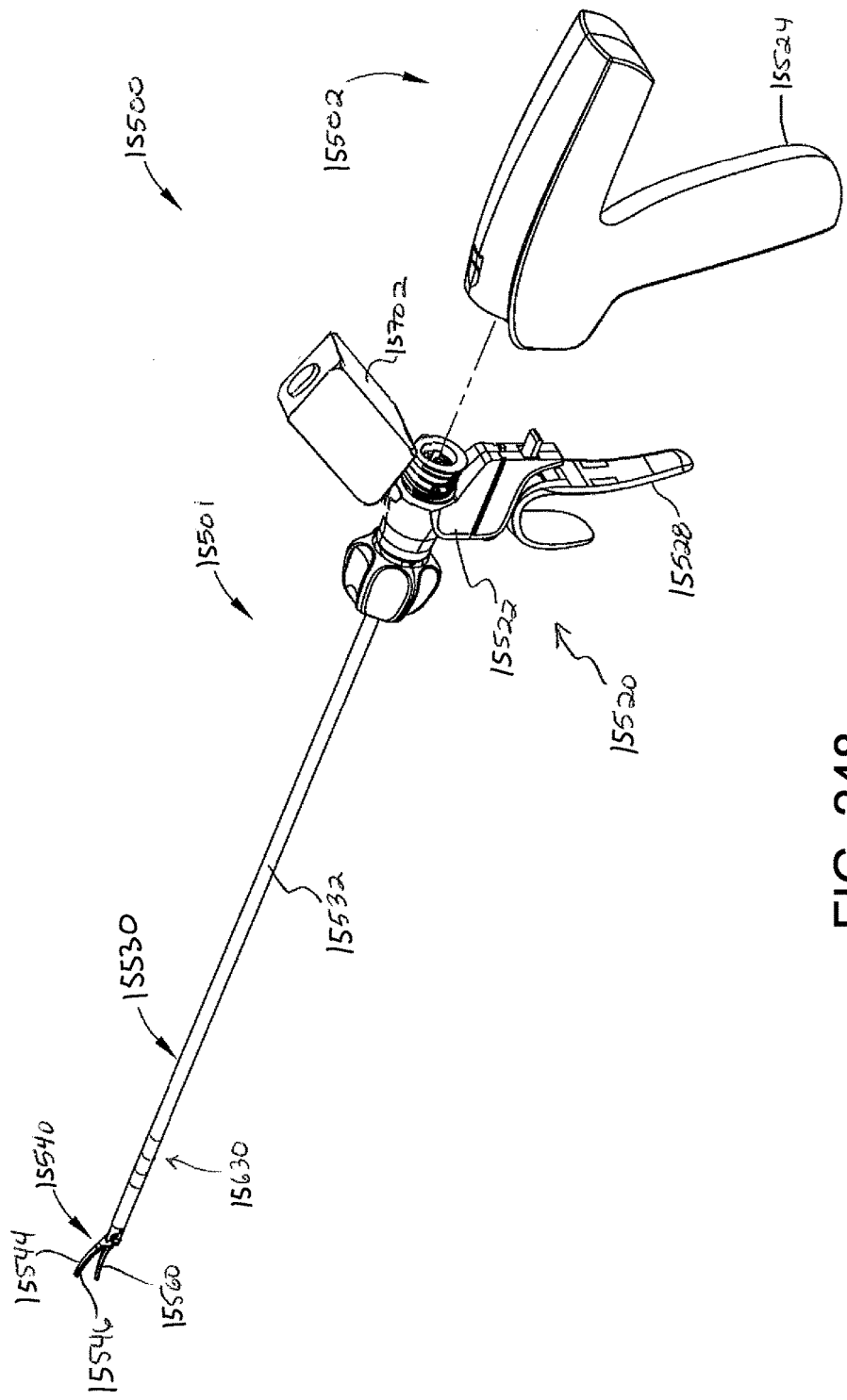
Figure 249:
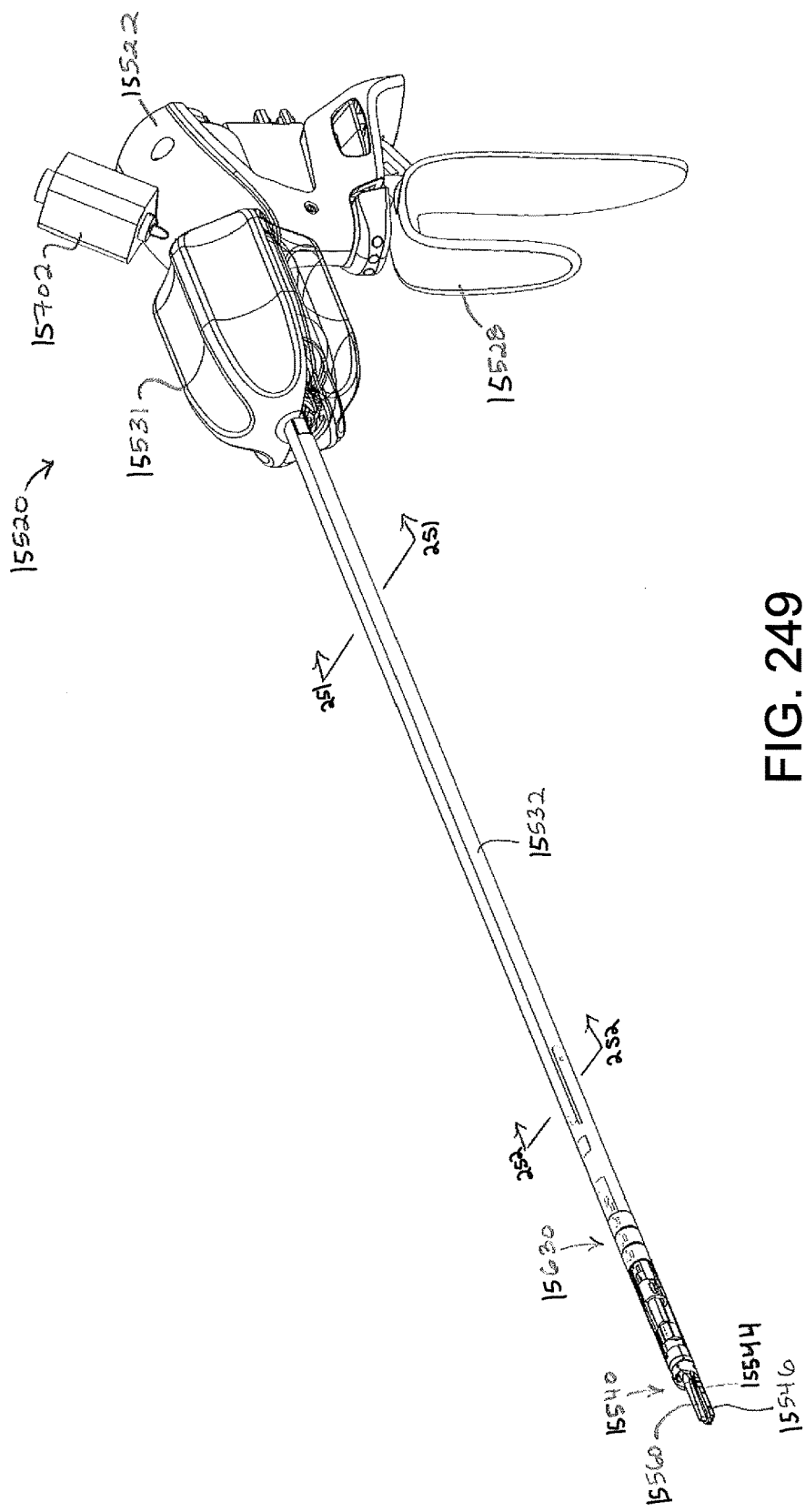
Figure 250:
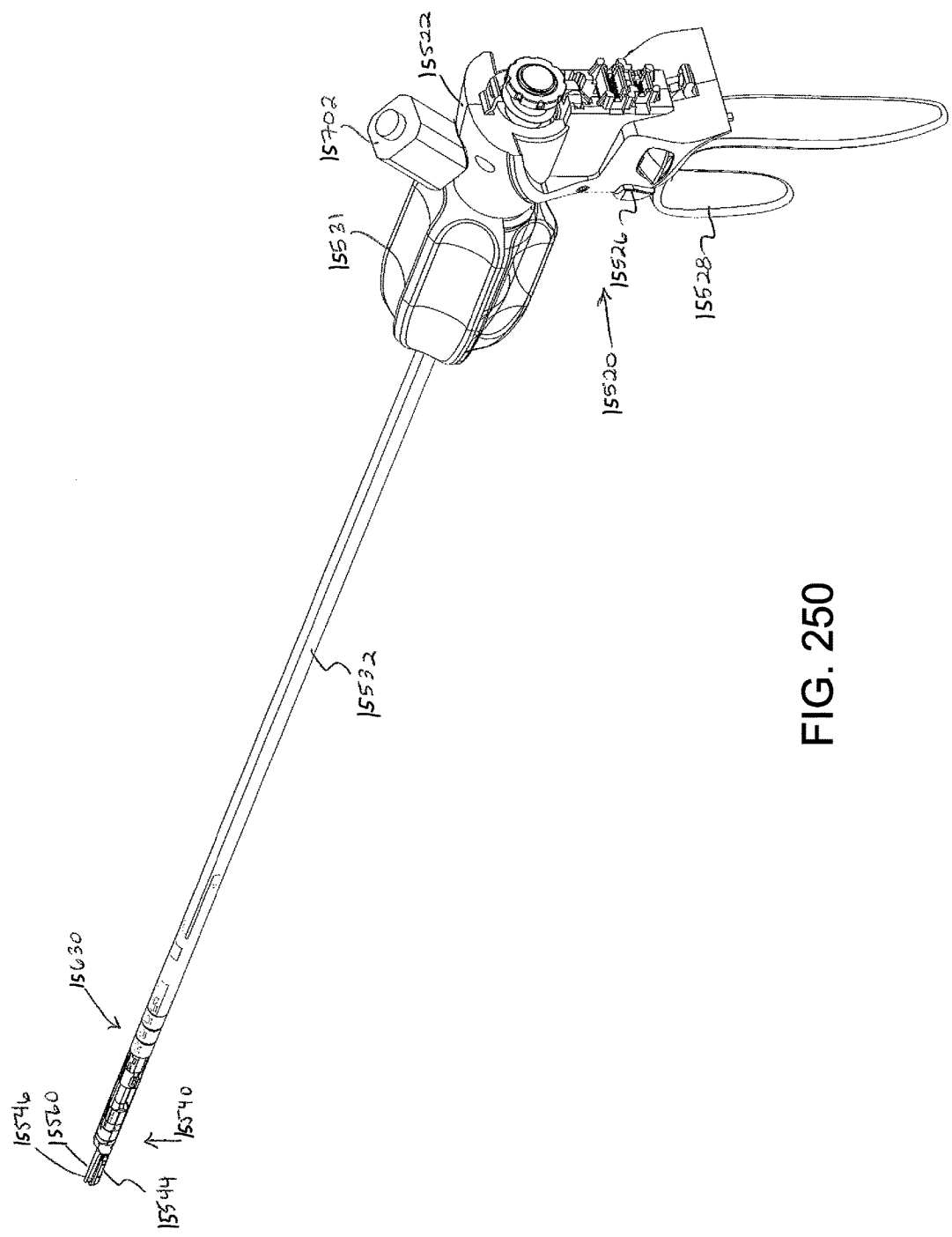
Figure 251:
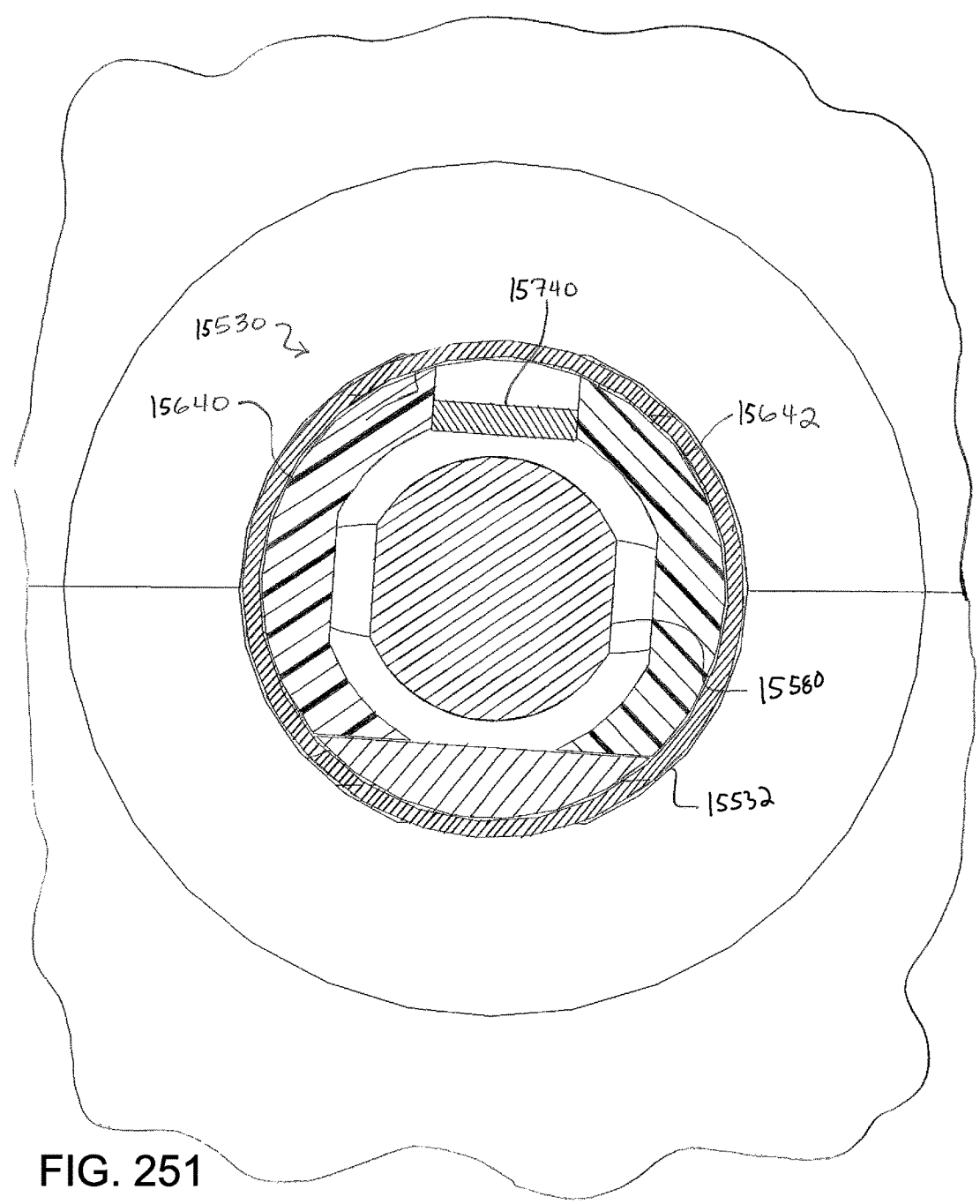
Figure 252:
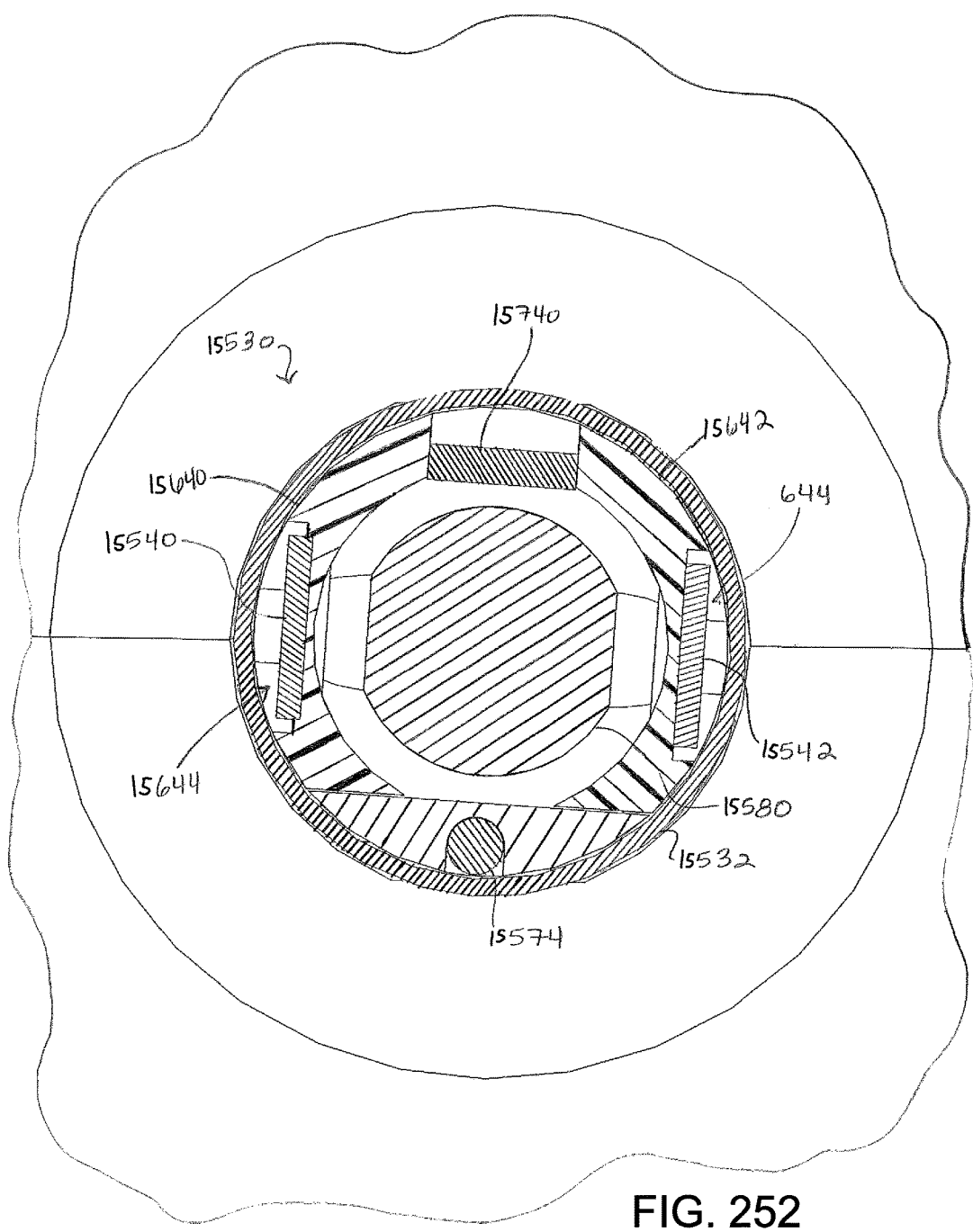
Figure 253:
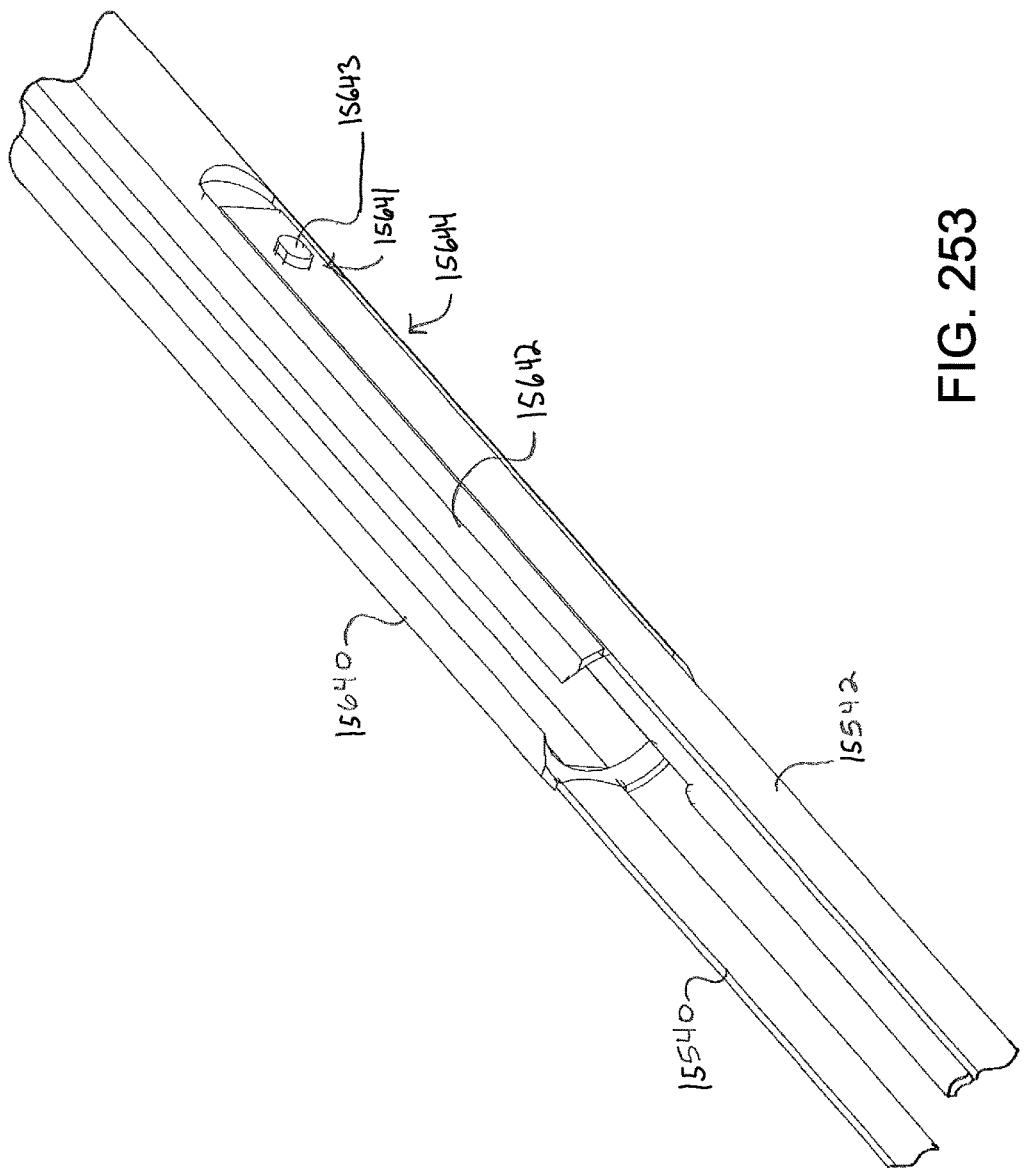
Figure 254:
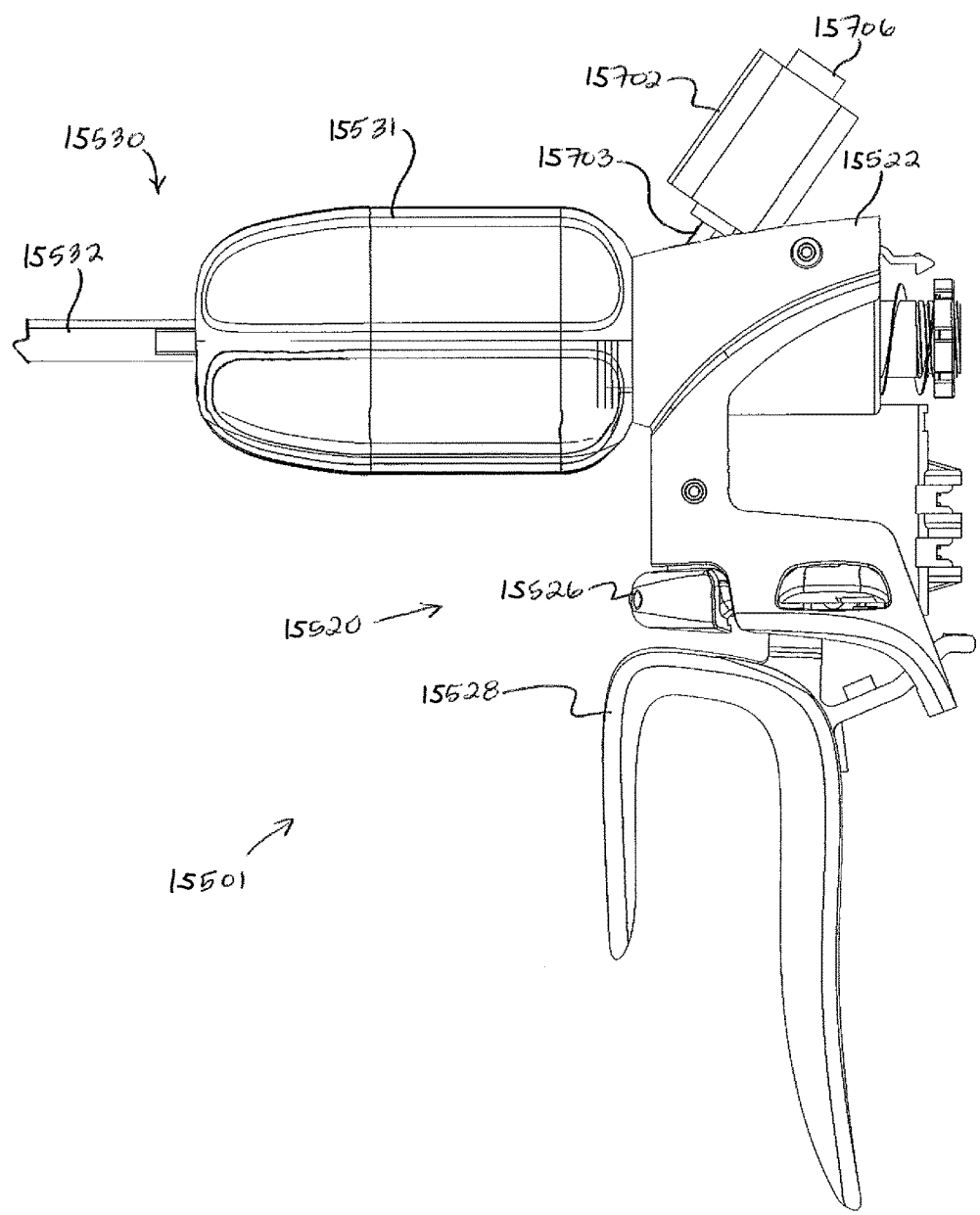
Figure 255:
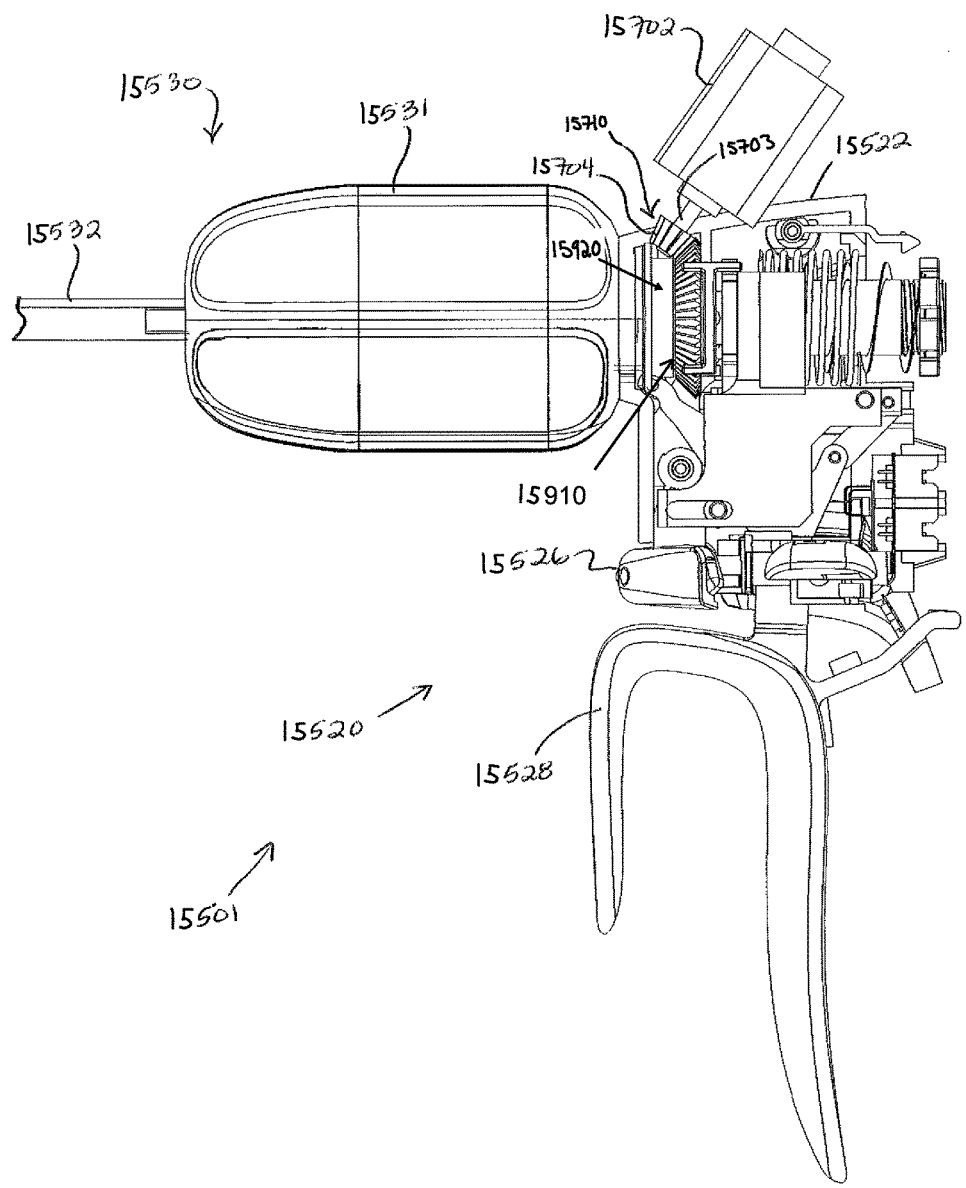
Figure 256:
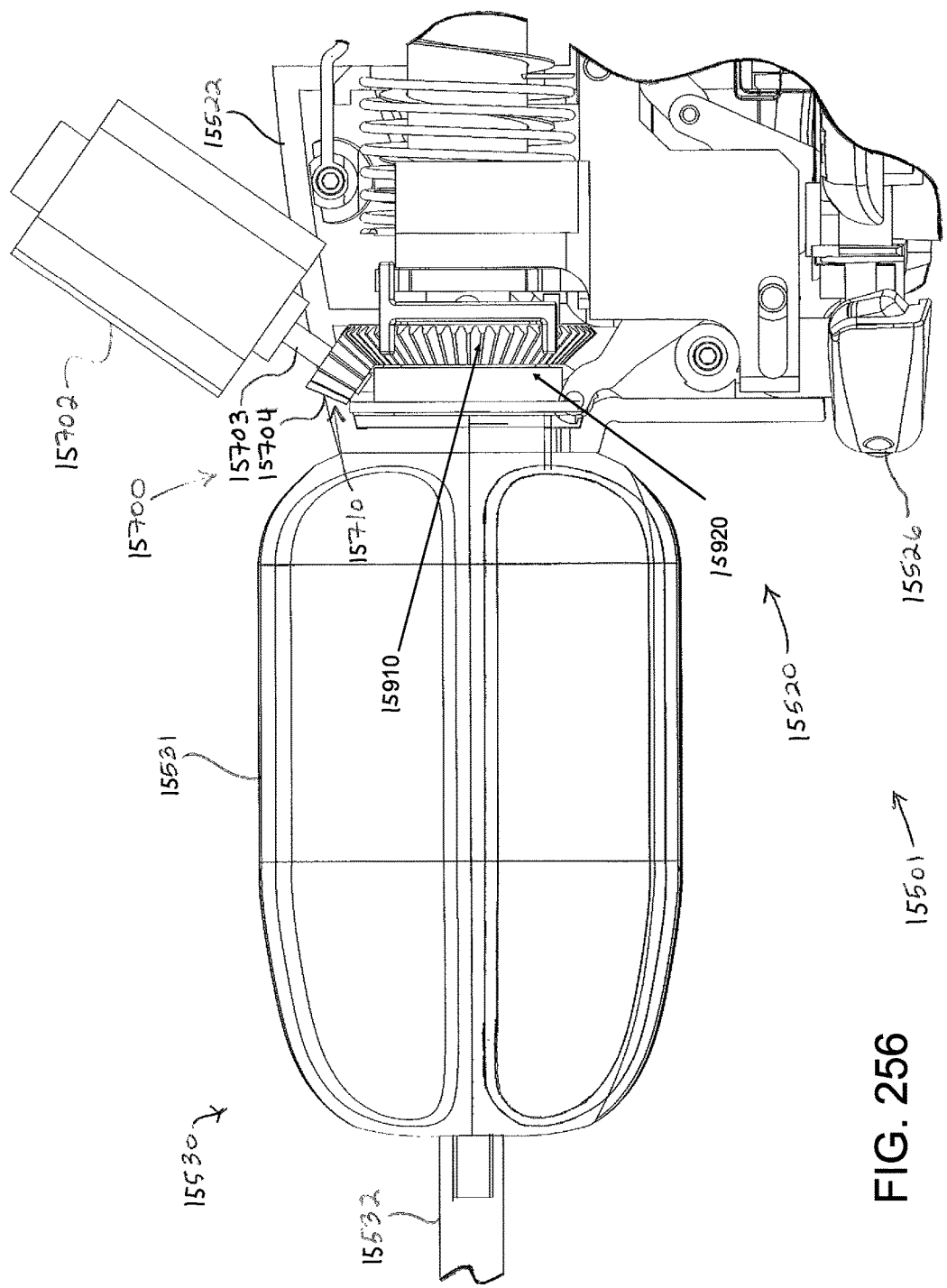
Figure 257:
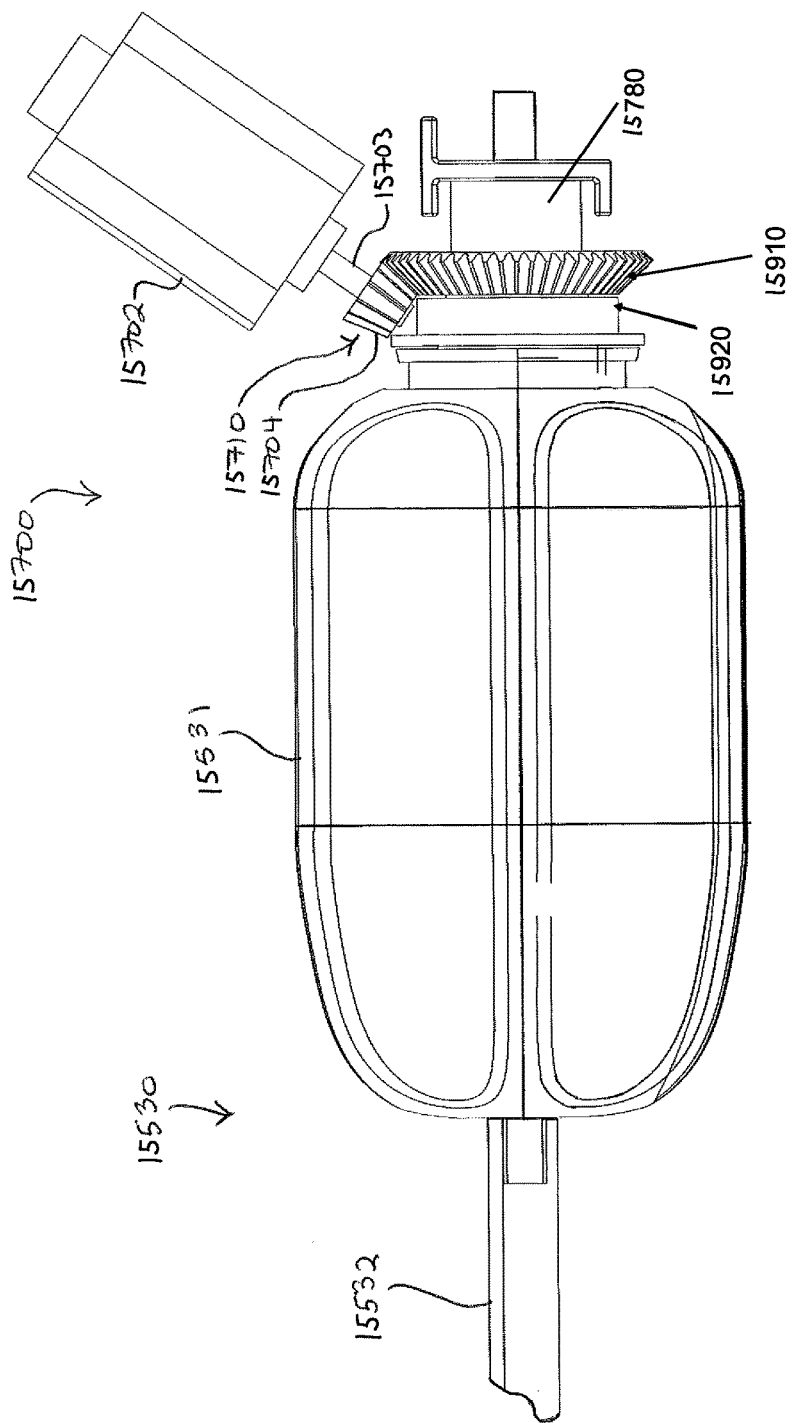
Figure 258:
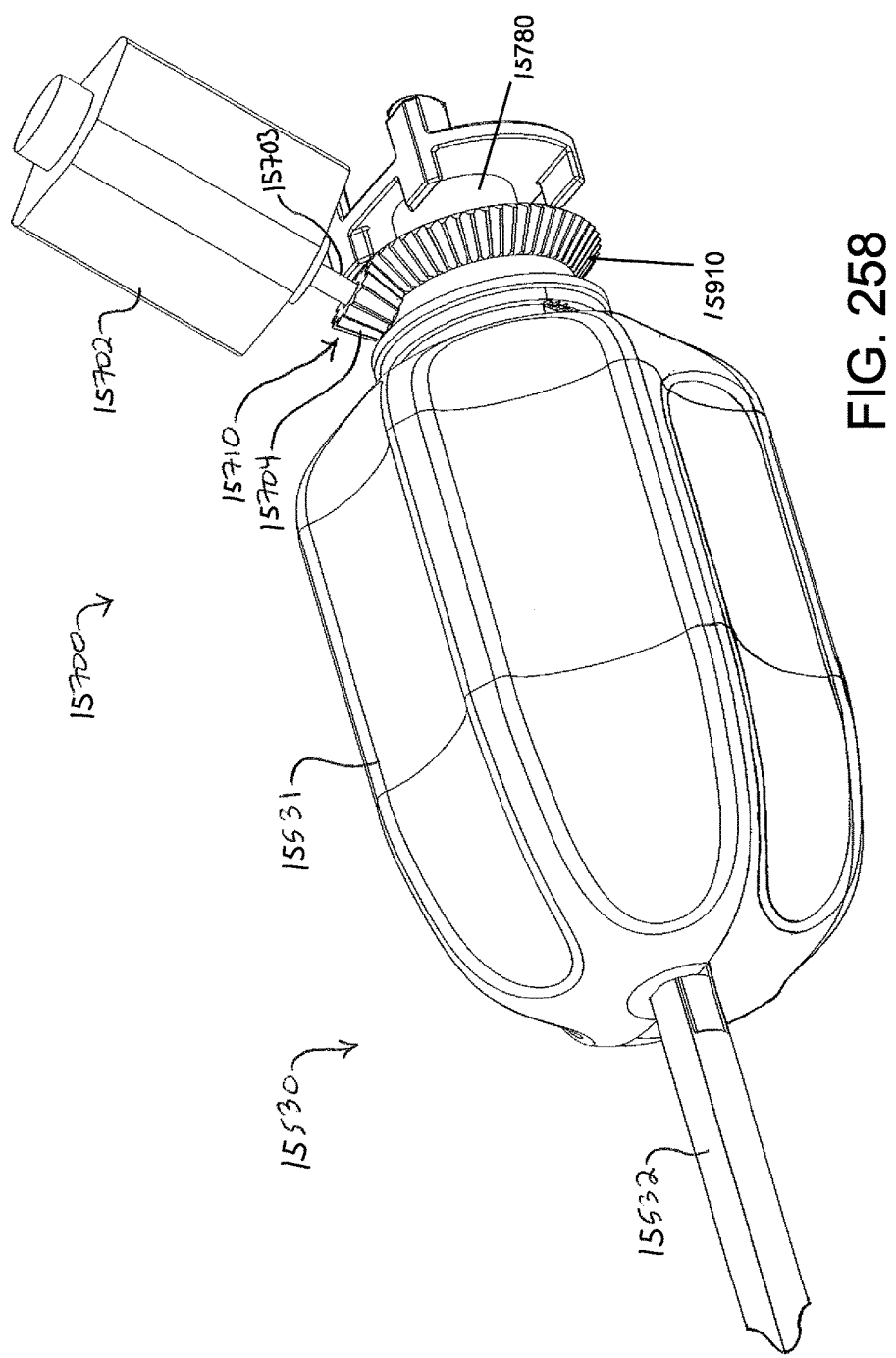
Figure 259A:
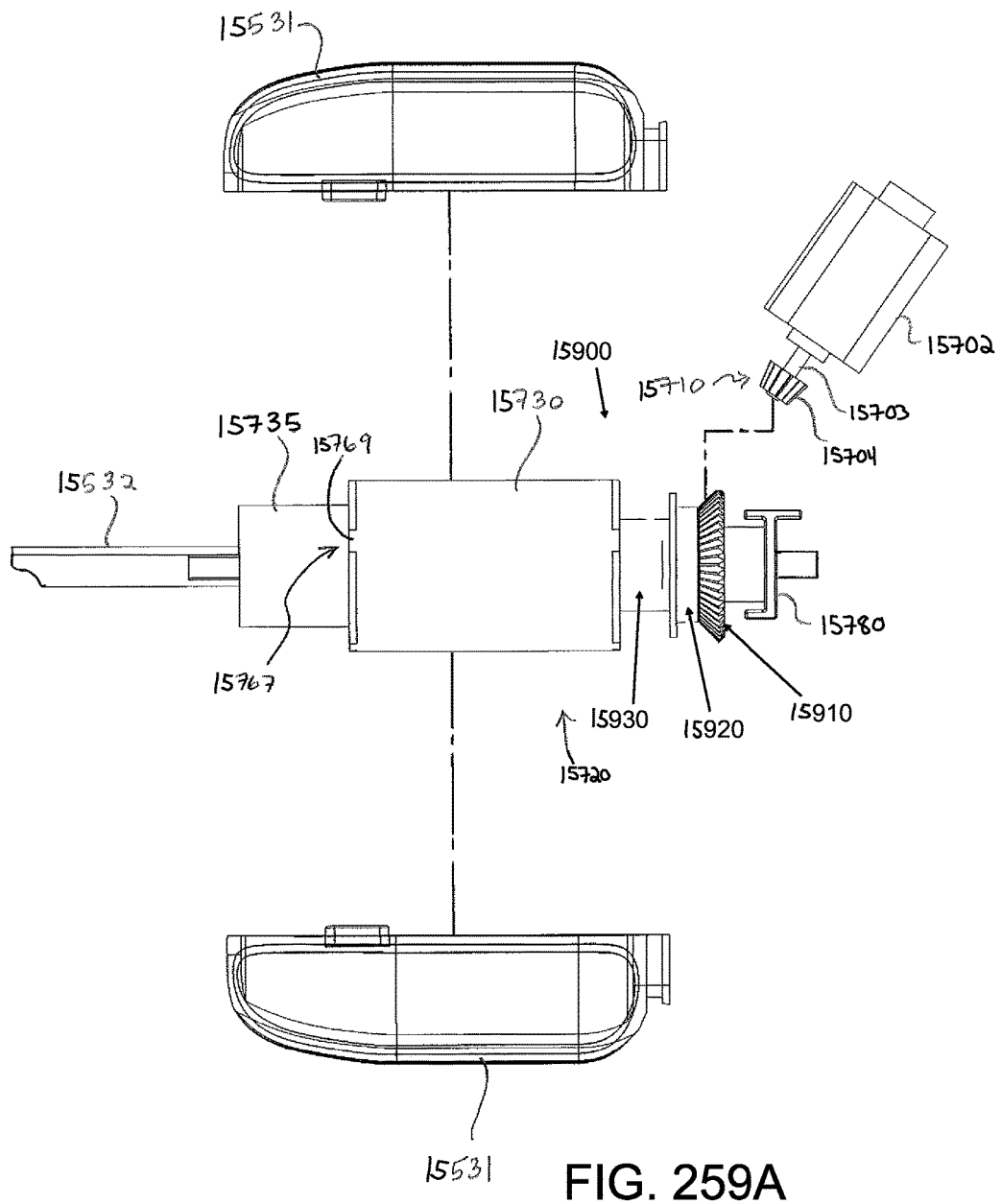
Figure 259B:
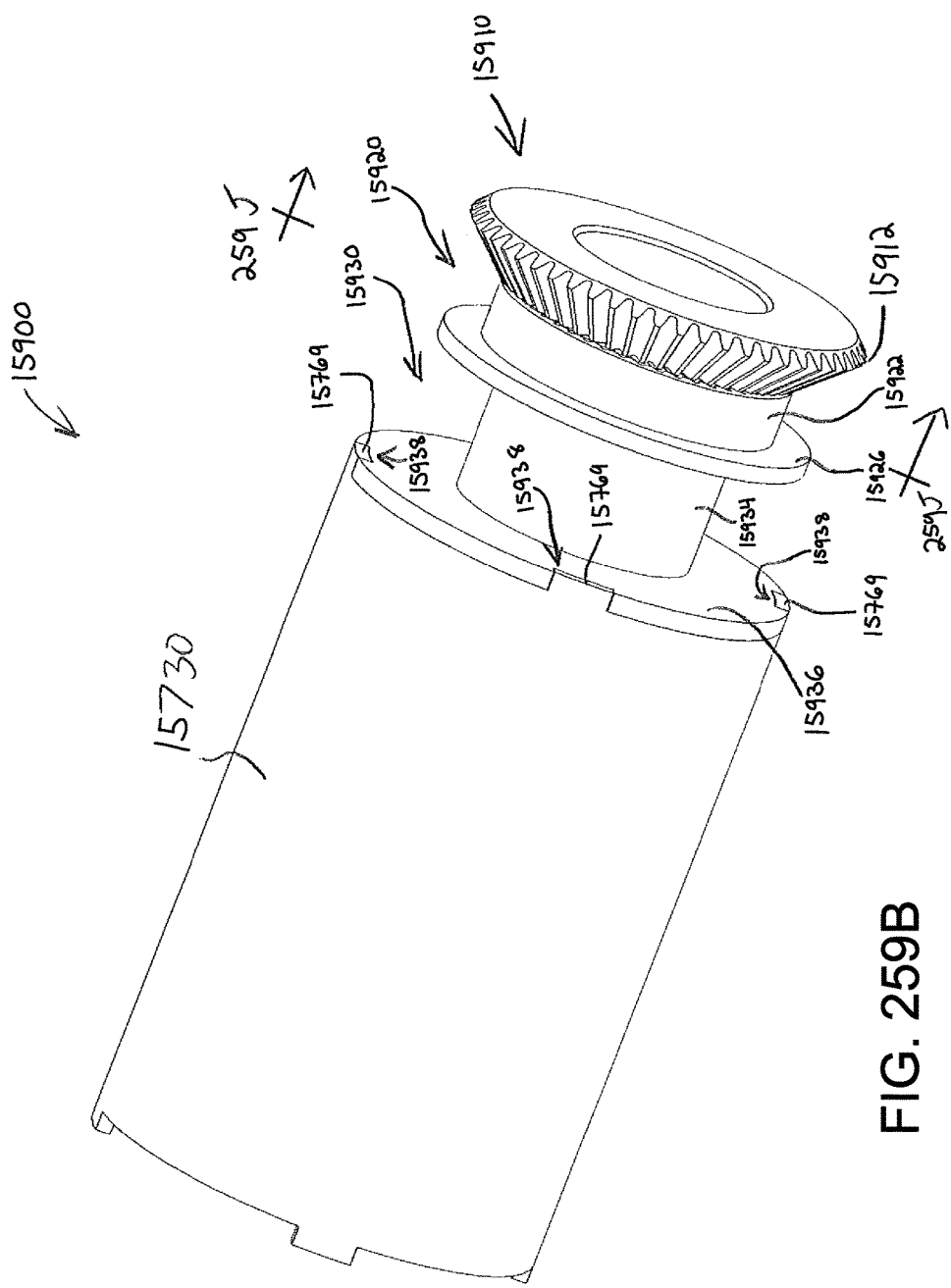
Figure 259C:
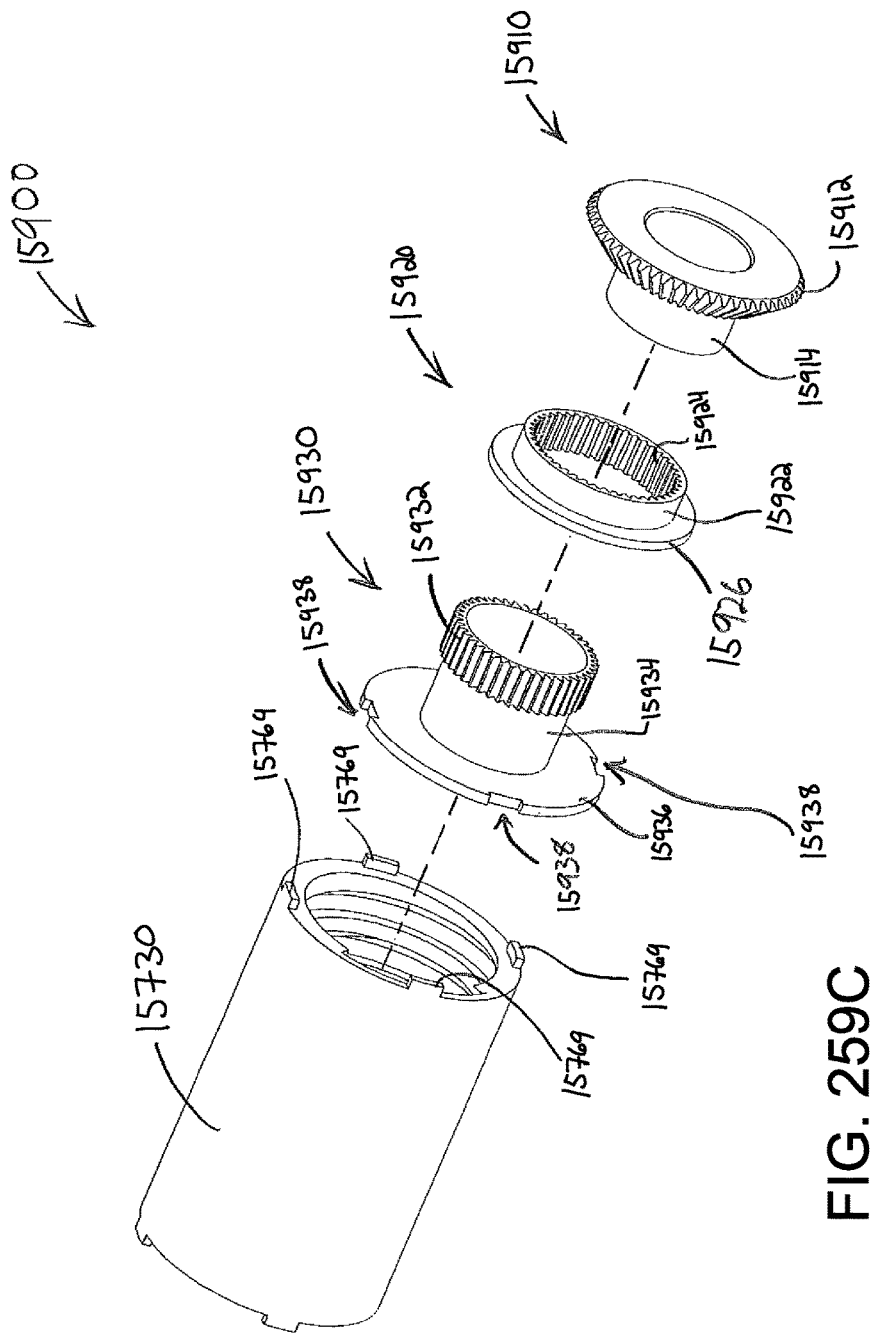
Figure 259D:
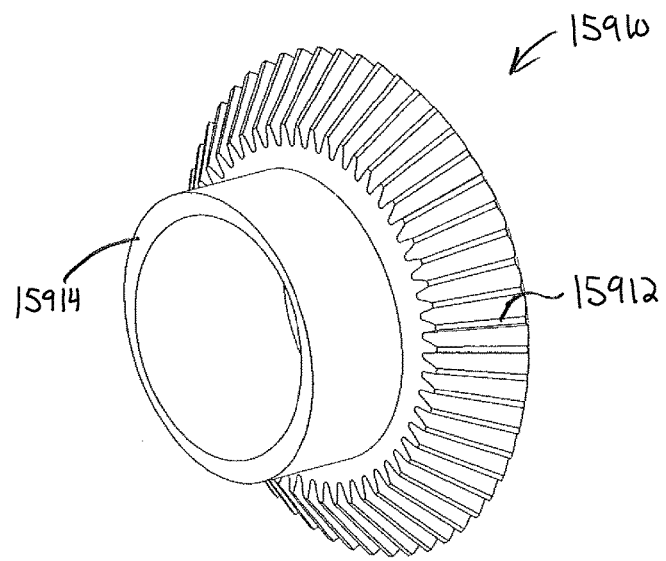
Figure 259E:
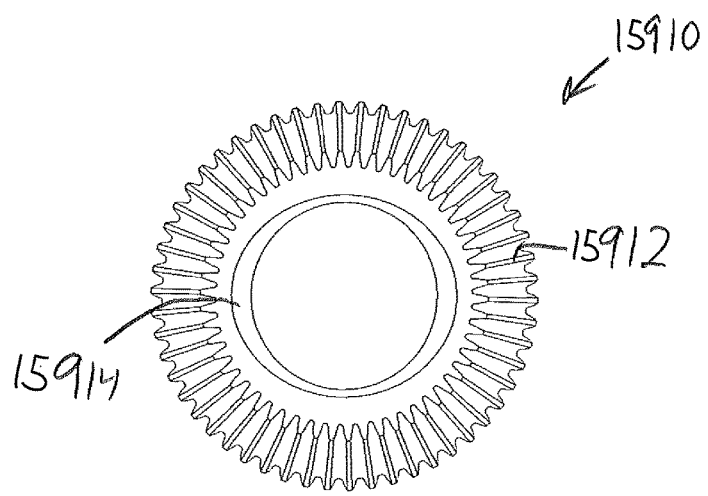
Figure 259F:
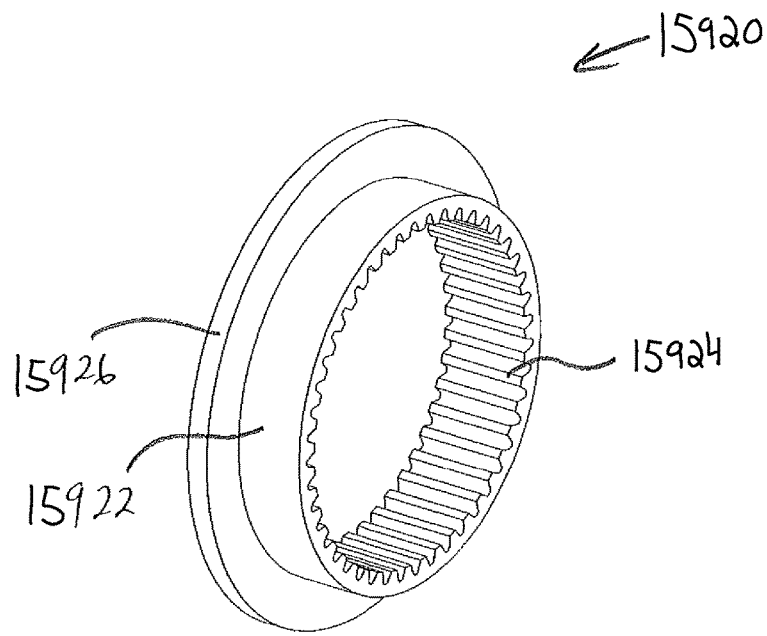
Figure 259G:
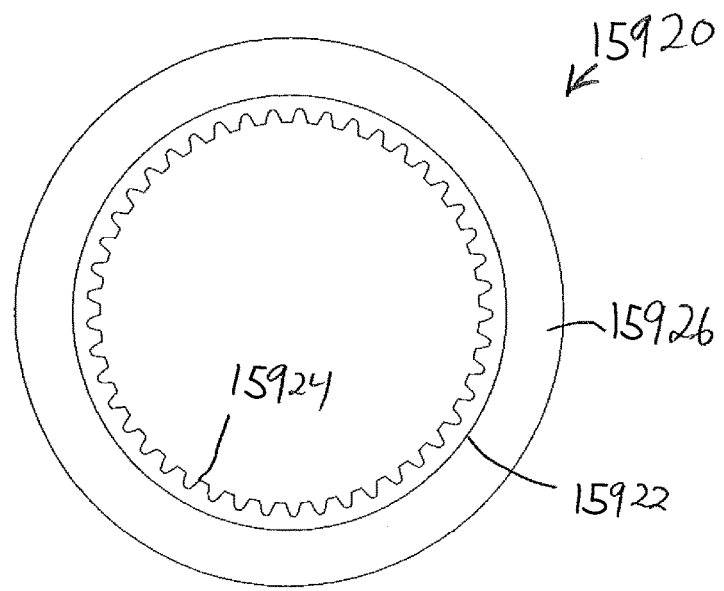
Figure 259H:
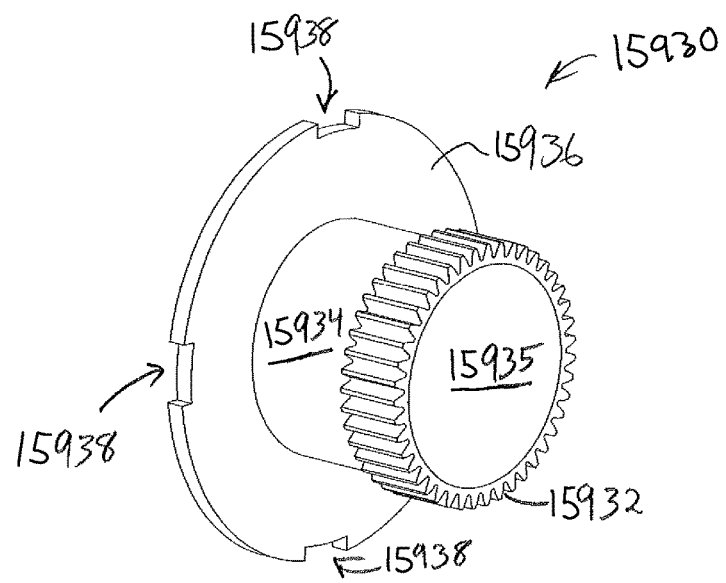
Figure 259I:
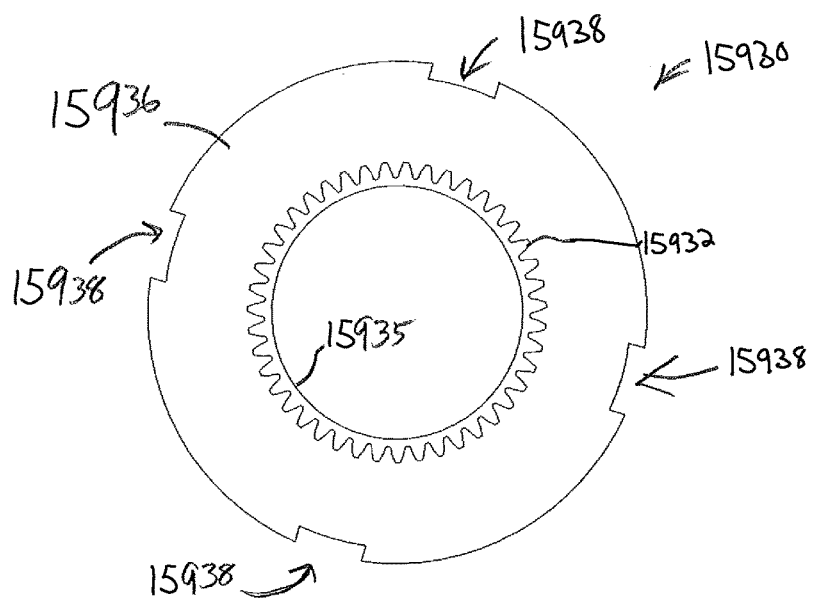
Figure 259J:
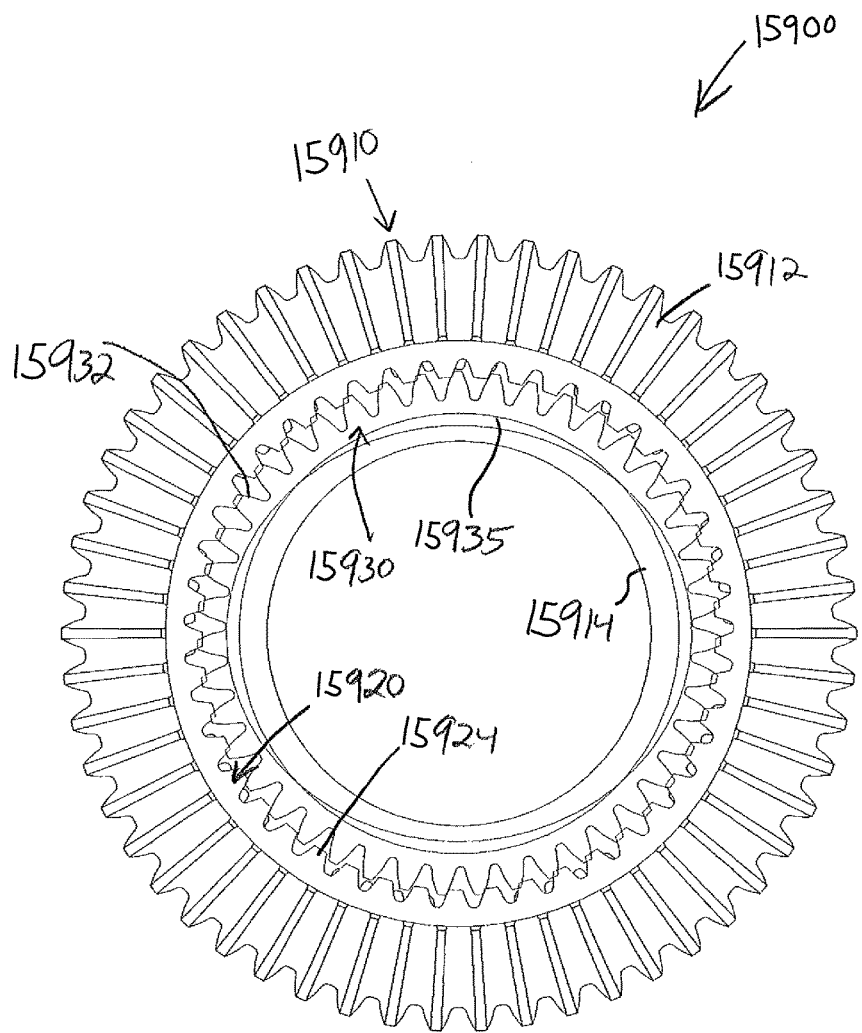
Figure 260:
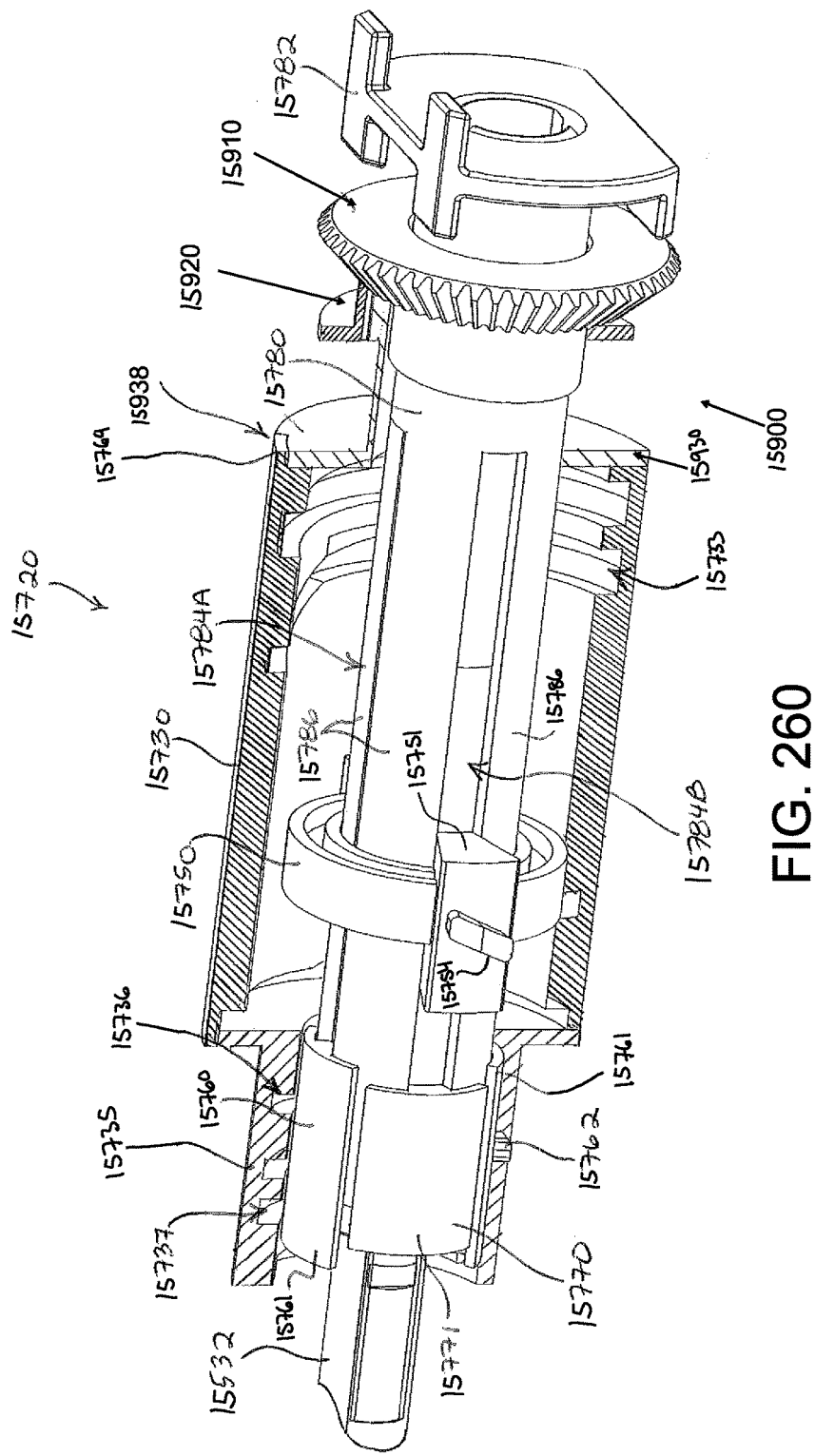
Figure 261:
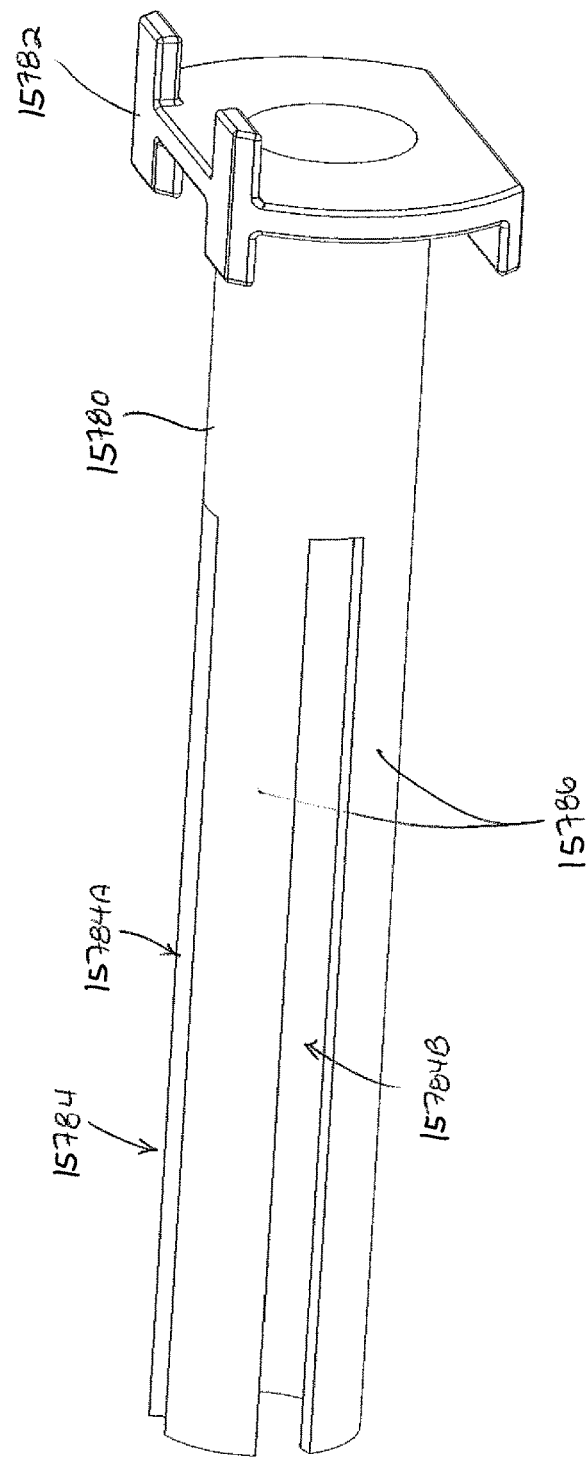
Figure 262:
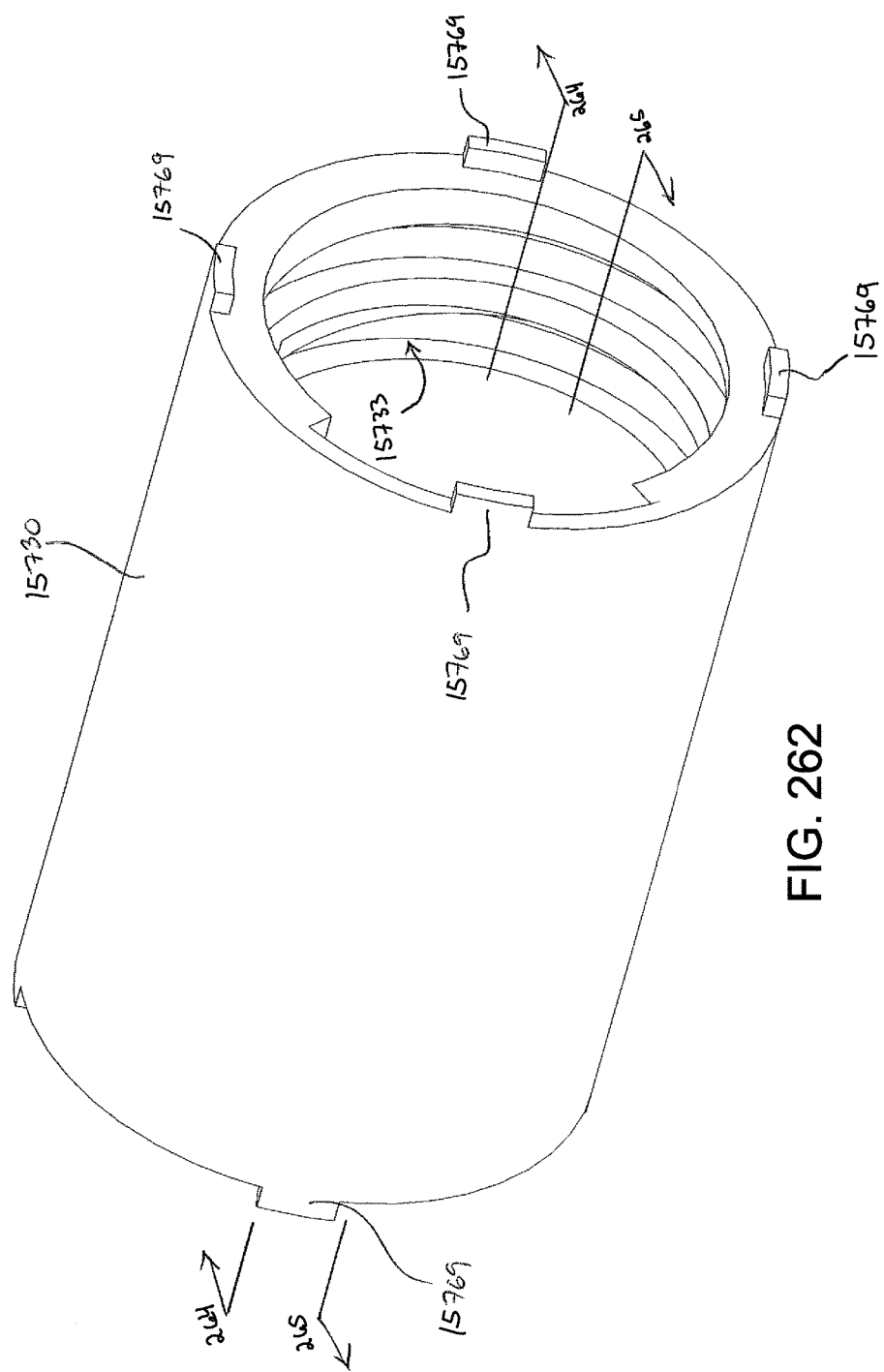
Figure 263:
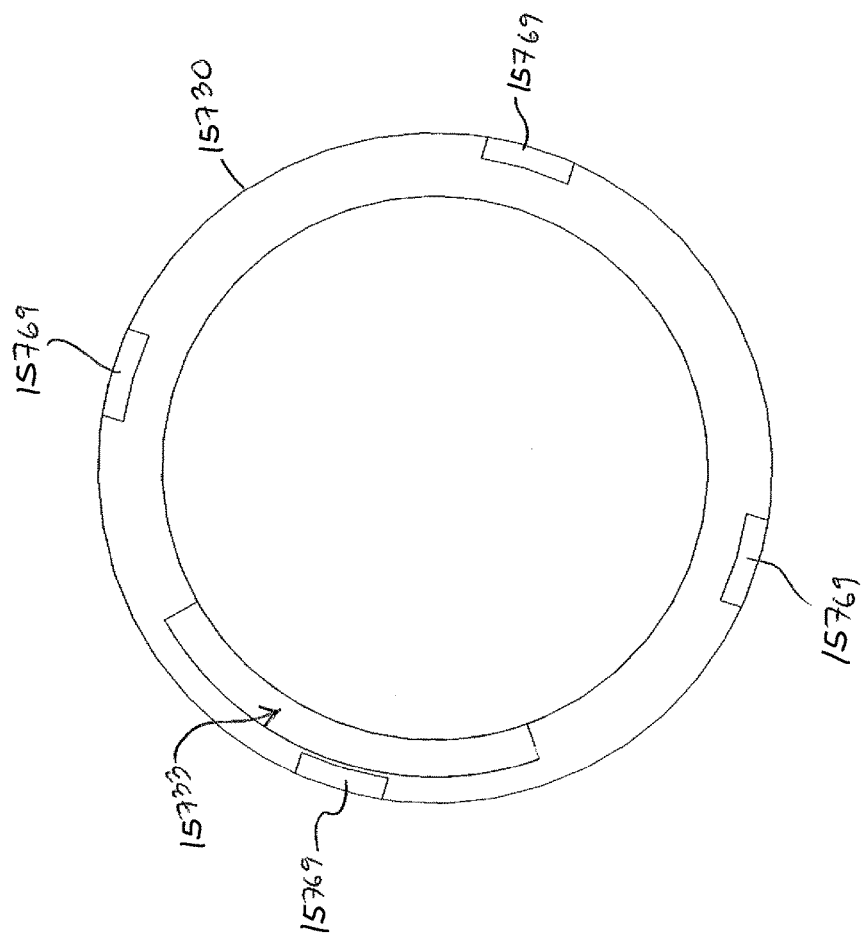
Figure 264:
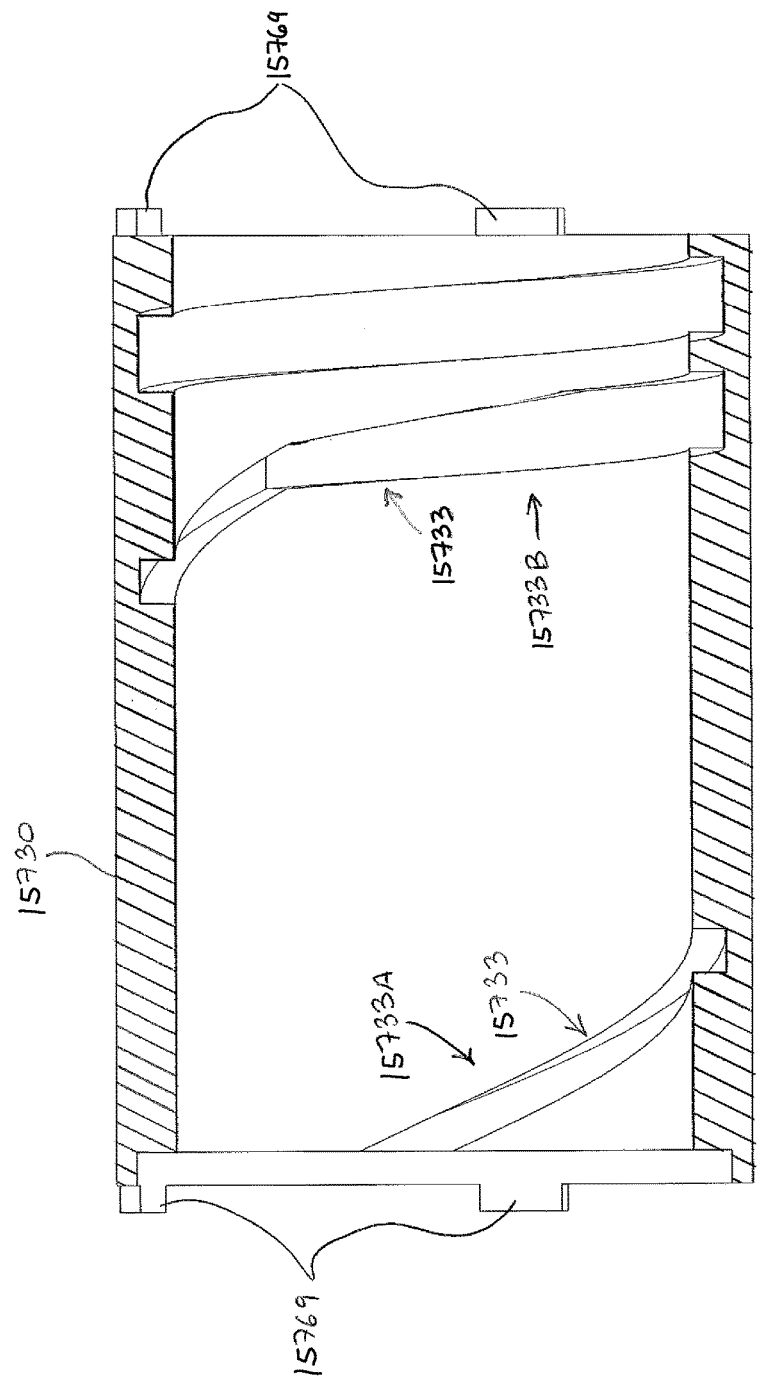
Figure 265:
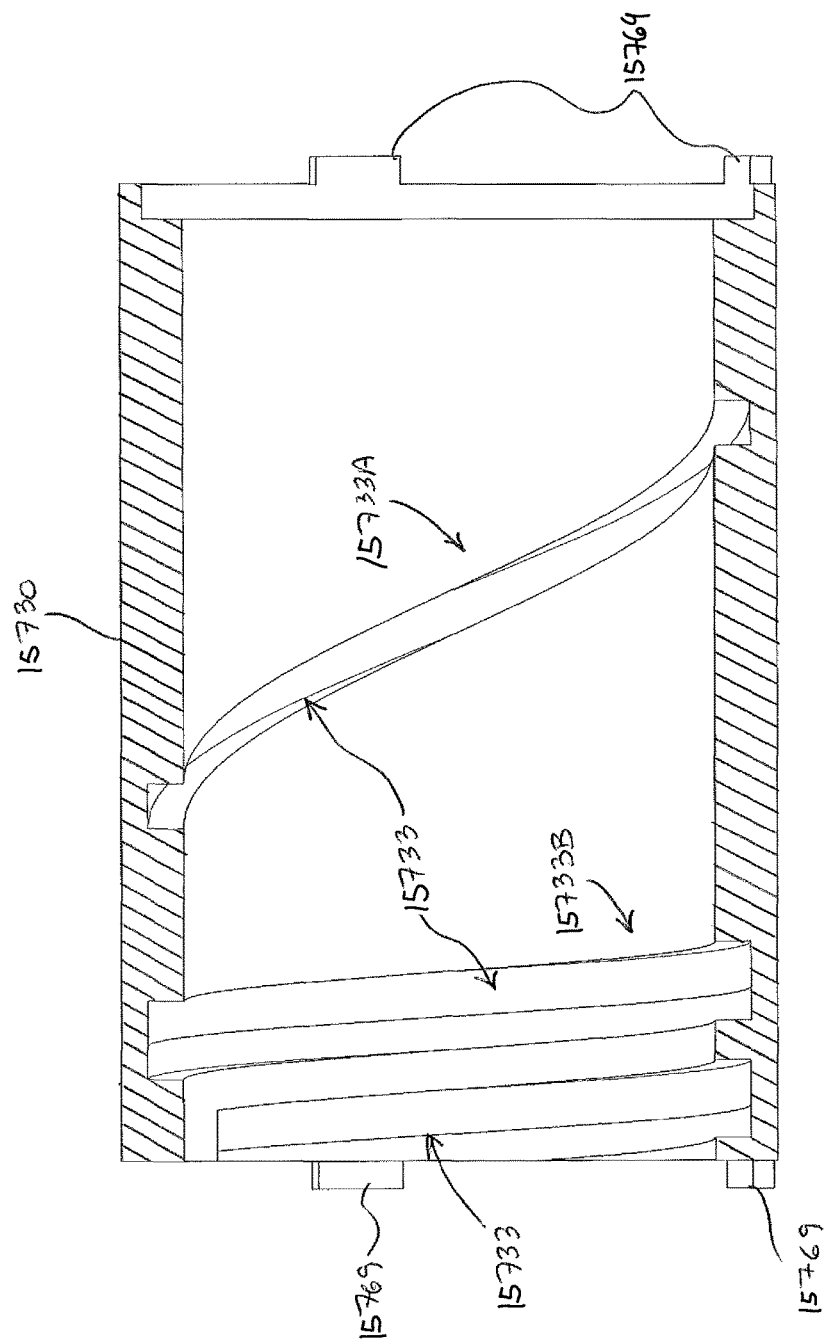
Figure 266:
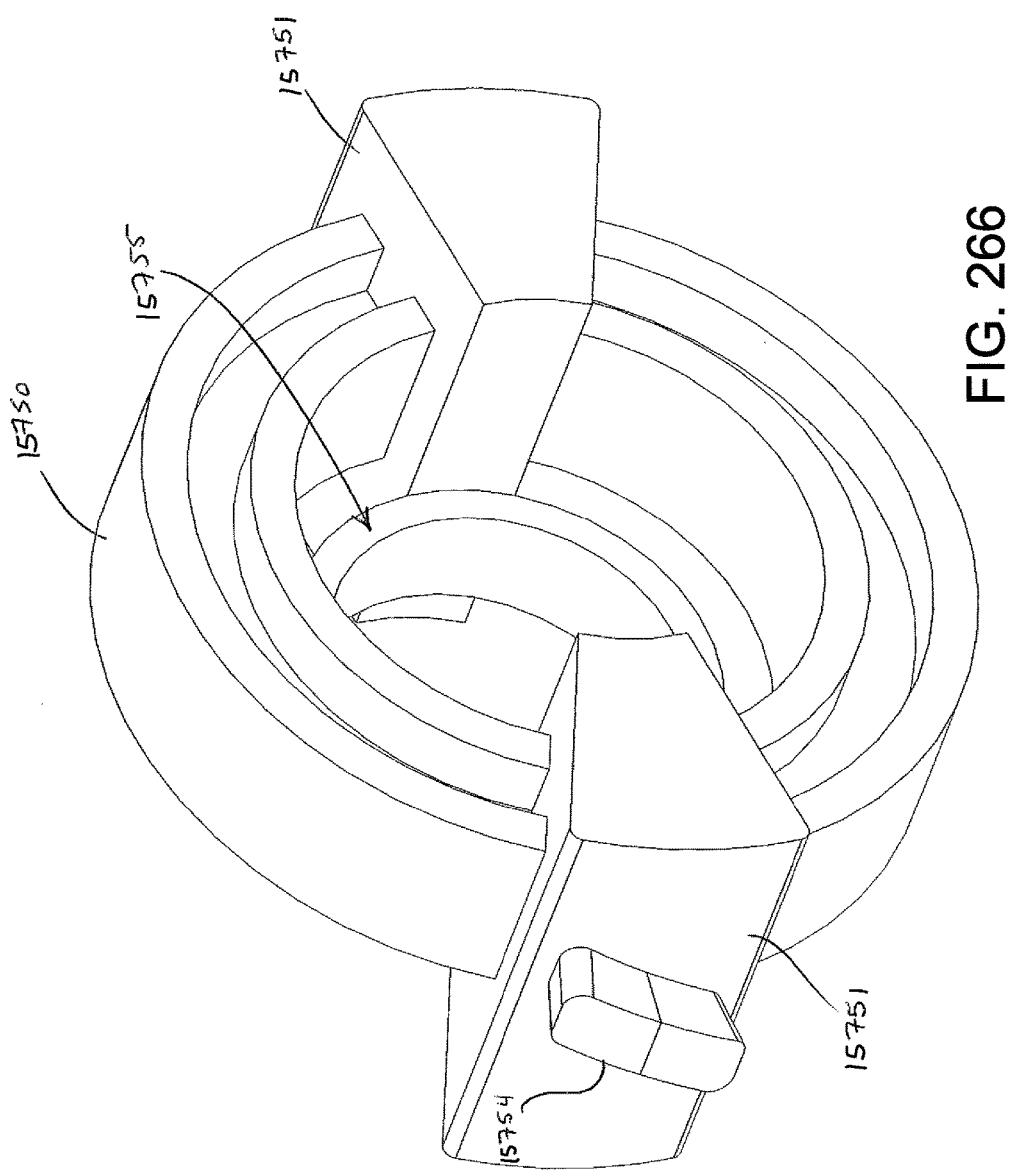
Figure 267:
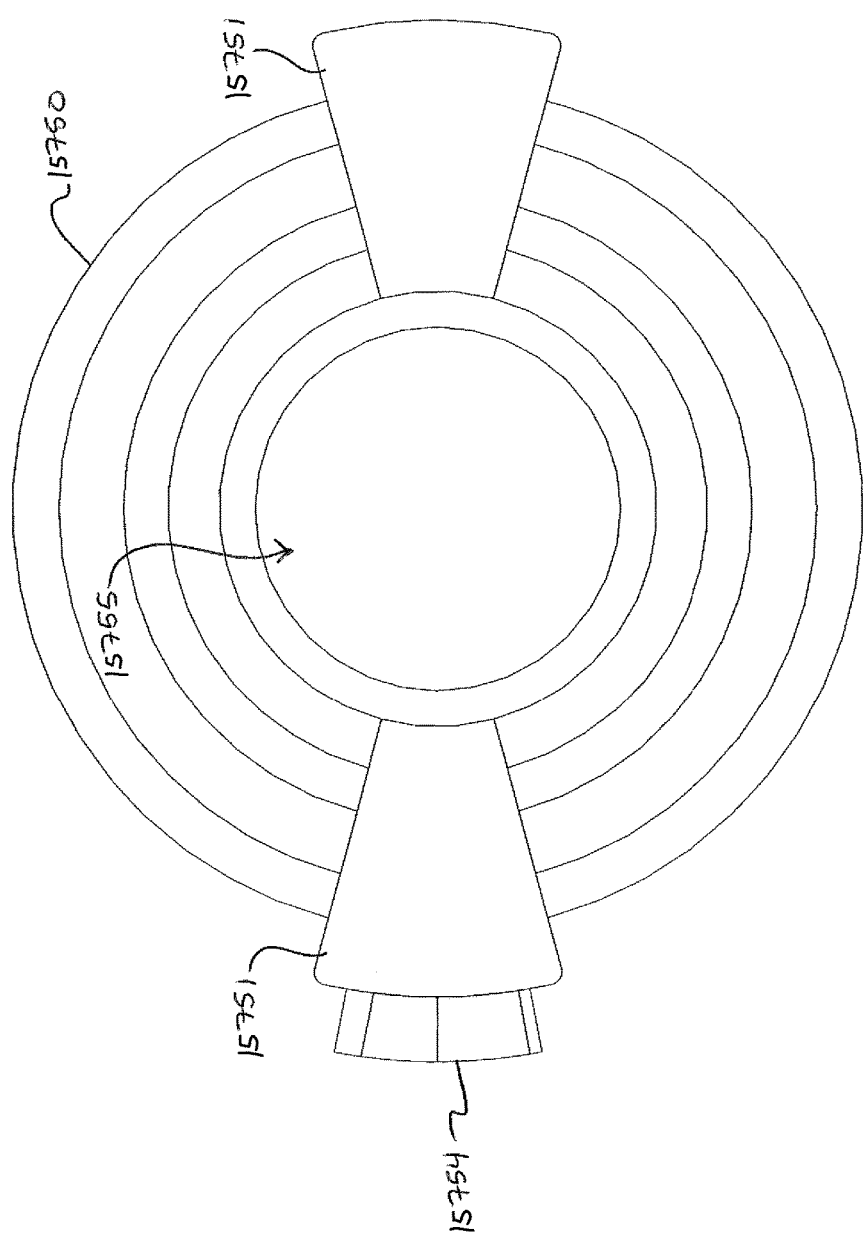
Figure 268:
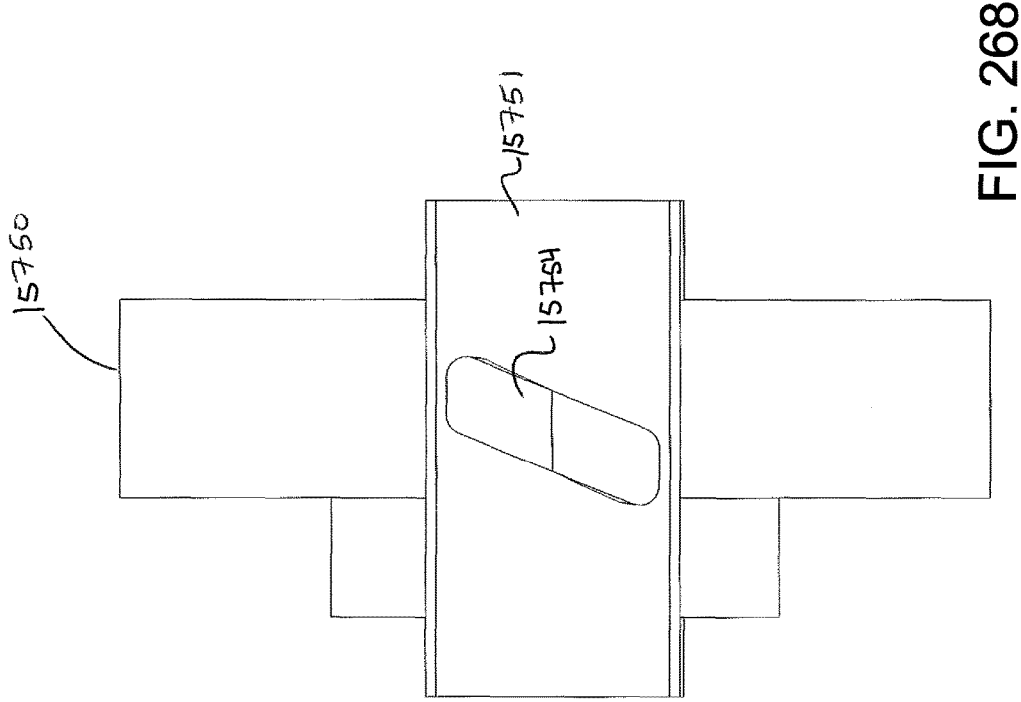
Figure 269:
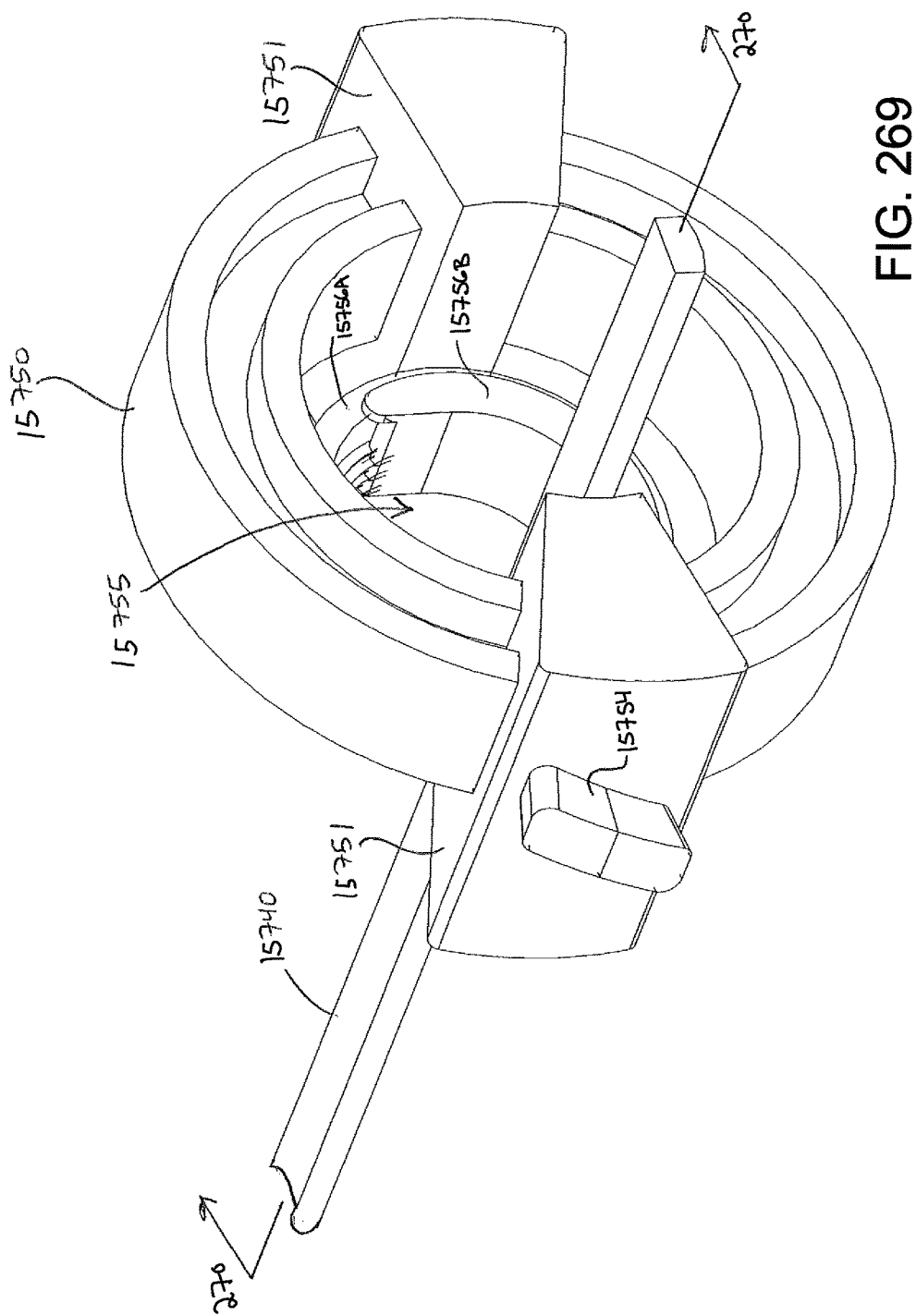
Figure 270:
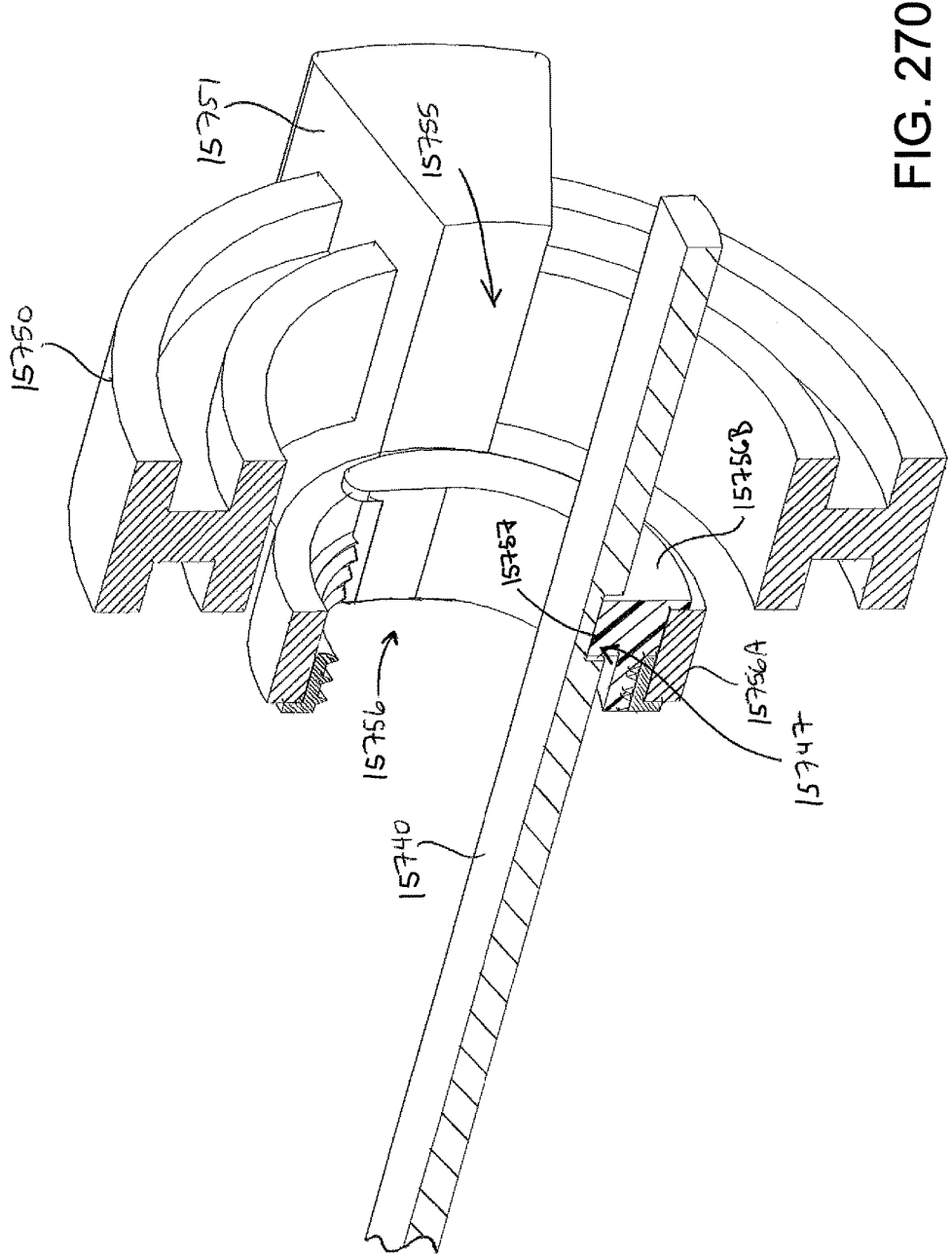
Figure 271:
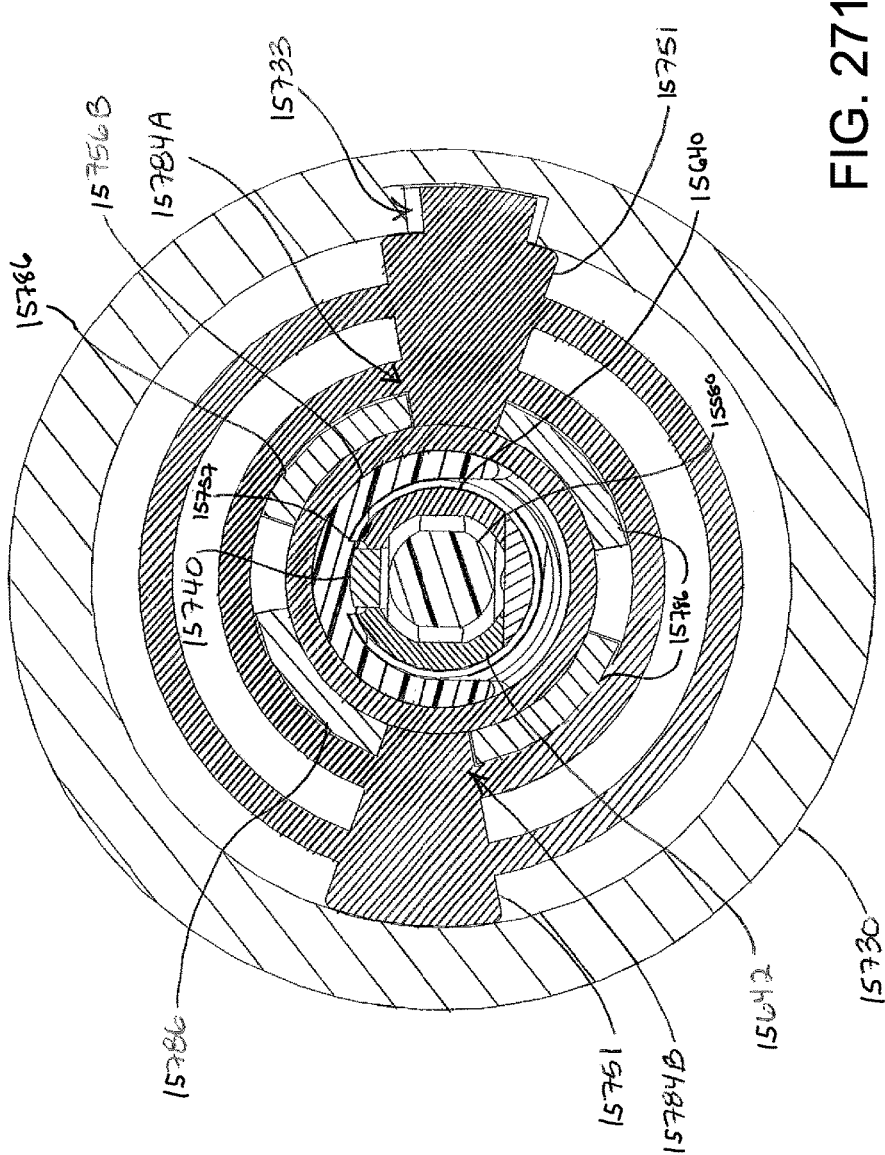
Figure 272:
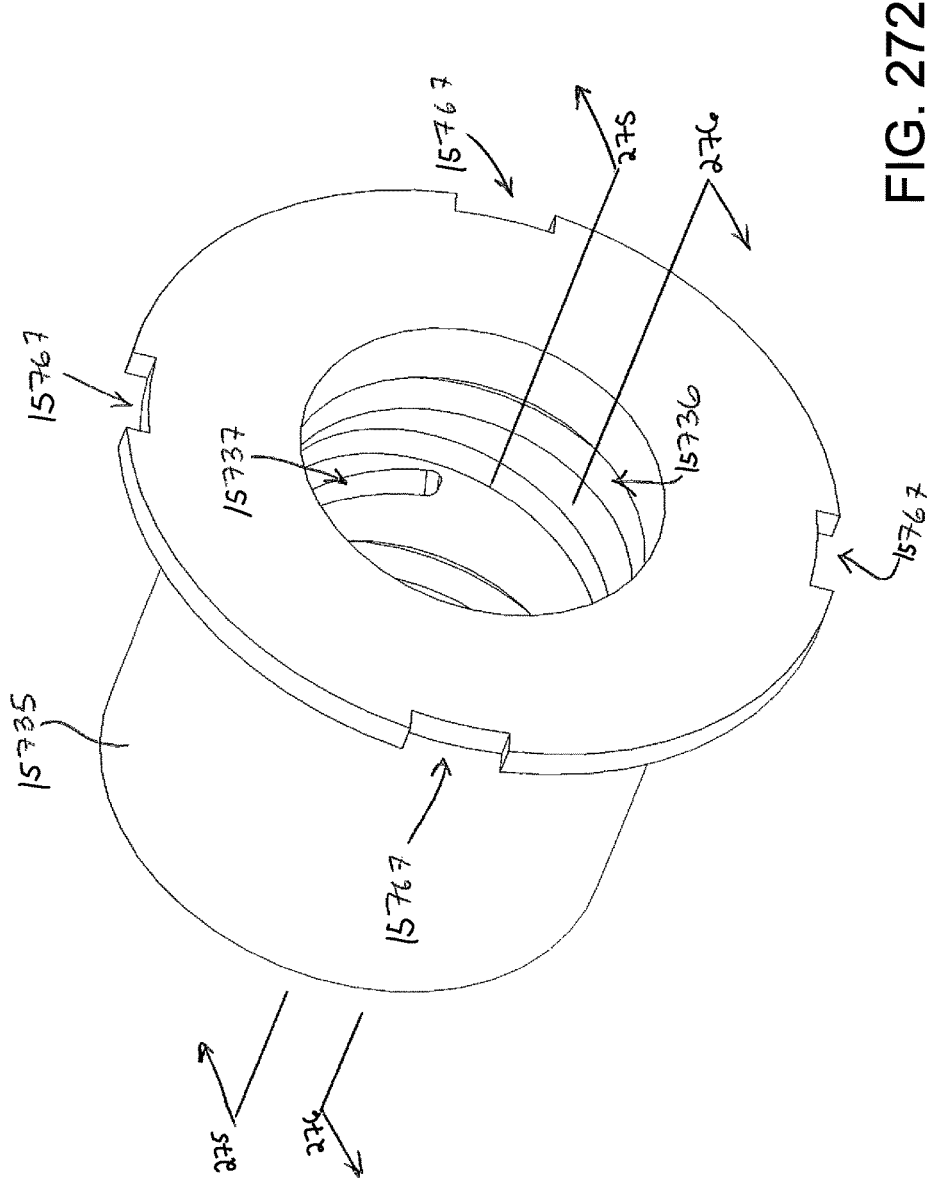
Figure 273:
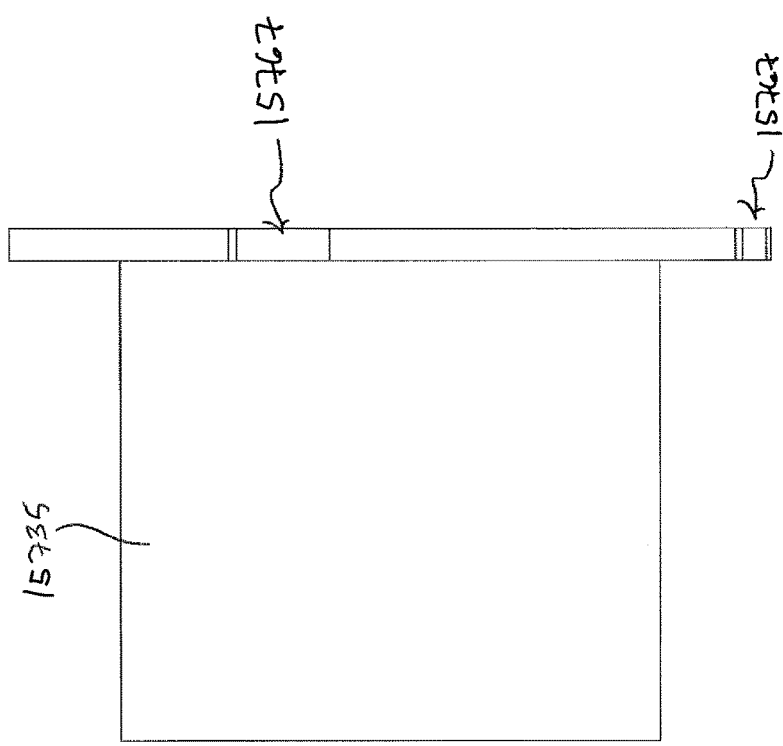
Figure 274:
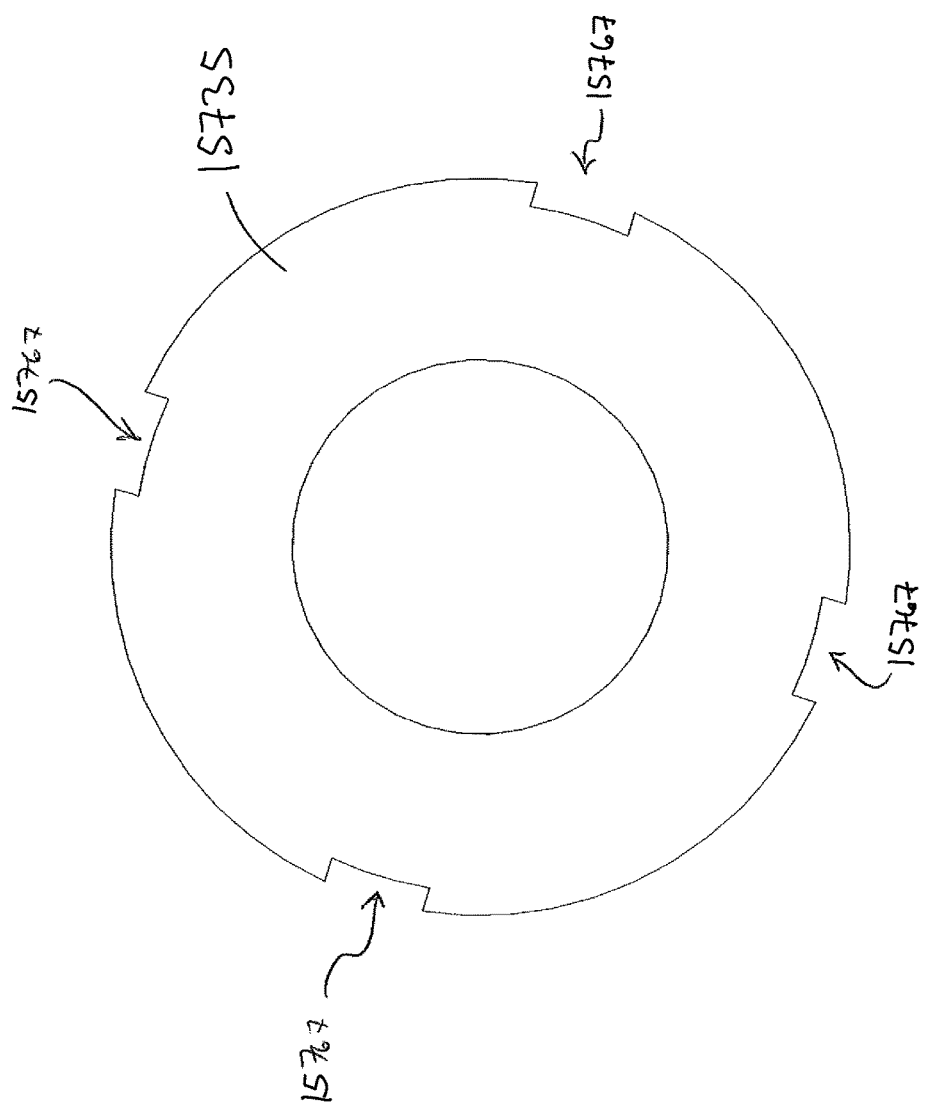
Figure 275:
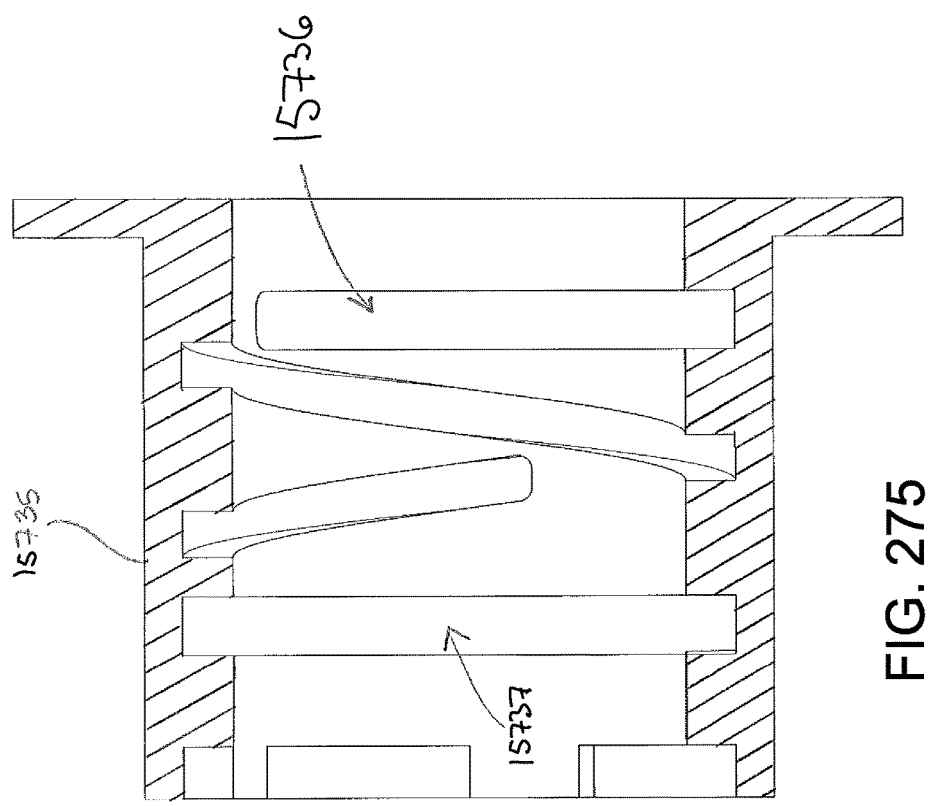
Figure 276:
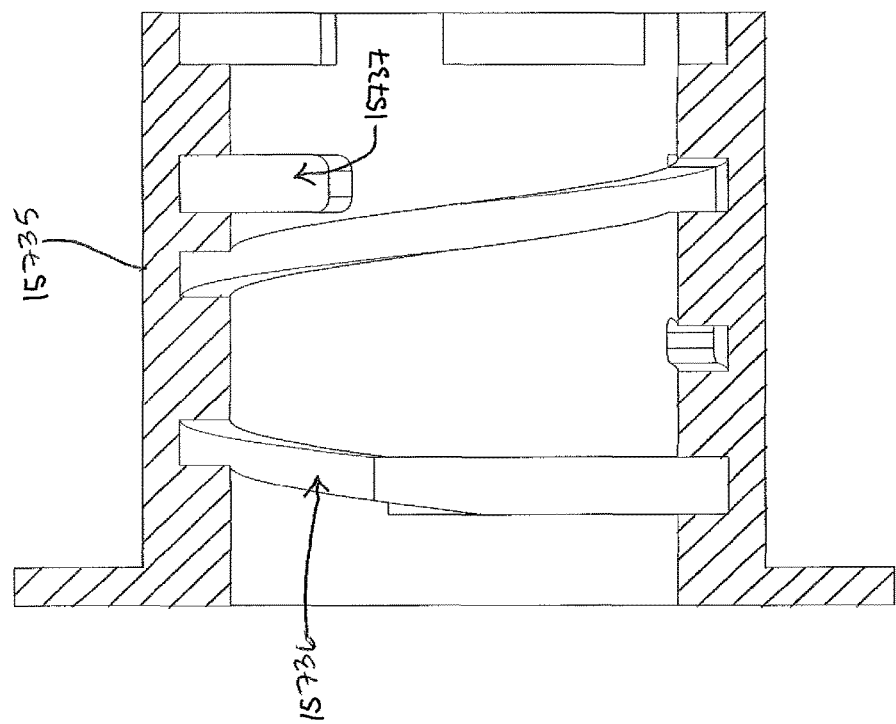
Figure 277:
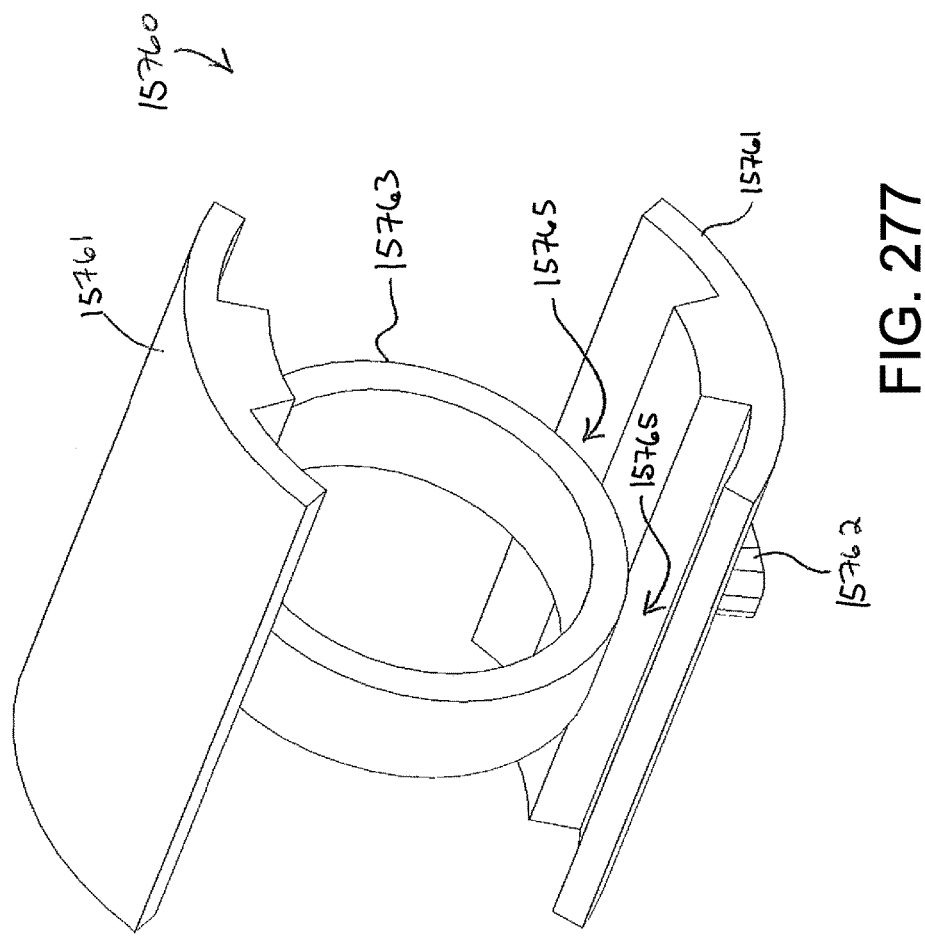
Figure 278:
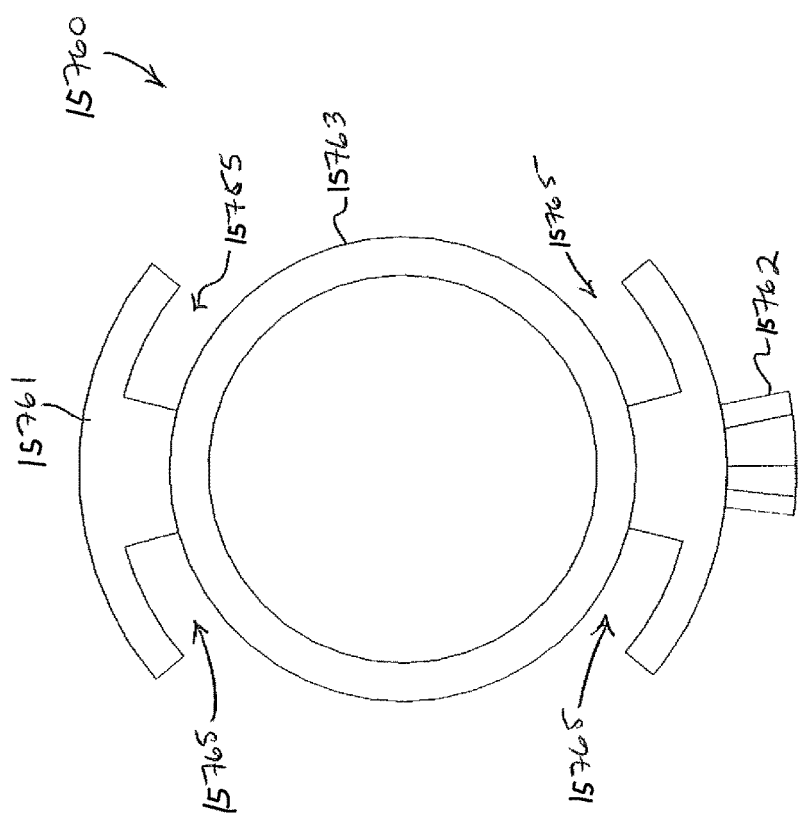
Figure 279:
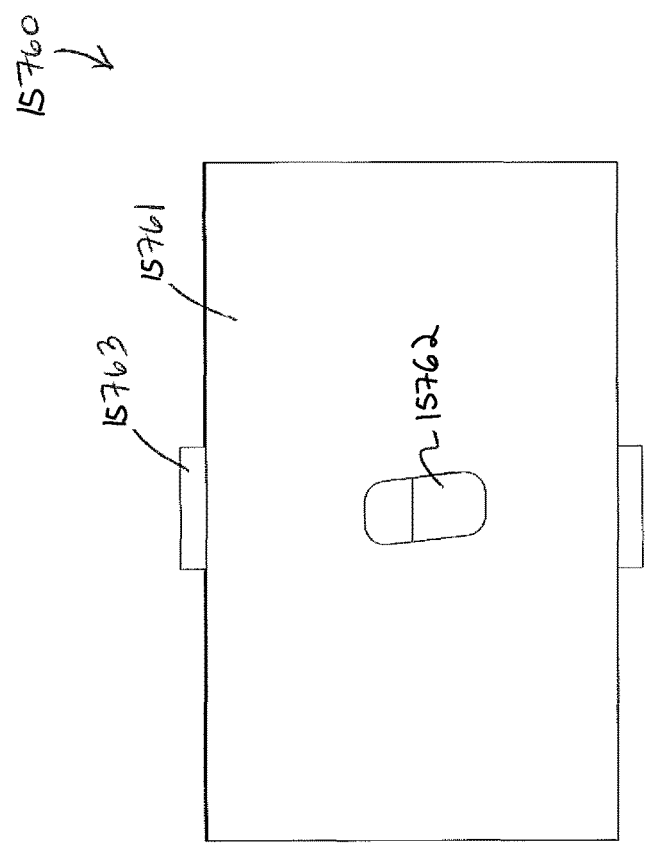
Figure 280:
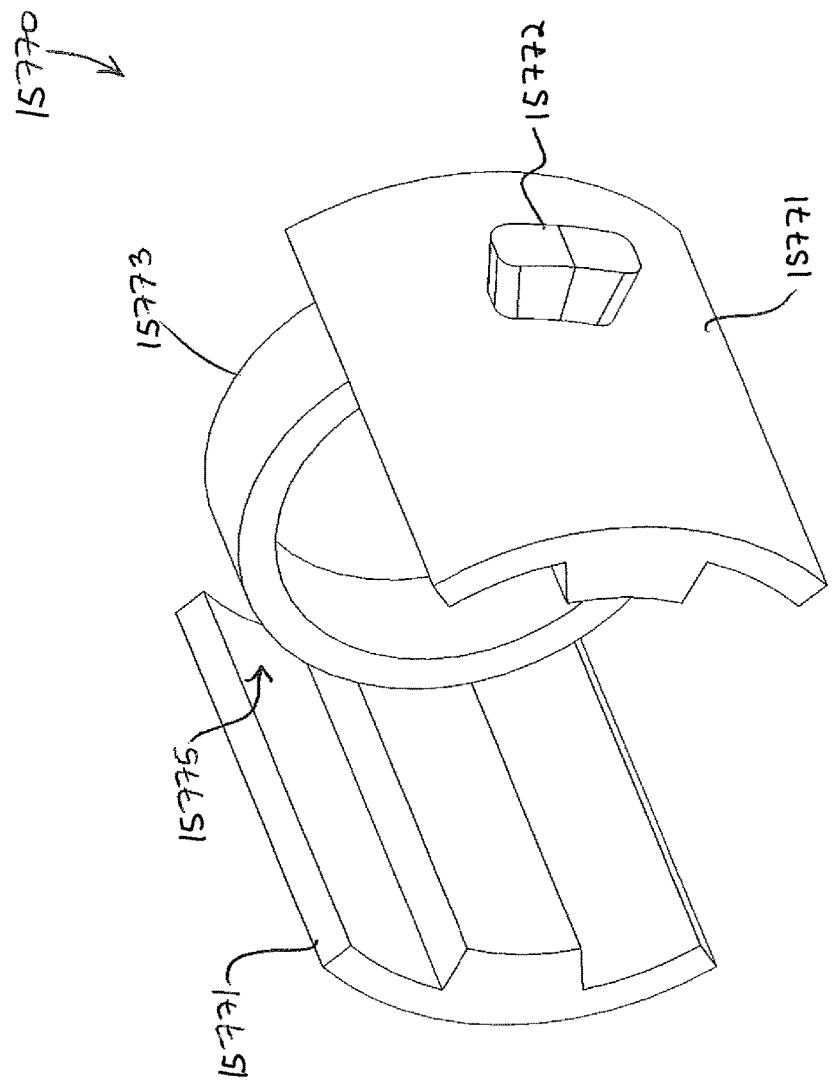
Figure 281:
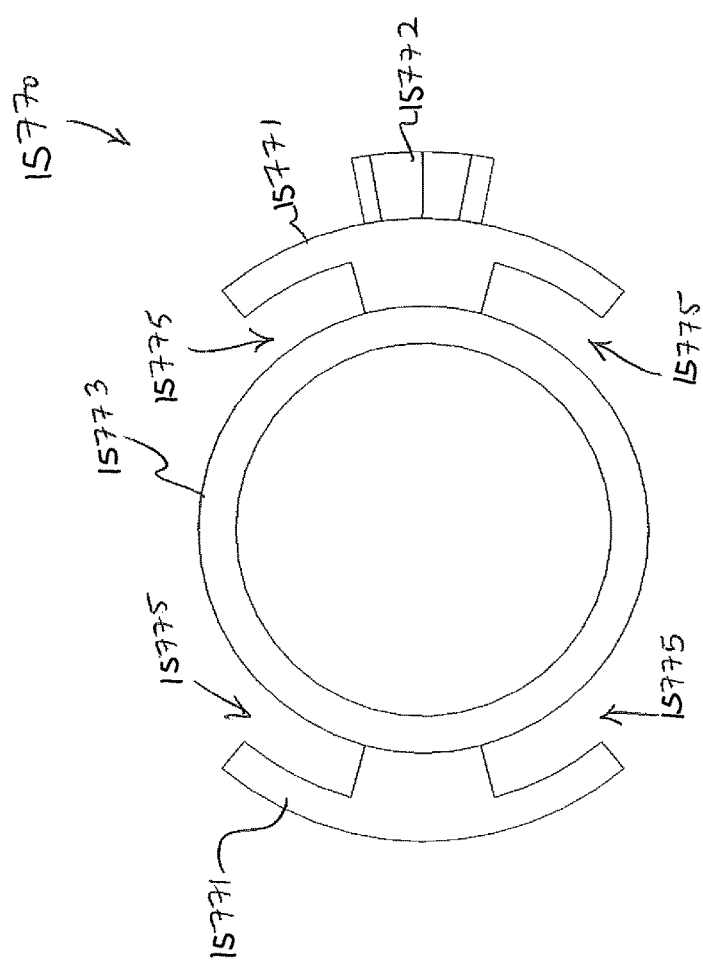
Figure 282:
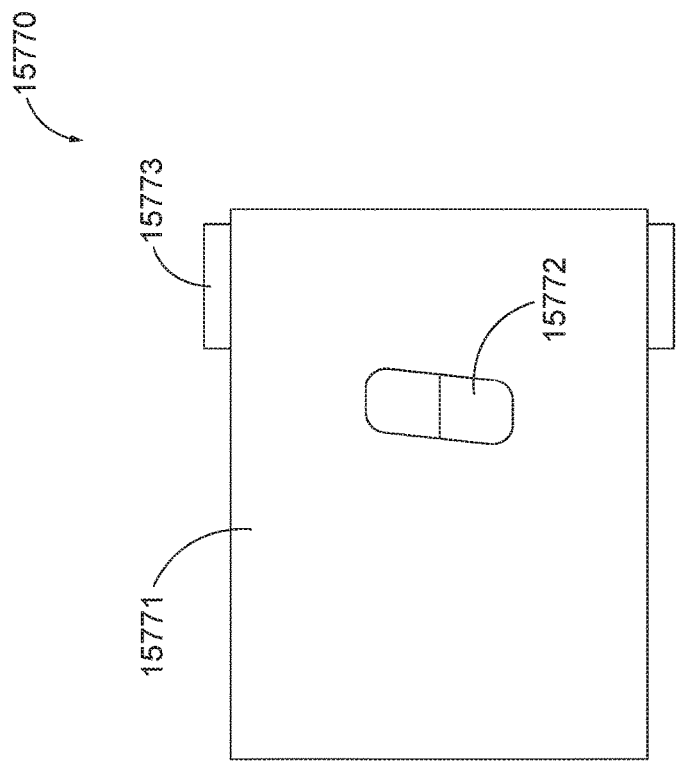
Figure 283:
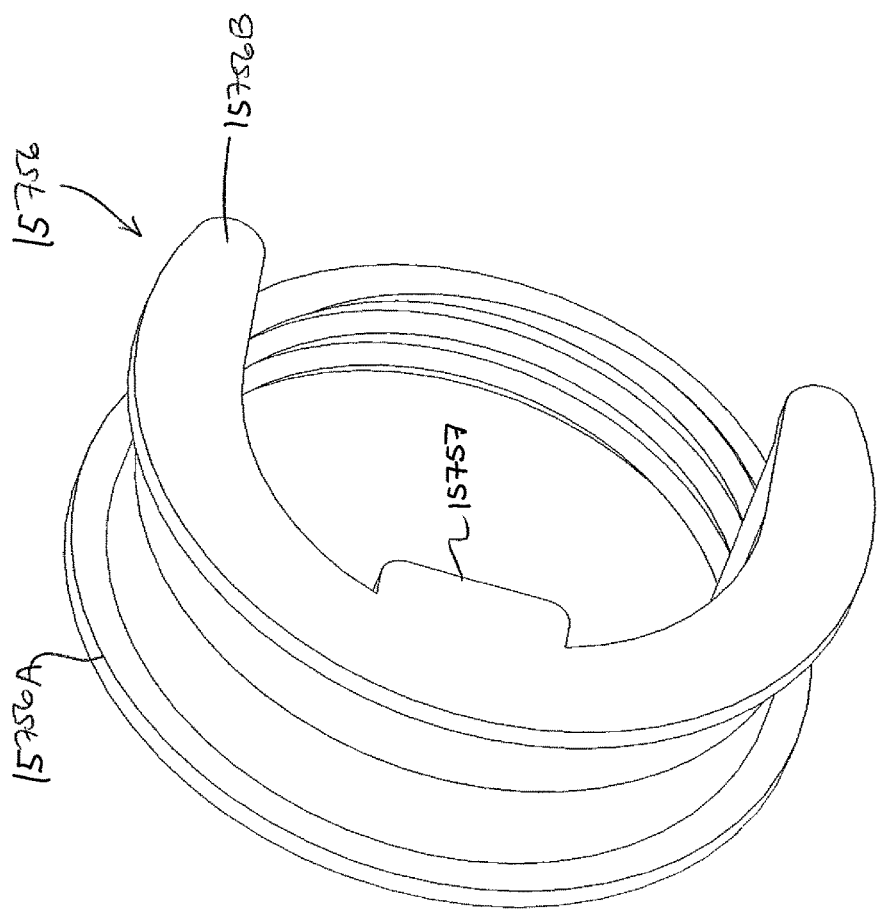
Figure 284:
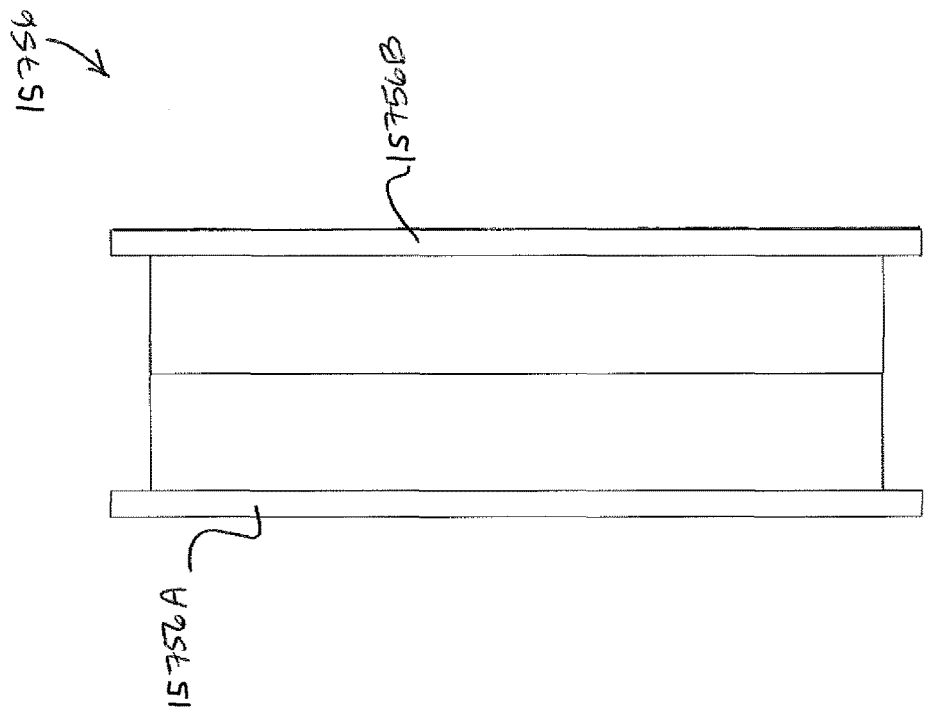
Figure 285:
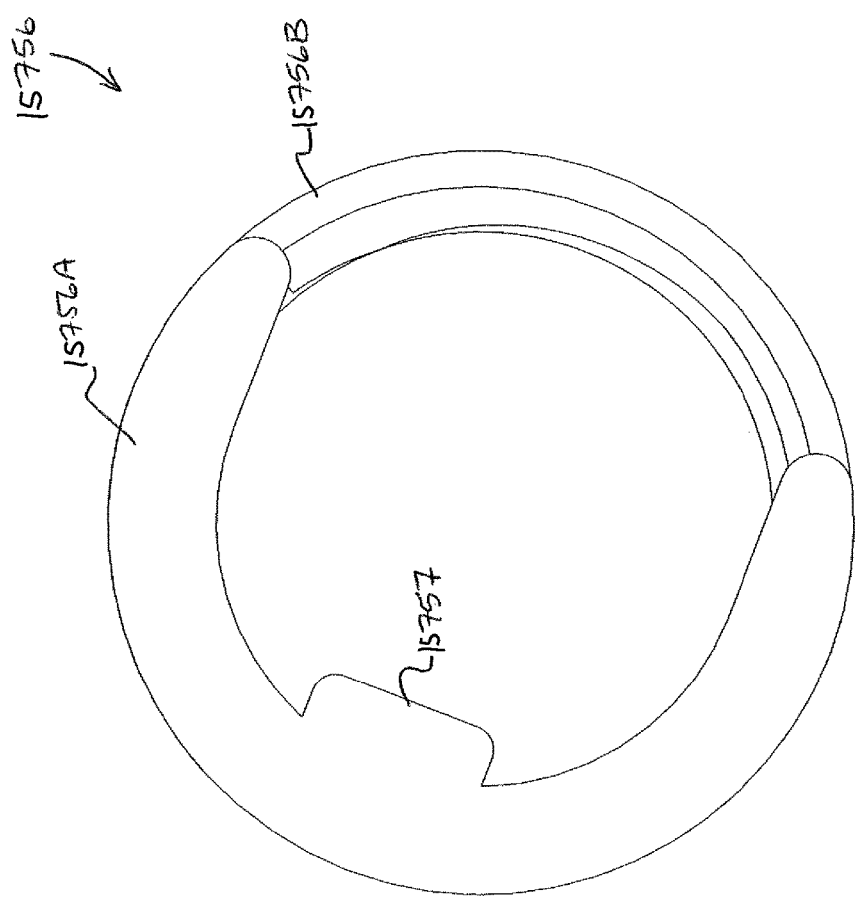
Figure 286:
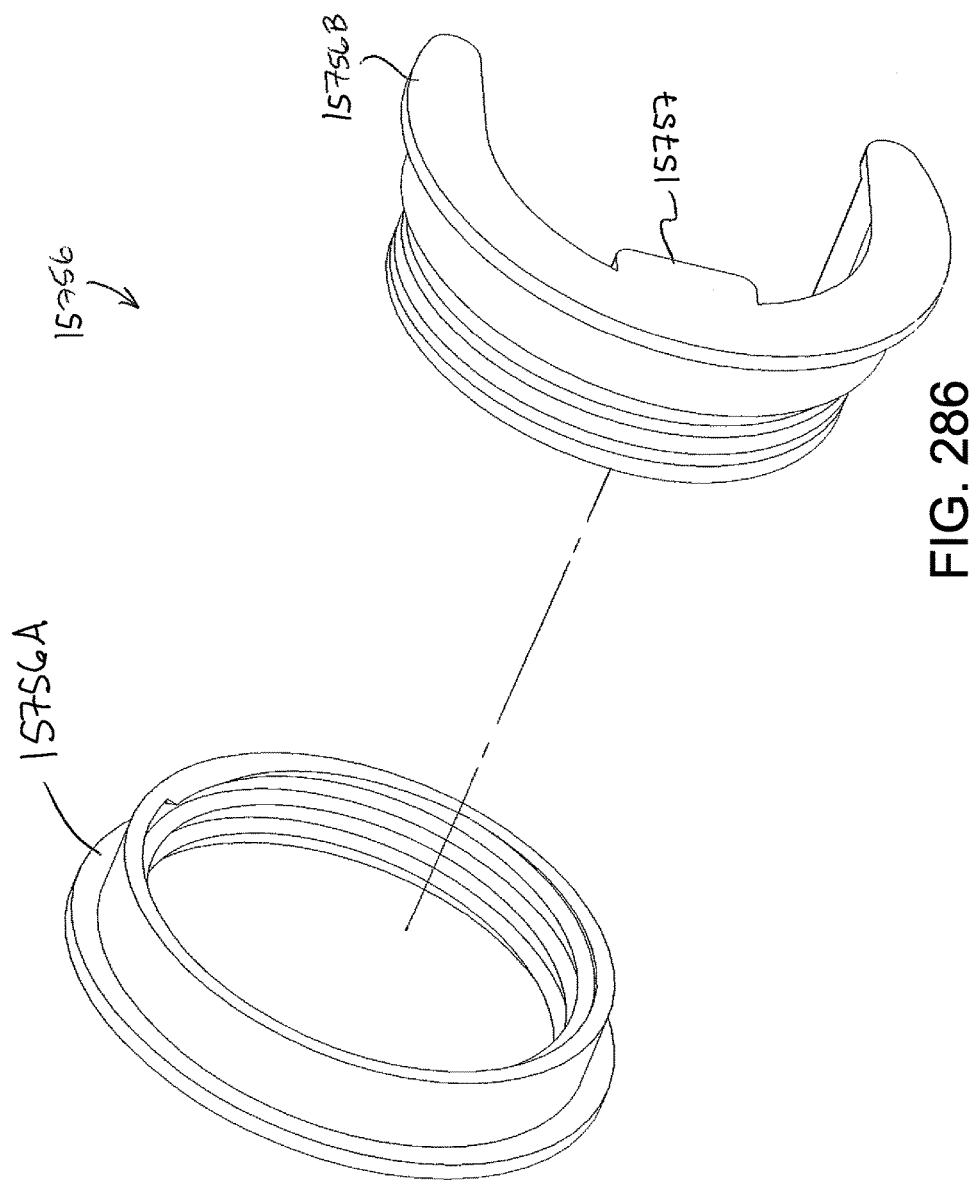
Figure 287:
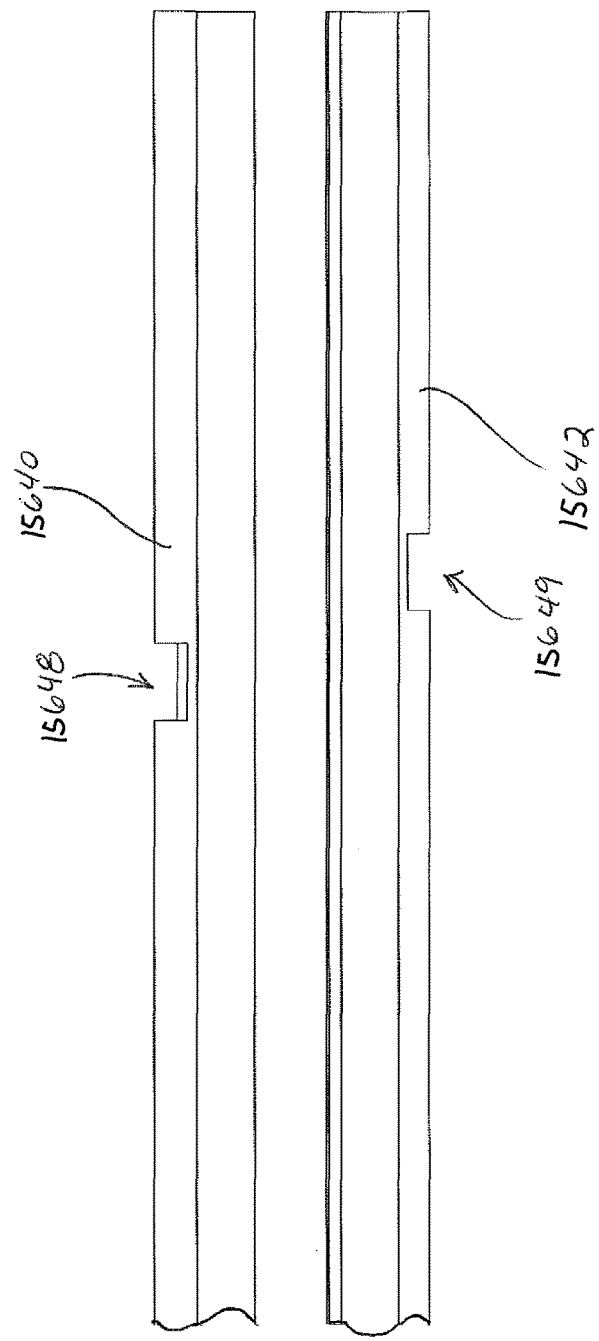
Figure 288:
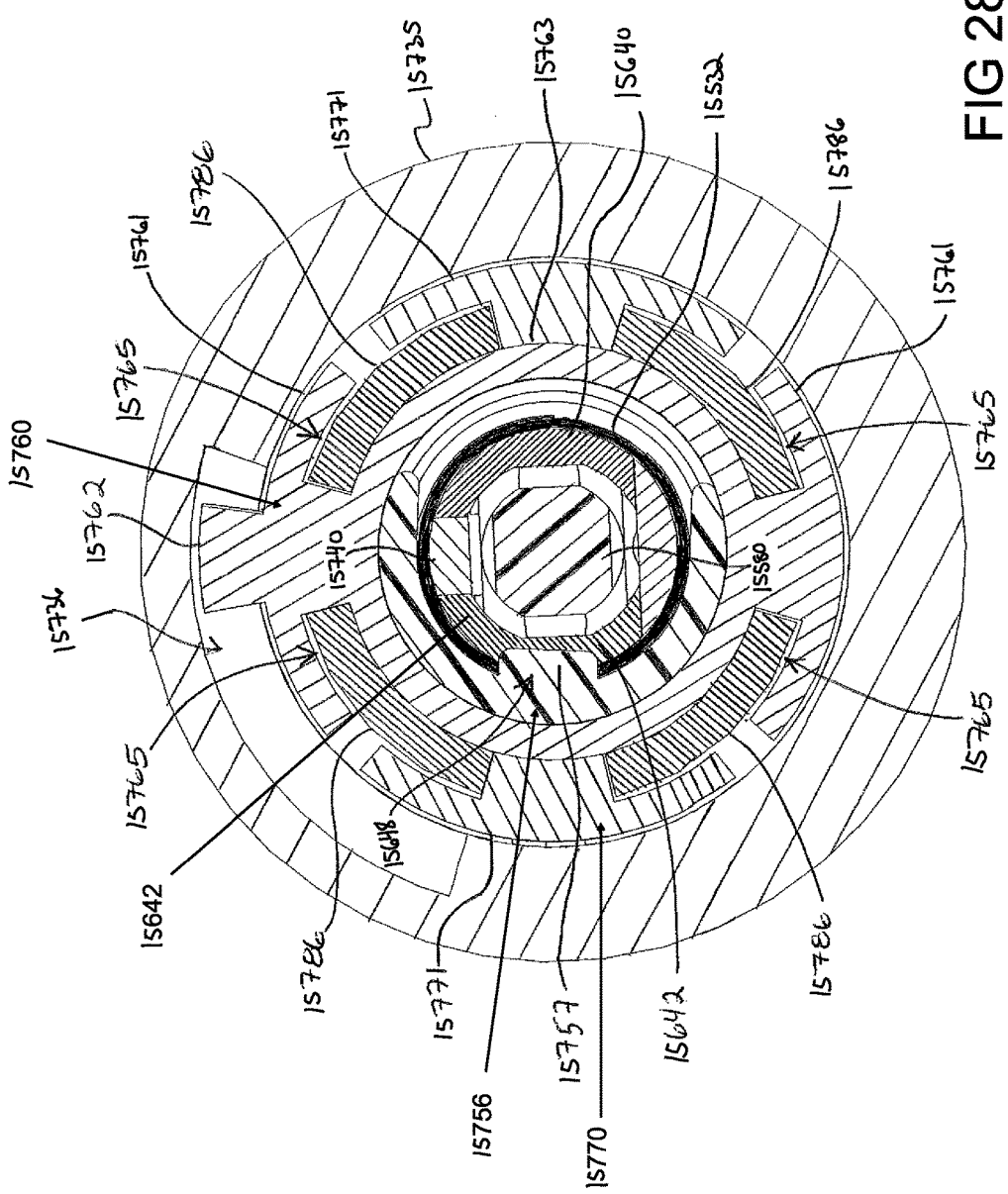
Figure 289:
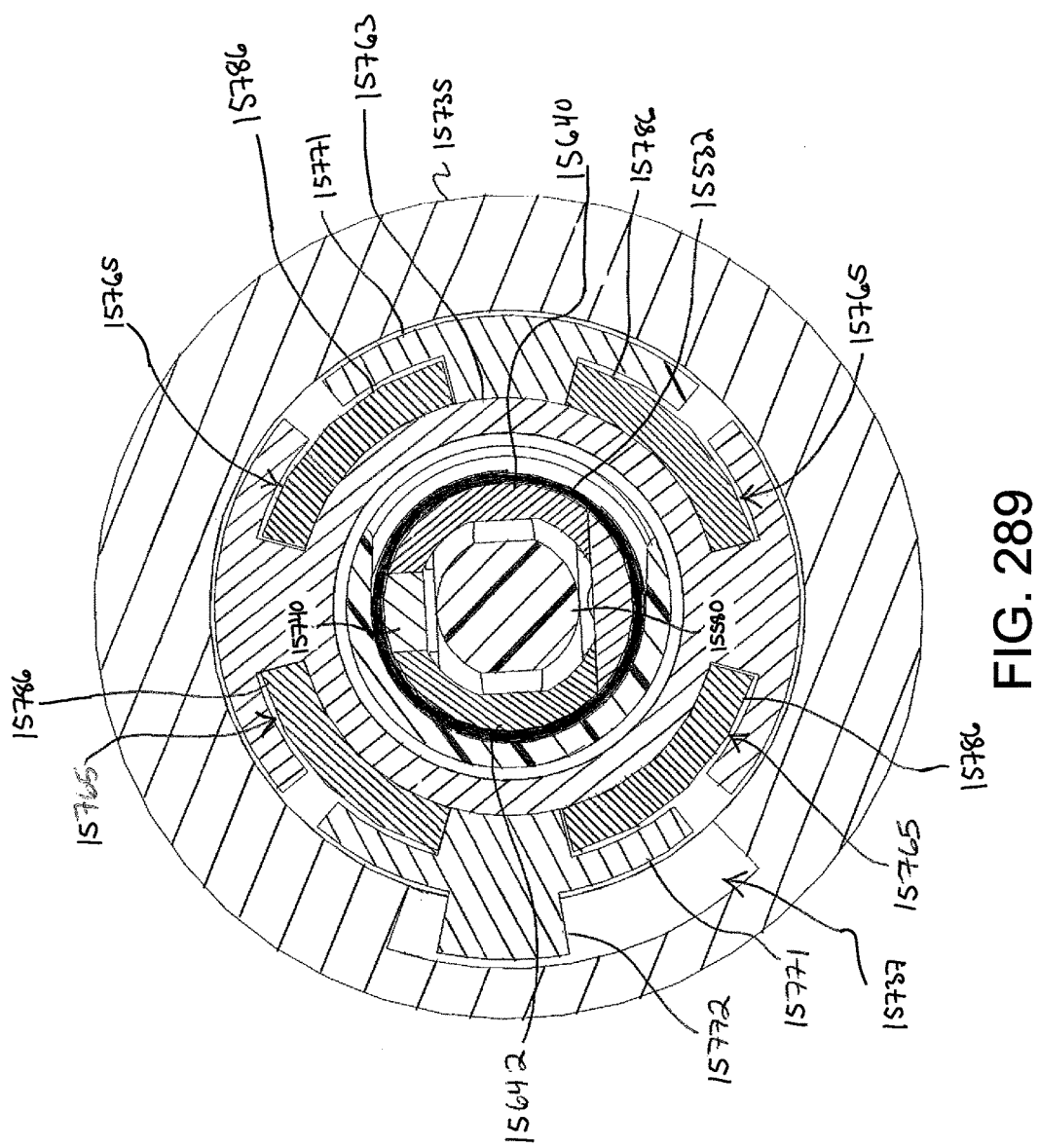
Figure 290:
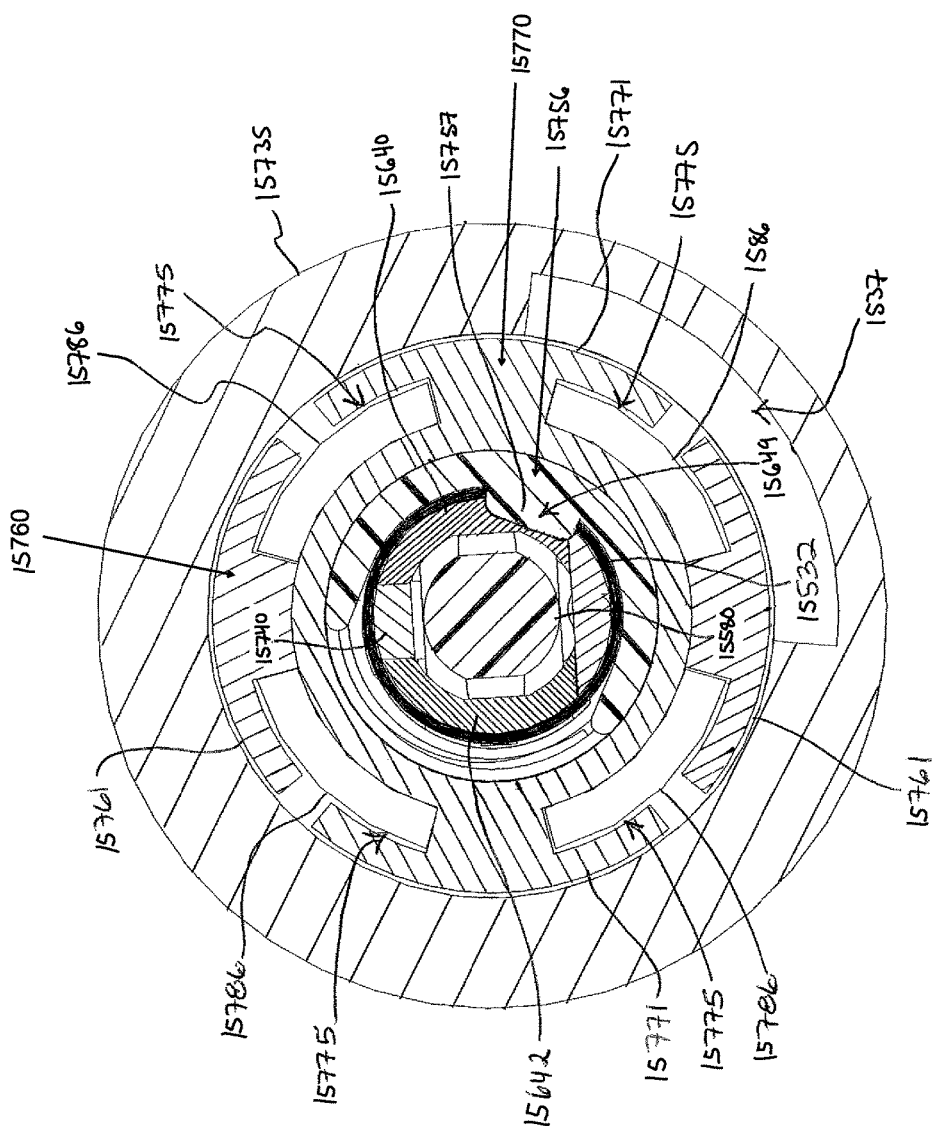
Figure 291A:
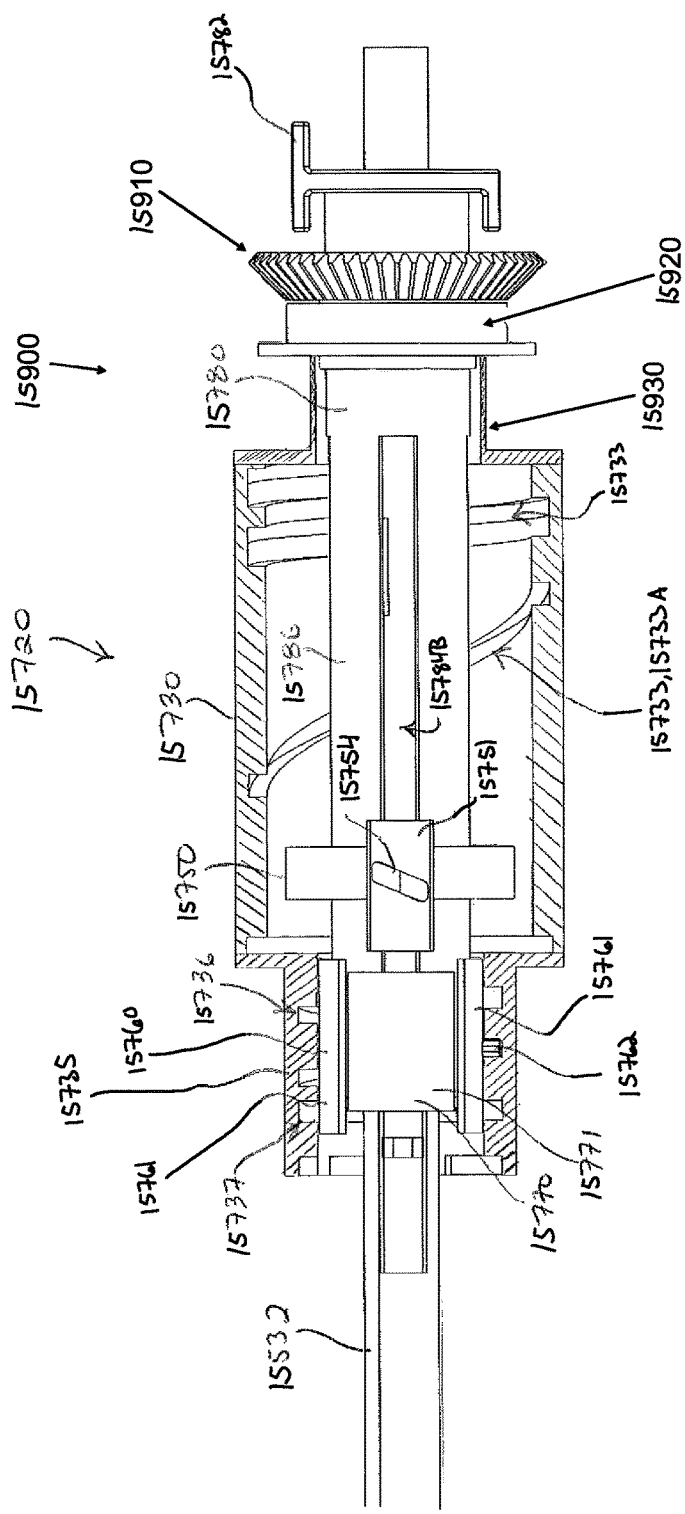
Figure 291B:
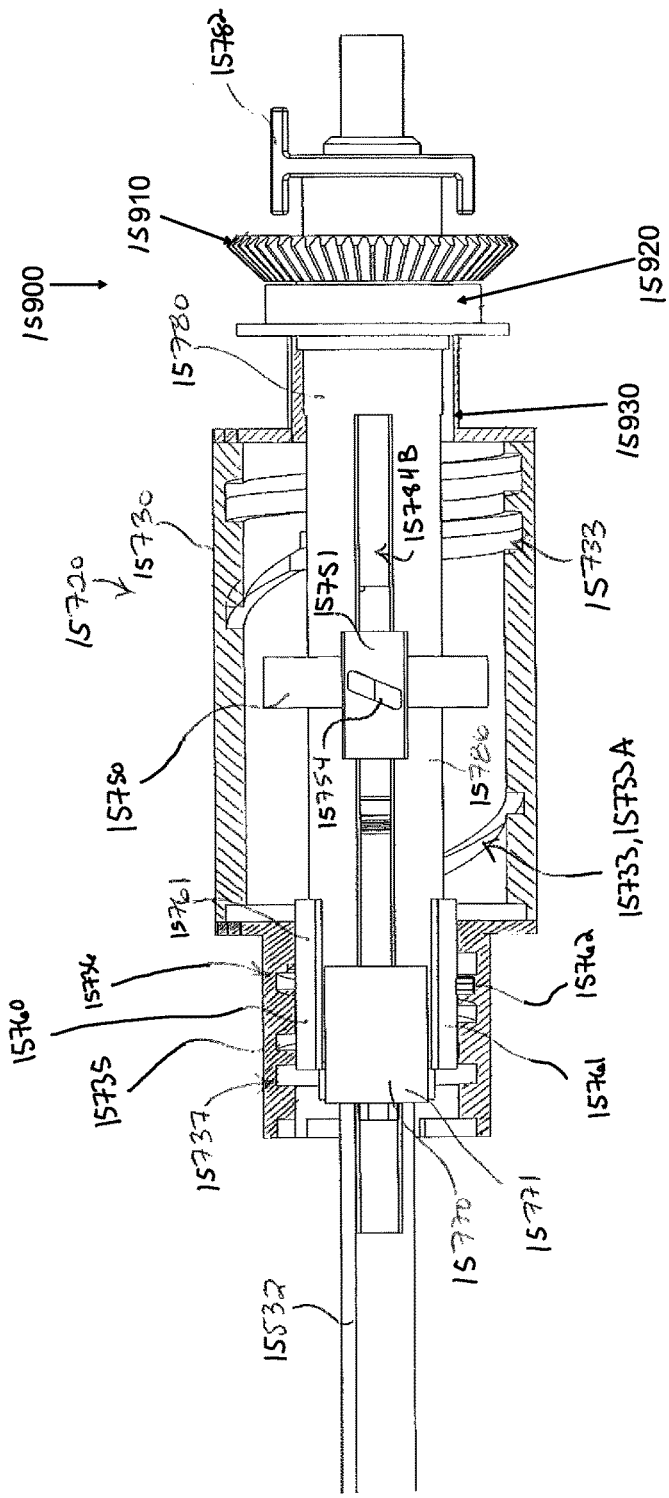
Figure 291C:
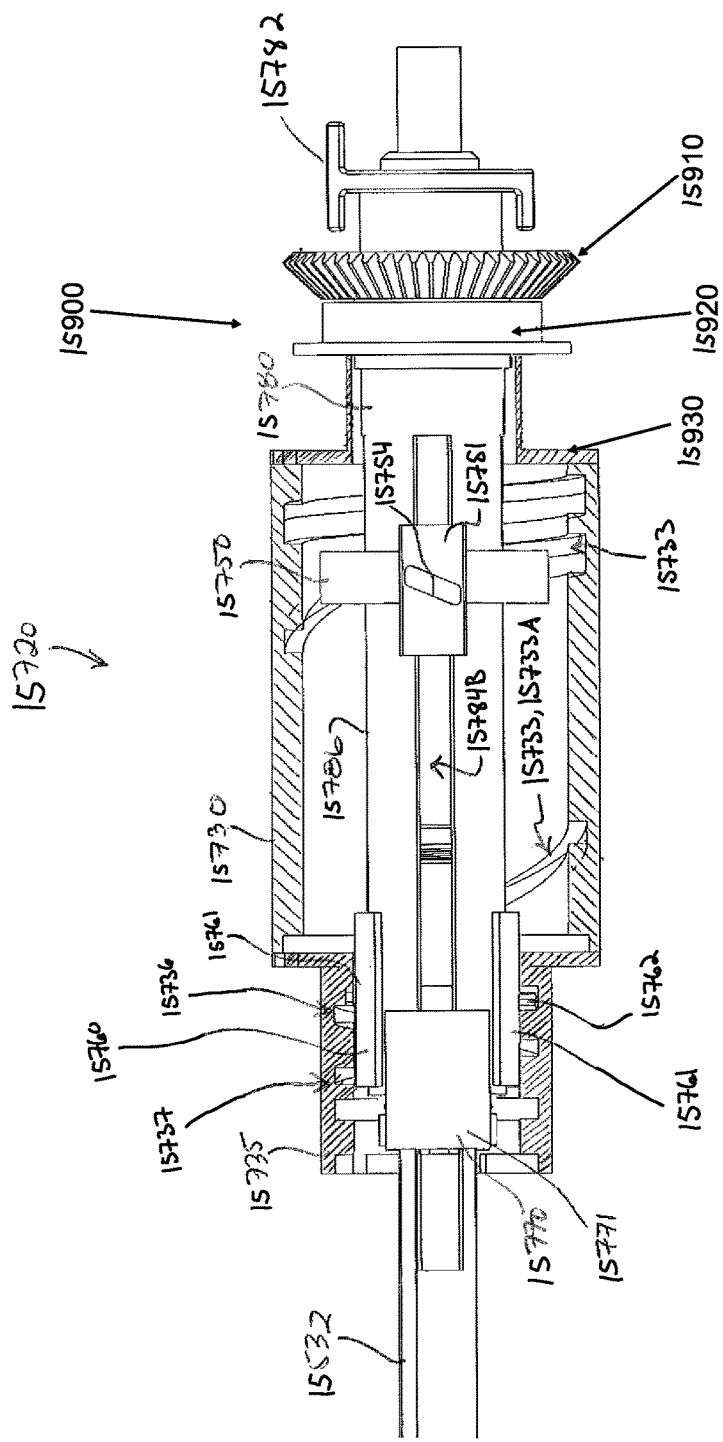
Figure 292A:
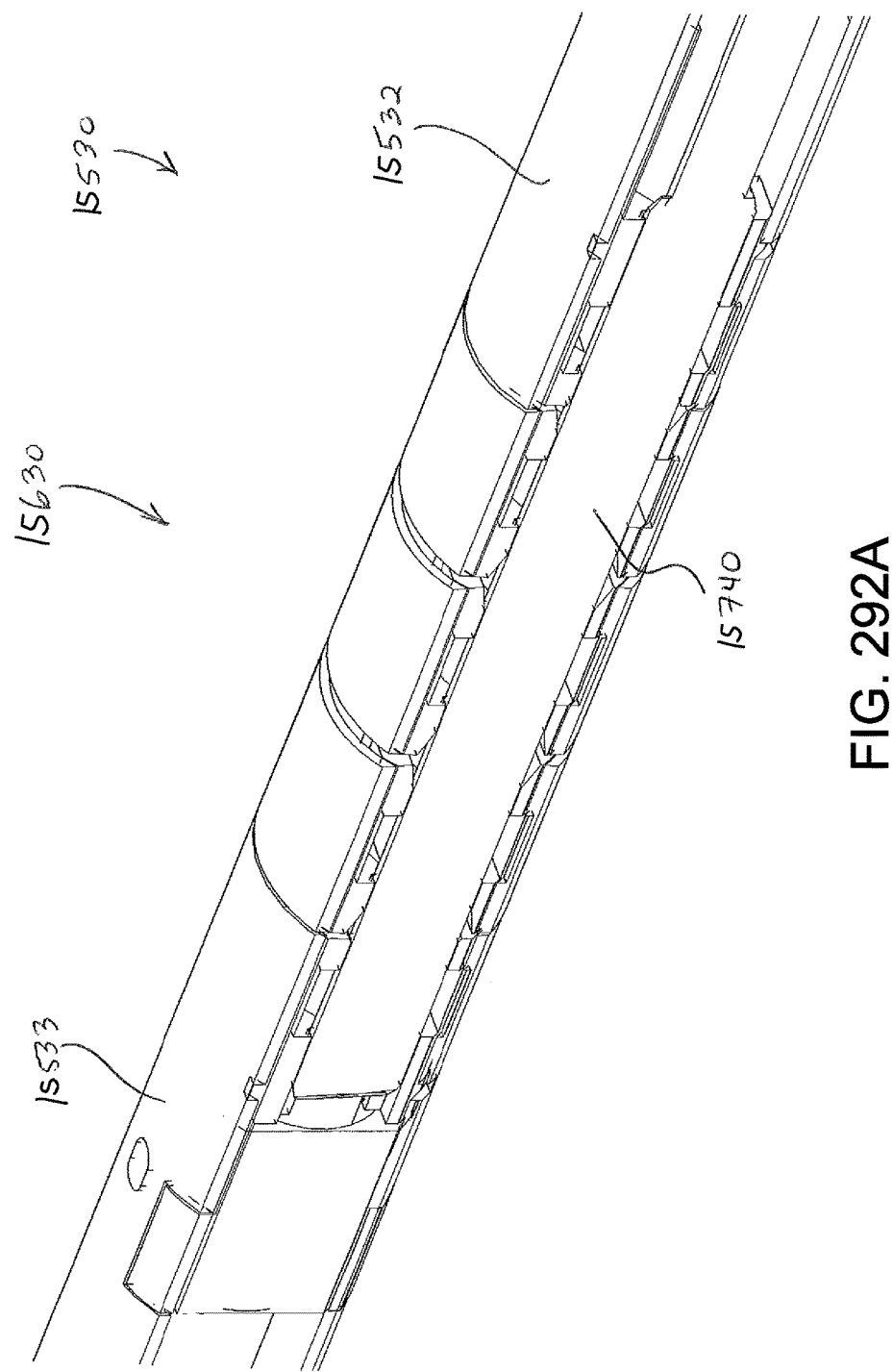
Figure 292B:
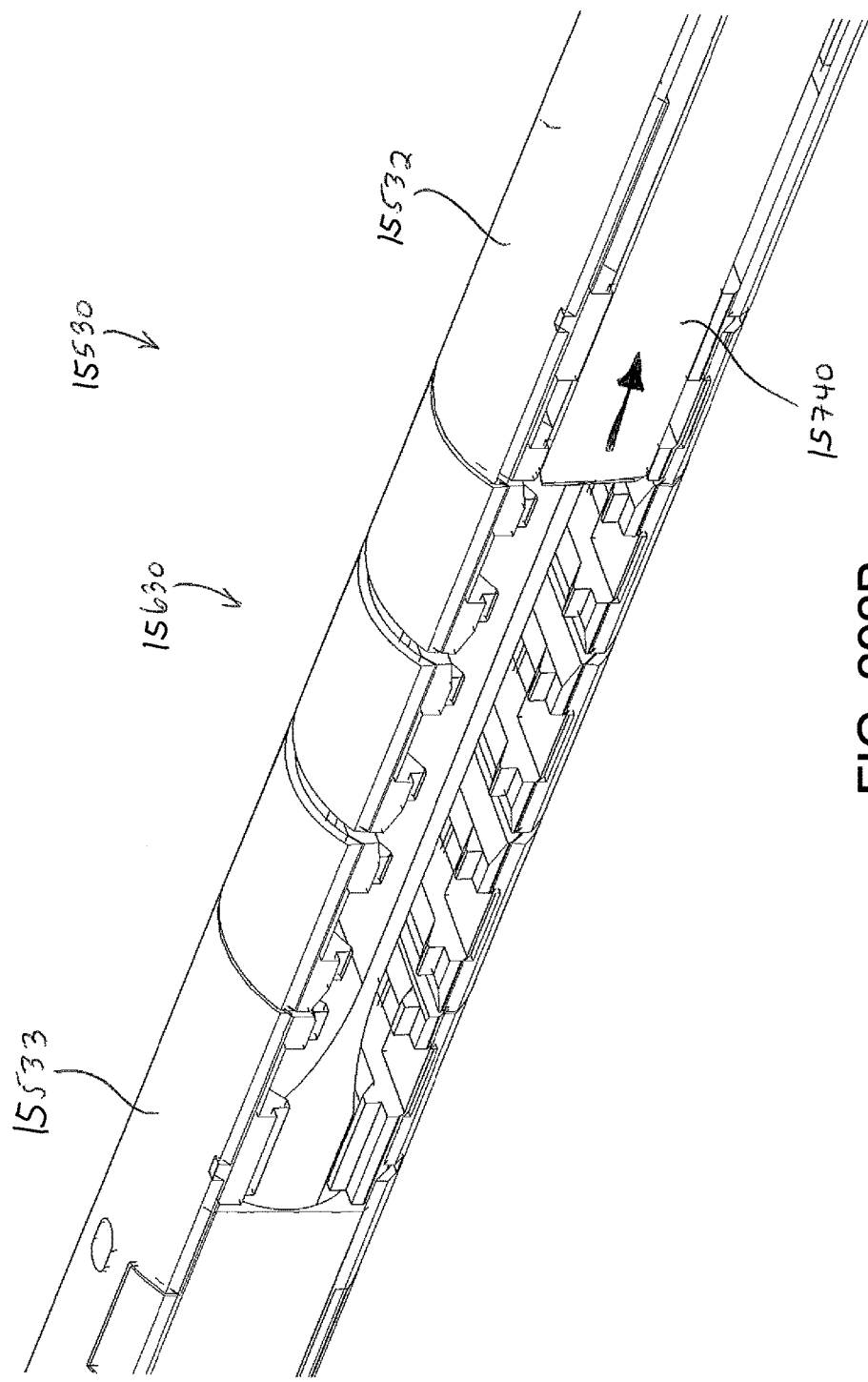
Figure 293A:
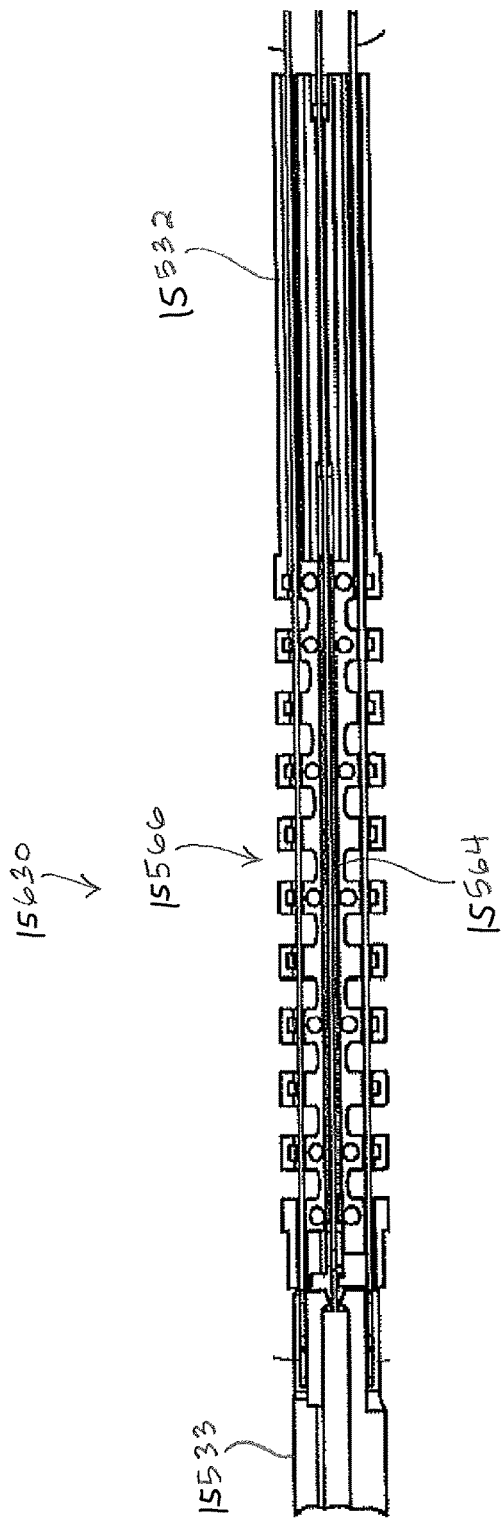
Figure 293B:
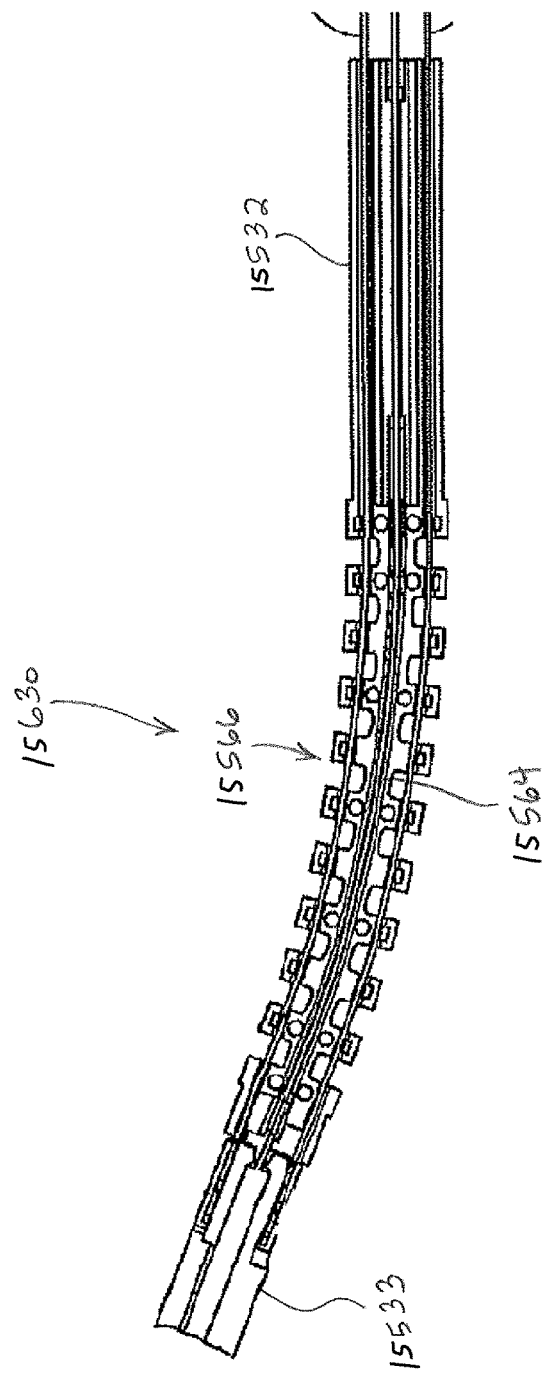
Figure 293C:
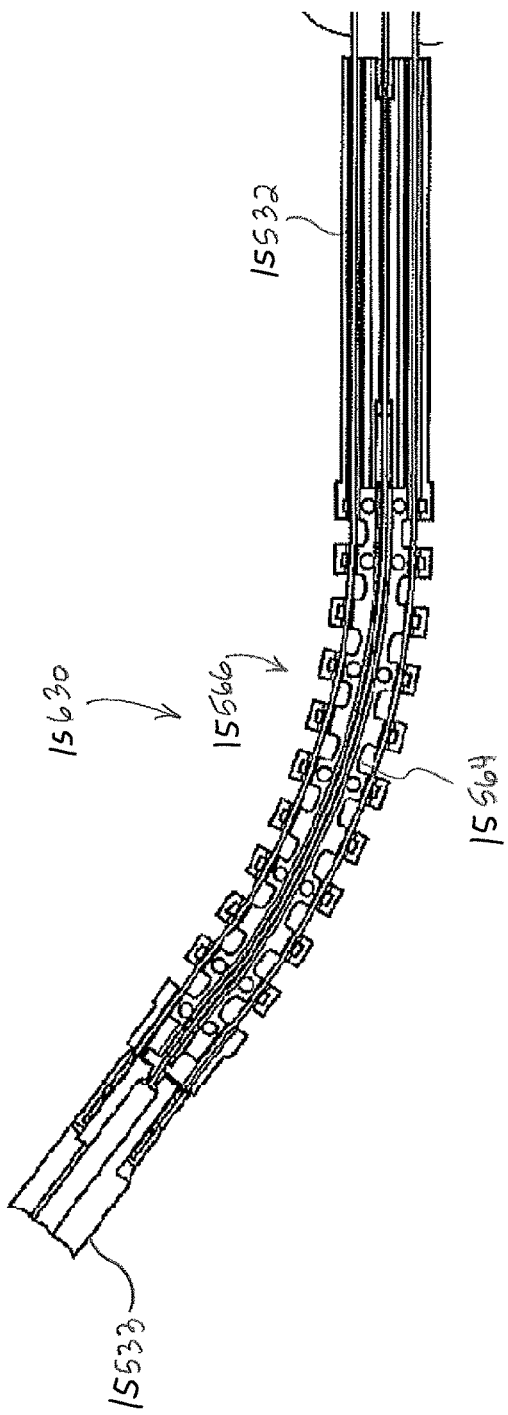
Figure 294:
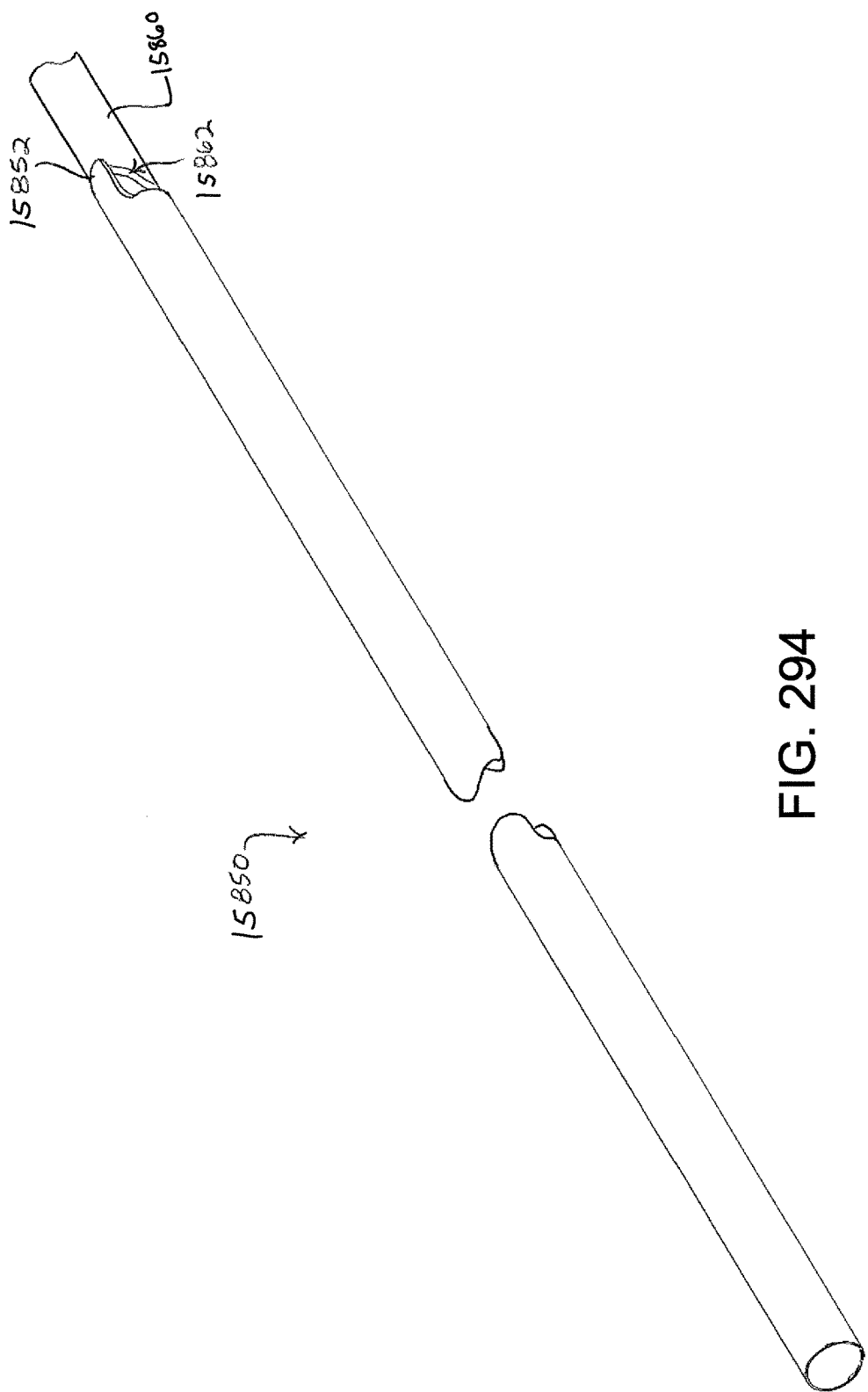
Figure 295:
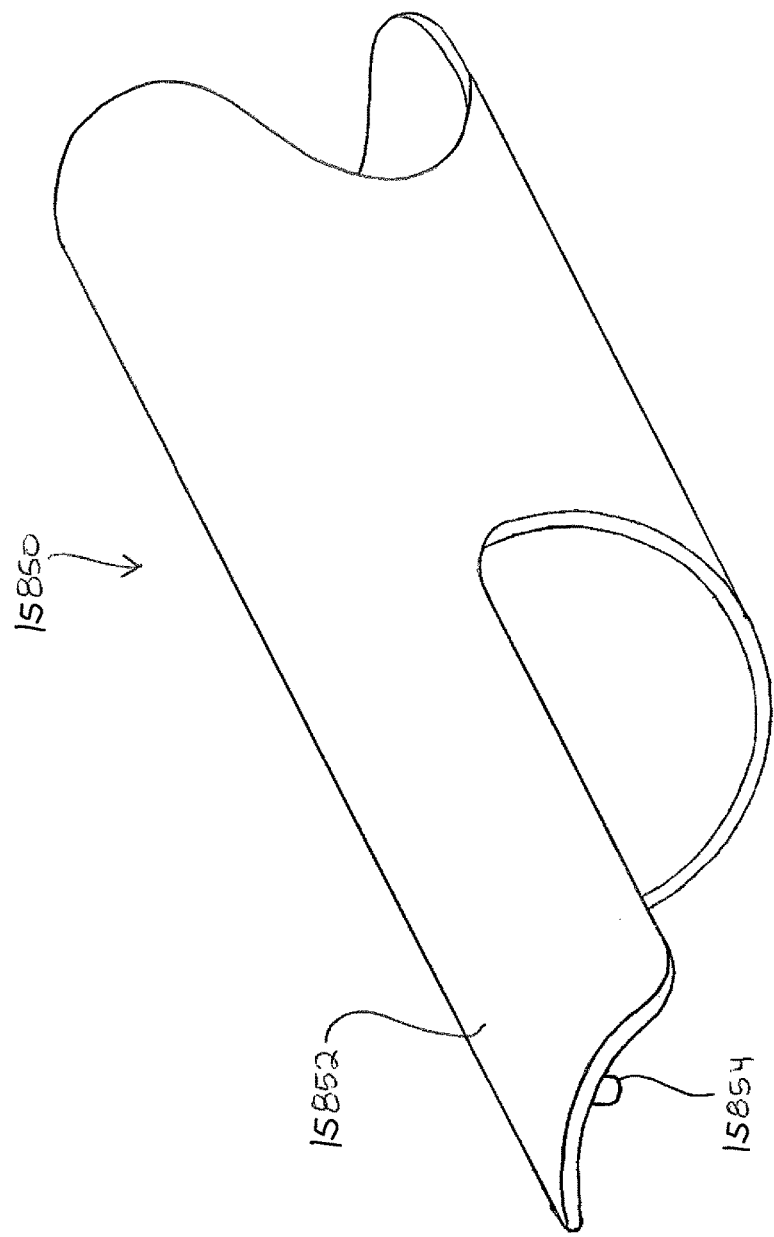
Figure 296:
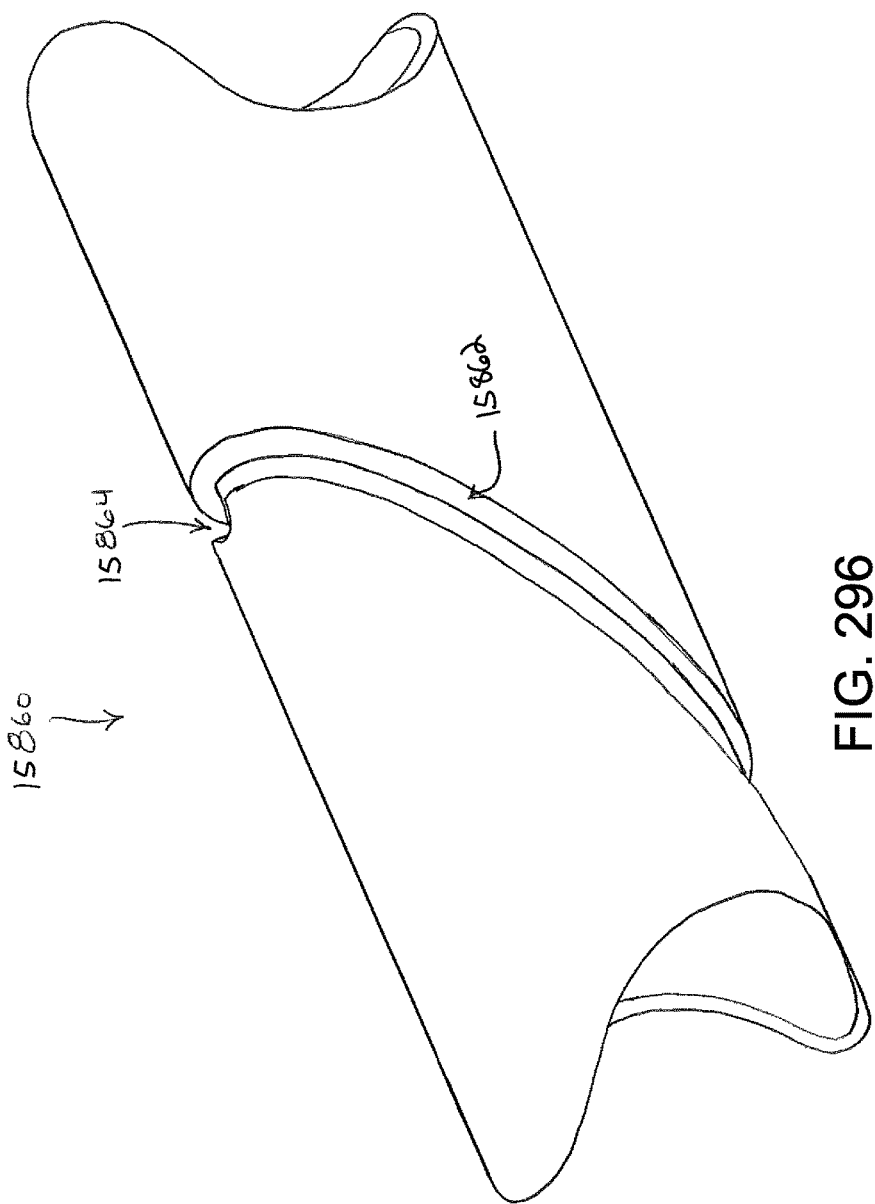
Figure 297A:
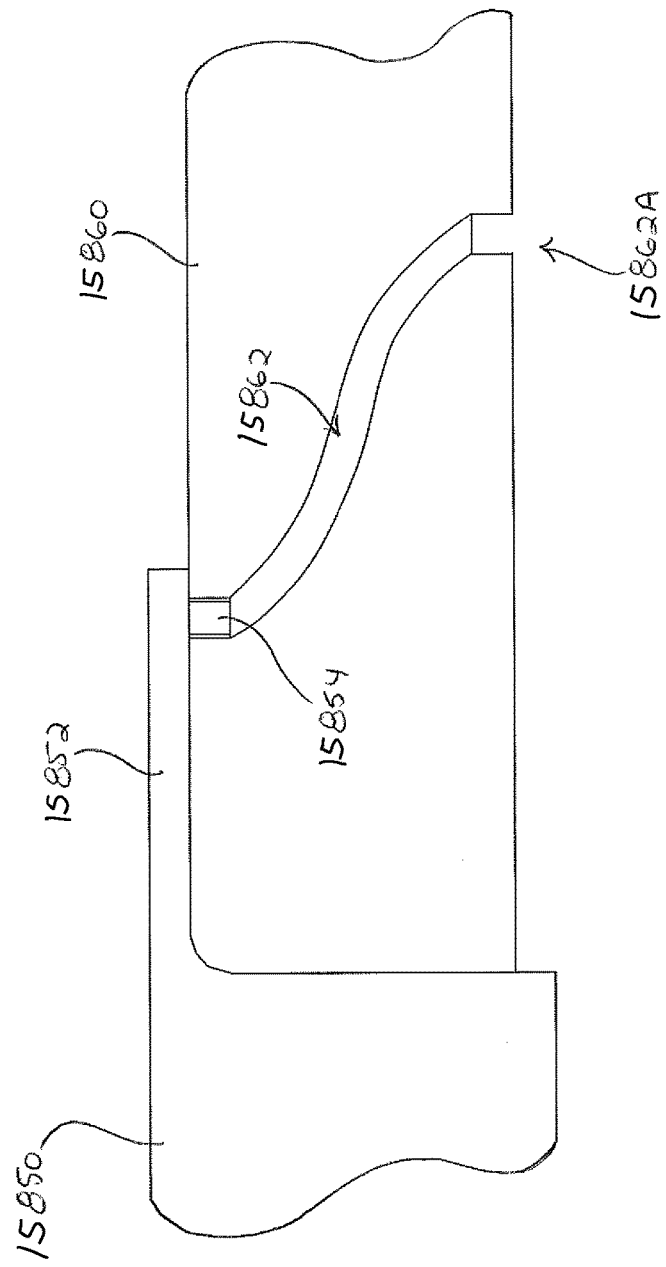
Figure 297B:
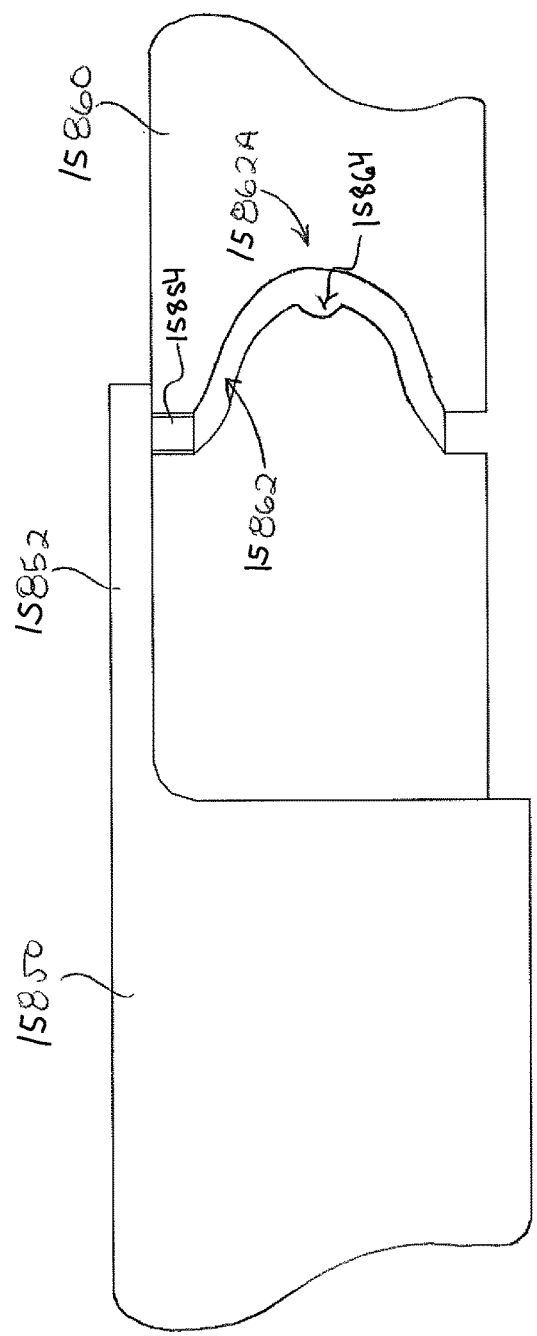
Figure 297C:
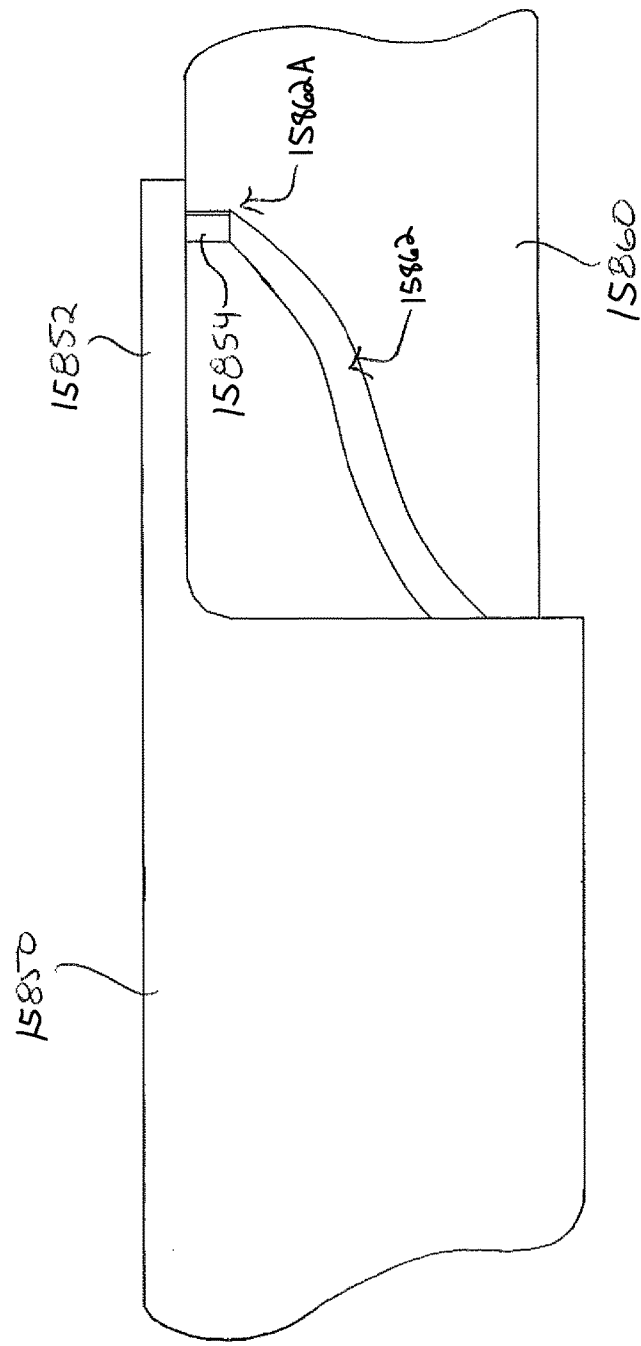
Figure 298A:
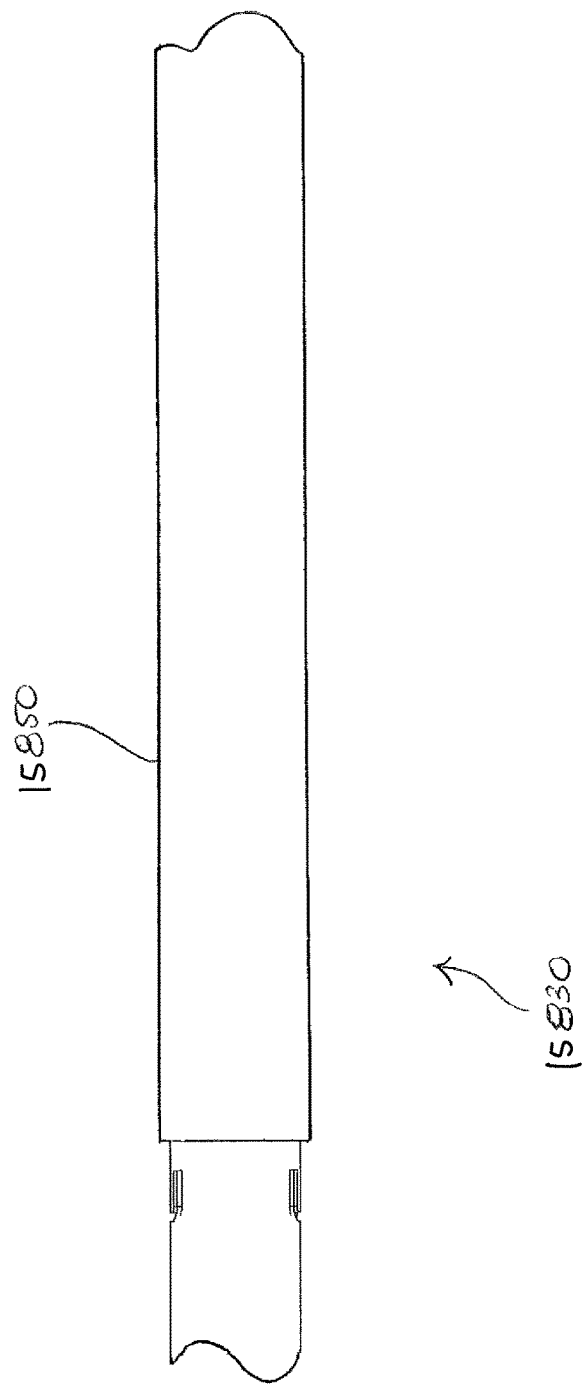
Figure 298B:
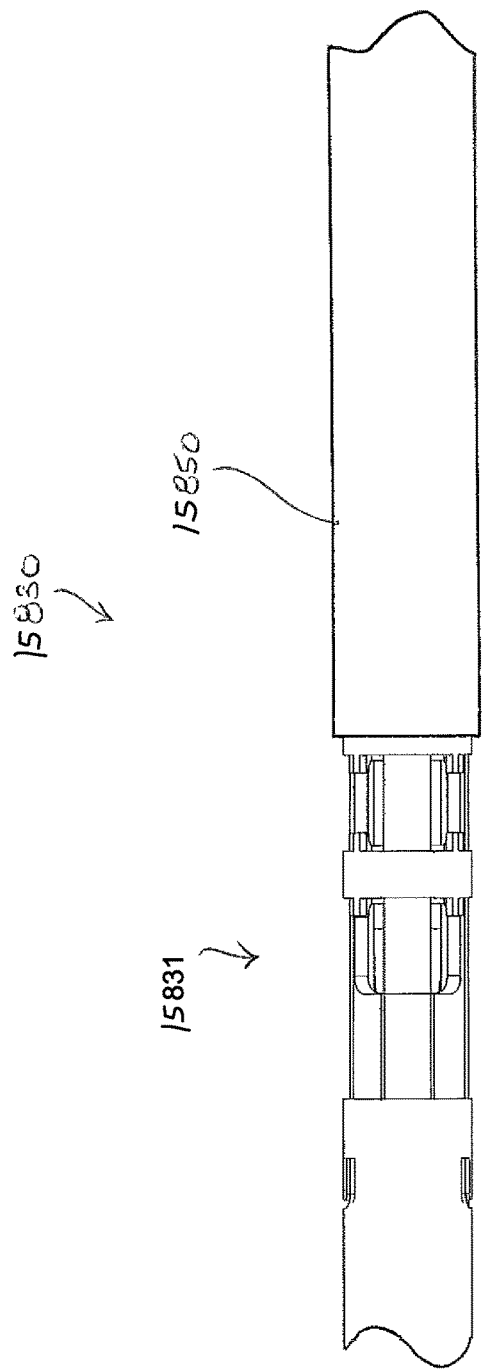
Figure 298C:
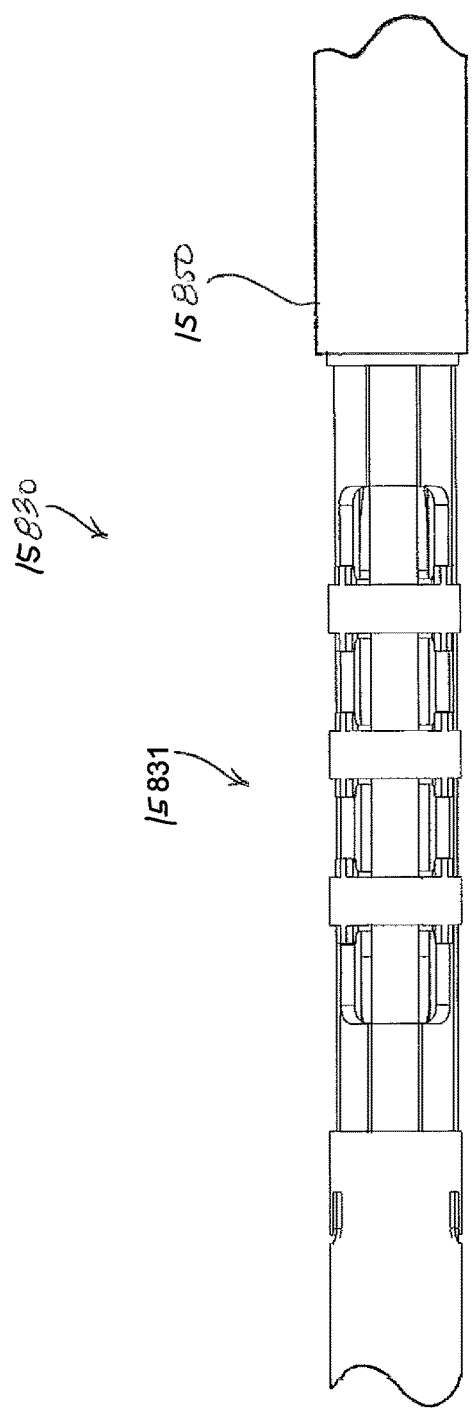

FIG. 99E depicts a cross sectional front view of the assembled rotation lock feature of FIG. 96 in the first unengaged position but rotated 90 degrees;

FIG. 100A depicts a side elevational view of another exemplary alternative surgical instrument, with a partially assembled rotation lock feature in an unlocked position;

FIG. 100B depicts a side elevational view of the instrument of FIG. 100A, with the partially assembled rotation lock feature in a locked position;

FIG. 101A depicts a top cross-sectional view of the instrument of FIG. 100A, with the rotation lock feature in the unlocked position;

FIG. 101B depicts a top cross-sectional view of the instrument of FIG. 100A, with the rotation lock feature in the locked position;

FIG. 102A depicts a top cross-sectional view of a partially assembled exemplary alternative rotation lock feature that may be incorporated into the instrument of FIG. 1 or the instrument of FIG. 95, with the rotation lock feature in an unlocked position;

FIG. 102B depicts a top cross-sectional view of the partially assembled rotation lock feature of FIG. 102A in a locked position;

FIG. 103A depicts a top cross-sectional view of a partially assembled exemplary alternative rotation lock feature that may be incorporated into the instrument of FIG. 1 or the instrument of FIG. 95, with the rotation lock feature in an unlocked position;

FIG. 103B depicts a top cross-sectional view of the partially assembled rotation lock feature of FIG. 103A in a locked position;

FIG. 104A depicts a top plan view of a modified version of the shaft assembly and end effector of FIG. 2 having an exemplary structural feature in a spaced-apart orientation;

FIG. 104B depicts a top plan view of the modified shaft assembly and end effector of FIG. 104A with the structural feature of FIG. 104A in a closed orientation;

FIG. 105 depicts a perspective view of another modified version of the shaft assembly and end effector of FIG. 2 having another exemplary structural feature;

FIG. 106A depicts a cross-sectional top view of the modified shaft assembly and end effector of FIG. 105 in a straight configuration with the structural feature of FIG. 105 deflated;

FIG. 106B depicts a cross-sectional top view of the modified shaft assembly and end effector of FIG. 105 in a straight configuration with the structural feature of FIG. 105 inflated;

FIG. 106C depicts a cross-sectional top view of the modified shaft assembly and end effector of FIG. 105 in an articulated configuration with the structural feature of FIG. 105 deflated;

FIG. 107 depicts a top plan view of another modified version of the shaft assembly and end effector of FIG. 2 having a plurality of couplers linked to one another;

FIG. 108A depicts a top plan view of yet another exemplary structural feature that may be incorporated into the shaft assembly of FIG. 107, in a contracted configuration;

FIG. 108B depicts a top plan view of the structural feature of FIG. 108A in an expanded configuration;

FIG. 109 depicts a top view of the shaft assembly and end effector of FIG. 107 in a straight configuration with the structural feature of FIG. 108A in the contracted configuration positioned therein;

FIG. 110A depicts detailed a top view of the shaft assembly of FIG. 107 in a straight configuration with the structural feature of FIG. 108A in the contracted configuration positioned therein;

FIG. 110B depicts detailed a top view of the shaft assembly of FIG. 107 in a straight configuration with the structural feature of FIG. 108A in the expanded configuration positioned therein;

FIG. 111A depicts a perspective view of a modified version of the articulation control assembly of FIG. 9 in a first rotational position and coupled with a linkage of the structural feature of FIG. 108A;

FIG. 111B depicts a perspective view of the modified articulation control assembly of FIG. 111A moved into a second rotational position so as to translate the linkage of FIG. 111A;

FIG. 112 depicts a perspective view of yet another exemplary structural feature that may be incorporated into the shaft assembly and end effector of FIG. 107;

FIG. 113 depicts a top plan view of the structural feature of FIG. 112;

FIG. 114A depicts detailed a top view of the shaft assembly of FIG. 107 in a straight configuration with the structural feature of FIG. 112 positioned therein in a first lateral position;

FIG. 114B depicts detailed a top view of the shaft assembly of FIG. 107 in a straight configuration with the structural feature of FIG. 112 positioned therein and moved to a second lateral position;

FIG. 115 depicts a top plan view of yet another exemplary structural feature that may be incorporated into the shaft assembly of FIG. 2;

FIG. 116A depicts a detailed top plan view of a modified version of the shaft assembly of FIG. 2 having a plurality of linkage members in a straight configuration with the structural feature of FIG. 115 positioned therein in a distal longitudinal position;

FIG. 116B depicts a detailed top plan view of the modified shaft assembly of FIG. 116A having a plurality of linkage members in a straight configuration with the structural feature of FIG. 115 positioned therein and moved into a proximal longitudinal position;

FIG. 116C depicts a detailed top plan view of the modified shaft assembly of FIG. 116A having a plurality of linkage members in an articulated configuration with the structural feature of FIG. 115 positioned therein in the proximal longitudinal position;

FIG. 117 depicts a perspective view of another modified version of the shaft assembly of FIG. 2 having yet another exemplary structural feature positioned therein;

FIG. 118 depicts a top plan view of the structural feature of FIG. 117;

FIG. 119 depicts a cross-sectional front view of the stiffening feature of FIG. 117, taken along line 119-119 of FIG. 118;

FIG. 120 depicts an exemplary alternative cross-sectional front view of the stiffening feature of FIG. 117;

FIG. 121 depicts a cross-sectional front view of the modified shaft assembly of FIG. 117 with the structural feature of FIG. 117 positioned therein, with the cross section taken along line 121-121 of FIG. 117;

FIG. 122A depicts a detailed cross-sectional top plan view of the modified shaft assembly of FIG. 117 in a straight configuration with the structural feature of FIG. 117 positioned therein in a distal longitudinal position, with the cross section taken along line 122-122 of FIG. 117;

FIG. 122B depicts a detailed cross-sectional top plan view of the modified shaft assembly of FIG. 117 in a straight configuration with the structural feature of FIG. 117 positioned therein and moved into a proximal longitudinal position, with the cross section taken along line 122-122 of FIG. 117;

FIG. 122C depicts a detailed cross-sectional top plan view of the modified shaft assembly of FIG. 117 in an articulated configuration with the structural feature of FIG. 117 positioned therein in the proximal longitudinal position, with the cross section taken along line 122-122 of FIG. 117;

FIG. 123 depicts a perspective view of yet another exemplary structural feature that may be incorporated into the shaft assembly of FIG. 2;

FIG. 124 depicts a cross-sectional front view of the rigidizing member of FIG. 123, taken along line 124-124 of FIG. 123;

FIG. 125A depicts a detailed cross-sectional top plan view of a modified version of the shaft assembly of FIG. 2 in a straight configuration with the structural feature of FIG. 123 positioned thereabout in a distal longitudinal position;

FIG. 125B depicts a detailed cross-sectional top plan view of the modified shaft assembly of FIG. 125A in a straight configuration with the structural feature of FIG. 123 positioned thereabout and moved into a proximal longitudinal position;

FIG. 125C depicts a detailed cross-sectional top plan view of the modified shaft assembly of FIG. 125A in an articulated configuration with the structural feature of FIG. 123 positioned thereabout in the proximal longitudinal position;

FIG. 126 depicts a perspective view of yet another exemplary structural feature that may be incorporated into the shaft assembly of FIG. 2;

FIG. 127 depicts a side view of the structural feature of FIG. 126;

FIG. 128 depicts a cross-sectional front view of the structural feature of FIG. 126, taken along line 128-128 of FIG. 127;

FIG. 129A depicts a detailed cross-sectional top plan view of a modified version of the shaft assembly of FIG. 2 in a straight configuration with the structural feature of FIG. 126 positioned thereabout in a distal longitudinal position;

FIG. 129B depicts a detailed cross-sectional top plan view of the modified shaft assembly of FIG. 129A in a straight configuration with the structural feature of FIG. 126 positioned thereabout and moved into a proximal longitudinal position;

FIG. 129C depicts a detailed cross-sectional top plan view of the modified shaft assembly of FIG. 129A in an articulated configuration with the structural feature of FIG. 126 positioned thereabout in the proximal longitudinal position;

FIG. 130A depicts a detailed cross-sectional top plan view of the modified shaft assembly of FIG. 129A in a straight configuration with a pair of the structural features of FIG. 126 positioned thereabout in a distal longitudinal position;

FIG. 130B depicts a detailed cross-sectional top plan view of the modified shaft assembly of FIG. 129A in a straight configuration with a pair of the structural features of FIG. 126 positioned thereabout and moved into a proximal longitudinal position;

FIG. 131 depicts a perspective view of yet another exemplary structural feature that may be incorporated into the shaft assembly of FIG. 2;

FIG. 132A depicts a detailed top plan view of the shaft assembly of FIG. 2 with the structural feature of FIG. 131 spaced apart therefrom;

FIG. 132B depicts a detailed top plan view of the shaft assembly of FIG. 2 with the structural feature of FIG. 131 positioned thereabout;

FIG. 133A depicts a detailed cross-sectional top plan view of a modified version of the shaft assembly of FIG. 2 having a pair of exemplary structural articulation bands in a straight configuration;

FIG. 133B depicts a detailed cross-sectional top plan view of the modified shaft assembly of FIG. 133A in an articulated configuration;

FIG. 134 depicts a side elevation view of an articulation band of the modified shaft assembly of FIG. 133A;

FIG. 135 depicts a side elevation view of another articulation band of the modified shaft assembly of FIG. 133A;

FIG. 136A depicts the articulation bands of FIG. 133A with "weak spots" of the articulation bands offset from one another;

FIG. 136B depicts the articulation bands of FIG. 133A with "weak spots" of the articulation bands aligned with one another;

FIG. 137 depicts a detailed cross-sectional top plan view of a modified version of the shaft assembly of FIG. 2 having yet another exemplary structural feature;

FIG. 138 depicts a detailed cross-sectional top plan view of a modified version of the shaft assembly of FIG. 2 having yet another exemplary structural feature;

FIG. 139 depicts a detailed cross-sectional top plan view of a modified version of the shaft assembly of FIG. 2 having yet another exemplary structural feature;

FIG. 140A depicts a detailed cross-sectional top plan view of a modified version of the shaft assembly of FIG. 2 in a straight configuration having yet another exemplary structural feature;

FIG. 140B depicts a detailed cross-sectional top plan view of the modified shaft assembly of FIG. 140A in an articulated configuration;

FIG. 141 depicts a partially exploded perspective view of an exemplary alternative articulation control assembly that may be incorporated into the instrument of FIG. 1;

FIG. 142 depicts a side elevational view of a rotatable knob of the articulation control assembly of FIG. 141;

FIG. 143 depicts a cross-sectional side view of the articulation control assembly of FIG. 141, with the knob in a first position;

FIG. 144 depicts another side cross-sectional view of the articulation control assembly of FIG. 141, with the knob in a second position;

FIG. 145 depicts a perspective view of another exemplary alternative articulation control assembly that may be incorporated into the instrument of FIG. 1;

FIG. 146 depicts a cross-sectional side view of the articulation control assembly of FIG. 145, with the cross-section taken along line 146-146 of FIG. 145, with a rotatable knob in a first position;

FIG. 147 depicts another cross-sectional side view of the articulation control assembly of FIG. 145, with the cross-section taken along line 146-146 of FIG. 145, with the rotatable knob pivoted to a second position;

FIG. 148 depicts a top plan view of an exemplary alternative articulation section that may be incorporated into the instrument of FIG. 1, with the articulation section in a straight configuration;

FIG. 149 depicts another top plan view of the articulation section of FIG. 148, with the articulation section in an articulated configuration;

FIG. 150 depicts a top plan view of an exemplary alternative housing that may be incorporated into the instrument of FIG. 1 for use with the articulation section of FIG. 148;

FIG. 151 depicts a top cross-sectional view of another exemplary alternative articulation section that may be incorporated into the instrument of FIG. 1;

FIG. 152 depicts a side elevational view of an exemplary alternative ultrasonic surgical instrument;

FIG. 153 depicts a detailed side cut-away view of the instrument of FIG. 152, with a tensioning assembly in a non-tensioning position;

FIG. 154 depicts a side cross-sectional view of a articulation control assembly of the instrument of FIG. 152;

FIG. 155 depicts a detailed side cut-away view of the instrument of FIG. 152, with a tensioning assembly in a tensioned position;

FIG. 156 depicts a side elevational view of another exemplary alternative surgical instrument;

FIG. 157 depicts a detailed top plan view of a tensioning assembly of the instrument of FIG. 156;

FIG. 158 depicts a side cross-sectional view of a collar of the tensioning assembly of FIG. 157, with the cross-section taken along line 158-158 of FIG. 157;

FIG. 159 depicts a detailed side elevational view of the tensioning assembly of FIG. 157, with the tensioning assembly in a non-tensioning position;

FIG. 160 depicts another detailed side elevational view of the tensioning assembly of FIG. 157, with the tensioning assembly in a tensioning position;

FIG. 161 depicts a top plan view of the shaft assembly and end effector of FIG. 2, including a movable sheath, with the sheath in a proximal position;

FIG. 162 depicts another top plan view of the shaft assembly and end effector of FIG. 2, with the movable sheath of FIG. 161 advanced to a distal position;

FIG. 163 depicts a top plan view of the shaft assembly and end effector of FIG. 2, including an exemplary alternative movable sheath, with the sheath in a first position;

FIG. 164 depicts another top plan view of the shaft assembly and end effector of FIG. 2, with the movable sheath of FIG. 163 retracted to a second position;

FIG. 165 depicts still another top plan view of the shaft assembly and end effector of FIG. 2, with the movable sheath of FIG. 163 advanced to a third position;

FIG. 166 depicts a perspective view of the articulation section of FIG. 2, the articulation section including a rotatable sheath, with the sheath in a first angular position;

FIG. 167 depicts a front cross-sectional view of the rotatable sheath of FIG. 166, the cross-section taken along line 167-167 of FIG. 166;

FIG. 168 depicts a top cross-sectional view of the articulation section and rotatable sheath of FIG. 166, the cross-section taken along line 168-168 of FIG. 166;

FIG. 169 depicts another perspective view of the articulation section of FIG. 2, with the rotatable sheath of FIG. 166 rotated to a second angular position;

FIG. 170 depicts a top cross-sectional view of the articulation section and rotatable sheath of FIG. 166, with the cross-section taken along line 170-170 of FIG. 169 and the sheath in the second angular position;

FIG. 171 depicts a perspective view of the articulation section of FIG. 2, the articulation section including an exemplary alternative rotatable sheath, with the sheath in a first angular position;

FIG. 172 depicts another perspective view of the articulation section and rotatable sheath of FIG. 171, with the sheath rotated to a second angular position;

FIG. 173 depicts a side elevational view of an exemplary alternative sheath assembly that may be incorporated into the instrument of FIG. 1, with an outer sheath in a first angular position;

FIG. 174 depicts a side cut-away view of the sheath assembly of FIG. 173;

FIG. 175 depicts another side elevational view of the sheath assembly of FIG. 173, with the outer sheath rotated to a second angular position;

FIG. 176 depicts a top plan view of the shaft assembly and end effector of FIG. 2, including a coil sheath assembly, with the coil sheath assembly in a first position;

FIG. 177 depicts another top plan view of the shaft assembly and end effector of FIG. 2, with the coil sheath assembly in a second position;

FIG. 178 depicts a top plan view of the shaft assembly and end effector of FIG. 2, including a linkage assembly, with the linkage assembly in a first configuration;

FIG. 179 depicts another top plan view of the shaft assembly and end effector of FIG. 2, with the linkage assembly in a second configuration;

FIG. 180 depicts a top plan view of the shaft assembly and end effector of FIG. 2, including a rigidizing plate assembly, with the rigidizing plate assembly in a proximal position;

FIG. 181 depicts a perspective view of the rigidizing member of the rigidizing plate assembly of FIG. 180;

FIG. 182 depicts another top plan view of the shaft assembly and end effector of FIG. 2, with the rigidizing plate assembly is a distal position;

FIG. 183 depicts a side elevational view of an exemplary alternative surgical instrument, with an outer sheath and actuation driver in a proximal position;

FIG. 184 depicts an exploded side view of the outer sheath and actuation driver of FIG. 30;

FIG. 185 depicts a front end view of the actuation driver of FIG. 183;

FIG. 186 depicts another side elevational view of the instrument of FIG. 183 with the outer sheath and actuation driver in a distal position;

FIG. 187 depicts a side elevational view of another exemplary alternative surgical instrument, with a rigidizing member and a drive member in a proximal position;

FIG. 188 depicts an exploded side view of the rigidizing member and drive member of FIG. 187;

FIG. 189 depicts a front end view of the drive member of FIG. 187;

FIG. 190 depicts a front cross-sectional view of a shaft assembly of the instrument of FIG. 187;

FIG. 191 depicts partial side elevational view of the instrument of FIG. 187, with the drive member in the proximal position;

FIG. 192 depicts a detailed side elevational view of a shaft assembly and end effector of the instrument of FIG. 187, with the rigidizing member in the proximal position;

FIG. 193 depicts another partial side elevational view of the instrument of FIG. 187, with the drive member in an intermediate position;

FIG. 194 depicts another detailed side elevational view of the shaft assembly and the end effector of the instrument of FIG. 187, with the rigidizing member in an intermediate position;

FIG. 195 depicts still another partial side elevational view of the instrument of FIG. 187, with the drive member in a distal position;

FIG. 196 depicts still another detailed side elevational view of the shaft assembly and the end effector of the instrument of FIG. 187, with the rigidizing member in a distal position;

FIG. 197 depicts an exploded view of an exemplary alternative rigidizing member and drive member that may be incorporated into the instrument of FIG. 187;

FIG. 198 depicts an front end view of the drive member of FIG. 197;

FIG. 199 depicts a cross-sectional view of the shaft assembly of the instrument of FIG. 34 incorporating the rigidizing member of FIG. 197;

FIG. 200 depicts a partial side elevational view of the instrument of FIG. 187 incorporating the rigidizing member and drive member of FIG. 197, with the drive member in a proximal position;

FIG. 201 depicts a detailed top plan view of a shaft assembly and end effector of the instrument of FIG. 187 incorporating the rigidizing member and drive member of FIG. 197, with the rigidizing member in a proximal position;

FIG. 202 depicts another partial side elevational view of the instrument of FIG. 187 incorporating the rigidizing member and drive member of FIG. 197, with the drive member in an intermediate position;

FIG. 203 depicts another detailed top plan view of the shaft assembly and the end effector of the instrument of FIG. 187, with the rigidizing member in an intermediate position;

FIG. 204 depicts still another partial side elevational view of the instrument of FIG. 187 incorporating the rigidizing member and drive member of FIG. 197, with the drive member in a distal position;

FIG. 205 depicts still another detailed top plan view of the shaft assembly and the end effector of the instrument of FIG. 187, with the rigidizing member in a distal position;

FIG. 206 depicts a perspective view of an exemplary alternative waveguide, including a curved blade;

FIG. 207 depicts a perspective view of a distal end of the waveguide of FIG. 206;

FIG. 208 depicts a top view of the distal end of the waveguide of FIG. 206, showing a bend angle of a blade of the waveguide;

FIG. 209 depicts a perspective view of an exemplary alternative articulation section of a shaft assembly and an end effector incorporating the waveguide of FIG. 206, which is suitable for incorporation into the surgical instrument of FIG. 1;

FIG. 210 depicts a perspective view of the articulation section of the shaft assembly and the end effector of FIG. 209, with certain parts omitted to show details;

FIG. 211 depicts an exploded perspective view of the articulation section of the shaft assembly and the end effector of FIG. 209;

FIG. 212 depicts a perspective view of a distal flex member of the articulation section of FIG. 209;

FIG. 213 depicts a cross-sectional view of the distal flex member of FIG. 212, with the cross section taken along line 213-213 of FIG. 212;

FIG. 214 depicts a perspective view of a proximal flex member of the articulation section of FIG. 209;

FIG. 215 depicts a front elevational view of the proximal flex member of FIG. 214;

FIG. 216 depicts a perspective view of a plurality of flex base members of the articulation section of FIG. 209, in an unflexed configuration;

FIG. 217 depicts a front elevational view of the plurality of flex base members of FIG. 216;

FIG. 218A depicts a top elevational view of the plurality of flex base members of FIG. 216, in an unflexed configuration;

FIG. 218B depicts a top elevational view of the flex base members of FIG. 216, in a flexed configuration;

FIG. 219 depicts a perspective view of a distal tube member of the articulation section of FIG. 14;

FIG. 220 depicts a top elevational view of the distal tube member of FIG. 219;

FIG. 221 depicts a perspective view of a proximal tube member of the articulation section of FIG. 209;

FIG. 222 depicts a top elevational view of the proximal tube member of FIG. 221;

FIG. 223 depicts a perspective view of a plurality of flex rings of the articulation section of FIG. 209 in an unflexed configuration;

FIG. 224A depicts a top elevational view of the plurality of flex rings of FIG. 223, in an unflexed configuration;

FIG. 224B depicts a top elevational view of the set of flex rings of FIG. 223, in a flexed configuration;

FIG. 225 depicts a perspective view of a collar of the articulation section of FIG. 209;

FIG. 226 depicts a front elevational view of the collar of FIG. 225;

FIG. 227A depicts a top elevational view of the articulation section of the shaft assembly and the end effector of FIG. 209, showing the articulation section in an unarticulated configuration;

FIG. 227B depicts a top elevational view of the articulation section of the shaft assembly and the end effector of FIG. 209, showing the articulation section in an articulated configuration;

FIG. 228A depicts a top cross-sectional view of the articulation section of the shaft assembly and the end effector of FIG. 209, showing the articulation section in an unarticulated configuration;

FIG. 228B depicts a top cross-sectional view of the articulation section of the shaft assembly and the end effector of FIG. 209, showing the articulation section in an articulated configuration;

FIG. 229 depicts a side elevational view of another exemplary ultrasonic surgical instrument;

FIG. 230 depicts a perspective view of the instrument of FIG. 229;

FIG. 231 depicts a side elevational view of a proximal portion of the instrument of FIG. 229 with a shrouding half removed;

FIG. 232 depicts a detailed side elevational view of the instrument of FIG. 229 with a shrouding half removed;

FIG. 233 depicts a cross-sectional front view of a shaft assembly of the instrument of FIG. 229;

FIG. 234 depicts a perspective view of internal components of the shaft assembly of FIG. 233;

FIG. 235 depicts a partially exploded perspective view of an articulation control assembly of the instrument of FIG. 229;

FIG. 236 depicts an exploded perspective view of a drive assembly of the articulation control assembly of FIG. 235;

FIG. 237 depicts another partially exploded perspective view of the drive assembly of FIG. 236;

FIG. 238 depicts a perspective view of a lead screw of the drive assembly of FIG. 236;

FIG. 239 depicts a front elevational view of the lead screw of FIG. 238;

FIG. 240 depicts a perspective view of another lead screw of the drive assembly of FIG. 236;

FIG. 241 depicts a front elevational view of the lead screw of FIG. 240;

FIG. 242A depicts a perspective view of a cylindrical guide of the drive assembly of FIG. 236;

FIG. 242B depicts a partially exploded perspective view of the cylindrical guide of FIG. 242A;

FIG. 243 depicts a cross-sectional perspective view of the drive assembly of FIG. 236, taken along the line 243-243 of FIG. 237;

FIG. 244 depicts a cross-sectional perspective view of the drive assembly of FIG. 236, taken along the line 244-244 of FIG. 237;

FIG. 245A depicts a detailed side elevational view of the instrument of FIG. 229 with a shrouding half removed, and a cross-sectional top view of an articulation section of the shaft assembly of FIG. 233, with the articulation section in a substantially straight configuration;

FIG. 245B depicts a detailed side elevational view of the instrument of FIG. 229 with a shrouding half removed, and a cross-sectional top view of the articulation section of FIG. 245A, with the articulation section in a first stage of articulation;

FIG. 245C depicts a detailed side elevational view of the instrument of FIG. 229 with a shrouding half removed, and a cross-sectional top view of the articulation section of FIG. 245A, with the articulation section in a second stage of articulation;

FIG. 246 depicts a side elevational view of yet another exemplary ultrasonic surgical instrument;

FIG. 247 depicts a perspective view of the instrument of FIG. 246;

FIG. 248 depicts a perspective view of the instrument of FIG. 246, with a disposable portion separated from a reusable portion;

FIG. 249 depicts a perspective view of an exemplary alternative disposable portion that may be used with the reusable portion of the instrument of FIG. 246;

FIG. 250 depicts another perspective view the disposable portion of FIG. 249;

FIG. 251 depicts a cross-sectional front view of a shaft assembly of the disposable portion of FIG. 249, taken along line 251-251 of FIG. 249;

FIG. 252 depicts another cross-sectional front view of a shaft assembly of the disposable portion of FIG. 249, taken along line 252-252 of FIG. 249;

FIG. 253 depicts a perspective view of internal components of the shaft assembly of FIG. 252;

FIG. 254 depicts a side elevational view of a body portion of the disposable portion of FIG. 249;

FIG. 255 depicts a side elevational view of the body portion of FIG. 254 with a shrouding half removed;

FIG. 256 depicts a detailed side elevational view of the body portion of FIG. 254 with a shrouding half removed;

FIG. 257 depicts a side elevational view of an articulation control assembly of the disposable portion of FIG. 249;

FIG. 258 depicts a perspective view of the articulation control assembly of FIG. 257;

FIG. 259A depicts a partially exploded side elevational view of the articulation control assembly of FIG. 257;

FIG. 259B depicts a perspective view of a gear reduction assembly of the articulation control assembly of FIG. 257;

FIG. 259C depicts an exploded perspective view of the gear reduction assembly of FIG. 259B;

FIG. 259D depicts a perspective view of a bevel gear of the gear reduction assembly of FIG. 259B;

FIG. 259E depicts a front elevational view of the bevel gear of FIG. 259D;

FIG. 259F depicts a perspective view of a fixed spline member of the gear reduction assembly of FIG. 259B;

FIG. 259G depicts a rear elevational view of the fixed spline member of FIG. 259F;

FIG. 259H depicts a perspective view of a flex spline member of the gear reduction assembly of FIG. 259B;

FIG. 259I depicts a rear elevational view of the flex spline member of FIG. 259H;

FIG. 259J depicts a cross-sectional view of the gear reduction assembly of FIG. 259B, taken along line 259J-259J of FIG. 259B;

FIG. 260 depicts a partial cross-sectional perspective view of a drive assembly of the articulation control assembly of FIG. 257;

FIG. 261 depicts a perspective view of a cylindrical guide of the drive assembly of FIG. 260;

FIG. 262 depicts a perspective view of a proximal rotatable housing of the drive assembly of FIG. 260;

FIG. 263 depicts a front elevational view of the proximal rotatable housing of FIG. 262;

FIG. 264 depicts a cross-sectional side view of the proximal rotatable housing of FIG. 262;

FIG. 265 depicts another cross-sectional side view of the proximal rotatable housing of FIG. 262;

FIG. 266 depicts a perspective view of a lead screw of the drive assembly of FIG. 260;

FIG. 267 depicts a front elevational view of the lead screw of FIG. 266;

FIG. 268 depicts a side elevational view of the lead screw of FIG. 266;

FIG. 269 depicts a perspective view of a translatable assembly of the drive assembly of FIG. 260;

FIG. 270 depicts a cross-sectional perspective view of the translatable assembly of FIG. 269, taken along line 270-270 of FIG. 269;

FIG. 271 depicts a cross-sectional rear view of the drive assembly of FIG. 260;

FIG. 272 depicts a perspective view of a distal rotatable housing of the drive assembly of FIG. 260;

FIG. 273 depicts a side elevational view of the distal rotatable housing of FIG. 272;

FIG. 274 depicts a front elevational view of the distal rotatable housing of FIG. 272;

FIG. 275 depicts a cross-sectional side view of the distal rotatable housing of FIG. 272, taken along line 275-275 of FIG. 272;

FIG. 276 depicts another cross-sectional side view of the second rotatable housing of FIG. 272, taken along line 276-276 of FIG. 272;

FIG. 277 depicts a perspective view of another lead screw of the drive assembly of FIG. 260;

FIG. 278 depicts a front elevational view of the lead screw of FIG. 277;

FIG. 279 depicts a bottom plan view of the lead screw of FIG. 277;

FIG. 280 depicts a perspective view of yet another lead screw of the drive assembly of FIG. 260;

FIG. 281 depicts a front elevational view of the lead screw of FIG. 280;

FIG. 282 depicts a side elevational view of the lead screw of FIG. 280;

FIG. 283 depicts a perspective view of a tensioner of the drive assembly of FIG. 260;

FIG. 284 depicts a side elevational view of the tensioner of FIG. 283;

FIG. 285 depicts a front elevational view of the tensioner of FIG. 283;

FIG. 286 depicts an exploded perspective view of the tensioner of FIG. 283;

FIG. 287 depicts a top plan view of a proximal end of a pair of translatable rods of the shaft assembly of FIG. 252;

FIG. 288 depicts another cross-sectional rear view of the drive assembly of FIG. 260;

FIG. 289 depicts yet another cross-sectional rear view of the drive assembly of FIG. 260;

FIG. 290 depicts yet another cross-sectional rear view of the drive assembly of FIG. 260;

FIG. 291A depicts a partial cross-sectional side view of the drive assembly of FIG. 260, with the lead screw of FIG. 266 in a first longitudinal position, with the lead screw of FIG. 277 in a first longitudinal position, and with the lead screw of FIG. 280 in a first longitudinal position;

FIG. 291B depicts a partial cross-sectional side view of the drive assembly of FIG. 260, with the lead screw of FIG. 266 moved to a second longitudinal position, with the lead screw of FIG. 277 moved to a second longitudinal position, and with the lead screw of FIG. 280 moved to a second longitudinal position;

FIG. 291C depicts a partial cross-sectional side view of the drive assembly of FIG. 260, with the lead screw of FIG. 266 moved to a third longitudinal position, with the lead screw of FIG. 277 moved to a third longitudinal position, and with the lead screw of FIG. 280 moved to a third longitudinal position;

FIG. 292A depicts a cross-sectional perspective view of the shaft assembly of FIG. 252, with a rod member in a first longitudinal position;

FIG. 292B depicts a cross-sectional perspective view of the shaft assembly of FIG. 252, with the rod member of FIG. 292A moved to a second longitudinal position;

FIG. 293A depicts a cross-sectional top view of the shaft assembly of FIG. 252, with an articulation section of the shaft assembly in a straight configuration;

FIG. 293B depicts a cross-sectional top view of the shaft assembly of FIG. 252, with the articulation section of FIG. 293B moved to a first articulated configuration;

FIG. 293C depicts a cross-sectional top view of the shaft assembly of FIG. 252, with the articulation section of FIG. 293B moved to a second articulated configuration;

FIG. 294 depicts a perspective view of a stiffening assembly that may be used with the ultrasonic surgical instruments of FIGS. 229 and 246;

FIG. 295 depicts a detailed perspective view of a proximal end of a tubular member of the stiffening assembly of FIG. 294;

FIG. 296 depicts a detailed perspective view of a tubular guide of the stiffening assembly of FIG. 294;

FIG. 297A depicts a detailed side elevational view of the tubular member of FIG. 295 coupled with the tubular guide of FIG. 296, with the tubular member in a first longitudinal position, and with the tubular guide in a first rotational position;

FIG. 297B depicts a detailed side elevational view of the tubular member of FIG. 295 coupled with the tubular guide of FIG. 296, with the tubular member moved to a second longitudinal position by rotation of the tubular guide to a second rotational position;

FIG. 297C depicts a detailed side elevational view of the tubular member of FIG. 295 coupled with the tubular guide of FIG. 296, with the tubular member moved to a third longitudinal position by rotation of the tubular guide to a third rotational position;

FIG. 298A depicts a detailed side elevational view of the tubular member of FIG. 295 in the first longitudinal position relative to an articulation section;

FIG. 298B depicts a detailed side elevational view of the tubular member of FIG. 295 moved to the second longitudinal position relative to the articulation section of FIG. 298A; and FIG. 298C depicts a detailed side elevational view of the tubular member of FIG. 295 moved to the third longitudinal position relative to the articulation section of FIG. 298A.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pat. No. 8,986,302, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 3:
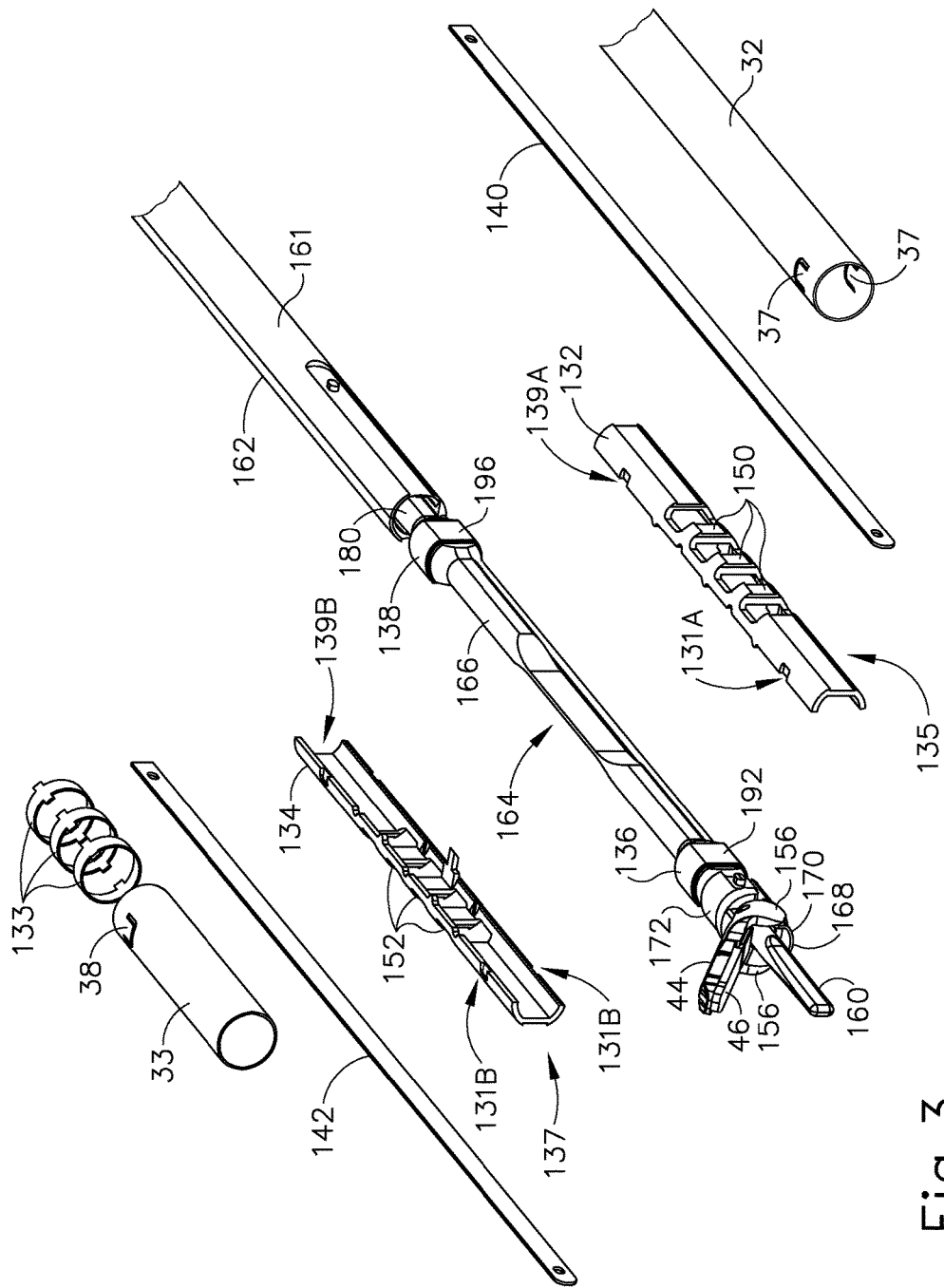
FIG. 3 depicts an exploded perspective view of an articulation section of the shaft assembly of FIG. 2.
Figure 4:
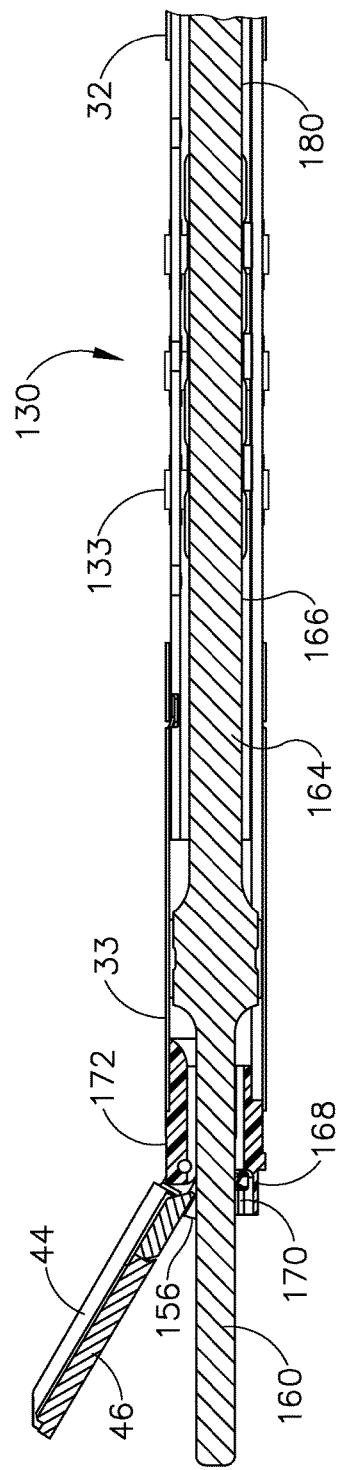
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
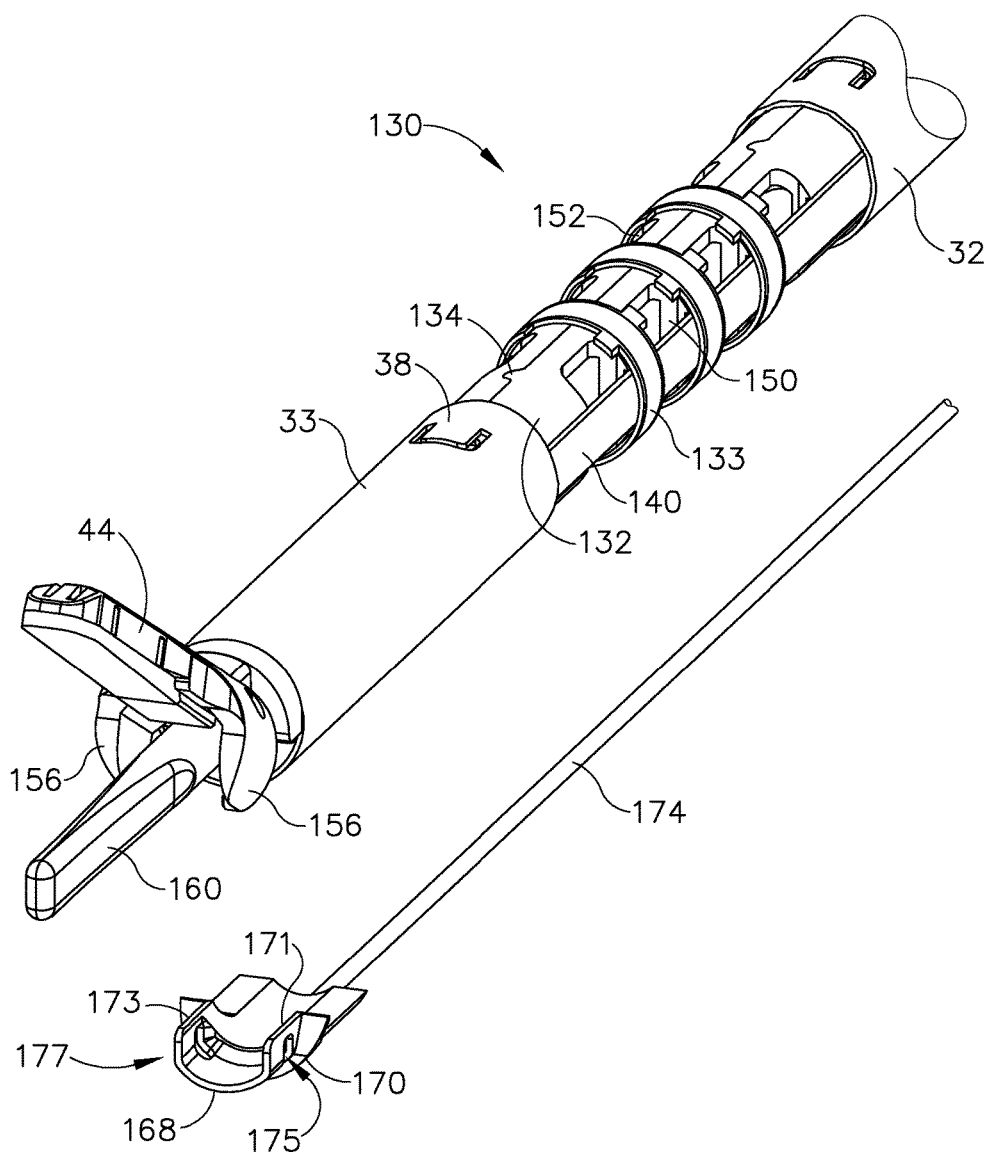
FIG. 7 depicts a partially exploded perspective view of the shaft assembly and end effector of FIG. 2.
Figure 8:
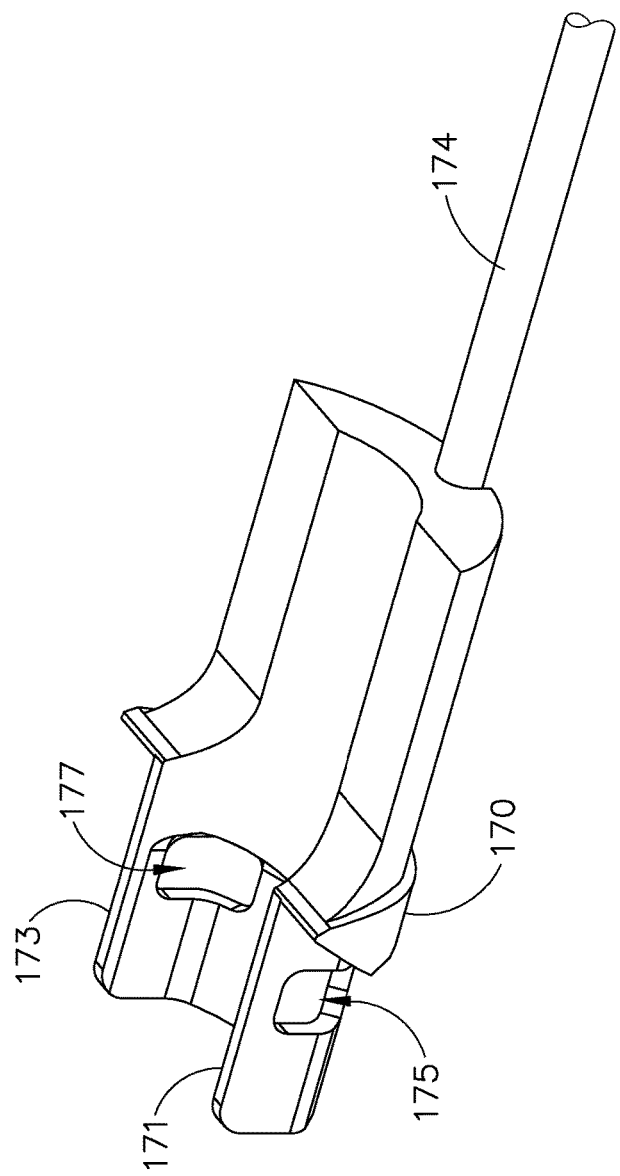
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
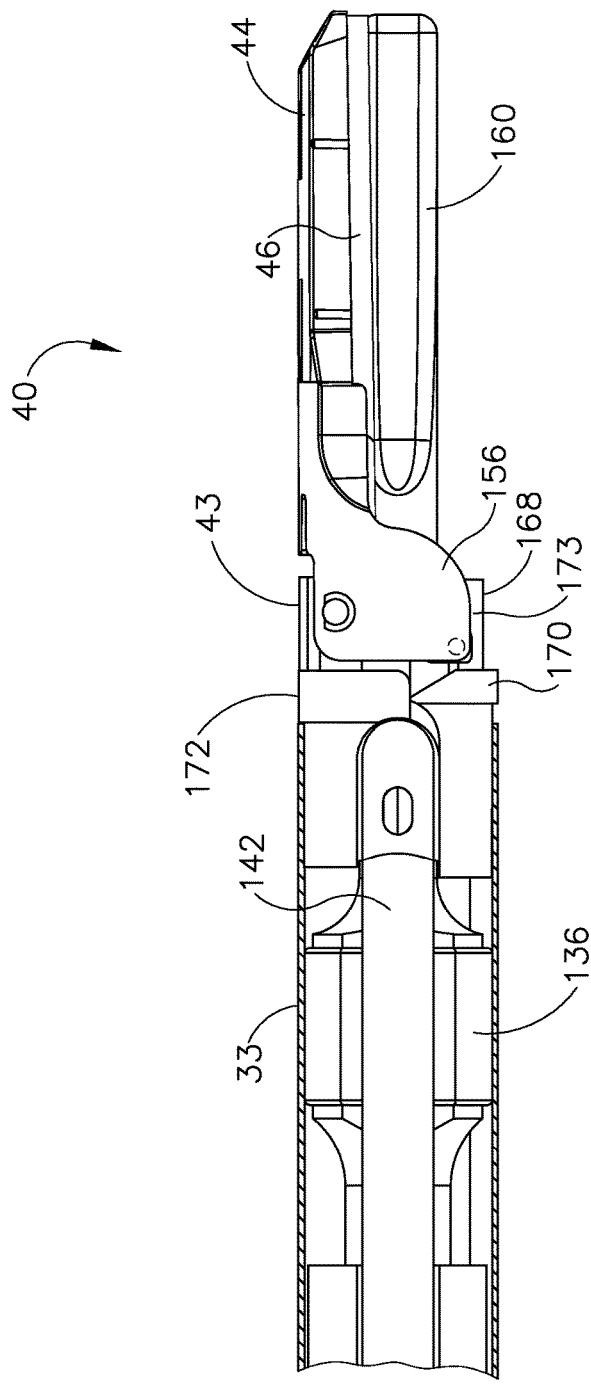
FIG. 10A depicts a side elevational view of an exemplary alternative end effector and the distal portion of a shaft assembly, configured for incorporation in the instrument of FIG. 1, with a clamp arm of the end effector in a closed position, and with an outer sheath shown in cross-section to reveal components within the outer sheath.
Figure 10B:
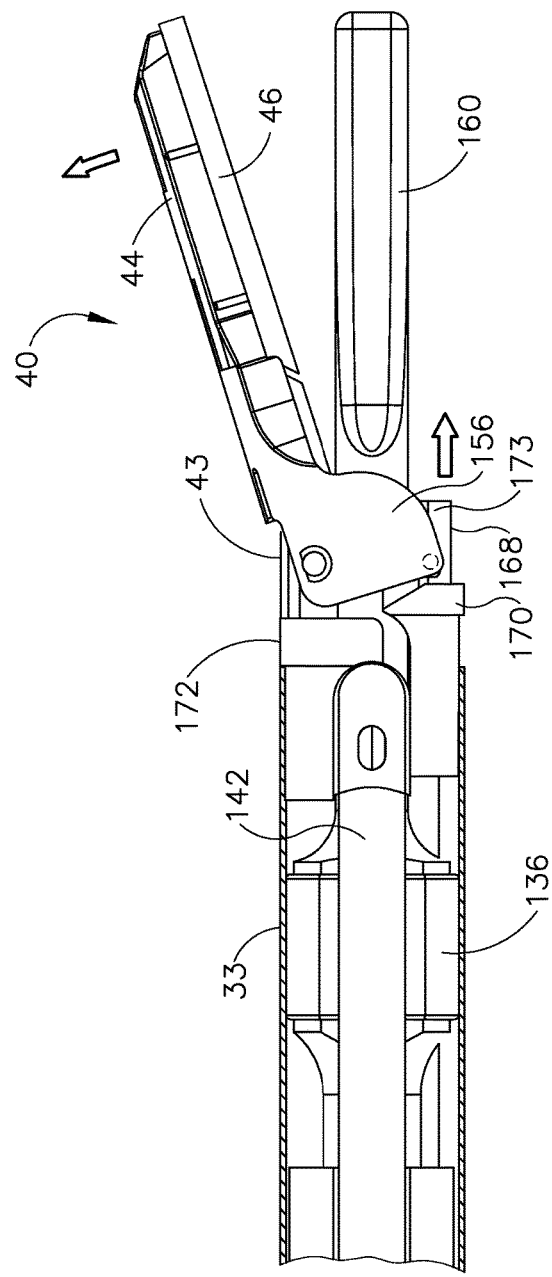
FIG. 10B depicts a side elevational view of the shaft assembly and end effector of FIG. 10A, with the clamp arm moved to a partially open position.
Figure 10C:
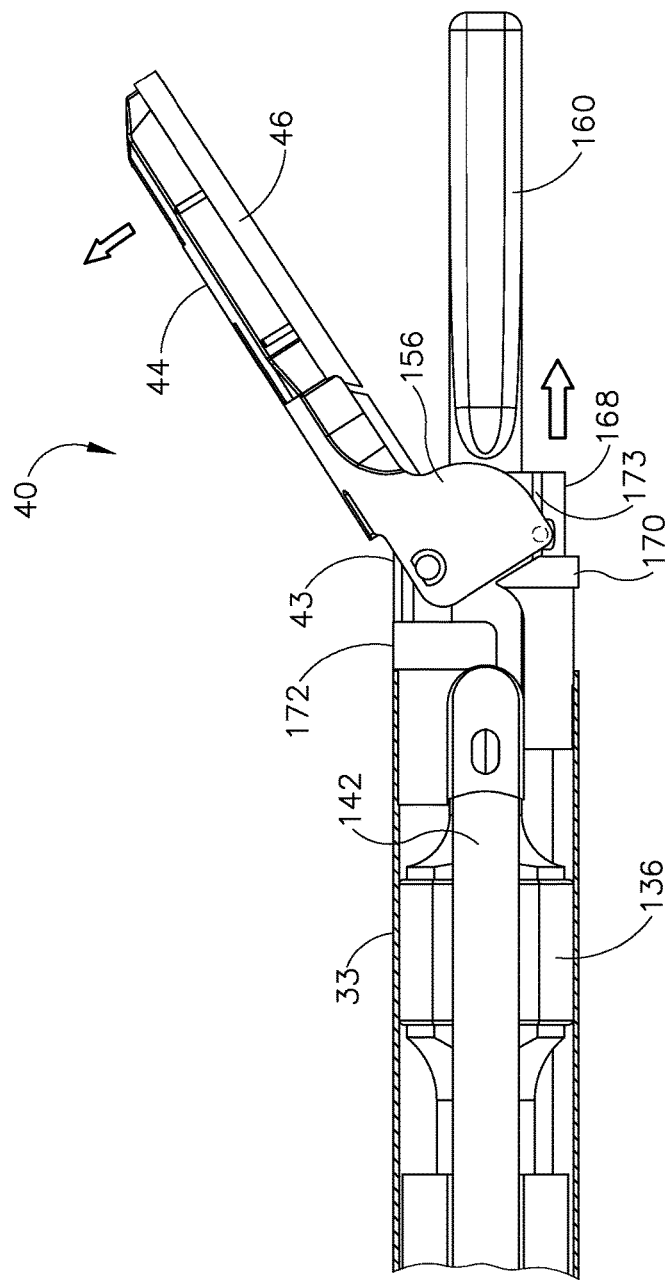
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, now issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, now issued as U.S. Pat. No. 9,393,037 on Jul. 19, 2016, and/or U.S. Pub. No. 2014/0114334, now issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
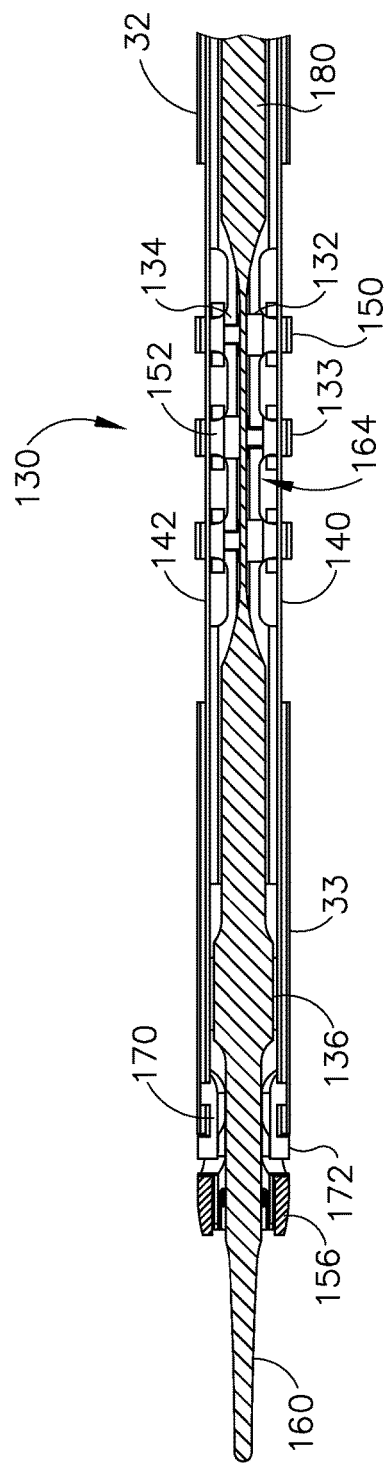
FIG. 6A depicts a cross-sectional top view of the shaft assembly and end effector of FIG. 2 in a straight configuration.
Figure 6B:
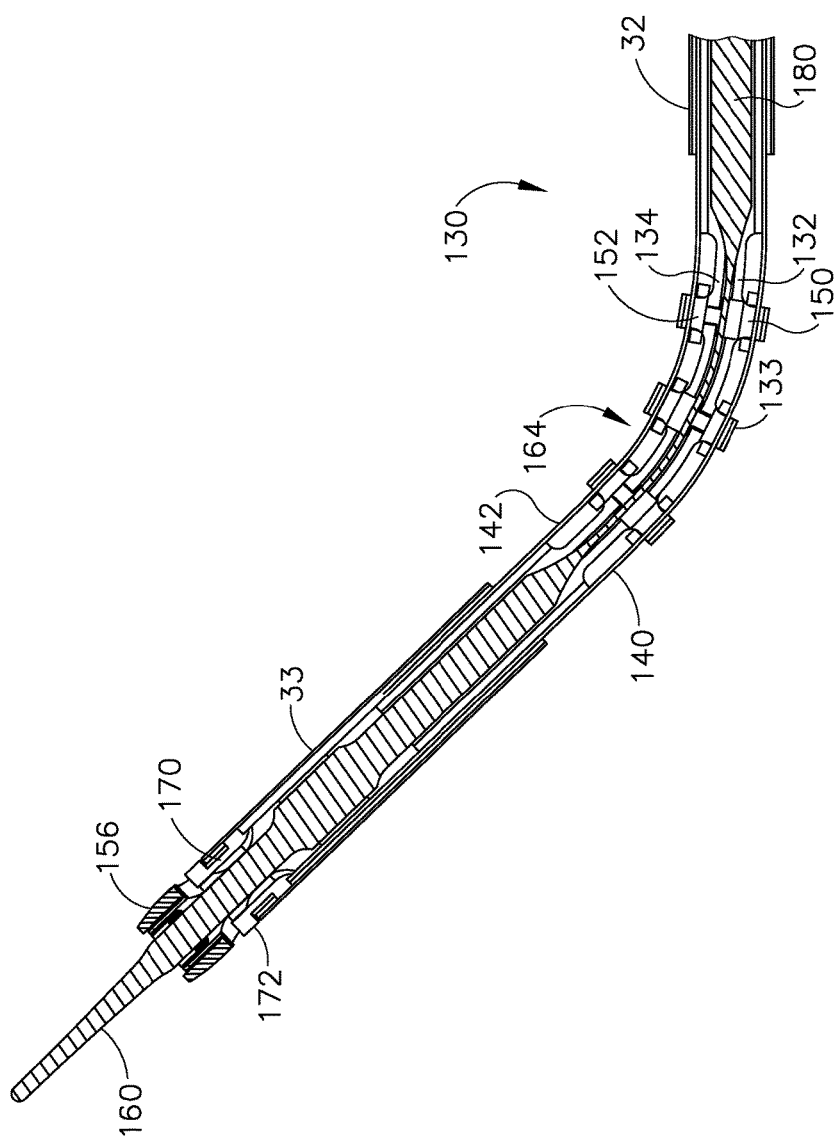
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

C. Exemplary Alternative End Effector and Shaft Assembly Configuration with Dual Role Bands and Flex Section as Ground FIGS. 11A-12B show an exemplary alternative shaft assembly (200) and end effector (240) that may be readily incorporated into instrument (10). Shaft assembly (200) of this example comprises a distal outer sheath (202), a proximal outer sheath (204), and an articulation section (210) configured to operate substantially similar to articulation section (130) discussed above except for the differences discussed below. In particular, articulation section (210) is operable to selectively position end effector (240) at various lateral deflection angles relative to a longitudinal axis defined by proximal outer sheath (204). End effector (240) includes an ultrasonic blade (242) and a pivoting clamp arm (244) having a clamp pad (245). End effector (240) is configured to operate substantially similar to end effector (40) discussed above except for the differences discussed below. In particular, clamp arm (244) of end effector (240) is operable to compress tissue against blade (242). When blade (242) is activated while clamp arm (244) compresses tissue against blade (242), end effector (240) simultaneously severs the tissue and denatures the proteins in adjacent tissue cells, thereby providing a coagulative effect.

Clamp arm (244) is operable to selectively pivot toward and away from blade (242) to selectively clamp tissue between clamp pad (245) and blade (242). Clamp arm (244) is pivotably secured to an upper distal end of distal outer sheath (202) via a pin (222). Distal outer sheath (202) is mechanically grounded to an instrument body (e.g., handle assembly (20), etc.) via articulation section (210) and proximal outer sheath (204). A pair of arms (247) extend transversely from clamp arm (244) and are pivotably secured to a collar (220) via a pin (224). Collar (220) is slidably disposed within distal outer sheath (202). Thus, it should be understood that longitudinal movement of collar (220) within distal outer sheath (202) causes pivoting of clamp arm (244) about pin (222) toward and away from blade (242). Collar (220) is longitudinally driven within distal outer sheath (202) as described in greater detail below.

Figure 11A:
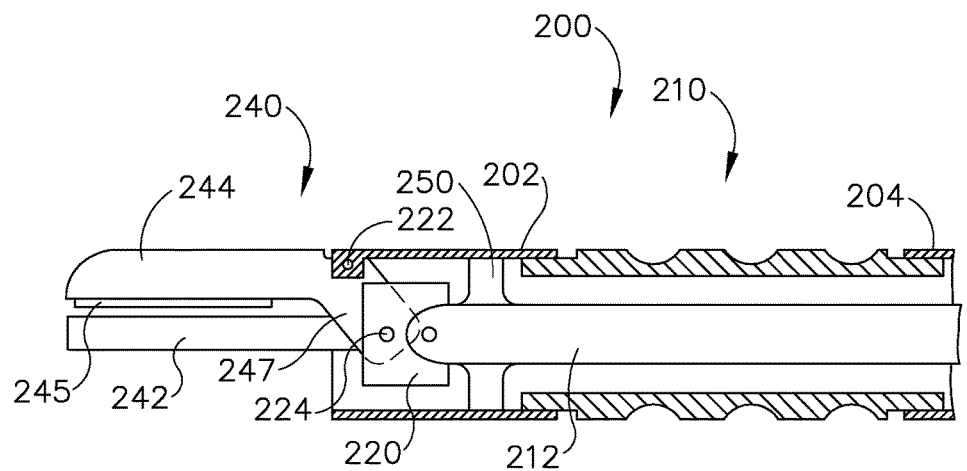
FIG. 11A depicts a side elevational view of another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 11B:
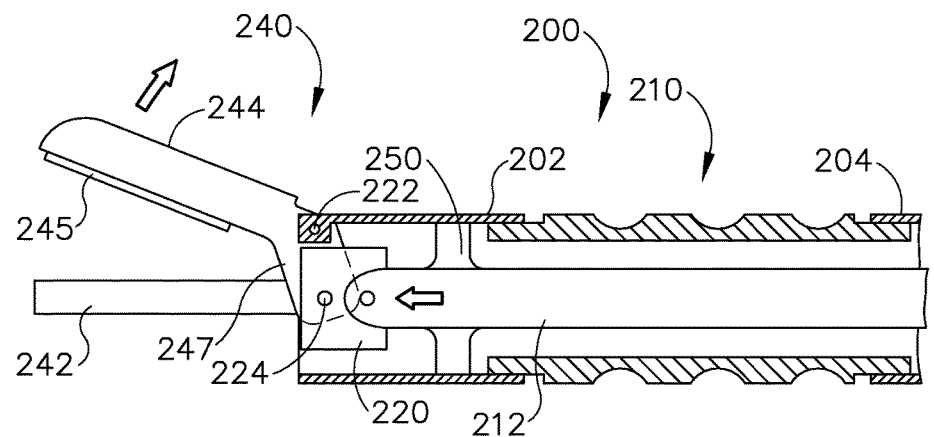
FIG. 11B depicts a side elevational view of the shaft assembly and end effector of FIG. 11A, with the clamp arm moved to an open position, and with the shaft assembly shown in side cross-section.

Blade (242) is positioned at the distal end of an acoustic drivetrain, which passes through an inner bore of collar (220) without contacting collar (220). This acoustic drivetrain includes a transducer assembly (not shown) and an acoustic waveguide (246). Waveguide (246) comprises a flexible portion (248). Flexible portion (248) of waveguide (246) includes a distal flange (250), a proximal flange (not shown), and a narrowed section (249) located between distal flange (250) and the proximal flange. In the present example, distal flange (250) and the proximal flange are located at positions corresponding to nodes associated with resonant ultrasonic vibrations communicated through flexible portion (248) of waveguide (246). Narrowed section (249) is configured to allow flexible portion (248) of waveguide (246) to flex without significantly affecting the ability of flexible portion (248) of waveguide (246) to transmit ultrasonic vibrations. As best seen in FIG. 11A-11B, distal flange (250) engages an interior surface of distal outer sheath (202). In some versions, a gap is defined between distal flange (250) and the interior surface of distal outer sheath (202). In some other versions, a dampening element such as an o-ring is interposed between distal flange (250) and the interior surface of distal outer sheath (202).

Figure 12A:
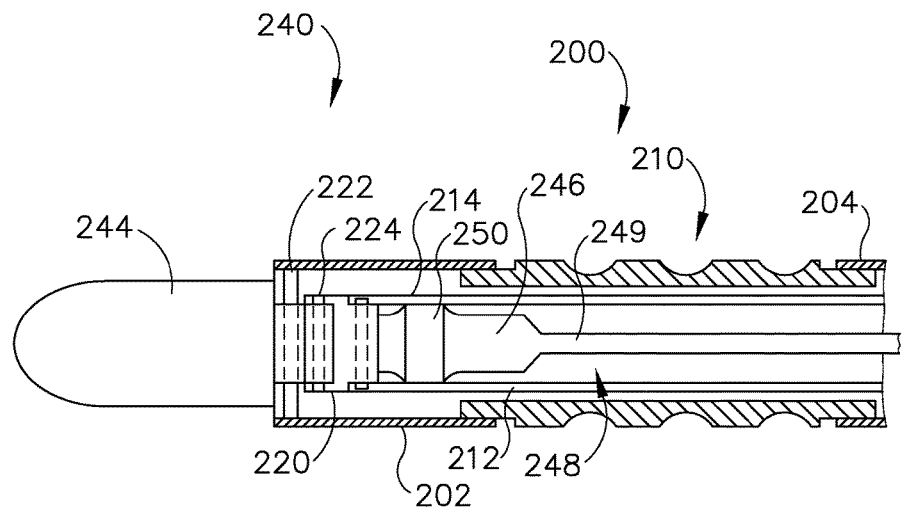
FIG. 12A depicts a top plan view of the shaft assembly and end effector of FIG. 11A in a substantially straight configuration, with the shaft assembly shown in top cross-section.
Figure 12B:
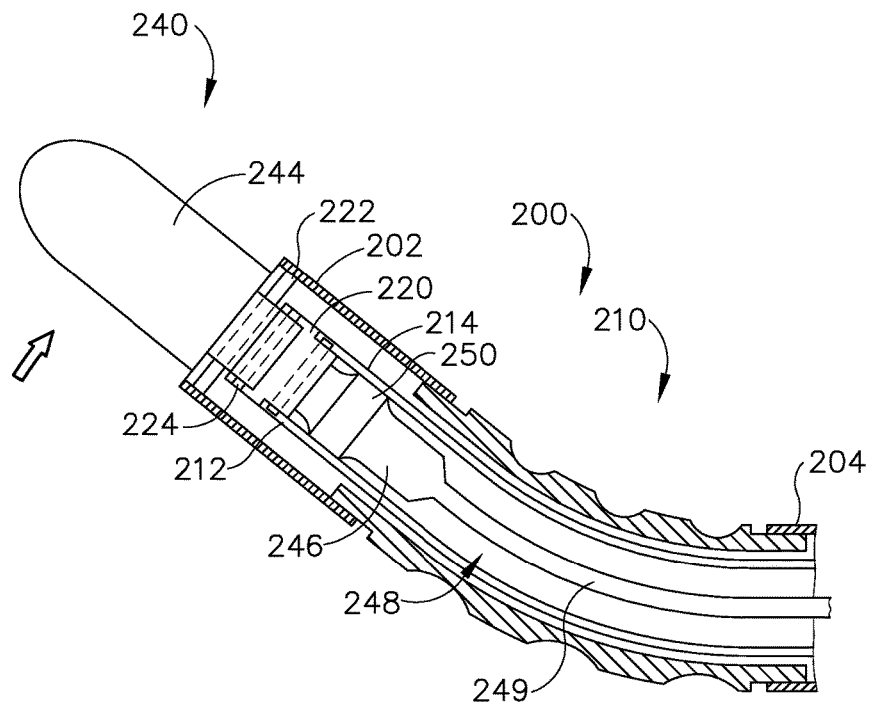
FIG. 12B depicts a top plan view of the shaft assembly and end effector of FIG. 11A in an articulated configuration, with the shaft assembly shown in top cross-section.

Shaft assembly (200) further comprises a pair of articulation bands (212, 214). Distal ends of articulation bands (212, 214) are secured to collar (220). Articulation bands (212, 214) are configured to operate substantially similar to articulation bands (140, 142) discussed above except for the differences discussed below. In particular, as shown in FIGS. 12A-12B, opposing longitudinal motion of articulation bands (212, 214) causes articulation of articulation section (210). When articulation bands (212, 214) are translated longitudinally in an opposing fashion, a moment is created and applied to a distal end of distal outer sheath (202) via pin (222), arms (247) of clamp arm (244), pin (224), and collar (220). This causes articulation section (210) and narrowed section (249) of flexible portion (248) of waveguide (246) to articulate, without transferring axial forces in articulation bands (212, 214) to waveguide (246).

As shown in FIGS. 11A-11B, when articulation bands (212, 214) are both translated in the same direction simultaneously, this simultaneous longitudinal movement of articulation bands (212, 214) causes concurrent longitudinal movement of collar (220) relative to distal outer sheath (202) and the other grounded components of shaft assembly (200). Thus, the simultaneous longitudinal motion of articulation bands (212, 214) in the same direction causes pivoting of clamp arm (244) toward and away from ultrasonic blade (242). It should therefore be understood that opposing longitudinal motion of articulation bands (212, 214) will cause articulation of articulation section (210); distal movement of both articulation bands (212, 214) simultaneously will cause clamp arm (244) to pivot away from blade (242); and proximal movement of both articulation bands (212, 214) simultaneously will cause clamp arm (244) to pivot toward blade (242).

Articulation bands (212, 214) may be driven to translate in an opposing fashion by a modified version of articulation control assembly (100). Articulation bands (212, 214) may be driven to translate in the same direction simultaneously by a modified version of trigger (28). For instance, pivoting of trigger (28) toward and away from pistol grip (24) may cause the entire modified articulation control assembly (100) to translate, which may thereby cause both articulation bands (212, 214) to translate simultaneously in the same direction. Various suitable ways in which articulation control assembly (100) and trigger (28) may be modified and coupled together will be apparent to those of ordinary skill in the art in view of the teachings herein. Similarly, other suitable ways in which articulation bands (212, 214) may be driven (in an opposing fashion and/or simultaneously in the same direction) will be apparent to those of ordinary skill in the art in view of the teachings herein.

D. Exemplary Alternative End Effector and Shaft Assembly Configuration with Dual Role Bands and Waveguide as Ground FIGS. 13A-14B show another exemplary alternative shaft assembly (300) and end effector (340) that may be readily incorporated into instrument (10). Shaft assembly (300) of this example comprises a distal outer sheath (302), a proximal outer sheath (304), and an articulation section (310) configured to operate substantially similar to articulation sections (130, 210) discussed above except for the differences discussed below. In particular, articulation section (310) is operable to selectively position end effector (340) at various lateral deflection angles relative to a longitudinal axis defined by proximal outer sheath (304). End effector (340) includes an ultrasonic blade (342) and a pivoting clamp arm (344) having a clamp pad (345). End effector (340) is configured to operate substantially similar to end effectors (40, 240) discussed above except for the differences discussed below. In particular, clamp arm (344) of end effector (340) is operable to compress tissue against blade (342). When blade (342) is activated while clamp arm (344) compresses tissue against blade (342), end effector (340) simultaneously severs the tissue and denatures the proteins in adjacent tissue cells, thereby providing a coagulative effect.

Clamp arm (344) is operable to selectively pivot toward and away from blade (342) to selectively clamp tissue between clamp pad (345) and blade (342). Clamp arm (344) is pivotably secured to an upper distal end of a distal outer sheath (302) via a pin (322). A pair of arms (347) extend transversely from clamp arm (344) and are pivotably secured to a collar (320) via a pin (324). Collar (320) is slidably disposed within distal outer sheath (302). Thus, it should be understood that longitudinal movement of collar (320) within distal outer sheath (302) causes pivoting of clamp arm (344) about pin (322) toward and away from blade (342).

Figure 13A:
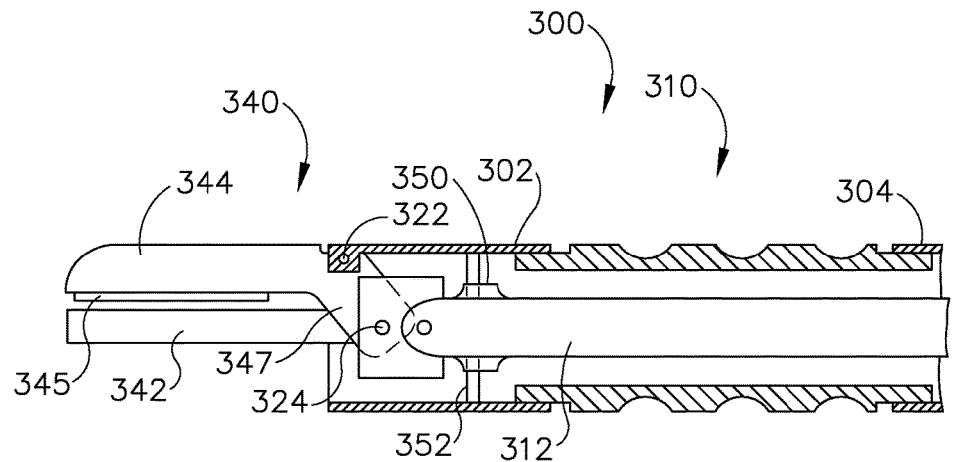
FIG. 13A depicts a side elevational view of yet another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 13B:
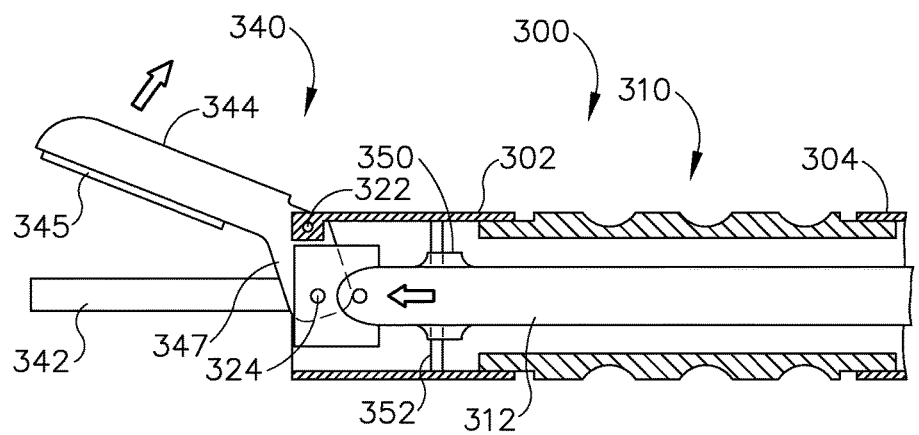
FIG. 13B depicts a side elevational view of the shaft assembly and end effector of FIG. 13A, with the clamp arm moved to an open position, and with the shaft assembly shown in side cross-section.

Blade (342) is positioned at the distal end of an acoustic drivetrain, which passes through an inner bore of collar (320) without contacting collar (320). This acoustic drivetrain includes a transducer assembly (not shown) and an acoustic waveguide (346). Waveguide (346) comprises a flexible portion (348). Flexible portion (348) of waveguide (346) includes a distal flange (350), a proximal flange (not shown), and a narrowed section (349) located between distal flange (350) and the proximal flange. In the present example, distal flange (350) and the proximal flange are located at positions corresponding to nodes associated with resonant ultrasonic vibrations communicated through flexible portion (348) of waveguide (346). Narrowed section (349) is configured to allow flexible portion (348) of waveguide (346) to flex without significantly affecting the ability of flexible portion (348) of waveguide (346) to transmit ultrasonic vibrations. As best seen in FIGS. 13A and 13B, distal flange (350) is secured to distal outer sheath (302) via a pin (352). Distal outer sheath (302) is thereby mechanically grounded to an instrument body (e.g., handle assembly (20), etc.) via waveguide (346).

Figure 14A:
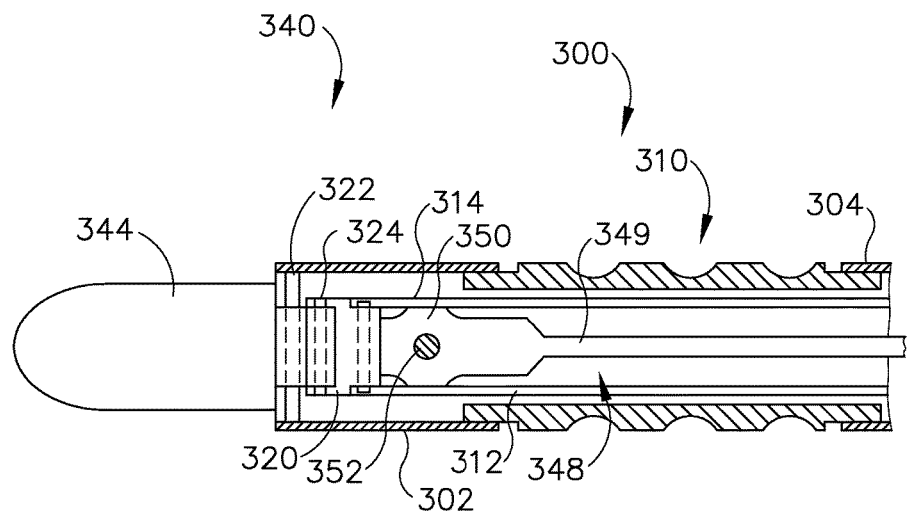
FIG. 14A depicts a top plan view of the shaft assembly and end effector of FIG. 13A in a substantially straight configuration, with the shaft assembly shown in top cross-section.
Figure 14B:
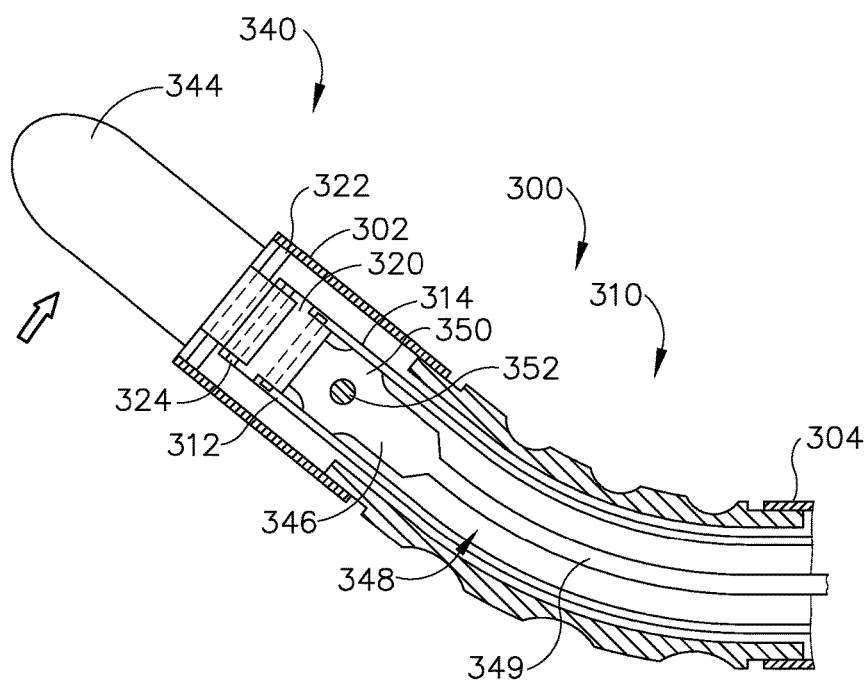
FIG. 14B depicts a top plan view of the shaft assembly and end effector of FIG. 13A in an articulated configuration, with the shaft assembly shown in top cross-section.

Shaft assembly (300) further comprises a pair of articulation bands (312, 314). Distal ends of articulation bands (312, 314) are secured to collar (320). Articulation bands (312, 314) are configured to operate substantially similar to articulation bands (140, 142, 212, 214) discussed above except for the differences discussed below. In particular, as shown in FIGS. 14A-14B, opposing longitudinal motion of articulation bands (312, 314) causes articulation of articulation section (310). Distal ends of articulation bands (312, 314) are secured to collar (320). When articulation bands (312, 314) are translated longitudinally in an opposing fashion, a moment is created and applied to a distal end of distal outer sheath (302) via pin (322), arms (347) of clamp arm (344), pin (324), and collar (320). This causes articulation section (310) and narrowed section (349) of flexible portion (348) of waveguide (346) to articulate, without transferring axial forces in articulation bands (312, 314) to waveguide (346).

As shown in FIGS. 13A-13B, when articulation bands (312, 314) are both translated in the same direction simultaneously, this simultaneous longitudinal movement of articulation bands (312, 314) causes concurrent longitudinal movement of collar (320) relative to distal outer sheath (302) and the other grounded components of shaft assembly (300). Thus, the simultaneous longitudinal motion of articulation bands (312, 314) in the same direction causes pivoting of clamp arm (344) toward and away from ultrasonic blade (342). It should therefore be understood that opposing longitudinal motion of articulation bands (312, 314) will cause articulation of articulation section (310); distal movement of both articulation bands (312, 314) simultaneously will cause clamp arm (344) to pivot away from blade (342); and proximal movement of both articulation bands (312, 314) simultaneously will cause clamp arm (344) to pivot toward blade (342).

Articulation bands (312, 314) may be driven to translate in an opposing fashion by a modified version of articulation control assembly (100). Articulation bands (312, 314) may be driven to translate in the same direction simultaneously by a modified version of trigger (28). For instance, pivoting of trigger (28) toward and away from pistol grip (24) may cause the entire modified articulation control assembly (100) to translate, which may thereby cause both articulation bands (312, 314) to translate simultaneously in the same direction. Various suitable ways in which articulation control assembly (100) and trigger (28) may be modified and coupled together will be apparent to those of ordinary skill in the art in view of the teachings herein. Similarly, other suitable ways in which articulation bands (312, 314) may be driven (in an opposing fashion and/or simultaneously in the same direction) will be apparent to those of ordinary skill in the art in view of the teachings herein.

E. Exemplary Alternative End Effector and Shaft Assembly Configuration with Clamp Arm Ball Joint FIGS. 15A-16B show yet another exemplary alternative shaft assembly (400) and end effector (440) that may be readily incorporated into instrument (10). Shaft assembly (400) comprises a distal outer sheath (402), a proximal outer sheath (404), and an articulation section (410) configured to operate substantially similar to articulation sections (130, 210, 310) discussed above except for the differences discussed below. In particular, articulation section (410) is operable to selectively position end effector (440) at various lateral deflection angles relative to a longitudinal axis defined by proximal outer sheath (404). End effector (440) includes an ultrasonic blade (442) and a pivoting clamp arm (444) having a clamp pad (445). End effector (440) is configured to operate substantially similar to end effectors (40, 240, 340) discussed above except for the differences discussed below. In particular, clamp arm (444) of end effector (440) is operable to compress tissue against blade (442). When blade (442) is activated while clamp arm (444) compresses tissue against blade (442), end effector (440) simultaneously severs the tissue and denatures the proteins in adjacent tissue cells, thereby providing a coagulative effect.

Figure 15A:
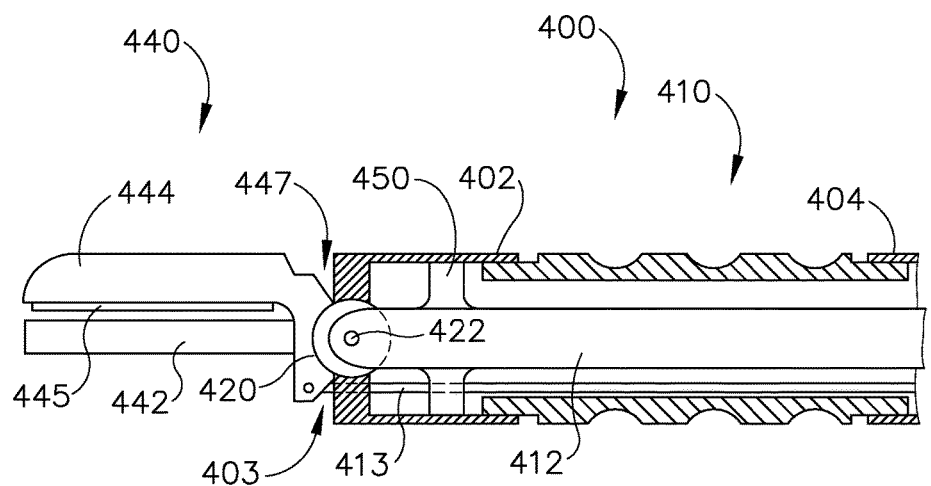
FIG. 15A depicts a side elevational view of yet another exemplary alternative end effector and the distal portion of a shaft assembly and end effector, configured for incorporation in the instrument of FIG. 1, with a clamp arm of the end effector in a closed position, and with the shaft assembly shown in side cross-section.
Figure 15B:
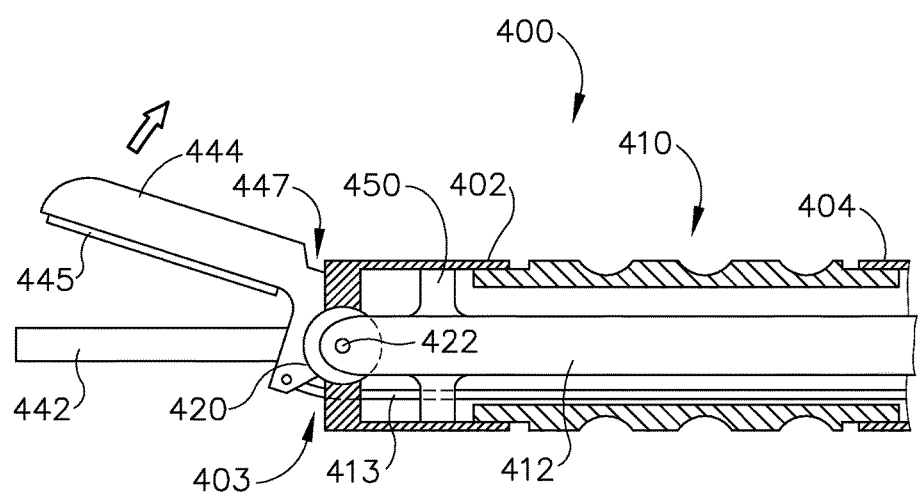
FIG. 15B depicts a side elevational view of the shaft assembly and end effector of FIG. 15A, with the clamp arm moved to an open position, and with the shaft assembly shown in side cross-section.

Clamp arm (444) is operable to selectively pivot toward and away from blade (442) to selectively clamp tissue between clamp pad (445) and blade (442). A proximal end of clamp arm (444) comprises a socket (447) configured to engage a sphere-shaped collar (420). A distal end of distal outer sheath (402) comprises a socket (403) that is also configured to engage sphere-shaped collar (420), such that sphere-shaped collar (420) is captured between sockets (403, 447). In other words, clamp arm (444), sphere-shaped collar (420), and distal outer sheath (402) engage one another in a ball-and-socket-like relationship. The proximal end of clamp arm (444) is pivotably coupled with sphere-shaped collar (420) and distal outer sheath (402) via a pin (422). Thus, it should be understood that clamp arm (444) is operable to rotate about pin (422), along sphere-shaped collar (420), toward and away from blade (442). A bottom portion of clamp arm (444) is pivotably coupled within a distal end of a rod (413). Rod (413) is slidably disposed within shaft assembly (400) such that rod (413) is freely translatable relative to articulation section (410). Thus, it should be understood that longitudinal movement of rod (413) causes pivoting of clamp arm (444) toward and away from blade (442) as shown in FIGS. 15A-15B. Rod (413) is coupled with a trigger (not shown) such that clamp arm (444) is pivotable toward and away from ultrasonic blade (442) in response to pivoting, sliding, or other actuation of the trigger.

Blade (442) is positioned at the distal end of an acoustic drivetrain, which passes through an inner bore of collar (420) without contacting collar (420). This acoustic drivetrain includes a transducer assembly (not shown) and an acoustic waveguide (446). Waveguide (446) comprises a flexible portion (448). Flexible portion (448) of waveguide (446) includes a distal flange (450), a proximal flange (not shown), and a narrowed section (449) located between distal flange (450) and the proximal flange. In the present example, distal flange (450) and the proximal flange are located at positions corresponding to nodes associated with resonant ultrasonic vibrations communicated through flexible portion (448) of waveguide (446). Narrowed section (449) is configured to allow flexible portion (448) of waveguide (446) to flex without significantly affecting the ability of flexible portion (448) of waveguide (446) to transmit ultrasonic vibrations. As best seen in FIG. 15A-15B, distal flange (450) engages an interior surface of distal outer sheath (402). In some versions, a gap is defined between distal flange (450) and the interior surface of distal outer sheath (402). In some other versions, a dampening element such as an o-ring is interposed between distal flange (450) and the interior surface of distal outer sheath (402).

Figure 16A:
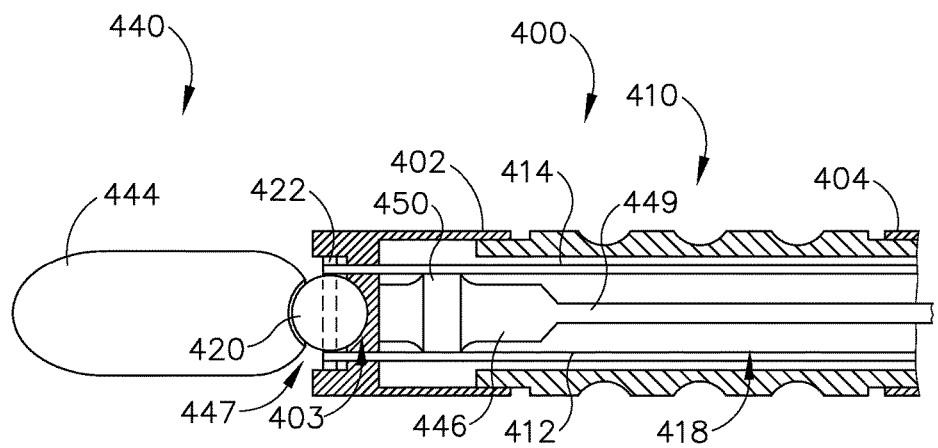
FIG. 16A depicts a top plan view of the shaft assembly and end effector of FIG. 15A in a substantially straight position, with the shaft assembly shown in top cross-section.
Figure 16B:
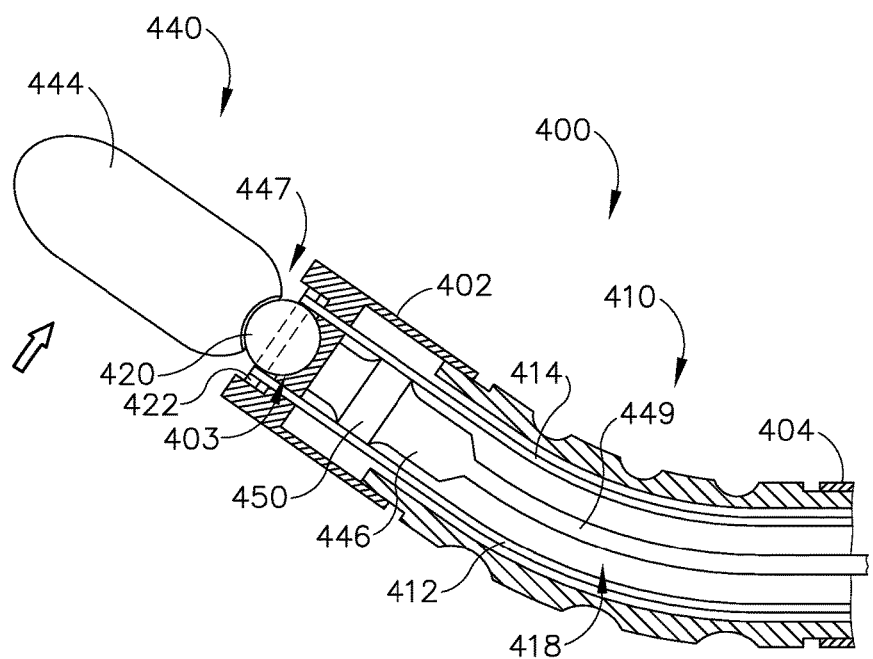
FIG. 16B depicts a top plan view of the shaft assembly and end effector of FIG. 15A moved into a bent configuration, with the shaft assembly shown in top cross-section.

Shaft assembly (400) further comprises a pair of articulation bands (412, 414). Distal ends of articulation bands (412, 414) are secured to distal outer sheath (402) and collar (420) via pin (422). Articulation bands (412, 414) are configured to operate substantially similar to articulation bands (140, 142, 212, 214, 312, 314) discussed above except for the differences discussed below. In particular, as shown in FIGS. 16A and 16B, opposing longitudinal motion of articulation bands (412, 414) is configured to cause articulation of articulation section (410). When articulation bands (412, 414) are translated longitudinally in an opposing fashion, a moment is created and applied to a distal end of distal outer sheath (402) via pin (422). This causes articulation section (410) and narrowed section (449) of flexible portion (448) of waveguide (446) to articulate, without transferring axial forces in articulation bands (412, 414) to waveguide (446). Articulation bands (212, 214) may be driven to translate in an opposing fashion by a version of articulation control assembly (100) or by any other suitable drive mechanism.

F. Fourth Exemplary Alternative End Effector and Shaft Assembly Configuration

Figure 17B:
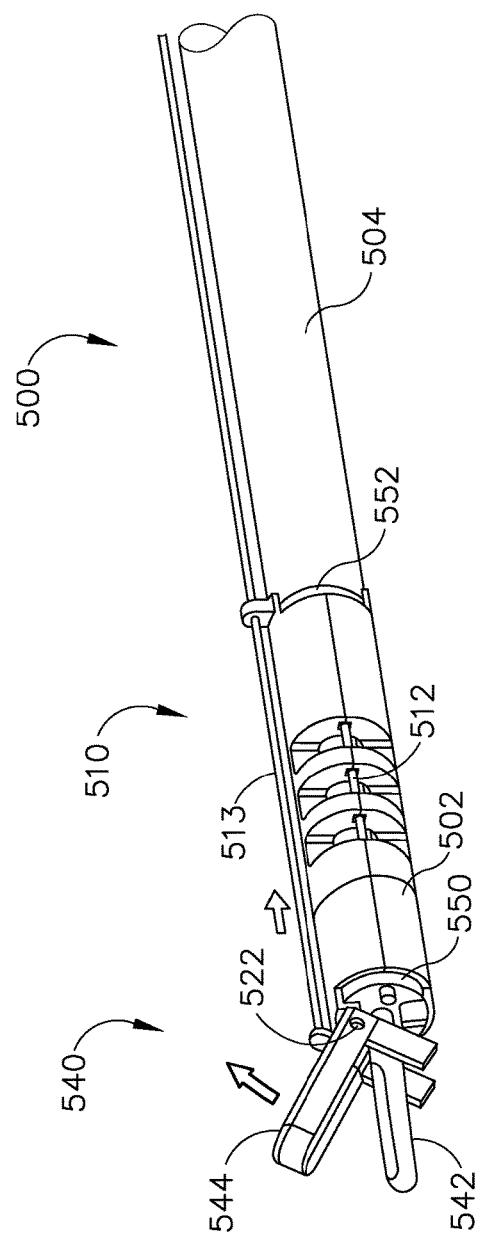
FIG. 17B depicts a perspective view of the shaft assembly and end effector of FIG. 17A, with the clamp arm moved to an open position.
Figure 18:
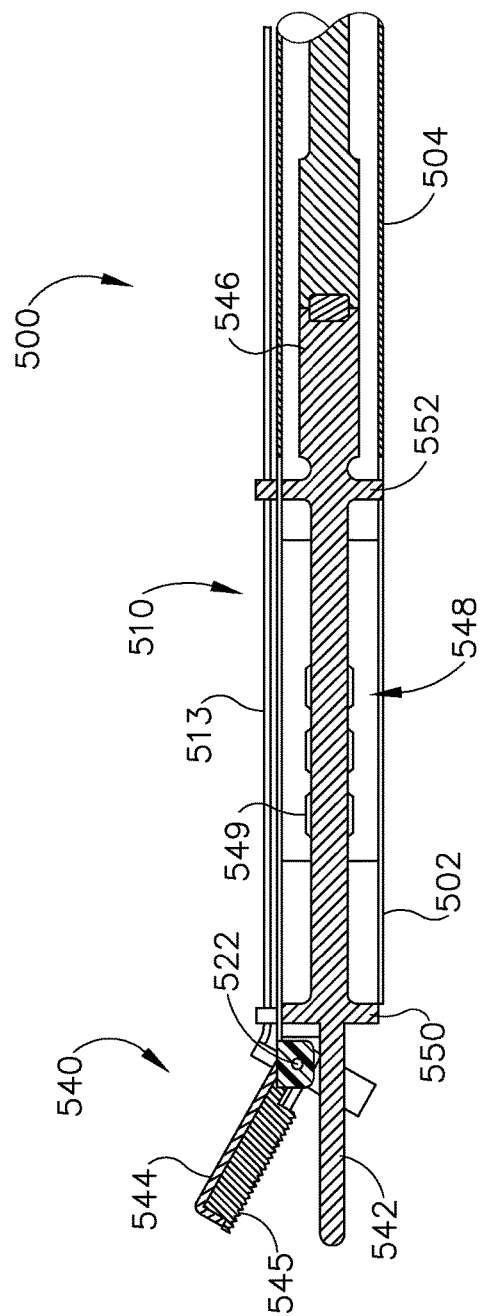
FIG. 18 depicts a side cross-sectional view of the shaft assembly and end effector of FIG. 17A, with the clamp arm in the open position.

FIGS. 17A-18 show yet another exemplary alternative shaft assembly (500) and end effector (540) that may be readily incorporated into instrument (10). Shaft assembly (500) comprises a distal outer sheath (502), a proximal outer sheath (504), and an articulation section (510) configured to operate substantially similar to articulation sections (130, 210, 310, 410) discussed above except for the differences discussed below. In particular, articulation section (510) is operable to selectively position end effector (540) at various lateral deflection angles relative to a longitudinal axis defined by proximal outer sheath (504). End effector (540) includes an ultrasonic blade (542) and a pivoting clamp arm (544) having a clamp pad (545). End effector (540) is configured to operate substantially similar to end effectors (50, 240, 340, 440) discussed above except for the differences discussed below. In particular, clamp arm (544) of end effector (540) is operable to compress tissue against blade (542). When blade (542) is activated while clamp arm (544) compresses tissue against blade (542), end effector (540) simultaneously severs the tissue and denatures the proteins in adjacent tissue cells, thereby providing a coagulative effect.

Clamp arm (544) is operable to selectively pivot toward and away from blade (542) to selectively clamp tissue between clamp pad (545) and blade (542). Clamp arm (544) is pivotably secured to an upper distal end of a distal outer sheath (502) via a pin (522). A top portion of clamp arm (544) is pivotably coupled within a distal end of a rod (513). Rod (513) is slidably secured to a top of shaft assembly (500) such that rod (513) is freely translatable relative to articulation section (510). Thus, it should be understood that longitudinal movement of rod (513) causes rotation of clamp arm (544) toward and away from blade (542). Rod (513) is coupled with a trigger (not shown) such that clamp arm (544) is pivotable toward and away from ultrasonic blade (542) in response to pivoting, sliding, or other actuation of the trigger.

Blade (542) is positioned at the distal end of an acoustic drivetrain. This acoustic drivetrain includes a transducer assembly (not shown) and an acoustic waveguide (546). Waveguide (546) comprises a flexible portion (548). Flexible portion (548) of waveguide (546) includes a distal flange (550), a proximal flange (552), and a narrowed section (549) located between flanges (550, 552). In the present example, flanges (550, 552) are located at positions corresponding to nodes associated with resonant ultrasonic vibrations communicated through flexible portion (548) of waveguide (546). Narrowed section (549) is configured to allow flexible portion (548) of waveguide (546) to flex without significantly affecting the ability of flexible portion (548) of waveguide (546) to transmit ultrasonic vibrations. It should be understood that rod (513) will also flex with flexible portion (548) when articulation section (510) is bent to an articulated state.

Shaft assembly (500) further comprises a pair of articulation cables (512). While only one articulation cable (512) is shown, it should be understood that another articulation cable (512) would be positioned on the other side of shaft assembly (500), 180° from the articulation cable (512) that is shown. The distal ends of articulation cables (512) are secured to distal flange (550) of waveguide (546). Articulation cables (512) are configured to operate substantially similar to articulation bands (140, 142, 212, 214, 312, 314, 412, 414) discussed above except for the differences discussed below. Opposing longitudinal motion of articulation cables (512) is configured to cause articulation of articulation section (510). Articulation cables (512) are secured to distal outer sheath (502) via a collar (520). When articulation cables (512) are translated longitudinally in an opposing fashion, a moment is created and applied to a distal end of distal outer sheath (502) via distal flange (550). This causes articulation section (510) and narrowed section (549) of flexible portion (548) of waveguide (546) to articulate, without transferring axial forces in articulation cables (512) to waveguide (546). Articulation bands (212, 214) may be driven to translate in an opposing fashion by a version of articulation control assembly (100) or by any other suitable drive mechanism.

In some versions of shaft assembly (500), shaft assembly includes an additional outer sheath that is disposed about outer sheaths (502, 504) and articulation section (510). In some such versions, clamp arm (544) is pivotally coupled with this additional outer sheath instead of being pivotally coupled with distal outer sheath (502). Rod (513) may be further coupled with this additional outer sheath such that rod (513) may translate relative to the additional outer sheath to pivot clamp arm (544) toward and away from blade (542). This additional outer sheath may be rotated relative to outer sheaths (502, 504) and articulation section (510). For instance, the additional outer sheath may include a knob to provide such rotation (e.g., in addition to or in lieu of a knob that provides rotation of the entire shaft assembly (500) as a unit). The additional outer sheath may also be configured to flex at articulation section (510), such that the additional outer sheath does not significantly impede the ability of articulation section (510) to achieve an articulated state. By way of example only, the additional outer sheath may be formed of a thin metal tube (e.g., approximately 0.002 inches thick) with laser cut features (e.g., a pattern of slots) that enable flexing at articulation section (510).

In versions where an additional outer sheath is provided as described above, clamp arm (544) and rod (513) may rotate with the additional outer sheath relative to outer sheaths (502, 504) and articulation section (510). Thus, the additional outer sheath may be used to rotate clamp arm (544) about the longitudinal axis of shaft assembly (500) to provide clamp arm (544) at different orbital orientations about blade (542). In versions of blade (542) that have a non-circular cross-sectional profile, this ability to orient clamp arm (544) may enable the operator to select a specific orientation that is particularly suited for the task at hand. For instance, the operator may orient clamp arm (544) to face a relatively broad flat face of blade (542) in order to provide relatively greater hemostasis in tissue compressed between clamp arm (544) and blade (542); or orient clamp arm (544) to face a relatively narrow edge region of blade (542) in order to provide relatively faster cutting of tissue compressed between clamp arm (544) and blade (542). Other suitable configurations and relationships will be apparent to those of ordinary skill in the art in view of the teachings herein. Similarly, other suitable ways in which an additional outer sheath may be formed and incorporated into shaft assembly (500) will be apparent to those of ordinary skill in the art in view of the teachings herein. While this additional outer sheath is described in the context of shaft assembly (500), it should be understood that such an additional outer sheath may also be incorporated into various other shaft assemblies described herein.

II. EXEMPLARY ALTERNATIVE SHAFT ASSEMBLY PROFILES

It may be desirable to change the profiles the components of shaft assembly (30). For instance, among other reasons, it may be desirable to change the profiles of the components of shaft assembly (30) to provide for more clearance within shaft assembly (30) while still enclosing the contents of shaft assembly (30) within an outer sheath. As will be discussed in more detail below, FIGS. 19-27 show various examples of how the profiles of the components of shaft assembly (30) may be changed. While various examples of how the profiles of the components of shaft assembly (30) may be changed will be described in greater detail below, other examples will be apparent to those of ordinary skill in the art according to the teachings herein. It should be understood that the examples of shaft assemblies and/or articulation sections described below may function substantially similar to shaft assembly (30) discussed above.

A. Exemplary Alternative Shaft Assembly Profile with Bands Defining Channels

Figure 19:
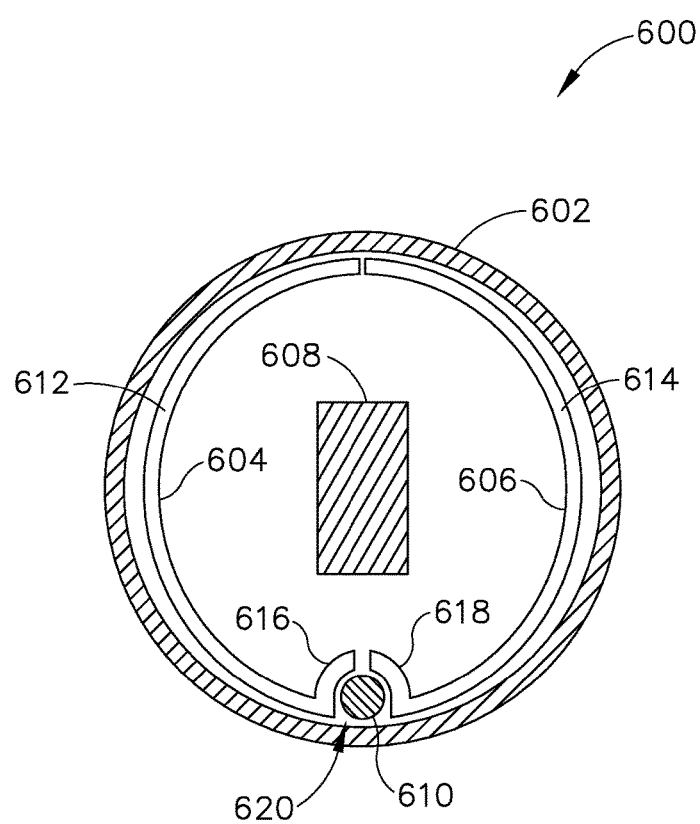
FIG. 19 depicts a front cross-sectional end view of yet another exemplary alternative shaft assembly and end effector, configured for incorporation in the instrument of FIG. 1.

FIG. 19 shows an exemplary alternative profile of yet another exemplary alternative shaft assembly (600) that may be used as a substitute for shaft assembly (30) in instrument (10). Shaft assembly (600) of this example comprises an outer sheath (602), a pair of articulation bands (604, 606), a waveguide (608), and a drive rod (610). Articulation bands (604, 606) are configured to operate substantially similar to articulation bands (140, 142), such that opposing longitudinal motion of articulation bands (604, 606) causes articulation of shaft assembly (600). Rod (610) is configured to operate substantially similar to cable (174) discussed above, such that longitudinal translation of rod (610) causes actuation of a clamp arm (not shown).

Outer sheath (602) has a circular cross-sectional profile. Each articulation band (604, 606) comprises a large semi-circular portion (612, 614) and a small semi-circular portion (616, 618). Small semi-circular portions (616, 618) extend inwardly from large semi-circular portions (612, 614). Articulation bands (604, 606) are arranged within outer sheath (602) such that small semi-circular portions (616, 618) are adjacent to one another, and form a channel (620) therebetween. Rod (610) is slidably disposed within channel (620) and is configured to longitudinally translate within channel (620) to thereby actuate the clamp arm. In the cross-sectional region shown in FIG. 19, waveguide (608) has a rectangular profile and passes within outer sheath (602) between articulation bands (604, 606). It should be understood that waveguide (608) may have any other suitable cross-sectional profile that fits within the space defined between articulation bands (604, 606). Moreover, the cross-sectional profile of waveguide (608) may vary along the length of waveguide (608).

Figure 20:
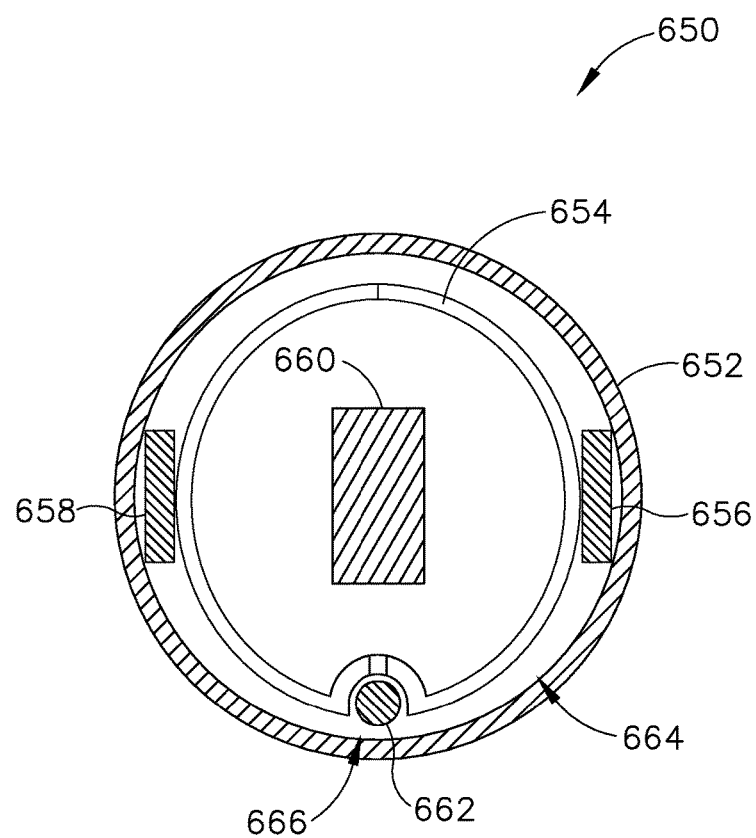
FIG. 20 depicts a front cross-sectional end view of yet another exemplary alternative shaft assembly and end effector, configured for incorporation in the instrument of FIG. 1.

B. Exemplary Alternative Shaft Assembly Profile Drive Features Between Inner Tube and Outer Tube FIG. 20 shows another exemplary alternative profile of yet another exemplary alternative shaft assembly (650) that may be used as a substitute for shaft assembly (30) in instrument (10). Shaft assembly (650) of this example comprises an outer sheath (652), an inner tube (654), a pair of articulation bands (656, 658), a waveguide (660), and a drive rod (662). Articulation bands (656, 658) are configured to operate substantially similar to articulation bands (140, 142), such that opposing longitudinal motion of articulation bands (656, 658) causes articulation of shaft assembly (650). Rod (662) is configured to operate substantially similar to cable (174) discussed above, such longitudinal translation of rod (662) actuates a clamp arm (not shown).

Outer sheath (652) has a circular cross-sectional profile. Inner tube (654) is slidably disposed within outer sheath (652) such that a space (664) is defined between an interior surface of outer sheath (652) and an exterior surface of inner tube (654). Articulation bands (656, 658) are slidably disposed within space (664) between inner tube (654) and outer tube (652). A semi-circular channel (666) is formed in the exterior surface of inner tube (654). Rod (662) is slidably disposed within channel (666) and is configured to longitudinally translate within channel (666) to thereby actuate the clamp arm. In the cross-sectional region shown in FIG. 20, waveguide (660) has a rectangular profile and passes within inner tube (654). It should be understood that waveguide (660) may have any other suitable cross-sectional profile that fits within the space defined within inner tube (654). Moreover, the cross-sectional profile of waveguide (660) may vary along the length of waveguide (660).

Figure 21:
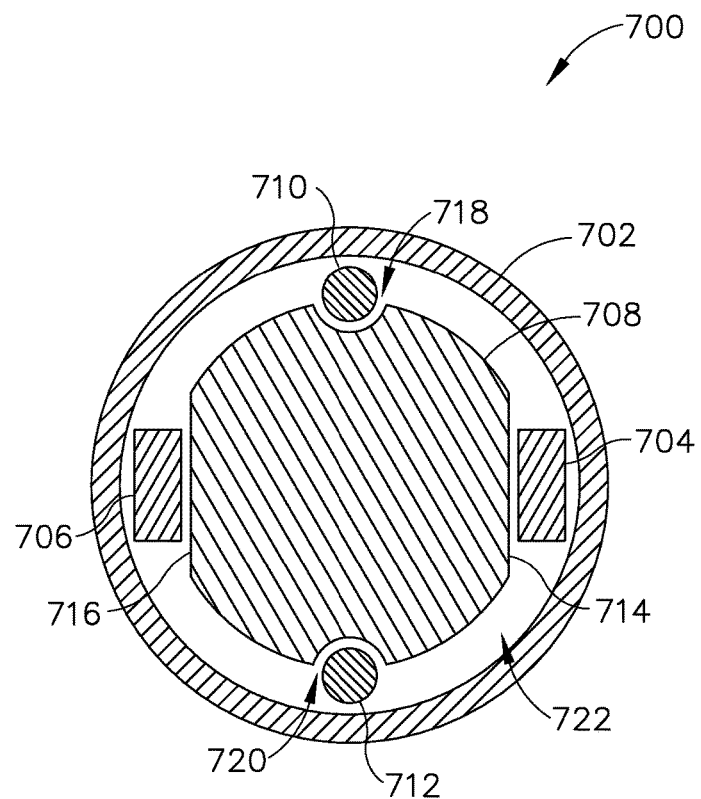
FIG. 21 depicts a front cross-sectional end view of yet another exemplary alternative shaft assembly and end effector, configured for incorporation in the instrument of FIG. 1.

C. Exemplary Alternative Shaft Assembly Profile with Waveguide Defining Channels and Dual Rods FIG. 21 shows yet another exemplary alternative profile of yet another exemplary alternative shaft assembly (700) that may be used as a substitute for shaft assembly (30) in instrument (10). Shaft assembly (700) of this example comprises an outer sheath (702), a pair of articulation bands (704, 706), a waveguide (708), and a pair of rods (710, 712). Articulation bands (704, 706) are configured to operate substantially similar to articulation bands (140, 142) discussed above, such that opposing longitudinal motion of articulation bands (704, 706) causes articulation of shaft assembly (700). Rods (710, 712) are configured to operate substantially similar to cable (174), such that longitudinal translation of rods (710, 712) provides actuation of a clamp arm (not shown). For instance, rod (710) may translate proximally while the other rod (712) translates distally to pivot a clamp arm away from an ultrasonic blade; and rod (710) may translate distally while the other rod (712) translates proximally to pivot the clamp arm toward the ultrasonic blade. Various suitable ways in which rods (710, 712) may be driven in such an opposing fashion will be apparent to those of ordinary skill in the art in view of the teachings herein. In some other versions, one of the rods (710, 712) is substituted with one or more wires that is/are configured to provide RF electrosurgical capabilities at an end effector that is at the distal end of shaft assembly (700).

Outer sheath (702) has a circular cross-sectional profile. Waveguide (708) has a generally circular cross-sectional profile with a pair of flats (714, 716) and a pair of semi-circular channels (718, 720) defined within an exterior surface of waveguide (708). Rods (710, 712) are slidably disposed within respective channels (718, 720) and are configured to longitudinally translate within channels (718, 720) to thereby actuate the clamp arm. Waveguide (708) is disposed within outer sheath (702) such that a space (722) is defined between an interior surface of outer sheath (702) and an exterior surface of waveguide (708). Articulation bands (704, 706) are slidably disposed within space (722) between outer sheath (702) and waveguide (708) adjacent to flats (714, 716) and are configured to longitudinally translate within space (722) to thereby cause articulation of shaft assembly (700).

Figure 22:
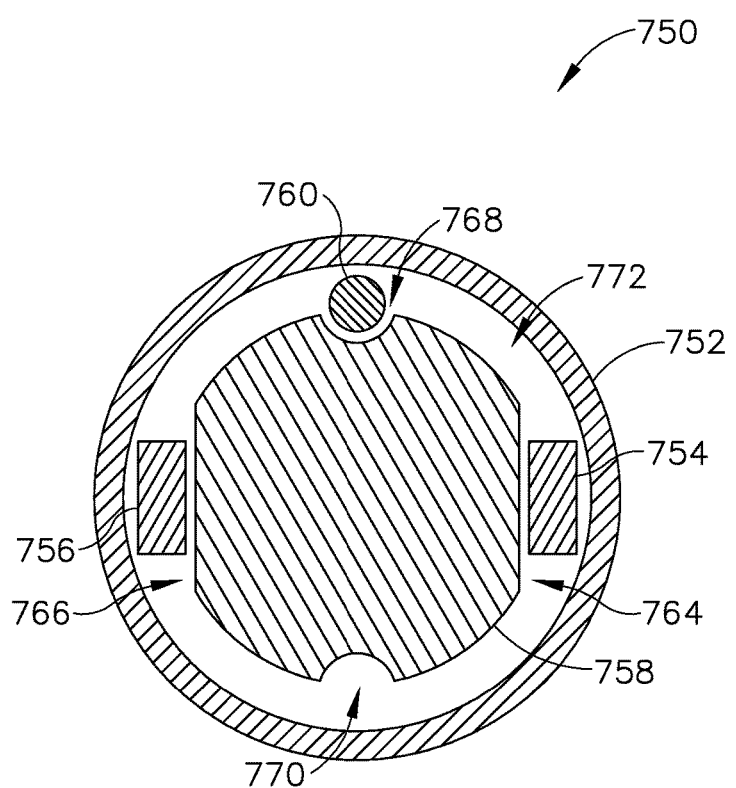
FIG. 22 depicts a front cross-sectional end view of yet another exemplary alternative shaft assembly and end effector, configured for incorporation in the instrument of FIG. 1.

D. Exemplary Alternative Shaft Assembly Profile with Waveguide Defining Channels and Single Upper Rod FIG. 22 shows yet another exemplary alternative profile of yet another exemplary alternative shaft assembly (750) that may be used as a substitute for shaft assembly (30) in instrument (10). Shaft assembly (750) of this example comprises an outer sheath (752), a pair of articulation bands (754, 756), a waveguide (758), and a rod (760). Articulation bands (754, 756) are configured to operate substantially similar to articulation bands (140, 142) discussed above, such that opposing longitudinal motion of articulation bands (754, 756) causes articulation of shaft assembly (750). Rod (760) is configured to operate substantially similar to cable (174), such that longitudinal translation of rod (760) provides actuation of a clamp arm (not shown).

Outer sheath (752) has a circular cross-sectional profile. Waveguide (758) has a generally circular cross-sectional profile with a pair of flats (764, 766) and a pair of semi-circular channels (768, 770) defined within an exterior surface of waveguide (758). Waveguide (758) is disposed within outer sheath (752) such that a space (772) is defined between an interior surface of outer sheath (752) and an exterior surface of waveguide (758). Articulation bands (754, 756) are slidably disposed within space (772) between outer sheath (752) and waveguide (758) adjacent to flats (764, 766) and are configured to longitudinally translate to thereby cause articulation of shaft assembly (750). Rod (760) is slidably disposed within channel (768) and is configured to longitudinally translate within channel (768) to thereby actuate the clamp arm. In this example, no component is disposed in channel (770). Thus, channel (770) may simply be omitted if desired. Alternative, one or more wires and/or other components may be positioned in channel (770).

Figure 23:
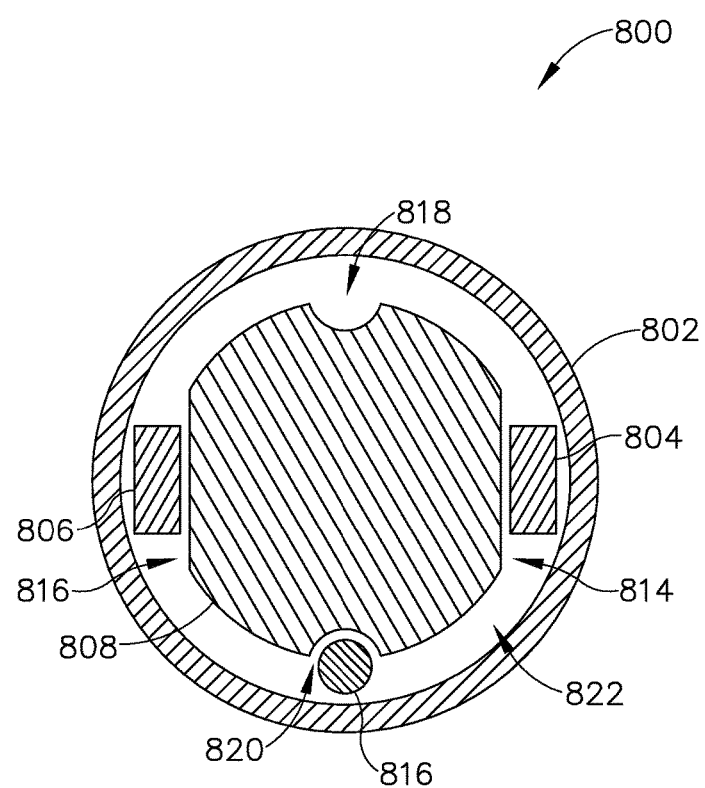
FIG. 23 depicts a front cross-sectional end view of yet another exemplary alternative shaft assembly and end effector, configured for incorporation in the instrument of FIG. 1.

E. Exemplary Alternative Shaft Assembly Profile with Waveguide Defining Channels and Single Lower Rod FIG. 23 shows yet another exemplary alternative profile of yet another exemplary alternative shaft assembly (800) that may be used as a substitute for shaft assembly (30) in instrument (10). Shaft assembly (800) of this example comprises an outer sheath (802), a pair of articulation bands (804, 806), a waveguide (808), and a rod (810). Articulation bands (804, 806) are configured to operate substantially similar to articulation bands (140, 142) discussed above, such that opposing longitudinal motion of articulation bands (804, 806) causes articulation of shaft assembly (800). Rod (810) is configured to operate substantially similar to cable (174) discussed above, such that longitudinal translation of rod (810) provides actuation of a clamp arm (not shown).

Outer sheath (802) has a circular cross-sectional profile. Waveguide (808) has a generally circular cross-sectional profile with a pair of flats (814, 816) and a pair of semi-circular channels (818, 820) defined within an exterior surface of waveguide (808). Waveguide (808) is disposed within outer sheath (802) such that a space (822) is defined between an interior surface of outer sheath (802) and an exterior surface of waveguide (808). Articulation bands (804, 806) are slidably disposed within space (822) between outer sheath (802) and waveguide (808) adjacent to flats (814, 816) and are configured to longitudinally translate to thereby cause articulation of shaft assembly (800). Rod (810) is slidably disposed within channel (820) and is configured to longitudinally translate within channel (820) to thereby actuate the clamp arm. In this example, no component is disposed in channel (818). Thus, channel (818) may simply be omitted if desired. Alternative, one or more wires and/or other components may be positioned in channel (818).

Figure 24:
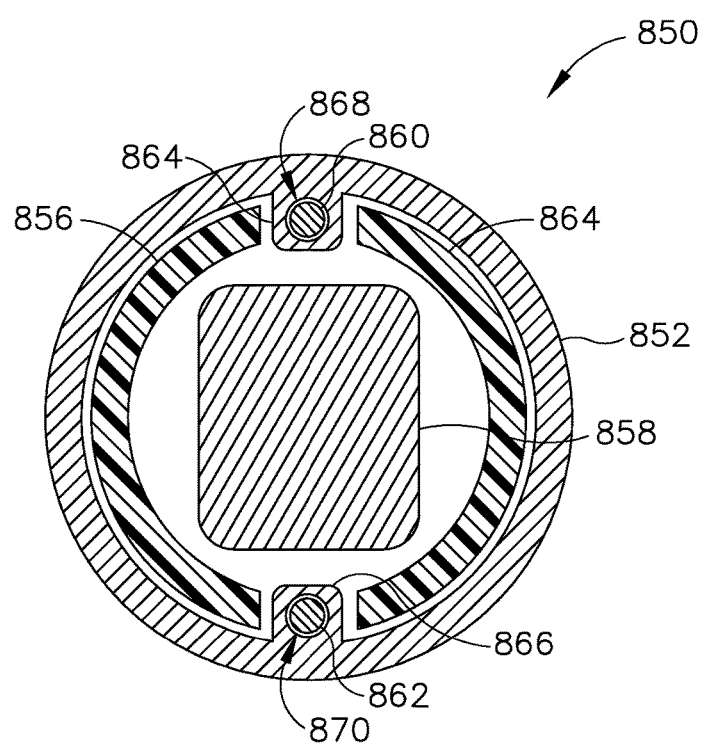
FIG. 24 depicts a front cross-sectional end view of yet another exemplary alternative shaft assembly and end effector, configured for incorporation in the instrument of FIG. 1.

F. Exemplary Alternative Shaft Assembly Profile with Outer Sheath Defining Channels for Upper and Lower Rods FIG. 24 shows yet another exemplary alternative profile of yet another exemplary alternative shaft assembly (850) that may be used as a substitute for shaft assembly (30) in instrument (10). Shaft assembly (850) of this example comprises an outer sheath (852), a pair of articulation bands (854, 856), a waveguide (858), and a pair of rods (860, 862). Articulation bands (854, 856) are configured to operate substantially similar to articulation bands (140, 142) discussed above, such that opposing longitudinal motion of articulation bands (854, 856) causes articulation of shaft assembly (850). Rods (860, 862) are configured to operate substantially similar to rods (710, 712) discussed above, such that longitudinal translation of rods (860, 862) is configured to cause rotation of a clamp arm (not shown). For instance, rod (860) may translate proximally while the other rod (862) translates distally to pivot a clamp arm away from an ultrasonic blade; and rod (860) may translate distally while the other rod (862) translates proximally to pivot the clamp arm toward the ultrasonic blade. Various suitable ways in which rods (860, 862) may be driven in such an opposing fashion will be apparent to those of ordinary skill in the art in view of the teachings herein. In some other versions, one of the rods (860, 862) is substituted with one or more wires that is/are configured to provide RF electrosurgical capabilities at an end effector that is at the distal end of shaft assembly (800).

Outer sheath (852) has a generally circular cross-sectional profile and includes a pair of inwardly extending projections (864, 866). Projections (864, 866) each define a respective through bore (868, 870). In some versions, outer sheath (852) is formed in an extrusion process (e.g., from plastic and/or metal, etc.). Of course, any suitable process may be used to form outer sheath (852). Rods (860, 862) are slidably disposed within through bores (868, 870) and are configured to longitudinally translate within through bores (868, 870) to thereby rotate the clamp arm. Articulation bands (854, 856) each have a semi-circular cross-sectional profile. Articulation bands (854, 856) are slidably disposed within outer sheath (852) between projections (864, 866) and are configured to longitudinally translate to thereby cause articulation of shaft assembly (850).

In the cross-sectional region shown in FIG. 24, waveguide (858) has a rectangular profile and passes within the space defined between articulation bands (854, 856). It should be understood that waveguide (858) may have any other suitable cross-sectional profile that fits within the space defined between articulation bands (854, 856). Moreover, the cross-sectional profile of waveguide (858) may vary along the length of waveguide (858).

Figure 25:
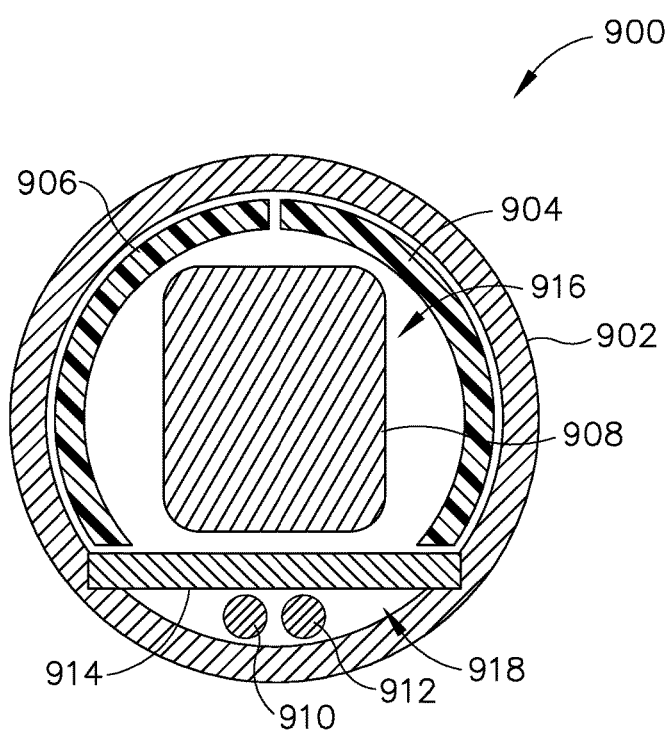
FIG. 25 depicts a front cross-sectional end view of yet another exemplary alternative shaft assembly and end effector, configured for incorporation in the instrument of FIG. 1.

G. Exemplary Alternative Shaft Assembly Profile with Outer Sheath Defining Channels for Dual Lower Rods FIG. 25 shows yet another exemplary alternative profile of yet another exemplary alternative shaft assembly (900) that may be used as a substitute for shaft assembly (30) in instrument (10). Shaft assembly (900) of this example comprises an outer sheath (902), a pair of articulation bands (904, 906), a waveguide (908), and a pair of rods (910, 912). Articulation bands (904, 906) are configured to operate substantially similar to articulation bands (140, 142) discussed above, such that opposing longitudinal motion of articulation bands (904, 906) causes articulation of shaft assembly (900). Rods (910, 912) are configured to operate substantially similar to cable (174) discussed above, such that longitudinal translation of rods (910, 912) actuates a clamp arm (not shown).

Outer sheath (902) has a circular cross-sectional profile. A partitioning member (914) extends between an interior surface of outer sheath (902) along a chord line, and divides the interior of outer sheath (902) into a first lumen (916) and a second lumen (918). Articulation bands (904, 906) each have a semi-circular profile. Articulation bands (904, 906) are slidably disposed within first lumen (916) of outer sheath (902) adjacent to one another and are configured to longitudinally translate to thereby cause articulation of shaft assembly (900). Rods (910, 912) are slidably disposed within second lumen (918) of outer sheath (902) and are configured to longitudinally translate within second lumen (918) to thereby actuate the clamp arm. In some versions, both rods (910, 912) translate longitudinally in the same direction simultaneously to actuate the clamp arm. In some other versions, rods (910, 912) translate longitudinally in an opposing fashion to actuate the clamp arm. In still other versions, one of the rods (910, 912) is substituted with one or more wires that is/are configured to provide RF electrosurgical capabilities at an end effector that is at the distal end of shaft assembly (900).

In the cross-sectional region shown in FIG. 25, waveguide (908) has a rectangular profile and passes within the space defined between articulation bands (904, 906) and partitioning member (914). It should be understood that waveguide (908) may have any other suitable cross-sectional profile that fits within the space defined between articulation bands (904, 906) and partitioning member (914). Moreover, the cross-sectional profile of waveguide (908) may vary along the length of waveguide (908).

Figure 26:
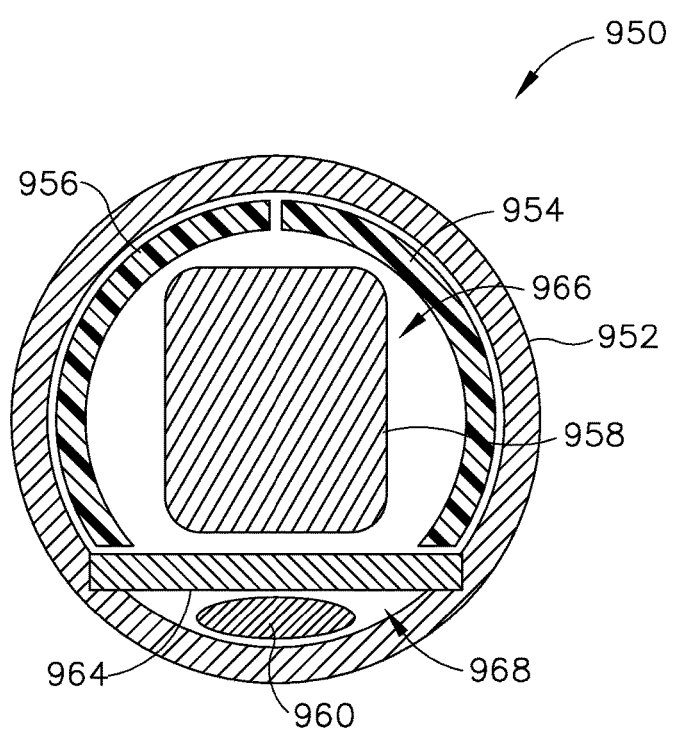
FIG. 26 depicts a front cross-sectional end view of yet another exemplary alternative shaft assembly and end effector, configured for incorporation in the instrument of FIG. 1.

H. Exemplary Alternative Shaft Assembly Profile with Partitioning Member Defining Channel for Single Lower Ribbon FIG. 26 shows yet another exemplary alternative profile of yet another exemplary alternative shaft assembly (950) that may be used as a substitute for shaft assembly (30) in instrument (10). Shaft assembly (950) of this example comprises an outer sheath (952), a pair of articulation bands (954, 956), a waveguide (958), and a ribbon (960). Articulation bands (954, 956) are configured to operate substantially similar to articulation bands (140, 142) discussed above, such that opposing longitudinal motion of articulation bands (954, 956) causes articulation of shaft assembly (950). Ribbon (960) is configured to operate substantially similar to cable (174), such that longitudinal translation of ribbon (960) actuates a clamp arm (not shown).

Outer sheath (952) has a circular cross-sectional profile. A partitioning member (964) extends between an interior surface of outer sheath (952) along a chord line, and divides the interior of outer sheath (952) into a first lumen (966) and a second lumen (968). Articulation bands (954, 956) each have a semi-circular profile. Articulation bands (954, 956) are slidably disposed within first lumen (966) of outer sheath (952) adjacent to one another and are configured to longitudinally translate to thereby cause articulation of shaft assembly (950). Ribbon (960) is slidably disposed within second lumen (968) of outer sheath (952) and is configured to longitudinally translate within second lumen (968) to thereby actuate the clamp arm.

In the cross-sectional region shown in FIG. 26, waveguide (958) has a rectangular profile and passes within the space defined between articulation bands (954, 956) and partitioning member (964). It should be understood that waveguide (908) may have any other suitable cross-sectional profile that fits within the space defined between articulation bands (954, 956) and partitioning member (964). Moreover, the cross-sectional profile of waveguide (958) may vary along the length of waveguide (958).

Figure 27:
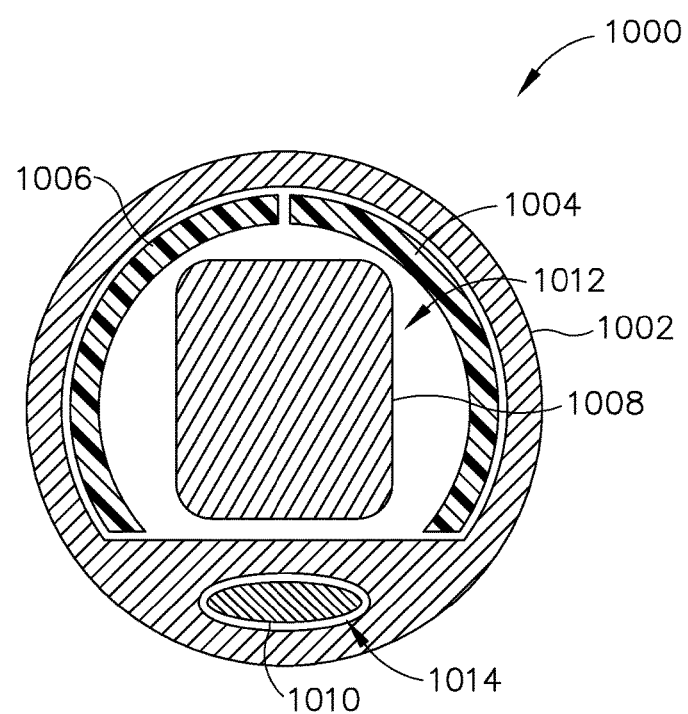
FIG. 27 depicts a front cross-sectional end view of yet another exemplary alternative shaft assembly and end effector, configured for incorporation in the instrument of FIG. 1.

I. Exemplary Alternative Shaft Assembly Profile with Outer Sheath Defining Channel for Single Lower Rod FIG. 27 shows yet another exemplary alternative profile of yet another exemplary alternative shaft assembly (1000) that may be used as a substitute for shaft assembly (30) in instrument (10). Shaft assembly (1000) of this example comprises an outer sheath (1002), a pair of articulation bands (1004, 1006), a waveguide (1008), and a ribbon (1010). Articulation bands (1004, 1006) are configured to operate substantially similar to articulation bands (140, 142) discussed above, such that opposing longitudinal motion of articulation bands (1004, 1006) causes articulation of shaft assembly (1000). Ribbon (1010) is configured to operate substantially similar to cable (174) discussed above, such that longitudinal translation of ribbon (1010) actuates a clamp arm (not shown).

Outer sheath (1002) defines a first lumen (1012) and a second lumen (1014). In some versions, outer sheath (1002) is formed in an extrusion process (e.g., from plastic and/or metal, etc.). Of course, any suitable process may be used to form outer sheath (852). Articulation bands (1004, 1006) each have a semi-circular profile. Articulation bands (1004, 1006) are slidably disposed within first lumen (1012) of outer sheath (1002) adjacent to one another and are configured to longitudinally translate to thereby cause articulation of shaft assembly (1000). Ribbon (1010) is slidably disposed within second lumen (1014) of outer sheath (1002) and is configured to longitudinally translate within second lumen (1018) to thereby actuate the clamp arm.

In the cross-sectional region shown in FIG. 27, waveguide (1008) has a rectangular profile and passes within the space defined between articulation bands (1004, 1006). It should be understood that waveguide (1008) may have any other suitable cross-sectional profile that fits within the space defined between articulation bands (1004, 1006). Moreover, the cross-sectional profile of waveguide (1008) may vary along the length of waveguide (1008).

III. EXEMPLARY ALTERNATIVE ACTUATION OF CLAMP ARM

It may be desirable to alter the operation of clamp arm (44) and/or articulation section (130). As will be discussed in more detail below, FIGS. 28-33B show various examples of how the operation of clamp arm (44) may be altered. While various examples of how the operation of clamp arm (44) may be altered will be described in greater detail below, other examples will be apparent to those of ordinary skill in the art according to the teachings herein. It should be understood that the examples of clamp arms described below may function substantially similar to clamp arm (44) discussed above. In particular, the examples of clamp arms described below are operable to compress tissue against an ultrasonic blade to thereby simultaneously sever the tissue and denature the proteins in adjacent tissue cells, thereby providing a coagulative effect.

A. Exemplary Alternative Clamp Arm Drive Assembly with Rod and Arcuate Arms

Figure 29:
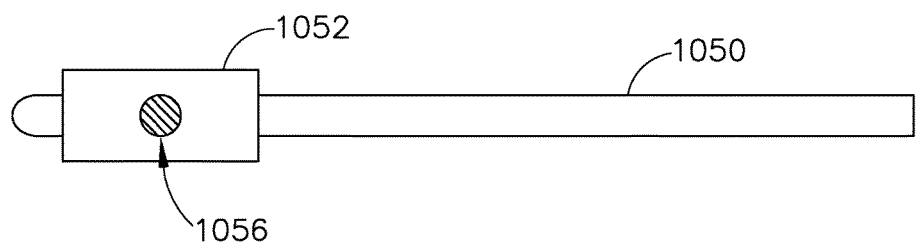
FIG. 29 depicts a side elevational view of the push/pull cable assembly of FIG. 28.
Figure 28:
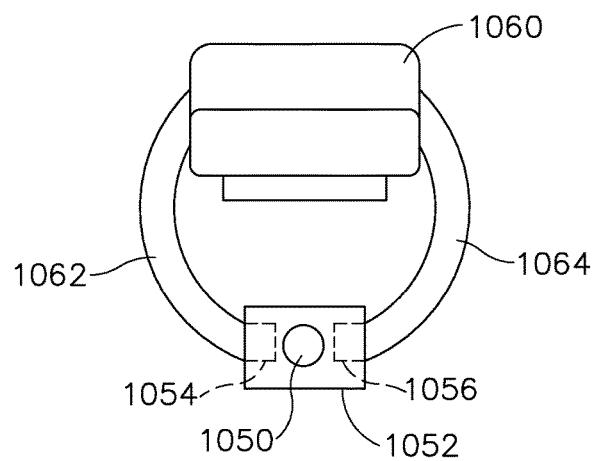
FIG. 28 depicts a front end view of a clamp arm coupled with an exemplary push/pull cable assembly configured for incorporation in any of the shaft assemblies and end effectors described herein.

FIGS. 28 and 29 show an exemplary rod (1050) and clamp arm (1060) that may be readily incorporated into instrument (10). Clamp arm (1060) is configured to operate substantially similar to clamp arm (44) discussed above, such that clamp arm (1060) is operable to selectively pivot toward and away from a blade (not shown) to selectively clamp tissue between clamp arm (1060) and the blade. Rod (1050) is configured to operate substantially similar to cable (174), such that longitudinal translation of rod (1050) causes actuation of clamp arm (1060) toward and away from the blade.

In the present example, a coupler (1052) is disposed at a distal end of rod (1050). Coupler (1052) comprises a pair of circular recesses (1054, 1056) formed in opposite sides of coupler (1052). A pair of arcuate arms (1062, 1064) extend transversely from clamp arm (1060). A circular projection (1066, 1068) extends inwardly from an interior surface of each arcuate arm (1062, 1064). Circular projections (1066, 1068) are rotatably disposed with respective circular recesses (1054, 1056) of coupler (1052). As discussed above with reference to instrument (10), clamp arm (1060) would be rotatably secured to a distal end of a longitudinally grounded shaft assembly (not shown), such that longitudinal movement of rod (1050) and coupler (1052) would pivotally actuate clamp arm (1060) toward and away from the blade.

B. Exemplary Alternative Clamp Arm Drive Assembly with Bent Rods

Figure 31:
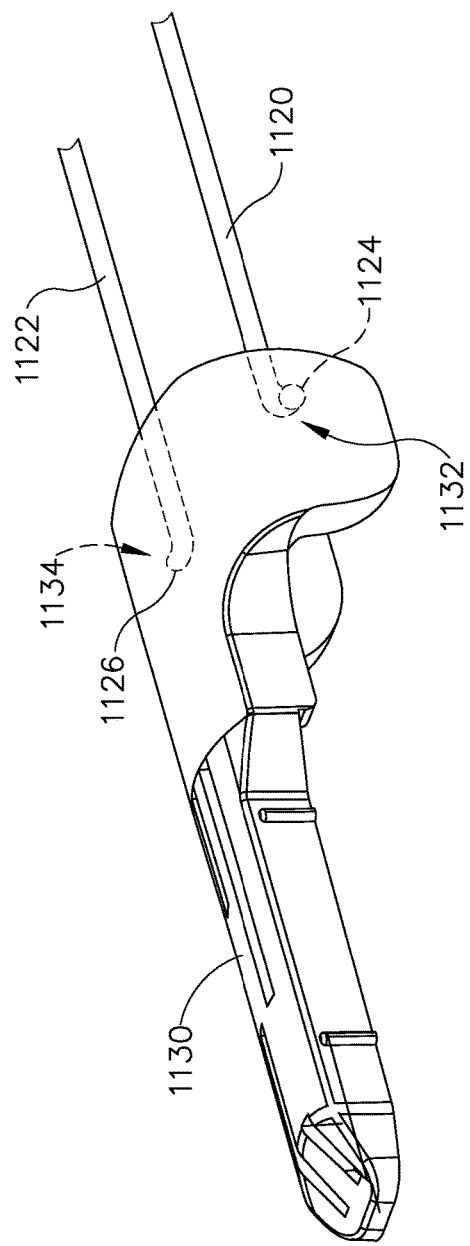
FIG. 31 depicts a perspective view of another exemplary alternative push/pull cable configured for incorporation in any of the shaft assemblies and end effectors described herein.

FIGS. 30 and 31 show additional examples of configurations that may be used to couple a pair of rods with a clamp arm to actuate the clamp arm. In the example shown in FIG. 30, a pair of rods (1100, 1102) each comprise a dog-leg feature (1104, 1106) at a distal end of rods (1100, 1102). A clamp arm (1110) comprises a pair of openings (1112, 1114). Dog-leg features (1104, 1106) of rods (1100, 1102) are pivotably disposed in openings (1112, 1114) of clamp arm (1110). As discussed above with reference to instrument (10), clamp arm (1110) would be rotatably secured to a distal end of a longitudinally grounded shaft assembly (not shown), such that longitudinal movement of rods (1100, 1102) would pivotally actuate clamp arm (1110) toward and away from a blade (not shown). In the present example, rods (1100, 1102) are directly coupled with clamp arm (1110). In some other versions, rods (1100, 1102) are coupled with clamp arm (1110) via some intermediary component. For instance, rods (1100, 1102) may instead be directly coupled with a collar or inner tube section, which may in turn be pivotally coupled with clamp arm (1110). Other suitable relationships will be apparent to those of ordinary skill in the art in view of the teachings herein.

In the example shown in FIG. 31, a pair of rods (1120, 1122) each comprise an outwardly projecting tab (1124, 1126) at a distal end of rods (1120, 1122). A clamp arm (1130) comprises a pair of openings (1132, 1134). Outwardly projecting tabs (1124, 1126) of rods (1120, 1122) are pivotably disposed in openings (1132, 1134) of clamp arm (1130). As discussed above with reference to instrument (10), clamp arm (1130) would be rotatably secured to a distal end of a longitudinally grounded shaft assembly (not shown), such that longitudinal movement of rods (1120, 1122) would pivotally actuate clamp arm (1130) toward and away from a blade (not shown). In the present example, rods (1120, 1122) are directly coupled with clamp arm (1130). In some other versions, rods (1120, 1122) are coupled with clamp arm (1130) via some intermediary component. For instance, rods (1120, 1122) may instead be directly coupled with a collar or inner tube section, which may in turn be pivotally coupled with clamp arm (1130). Other suitable relationships will be apparent to those of ordinary skill in the art in view of the teachings herein.

C. Exemplary Alternative Clamp Arm with Oblique Coupling Projection

Figure 32:
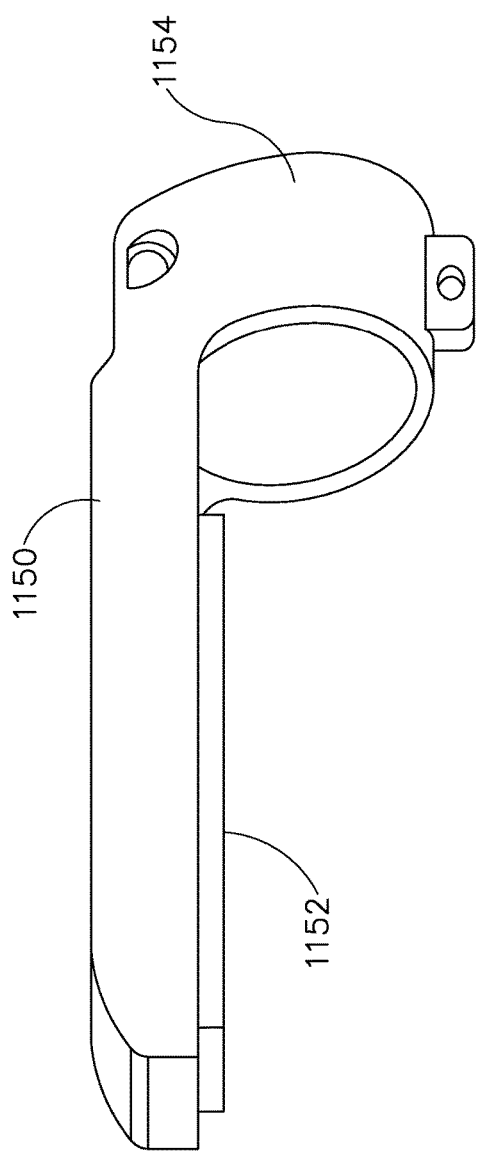
FIG. 32 depicts a perspective view of an exemplary clamp configured for incorporation in any of the end effectors described herein.
Figure 33A:
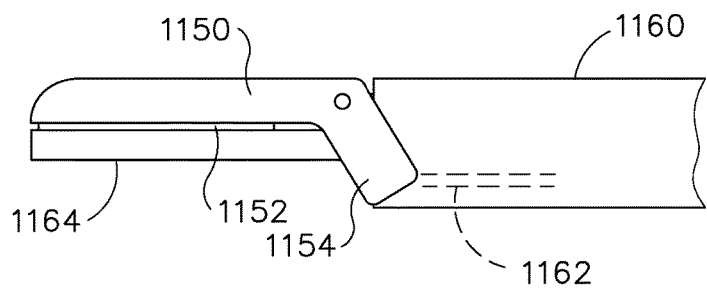
FIG. 33A depicts a side elevational view of an end effector having the clamp arm of FIG. 32, with the clamp arm in a closed position.
Figure 33B:
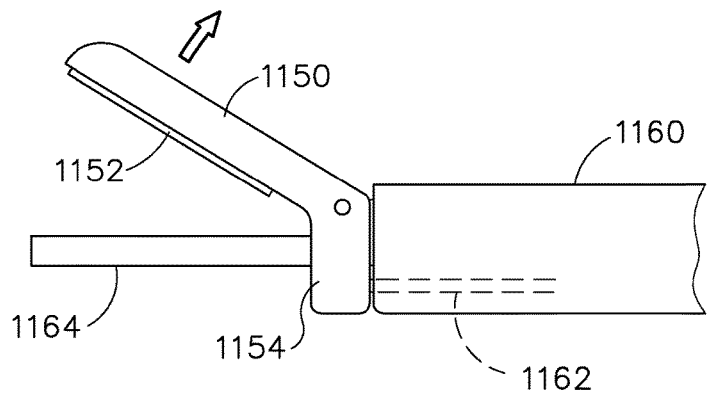
FIG. 33B depicts a side elevational view of the end effector of FIG. 33A, with the clamp arm moved to an open position.

FIGS. 32-33B show yet another exemplary alternative clamp arm (1150) that may be readily incorporated into instrument (10). Clamp arm (1150) of this example includes a clamp pad (1152) that is secured to the underside of clamp arm (1150). As shown in FIGS. 33A-33B, clamp arm (1150) is pivotably secured to a distal end of an exemplary alternative shaft assembly (1160). A tubular projection (1154) extends obliquely from clamp arm (1150) and is pivotably secured to a rod (1162). Rod (1162) is operable to translate longitudinally to thereby selectively pivot clamp arm (1150) toward and away from a blade (1164). As shown in FIG. 33A, tubular projection (1154) extends from clamp arm (1150) at an oblique angle relative to the longitudinal axis of shaft assembly (1160) when clamp arm (1150) is in a closed position. As shown in FIG. 33B, tubular projection (1154) extends from clamp arm (1150) perpendicularly to the longitudinal axis of shaft assembly (1160) when clamp arm (1150) is in an open position. It should be appreciated that, with tubular projection (1154) extending from clamp arm (1150) at an oblique angle relative to shaft assembly (1160), tubular projection (1154) will not contact blade (1164) when clamp arm (1150) is opened to a substantially wide open position.

D. Exemplary Alternative Articulation Section Drivers with Racks and Idler

FIGS. 34A-37 show yet another exemplary alternative shaft assembly (1200) and end effector (1210) that may be readily incorporated into instrument (10). Shaft assembly (1200) comprises a pair of articulation drive bands (1202, 1204) and a pair of jaw closure bands (1206, 1208). A distal end of each articulation drive band (1202, 1204) is secured to a distal end of shaft assembly (1200) via a distal flange (1203) of a flexible waveguide (1230). When articulation drive bands (1202, 1204) are translated longitudinally in an opposing fashion, a moment is created and applied to the distal end of shaft assembly (1200) via distal flange (1203). Thus, opposing longitudinal motion of articulation drive bands (1202, 1204) causes articulation of shaft assembly (1200). Articulation drive bands (1202, 1204) may be driven using a version of articulation control assembly (100) described above or any other suitable mechanism.

Jaw closure bands (1206, 1208) pass slidably through flange (1203). A distal end of each jaw closure band (1206, 1208) is pivotably secured to a clamp arm (1212). It should be understood that FIGS. 34A-34B only show transverse coupling arms (1213) of clamp arm (1212). As discussed above with reference to instrument (10), clamp arm (1212) would be rotatably secured to a distal end of a longitudinally grounded shaft assembly (1200), such that simultaneous longitudinal translation of jaw closure bands (1206, 1208) pivotally actuates clamp arm (1212) toward and away from an ultrasonic blade (1214).

Figure 36:
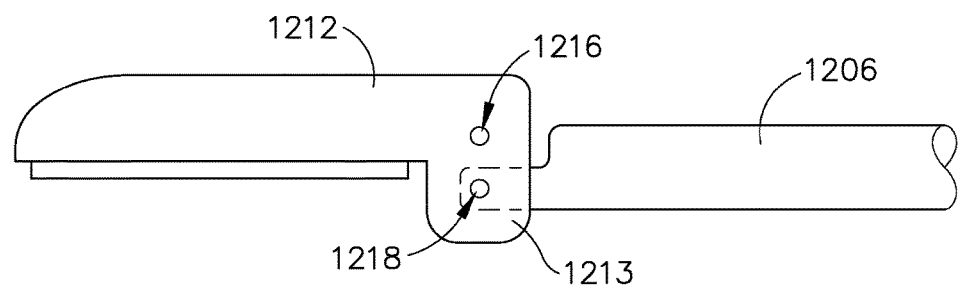
FIG. 36 depicts a side elevational view of an exemplary relationship between articulation bands and the clamp arm of the shaft assembly and end effector of FIG. 34A.
Figure 37:
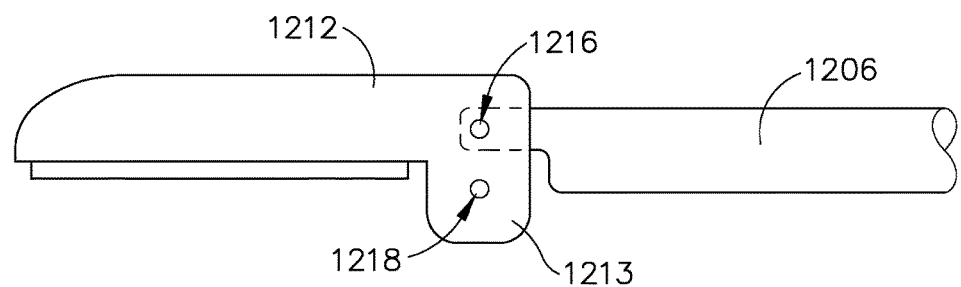
FIG. 37 depicts a side elevational view of another exemplary relationship between articulation bands and the clamp arm of the shaft assembly and end effector of FIG. 34A.

As shown in FIG. 36, jaw closure bands (1206, 1208) may be pivotably secured to a bottom pivot opening (1218) in each arm (1213) of clamp arm (1212) in those versions of end effector (1210) where a top portion of clamp arm (1212) is pivotably secured to shaft assembly (1200) via a top pivot opening (1216) in each arm (1213), such that simultaneous longitudinal translation of jaw closure bands (1206, 1208) causes pivoting of clamp arm (1212) toward and away from an ultrasonic blade (1214). As shown in FIG. 37, jaw closure bands (1206, 1208) may be pivotably secured to top pivot opening (1216) in each arm (1213) of clamp arm (1212) in those versions of end effector (1210) where a bottom portion of clamp arm (1212) is pivotably secured to shaft assembly (1200) via bottom pivot opening (1218) in each arm (1213), such that simultaneous longitudinal translation of jaw closure bands (1206, 1208) causes pivoting of clamp arm (1212) toward and away from an ultrasonic blade (1214).

Figure 34B:
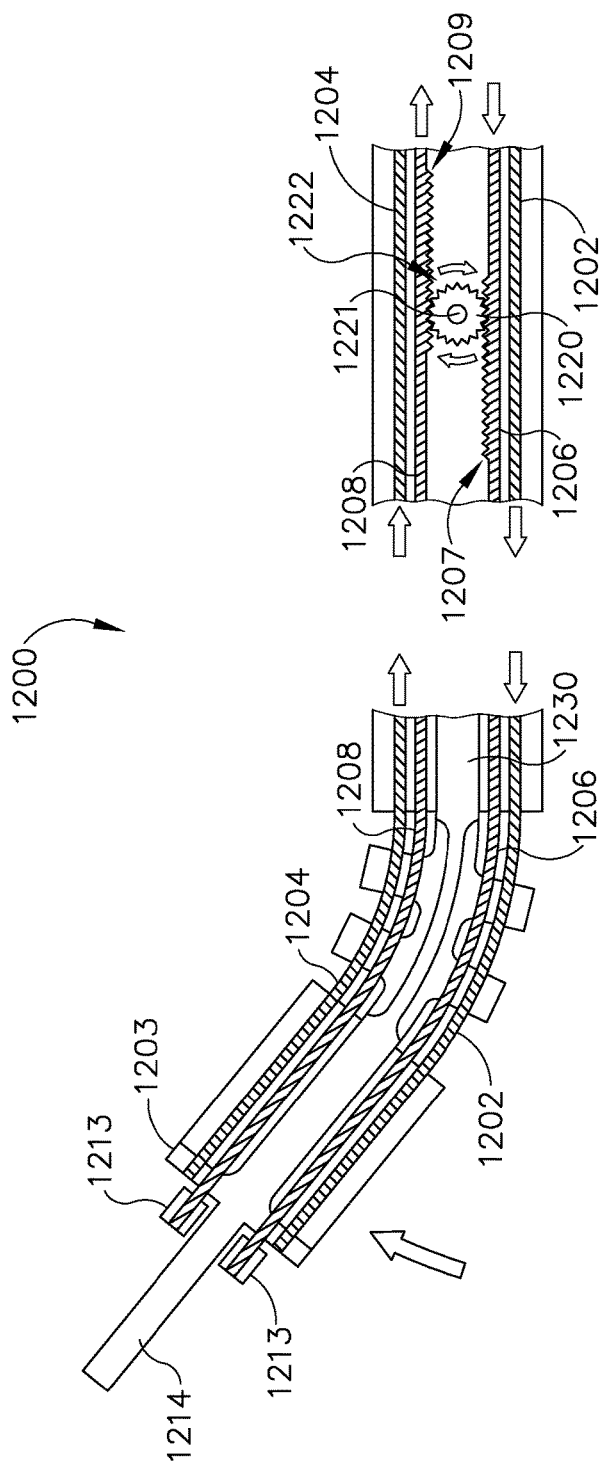
FIG. 34B depicts a cross-sectional top view of the shaft assembly and end effector of FIG. 34A moved into an articulated configuration.

Referring back to FIGS. 34A-34B, the proximal region of each jaw closure band (1206, 1208) includes a respective, inwardly directed rack (1207, 1209). Shaft assembly (1200) of the present example further comprises a gear (1220) positioned between racks (1207, 1209) of articulation jaw closure bands (1206, 1208). Gear (1220) comprises a plurality of teeth (1222) that mesh with complementary teeth of racks (1207, 1209). Gear (1220) is configured to rotate freely about a central axle (1221), such that gear (1220) serves as an idler. Thus, as shaft assembly (1200) is articulated by opposing longitudinal translation of articulation bands (1202, 1204), gear (1220) engages second pair of articulation bands (1206, 1208) and provides for guided, opposing longitudinal translation of jaw closure bands (1206, 1208) as shown in FIG. 34B. In other words, gear (1220) allows jaw closure bands (1206, 1208) to move in relation to each other to accommodate articulation of shaft assembly (1200).

Also in the present example, gear (1220) is operable to drive jaw closure bands (1206, 1208) longitudinally in the same direction in order to actuate clamp arm (1212). In particular, axle (1221) is configured to slide longitudinally relative to shaft assembly (1200), thereby providing longitudinal movement of gear (1220) relative to shaft assembly (1200). Due to engagement of teeth (1222) with racks, (1207, 1209), this will provide corresponding and simultaneous longitudinal movement of both jaw closure bands (1206, 1208) relative to shaft assembly (1200). Various suitable features that may be used to drive axle (1221) longitudinally will be apparent to those of ordinary skill in the art in view of the teachings herein.

Figure 35:
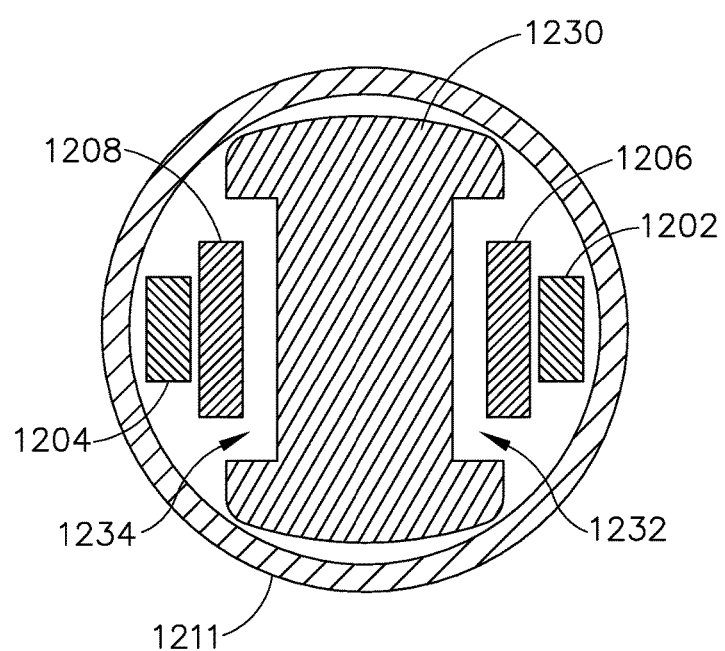
FIG. 35 depicts a cross-sectional view of the shaft assembly of FIG. 34A, taken along line 35-35 of FIG. 34A.

FIG. 35 shows a cross-sectional view of shaft assembly (1200). At this cross-sectional region, waveguide (1230) has an I-shaped cross-sectional profile with a pair of rectangular channels (1232, 1234) defined on opposite sides of waveguide (1230). Articulation bands (1202, 1204) are slidably disposed within channel (1232) between waveguide (1230) and an interior surface of an outer sheath (1211). Articulation bands (1206, 1208) are slidably disposed within channel (1234) between waveguide (1230) and an interior surface of an outer sheath (1211). Of course, any other suitable configurations may be used.

E. Exemplary Shaft Assembly with Clamp Arm Actuation Via Flexible Outer Sheath

Figure 38:
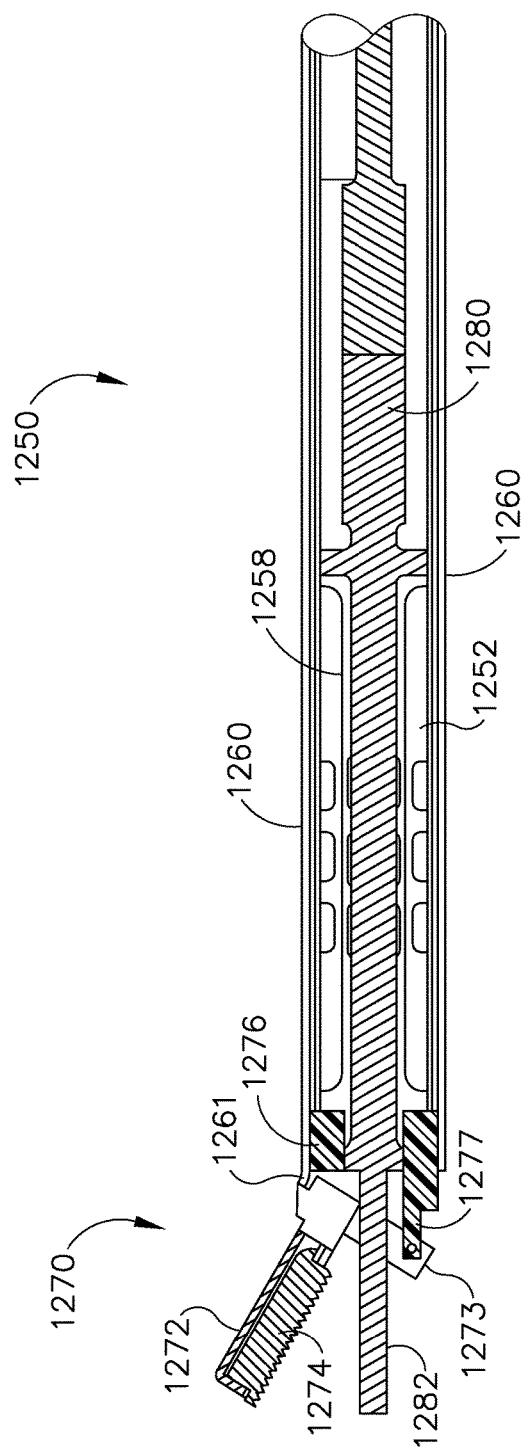
FIG. 38 depicts a cross-sectional side view of yet another exemplary alternative shaft assembly and end effector configured for incorporation in the instrument of FIG. 1.
Figure 39:
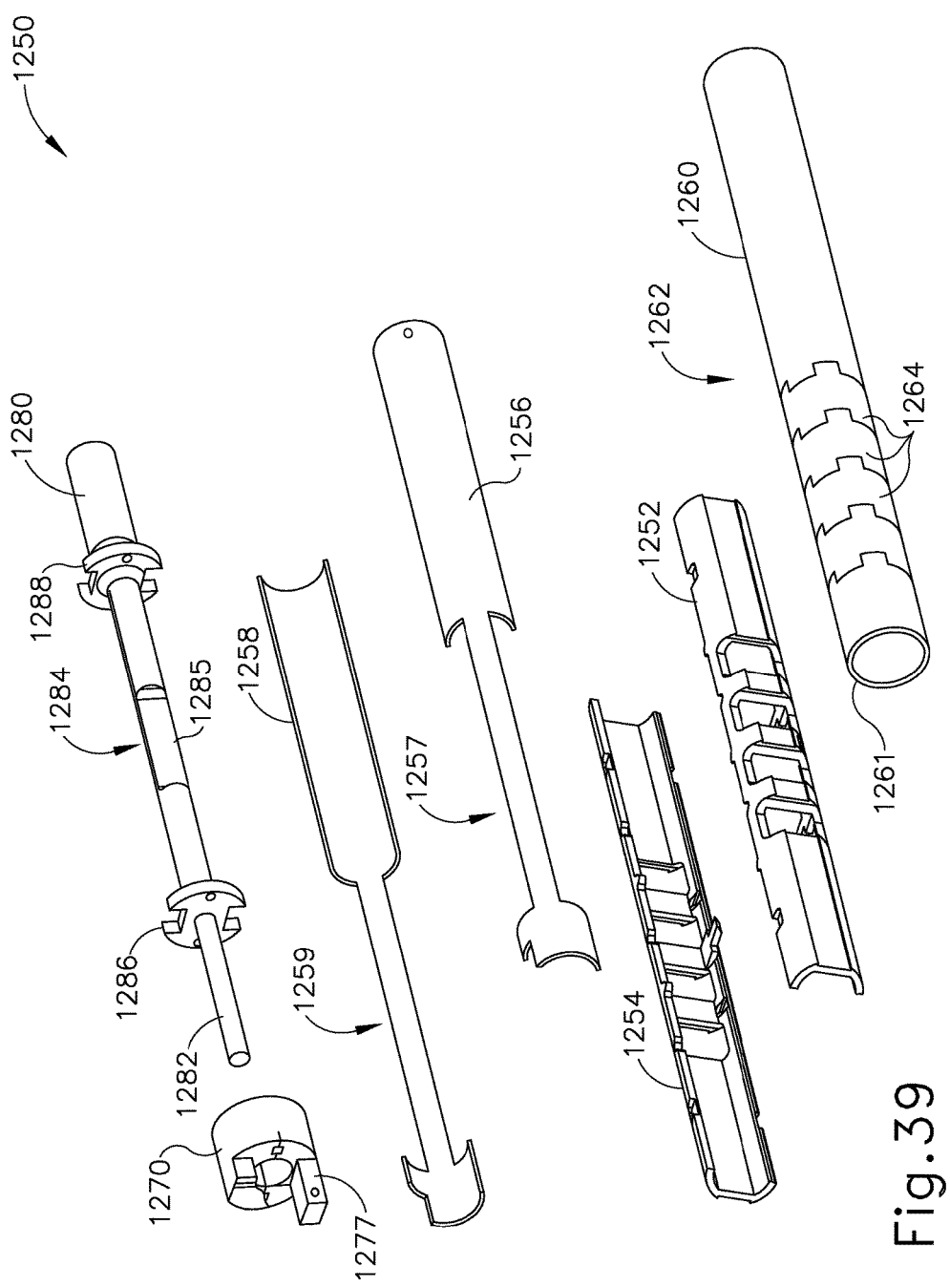
FIG. 39 depicts an exploded perspective view of the shaft assembly of FIG. 38.

FIGS. 38-39 show yet another exemplary alternative shaft assembly (1250) and end effector (1270) that may be readily incorporated into instrument (10). Shaft assembly (1250) comprises an outer sheath (1260), a pair of ribbed body portions (1252, 1254), a pair of articulation bands (1256, 1258), and a waveguide (1280). End effector (1270) includes an ultrasonic blade (1282) and a pivoting clamp arm (1272) having a clamp pad (1274). End effector (1270) is configured to operate substantially similar to end effector (40), such clamp arm (1272) of end effector (1270) is operable to compress tissue against blade (1282). When blade (1282) is activated while clamp arm (1272) compresses tissue against blade (1282), end effector (1270) simultaneously severs the tissue and denatures the proteins in adjacent tissue cells, thereby providing a coagulative effect.

Clamp arm (1272) is operable to selectively pivot toward and away from blade (1282) to selectively clamp tissue between clamp arm (1272) and blade (1282). A pair of arms (1273) extend transversely from clamp arm (1272). Arms (1273) are pivotably secured to a distally projecting tongue (1277) of a collar (1276). Collar (1276) is secured to a distal flange (1286) of waveguide (1280). Waveguide (1280) provides a longitudinal mechanical ground for collar (1276), which in turn provides a longitudinal mechanical ground to clamp arm (1272). Clamp arm (1272) is also pivotably secured with a distally projecting tongue (1261) of outer sheath (1260). Outer sheath (1260) is operable to translate longitudinally relative to waveguide (1280) and the other components of shaft assembly (1250) that are longitudinally mechanically grounded. It should therefore be understood that outer sheath (1260) is operable to actuate clamp arm (1272) toward and away from blade (1282). A trigger such as trigger (28) or any other suitable feature may be operable to translate outer sheath (1260) longitudinally, to thereby actuate clamp arm (1272) toward and away from blade (1282).

Blade (1282) is positioned at the distal end of an acoustic drivetrain. This acoustic drivetrain includes a transducer assembly (not shown) and waveguide (1280). Waveguide (1280) comprises a flexible portion (1284). Flexible portion (1284) of waveguide (1280) includes a distal flange (1286), a proximal flange (1288), and a narrowed section (1285) located between distal flanges (1286, 1288). In the present example, flanges (1286, 1288) are located at positions corresponding to nodes associated with resonant ultrasonic vibrations communicated through flexible portion (1284) of waveguide (1280). Narrowed section (1285) is configured to allow flexible portion (1284) of waveguide (1280) to flex without significantly affecting the ability of flexible portion (1284) of waveguide (1280) to transmit ultrasonic vibrations.

Outer sheath (1260) further comprises an articulation section (1262) having a series of interlocking rings (1264). Rings (1264) are configured to engage one another in a manner such that articulation section (1262) is operable to selectively flex at various lateral deflection angles relative to a longitudinal axis defined by shaft assembly (1250). Rings (1264) also allow outer sheath (1260) to translate along a bent region of shaft assembly (1250) when shaft assembly (1250) is in an articulated state.

Ribbed body portions (1252, 1254) are configured to selectively flex at various lateral deflection angles relative to the longitudinal axis defined by shaft assembly (1250) and to further provide for guidance of articulation bands (1256, 1258). In particular, ribbed body portions (1252, 1254) prevent articulation bands (1256) from contacting the region of waveguide (1280) between flanges (1286, 1288).

Articulation bands (1256, 1258) are configured to operate substantially similar to articulation bands (140, 142), such opposing longitudinal motion of articulation bands (1256, 1258) causes articulation of shaft assembly (1250). Articulation bands (1256, 1258) each comprise a flexible portion (1257, 1259) that is configured to align with the articulation section of shaft assembly (1250). Distal ends of articulation bands (1256, 1258) are secured to collar (1276). When articulation bands (1256, 1258) are translated longitudinally in an opposing fashion, a moment is created and applied to distal flange (1286) via collar (1276). This causes the articulation section of shaft assembly (1250), in particular articulation section (1262), ribbed body portions (1252, 1254), flexible portion (1257, 1259) of articulation bands (1256, 1258), and narrowed section (1285) of flexible portion (1284) of waveguide (1280), to articulate, without transferring axial forces in articulation bands (1256, 1258) to waveguide (1280).

Figure 40:
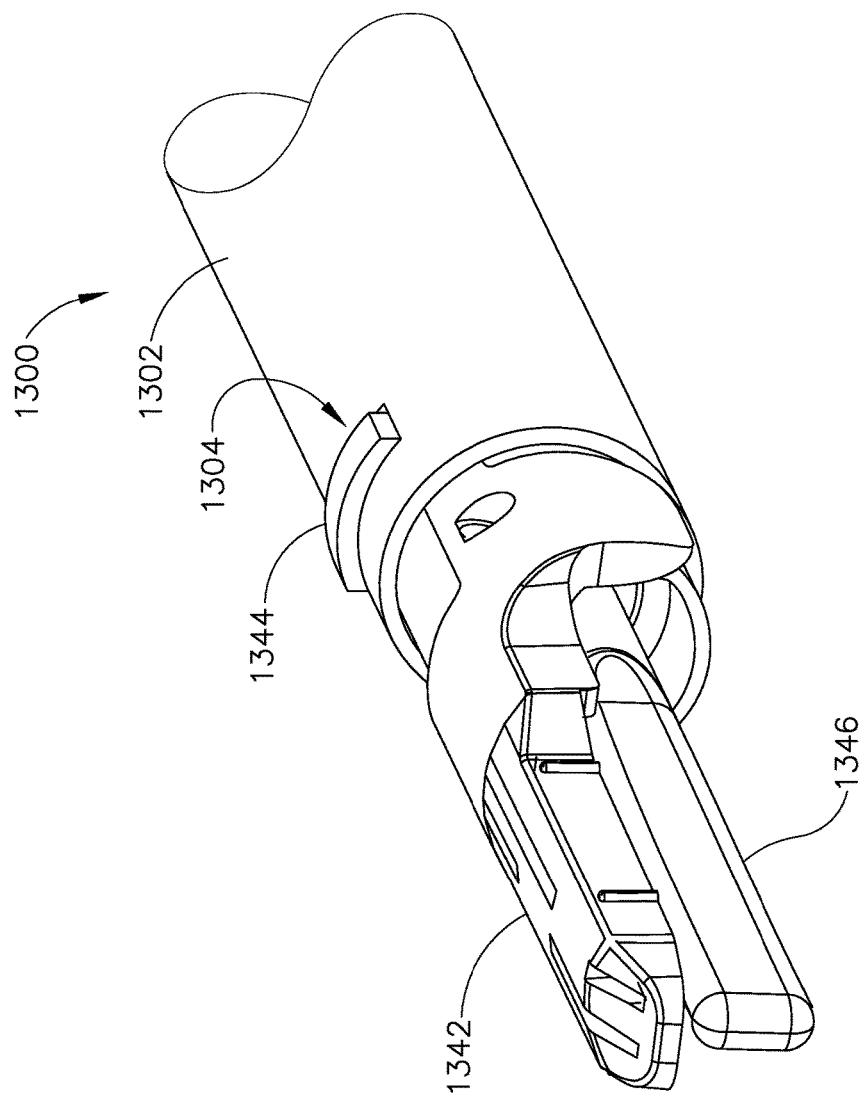
FIG. 40 depicts a detailed perspective view of yet another exemplary alternative shaft and end effector assembly configured for incorporation in the instrument of FIG. 1.

F. Exemplary Alternative Configuration for Outer Closure Tube for Actuation of Clamp Arm FIG. 40 shows yet another exemplary alternative shaft assembly (1300) and end effector (1340) that may be readily incorporated into instrument (10). Shaft assembly (1300) of this example comprises an outer sheath (1302) that is configured to translate longitudinally relative to end effector (1340) to pivotally actuate a clamp arm (1342) toward and away from an ultrasonic blade (1346). Shaft assembly (1300) and end effector (1340) thus operate similar to shaft assembly (1250) and end effector (1270) described above. However, in this example, a distal end of outer sheath (1302) defines a slot (1304). Clamp arm (1342) of end effector (1340) comprises a proximal projection (1344) extending upwardly from clamp arm (1342). Proximal projection (1344) is disposed within slot (1304). As discussed above with reference to instrument (10), clamp arm (1304) is pivotally secured to a longitudinally grounded component of shaft assembly (1300), such that longitudinal translation of outer sheath (1302) causes pivoting of clamp arm (1342) toward and away from blade (1346) via engagement of projection (1344) with slot (1304). Other suitable ways in which clamp arm (1342) may be coupled with a translating outer sheath (1302) will be apparent to those of ordinary skill in the art in view of the teachings herein.

G. Exemplary Alternative Actuation of Articulation Section

Figure 41:
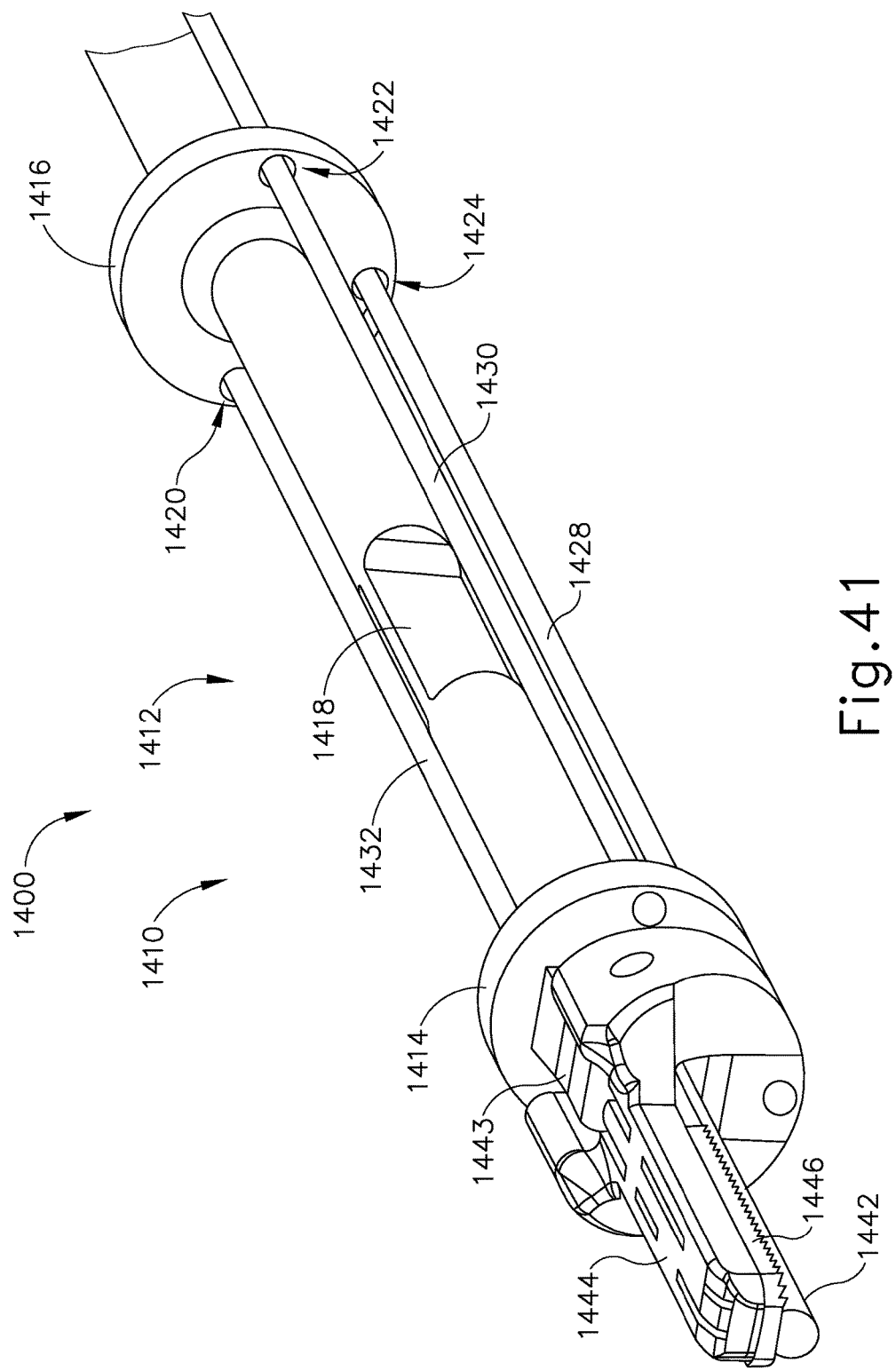
FIG. 41 depicts a perspective view of components of yet another exemplary alternative shaft assembly configured for incorporation in the instrument of FIG. 1.

FIGS. 41-42B show exemplary alternative internal components of yet another exemplary alternative shaft assembly (1400) and end effector (1440) that may be readily incorporated into instrument (10). End effector (1440) of this example comprises an ultrasonic blade (1442) and a clamp arm (1444). Clamp arm (1444) includes a clamp pad (1446) that is secured to the underside of clamp arm (1444), facing blade (1442). Blade (1442) of the present example is configured to operate substantially similar to blade (160) discussed above, such that blade (1442) is operable to vibrate at ultrasonic frequencies in order to effectively cut through and seal tissue, particularly when the tissue is being compressed between clamp pad (1446) and blade (1442). Blade (1442) is positioned at the distal end of an acoustic drivetrain. This acoustic drivetrain includes transducer assembly (12) and an acoustic waveguide (1410). The transducer assembly is operable to convert electrical power into ultrasonic vibrations, which are then transmitted along waveguide (1410), including flexible portion (1412) of waveguide (1410), to blade (1442) in accordance with known configurations and techniques. By way of example only, this portion of the acoustic drivetrain may be configured in accordance with various teachings of various references that are cited herein.

Figure 42A:
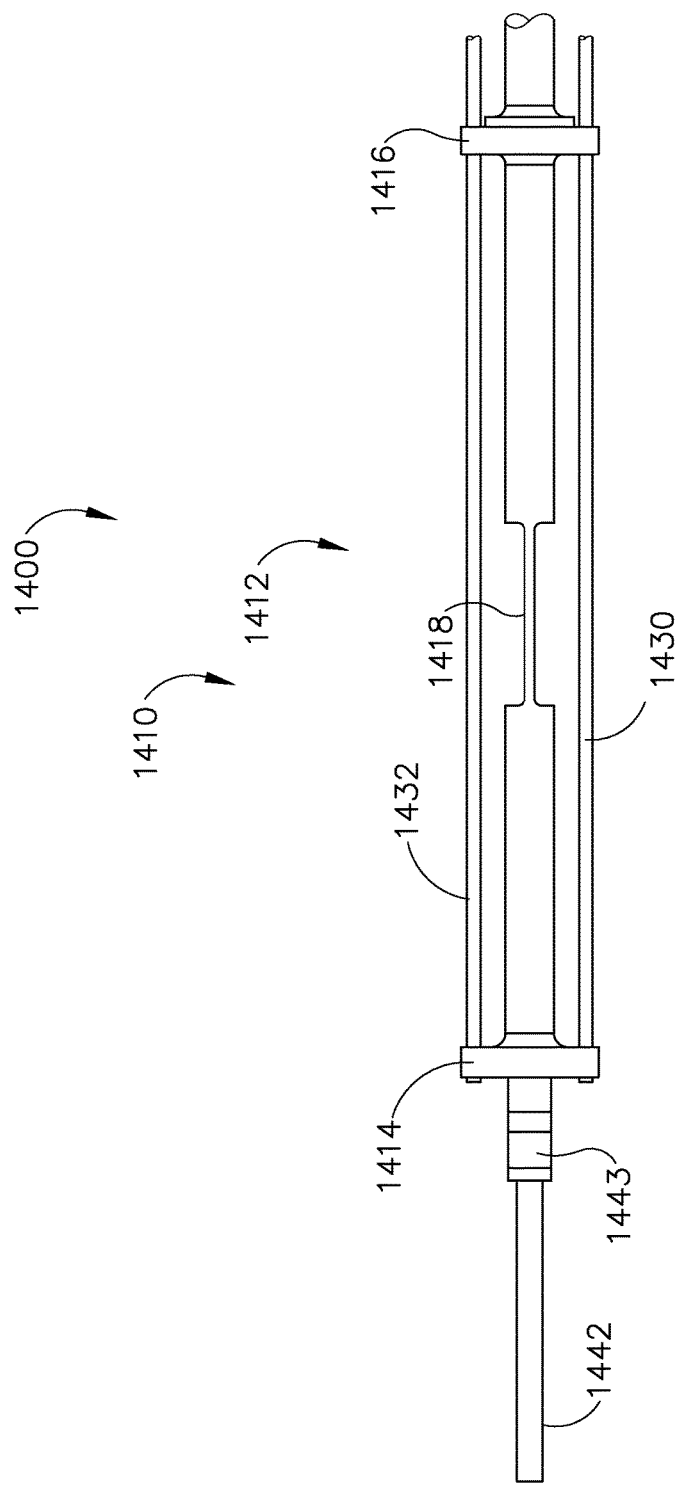
FIG. 42A depicts a top plan view of the shaft assembly of FIG. 41 in a straight configuration.

Waveguide (1410) comprises a flexible portion (1412), a distal flange (1414), and a proximal flange (1416). As best seen in FIGS. 42A and 42B, flexible portion (1412) of waveguide (1410) includes a narrowed section (1418) located between flanges (1414, 1416). In the present example, flanges (1414, 1416) are located at positions corresponding to nodes associated with resonant ultrasonic vibrations communicated through flexible portion (1412) of waveguide (1410). Narrowed section (1418) is configured to allow flexible portion (1412) of waveguide (1410) to flex without significantly affecting the ability of flexible portion (1412) of waveguide (1410) to transmit ultrasonic vibrations. By way of example only, narrowed section (1418) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (1410) may be configured to amplify mechanical vibrations transmitted through waveguide (1410). Furthermore, waveguide (1410) may include features operable to control the gain of the longitudinal vibrations along waveguide (1410) and/or features to tune waveguide (1410) to the resonant frequency of the system.

In the present example, the distal end of blade (1442) is located at a position corresponding to an anti-node associated with resonant ultrasonic vibrations communicated through flexible portion (1412) of waveguide (1410), in order to tune the acoustic assembly to a preferred resonant frequency $f_o$ when the acoustic assembly is not loaded by tissue. When transducer assembly (12) is energized, the distal end of blade (1442) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (1410) to reach blade (1442), thereby providing oscillation of blade (1442) at the resonant ultrasonic frequency. Thus, when tissue is compressed between blade (1442) and clamp pad (1446), the ultrasonic oscillation of blade (1442) may simultaneously sever the tissue and denature the proteins in adjacent tissue cells, thereby providing a coagulative effect with relatively little thermal spread. In some versions, an electrical current may also be provided through blade (1442) and clamp arm (1444) to also cauterize the tissue. Other suitable configurations for an acoustic transmission assembly and transducer assembly will be apparent to one or ordinary skill in the art in view of the teachings herein. Similarly, other suitable configurations for end effector (1440) will be apparent to those of ordinary skill in the art in view of the teachings herein.

The internal components of shaft assembly (1400) further comprise a pair of articulation cables (1430, 1432). Proximal flange (1416) of flexible portion (1412) of waveguide (1410) comprises a plurality of through bores (1420, 1422, 1424). The distal ends of articulation cables (1430, 1432) are unitarily secured to distal flange (1414) of flexible portion (1412) of waveguide (1410). Articulation cables (1430, 1432) extend proximally from distal flange (1414) and pass freely through bores (1420, 1422) within shaft assembly (1400). As one articulation cable (1430, 1432) is pulled proximally, this will cause an articulation section of shaft assembly (1400) to bend, thereby laterally deflecting end effector (1440) away from a longitudinal axis of shaft assembly (1400) at an articulation angle as shown in FIG. 42B. In particular, end effector (1440) will be articulated toward the articulation cable (1430, 1432) that is being pulled proximally. During such articulation, the other articulation cable (1430, 1432) will be pulled distally by distal flange (1414) of flexible portion (1412) of waveguide (1410). Flexible portion (1412) is configured to effectively communicate ultrasonic vibrations from waveguide (1410) to blade (1442) even when the articulation section of shaft assembly (1440) is in an articulated state as shown in FIG. 42B.

Distal flange (1414) of flexible portion (1412) of waveguide (1410) is fixedly secured to a distal end of shaft assembly (1400). When articulation cables (1430, 1432) are translated longitudinally in an opposing fashion, a moment is created and applied to the distal end shaft assembly (1400)

via distal flange (1414). This causes the articulation section of shaft assembly (1400) and narrowed section (1418) of flexible portion (1412) of waveguide (1410) to articulate, without transferring axial forces in articulation cables (1430, 1432) to waveguide (1410). It should be understood that one articulation cable (1430, 1432) may be actively driven distally while the other articulation cable (1430, 1432) is passively permitted to retract proximally. As another merely illustrative example, one articulation cable (1430, 1432) may be actively driven proximally while the other articulation cable (1430, 1432) is passively permitted to advance distally. As yet another merely illustrative example, one articulation cable (1430, 1432) may be actively driven distally while the other articulation cable (1430, 1432) is actively driven proximally. Various suitable ways in which articulation cables (1430, 1432) may be driven will be apparent to those of ordinary skill in the art in view of the teachings herein. It should also be understood that one or more spacers may be used to prevent articulation cables (1430, 1432) from contacting waveguide (1410) between flanges (1414, 1416).

An upper portion of clamp arm (44) is pivotally secured to a distally projecting tongue (1443) of distal flange (1414) of waveguide (1410). Clamp arm (1444) is operable to selectively pivot toward and away from blade (1442) to selectively clamp tissue between clamp pad (1446) and blade (1442). A cable (1428) is secured to a lower portion of clamp arm (1444). Cable (1428) extends proximally from clamp arm (1444) and passes freely through distal flange (1414) and freely through bore (1424) of proximal flange (1416) within shaft assembly (1400). Cable (1428) is operable to translate longitudinally relative to the articulation section of shaft assembly (1400) to selectively pivot clamp arm (1444) toward and away from blade (1442). Cable (1428) may be coupled with a trigger such that clamp arm (1444) pivots toward and away from blade (1442) in response to pivoting of the trigger. Clamp arm (1444) may be biased toward the open position, such that (at least in some instances) the operator may effectively open clamp arm (1444) by releasing a grip on the trigger.

IV. EXEMPLARY ALTERNATIVE WAVEGUIDE CONFIGURATIONS

It may be desirable to provide for alternative engagement between waveguide (180) and shaft assembly (30). As will be discussed in more detail below, FIGS. 43-50 show various examples of how waveguide (180) may engage shaft assembly (30). While various examples of how waveguide (180) may engage shaft assembly (30) will be described in greater detail below, other examples will be apparent to those of ordinary skill in the art according to the teachings herein. It should be understood that the examples of waveguides described below may function substantially similar to clamp waveguide (180) discussed above. In particular, the examples of waveguides described below are operable to transmit ultrasonic vibrations from transducer (12) to an ultrasonic blade.

FIGS. 43-46 show an exemplary alternative waveguide (1500) that may be readily incorporated into instrument (10). Waveguide (1500) of this example comprises an ultrasonic blade (1502) and a flexible portion (1504). Blade (1502) of the present example is configured to operate substantially similar to blade (160) discussed above except for the differences discussed below. In particular, blade (1502) of the present example is operable to vibrate at ultrasonic frequencies in order to effectively cut through and seal tissue. As discussed above, transducer assembly (12) is operable to convert electrical power into ultrasonic vibrations, which are then transmitted along waveguide (1502), including flexible portion (1504) of waveguide (1502) to blade (1502) in accordance with known configurations and techniques. By way of example only, this portion of the acoustic drivetrain may be configured in accordance with various teachings of various references that are cited herein.

Figure 43:
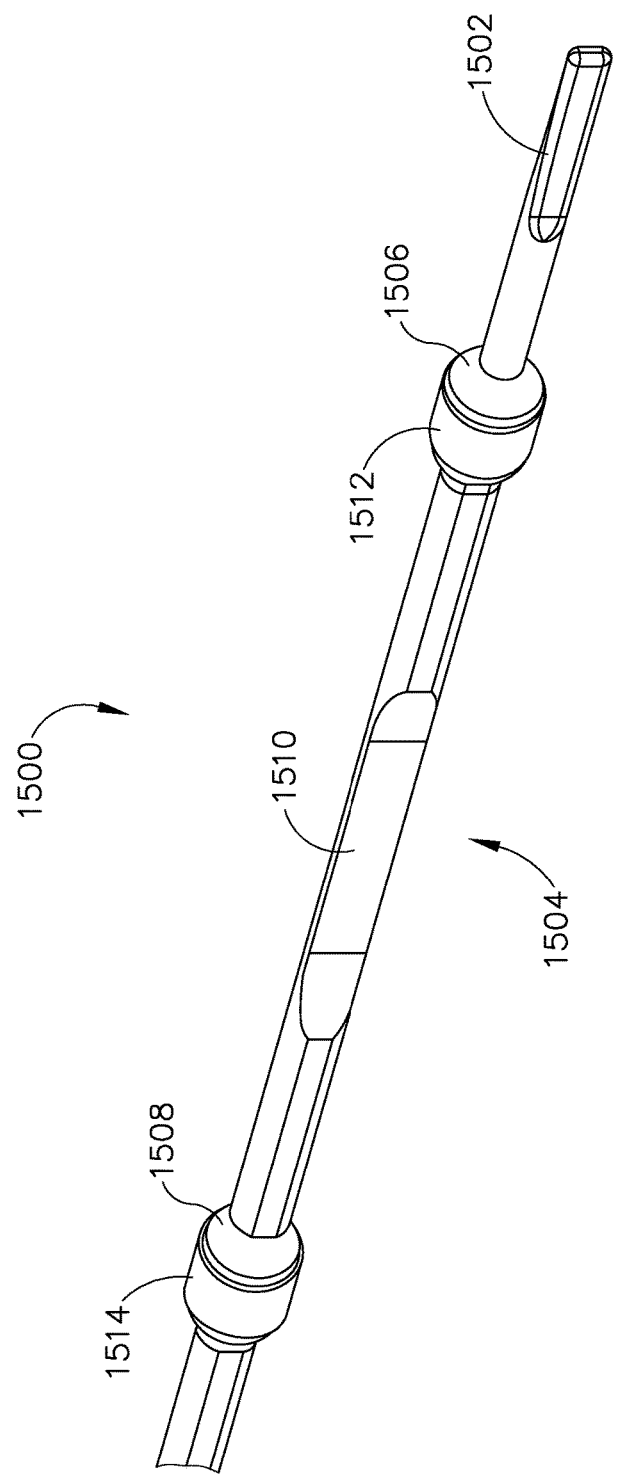
FIG. 43 depicts a perspective view of an exemplary alternative waveguide configured for incorporation in the instrument of FIG. 1.

As best seen in FIG. 43, flexible portion (1504) of waveguide (1500) includes a distal flange (1506), a proximal flange (1508), and a narrowed section (1510) located between flanges (1506, 1508). In the present example, flanges (1506, 1508) are located at positions corresponding to nodes associated with resonant ultrasonic vibrations communicated through flexible portion (1504) of waveguide (1500). Narrowed section (1510) is configured to allow flexible portion (1504) of waveguide (1500) to flex without significantly affecting the ability of flexible portion (1504) of waveguide (1500) to transmit ultrasonic vibrations. By way of example only, narrowed section (1510) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (1500) may be configured to amplify mechanical vibrations transmitted through waveguide (1500). Furthermore, waveguide (1500) may include features operable to control the gain of the longitudinal vibrations along waveguide (1500) and/or features to tune waveguide (1500) to the resonant frequency of the system.

In the present example, the distal end of blade (1502) is located at a position corresponding to an anti-node associated with resonant ultrasonic vibrations communicated through flexible portion (1504) of waveguide (1500), in order to tune the acoustic assembly to a preferred resonant frequency $f_o$ when the acoustic assembly is not loaded by tissue. When transducer assembly (12) is energized, the distal end of blade (1502) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (1500) to reach blade (1502), thereby providing oscillation of blade (1502) at the resonant ultrasonic frequency. Thus, the ultrasonic oscillation of blade (1502) may simultaneously sever the tissue and denature the proteins in adjacent tissue cells, thereby providing a coagulative effect with relatively little thermal spread. In some versions, an electrical current may also be provided through blade (1502) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein.

Figure 44:
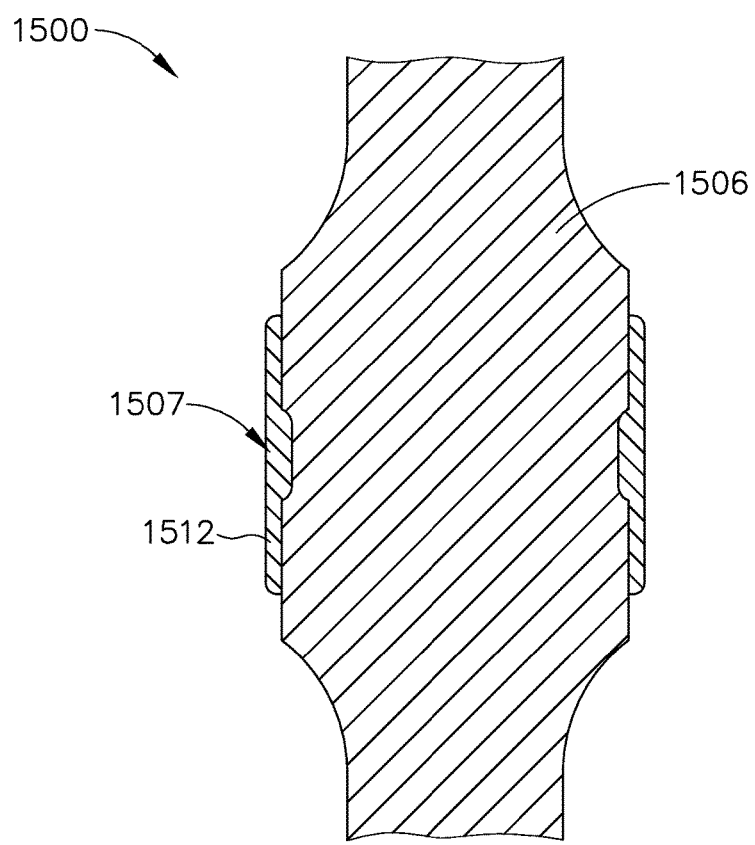
FIG. 44 depicts a cross-sectional top view of a flange of the waveguide of FIG. 43.

Waveguide (1500) further comprises a pair of overmolds (1512, 1514) secured about an exterior of flanges (1506, 1508). Overmolds (1512, 1514) of flanges (1506, 1508) are configured to engage an interior surface of shaft assembly (30). Overmolds (1512, 1514) provide an acoustic barrier between waveguide (1500) and shaft assembly (30) to thereby lessen the effect that engagement between waveguide (1500) and shaft assembly (30) may have upon transmission of ultrasonic vibrations within waveguide (1500). As shown in FIG. 44, flanges (1506, 1508) of the present example comprise an annular groove (1507) formed in an exterior surface of flanges (1506, 1508). Overmolds (1512, 1514) may be disposed within groove (1507) to thereby improve engagement between overmolds (1512, 1514) and flanges (1506, 1508). Overmolds (1512, 1514) may comprise polytetraflouroethylene (PTFE), rubber, silicone, plastic, and/or any other suitable material(s).

As best seen in FIG. 46, flanges (1506, 1508) of the present example have a circular cross-sectional profile. It should be understood, however, that any other suitable shapes may be used. For instance, FIGS. 47-48 show an exemplary alternative waveguide (1550) with a flange (1556) having an oblong shape. In particular, flange (1556) includes a pair of flats (1557). A blade (1552) is located distal to flange (1556). An overmold (1562) is positioned about flange (1556) and has a cross-sectional profile complementing the cross-sectional profile of flange (1556). FIGS. 49-50 show another exemplary alternative waveguide (1600) with a flange (1606) having an oblong shape. In particular, flange (1606) includes a pair of flats (1607) and a pair of longitudinally extending grooves (1609). A blade (1602) is located distal to flange (1606). An overmold (1612) is positioned about flange (1606) and has a cross-sectional profile complementing the cross-sectional profile of flange (1606). Other suitable configurations that may be used for flanges will be apparent to those of ordinary skill in the art in view of the teachings herein.

V. EXEMPLARY ALTERNATIVE INSTRUMENT WITH DUAL ROLE BANDS AND DUAL ACTUATORS

Figure 51:
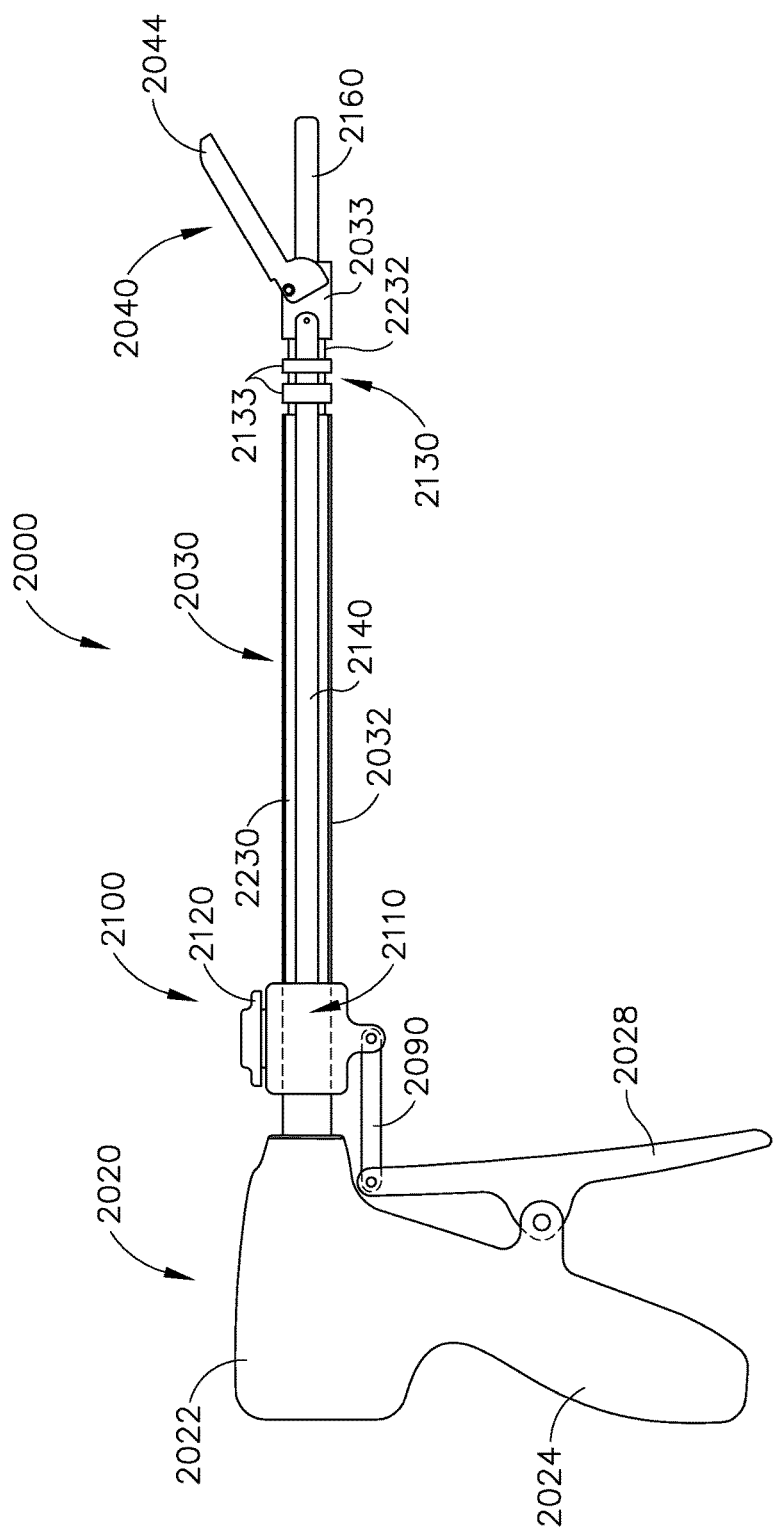
FIG. 51 depicts a side elevational view of an exemplary alternative ultrasonic surgical instrument.
Figure 52:
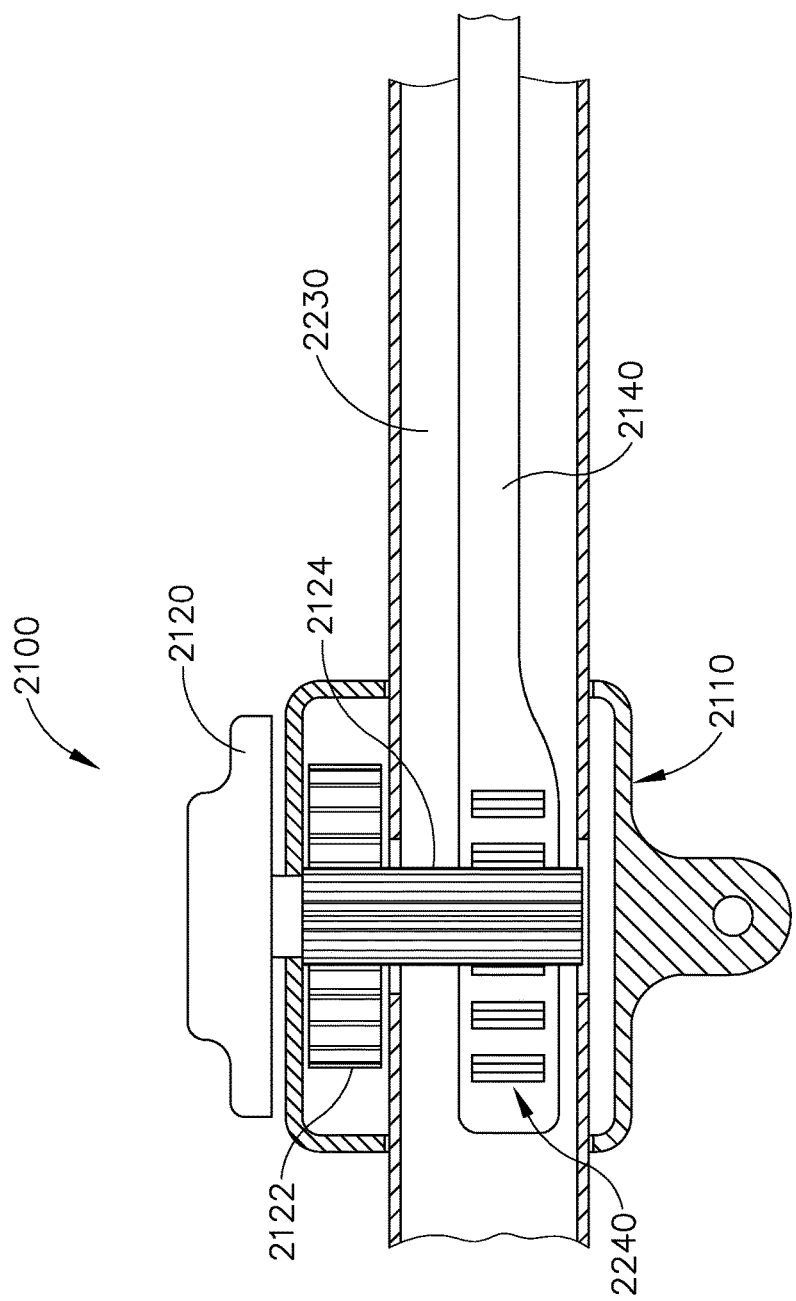
FIG. 52 depicts an enlarged side elevational view of an exemplary articulation control assembly of the instrument of FIG. 51, with a housing of the assembly shown in cross-section.
Figure 53:
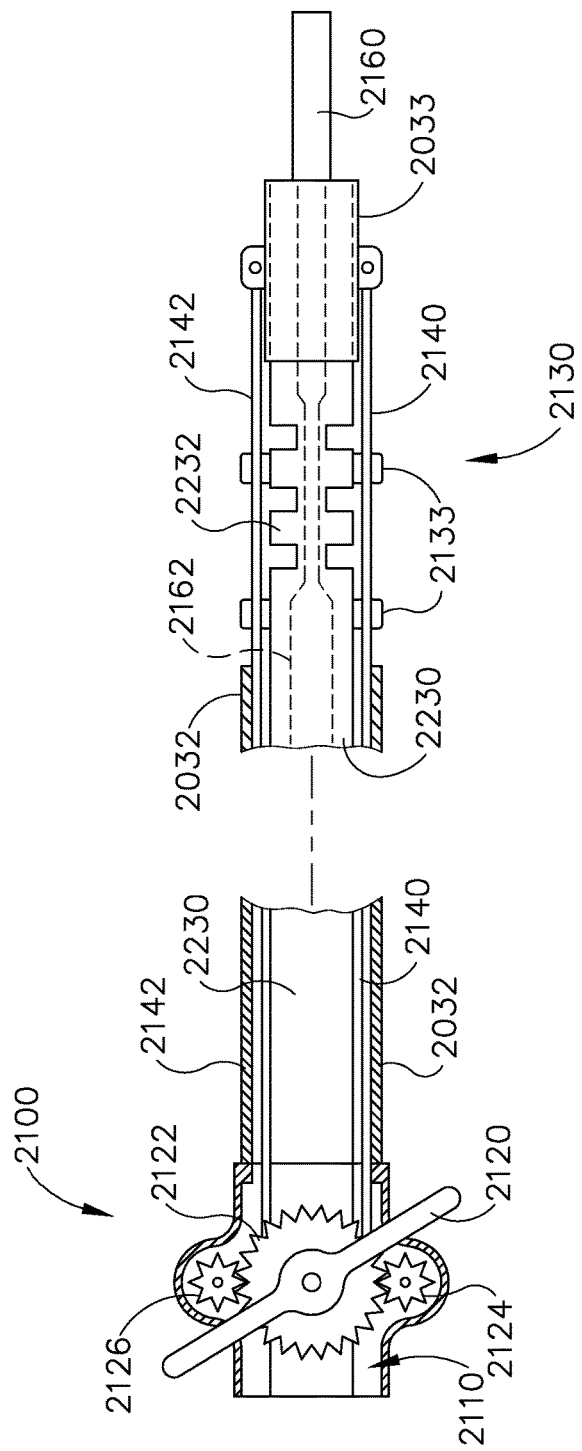
FIG. 53 depicts a top plan view of the articulation control assembly of FIG. 52, with the housing of the assembly shown in cross-section, and the end effector of the instrument of FIG. 51.

FIGS. 51-53 show another exemplary ultrasonic surgical instrument (2000) that is configured and operable substantially similar to instrument (10) except for the differences discussed below. Instrument (2000) of this example comprises a handle assembly (2020), a shaft assembly (2030), and an end effector (2040). Handle assembly (2020) includes a body (2022) that defines a pistol grip (2024). A trigger (2028) is pivotally coupled with body (2022) such that trigger (2028) is pivotable toward and away from pistol grip (2024). An articulation and closure actuation assembly (2100) is slidably coupled with handle assembly (2020) as will be described in greater detail below. It should be understood that handle assembly (2020) may also include a transducer assembly like transducer assembly (12), buttons like buttons (26), and/or various other features as described above with respect to handle assembly (20).

Shaft assembly (2030) of the present example comprises a proximal outer sheath (2032), a distal outer sheath (2033), an inner tubular body (2230), and a flex housing (2232). It should be understood that proximal outer sheath (2032) is shown in cross-section in FIGS. 51 and 53 to reveal internal components of shaft assembly (2030). Shaft assembly (2030) further includes an articulation section (2130), which enables end effector (2040) to be deflected laterally away from the longitudinal axis of the proximal portion of shaft assembly (2030). Proximal outer sheath (2032) distally terminates at the proximal end of articulation section (2130). Distal outer sheath (2033) proximally terminates at the distal end of articulation section (2130). Articulation section (2130) is thus longitudinally interposed between outer sheaths (2032, 2033). Inner tubular body (2230) also distally terminates at the proximal end of articulation section (2130). Flex housing (2232) extends along the length of articulation section (2130). Flex housing (2232) is longitudinally secured relative to inner tubular body (2230), which is further longitudinally secured relative to handle assembly (2020). Flex housing (2232) is thus longitudinally grounded relative to handle assembly (2020), though flex housing (2232) is still configured to bend in lateral deflection during articulation. In some versions, flex housing (2232) is configured similar to the combination of ribbed body portions (132, 134) described above.

Shaft assembly (2030) of the present example further includes a pair of articulation bands (2140, 2142). The distal ends of articulation bands (2140, 2142) are secured to distal outer sheath (2033). The proximal ends of articulation bands (2140, 2142) are coupled with articulation and closure actuation assembly (2100), as will be described in greater detail below. Articulation bands (2140, 2142) pass through a space defined between inner tubular body (2230) and proximal outer sheath (2032). A set of retention collars (133) are positioned about articulation bands (2140, 2142) in articulation section (2130). Articulation bands (2140, 2142) are operable to actuate articulation section (2130), to thereby deflect end effector (2040) laterally to an articulated position. In particular, articulation bands (2140, 2142) translate in an opposing fashion to create and apply a moment to distal outer sheath (2033), thereby providing articulation of articulation section (2130) and end effector (2040), similar to bands (140, 142) described above. It should therefore be understood that end effector (2040) will deflect laterally in the direction of whichever articulation band (2140, 2142) is moving proximally; while the other articulation band (2140, 2142) moves distally.

End effector (2040) of the present example comprises a clamp arm (2044) and an ultrasonic blade (2160). Ultrasonic blade (2160) is formed at the distal end of a waveguide (2162). In the present example, waveguide (2162) is configured and operable identically to waveguide (180) described above, such that waveguide (2162) is configured to bend with articulation section (2130) to achieve an articulated state. Clamp arm (2044) is operable to pivot toward and away from ultrasonic blade (2160), to thereby capture and compress tissue against ultrasonic blade (2160). In particular, one portion of clamp arm (2044) is pivotally coupled with the distal end of flex housing (2232) (or some component that is longitudinally grounded to flex housing (2232)). Another portion of clamp arm (2044) is pivotally coupled with distal outer sheath (2033). Distal outer sheath (2033) is operable to translate longitudinally relative to flex housing (2232) and the other components of shaft assembly (2030) that are longitudinally grounded relative to handle assembly (2022). It should therefore be understood that clamp arm (2044) will pivot relative to blade (2160) in response to longitudinal translation of distal outer sheath (2033) relative to flex housing (2232) and the other components of shaft assembly (2030) that are longitudinally grounded relative to handle assembly (2022).

Articulation and closure actuation assembly (2100) of the present example comprises a housing (2110) and a control knob (2126), which is rotatable relative to housing (2110). As best seen in FIGS. 52-53, where housing (2110) is shown in cross-section, a pinion gear (2122) is unitarily secured to control knob (2126), such that pinion gear (2122) rotates unitarily with control knob (2126) relative to housing (2110). Intermediate gears (2124, 2126) are positioned on opposite sides of pinion gear (2122) and mesh with pinion gear (2122), such that intermediate gears (2124) rotate in response to rotation of control knob (2126) and pinion gear (2122). As shown in FIG. 52, intermediate gear (2124) extends vertically to mesh with a rack (2240) of articulation band (2140), providing a rack and pinion relationship between intermediate gear (2124) and articulation band (2140). Thus, when intermediate gear (2124) rotates, articulation band (2140) translates longitudinally. Articulation band (2140) will therefore translate longitudinally in response to rotation of control knob (2126). While not shown, intermediate gear (2126) meshes with a rack of articulation band (2142) in a similar fashion. Articulation bands (2140, 2142) will thus translate longitudinally in an opposing fashion in response to rotation of control knob (2126). It should therefore be understood that articulation section (2130) will bend to deflect end effector (2040) in a first direction when control knob (2126) is rotated in a first direction; and will bend to deflect end effector (2040) in a second direction when control knob (2126) is rotated in a second direction. In some versions, knob (2126) is oriented to extend along a plane that is parallel with the longitudinal axis of shaft assembly (2030) when articulation section (213) is straight; and obliquely relative to the longitudinal axis of shaft assembly (2030) when articulation section (213) is bent, such that control knob (2126) provides visual feedback indicating the state of articulation.

As noted above, articulation and closure actuation assembly (2100) is configured to slide longitudinally relative to handle assembly (2020). Articulation and closure actuation assembly (2100) is pivotally coupled with trigger (2028) via a link (2090). In particular, one end of link (2090) is pivotally coupled with the underside of housing (2110) and another end of link (2090) is pivotally coupled with the upper end of trigger (2028). Thus, as trigger (2028) is pivoted toward pistol grip (2024), link (2090) drives articulation and closure actuation assembly (2100) distally relative to handle assembly (2020). As trigger (2028) is pivoted back away from pistol grip (2024), link (2090) drives articulation and closure actuation assembly (2100) proximally relative to handle assembly (2020). When articulation and closure actuation assembly (2100) translates relative to handle assembly (2020), intermediate gears (2124, 2126) drive articulation bands (2140, 2142) longitudinally together in the same direction simultaneously. When articulation bands (2140, 2142) translate longitudinally together in the same direction simultaneously, articulation bands (2140, 2142) drive distal outer sheath (2033) longitudinally. Such longitudinal motion of distal outer sheath (2033) actuates clamp arm (2044) as described above. It should therefore be understood that, as trigger (2028) is pivoted toward pistol grip (2024), clamp arm (2044) is driven toward blade (2160) via link (2090), articulation and closure actuation assembly (2100), articulation bands (2140, 2142), and distal outer sheath (2033). Likewise, as trigger (2028) is pivoted away from pistol grip (2024), clamp arm (2044) is driven away from blade (2160) via link (2090), articulation and closure actuation assembly (2100), articulation bands (2140, 2142), and distal outer sheath (2033).

It should be understood that articulation and closure actuation assembly (2100) may include one or more features that are operable to selectively lock the straight/articulation state of articulation section (2130) or at least resist a change in the straight/articulation state of articulation section (2130). By way of example only, such resistance may be provided through friction, detent features, etc. Other suitable ways in which articulation and closure actuation assembly (2100) may selectively lock the straight/articulation state of articulation section (2130) or at least resist a change in the straight/articulation state of articulation section (2130) will be apparent to those of ordinary skill in the art in view of the teachings herein.

VI. EXEMPLARY ULTRASONIC SURGICAL INSTRUMENT WITH MOTORIZED ARTICULATION

Figure 54:
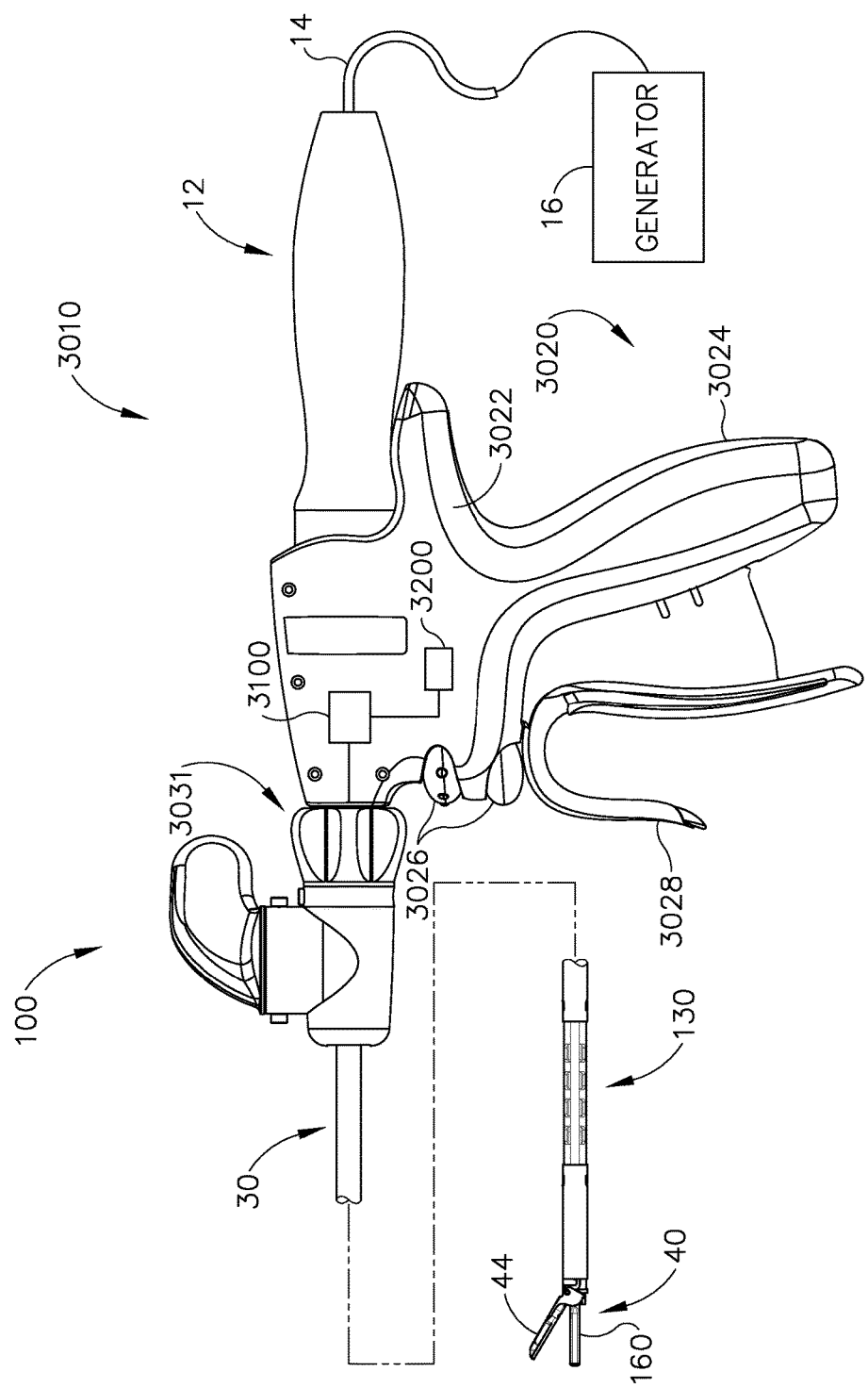
FIG. 54 depicts a side elevational view of an exemplary alternative ultrasonic surgical instrument.

The above examples are discussed in the context of manual control of articulation in a shaft assembly. However, it should also be understood that articulation may be motorized. For instance, FIG. 54 shows an exemplary instrument (3010) that is in many ways similar to instrument (10) described above. Instrument (3010) of this example includes a handle assembly (3020), a shaft assembly (30), and an end effector (40). Handle assembly (3020) comprises a body (3022) including a pistol grip (3028) and a pair of buttons (3026). Handle assembly (3020) also includes a trigger (3028) that is pivotable toward and away from pistol grip (3024). End effector (40) includes an ultrasonic blade (160) and a pivoting clamp arm (44). Clamp arm (44) is coupled with trigger (3028) such that clamp arm (44) is pivotable toward ultrasonic blade (160) in response to pivoting of trigger (3028) toward pistol grip (3024); and such that clamp arm (44) is pivotable away from ultrasonic blade (160) in response to pivoting of trigger (3028) away from pistol grip (3024).

An ultrasonic transducer assembly (12) extends proximally from body (3022) of handle assembly (3020). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12).

Shaft assembly (30) of the present example extends distally from handle assembly (3020). Shaft assembly (30) includes an articulation section (130), which is located at a distal portion of shaft assembly (30), with end effector (40) being located distal to articulation section (130). A knob (3031) is secured to a proximal portion of proximal outer sheath (32). Knob (3031) is rotatable relative to body (3022), such that shaft assembly (30) is rotatable about a longitudinal axis relative to handle assembly (3020). Such rotation may provide rotation of end effector (40), articulation section (130), and shaft assembly (30) unitarily. Of course, rotatable features may simply be omitted if desired. Articulation section (130) is operable to selectively position end effector (40) at various lateral deflection angles relative to a longitudinal axis defined by outer sheath (32). Articulation section (130) may take a variety of forms, including but not limited to any of the forms described herein.

It should be understood that all of the above described features of instrument (3010) are substantially identical to the same features of instrument (10), except for the differences described below. In particular, instrument (3010) of this example lacks manually operated articulation control assembly (100). Instead, instrument (3010) includes a motor (3100) that is coupled with articulation section (130) to drive articulation section (130) in a motorized fashion. Various suitable ways in which motor (3100) may be coupled with articulation section (130) to drive articulation section (130) in a motorized fashion will be apparent to those of ordinary skill in the art in view of the teachings herein. A user input feature (3200) is in communication with motor (3100) and is operable to selectively activate motor (3100) in response to user input. Various suitable forms that user input feature (3200) may take will be apparent to those of ordinary skill in the art in view of the teachings herein. It should also be understood that more than one user input feature (3200) may be provided (e.g., one user input feature (3200) for each direction of articulation, etc.).

In some versions, motor (3100) receives power from an external source (e.g., generator (16), etc.) via cable (14). In some other versions, motor (3100) receives power from an internal source (e.g., one or more batteries or other portable power sources in body (3022) of handle assembly (3020), etc.). It should also be understood that motor (3100) may be located at any suitable position within body (3022) of handle assembly (3020). Alternatively, motor (3100) may be located external to body (3022). Other suitable ways in which motor (3100) may be incorporated in instrument (3010) to drive articulation section (130) will be apparent to those of ordinary skill in the art in view of the teachings herein.

While instrument (3010) is described above as providing motorized driving of articulation section (130), it should be understood that instrument (3010) may instead incorporate any of the other articulation sections described herein. In other words, any of the articulation sections described herein may be driven in a motorized fashion.

VII. EXEMPLARY ULTRASONIC SURGICAL INSTRUMENT WITH RESTRICTED ARTICULATION

In some instances, it may be desirable to restrict the articulation angle of waveguide (180). For instance, if waveguide (180) is articulated from the longitudinal axis defined by proximal outer sheath (32) at too steep an angle, waveguide (180) could permanently deform leading to undesirable effects. Restricting the maximum articulation of waveguide (180) may therefore help maintain the structural integrity of waveguide (180). A merely illustrative example of how the articulation angle may be restricted will be described in greater detail below.

A. Exemplary End Effector and Acoustic Drivetrain

Figure 55A:
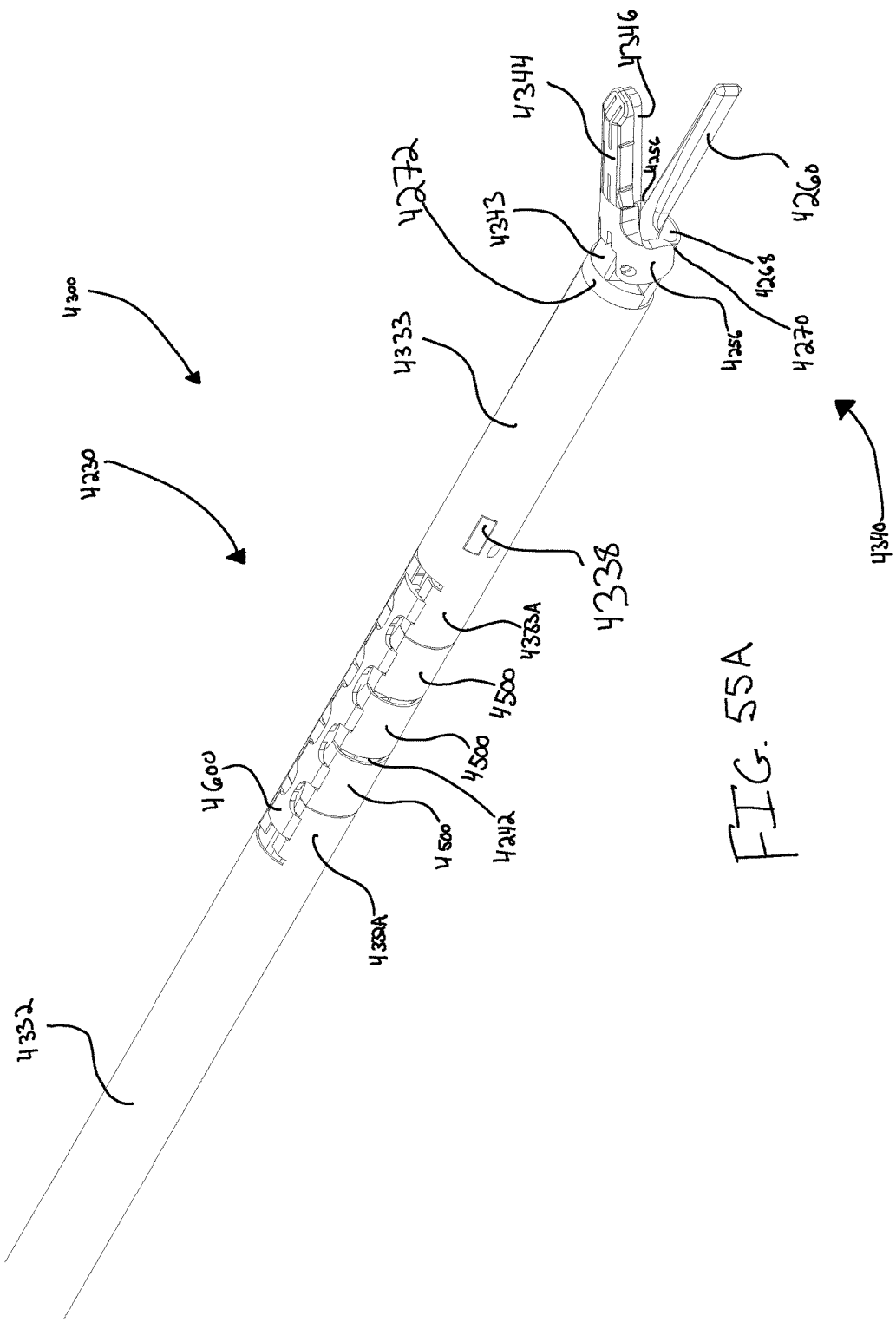
FIG. 55A depicts a perspective view of an articulation section of an exemplary alternative shaft assembly and an end effector that may be incorporated into the instrument of FIG. 1.

FIG. 55A illustrates an exemplary shaft assembly (4300) and an exemplary end effector (4340). Shaft assembly (4300) and end effector (4340) can be utilized in instrument (10), substituting for shaft assembly (30) and end effector (40). End effector (4340) is substantially similar to end effector (40). End effector (4340) includes an ultrasonic blade (4260) and a pivoting clamp arm (4344). Claim arm (4344) includes a clamp pad (4346) that is secured to the underside of clamp arm (4344), facing ultrasonic blade (4260). Clamp pad (4346) may comprise polytetrafluoroethylene (PTFE) and/or any other suitable material(s).

Clamp arm (4344) is pivotally secured to a distally projecting tongue (4343) of an upper distal shaft element (4272), which is fixedly secured within a distal portion of a distal outer sheath (4333). Lower distal shaft element (4270) is slidably disposed within the distal portion of distal outer sheath (4333). Trigger (28) is operable to translate lower distal shaft element (4270) along a path that is parallel to the longitudinal axis defined by distal outer sheath (4333). Specifically, trigger (28) can translate lower distal shaft element (4272) proximally when trigger (28) is pivoted toward pistol grip (24) and distally when trigger (28) is pivoted away from pistol grip (24). A pair or arms (4256) extend transversely from clamp arm (4344) and are pivotally secured to lower distal shaft element (4270). Therefore, clamp arm (4344) is coupled with trigger (28) such that clamp arm (4344) is pivotable toward ultrasonic blade (4260) in response to pivoting of trigger (28) toward pistol grip (24); and such that clamp arm (4344) is pivotable away from ultrasonic blade (4260) in response to pivoting of trigger (28) away from pistol grip (24). Various suitable ways in which clamp arm (4344) may be coupled with trigger (28) will be apparent to those of ordinary skill in the art in view of the teachings herein. In some versions, one or more resilient members are used to bias clamp arm (4344) and/or trigger (28) to the open position shown in FIG. 55A. Drive features enabling trigger (28) to close clamp arm (4344) are the same for the drive features described above enabling trigger (28) to close clamp arm (44).

Blade (4260) of the present example is operable to vibrate at ultrasonic frequencies in order to effectively cut through and seal tissue, particularly when the tissue is being compressed between clamp pad (4346) and blade (4260). Blade (4260) is positioned at the distal end of an acoustic drivetrain. This acoustic drivetrain includes transducer assembly (12) and an acoustic waveguide (4280). Acoustic waveguide (4280) comprises a flexible portion (4266). Transducer assembly (12) includes a set of piezoelectric discs (not shown) located proximal to a horn (not shown) of waveguide (4280). The piezoelectric discs are operable to convert electrical power into ultrasonic vibrations, which are then transmitted along waveguide (4280), including flexible portion (4266) of waveguide (4280) to blade (4260) in accordance with known configurations and techniques. By way of example only, this portion of the acoustic drivetrain may be configured in accordance with various teachings of various references that are cited herein.

Figure 56:
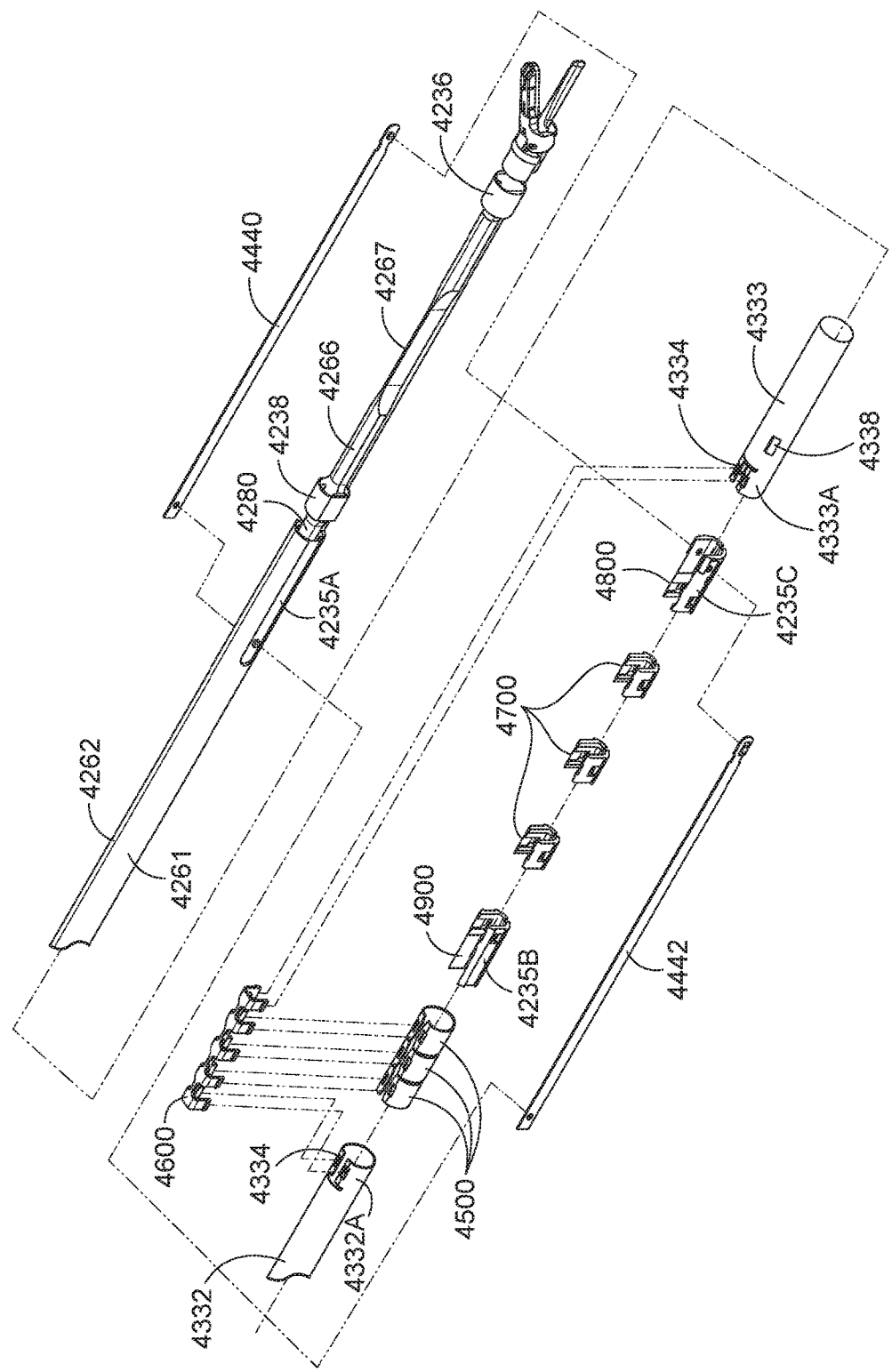
FIG. 56 depicts an exploded perspective view of the articulation section of FIG. 55A.

As best seen in FIG. 56, flexible portion (4266) of waveguide (4280) includes a distal flange (4236), a proximal flange (4238), and a narrowed section (4267) located between flanges (4236, 4238). In the present example, flanges (4236, 4238) are located at positions corresponding to nodes associated with resonant ultrasonic vibrations communicated through flexible portion (4266) of waveguide (4280). Narrowed section (4267) is configured to allow flexible portion (4266) of waveguide (4280) to flex without significantly affecting the ability of flexible portion (4266) of waveguide (4280) to transmit ultrasonic vibrations. By way of example only, narrowed section (4267) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (4280) may be configured to amplify mechanical vibrations transmitted through waveguide (4280). Furthermore, waveguide (4280) may include features operable to control the gain of the longitudinal vibrations along waveguide (4280) and/or features to tune waveguide (4280) to the resonant frequency of the system. Various suitable ways in which waveguide (4280) may be mechanically and acoustically coupled with transducer assembly (12) will be apparent to those of ordinary skill in the art in view of the teachings herein.

In the present example, the distal end of blade (4260) is located at a position corresponding to an anti-node associated with resonant ultrasonic vibrations communicated through flexible portion (4266) of waveguide (4280), in order to tune the acoustic assembly to a preferred resonant frequency $f_o$ when the acoustic assembly is not loaded by tissue. When transducer assembly (12) is energized, the distal end of blade (4260) is configured to move longitudinally in the range of, for example, approximately 10 to 500 microns peak-to-peak, and in some instances in the range of about 20 to about 200 microns at a predetermined vibratory frequency f$_o$ of, for example, 55.5 kHz. When transducer assembly (12) of the present example is activated, these mechanical oscillations are transmitted through waveguide (4280) to reach blade (4260), thereby providing oscillation of blade (4260) at the resonant ultrasonic frequency. Thus, when tissue is secured between blade (4260) and clamp pad (4346), the ultrasonic oscillation of blade (4260) may simultaneously sever the tissue and denature the proteins in adjacent tissue cells, thereby providing a coagulative effect with relatively little thermal spread. In some versions, an electrical current may also be provided through blade (4260) and clamp arm (4344) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (4340) will be apparent to those of ordinary skill in the art in view of the teachings herein.

B. Exemplary Shaft Assembly and Alternative Articulation Section

When incorporated into instrument (10) described above, shaft assembly (4300) of the present example would extend distally from handle assembly (20). As shown in FIGS. 55A-56, shaft assembly (4300) includes distal outer sheath (4333) and a proximal outer sheath (4332) that encloses clamp arm (4344) drive features and the above-described acoustic transmission features. Shaft assembly (4300) further includes an articulation section (4230), which is located at a distal portion of shaft assembly (4300), with end effector (4340) being located distal to articulation section (4230).

Similar to articulation section (130), articulation section (4230) is operable to selectively position end effector (4340) at various lateral deflection angles relative to a longitudinal axis defined by outer sheath (4332). Articulation section (4230) may take a variety of forms. By way of example only, articulation section (4230) may be configured in accordance with one or more teachings of U.S. Pub. No. 2012/0078247, issued as U.S. Pat. No. 9,402,682 on Aug. 2, 2016. the disclosure of which is incorporated by reference herein. As another merely illustrative example, articulation section (4230) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. Various other suitable forms that articulation section (4230) may take will be apparent to those of ordinary skill in the art in view of the teachings herein.

As illustrated in FIGS. 55A-56, articulation section (4230) of this example comprises a set of three retention collars (4500), a distal mating feature (4332A) of proximal outer sheath (4332), a proximal mating feature (4333A) of distal outer sheath (4333), a set of body portions (4700, 4800, 4900), a flexible locking feature (4600), and a pair of articulation bands (4440, 4442) extending along channels (4235A-C) defined by translation members (4261, 4262), proximal body portion (4900) and distal body portion (4800). Distal mating feature (4332A) and proximal mating feature (4333A) both comprise insert holes (4334).

Figure 57:
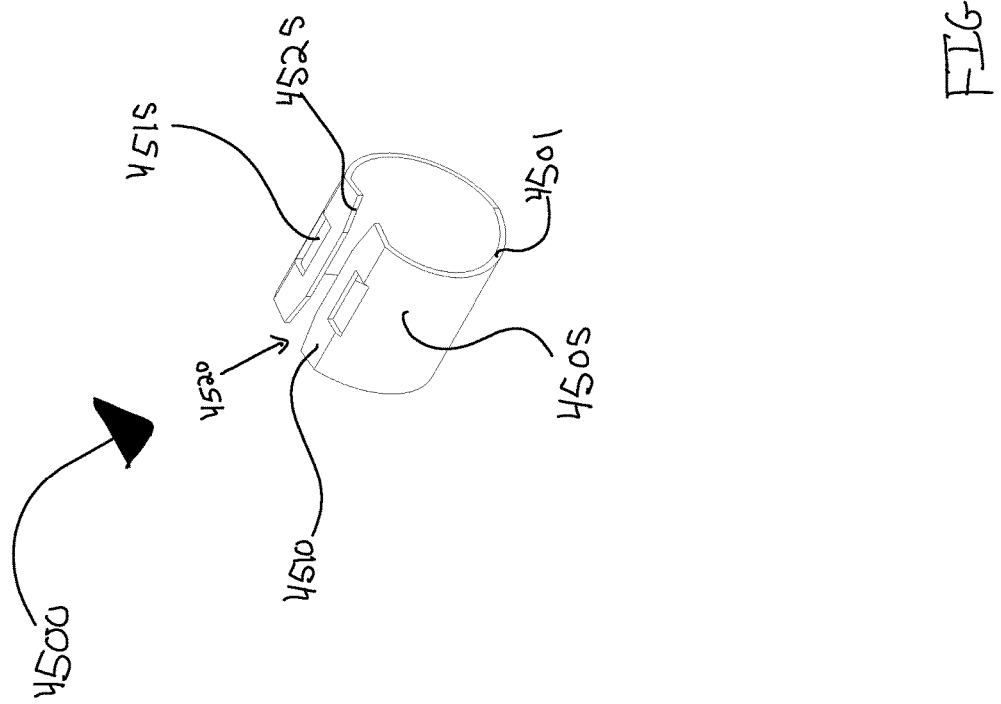
FIG. 57 depicts a perspective view of a retention collar of the articulation section of FIG. 55A.
Figure 58:
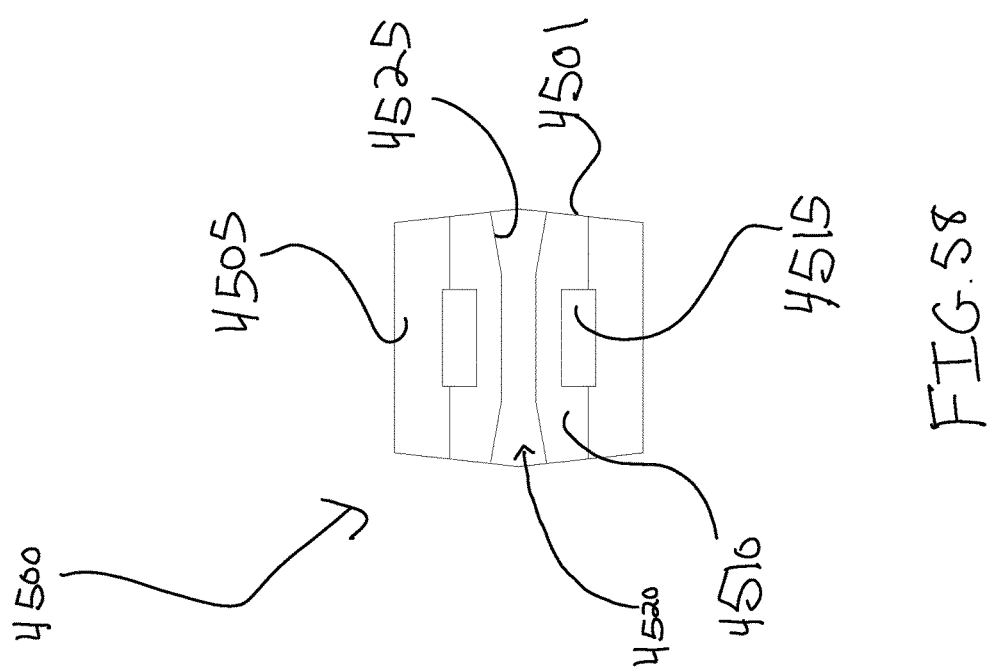
FIG. 58 depicts a top elevational view of the retention collar of FIG. 55A.
Figure 68:
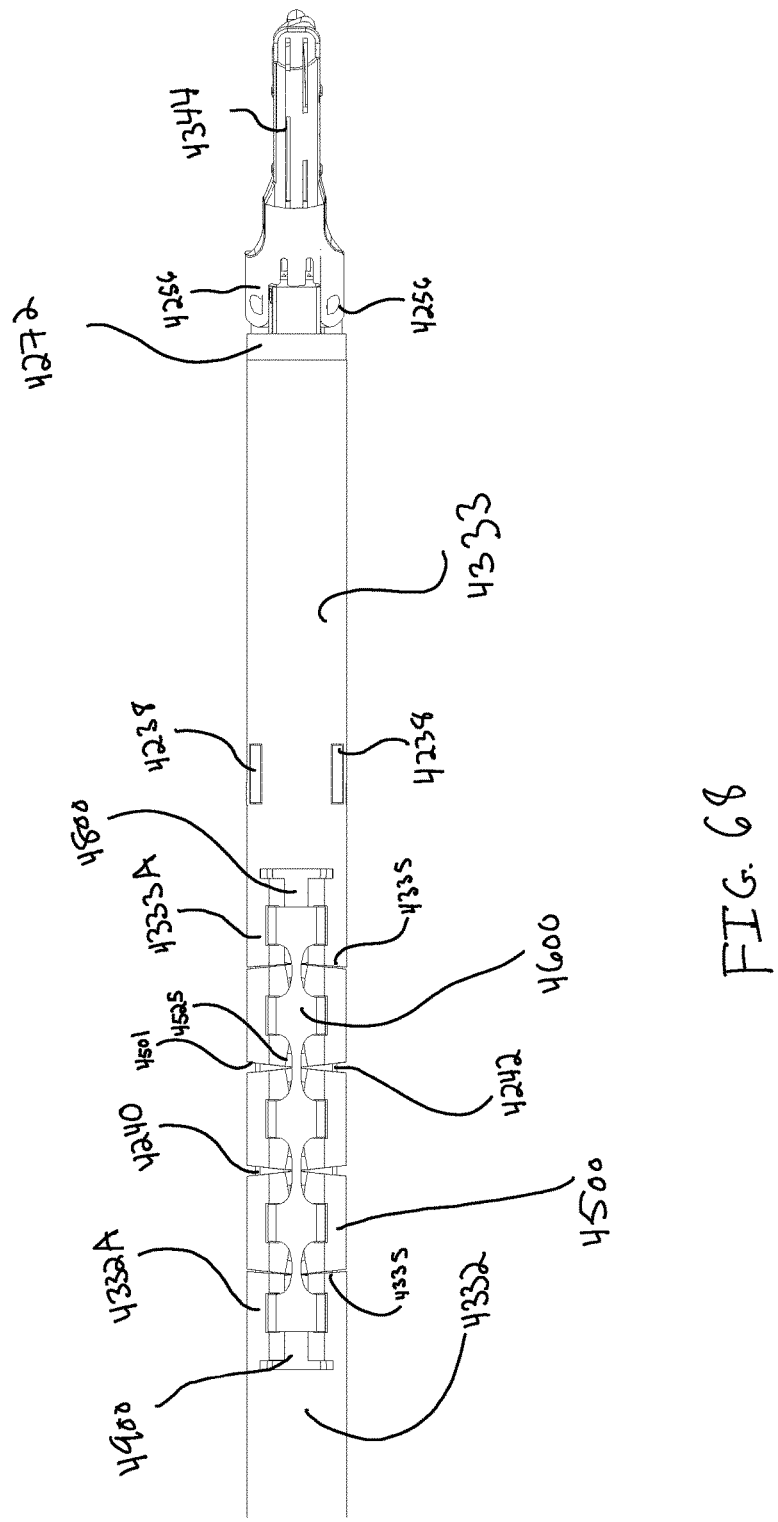
FIG. 68 depicts a top elevational view of the articulation section of the shaft assembly and the end effector of the surgical instrument of FIG. 55A.

As illustrated in FIGS. 57-58, each retention collar (4500) comprises a first angled contact surface (4501), a second angled contact surface (4525), a circular segment surface (4505), and a pair of flattened surfaces (4510) extending inwardly from circular segment surface (4505). Flattened surfaces (4510) define a pathway (4520) and a pair of insert holes (4515). First angled contact surface (4501) is configured to contact a complementary first angled contact surface (4501) of another retention collar (4500). Distal mating feature (4332A) of proximal outer sheath (4332) and proximal mating feature (4333A) of distal outer sheath (4333) are substantially similar to retention collar (4500), but without first angled contact surface (4501) and second angled contact surface (4525). As best seen in FIG. 68, distal mating feature (4332A) and proximal mating feature (4333A) each have a first angled contact surface (4335) that complements first angled contact surfaces (4501) of retention collars (4501).

Figure 60:
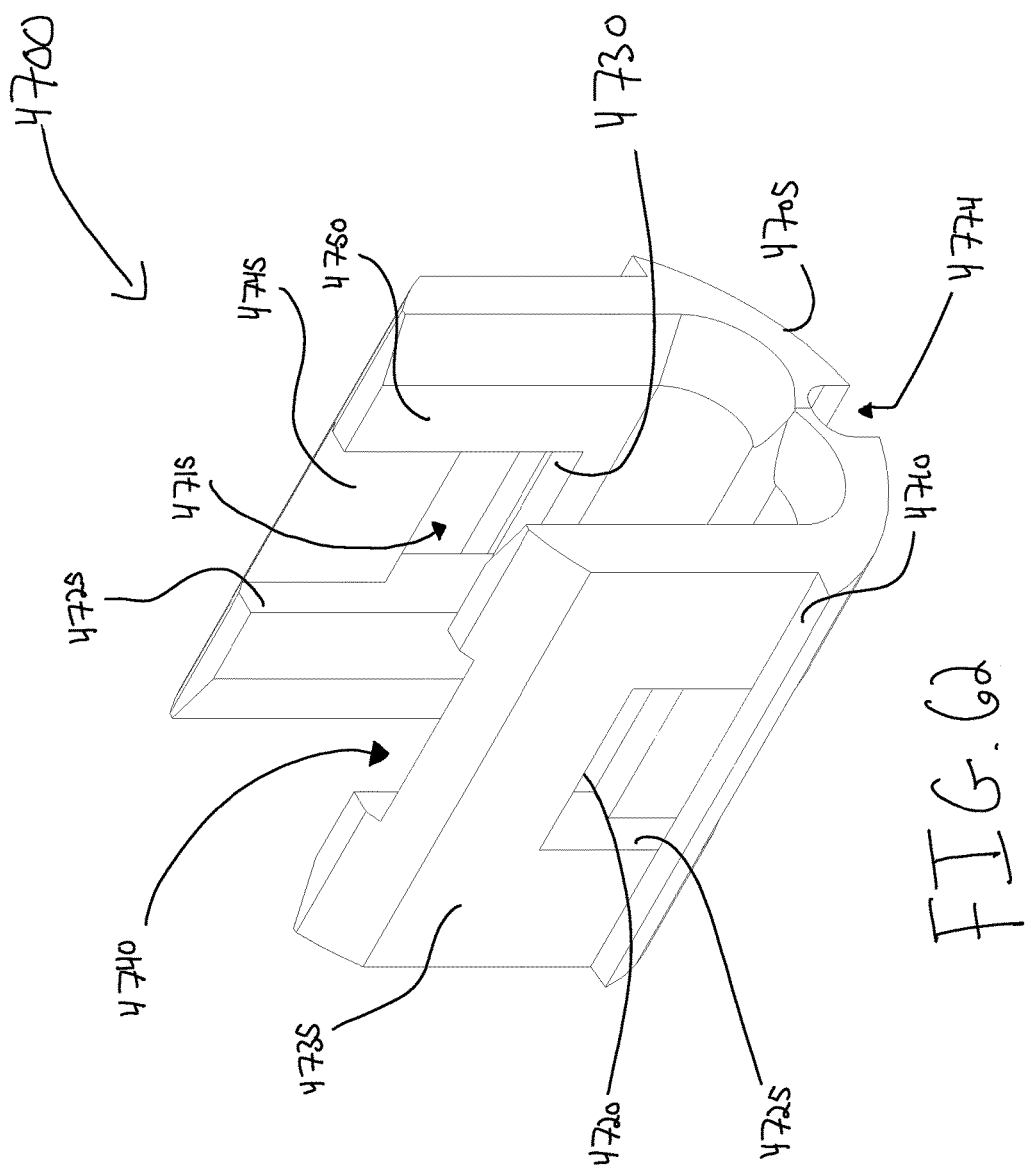
FIG. 60 depicts a front elevational view of the flexible locking feature of FIG. 55A.

As illustrated in FIGS. 59-60, flexible locking feature (4600) comprises a connecting spine (4630), pairs of resilient legs (4625) extending from connecting spine (4630), tabs (4620) located at the termination of each resilient leg (4625), and a rib (4605) running longitudinally along connecting spine (4630) and in between each pair of resilient legs (4625). Each tab (4625) further comprises an angled surface (4610) and a transverse surface (4615).

As illustrated in FIGS. 62-63, each intermediate body portion (4700) comprises an arched base (4705), an articulation band ledge (4710), a tab window (4715), an exterior surface (4735), an interior surface (4750), a leg channel (4740), and a cable channel (4774). Tab window (4715) is defined by transverse walls (4725), tab floor (4730), and tab ceiling (4720). Leg channel (4740) is defined by interior tab contact surface (4745) and transverse walls (4725). Articulation band ledge (4710) extends transversely from exterior surface and terminates at arched base (4705). Each articulation band ledge (4710) is configured to at least partially support or otherwise accommodate a corresponding articulation band (4440, 4442) between second channel for articulation band (4235B) and third channel for articulation band (4235C). Leg channel (4740) is configured and dimensioned to act as a guide for insertion of resilient legs (4625) of flexible locking feature (4600). Cable channel (4774) provides a linear path for a drive feature (e.g., cable (174) as described above) to communicate with trigger (28) in order to move clamp arm (4344).

Figure 64:
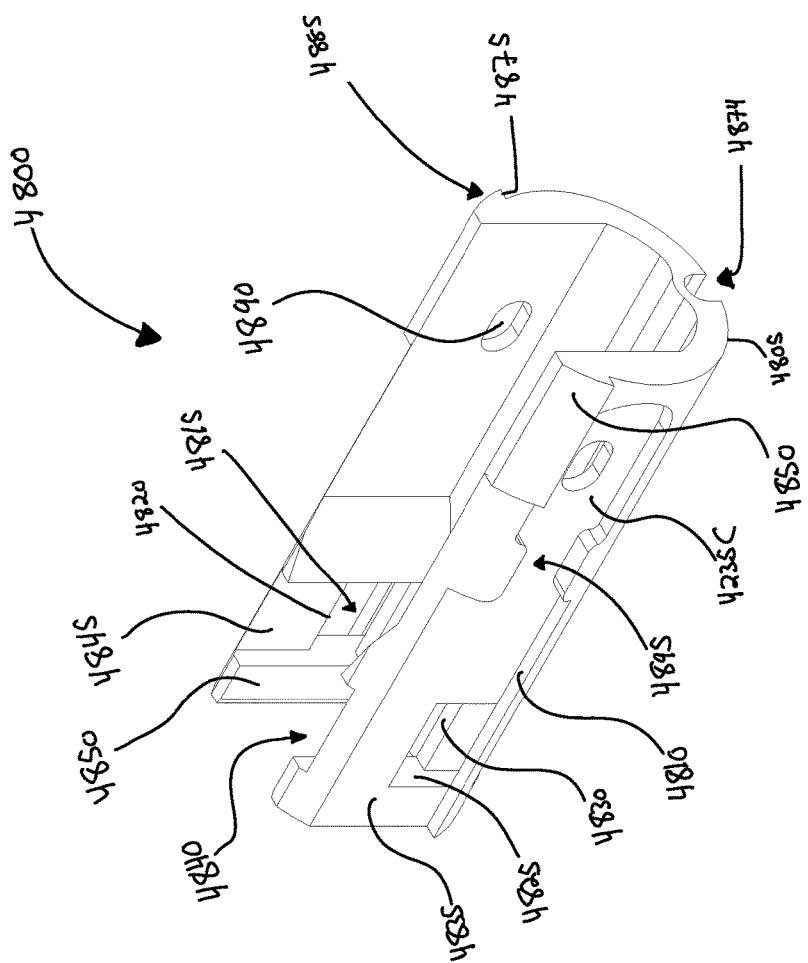
FIG. 64 depicts a perspective view of the distal body portion of FIG. 55A.
Figure 65:
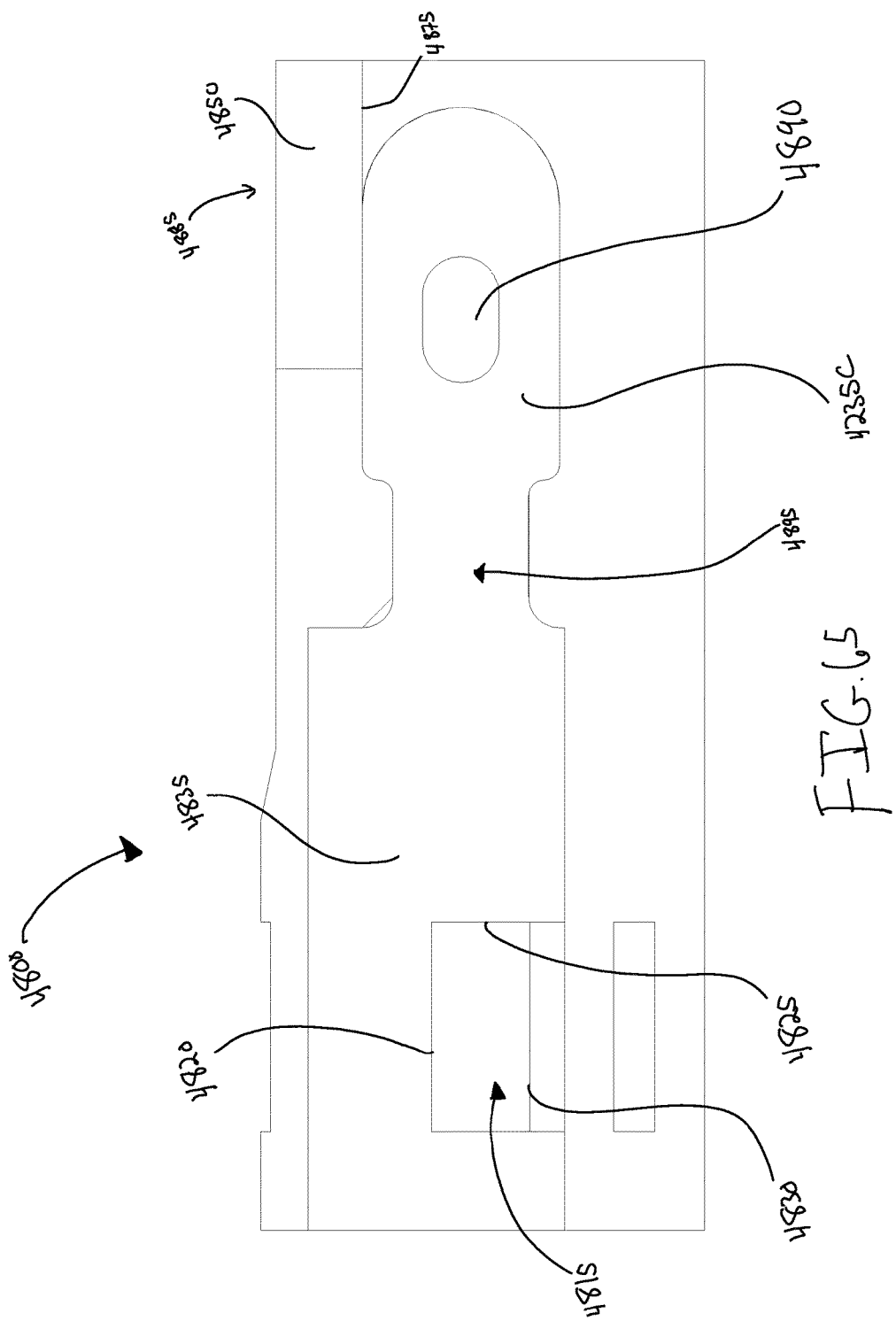
FIG. 65 depicts a side elevational view of the distal body portion of FIG. 55A.

FIGS. 64-65 illustrate distal body portion (8400). Similarly to intermediate body portion (4700), distal body portion (4800) comprises an arched base (4805), an articulation band ledge (4810), a tab window (4815), an exterior surface (4835), an interior surface (4850), a leg channel (4840), and a cable channel (4874). Tab window (4815) is defined by transverse walls (4825), tab floor (4830), and tab ceiling (4820). Leg channel (4840) is defined by interior tab contact surface (4845) and transverse walls (4825).

All of the features mentioned above for the distal body portion (4800) are substantially the same as their counterparts of intermediate body portion (4700). However, distal body portion (4800) additionally comprises a resilient tab (4885), a mating feature for articulation band (4890), a narrowed pathway (4895), and third channel for articulation band (4235C). Resilient tab (4885) further comprises a transverse surface (4875) and an extending surface (4850). Articulation band ledge (4810) extends transversely from exterior surface and terminates at arched base (4805). Each articulation band ledge (4810) is configured to at least partially support or otherwise accommodate a corresponding articulation band (4440, 4442) between second channel for articulation band (4235B) and third channel for articulation band (4235C). Leg channel (4840) is configured and dimensioned to act as a guide for insertion of resilient legs (4625) of flexible locking feature (4600). Cable channel (4874)

provides a linear path for a drive feature (e.g., cable (174) as described above) to communicate with trigger (28) in order to move clamp arm (4344).

Figure 66:
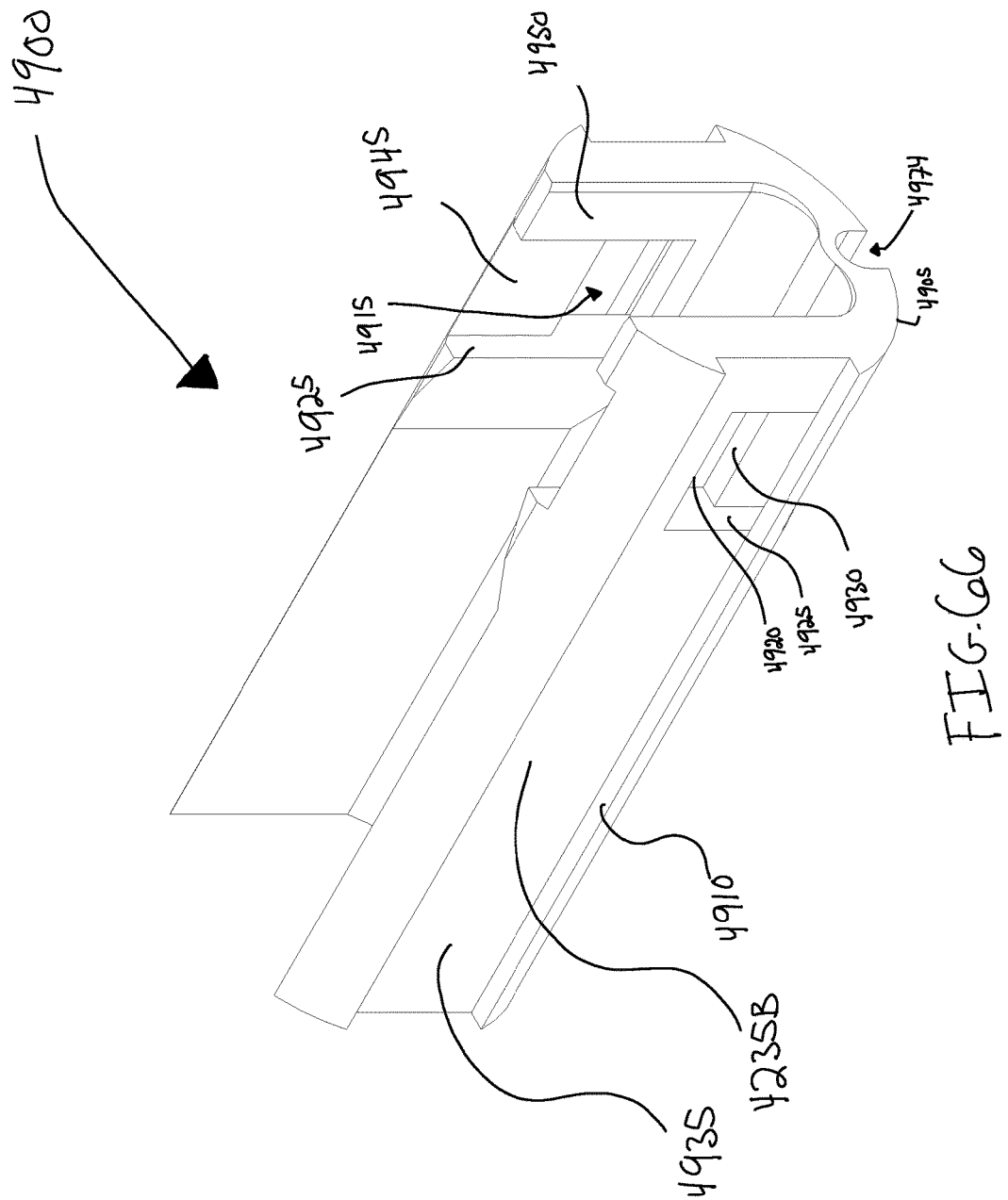
FIG. 66 depicts a perspective view of the proximal body portion of FIG. 55A.

FIG. 66 illustrates proximal body portion (4900). Similarly to intermediate body portion (4700), proximal body portion (4900) comprises an arched base (4905), an articulation band ledge (4910), a tab window (4915), an exterior surface (4935), an interior surface (4950), a leg channel (4940), and a cable channel (4974). Tab window (4915) is defined by transverse walls (4925), tab floor (4930), and tab ceiling (4920). Leg channel (4940) is defined by interior tab contact surface (4945) and transverse walls (4925).

All of the features mentioned above for the proximal body portion (4900) are substantially the same as their counterparts for both intermediate body portions (4700) and distal body portion (4900). However, proximal body portion (4900) additionally comprises second channel (4235B) for articulation band (4440, 4442). Articulation band ledge (4910) extends transversely from exterior surface and terminates at arched base (4905). Each articulation band ledge (4910) is configured to at least partially support or otherwise accommodate a corresponding articulation band (4440, 4442) as articulation band ledge (4910) helps partially define second channel (4235B) for articulation band (4440, 4442). Leg channel (4940) is configured and dimensioned to act as a guide for insertion of resilient legs (4625) of flexible locking feature (4600). Cable channel (4974) provides a linear path for a drive feature (e.g., cable (174) as described above) to communicate with trigger (28) in order to move clamp arm (4344).

Figure 55B:
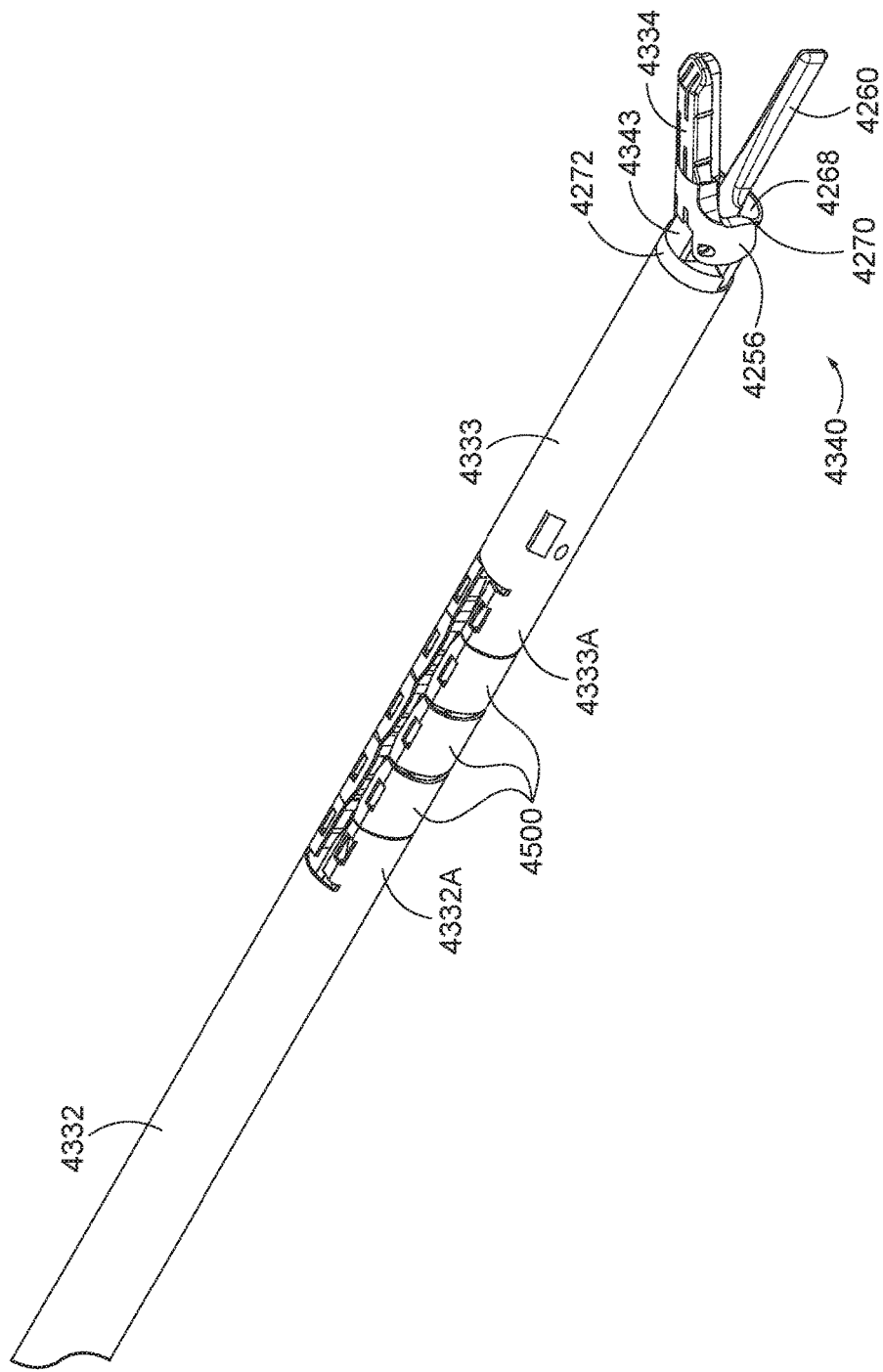
FIG. 55B depicts a perspective view of the articulation section of the shaft assembly and the end effector of FIG. 55A with certain elements omitted to show greater detail.
Figure 55D:
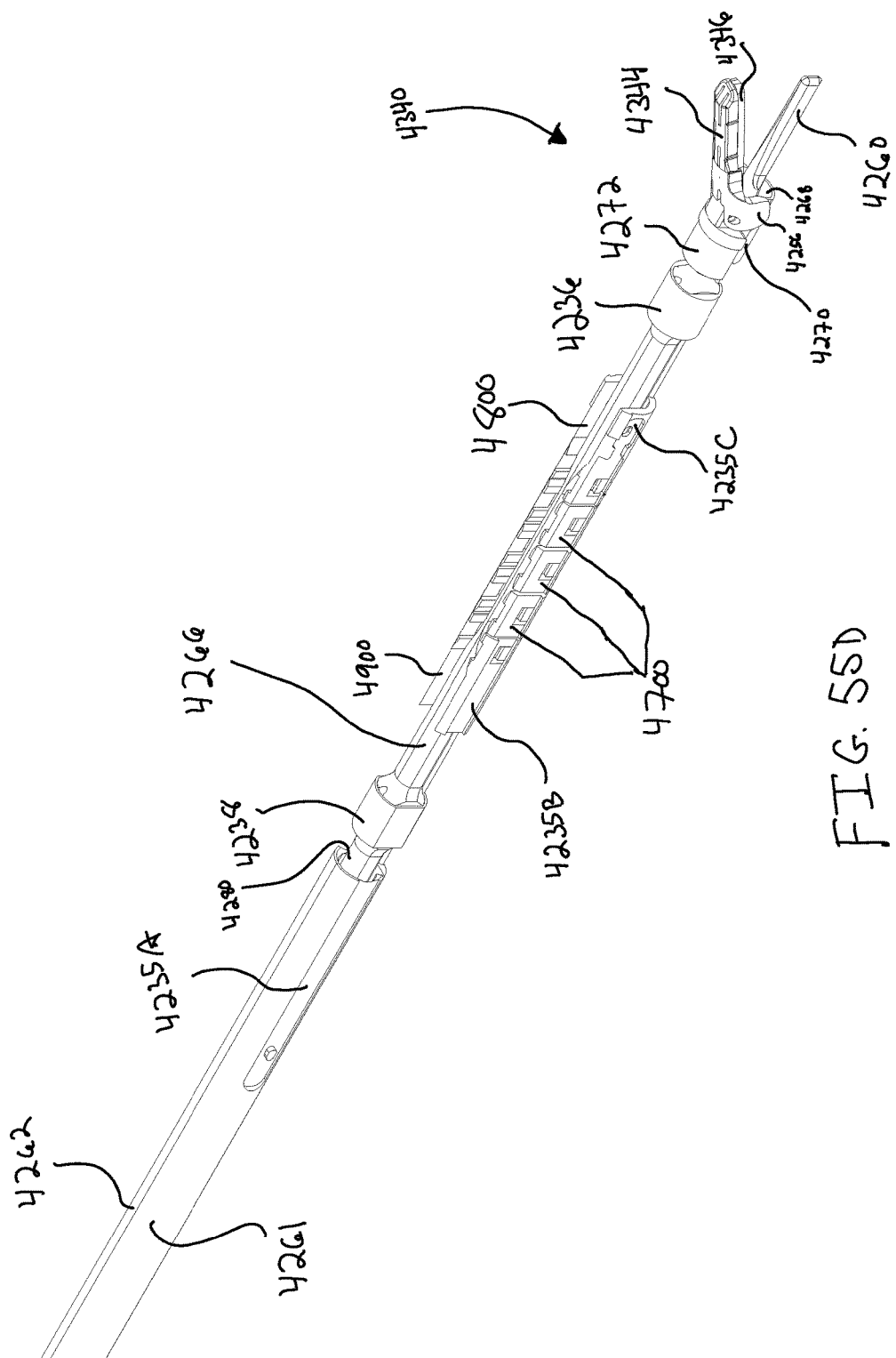
FIG. 55D depicts a perspective view of the articulation section of the shaft assembly and the end effector of FIG. 55A with certain elements omitted to show greater detail.

FIGS. 55A-56 illustrate the assembly of articulation section (4230). As illustrated in FIGS. 55D, 56, and 61, body portions (4700, 4800, 4900) are longitudinally aligned with one another between flanges (4236, 4238). In the present example, body portions (4700, 4800, 4900) are formed as discrete pieces positioned adjacent to each other, thereby promoting lateral flexing of articulation section (4230). Alternatively, body portions (4700, 4800, 4900) may be joined together by living hinges or any other structures that provide lateral flexing of articulation section (4230) as will be apparent to those of ordinary skill in the art in view of the teachings herein. In the current example, there is one proximal body portion (4900), three intermediate body portions (4700), and one distal body portion (4800). Of course, any suitable number of intermediate body portions (4700) may be provided.

As illustrated in FIGS. 55C and 56, body portions (4700, 4800, 4900) also partially define a channel (4235B, 4235C) that is configured to receive articulation band (4440) while allowing articulation band (4440) to slide relative to proximal body portion (4900) and intermediate body portions (4700). Unlike the previously mentioned articulation section (130), articulation bands (4440, 4442) are fixed to distal body portion (4800) rather than distal flange (4236). Because of this, distal flange (4236) does not require features, such as flats (192) to accommodate articulation bands (4440, 4442). Additionally, the shortened distance of articulation bands (4440, 4442) provides a user with greater control of articulation. During longitudinal deflection, more force is required from the shortened length of articulation bands (4440, 4442) to provide an equivalent moment as provided by longer articulation bands (140, 142). Therefore, a user has more tolerance control of the articulation angle due to the greater force required with shorter articulation bands (4440, 4442) than longer articulation bands (140, 142).

As illustrated in FIG. 55B, Proximal body portion (4900) is located within distal mating feature (4332A) of proximal outer sheath (4332) while distal body portion (4800) is located within proximal mating feature (4333A) of distal outer sheath (4333). Intermediate body portions (4700) are located in between proximal outer sheath (4332) and distal outer sheath (4333). More specifically, insert holes (4515) are located directly above leg channels (4740, 4840, 4940) of body portions (4700, 4800, 4900) in order to provide an insertion pathway for resilient legs (4625) of flexible locking feature (4600). In other words, retention collars (4500) are located at longitudinal positions corresponding to intermediate body portions (4700) while proximal mating feature (4333A) and distal mating feature (4332A) are located at longitudinal positions corresponding to distal body portion (4800) and proximal body portion (4900) respectively. Additionally, resilient tab (4885) of distal body portion (4800) is sized to fit within coupling features (4338) of distal outer sheath (4333), thereby ensuring distal body portion (4800) is fixed relative to distal outer sheath (4333). Of course, a similar feature can be added to proximal body portion (4900) to ensure sufficient attachment to proximal outer sheath (4332).

Figure 67:
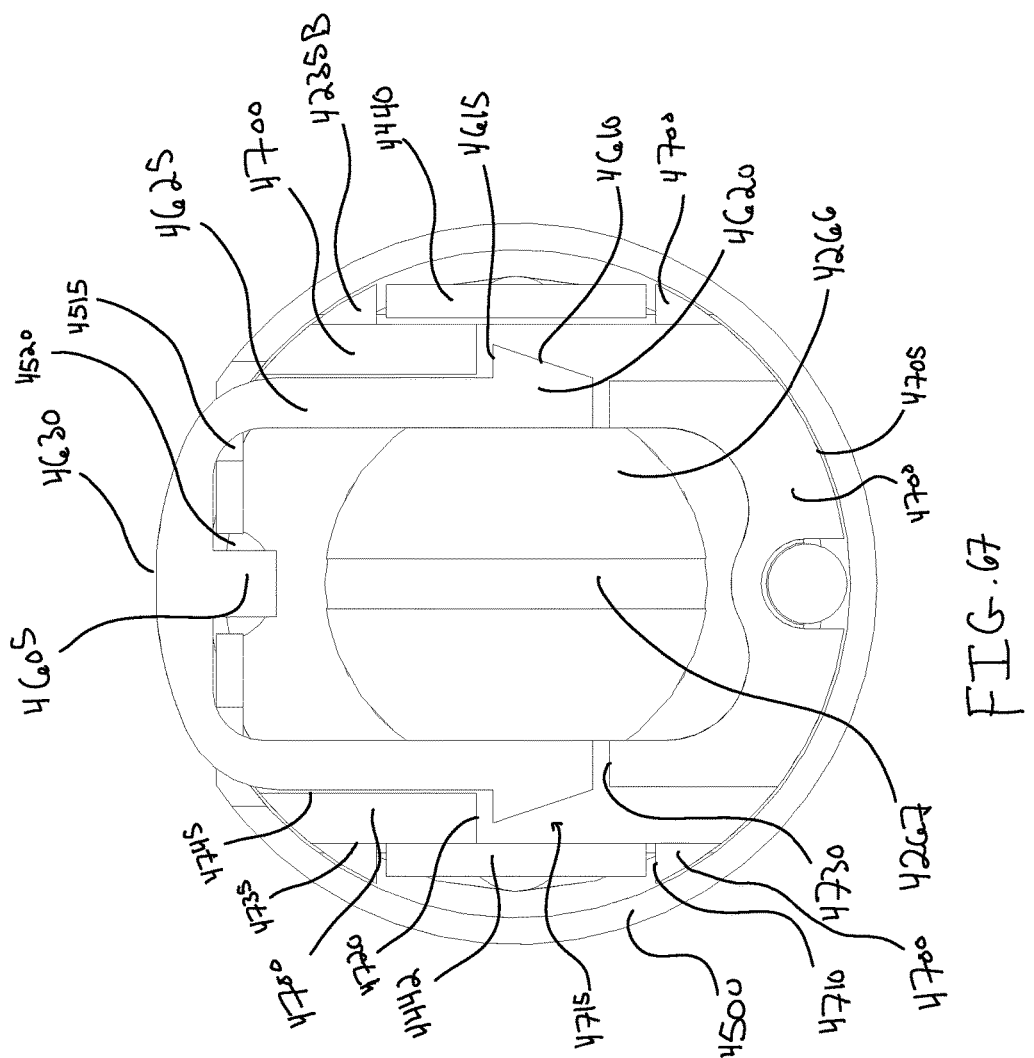
FIG. 67 depicts a cross sectional view of the articulation section of FIG. 55A across the intermediate body portion.

As illustrated in FIGS. 55A and 67-68, flexible locking feature (4600) is inserted into distal mating feature (4332A), retention collars (4500), proximal mating feature (4333A), proximal body portion (4900), intermediate body portions (4700), and distal body portion (4800). Flexible locking feature (4600) unitarily couples distal mating feature (4332A), retention rings (4500), and proximal mating feature (4333A) with proximal body portion (4900), intermediate body portions (4700), and distal body portion (4800) respectively. This coupling can be seen in greater detail in FIG. 67. When tabs (4620) of resilient legs (4625) are first inserted into insert holes (4515), resilient legs (4625) must be compressed inwardly to accommodate transverse surface (4615). Contact between interior tab contact surface (4745) and tab (4620) keeps resilient legs (4625) in a compressed position. Once transverse surface (4615) passes interior tab contact surface (4745) to tab window (4715), resilient legs (4625) transition from a compressed state to an original state substantially parallel with each other. Tab (4620) then enters through tab window (4715). At this point, flexible locking member (4600) is locked in place through a snap fit due to overlapping dimensions of tab ceiling (4720) and transverse surface (4615). Rib (4605) is now located within pathway (4520) of retention collar (4500). No object is in contact with the narrow section of waveguide (4267).

Due to the insertion of resilient legs (4625) into insert holes (4515) and leg channel (4740), retention collar (4500) is fixed along the longitudinal axis relative to intermediate body portions (4700). Similarly, due to the insertion of resilient legs (4625) into insert holes (4334) and leg channel (4840, 4940), proximal body portion (4900) and distal body portion (4800) are fixed along the longitudinal axis relative to distal mating feature (4332A) and proximal mating feature (4333A).

As mentioned before, the distal ends of articulation bands (4440, 4442) are unitarily secured to distal body portion (4800) via mating feature for articulation band (4890). When articulation bands (4440, 4442) translate longitudinally in an opposing fashion (e.g., one articulation band (4440) translating distally while the other articulation band (4442) simultaneously translates proximally), this will cause articulation section (4330) to bend due to creation of a moment applied to a distal end of distal outer sheath (4333) via upper distal shaft element (4272). The force provided by translation of articulation bands (4440, 4442) is communicated to distal body portion (4800) via a mating feature for articulation band (4890), which in turn is communicated to distal outer sheath (4333) via the connection of resilient tab (4885) of distal body portion (4800) and coupling feature (4338) of distal outer sheath (4333).

Figure 69B:
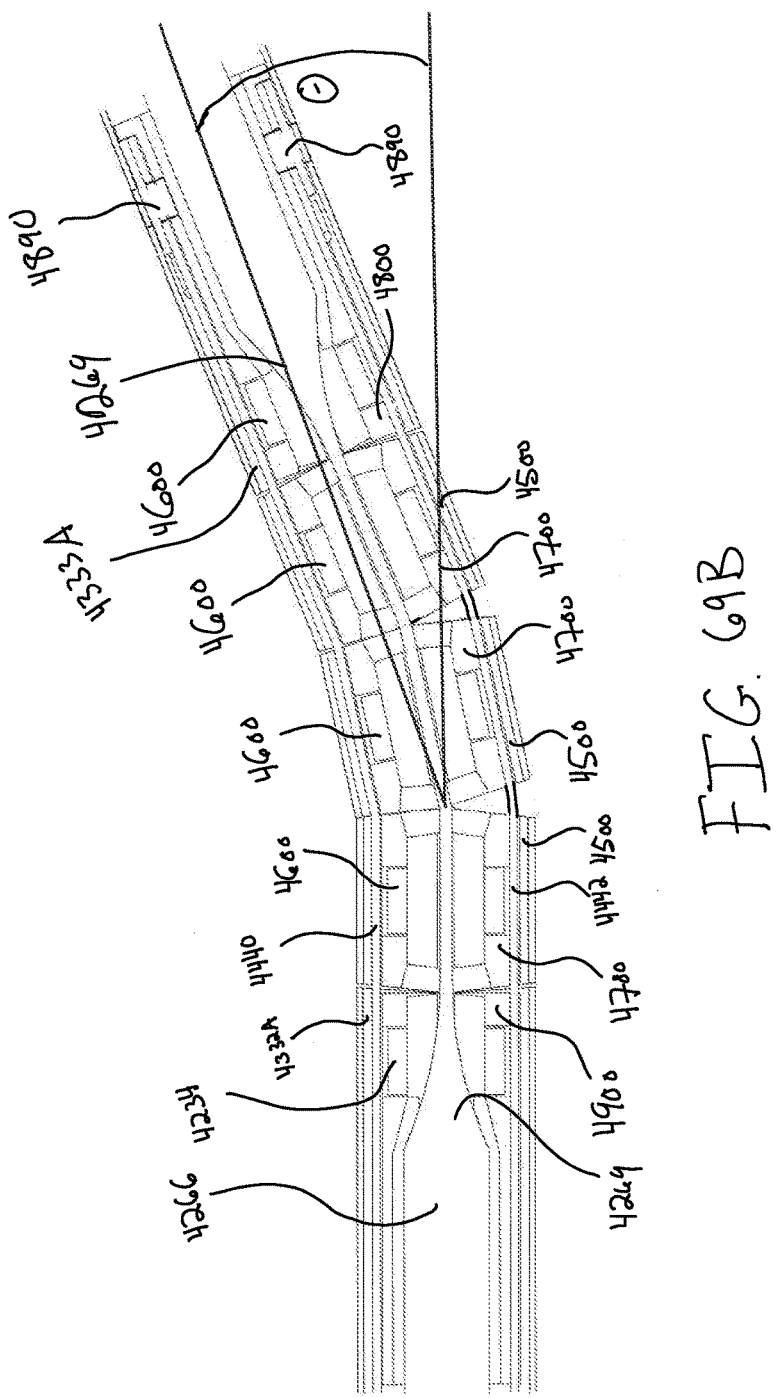
FIG. 69B depicts a cross sectional top view of the articulation section of the shaft assembly of the surgical instrument of FIG. 55A, with the articulation section in an articulated state.

Distal outer sheath (4333) is secured to waveguide (4280) at distal flange (4236), which is located at a position corresponding a node associated with resonant ultrasonic vibrations communicated through waveguide (4280). Therefore, the force required to bend waveguide (4280) for articulation is still communicated to waveguide (4280) at the nodal position of distal flange (4236), similar to waveguide (180). The bend thereby laterally deflects end effector (4340) away from the longitudinal axis of shaft assembly (4300) from a straight configuration as shown in FIGS. 68-69A to an articulated configuration as shown in FIG. 69B. In particular, end effector (4340) will be articulated toward the articulation band (4440, 4442) that is being pulled proximally. During such articulation, the other articulation band (4440, 4442) may be pulled distally by upper distal shaft element (4272). Alternatively, the other articulation band (4440, 4442) may be driven distally by an articulation control.

Flexible locking feature (4600) and narrowed section (4267) are sufficiently flexible to accommodate the above-described articulation of end effector (4340). Intermediate body portions (4700) and retention collars (4500) are able to articulate by moving relative to each other due to force provided by flexible locking feature (4600). Furthermore, flexible acoustic waveguide (4266) is configured to effectively communicate ultrasonic vibrations from waveguide (4280) to blade (4260) even when articulation section (4230) is in an articulated state as shown in FIG. 69B.

However, the flexible locking feature (4600) and the narrowed section (4267) are limited in articulation due to the geometry of retention collars (4500) and flexible locking element (4600). As best illustrated in FIG. 68, second angled contact surface (4525) of retention collar (4500) is dimensioned to allow a certain amount of clearance between articulation between rib (4605) of flexible locking member (4600) and retention collar (4500), thereby permitting articulation.

As best shown in FIG. 69A-B, first angled contact surface (4501) of one retention collar (4500) is dimensioned to abut against first angled contact surface (4501) of a second retention collar (4500), thereby providing a stop to limit articulation at a predetermined angle. As seen in FIG. 69A, angles X and Z are formed between first angled contact surfaces (4501) in an unarticulated position. While in this example, the angles X and Z are substantially similar, there is no requirement that the angles formed by first angled contact surfaces (4501) be identical. Alternatively, X could be twice the amount as Z, or X could be 0 degrees and Z could determine the entire articulation range. FIG. 69B shows articulation section (4230) in a maximum articulated state. First angled contact surfaces (4501) on one side of retention collars (4500) lock each other while the opposite side of first angled contact surfaces (4501) are further apart. Accordingly, the maximum articulation is limited to theta. In the present example, the maximum articulation angle is 30°.

Similar to articulation feature (130), articulation bands (4440, 4442) are laterally interposed within channels (4235B, 4235C) between retention collars (4500) and intermediate body portions (4700). Retention collars (4500) are configured to keep articulation bands (4440, 4442) in a parallel relationship with each other, particularly when articulation section (4330) is in a bent configuration (e.g., similar to the configuration shown in FIG. 69B). In other words, when articulation band (4440) is on the inner diameter of a curved configuration presented by a bent articulation section (4330), retention collars (4500) may retain articulation band (4440) such that articulation band (4440) follows a curved path that complements the curved path followed by articulation band (4442). It should be understood that channels (4235B, 4235C) are sized to accommodate respective articulation bands (4440, 4442) in such a way that articulation bands (4440, 4442) may still freely slide through articulation section (4330), even with retention collars (4500) being secured to intermediate body portions (4700). It should also be understood that retention collars (4500) may be secured to body portions (4700, 4800, 4900) in various ways, including but not limited to interference fitting, adhesives, welding, etc.

VIII. EXEMPLARY DISTAL FLANGE WITH CRUSH RIBS

Figure 71:
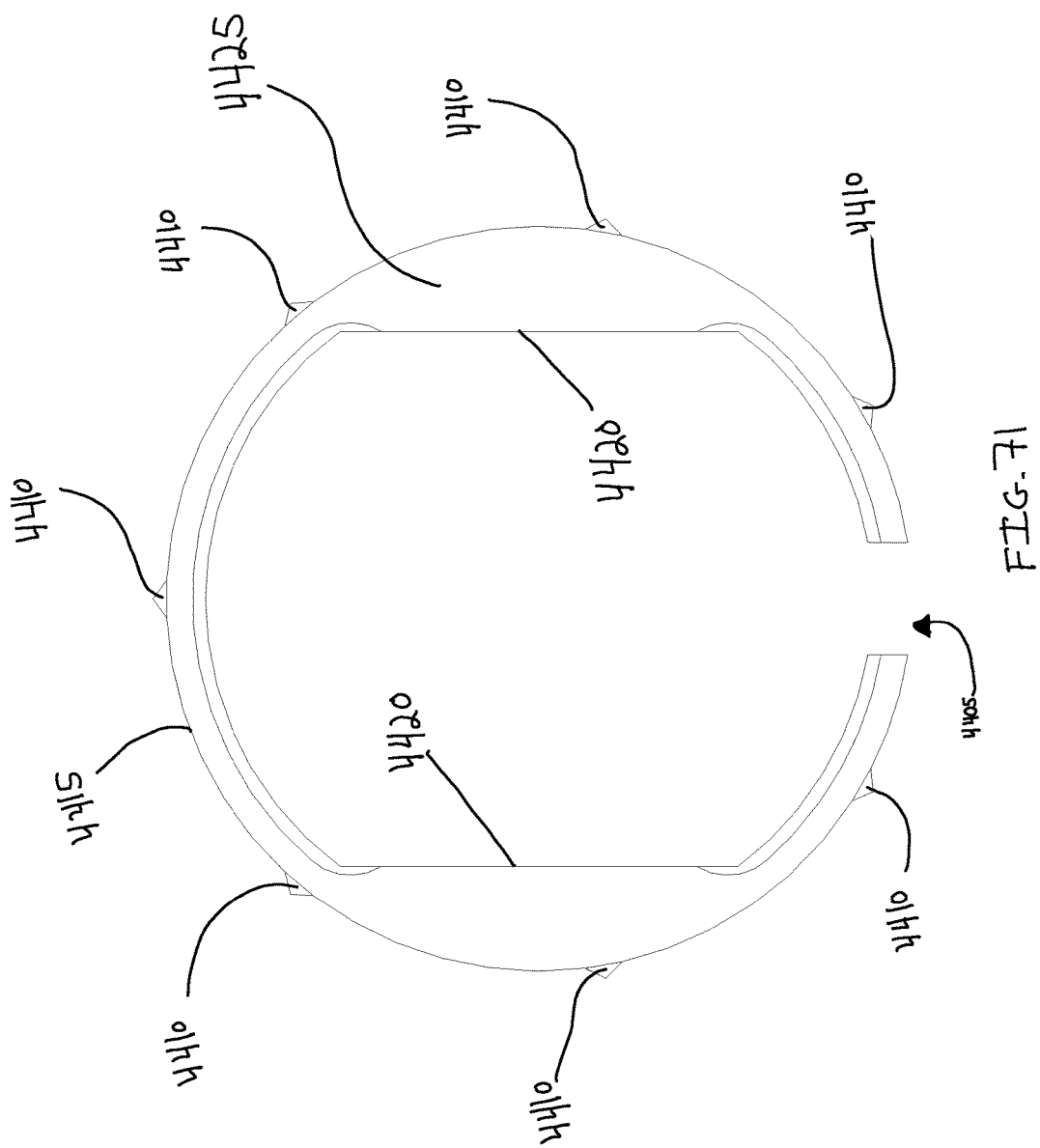
FIG. 71 depicts a front elevational view of the distal node bumper of FIG. 70.

In some instances it may be desirable for distal outer sheath (33, 4333) to be secured against distal flange (136, 4236) while maintaining minimal contact with distal flange (136, 4236). Minimal contact between distal outer sheath (33, 4333) and distal flange (136, 4236) may be desirable in order to limit the amount energy absorbed by outer sheath (33, 4333) in order to maintain a structurally secured connection between distal outer sheath (33, 4333) and distal flange (136, 4236). To that end, FIGS. 70-71 show an exemplary distal node bumper (4400) that may be used to secure distal outer sheath (33, 4333) to distal flange (136, 4236).

Distal node bumper (4400) of the present example is formed of an elastomeric material (e.g., silicone, etc.) and comprises a pair of flats (4420), a slot (4405), an outer surface (4415), crush ribs (4410) longitudinally disposed on surface (4415), and a face (4425). Flats (4420) complement flats of distal flange (136), thereby ensuring a secure connection between distal node (136) and distal node bumper (4400). Slot (4405) allows space for cable (174) to pass through distal node bumper (4400). Crush ribs (4410) are resilient, but compress within distal outer sheath (33) in order to provide a secure connection between distal flange (136) and distal outer sheath (33). Crush ribs (4410) also provide limited contact between distal flange (136) and distal outer sheath (33), thereby transferring minimal ultrasonic vibration energy to distal outer sheath (33), helping maintain a structurally secured connection between distal outer sheath (33) and distal flange (136).

IX. WAVEGUIDE WITH KEYHOLE CROSS SECTIONAL PROFILE

In some instances, articulation of waveguide (180, 4280) might lead to varied location of interaction between clamp pad (46, 4346) and blade (60, 4260) about the longitudinal axis when clamp pad (46, 4346) is in a closed position. For instance, when the articulation section (130, 4230) is in a non-articulated state, and clamp pad (46, 4346) is pivoted toward and away from blade (60, 4260), clamp pad (46, 4346) may traverse a vertically oriented path that is on-plane with a vertical plane that laterally bisects blade (60, 4260).

In some instances when the articulation section (130, 4320) is in an articulated state, and clamp pad (46, 4346) is pivoted toward and away from blade (60, 4260), clamp pad (46, 4346) may traverse an obliquely oriented path that is off-plane with a vertical plane that laterally bisects blade (60, 4260). In other words, the path that is traversed by clamp pad (46, 4346) may be obliquely oriented relative to a vertical plane that laterally bisects blade (60, 4260). This may be caused by a tolerance stack in the shaft assembly (30, 4300) and/or due to other factors. If this occurs to a blade that has a radius that varies along the surface range at which clamp pad (46, 4346) may compress tissue, such off-plane closure of clamp pad (34, 4346) may result in a compression force profile on the tissue that differs from the compression force profile that would be encountered by the tissue when clamp pad (46, 4346) is closed on-plane with articulation section (130, 4230) in a non-articulated state. In other words, the compression force profile on the tissue may vary based on whether articulation section (130, 4230) in an articulated state or a non-articulated state. For instance, such variation may lead to different times required to cut and/or seal tissue (e.g., by denaturing proteins in tissue cells). This inconsistency may cause an operator to expose blade (60, 4260) to direct contact with clamp pad (46, 4346) for a longer amount of time than desired. Direct contact between blade (60, 4260) and clamp pad (46, 4346) could lead to higher operating temperatures, possibly leading to deformation of blade (60, 4260) and/or clamp pad (46, 4346). It may therefore be desirable to prevent such variance in the compression force profile, thereby providing an end effector that provides a more consistent and predictable performance.

One method of providing uniform times for cutting and/or sealing is to use a blade (5000) with a keyhole cross sectional area, as shown in FIGS. 72-74. Blade (1000) of this example comprises a clamping surface (5003), an elongated surface (5002), and a back-cutting surface (5001). Clamping surface is substantially circular in shape, with a constant radius of curvature, and with a circumference large enough to prevent clamp pad (46) from clamping tissue on any other surface of blade (5000). By way of example only, the constant radius of curvature may extend for at least 180° of the cross-sectional area of blade (5000), or more particularly for at least 270° of the cross-sectional area of blade (5000), or more particularly for at least 320° of the cross-sectional area of blade (5000). Since clamping surface is substantially circular in shape, the tissue (6000) surface area exposed to blade (5000) is uniform regardless of articulation location, and regardless of whether clamp pad (46) is on-plane or off-plane with blade (5000) during closure. Elongated surface (5002) is relatively thin compared to clamping surface (5003). Elongated surface (5002) also extends from the bottom of clamping surface (5003). The shape and location of elongated surface (5002) ensures elongated surface (5002) will not come into contact with tissue (6000) clamped between clamp pad (46) and blade (5000). Back-cutting surface (5001) is located furthest away from clamp pad (46). Back-cutting surface (5001) is operable to cut and/or seal tissue (e.g., by denaturing proteins in tissue cells) without clamping tissue beforehand. It should also be understood that back-cutting surface (5001) may be used to perform back-cutting on tissue.

X. EXEMPLARY ALTERNATIVE FEATURES FOR SELECTIVELY LOCKING ARTICULATION SECTION

In some versions of instrument (10) it may be desirable to provide features that are configured to selectively lock articulation section (130) at a selected state of articulation. For instance, when articulation section (130) is in a straight configuration, it may be desirable to lock articulation section (130) in the straight configuration in order to prevent inadvertent lateral deflection of end effector (40) at articulation section (130). Similarly, when articulation section (130) is bent to a selected articulation angle, it may be desirable to lock articulation section (130) at that selected articulation angle in order to prevent inadvertent lateral deflection of end effector (40) way from that selected articulation angle at articulation section (130). Various examples of features that are configured to selectively lock articulation section (130) at a selected state of articulation will be described in greater detail below. Other examples will be apparent to those of ordinary skill in the art according to the teachings herein.

Figure 75:
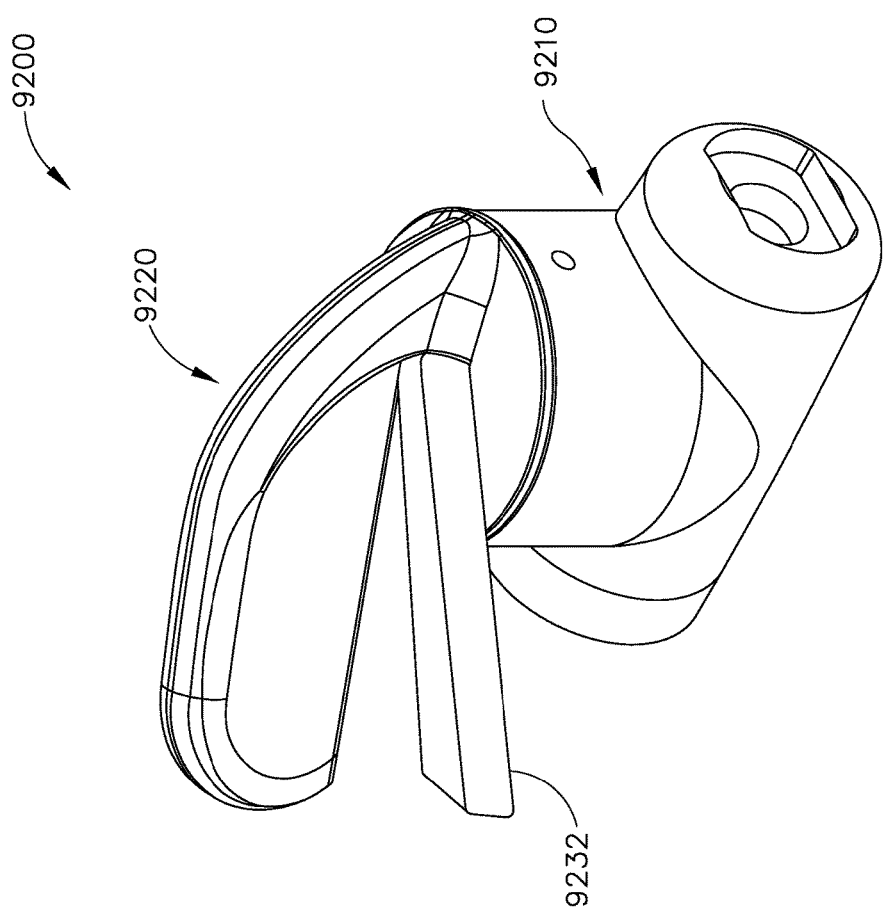
FIG. 75 shows a perspective view of an exemplary alternative articulation control assembly that may be incorporated into the instrument of FIG. 1, with a locking feature in a locked configuration.

A. Articulation Control Assembly with Resiliently Biased Locking Paddle on Knob FIGS. 75-76B show an exemplary articulation control assembly (9200) that may be readily incorporated into instrument (10) in place of articulation control assembly (100). Except as otherwise described below, articulation control assembly (9200) is configured and operable just like articulation control assembly (100) described above. Articulation control assembly (9200) of this example comprises a housing (9210) and a knob (9220). Rotation of rotation knob (9220) relative to housing (9210) causes articulation of an articulation section of a shaft assembly, such as articulation section (130) of shaft assembly (30). Articulation control assembly (9200) of this example further comprises a locking feature (9230) that is configured to selectively prevent the rotation of knob (9220). It should be understood that, by preventing rotation of knob (9220), locking feature (9230) further prevents articulation of the articulation section of the shaft assembly. Locking feature (9230) may be used in lieu of, or in addition to, other features discussed herein that selectively prevent rotation of knob (9220); and that selectively lock articulation section (9130) in a particular deflected position relative to the longitudinal axis defined by outer sheath (32).

Figure 76A:
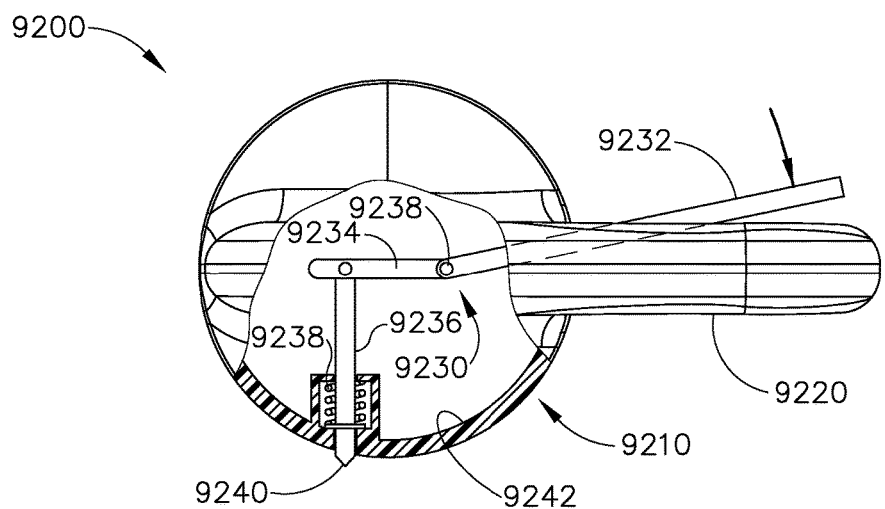
FIG. 76A depicts a top plan view of the articulation control assembly of FIG. 75, with the locking feature in the locked configuration.
Figure 76B:
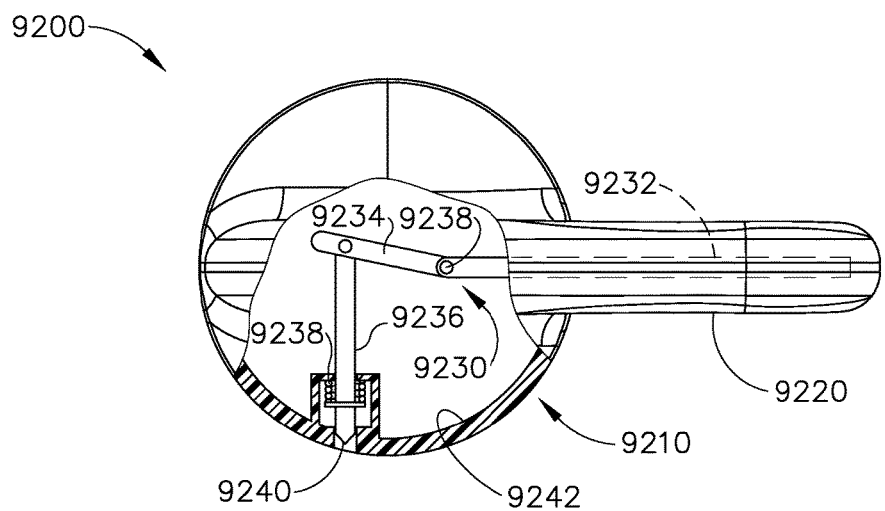
FIG. 76B depicts a top plan view of the articulation control assembly of FIG. 75, with the locking feature in an unlocked configuration.

As shown in FIGS. 75-76B, locking feature (9230) of the present example includes a paddle (9232), a lever member (9234), a lock arm (9236), and a spring (9238). In the present example, paddle (9232) is operably coupled to lever member (9234) at pivot point (9238). Paddle (9232) and lever member (9234) together form an oblique angle at pivot point (9238). Pivot point (9238) provides a pivotal coupling of paddle (9232) and lever member (9234) to the underside of knob (9220). Paddle (9232) and lever member (9234) are rigidly coupled together such that the pivoting of paddle (9232) about pivot point (9238) causes lever member (9234) to rotate or pivot in the same direction about pivot point (9238). In particular, paddle (9232) and lever member (9234) are pivotable between a first position (FIG. 76A) and a second position (FIG. 76B). In the first position, paddle (9232) is oriented obliquely relative to a vertical plane (going into and out of the page in the views shown in FIGS. 76A-76B) that is defined by knob (9220); while lever member (9234) extends along the vertical plane defined by knob (9220). In the second position, paddle (9232) extends along the vertical plane defined by knob (9220); while lever member (9234) is oriented obliquely relative to the vertical plane defined by knob (9220).

Lever member (9234) is pivotably coupled to lock arm (9236). Lock arm (9236) is resiliently biased toward inner wall (9242) housing (9210) by spring (9238). In the locked configuration (FIG. 76A), lock arm (9236) positively engages housing (9210) and thereby prevents rotation of knob (9220) relative to housing (9210). Lock arm (9236) is configured to translate along a path that is transverse to the vertical plane defined by knob (9220). In particular, lock arm (9236) translates along this path in response to pivoting of paddle (9232) and lever member (9234) between the first and second positions as described above. By way of example only, the underside of knob (9220) may include a channel that is sized to receive and guide lock arm (9236) in order to keep lock arm (9236) on this linear path of travel. As another merely illustrative example, one or more guiding features (e.g., rails, etc.), may be configured to receive and guide lock arm (9236) in order to keep lock arm (9236) on this linear path of travel.

In the example shown, lock arm (9236) includes a pointed end (9240) that is configured to frictionally engage an inner wall (9242) of housing (9210). In some examples, inner wall (9242) of housing (9210) includes one or more features to enhance the positive engagement between lock arm (9236) and housing (9210). For example, inner wall (9242) of housing (9210) may include notches, splines, detents, frictional coatings, frictional surface treatments, etc., with which the lock arm (9236) may engage. It should also be understood that pointed end (9240) may include an elastomeric material and/or any other suitable feature(s) to promote a locking relationship between pointed end (9240) and inner wall (9242) of housing (9210).

When articulation control assembly (9200) is in the configuration shown in FIG. 76A, articulation control assembly (9200) is in a locked state due to engagement between pointed end (9240) of lock arm (9242) and inner wall (9242) of housing (9210). This locked state provides locking of the articulation state of the articulation section of the shaft assembly, regardless of whether the articulation section is in a straight configuration or a bent configuration. In order to unlock articulation control assembly (9200) in order to change the articulation state of the articulation section, an operator may drive paddle (9232) from the position shown in FIG. 76A to the position shown in FIG. 76B by pinching paddle (9232) toward knob (9220). This causes paddle (9232) to pivot about pivot point (9238) toward knob (9220), which in turn causes pivoting of lever member (9234) in the same angular direction about pivot point (9238). This pivoting of lever member (9234) pulls lock arm (9236) away from inner wall (9242) of housing (9210), such that pointed end (9240) disengages inner wall (9242) of housing (9210). With pointed end (9240) disengaged from inner wall (9242) of housing (9210), articulation control assembly (9200) is in an unlocked state, such that knob (9220) may be rotated relative to housing (9210) to change the articulation state of the articulation section of the shaft assembly.

Once the user has reached the desired articulation state, the operator may release paddle (9232). When the operator releases paddle (9232), the resilience of spring (9238) may return lock arm (9236), lever member (9234), and paddle (9232) back to the locked configuration (FIG. 76A). The articulation section will thus be re-locked at the adjusted articulation state.

B. Articulation Control Assembly with Upwardly Biased Clutching Lock

Figure 78:
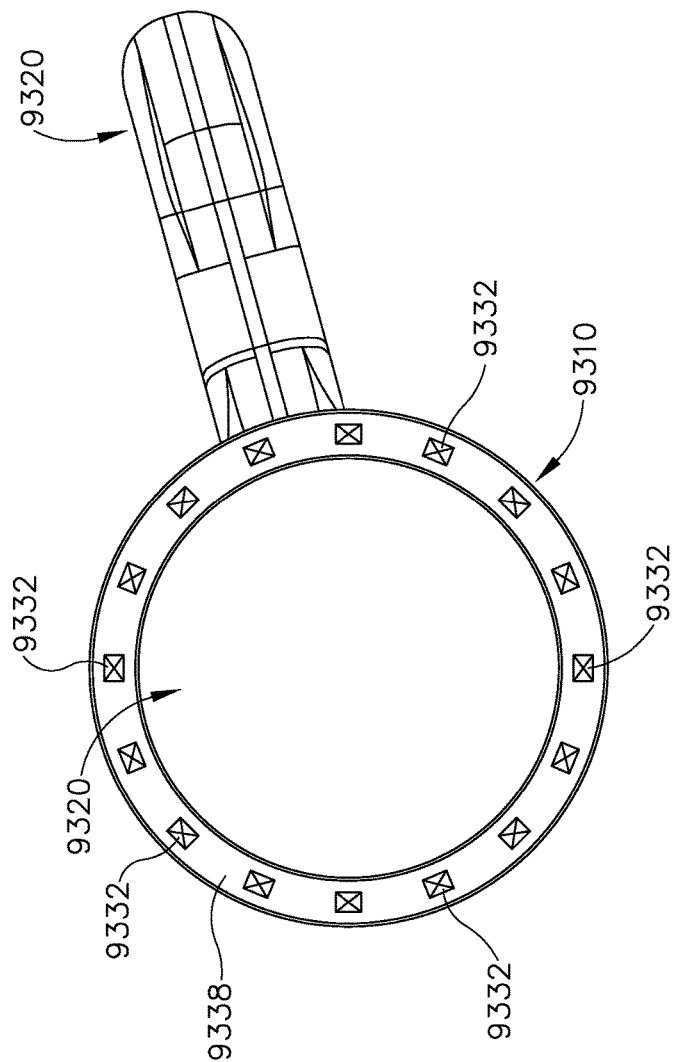
FIG. 78 depicts a bottom cross-sectional view of a knob of the articulation control assembly of FIG. 77, taken along line 78-78 of FIG. 77.

FIGS. 77-78 show another exemplary articulation control assembly (9300) that may be readily incorporated into instrument (10) in place of articulation control assembly (100). Except as otherwise described below, articulation control assembly (9300) is configured and operable just like articulation control assembly (100) described above. Articulation control assembly (9300) of this example comprises a housing (9310) and a knob (9320). Rotation of rotation knob (9320) relative to housing (9310) causes articulation of an articulation section of a shaft assembly, such as articulation section (130) of shaft assembly (30). Articulation control assembly (9300) of this example further comprises a locking feature (9330) that is configured to selectively prevent the rotation of knob (9320). It should be understood that, by preventing rotation of knob (9320), locking feature (9330) further prevents articulation of the articulation section of the shaft assembly. Locking feature (9330) may be used in lieu of, or in addition to, other features discussed herein that selectively prevent rotation of knob (9320); and that selectively lock articulation section (130) in a particular deflected position relative to the longitudinal axis defined by outer sheath (32).

As shown in FIGS. 77-77B, locking feature (9330) of the present example includes a plurality of female spline features (9332) disposed on housing (9310), and a male spline feature (9334) coupled to knob (9320). Female spline features (9332) are more particularly defined as recesses disposed circumferentially and presented downwardly along an annular lip (9338) (FIG. 78) that surrounds a body portion (9340) of knob (9320) (when knob is received within housing (9310)). Male spline feature (9334) includes a first portion (9334a) that extends radially outwardly from body portion (9340) and a second portion (9334b) that extends upwardly, perpendicular to the first portion (9334b). While only one male spline feature (9334) is shown, it should be understood that body portion (9340) may include two more male spline features (9334). For instance, a plurality of male spline features (9334) may be angularly spaced along at least a portion of the perimeter of body portion (9340). It should also be understood that female spline features (9332) may be angularly spaced along any suitable angular range along the circumference of annular lip (9338).

As shown, female and male spline members (9334, 9332) are similarly shaped such that the female spline members (9332) are defined as cavities having shapes that complement the end (9339) of the male spline feature (9334). FIG. 77A shows male spline feature (9334) received in female spline feature (9332). In this state, locking feature (9330) prevents knob (9320) from rotating relative to housing (9310), thereby locking articulation section (130) in its current articulated (or non-articulated) position relative to the longitudinal axis defined by outer sheath (32). In the present example, female spline feature (9332) and end (9339) of male spline features (9334) define pyramidal shapes with pointed portions. In some other examples, spline features (9332, 9334) are substituted with a plurality of complementary teeth arranged in a starburst pattern. Various suitable other ways in which spline features (9332, 9334) may be may be configured will be apparent to those of ordinary skill in the art in view of the teachings herein.

In the present example, a resilient element (9336) biases knob (9320) upwardly into a position where an end (9339) of male spline feature (9334) is received with and engages one of the female spline features (9332), thereby preventing the rotation of knob (9320) relative to housing (9310). Resilient element (9336) may comprise a coil spring, a wave spring, a leaf spring, and/or any other suitable kind of resilient feature. In some examples, locking feature (9330) may be configured to act as a slipping clutch mechanism. That is, in some such examples, the engagement of male spline feature (9334) with one of the female spline features (9332) may be overcome by a user applying sufficient rotational force to knob (9320); but absent such force, the engagement will suffice to maintain the straight or articulated configuration of articulation section (130). It should therefore be understood that the ability to selectively lock knob (9320) in a particular rotational position will provide selective locking of articulation section (130) in a particular deflected position relative to the longitudinal axis defined by outer sheath (32).

In some other examples, the male spline feature (9334) and female spline features (9332) are configured such that that it is difficult to overcome that engagement between male spline feature (9334) and female spline features (9332) by simply providing a rotational force to knob (9320); or such that the rotational force required to overcome the engagement may cause unintended damage to one or more components of the instrument (10). Such a configuration, where a relatively higher rotational force is required to rotate knob (9320), may be provided for the prevention of unintended articulation as a result of inadvertent rotation of knob (9320).

In the example shown, in order to enable rotation of knob (9320), the operator must press knob (9320) in a direction (defined by arrow (9341)), along an axis that is perpendicular to the longitudinal axis of shaft assembly (30). In the present example, knob (9320) is pressed along the same axis about which knob (9320) is rotated in order to drive articulation of articulation section (130). When the user depresses knob (9320) with a sufficient force to overcome the bias of a resilient element (9336), end (9339) of male spline feature (9334) disengages from female spline feature (9332) as shown in FIG. 77B. Knob (9320) is then free to rotate relative to housing (9310) as the operator continues to press downwardly on knob (9320). In examples where the engagement between male spline feature (9334) and female spline features (9332) may be overcome by applying sufficient rotational disengagement force to knob (9320), the rotational force required to rotate the knob (9320) in the unlocked configuration is less than the rotational force required to disengage male spline feature (9334) from female spline feature (9332).

When the operator rotates knob (9320) while knob (9320) is in the downward, unlocked position, such rotation of knob (9320) causes the articulation of articulation section (130). Once the user has articulated articulation section (130) a desired amount (whether to or from an articulated state), the user may release the downward force (in the direction of arrow (9341)) on knob (9320). Resilient element (9336) will then resiliently urge knob (9320) back to the locked configuration of FIGS. 77 and 77A, such that articulation section (130) is locked in the adjusted articulation state relative to the longitudinal axis defined by outer sheath (32). In some examples, the operator may need to ensure the proper alignment of corresponding male spline feature (9334) and a particular female spline feature (9332) to enable the knob (9320) to return to the locked configuration. However, in some examples, locking feature (9330) may be configured to circumferentially align corresponding male spline feature (9334) with a circumferentially adjacent female spline feature (9332) to ensure a smooth transition to the locked configuration. In other words, spline features (9332, 9334) may be configured to self-align with each other. Various suitable ways in which locking feature (9330) may be may be configured will be apparent to those of ordinary skill in the art in view of the teachings herein.

C. Articulation Control Assembly with Downwardly Biased Clutching Lock

FIGS. 79A-81 show another exemplary articulation control assembly (9400) that may be readily incorporated into instrument (10) in place of articulation control assembly (100). Except as otherwise described below, articulation control assembly (9400) is configured and operable just like articulation control assembly (100) described above. Articulation control assembly (9400) of this example comprises a housing (9410) and a knob (9420). Rotation of rotation knob (9420) relative to housing (9410) causes articulation of an articulation section of a shaft assembly, such as articulation section (130) of shaft assembly (30). Articulation control assembly (9400) of this example further comprises a locking feature (9430) that is configured to selectively prevent the rotation of knob (9420). It should be understood that, by preventing rotation of knob (9420), locking feature (9430) further prevents articulation of the articulation section of the shaft assembly. Locking feature (9430) may be used in lieu of, or in addition to, other features discussed herein that selectively prevent rotation of knob (9420); and that selectively lock articulation section (130) in a particular deflected position relative to the longitudinal axis defined by outer sheath (32). Locking feature (9430) is shown in a locked configuration in FIG. 79A and an unlocked configuration in FIG. 79B.

Locking feature (9430) of the present example comprises a plurality of male spline features (9432) and a plurality of female spline features (9436). As best seen in FIG. 79B, male spline features (9432) extend downwardly (direction defined by defined by arrow (9438)) from lip (9434) of knob (9420). As best seen in FIG. 80, male spline features (9432) are angularly spaced in an annular array along the underside of lip (9434). Male spline features (9432) of the present example are generally rectangular in shape. Alternatively, male spline features (9432) may instead have a pyramidal shape, a starburst configuration, and/or any other suitable configuration.

Figure 79A:
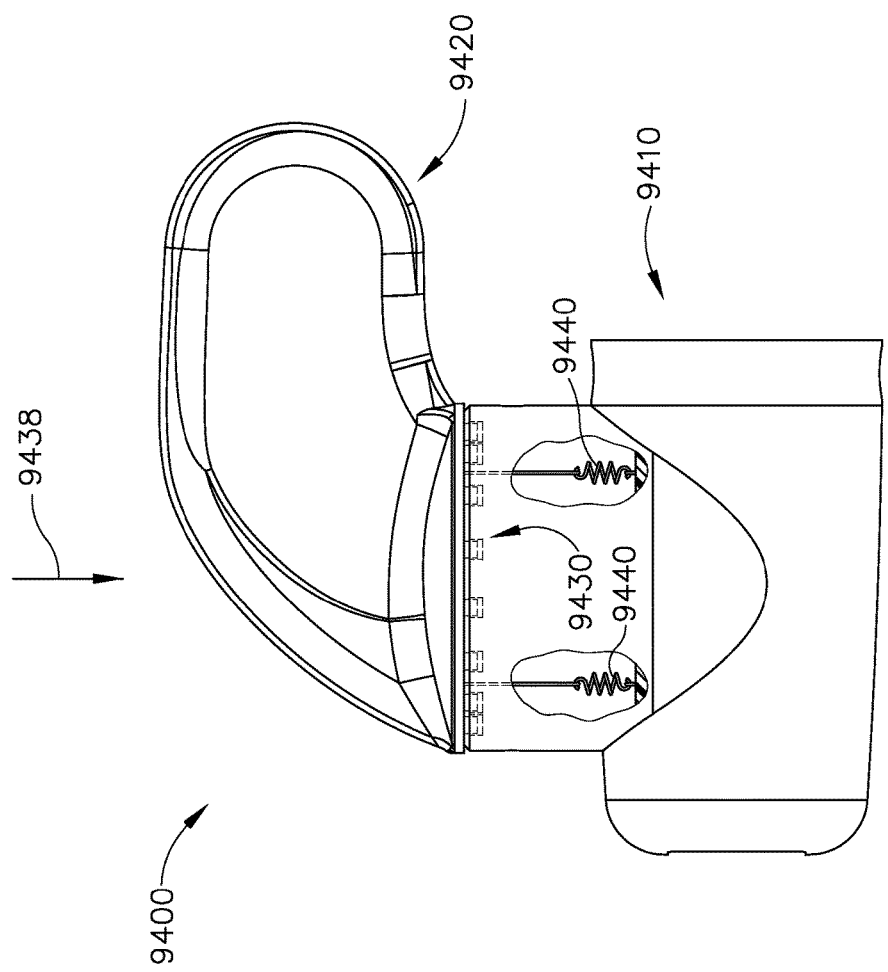
FIG. 79A depicts a side elevational view of yet another exemplary alternative articulation control assembly that may be incorporated into the instrument of FIG. 1, with a locking feature in a locked configuration.
Figure 80:
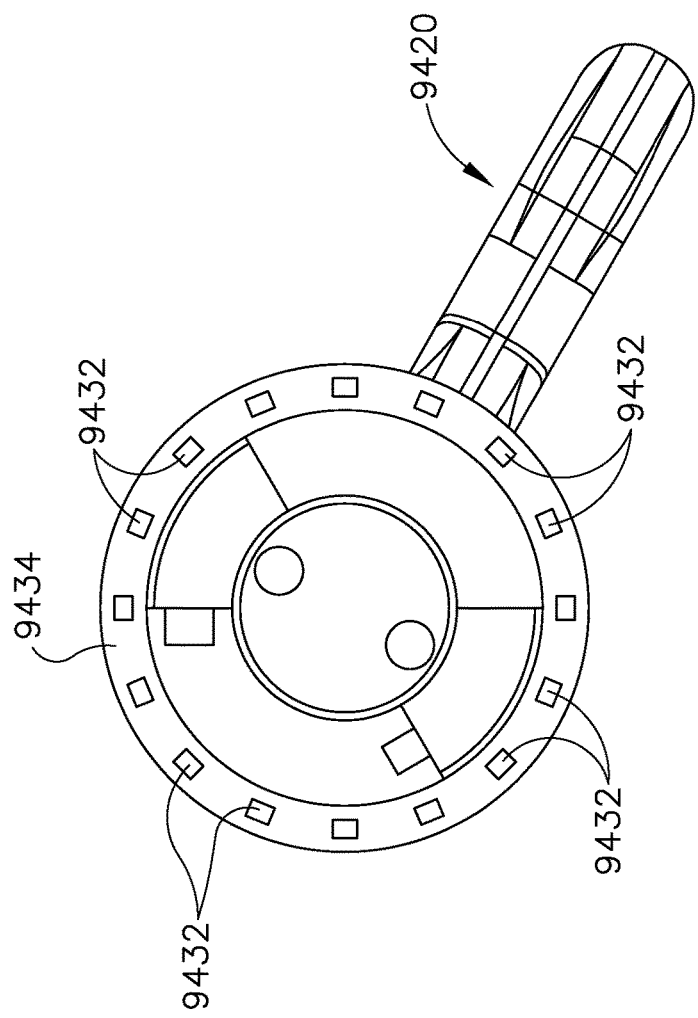
FIG. 80 a bottom plan view of a knob of the articulation control assembly of FIG. 79A.
Figure 81:
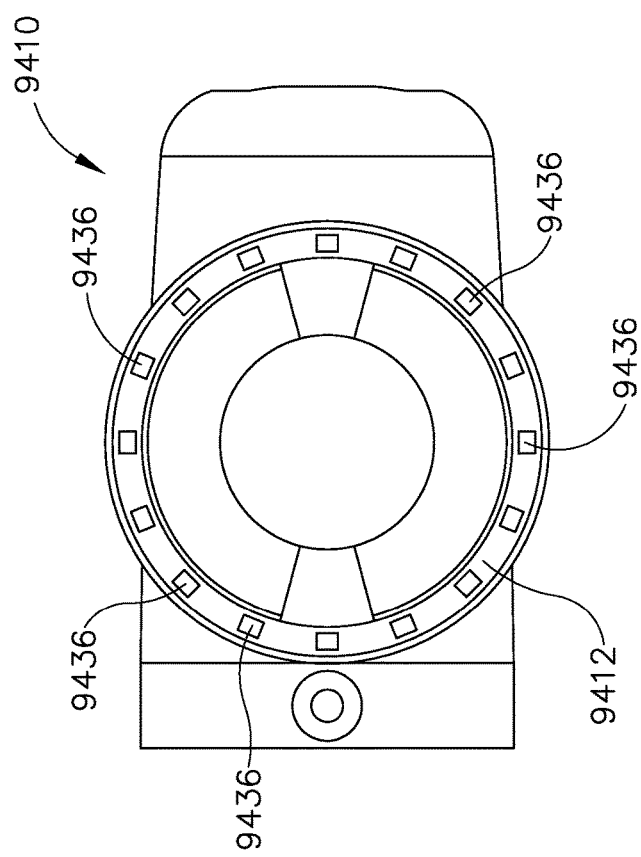
FIG. 81 depicts a top plan view of a housing of the articulation control assembly of FIG. 79A.

As best seen in FIG. 79B, female spline features (9436) comprise recesses that are formed in an upwardly facing surface (9412) of housing (9410). As best seen in FIG. 81, female spline features (9436) are angularly spaced in an annular array along upwardly facing surface (9412) with spacing that complements the spacing of male spline features (9432). Female spline features (9436) are shaped similarly to male spline features (9432) such that female spline features (9436) define generally rectangular recesses, and are spaced apart from one another circumferentially such that female spline features (9436) may receive correspondingly shaped and angularly spaced male spline features (9432) as shown in FIG. 79A. In the present example, there are an equal number of male and female spline features (9432, 9436). However, in other examples, there may be fewer male spline features (9432) than female spline features (9436), provided that the male spline features (9432) are configured to be received in corresponding female spline features (9436) (9 e.g., proper sizing and angular spacing). When male spline features (9432) are positioned in female spline features (9436), the engagement between spline features (9432, 9436) prevents knob (9420) from rotating relative to housing (9410). Thus, when locking feature (9430) is in a locked state due to engagement between spline features (9432, 9436), locking feature (9430) locks the articulation section at its current state of articulation relative to the longitudinal axis of the shaft assembly.

In the present example, a pair of coil springs (9440) is operably coupled to knob (9420) via a pair of links (9441) that resiliently bias knob (9420) downwardly (9 in the direction defined by arrow (9438)). Springs (9440) thus bias knob (9420) and male spline features (9432) into the locked position shown in FIG. 79A. Due to the engagement between male and female spline features (9432, 9436), knob (9420) is unable to rotate relative to housing (9410). Of course, any other suitable kind of resilient member(s) may be used in addition to or in lieu of coil springs (9440).

In some examples, locking feature (9430) may be configured to act as a slipping clutch mechanism such that a sufficient amount of angular force on knob (9420) causes male spline features (9432) to slip between female spline features (9436). In some such examples, male and/or female spline features (9432, 9436) may include ramped or cammed surfaces to enable the slipping clutch action therebetween. In some such examples, the engagement of male spline features (9432) with one of the female spline features (9436) may be overcome by a user applying sufficient rotational force to knob (9420); but absent such force, the engagement will suffice to maintain the straight or articulated configuration of articulation section (130). It should therefore be understood that the ability to selectively lock knob (9420) in a particular rotational position lock will enable an operator to selectively lock articulation section (130) in a particular deflected position relative to the longitudinal axis defined by outer sheath (32).

In the example shown, in order to enable rotation of knob (9420), the operator must pull knob (9420) in the direction of arrow (9442) along an axis that is perpendicular to the longitudinal axis of shaft assembly (30), into the unlocked configuration shown in FIG. 79B. In the present example, knob (9420) is pulled along the same axis about which knob (9420) is rotated in order to drive articulation of articulation section (130). As shown, in the unlocked configuration, male spline features (9432) are disengaged from female spline features (9436) (i.e., male spline features (9432) are spaced from female spline features (9436)). Thus, in the unlocked configuration, knob (9420) is able to rotate relative to housing (9410) along an axis that is perpendicular to the longitudinal axis of outer sheath (32) and cause articulation of articulation section (130), for example. In examples where the engagement between male spline features (9432) and female spline features (9436) may be overcome by applying sufficient rotational disengagement force to knob (9420), the rotational force required to rotate the knob (9420) in the unlocked configuration is less than the rotational force required to disengage male spline features (9432) from female spline features (9436).

When the operator rotates knob (9420) while knob (9420) is in the upward, unlocked position, such rotation of knob (9420) causes the articulation of articulation section (130). Once the user has articulated articulation section (130) a desired amount (whether to or from an articulated state), the user may release the upward force on knob (9420). Springs (9440) will then resiliently urge knob (9420) back to the locked configuration of FIG. 79A, such that articulation section (130) is locked in the adjusted articulation state relative to the longitudinal axis defined by outer sheath (32). In some examples, the operator may need to ensure the proper alignment of male spline features (9432) with female spline features (9436) to enable the knob (9420) to return to the locked configuration. However, in some examples, locking feature (9430) may be configured to circumferentially align male spline features (9432) with circumferentially adjacent female spline features (9332) to ensure a smooth transition to the locked configuration. In other words, spline features (9432, 9436) may be configured to self-align with each other. Various suitable ways in which locking feature (9430) may be may be configured will be apparent to those of ordinary skill in the art in view of the teachings herein.

D. Articulation Control Assembly with Button Actuated Locking Feature

Figure 82:
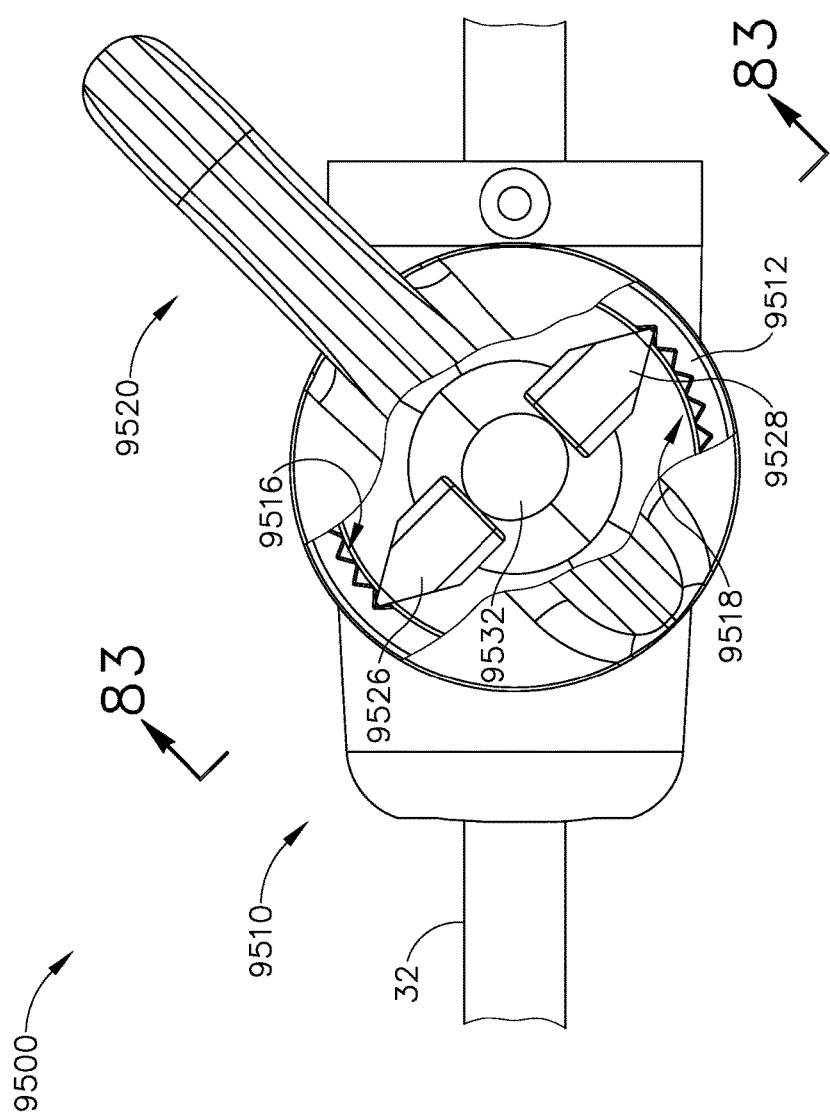
FIG. 82 depicts a top elevational view of yet another exemplary alternative articulation control assembly that may be incorporated into the instrument of FIG. 1, with a locking feature in a locked configuration.
Figure 83A:
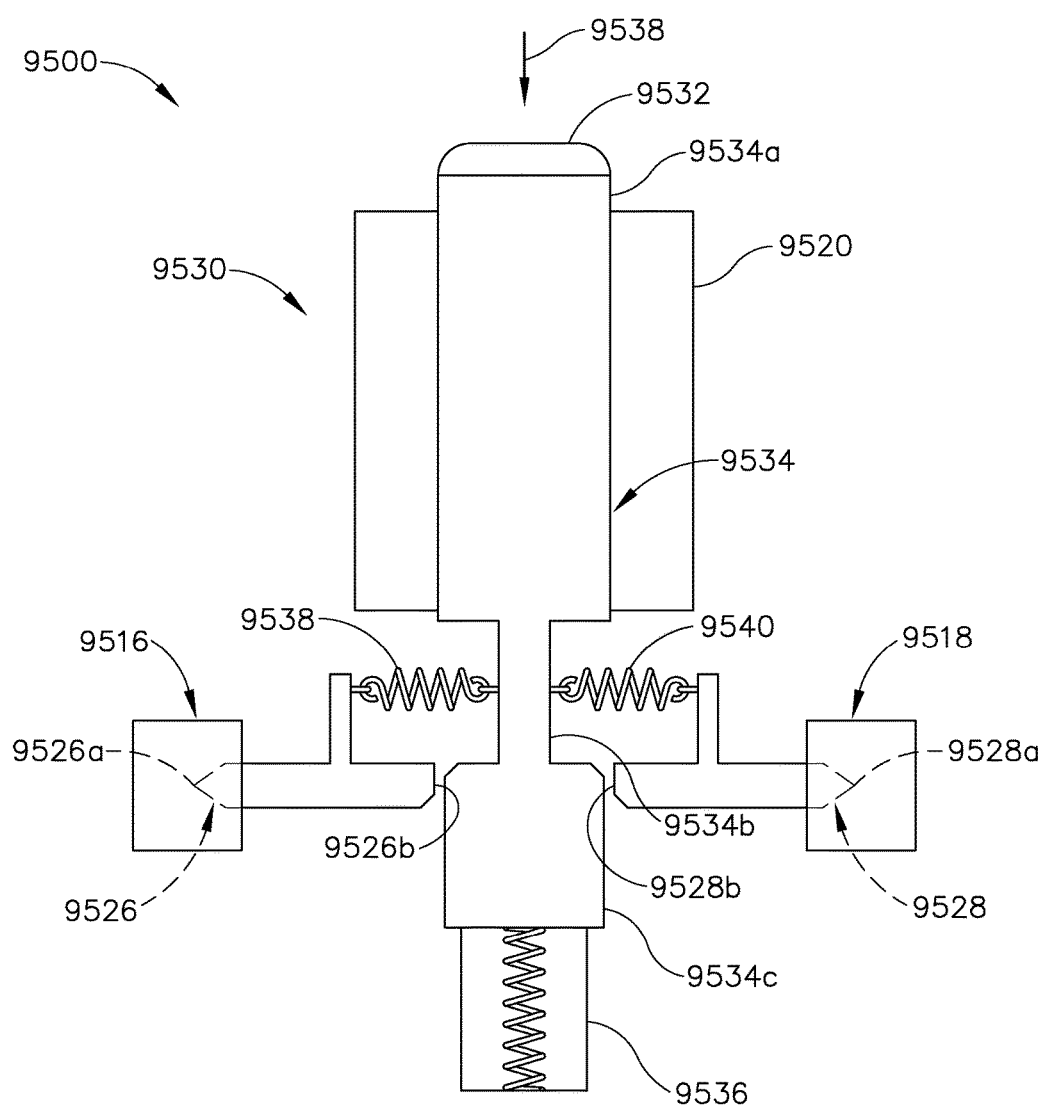
FIG. 83A depicts a partial, side cross-sectional view of the articulation control assembly of FIG. 82, with the locking feature in a locked configuration, with the cross section taken along line 83-83 of FIG. 82.
Figure 83B:
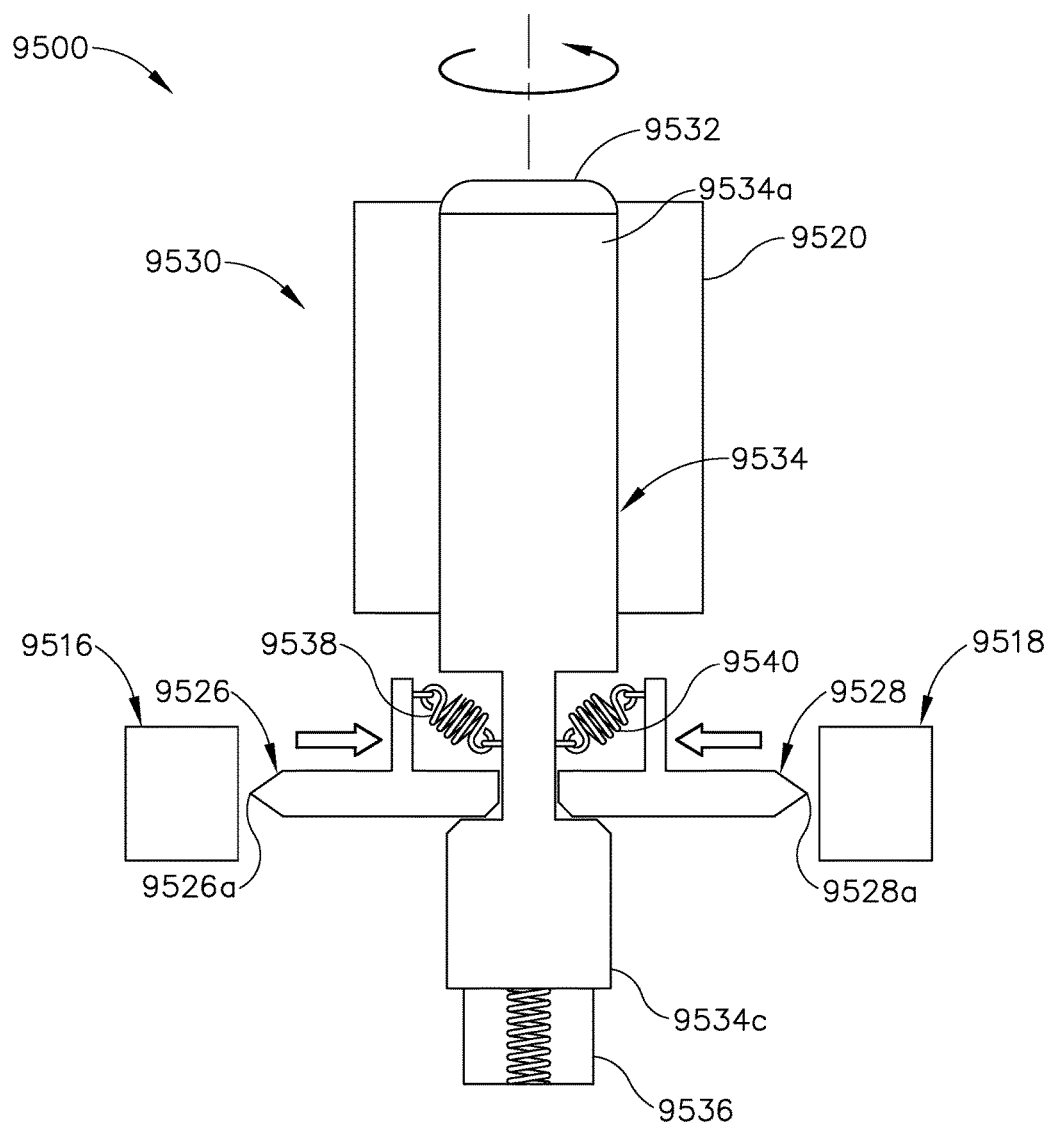
FIG. 83B depicts a partial, side cross-sectional view of the articulation control assembly of FIG. 82, with the locking feature in an unlocked configuration.

FIGS. 82-83B show another exemplary articulation control assembly (9500) that may be readily incorporated into instrument (10) in place of articulation control assembly (100). Except as otherwise described below, articulation control assembly (9500) is configured and operable just like articulation control assembly (100) described above. Articulation control assembly (9500) of this example comprises a housing (9510) and a knob (9520). Rotation of rotation knob (9520) relative to housing (9510) causes articulation of an articulation section of a shaft assembly, such as articulation section (130) of shaft assembly (30). Articulation control assembly (9500) of this example further comprises a locking feature (9530) that is configured to selectively prevent the rotation of knob (9520). It should be understood that, by preventing rotation of knob (9520), locking feature (9530) further prevents articulation of the articulation section of the shaft assembly. Locking feature (9530) may be used in lieu of, or in addition to, other features discussed herein that selectively prevent rotation of knob (9520); and that selectively lock articulation section (130) in a particular deflected position relative to the longitudinal axis defined by outer sheath (32).

In the present example, locking feature (9530) comprises a button (9532) that is operably coupled to a shaft (9534). Shaft (9534) is slidably received in knob (9520) along the same axis about which knob (9520) rotates relative to housing (9510). Shaft (9534) has a first portion (9534a), a second portion (9534b), and a third portion (9534c). Button (9532) is positioned on top of first portion (9534a) and is configured to protrude above the upper surface of knob (9520) to enable an operator to readily depress button (9532) as described below. As shown, first portion (9534a) of shaft (9534) and button (9532) are shown to be separate components, but in other examples, button (9532) may be unitarily formed with shaft (9534). As shown, second portion (9534b) of shaft (9534) includes a smaller cross-sectional dimension (e.g., diameter) than the first and second portions (9534a, 9534c). Locking feature (9530) further comprises a resilient feature (536), which in the present example is shown as a coil spring, but in other examples may be other types of resilient features. Resilient feature (9536) biases shaft (9534) upwardly into the position shown in FIG. 83A, whereby locking feature (9530) is in a locked configuration.

In the present example, locking feature (9530) further comprises a pair of outwardly extending engagement members (9526, 9528) including pointed ends (9526a, 9528a). Housing (9510) includes a first cylindrical portion (9512) that has inwardly presented teeth (9516, 9518). Teeth (9516, 9518) are configured to complement engagement members (9526, 9528). In particular, engagement members (9526, 9528) are configured to engage teeth (9516, 9518) in a detent relationship to thereby selectively lock the rotational position of knob (9520) relative to housing (510). Engagement members (9526, 9528) and teeth (9516, 9518) are configured to operate substantially similar to engagement members (126, 128) with teeth (116, 118) as described above. However, in the present example, engagement members (9526, 9528) are retractable radially inwardly to disengage teeth (9516, 9518). A set of resilient members (9538, 9540) bias engagement members (9526, 9528) inwardly. Shaft (534) selectively resists this inward bias of engagement members (9526, 9528), depending on whether third portion (534c) is positioned on the same lateral plane as engagement members (9526, 9528) or second portion (9534b) is positioned on the same lateral plane as engagement members (9526, 9528).

Shaft (9534) translates along a vertical axis to selectively position portions (9534b, 9534c) on the same lateral plane as engagement members (9526, 9528) in response to depression and release of button (9532). In particular, when button (9532) is not being depressed, shaft (9534) is in an upper, home position as shown in FIG. 83A due to the bias of resilient feature (9536). In this state, third portion (9534c) of shaft (9534) is positioned on the same lateral plane as engagement members (9526, 9528). Due to the relatively larger size of the diameter of third portion (9534c), third portion (9534c) holds engagement members (9526, 9528) in an outward position, such that pointed ends (9526a, 9528a) are engaged with teeth (9516, 9518). This engagement between pointed ends (9526a, 9528a) and teeth (9516, 9518) prevents knob (9520) from rotating relative to housing (9510), thereby preventing articulation section (130) from articulating relative to the rest of shaft assembly (30). Thus, articulation section (130) is locked at its current state of articulation when locking feature (9530) is in the state shown in FIG. 83A.

In order to unlock knob (9520), and thereby unlock articulation section (130), the operator may press button (9532) downwardly (in the direction of arrow (9538)). When button (9532) is depressed downwardly, shaft (9534) overcomes the bias of resilient feature (9536) and shaft (9534) moves downwardly. As shaft (9534) moves downwardly, radially inward portions (9526b, 9528b) of engagement features (9526, 9528) ride along third portion (9534c) and engagement members (9526, 9528) are eventually urged inwardly by resilient members (9538, 9540) as radially inward portions (9526b, 9528b) become coincident with second portion (9534b) of shaft (9534), which has a smaller diameter than third portion (9534c) of shaft (9534). As engagement features (9526, 9528) move inwardly as shown in FIG. 83B, pointed ends (9526a, 9528a) of engagement features disengage from teeth (9516, 9518), respectively, and knob (9520) is free to rotate relative to housing (9510). The operator may thus rotate knob (9520) while holding button (9532) in the depressed state in order to adjust the articulation state of articulation section (130).

Once the operator has adjusted the articulation state of articulation section (130) to a desired amount (whether to or from an articulated state), the operator releases button (9532). When the operator releases button (9532), resilient feature (9536) urges button (9532) and shaft (9534) upwardly (in a direction opposite to arrow (9538)). As shaft (9534) travels upwardly, third portion (9534c) of shaft (9534) eventually engages radially inward portions (9526b, 9528b) of engagement features (9526, 9528), thereby driving engagement features (9526, 9528) outwardly back to the positions shown in FIG. 83A. Engagement features (9526, 9528) thus re-engage teeth (9516, 9518) respectively, thereby re-locking the rotational position of knob (9520) relative to housing (9510), and further thereby locking the adjusted articulation state of articulation section (130). While shaft (9534) is shown as providing a stepped transition between portions (9534b, 9534c), it should be understood that shaft (9534) may instead provide a tapered transition between portions (9534b, 9534c). Radially inner portions (9526b, 9528b) of engagement members (9526, 9528) may slidably cam along such a tapered transition portion during the transition between the locked configuration (FIGS. 82, 83A) and unlocked configuration (FIG. 83B). Various other suitable ways in which locking feature (9530) may be may be configured will be apparent to those of ordinary skill in the art in view of the teachings herein.

E. Articulation Control Assembly with Biased and Keyed Locking Feature

FIGS. 84-89 show another exemplary articulation control assembly (9600) that may be readily incorporated into instrument (10) in place of articulation control assembly (100). Except as otherwise described below, articulation control assembly (9600) is configured and operable just like articulation control assembly (100) described above. Articulation control assembly (9600) of this example comprises a housing (9610) and a knob (9620). Rotation of rotation knob (9620) relative to housing (9610) causes articulation of an articulation section of a shaft assembly, such as articulation section (130) of shaft assembly (30). Articulation control assembly (9600) of this example further comprises a locking feature (9630) that is configured to selectively prevent the rotation of knob (9620). It should be understood that, by preventing rotation of knob (9620), locking feature (9630) further prevents articulation of the articulation section of the shaft assembly. Locking feature (9630) may be used in lieu of, or in addition to, other features discussed herein that selectively prevent rotation of knob (9620); and that selectively lock articulation section (130) in a particular deflected position relative to the longitudinal axis defined by outer sheath (32).

Figure 84:
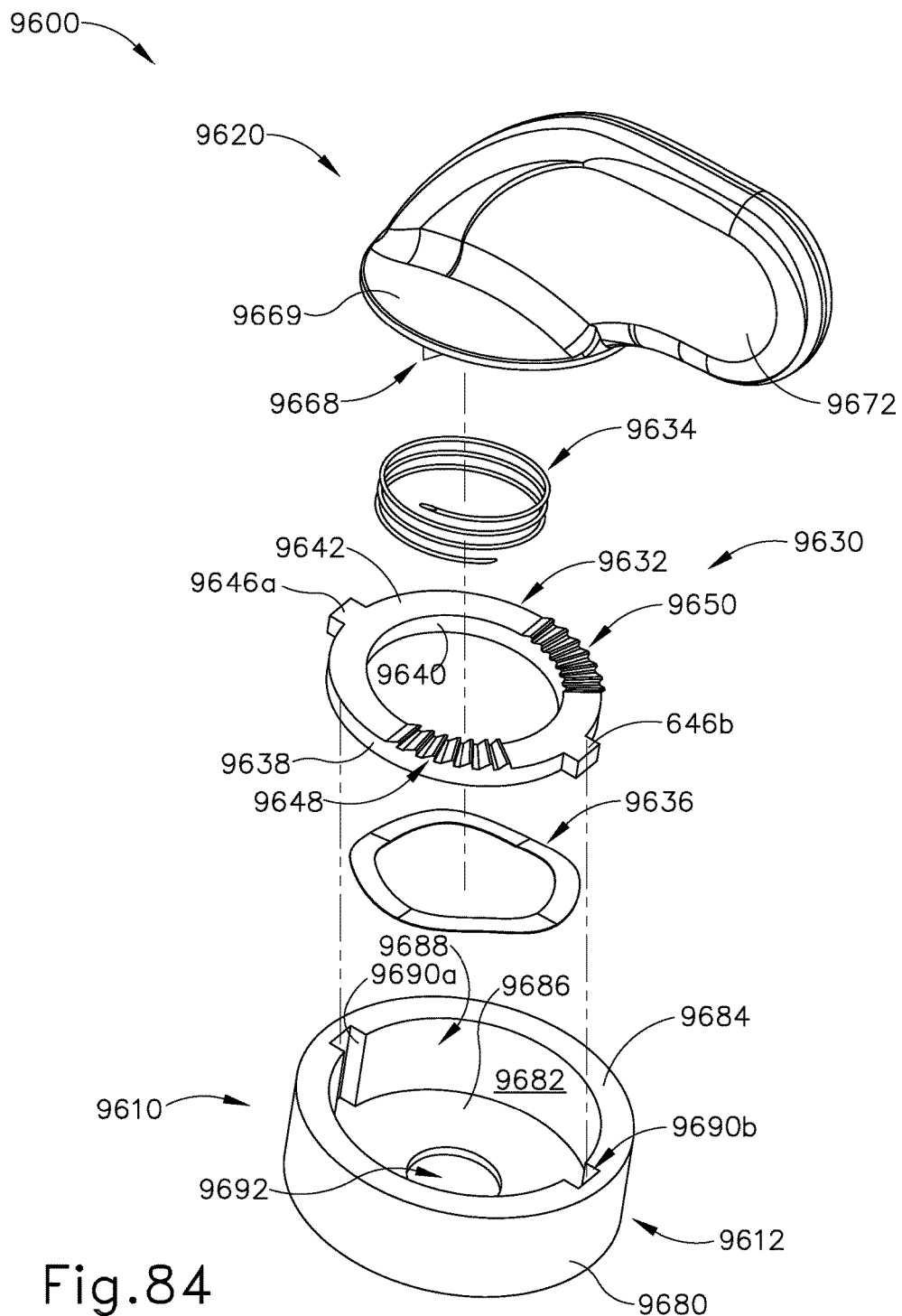
FIG. 84 depicts an exploded perspective view of another exemplary alternative articulation control assembly that may be incorporated into the instrument of FIG. 1.

As best seen in FIG. 84, locking feature (9630) of the present example includes a generally annular locking plate (9632), a coil spring (9634), and a wave spring (9636). Annular locking plate (9632) includes a radially outer edge (9638), a radially inner edge (9640), a first side (9642) and a second side (9644) (FIGS. 88A-B). Annular locking plate (9632) further includes a pair of opposing male keying features (9646a, 9646b) extending radially outwardly from outer edge (9638), a set of first locking teeth (9648), and a set of second locking teeth (9650). Each set of teeth (9648, 9650) has a sawtooth configuration and extends along only a respective portion of the angular range of first side (9642).

Figure 85:
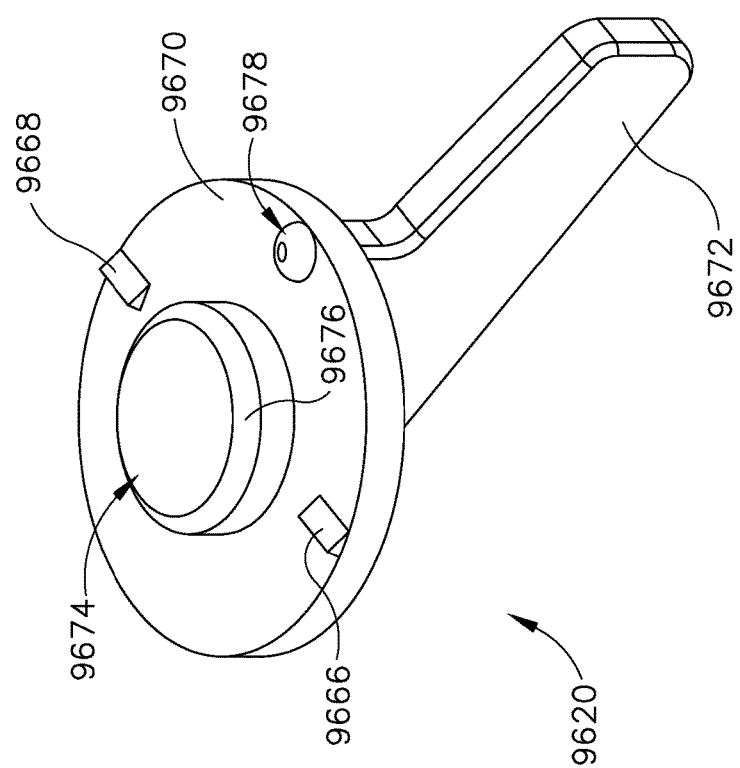
FIG. 85 depicts a bottom perspective view of a knob of the articulation control assembly of FIG. 84.

Different components of the locking feature (9630) are also included on the knob (9620) and housing (9610). In particular, and as best seen in FIG. 85, knob (9620) includes a first surface (9669) and a second surface (9670). A handle (9672) extends upwardly from first surface (9669). Teeth (9666, 9668) extend downwardly from second surface (9670). Tooth (9666) is angularly separated from tooth (9668) by 180°. Teeth (9666, 9668) each have a sawtooth configuration such that teeth (9666, 9668) are configured to engage locking teeth (9648, 9650), respectively, to selectively lock the rotational position of knob (9620) relative to housing (9610). The complementary sawtooth configuration of tooth (9666) and teeth (9650) is such that tooth (9666) may slide along teeth (9650) in a ratcheting fashion as knob (9620) is rotated in a first angular direction, yet the configuration of teeth (9666, 9650) will prevent knob (9620) from rotating in a second angular direction (opposite to the first angular direction) when teeth (9666, 9650) are engaged. Likewise, the complementary sawtooth configuration of tooth (9668) and teeth (9648) is such that tooth (9668) may slide along teeth (9648) in a ratcheting fashion as knob (9620) is rotated in the second angular direction, yet the configuration of teeth (9668, 9648) will prevent knob (9620) from rotating in the first angular direction when teeth (9668, 9648) are engaged.

As also best seen in FIG. 85, knob (9620) also includes a generally cylindrical projection (9674) extending downwardly from surface (9670) and having a chamfered edge (9676). Cylindrical projection (9674) is configured to engage a coil spring (9634) as described below. Knob (9620) further includes a generally hemispherical protrusion (9678) extending downwardly from surface (9670). Protrusion (9678) is angularly positioned at 90° between teeth (9666, 9668). Protrusion (9678) and handle (9672) both lie along an imaginary vertical plane (9679) (FIG. 88A) that laterally bisects knob (9670). Plane (9678) also laterally bisects handle (9672) and protrusion (9678).

In the present example, only a first cylindrical portion (9612) of housing (9610) is shown. It should be understood, however, that housing (9610) may further include a second cylindrical portion (not shown) that is configured and operable substantially similar to second cylindrical portion (114) of articulation assembly housing (110). First cylindrical portion (9612) of housing (9610) is defined as a generally cylindraceous body having a generally cylindraceous cavity. Particularly, and as best seen in FIG. 84, cylindrical portion (9612) includes a radially outer wall (9680), a radially inner wall (9682), an upper edge (9684), and a generally circular inner surface (9686). Radially inner wall (9682) and inner surface (9686) define a generally cylindraceous cavity (9688) that also includes female keying features (9690a, 9690b) extending radially outward therefrom. An aperture (9692) extends through surface (9684) and through outer bottom surface (9688). Aperture (9692) provides a path for knob (9620) to couple with features like translatable members (161, 162) to thereby drive articulation bands (140, 142) in opposing longitudinal directions in order to thereby drive articulation of articulation section (130).

As shown best in FIGS. 84 and 86-88B, locking plate (9632), coil spring (9634), and wave spring (9636) are received in cavity (9688). Particularly, locking plate (9632), coil spring (9634), and wave spring (9636) are situated in cavity (9688) in a coaxial arrangement. Wave spring (9636) abuts surface (9686). Locking plate (9632) is positioned above wave spring (9636) such that portions of surface (9644) of locking plate (9632) abut wave spring (9636). Female keying portions (9690a, 9690b) of first cylindrical portion (612) receive male keying portions (9646a, 9646b) of locking plate (9632). The relationship between keying portions (9646a, 9646b, 9690a, 9690b) permits locking plate (9632) to translate vertically within first cylindrical portion (9612) but prevents locking plate (9632) from rotating relative to first cylindrical portion (9612). Coil spring (9634) is sized such that the effective outer diameter of coil spring (9634) is less than the inner diameter defined by radially inner edge (9640) of locking plate (9632).

Knob (9620) is placed relative to the cavity (9688) such that locking plate (9632) is generally interposed between knob (9620) and wave spring (9636). Moreover, knob (9620) is placed relative to the cavity such that surface (9669) of knob (9620) is generally flush with edge (9684) of cylindrical portion (9612). A retention feature (not shown) is provided in order prevent knob (9620) from moving above edge (9684) to a point where surface (9669) is above edge (9684). For instance, after the above components are assembled together, a retaining ring may be placed over edge (9684) to restrict upward vertical movement of knob (9620) relative to first cylindrical portion (9612). Coil spring (9634) is further sized such that the effective inner diameter of coil spring (9634) is less than the outer diameter of cylindrical projection (9674) of knob (9620). Coil spring (9634) thus receives cylindrical projection (9674) such that cylindrical projection (9674) maintains the axial orientation of coil spring (9634) within first cylindrical member (9612).

Figure 86:
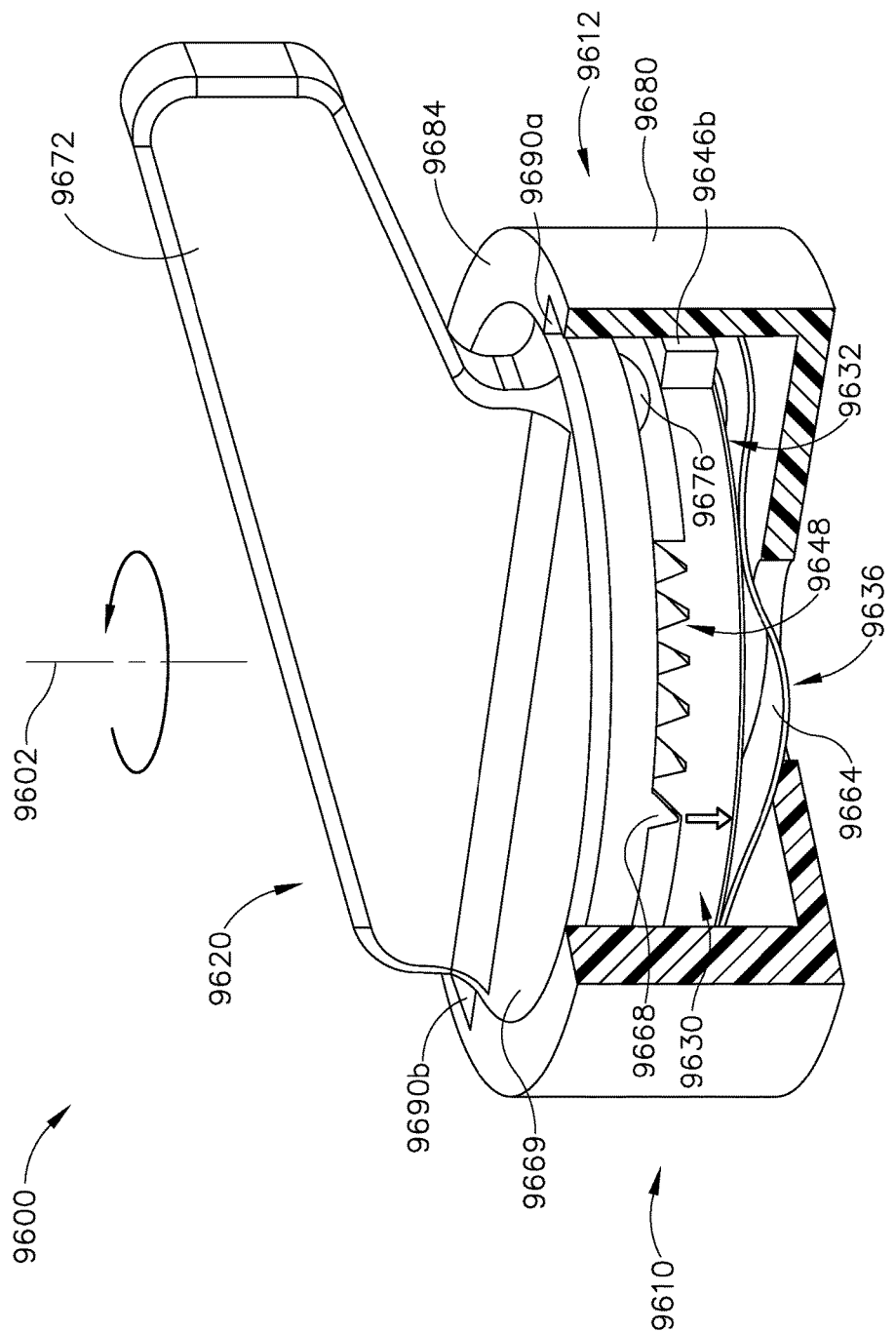
FIG. 86 depicts a perspective view of the articulation control assembly of FIG. 84, with part of the housing broken away to show details of the components.
Figure 87:
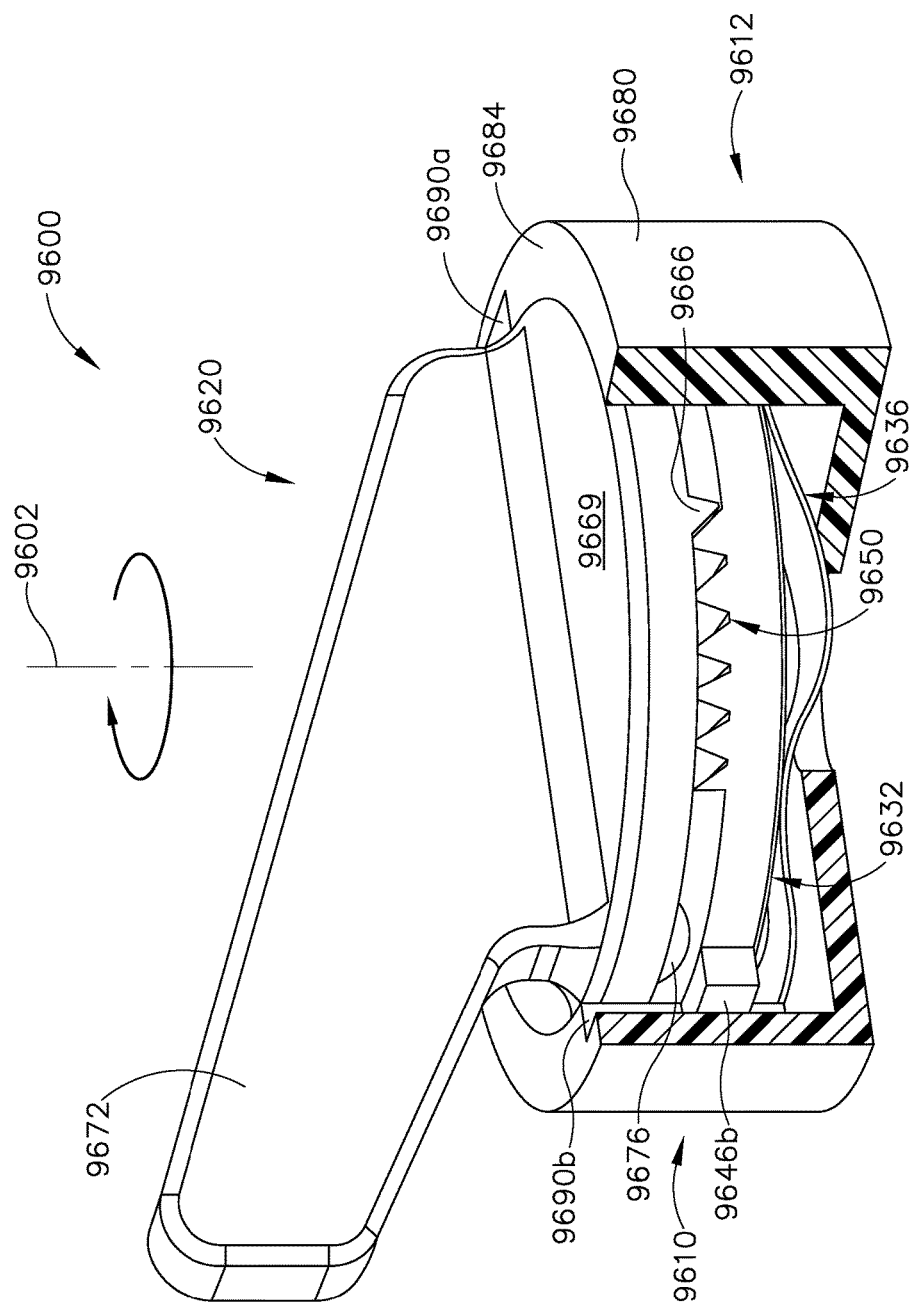
FIG. 87 depicts another perspective view of the articulation control assembly of FIG. 84, with part of the housing broken away to show details of the components.

As shown in FIGS. 86-87, knob (9620) is initially placed such that locking teeth (9666, 9668) are adjacent to but do not yet engage the detent features (9648, 9650), respectively. Knob (9620) is horizontally oriented such that surfaces (9669, 9670) are parallel to sides (9642, 9644) of locking plate (9632) and inner surface (9686) of cylindrical portion (9612). At this point, knob (9620) is free to rotate relative to housing (9610) in either a first direction or second direction about a vertical axis (9602) in order to articulate the articulation section in a first or second direction. For example, rotation of knob (9620) from the neutral position shown in FIGS. 86-87 in a first angular direction about axis (9602) will cause articulation of the articulation section in a first direction. As knob (9620) is rotated in the first direction, tooth (9668) ratchets along teeth (9648). Tooth (9666) simply slides along (or moves freely above) first side (9642) of locking plate (9632). When the operator thereafter releases knob (9620), engagement between teeth (9668, 9648) will lock the articulation section in the selected state of articulation. In other words, engagement between teeth (9668, 9648) will lock articulation control assembly (9600), thereby locking the articulation section in an articulated state.

Similarly, rotation of knob (9620) from the neutral position shown in FIGS. 86-87 in a second angular direction about axis (9602) will cause articulation of the articulation section in a second direction. As knob (9620) is rotated in the second direction, tooth (9666) ratchets along teeth (9650). Tooth (9668) simply slides along (or moves freely above) first side (9642) of locking plate (9632). When the operator thereafter releases knob (9620), engagement between teeth (9666, 9650) will lock the articulation section in the selected state of articulation. In other words, engagement between teeth (9666, 9650) will lock articulation control assembly (9600), thereby locking the articulation section in an articulated state.

When the operator wishes to unlock articulation control assembly (9600) and the articulation section (e.g., to return the articulation section to a straight configuration), the operator may tilt the proximal end of knob (9620) downwardly about a horizontal axis (9696) as shown in FIGS. 88A-89. In particular, FIG. 88A shows articulation control assembly (9600) before knob (9620) is tilted, while articulation control assembly (9600) is still in a locked state. As the proximal end of knob (9620) is tilted downwardly about horizontal axis (9696), protrusion (9678) bears downwardly on first side (9642) of locking plate (9632), thereby driving locking plate (9632) downwardly as shown in FIGS. 88B and 89. As locking plate (9632) is driven downwardly, whichever tooth (9666, 9668) that was previously engaged with the corresponding teeth (9650, 9648) will disengage teeth (9650, 9648), thereby transitioning articulation control assembly (9600) to an unlocked state. While holding knob (9620) in the tilted orientation, the operator may rotate knob (9620) in either direction about axis (9602) to re-adjust the state of articulation of the articulation section. Once the articulation section has reached the desired re-adjusted state, the operator may release knob (9620). At this point, the resilience of coil spring (9634) will drive knob (9620) back to the horizontal orientation shown in FIGS. 86-88A.

Figure 90A:
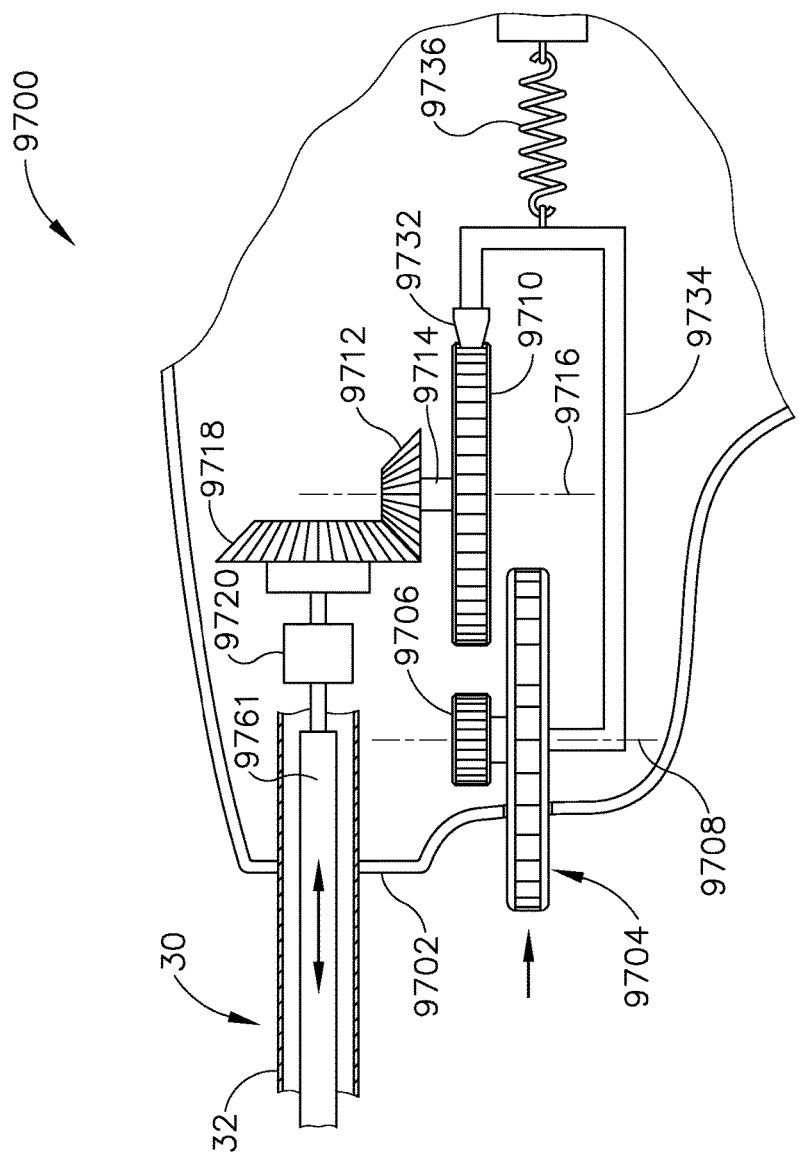
FIG. 90A depicts a partial, schematic, side elevational view of an exemplary alternative articulation control assembly that may be incorporated into the instrument of FIG. 1, with a locking feature in a locked configuration.
Figure 90B:
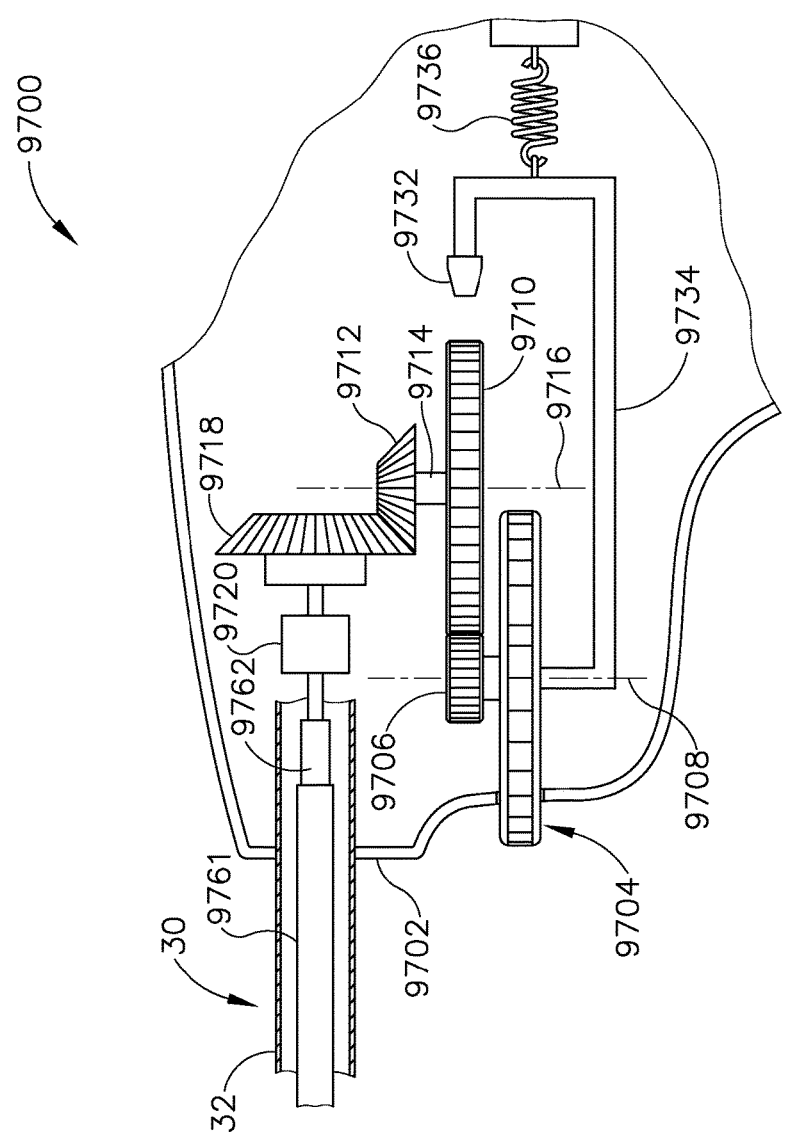
FIG. 90B depicts a partial, schematic, side elevational view of the articulation control assembly of FIG. 90A, with the locking feature in an unlocked configuration.
Figure 91B:
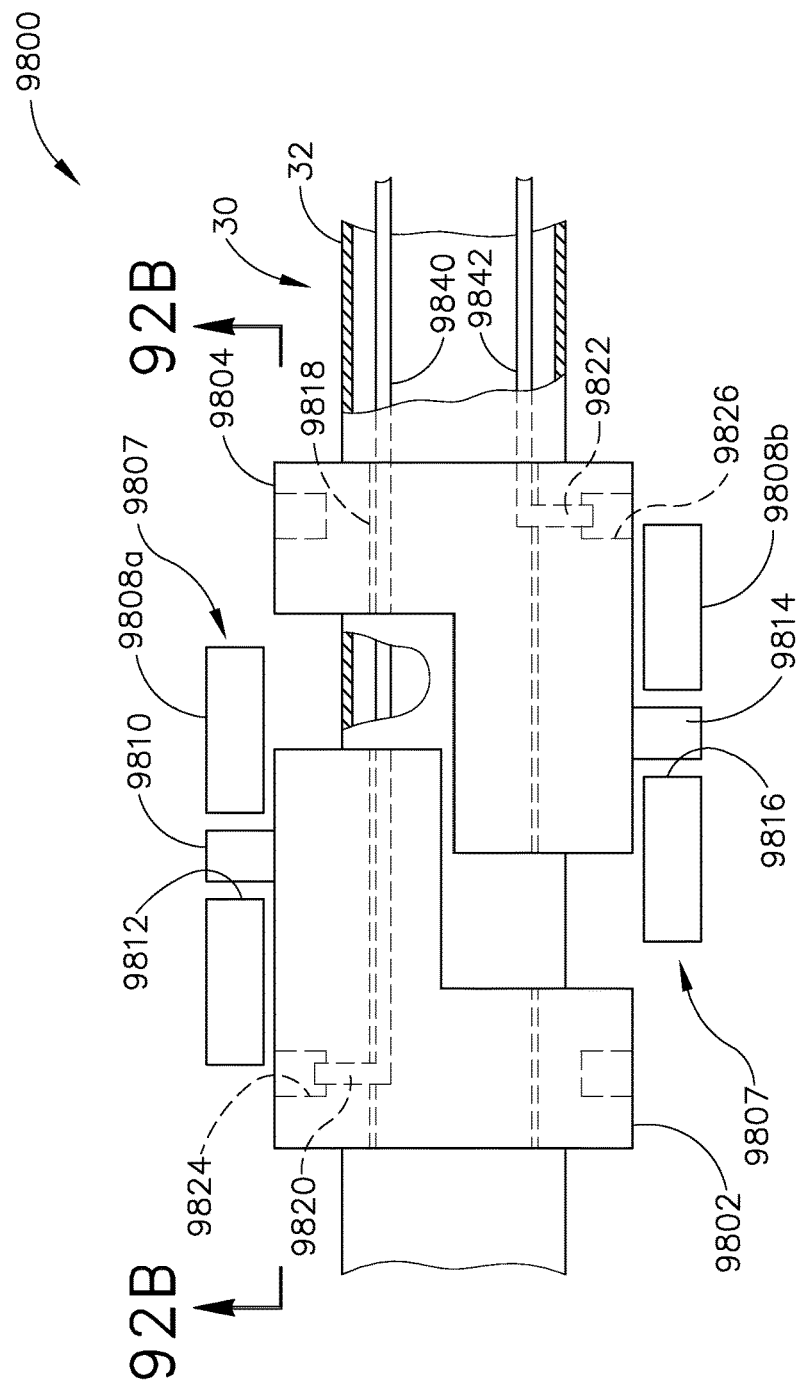
FIG. 91B depicts a top plan view of the articulation control assembly of FIG. 91A, with the articulation control assembly in a second configuration.

F. Articulation Control Assembly with Resiliently Biased Control Wheel and Locking Feature FIGS. 90A-90B show exemplary alternative articulation control assembly (9700) that may be readily incorporated into instrument (10) in place of articulation control assembly (100). Articulation control assembly (9700) of the present example is configured to articulate articulation section (130) in a substantially similar manner to articulation control assembly (100), except for the differences described below. Articulation control assembly (9700) is secured to a proximal portion of outer sheath (32) of shaft assembly (30). Articulation control assembly (9700) is located within a body (9702) of a handle assembly. Except as otherwise described herein, body (9702) and the rest of the handle assembly may be configured similar to body (22) and the rest of handle assembly (20) of instrument (10).

Articulation control assembly (9700) of the present example includes a rotatable input wheel (9704) that is configured to translate and rotate relative to body (9702). Input wheel (9704) includes an integral gear (9706). Wheel (9704) and gear (9706) are rotatable about an axis (9708). Wheel (9704) and gear (9706) are further coupled with a rigid arm (9734). Arm (9734) is further coupled with a pawl (9732) and a resilient member (9736). Resilient member (9736) is mounted to body (9702) and is configured to bias wheel (9704) and gear (9706) to the position shown in FIG. 90A.

Articulation control assembly (9700) of the present example further includes a transmission gear (9710), a first bevel gear (9712), and a second bevel gear (9718). Transmission gear (9710) and first bevel gear (9712) are unitarily coupled together via a shaft (9714), such that gears (9710, 9712) rotate together unitarily. Bevel gears (9712, 9718) are in a meshing relationship with each other, such that rotation of first bevel gear (9712) will provide rotation of second bevel gear (9718). Second bevel gear (9718) is coupled with an opposing thread transmission assembly (9720), which is further coupled with translating members (9761, 9762). Transmission assembly (9720) is configured to convert a rotary output from second bevel gear (9718) into opposing longitudinal motion of translating members (9761, 9762). Translating members (9761, 9762) are coupled with respective articulation bands similar to articulation bands (140, 142), such that opposing longitudinal motion of translating members (9761, 9762) provides articulation of an articulation section in a shaft assembly.

In some versions, transmission assembly (9720) comprises a first nut and lead screw assembly associated with first translating member (9761); and a second nut and lead screw assembly associated with second translating member (9761). The second nut and lead screw assembly may have a thread orientation that is opposite from the thread orientation of the first nut and lead screw assembly, such that the lead screw assemblies may provide opposing longitudinal motion from a single rotary input that is shared by both of the lead screw assemblies. By way of example only, transmission assembly (9720) may be configured in accordance with at least some of the teachings of U.S. Pub. No. 2013/0023868, issued as U.S. Pat. No. 9,545,253 on Jan. 17, 2017, entitled "Surgical Instrument with Contained Dual Helix Actuator Assembly," published Jan. 24, 2013, the disclosure of which is incorporated by reference herein. Other suitable configurations for transmission assembly (9720) will be apparent to those of ordinary skill in the art in view of the teachings herein.

Articulation control assembly (9700) is configured to transition between a locked state (FIG. 90A) and a driving state (FIG. 90B). In the locked state, gear (9706) is disengaged from gear (9710) and pawl (9732) is engaged with gear (9710). Pawl (9732) prevents gear (9710) from rotating. With gear (9710) locked by pawl (9732), gears (9712, 9718) and transmission assembly (9720) are also locked. With transmission assembly (9720) locked, translating members (9761, 9762) are also locked, thereby locking the articulation section in its current state of articulation. If the operator attempts to rotate wheel (9704) about axis (9708) when articulation control assembly (9700) is in the locked state, wheel (9704) will simply rotate freely without having any other effect. Alternatively, body (9702) may include an integral pawl feature that engages wheel (9704) or gear (9706) when articulation control assembly (9700) is in the locked state. Such a pawl may prevent wheel (9704) from rotating when articulation control assembly (9700) is in the locked state, thereby providing tactile feedback to the operator to indicate that articulation control assembly (9700) is in the locked state.

When the operator wishes to change the articulation state of the articulation section (e.g., articulation section (130) described above), the operator may transition articulation control assembly (9700) to the driving state by pushing/pulling wheel (9704) proximally from the position shown in FIG. 90A to the position shown in FIG. 90B. This will eventually bring gear (9706) into engagement with gear (9710). In addition, the proximal movement of wheel (9704) will be communicated to pawl (9732) via arm (9734), such that pawl (9732) will disengage gear (9710) as shown in FIG. 90B. The proximal movement of arm (9734) also compresses resilient member (9736). With pawl (9732) disengaged from gear (9710), gear (9710) is free to rotate. With gear (9706) engaged with gear (9710), rotation of wheel (9704) will cause rotation of gear (9710). It should therefore be understood that rotation of wheel (9704) will actuate transmission assembly (9720), thereby providing opposing longitudinal motion of translating members (9761, 9762), when articulation control assembly (9700) is in the driving as shown in FIG. 90B. In other words, rotation of wheel (9704) about axis (9708) will drive articulation of the articulation section of the shaft assembly when articulation control assembly (9700) is in the driving as shown in FIG. 90B.

Once the operator has achieved the desired state of articulation in the articulation section of the shaft assembly, the operator may simply release wheel (9704). When the operator releases wheel (9704), resilient member (9736) will drive wheel (9704), gear (9706), and pawl (9732) back to the positions shown in FIG. 90A, thereby transitioning articulation control assembly (9700) back to the locked state. This will lock the articulation assembly in the adjusted state of articulation. Various other suitable ways in which articulation control assembly (9700) may be configured and operated will be apparent to a person skilled in the art in view of the teachings herein.

G. Articulation Control Assembly with Self-Locking Linear Cam Features

FIGS. 91A-92B show another exemplary alternative articulation control assembly (9800) that may be readily incorporated into instrument (10) in place of articulation control assembly (100). Articulation control assembly (9800) is configured to articulate articulation section (130) in a substantially similar manner to articulation control assembly (100), except for the differences described below. Articulation control assembly (9800) is secured to a proximal portion of outer sheath (32) of shaft assembly (30).

Figure 92A:
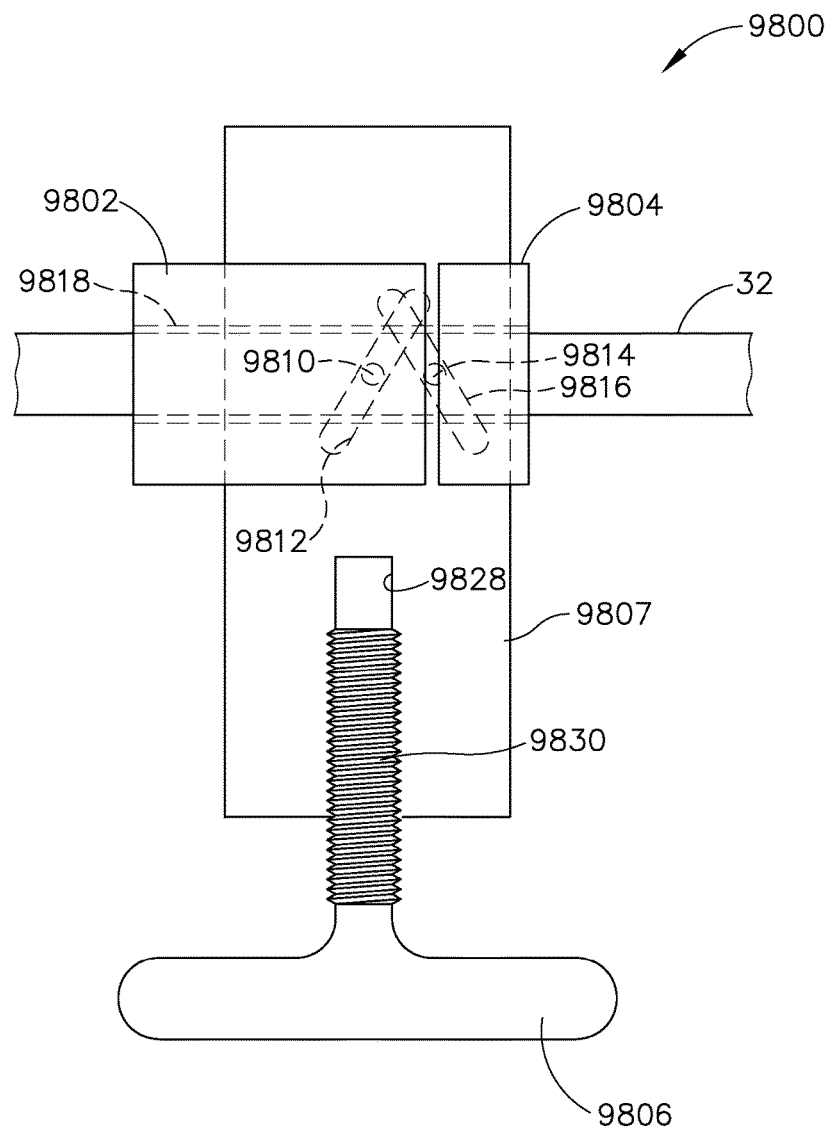
FIG. 92A depicts a partial side elevational view of the articulation control assembly of FIG. 91A, with the articulation control assembly in the first configuration, with the cross section taken along line 92A-92A of FIG. 91A.
Figure 92B:
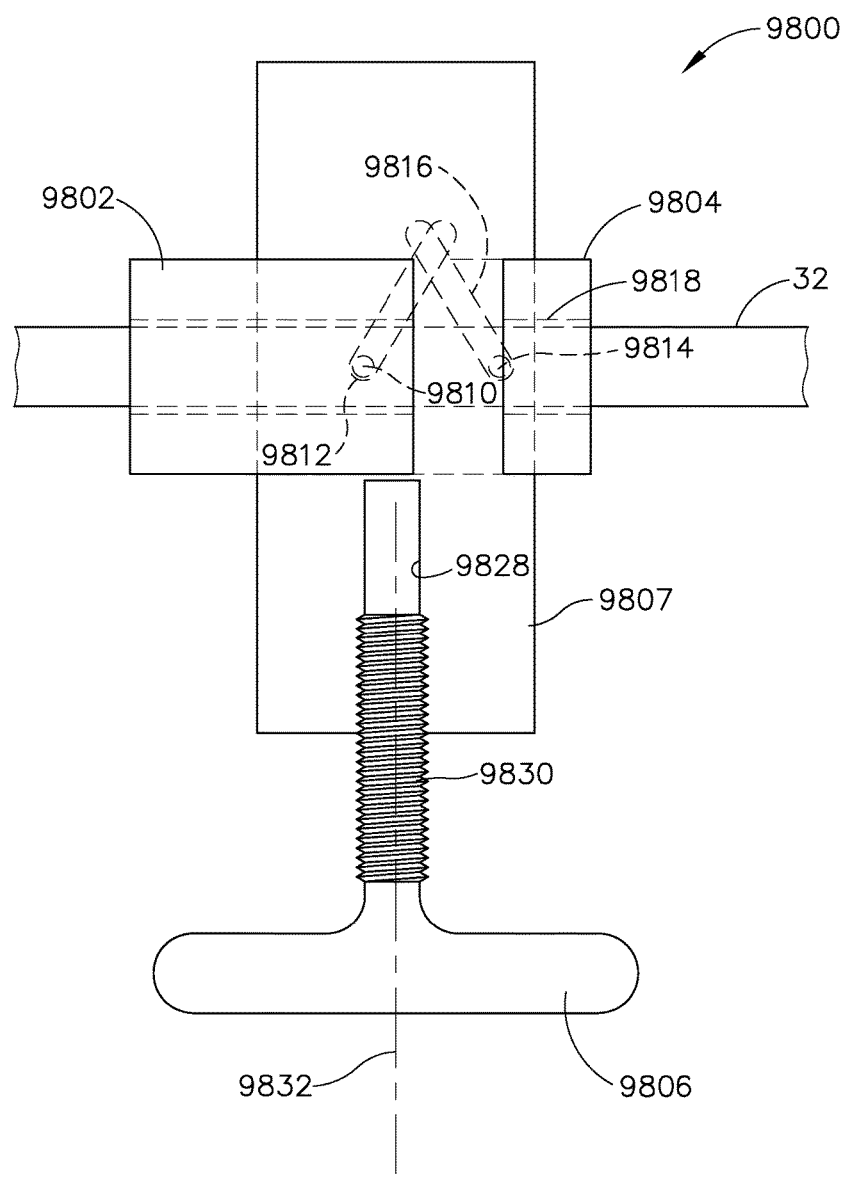
FIG. 92B depicts a partial side elevational view of the articulation control assembly of FIG. 91A, with the articulation control assembly in the second configuration, with the cross section taken along line 92B-92B of FIG. 91B.
Figure 93A:
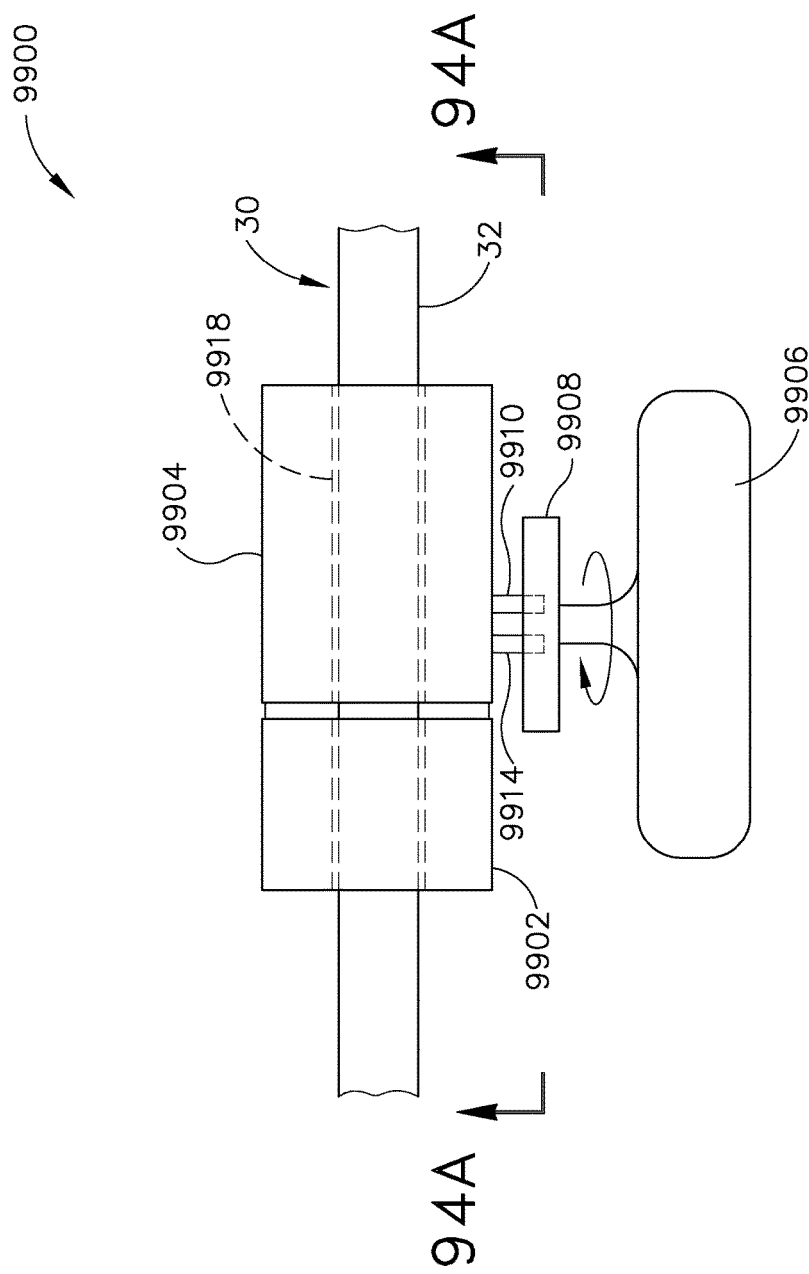
Figure 93B:
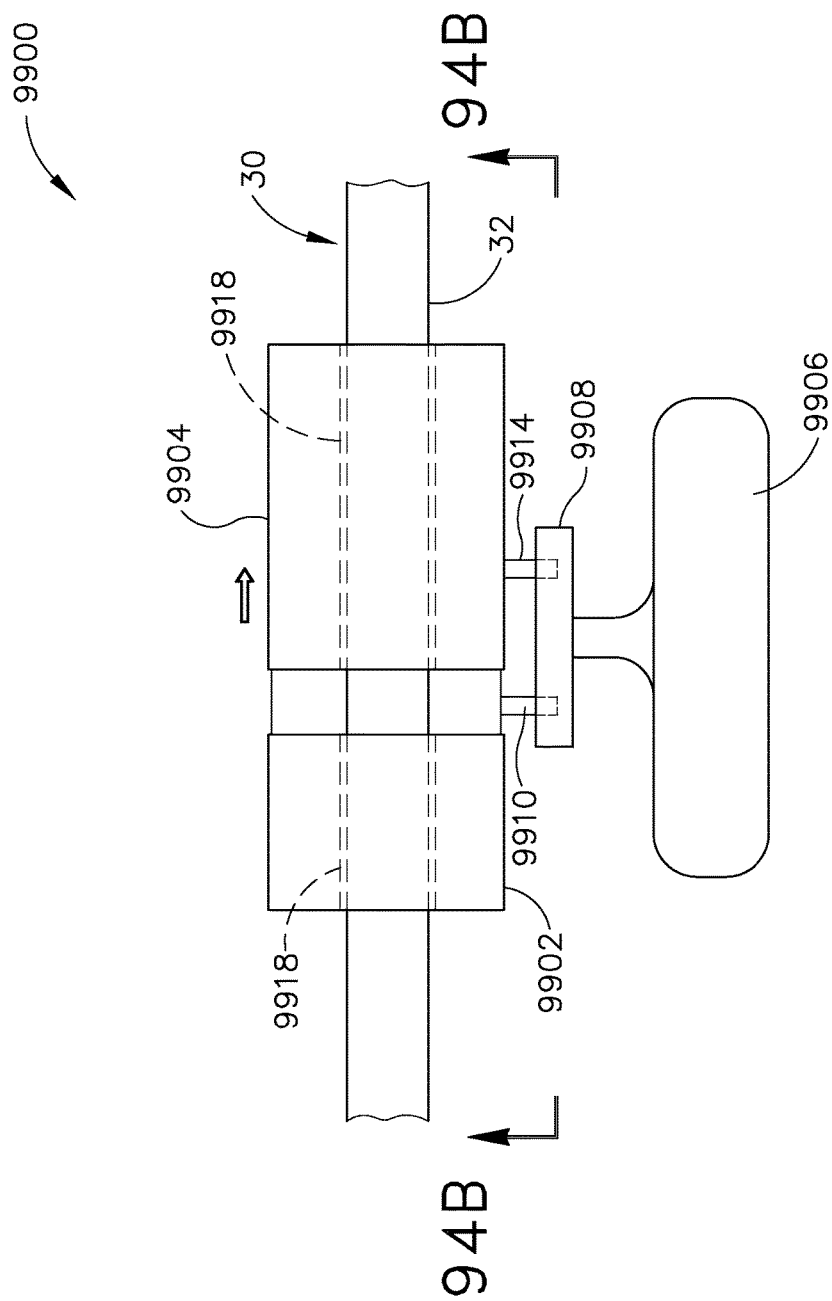

In the present example, articulation control assembly (9800) comprises a first collar (9802), a second collar (9804), and a rotatable knob (9806). Rotation of knob (9806) causes the articulation of articulation section (130), as discussed in more detail below. Articulation control assembly (9900) further includes an actuator (9807) with opposing first and second cam plates (9808*a*, 9808*b*). First collar (9802) includes a first pin (9810) extending transversely therefrom. First pin (9810) is received in a first cam channel (9812) of cam plate (9808*a*). Second collar (9804) includes a second pin (9814) extending transversely therefrom. Second pin (9814) is received in a second cam channel (9816) of cam plate (9808). As best seen in FIGS. 92A-92B, cam channels (9812, 816) each extend obliquely relative to a vertical axis (9832). In addition, first cam channel (9812) tilts distally while second cam channel (9816) tilts proximally.

Shaft assembly (30) comprises a pair of articulation bands (9840, 9842) that are coupled to first and second collars (9802, 9804) via pins (9820, 9822), respectively. Articulation bands (9840, 9842) are configured to operate substantially similar to articulation bands (140, 142), such that opposing longitudinal translation of articulation bands (9840, 9842) causes articulation of articulation section (130). Articulation bands (9840, 9842) extend slidably and longitudinally through the proximal portion of outer sheath (32). Pin (9820) is received within annular groove (9824) of first collar (9802), and pin (9822) is received within annular groove (9826) of second collar (9804). Thus, as shaft assembly (30) rotates relative to articulation control assembly (9800), pin (9820) rotates within annular groove (9824), and pin (9822) rotates within annular groove (9826). Pins (9820, 9822) are mechanically coupled with respective articulation bands (9840, 9842), respectively, such that longitudinal translation of pin (9820) causes longitudinal translation of articulation band (9840), and such that longitudinal translation of pin (9822) causes longitudinal translation of articulation band (9842).

Actuator (9807) of the present example includes a threaded bore (9828) that is configured to threadably couple with a threaded rod (9830) that is coupled to knob (9806). Knob (9806) and threaded rod (9830) are fixed together along an axis (9832) such that rotation of knob (9806) causes actuator to move longitudinally along axis (9832) due to the threaded coupling between threaded rod (9830) and actuator (9807). For example, rotating knob (9806) in a first direction causes actuator (9807) to move in a direction away from knob (9806) along axis (9832), and along a plane that is perpendicular to the longitudinal axis of outer sheath (32). Rotating knob (9806) in a second direction causes actuator (9807) to move toward knob (9807) along axis (9832), and along a plane that is perpendicular to the longitudinal axis of outer sheath (32).

As shown in the transition from FIG. 92A to FIG. 92B, knob (9806) has been rotated in a direction that has caused actuator (9807) to move away from knob (9806). Due to the configuration of cam channels (9812, 9816), the movement of actuator (9807) away from knob (9806) causes pins (9810, 9814) to follow cam channels (9812, 9816). Thus, pin (9810) is urged in a proximal direction by cam channel (9812), thereby causing proximal translation of collar (9802). Similarly, pin (9814) is urged in a distal direction by cam channel (9816), thereby causing distal translation of collar (9804). Due to the coupling engagement between collar (9902) and articulation band (9940), the proximal translation of collar (9802) causes the proximal translation of articulation band (9840). Similarly, due to the coupling engagement between collar (9804) and articulation band (9842), the distal translation of collar (9804) causes the distal translation of articulation band (9842). Thus, articulation bands (9840, 9842) translate simultaneously in opposing longitudinal directions in response to rotation of knob (9806). Rotation of knob (9806) will thereby change the articulation state of articulation section (130).

It should be understood that pins (9810, 9814) and cam channels (9812, 9816) may be positioned and arranged such that rotation of knob (9806) in a first angular direction will cause articulation section (130) to deflect in a first lateral direction away from the longitudinal axis of outer sheath (32); while rotation of knob (9806) in a second angular direction will cause articulation section (130) to deflect in a second lateral direction away from the longitudinal axis of outer sheath (32). It should also be understood that, due to the configuration and arrangement of pins (9810, 9814) and cam channels (9812, 9816), articulation control assembly (9800) may provide self-locking of articulation section (9130). In other words, friction between pins (9810, 9814) and cam channels (9812, 9816) may prevent articulation section (130) from inadvertently deflecting away from a selected state of articulation unless and until the operator rotates knob (9806).

H. Articulation Control Assembly with Self-Locking Rotary Cam Features

FIGS. 93A-94B show another exemplary alternative articulation control assembly (9900) that may be readily incorporated into instrument (10) in place of articulation control assembly (100). Articulation control assembly (9900) is configured to articulate articulation section (130) in a substantially similar manner to articulation control assembly (100), except for the differences described below. Articulation control assembly (9900) is secured to a proximal portion of outer sheath (32) of shaft assembly (30).

Articulation control assembly (9900) comprises a first collar (9902), a second collar (9904), a rotatable knob (9906), and a cam plate (9908). Cam plate (9908) is coupled to rotatable knob (9906) such that rotation of rotatable knob (9906) causes rotation of cam plate (9908). First collar (9902) includes a first pin (9910) extending transversely therefrom. First pin (9910) is received in a first cam channel (9912) of cam plate (9908). Second collar (9904) includes a second pin (9914) extending transversely therefrom. Second pin (9914) is received in a second cam channel (9916) of cam plate (9908).

Shaft assembly (30) comprises a pair of articulation bands (9940, 942) that are coupled to first and second collars (9902, 904) via pins (9920, 9922), respectfully. Articulation bands (9940, 9942) are configured to operate substantially similar to articulation bands (140, 142), such that opposing longitudinal translation of articulation bands (9940, 9942) causes articulation of articulation section (130). Articulation bands (9940, 9942) extend slidably and longitudinally through the proximal portion of outer sheath (32). Pin (9920) is received within annular groove (9924) of first collar (9902), and pin (9922) is received within annular groove (9926) of second collar (9904). Thus, as shaft assembly (30) rotates relative to articulation control assembly (9900), pin (9920) rotates within annular groove (9924) and pin (9922) rotates within annular groove (9926). Pins (9920, 9922) are mechanically coupled with respective articulation bands (9940, 9942) such that longitudinal translation of pin (9920) causes longitudinal translation of articulation band (9940), and such that longitudinal translation of pin (9922) causes longitudinal translation of articulation band (9942).

As shown in the transition from FIG. 94A to FIG. 94B, knob (9906) has been rotated in a direction that has caused cam plate (9908) to move counterclockwise. Due to the configuration of cam channels (9912, 9916), the counterclockwise rotation of cam plate (9908) causes pins (9910, 9914) to follow cam channels (9912, 9916) such that pin (9910) is urged distally while pin (9914) is urged proximally. The proximal movement of pin (9910) provides proximal movement of collar (9902), which in turn causes proximal movement of articulation band (9940). The distal movement of pin (9914) provides distal movement of collar (9904), which in turn causes distal movement of articulation band (9942). Thus, articulation bands (9940, 9942) translate simultaneously in opposing longitudinal directions in response to rotation of knob (9906). Rotation of knob (9906) will thereby change the articulation state of articulation section (130).

It should be understood that pins (9910, 9914) and cam channels (9912, 9916) may be positioned and arranged such that rotation of knob (9906) in a first angular direction will cause articulation section (130) to deflect in a first lateral direction away from the longitudinal axis of outer sheath (32); while rotation of knob (9906) in a second angular direction will cause articulation section (130) to deflect in a second lateral direction away from the longitudinal axis of outer sheath (32). It should also be understood that, due to the configuration and arrangement of pins (9910, 9914) and cam channels (9912, 9916), articulation control assembly (9900) may provide self-locking of articulation section (130). In other words, friction between pins (9910, 9914) and cam channels (9912, 9916) may prevent articulation section (130) from inadvertently deflecting away from a selected state of articulation unless and until the operator rotates knob (9906).

XI. INSTRUMENT WITH ROTATABLE SHAFT HAVING PLURALITY OF LOCKING POSITIONS

As noted above, ultrasonic surgical instrument (10) has a shaft assembly (30) that is rotatable via knob (31). It should be understood that other instruments may also have rotatable shaft assemblies. For instance, FIG. 95 shows an exemplary electrosurgical instrument (10110). By way of example only, electrosurgical instrument (10110) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 8,888,809; U.S. Pub. No. 2011/0087218, issued as U.S. Pat. No. 8,939,974 on Jan. 27, 2015; U.S. Pub. No. 2012/0116379, issued as U.S. Pat. No. 9,161,803 on Oct. 20, 2015; U.S. Pub. No. 2012/0078243; U.S. Pub. No. 2012/0078247, issued as U.S. Pat. No. 9,402,682 on Aug. 2, 2016; U.S. Pub. No. 2013/0030428, issued as U.S. Pat. No. 9,089,327 on Jul. 28, 2015; and/or U.S. Pub. No. 2013/0023868, issued as U.S. Pat. No. 9,545,253 on Jan. 17, 2017. As described therein and as will be described in greater detail below, electrosurgical instrument (10110) is operable to cut tissue and seal or weld tissue (e.g., a blood vessel, etc.) substantially simultaneously. In other words, electrosurgical instrument (10110) operates similar to an endocutter type of stapler, except that electrosurgical instrument (10110) provides tissue welding through application of bipolar RF energy instead of providing lines of staples to join tissue.

It should also be understood that electrosurgical instrument (10110) may have various structural and functional similarities with the ENSEAL®. Tissue Sealing Device by Ethicon Endo-Surgery, Inc., of Cincinnati, Ohio. Furthermore, electrosurgical instrument (10110) may have various structural and functional similarities with the devices taught in any of the other references that are cited and incorporated by reference herein. To the extent that there is some degree of overlap between the teachings of the references cited herein, the ENSEAL®. Tissue Sealing Device by Ethicon Endo-Surgery, Inc., of Cincinnati, Ohio, and the following teachings relating to electrosurgical instrument (10110), there is no intent for any of the description herein to be presumed as admitted prior art. Several teachings below will in fact go beyond the scope of the teachings of the references cited herein and the ENSEAL®. Tissue Sealing Device by Ethicon Endo-Surgery, Inc., of Cincinnati, Ohio.

Electrosurgical instrument (10110) of the present example includes a handle assembly (10120), a shaft assembly (10130) extending distally from handle assembly (10120), and an end effector (10140) disposed at a distal end of shaft assembly (10130). Handle assembly (10120) of the present example includes a body (10122), a pistol grip (10124), an activation button (10126), and a pivoting trigger (10128). Trigger (10128) is pivotable toward and away from pistol grip (10124) to selectively actuate end effector (10140) as will be described in greater detail below. Activation button (10126) is operable to selectively activate RF circuitry that is in communication with end effector (10140), as will also be described in greater detail below. In some versions, activation button (10126) also serves as a mechanical lockout against trigger (10128), such that trigger (10128) cannot be fully actuated unless button (10126) is being pressed simultaneously. Examples of how such a lockout may be provided are disclosed in one or more of the references cited herein. It should be understood that pistol grip (10124), trigger (10128), and button (10126) may be modified, substituted, supplemented, etc. in any suitable way, and that the descriptions of such components herein are merely illustrative.

Shaft assembly (10130) of the present example includes an outer sheath (10132). In some merely illustrative variations, shaft assembly (10130) also includes an articulation section (not shown) that is operable to selectively position end effector (10140) at various angles relative to the longitudinal axis defined by sheath (10132). Handle assembly (10120) may include one or more control features that are operable to drive articulation of the articulation section. By way of example only, an articulation section and associated control features may be configured in accordance with at least some of the teachings of the various references cited herein. Of course, as in the present example, shaft assembly (10130) may simply lack an articulation section if desired.

End effector (10140) of the present example comprises a first jaw (10142) and a second jaw (10144). In the present example, first jaw (10142) is substantially fixed relative to shaft assembly (10130); while second jaw (10144) pivots relative to shaft assembly (10130), toward and away from second jaw (10142). In some versions, actuators such as rods or cables, etc., may extend through sheath (10132) and be joined with second jaw (10144) at a pivotal coupling (not shown), such that longitudinal movement of the actuator rods/cables/etc. through shaft assembly (10130) provides pivoting of second jaw (10144) relative to shaft assembly (10130) and relative to first jaw (10142) in response to pivoting of trigger (10128) relative to pistol grip (10124). Of course, jaws (10142, 10144) may instead have any other suitable kind of movement and may be actuated in any other suitable fashion.

In the present example, each jaw (10142, 10144) includes at least one electrode surface that is in communication with an electrical source (10116). Electrical source (10116) is operable to deliver RF energy to those electrodes at respective polarities such that RF current flows between the electrode surfaces of jaws (10142, 10144) and thereby through tissue captured between jaws (10142, 10144). The RF energy may be delivered in response to the operator pressing button (10126) while tissue is clamped between jaws (10142, 10144). While electrical source (10116) is shown as being external to electrosurgical instrument (10110), electrical source (10116) may be integral with electrosurgical instrument (10110) (e.g., in handle assembly (10120), etc.), as described in one or more references cited herein or otherwise. A controller (not shown) regulates delivery of power from electrical source (10116) to the electrode surfaces. The controller may also be external to electrosurgical instrument (10110) or may be integral with electrosurgical instrument (10110) (e.g., in handle assembly (10120), etc.), as described in one or more references cited herein or otherwise. It should also be understood that the electrode surfaces may be provided in a variety of alternative locations, configurations, and relationships.

In some versions, end effector (10140) includes one or more sensors (not shown) that are configured to sense a variety of parameters at end effector (10140), including but not limited to temperature of adjacent tissue, electrical resistance or impedance of adjacent tissue, voltage across adjacent tissue, forces exerted on jaws (10142, 10144) by adjacent tissue, etc. By way of example only, end effector (10140) may include one or more positive temperature coefficient (PTC) thermistor bodies (e.g., PTC polymer, etc.), located adjacent to the electrodes and/or elsewhere. Data from sensors may be communicated to the controller. The controller may process such data in a variety of ways. By way of example only, the controller may modulate or otherwise change the RF energy being delivered to the electrode surfaces, based at least in part on data acquired from one or more sensors at end effector (10140). In addition or in the alternative, the controller may alert the operator to one or more conditions via an audio and/or visual feedback device (e.g., speaker, lights, display screen, etc.), based at least in part on data acquired from one or more sensors at end effector (10140). It should also be understood that some kinds of sensors need not necessarily be in communication with the controller, and may simply provide a purely localized effect at end effector (10140). For instance, PTC thermistor bodies at end effector (10140) may automatically reduce the energy delivery at the electrode surfaces as the temperature of the tissue and/or end effector (10140) increases, thereby reducing the likelihood of overheating, in accordance with the teachings of one or more references cited herein. Various ways in which sensors that may be incorporated into electrosurgical instrument (10110) will be apparent to those of ordinary skill in the art in view of the teachings herein.

By way of example only, and as is described in various references cited herein, jaws (10142, 10144) may be actuated and thus closed by longitudinal translation of a firing beam (not shown). The firing beam may be longitudinally movable along part of the length of end effector (10140). The firing beam may be coaxially positioned within shaft assembly (10130), extend along the length of shaft assembly (10130), and translate longitudinally within shaft assembly (10130). The firing beam may include a sharp distal blade that severs tissue that is captured between jaws (10142, 10144). The firing beam may also include a set of flanges that engage jaws (10142, 10144) and thereby drive jaw (10144) toward jaw (10142) as the firing beam is advanced distally through end effector (10140). The flanges may also drive jaw (10144) away from jaw (10142) as the firing beam is retracted to a proximal position. The flanges may provide the firing beam with an "I-beam" type of cross section at the distal end of the firing beam. Alternatively, pins or other structural features may be used instead of flanges. In some versions, the firing beam is also electrically grounded, providing a return path for RF energy that is delivered to the captured tissue via the electrodes in jaws (10142, 10144).

As shown in FIG. 95, a knob (10134) is secured to a proximal portion of outer sheath (10132). Knob (10134) is rotatable relative to body (10122), such that shaft assembly (10130) is rotatable about the longitudinal axis defined by outer sheath (10132), relative to handle assembly (10120). Such rotation may provide rotation of end effector (10140) and shaft assembly (10130) unitarily. It may be desirable to actuate knob (10134) to rotate end effector (10140) and shaft assembly (10130) in order to suitably orient the clamping plane of jaws (10142, 10144) relative to targeted tissue.

In some instances, it may be desirable to selectively prevent and permit rotatability of shaft assembly (10130) relative to handle assembly (10120) by locking and unlocking features of shaft assembly (10130) relative to handle assembly (10120). For instance, it may be desirable to prevent shaft assembly (10130) from being inadvertently rotated about its longitudinal axis due to incidental contact between the operator's hand and knob (10134), due to incidental contact between end effector (10140) and an anatomical structure in the patient, and/or due to other conditions. It may be particularly desirable to prevent shaft assembly (10130) from being inadvertently rotated about its longitudinal axis once end effector (10140) has been positioned adjacent to targeted tissue, right before or during actuation of clamp arm or second jaw (10144) to compress the tissue against blade or first jaw (10142), respectively. In the context of instrument (10) where shaft assembly (30) includes an articulation section (36), it may be desirable to prevent rotation of shaft assembly (30) about the longitudinal axis after articulation section (36) has been bent or otherwise deflected to an articulated state. In any of the foregoing scenarios, inadvertent rotation of shaft assembly (30, 10130) may frustrate the operator and require the operator to reposition end effector (40, 10140) relative to the targeted tissue.

Thus, it may be desirable to provide rotatability of shaft assembly (10130) before and during positioning of end effector (10140); yet prevent rotatability of shaft assembly (10130) once end effector (10140) has been suitably positioned relative to targeted tissue. Various examples of how rotatability of shaft assembly (10130) may be selectively locked and unlocked will be described in greater detail below. Other examples will be apparent to those of ordinary skill in the art in view of the teachings herein.

While several of the teachings below are described as variations to ultrasonic surgical instrument (10) and/or electrosurgical instrument (10110), it should be understood that various teachings below may also be incorporated into various other types of devices. By way of example only, in addition to being readily incorporated into ultrasonic surgical instrument (10) and electrosurgical instrument (10110), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

A. Exemplary Knob-Driven Clamping Lock for Shaft Assembly

One exemplary feature that may be used to prevent inadvertent rotation of end effector (10140) about the longitudinal axis defined by sheath (10132) is a spring clamp (10200), as shown in FIGS. 96-99E. As best seen in FIG. 96, a shaft assembly (10260) extends distally from a handle assembly (10210), which comprises a pair of housing halves (10212, 10214). Handle assembly (10210) may be configured like handle assembly (20), like handle assembly (10120), or have any other suitable configuration. Each housing half (10212, 10214) in this example comprises a respective, distally extending boss (10216, 10218). Bosses (10216, 10218) cooperate to form an annular shape. This annular shape formed by bosses (10216, 10218) is concentric with shaft assembly (10260). Shaft assembly (10260) comprises an outer sheath (10262) and a rotation knob (10270), which is operable to rotate outer sheath (10262) and other components of shaft assembly (10260) relative to handle assembly (10210) as described in greater detail below. Shaft assembly (10260) may be configured like shaft assembly (30), like shaft assembly (10130), or have any other suitable configuration. It should be understood that the distal end of shaft assembly (10260) may include an end effector like end effector (40), an end effector like end effector (10140), and/or any other suitable kind of end effector.

Spring clamp (10200) comprises a resilient annular surface (10220), notches (10225, 10240), a proximal edge (10245), an offset distal edge (10235), and strips (10230, 10231, 10232) that terminate into radially extending tabs (10205, 10210, 10215). Resilient annular surface (10220) terminates on one end with single strip (10232) and terminates on the other end with two strips (10230, 10231). Two strips (10230, 10231) form a U-shaped pathway that is configured to receive single strip (10232). The resilient properties of spring clamp (10200) ensure that single strip (10232) and two strips (10230, 10231) angularly overlap toward each other in such a way as to conform to bosses (10216, 10218). In other words, spring clamp (10230) is resiliently biased in a first position where interior of resilient annular surface (10220) engages bosses (10216, 10218) in such a way that spring clamp (10230) and bosses (10216, 10218) are fixed relative to one another in the first position. Proximal edge (10245) is positioned against handle housing halves (10212, 10214) while offset distal edge (10235) aligns flush with the distal ends of bosses (10216, 10218). Notches (10225, 10240) extend longitudinally past bosses (10216, 10218) as best seen in FIG. 96. While notches (10225, 10240) are used in the current examples, other features can be implemented onto spring clamp (10200) such as slots or bent tabs similar to radially extending tabs (10205, 10210, 10215).

Figure 97:
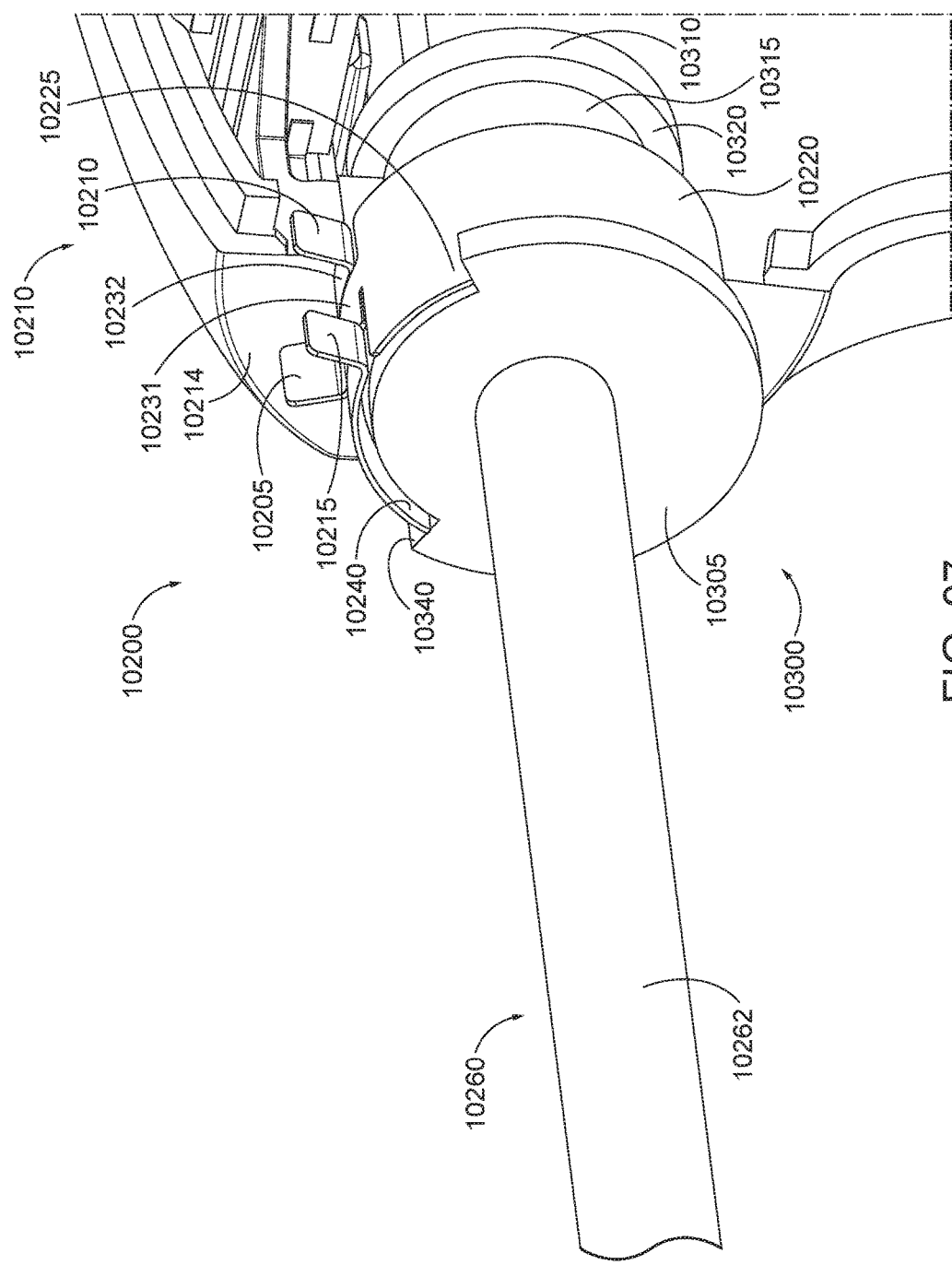

As best seen in FIG. 97, notches (10225) are in contact with a shaft retainer (10300). Shaft retainer (10300) is unitarily fixed to distal outer sheath (10262), such that rotation of shaft retainer (10300) rotates outer sheath (10262) and the rest of shaft assembly (10260) relative to handle assembly (10210). Shaft retainer (10300) comprises a proximal annular flange (10210), a body (10315), and a distal annular flange (10305) with a cutout (10340). Body (10315) is dimensioned to fit within bosses (10216, 10218). The outer diameter of body (10315) is less than the inner diameter defined by bosses (10216, 10218), such that shaft retainer (10300) may freely rotate within bosses (10216, 10218) when spring clamp (10200) is in an unlocked state (i.e., in the second position). Outer sheath (10262) is fixedly secured within the interior of body (10315). Body (10315) also connects proximal annular flange (10210) with distal annular flange (10305). Proximal annular flange (10210) further comprises contact surface (10320) that is configured to engage the proximal ends of bosses (10216, 10218). Spring clamp (10200) engages shaft retainer (10300) due to contact between the outer edges of notches (10225) and the inner edges of cutout (10340).

Figure 98:
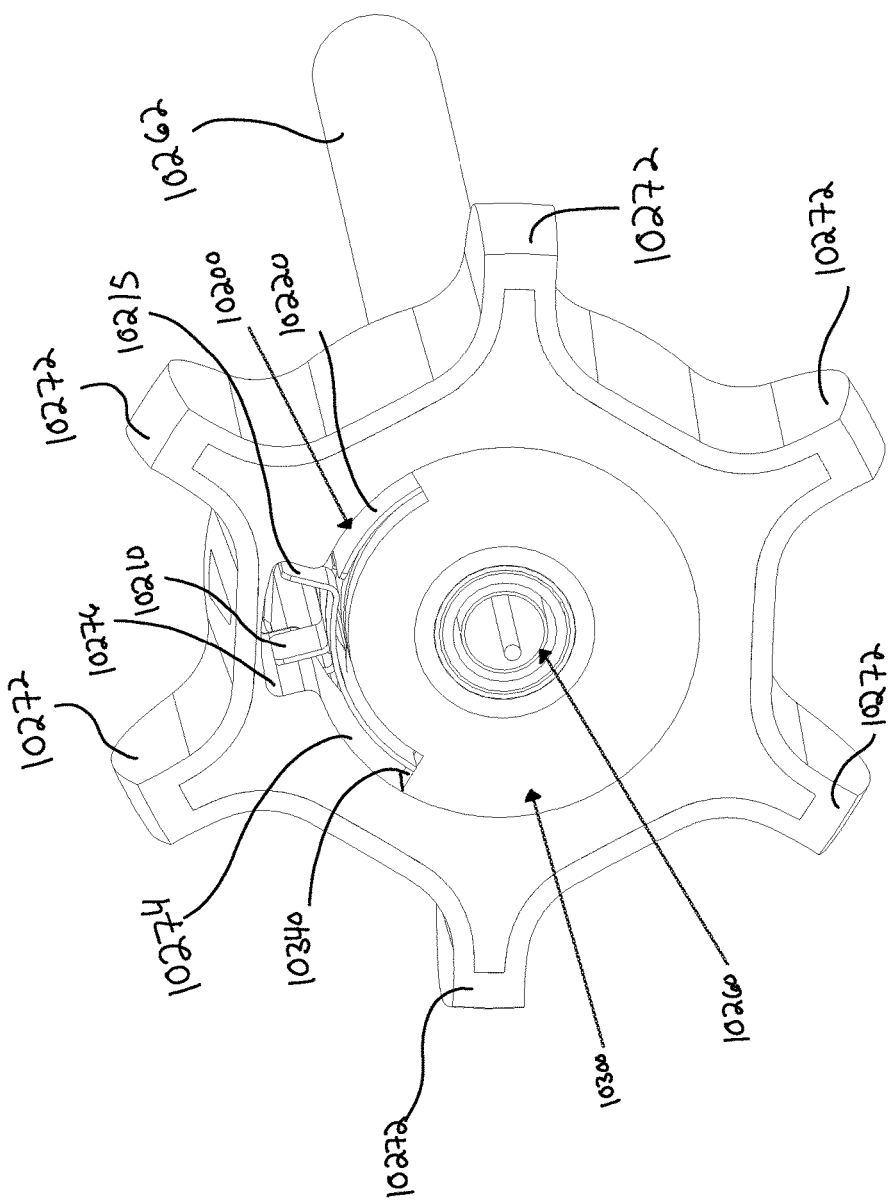

As best seen in FIG. 98, rotation knob (10270) encompasses bosses (10216, 10218), spring clamp (10200) and at least a portion of shaft retainer (10300). Rotation knob (10270) comprises a plurality of rotation grips (10272), a rotation channel (10274), and a key slot (10276) extending from a portion of rotation channel (10274). Rotation channel (10274) forms a recess that encompasses bosses (10216, 10218), a portion of spring clamp (10200), and a portion of shaft retainer (10300). Key slot (10276) provides additional space for radially extending tabs (10205, 10210, 10215). However, rotation knob (10270) is not directly in contact with shaft retainer (10300) or outer sheath (10262). Therefore, rotation of knob (10270) does not directly correlate to rotation of shaft assembly (10260).

As described below, knob (10270) is configured to interact with spring clamp (10200) in order to transition spring clamp (10200) from first position to a second position. When spring clamp (10200) is in the first position, spring clamp (10200) resiliently bears radially inwardly against bosses (10216, 10218), such that spring clamp (10200) is effectively locked to handle assembly (10210) due to a frictional braking effect. This effect is transferred to shaft assembly (10260) via shaft retainer (10300) due to engagement between the outer edges of notches (10225) and the inner edges of cutout (10340). In other words, when spring clamp (10200) is in the first position, shaft retainer (10300), spring clamp (10200), and bosses (10216, 10218) all cooperate to effectively lock the rotational position of shaft assembly (10260) relative to handle assembly (10210). When spring clamp (10200) transitions to the second position, the grip of spring clamp (10200) against bosses (10216, 10217) is relieved, reducing or eliminating frictional braking of spring clamp (10200) against bosses (10216, 10217), thereby allowing shaft assembly (10260) to rotate relative to handle assembly (10210).

The fact that spring clamp (10200) transitions from the first position to the second position in response to actuation of rotation knob (10270) may also provide other results. For example, if outer sheath (10262) encounters incidental rotational forces due to the end effector bearing against anatomical structures of the patient during operation of the instrument in a surgical procedure, these incidental rotation forces will not cause spring clamp (10200) to release. Instead, these incidental rotation forces will further tighten spring clamp (10200), such that spring clamp (10200) will provide further resistance to rotation of shaft assembly (10260). Thus, actual rotation of knob (10270) will be required in order to release spring clamp (10200) to permit rotation of shaft assembly (10260).

FIG. 99A shows rotation knob (10270) and spring clamp (10200) in a non-engaged relationship, such that tabs (10205, 10210, 10215) are positioned within key slot (10276) without engaging any interior surfaces of knob (10270) that define key slot (10276). At this point, spring clamp (10200) is still in a first position, clamping against bosses (10216, 10218), thereby effectively locking the rotational position of shaft assembly (10260) relative to handle assembly (10210). FIG. 99B shows rotation knob (10270) rotated to an angular position where an interior surface of knob (10270) defining key slot (10276) is in contact with radially extending tab (10215), but where spring clamp (10200) is still in the first position. This is the maximum amount of rotation that knob (10270) is allowed without rotating shaft assembly (10260) via shaft retainer (10300). It should therefore be understood that there is some "play" between knob (10270) and shaft assembly (10260), such that there is lost motion between knob (10270) and shaft assembly (10260) as knob (10270) is rotated through a first range of angular motion from the position shown in FIG. 99A to the position shown in FIG. 99B.

FIG. 99C shows rotation knob (10270) rotated further to an angular position where the surface of key slot (10276) that initially contacted tab (10215) at the stage shown in FIG. 99B is now bearing against tab (10215) with enough force to cause spring clamp (10200) to deform to the second position. As noted above, when spring clamp (10200) is in the second position, spring clamp (10200) the braking force of spring clamp (10200) against bosses (10216, 10218) is substantially relieved such that spring clamp (10200) may be rotated relative to bosses (10216, 10218). Therefore, as seen in the transition from the stage shown in FIG. 99C to the stage shown in FIG. 99D, further rotation of knob (10270) provides rotation of spring clamp (10200) about bosses (10216, 10218). Additionally, since notches (10225, 10240) are in direct contact with cutouts (10340) of distal annular flange (10305), rotation of spring clamp (10200) also rotates shaft retainer (10300), thereby rotating shaft assembly (10260) (and the end effector (not shown) at the distal end of shaft assembly (10260)). In other words, as key slot (10276) of rotation knob (10270) engages radially extending tab (10215) of spring clamp (10200), spring clamp (10200) becomes free to rotate relative to handle housing halves (10212, 10214) while simultaneously rotating shaft assembly (10260) due to contact between spring clamp (10200) and shaft retainer (10300).

As seen in the transition from the stage shown in FIG. 99C to the stage shown in FIG. 99D, once the operator has rotated knob (10270) to orient shaft assembly (10260) at the desired angular position, the operator then release knob (10270). When the operator releases knob (10270), the resilient properties of spring clamp (10200) pushes spring clamp from the second position back to the first position. Spring clamp (10200) is then again rotationally fixed relative to bosses (10216, 218), thereby effectively locking the rotational position of shaft assembly (10260) relative to handle assembly (10210). While FIG. 99A depict rotation of knob (10270) and shaft assembly (10260) in just one angular direction, it should be understood that the above described components will operate in the same fashion when knob (10270) and shaft assembly (10260) are rotated in the opposite angular direction.

FIGS. 96-99E show spring clamp (10200) in a flat spring form. However, spring clamp (10200) may take a variety of alternative forms such as a round wire form. Additionally, spring clamp (10200) can have other features for engaging key slot (10276) instead of radially extending tabs (10205, 10210, 10215). Additionally, it is not necessary for spring clamp (10200) to comprise two strips (10230, 10231) in order to form a U-shaped pathway and angularly overlap toward single strip (10232). For instance, two strips (10230, 10231) could be a single strip that does not overlap single strip (10232) of the present example. In some such versions, a boss could be inserted on knob (10270) instead of key slot (10276) to engage either strip. Various suitable alternative configurations and relationships for spring clamp (10200) and knob (10270) will be apparent to those of ordinary skill in the art in view of the teachings herein.

B. Exemplary Trigger-Driven Clutching Lock for Shaft Assembly

In some circumstances, it may be desirable to tie the locking of the angular position of shaft assembly (10130) to some other operation of instrument (10100). For instance, it may be desirable to lock rotation of shaft assembly (10130) relative to handle assembly (10120) when trigger (10128) is being actuated; yet permit shaft assembly (10130) to be rotated relative to handle assembly (10120) when trigger (10128) is not being actuated. FIGS. 100A-100B show an exemplary instrument (10400) that is configured to provide such functionality.

Instrument (10400) of the present example comprises a handle assembly (10410) and a shaft assembly (10450). Handle assembly (10410) comprises a housing (10412), a pistol grip (10414), and a trigger (10425) that is pivotable toward and away from pistol grip (10414). It should be understood that handle assembly (10410) may further include any of the other features of handle assembly (20), any of the other features of handle assembly (10120), and/or any other suitable features. Shaft assembly (10450) is selectively rotatable relative to handle assembly (10410) as will be described in greater detail below. Shaft assembly (10450) comprises an outer sheath (10452) and an inner tubular actuating member (10454) Inner tubular actuating member (10454) is configured to translate within outer sheath (10452) to thereby actuate an element of an end effector (10450) at the distal end of shaft assembly. For instance, such an element may be similar to clamp arm (44) or second jaw (10144). It should therefore be understood that the distal end of shaft assembly (10450) may include an end effector like end effector (40), an end effector like end effector (10140), and/or any other suitable kind of end effector. Moreover, shaft assembly (10450) may be configured like shaft assembly (30), like shaft assembly (10130), or have any other suitable configuration.

Instrument (10400) further includes a rotation knob (10405), which is fixedly secured to outer sheath (10452). Rotation knob (10405) is rotatably supported by housing (10412) of handle assembly (10410) via an annular flange (10406). In particular, housing (10412) supports rotation knob (10405) via flange (10406) while still permitting rotation knob (10405) to rotate via flange (10406). The proximal end of rotation knob (10405) includes an angular array of proximally presented locking recesses (10420), which will be described in greater detail below. When rotation knob (10405) is in an unlocked state, the operator may grasp rotation knob (10405) and rotate shaft assembly (10450) relative to handle assembly (10410) via rotation knob (10405). When rotation knob (10405) is in a locked state, shaft assembly (10450) cannot be rotated relative to handle assembly (10410).

Trigger (10425) is pivotably mounted to housing (10410) via a pin (10430). Trigger (10425) further comprises an actuating arm (10440) and a locking arm (10435). Actuating arm (10440) is coupled to an actuating collar (10415) via pin (10445). Actuating collar (10415) is fixed to inner tubular actuating member (10454). Therefore, closure of trigger (10425) toward pistol grip (10414) rotates actuating arm (10440) via pin (10430), which in turn translates actuating collar (10415) and inner tubular actuating member (10454) distally. Additionally, locking arm (10435) pivots about pin (10430) in response to closure of trigger (10425).

As best seen in FIGS. 101A-101B, locking arm (10435) includes a pair of distally oriented projections (10436) that are positioned to selectively engage locking recesses (10420) of knob (10405). In particular, when trigger (10425) is in the relaxed state as shown in FIGS. 100A and 101A, projections (10436) are spaced away from recesses (10420), With projections (10436) being spaced away from recesses (10420), knob (10405) and shaft assembly (10450) are free to rotate relative to handle assembly (10410). It should also be understood that the movable element of the end effector that is coupled with inner tubular actuating member (10454)

will be in a non-actuated state when trigger (10425) is in the relaxed state as shown in FIGS. 100A and 101A. When trigger (10425) is pivoted toward pistol grip (10414), trigger (10452) reaches the position shown in FIGS. 100B and 101B. At this stage, inner tubular actuating member (10454) is advanced distally via actuating collar (10415), thereby actuating the movable element of the end effector that is coupled with inner tubular actuating member (10454). In addition, locking arm (10435) is pivoted to a position where projections (10436) are received in recesses (10420). The engagement of projections (10436) in recesses (10420) will effectively lock knob (10405) such that knob (10405) and shaft assembly (10450) are prevented from rotating relative to handle assembly (10410) when trigger (10425) is in the actuated position shown in FIGS. 100B and 101B. When the operator releases trigger (10425), instrument (10400) returns back to the state shown in FIGS. 100A and 101A. It should therefore be understood that the instrument (10400) prevents rotation of shaft assembly (10450) relative to handle assembly (10410) when a movable element of the end effector is being actuated; yet permits rotation of shaft assembly (10450) relative to handle assembly (10410) when the movable element of the end effector is not being actuated.

In some versions, locking arm (10435) is deformable in the plane along which trigger (10425) pivots; yet is substantially non-deformable along a path that is transverse to the pivot plane. For instance, locking arm (10435) may be configured such that projections (10436) are received in recesses (10420) as soon as trigger (10425) pivots through a first range of motion toward pistol grip (10414); and such that locking arm (10435) deforms (with projections (10436) still being received in recesses (10420)) as trigger (10425) pivots through a second range of motion toward pistol grip (10414). In some such versions, trigger (10425) does not complete the actuation of the movable element of the end effector until trigger (10425) completes the second range of motion. Thus, locking arm (10435) may prevent rotation of shaft assembly (10450) relative to handle assembly (10410) before the movable element of the end effector is fully actuated. Locking arm (10435) may be configured such that projections (10436) engage recesses (10420) to prevent rotation of shaft assembly (10450) relative to handle assembly (10410) at any suitable stage of actuation of the movable element of the end effector.

In some other variations, locking arm (10435) is pivotably mounted to trigger (10425), such that locking arm (10435) pivots relative to trigger (10425) as trigger (10425) pivots through the second range of motion relative to pistol grip (10414). In some such versions, a resilient member may bias locking arm (10435) to engage recesses (10420) as soon as trigger (10425) pivots through the first range of motion toward pistol grip (10414). Other suitable configurations for locking arm (10435) will be apparent to those of ordinary skill in the art in view of the teachings herein. Similarly, other suitable relationships between trigger (10425) and locking arm (10435) will be apparent to those of ordinary skill in the art in view of the teachings herein. As yet another merely illustrative alternative, locking arm (104350 may be omitted, and projections (10436) may be secured to actuating collar (10415) or inner tubular actuating member (10454). In versions where projections (10436) are secured to inner tubular actuating member (10454), projections (10456) may be incorporated into a locking collar that is fixedly secured to inner tubular actuating member (10454).

Since knob (10405) has a finite number of recesses (10420), there may be occasions where the operator actuates trigger (10425) when projections (10436) are not perfectly angularly aligned with corresponding recesses (10420). Thus, projections (10436) and/or recesses (10420) may include obliquely angled cam features, curved cam features, and/or other kinds of features that are configured to provide self-alignment to thereby fully seat projections (10436) in recesses (10420). In other words, such self-alignment features may provide whatever further minimal rotation of shaft assembly (10450) that might be necessary in order to fully seat projections (10436) in recesses (10420) as trigger (10425) completes a range of pivotal motion toward pistol grip (10414). In such versions, it may be desirable to maximize the number of recesses (10420) in order to minimize the amount of further rotation that might be required in order for self-alignment features to fully seat projections (10436) in recesses (10420). Minimizing the amount of further rotation that is required in order to fully seat projections (10436) in recesses (10420) may minimize the risk of operator frustration, as it will make the final angular orientation of shaft assembly (10450) as close as possible to the angular orientation selected by the operator.

C. Exemplary Cam-Driven Clutching Lock for Shaft Assembly

In some instances, it may be desirable to lock rotation of shaft assembly (10130) relative to handle assembly (10120) whenever the operator is not attempting to rotate knob (10134); and to only unlock rotation of shaft assembly (10130) relative to handle assembly (10120) when the operator is actively rotating knob (10134). To that end, FIGS. 102A-102B show a locking mechanism (10500) comprising a rotation knob (10510), and a biased locking member (10563). Rotation knob (10510) is secured to a shaft assembly (10505) and is thereby operable to selectively rotate shaft assembly (10505) relative to a handle assembly (10546). It should be understood that handle assembly (10546) may further include any of the other features of handle assembly (1020), any of the other features of handle assembly (10120), and/or any other suitable features. Shaft assembly (10505) may be configured like shaft assembly (30), like shaft assembly (10130), or have any other suitable configuration. Moreover, the distal end of shaft assembly (10505) may include an end effector like end effector (40), an end effector like end effector (10140), and/or any other suitable kind of end effector.

Rotation knob (10510) is rotatably supported by handle assembly (10546) via an annular flange (10506). In particular, handle assembly (10546) supports rotation knob (10510) via flange (10506) while still permitting rotation knob (10510) to rotate via flange (10506). Rotation knob (10510) further comprises a channel (10508), a linear slot (10525), and a V-shaped slot (10520). V-shaped slot (10520) includes a pair of obliquely angled slot legs. It should be understood that slot (10520) may have various other suitable configurations, such that a "V" shape is not necessary. Other suitable shapes that slot (10520) may have will be apparent to those of ordinary skill in the art in view of the teachings herein.

A proximal portion of shaft assembly (10505) that protrudes proximally from knob (10510) comprises an annular array of proximally oriented teeth (10507). Shaft assembly (10505) further includes transversely oriented pin (10535) that is received in linear slot (10525) of rotation knob (10510). Biased locking member (10563) further comprises a fixed member (10590), a resilient member (10580), a guide channel (10570), a rotation lock base (10562), a rotation lock body (10560), a rotation lock shaft (10540), and a rotation lock pin (10530). Rotation lock body (10560) further comprises a set of distally oriented lock teeth (10561) that are configured to selectively engage teeth (10507) of shaft assembly (10505).

One end of resilient member (10580) is engaged with fixed member (10590), while the other end of resilient member (10580) is engaged with lock base (10562). Fixed member (10590) is fixedly secured to handle assembly (10546). Resilient member (10580) is configured to resiliently bias lock base (10562) distally. In the present example, resilient member (10580) comprises a coil spring, though it should be understood that any other suitable kind of resilient member may be used. Guide channel (10570) ensures that resilient member (10580) is facing the appropriate direction, preventing resilient member (10580) from buckling laterally or otherwise deviating from a path that is parallel to the longitudinal axis of shaft assembly (10505).

Rotation lock body (10560) is secured to lock base (10562), such that resilient member (10580) biases rotation lock body (10560) distally via lock base (10562). Rotation lock body (10560) and lock base (10562) are configured to translate within handle assembly (10546) but are prevented from rotating within handle assembly (10546). For instance, rotation lock body (10560) and/or lock base (10562) may be engaged with handle assembly (10546) via a complementary key and keyway. As another merely illustrative example, rotation lock body (10560) and/or lock base (10562) may have a non-circular cross-sectional profile that is received in a complementary recess or other mounting structure in handle assembly (10546). Other suitable configurations will be apparent to those of ordinary skill in the art in view of the teachings herein.

The proximal end of rotation lock shaft (10540) is engaged with lock base (10562) such that lock shaft (10540) and lock base (10562) translate with each other relative to handle assembly (10546). However, unlike lock base (10562), lock shaft (10540) is configured to rotate relative to handle assembly (10546) once lock shaft (10540) has reached a fully proximal position in an unlocked state, as described in greater detail below. The distal end of lock shaft (10540) includes a transversely oriented pin (10530), which is disposed within V-shaped slot (10520). Various suitable ways in which lock shaft (10540) may coupled with lock base (10562) in order to provide such functionality will be apparent to those of ordinary skill in the art in view of the teachings herein. For example, fins/pins could be implemented on lock shaft (10540) or pin (10530), where fins/pins are configured to interface with short grooves in any fixed element, such as handle assembly (10546), guide channel (10570) or fixed member (10590). Additionally, fins/pins do not necessarily need to be implemented on lock shaft (10540), as lock shaft (10540) could be fixed to lock base (10562) or lock body (10560), in which lock base (10562) or lock body (10560) could have fins/pins configured to rotate lock base (10562) or lock body (10560) once fully proximal, but limiting rotation in a distal position.

FIG. 102A shows locking mechanism (10500) in a locked state. In this state, resilient member (10580) urges lock body (10560) to a distal position, such that teeth (10561) are engaged with teeth (10507). Pin (10530) is positioned at the vertex of the angle defined by the oblique legs of slot (10520). With teeth (10561, 10507) engaged, lock body (10560) prevents shaft assembly (10505) from rotating relative to handle assembly (10546). When in a locked state, lock shaft (10540) is configured to only translate, so when the operator rotates knob (10510) relative to handle assembly (10546), V-shaped slot (10520) provides a camming action against pin (10530), driving lock body (10560) proximally via lock shaft (10540). This moves lock body (10560) to a proximal position as shown in FIG. 102B, where teeth (10561) are disengaged from teeth (10507). With teeth (10561, 10507) disengaged, locking mechanism (10500) is now in an unlocked state. When locking mechanism (10500) is in an unlocked state, shaft assembly (10505) is now rotatable relative to handle assembly (10546). Additionally, as mentioned above, when locking mechanism (10500) is in an unlocked state, lock shaft (10540) is now free to rotate relative to lock base (10562). It should be noted that, at this stage of operation, pin (10535) of shaft assembly (10505) has reached the end of slot (10525). Thus, further rotation of knob (10510) will cause shaft assembly (10505) to rotate due to engagement between pin (10535) and the end of slot (10525). Pin (10535) does not reach the end of slot (10525) until locking mechanism (10500) has reached the unlocked state shown in FIG. 102B.

Once the operator has achieved the desired rotational position of shaft assembly (10505), the operator may simply release knob (10510). When the operator releases knob (10510), the bias of resilient member (10580) will urge lock base (10562) and lock body (10560) back to the distal position shown in FIG. 102A, such that teeth (10561, 10507) will be reengaged to lock the adjusted rotational position of shaft assembly (10505) relative to handle assembly (10546). Pin (10530) will provide a camming action against slot (10525), rotating knob (10510) as pin (10530) and lock shaft (10540) travel distally until pin (10530) again reaches the apex of V-shaped slot (10520) as also shown in FIG. 102A. Locking mechanism (10500) will thus automatically transition back to the locked state after the operator releases knob (10510).

D. Exemplary Knob-Driven Braking Lock for Shaft Assembly

In some instances, it may be desirable to provide a separate, dedicated input feature for the operator to selectively lock and unlock rotation of shaft assembly (10130) relative to handle assembly (10120). To that end, FIGS. 103A-103B show an exemplary locking mechanism (10600) comprising a rotation knob (10605), a bearing washer (10615), a wave spring (10680), a cam interface plate (10620), and a locking knob (10630). Locking knob (10630) is rotatably fixed to body (10646). Locking feature comprises a locking arm (10631), and a locking body (10632) with a pair of cam lobes (10622, 10633). Cam interface plate (10620) further comprises a concave surface (10622) facing locking knob (10630) and a flat surface facing wave spring (10680).

Rotation knob (10605) is secured to shaft assembly (10608) such that rotation knob (10605) is operable to rotate shaft assembly (10608) relative to handle assembly (10646). It should be understood that handle assembly (10646) may further include any of the other features of handle assembly (20), any of the other features of handle assembly (10120), and/or any other suitable features. Shaft assembly (10608) may be configured like shaft assembly (1030), like shaft assembly (10130), or have any other suitable configuration. Moreover, the distal end of shaft assembly (10608) may include an end effector like end effector (40), an end effector like end effector (10140), and/or any other suitable kind of end effector.

Rotation knob (10605) further comprises an annular flange (10606) and a wave spring channel (10610). Bearing washer (10615) is placed in between flange (10606) and wave spring (10680), within wave spring channel (10610). Rotation knob (10605) is rotatably supported by handle assembly (10646) via annular flange (10606). In particular, handle assembly (10646) supports rotation knob (10605) via flange (10606) while still permitting rotation knob (10605) to rotate via flange (10606).

The operator may selectively rotate knob (10630) in order to selectively prevent or permit rotation of shaft assembly (10608) relative to handle assembly (10646). In particular, FIG. 103A shows locking mechanism (10600) in an unlocked state. In this state, wave spring (10680) is not being compressed against bearing washer (10615), such that shaft assembly is not encountering any substantial resistance to rotation relative to handle assembly (10646). When the operator rotates knob (10630) to transition locking mechanism to a locked state shown in FIG. 103B, cam lobe (10633) bears against cam interface plate (10620), driving cam interface plate (10620) distally. This in turn compresses wave spring (10680) against bearing washer (10615), generating a frictional braking effect against flange (10606) via bearing washer (10615). This effectively locks rotation of shaft assembly (10608) relative to handle assembly (10646). When the operator wishes to again rotate shaft assembly (10608) relative to handle assembly (10646), the operator may rotate knob (10630) back to the position shown in FIG. 103A, thereby transitioning locking mechanism (10600) back to the unlocked state.

It should be understood that either cam lobe (10633) or cam lobe (10644) may be used to drive cam interface plate (10620) distally, depending on the direction in which knob (10630) is rotated. In some other versions, knob (10630) is only rotatable in one direction to selectively lock rotation of shaft assembly (10608) relative to handle assembly (10646). Thus, one of cam lobes (10633, 644) may be omitted. It should also be understood that wave spring (10680) may be omitted. For instance, cam interface plate (10620) may be positioned and configured to bear directly against bearing washer (10615). In some variations, locking mechanism (10600) relies on selective engagement between teeth at the distal face of cam interface plate (10620) and at the proximal face of knob (10605) in order to provide selective locking, in a manner similar to locking mechanism (10500). It should also be understood that while knob (10630) can act as a manual input to lock and unlock rotation of shaft assembly (10608), knob (10630) could also be configured to provide additional action, including but not limited to driving articulation of an articulation section in shaft assembly (10608). Still other suitable variations will be apparent to those of ordinary skill in the art in view of the teachings herein.

XII. ULTRASONIC SURGICAL INSTRUMENT WITH ARTICULATION JOINT HAVING INTEGRAL STIFFENING MEMBERS

In some versions of instrument (10) it may be desirable to provide features that are configured to selectively provide rigidity to articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Features may thus be provided to selectively rigidize articulation section (130). Various examples of features that are configured to selectively provide rigidity to articulation section (130) and/or to limit or prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof such that the already existing rigidity of articulation section (130) may be increased. Thus, terms such as "provide rigidity" and "providing rigidity" shall be understood to include just increasing rigidity that is already present in some degree. The terms "provide rigidity" and "providing rigidity" should not be read as necessarily requiring articulation section (130) to completely lack rigidity before the rigidity is "provided."

A. Exemplary Collapsible and Expandable Rigidizing member

FIGS. 104A and 104B show shaft assembly (11030) of instrument (11010) described above having a collapsible and expandable tube (11200) added thereon. As will be described in more detail below, tube (11200) may function to selectively provide rigidity to articulation section (11130) and/or to prevent inadvertent deflection of end effector (11040) relative to outer sheath (11032). Tube (11200) of the present example comprises a plurality of annular members (11202) disposed about shaft assembly (11030), including articulation section (11130). As will be described in more detail below, annular members (11202) are longitudinally translatable along a length of shaft assembly (11030) relative to one another between an expanded configuration (FIG. 104A) and a collapsed configuration (FIG. 104B). Also as will be described in more detail below, when in the collapsed configuration, annular members (11202) function to provide rigidity to articulation section (11130) and/or to prevent inadvertent deflection of end effector (11040) relative to outer sheath (11032).

A distal-most ring-shaped member (11202A) of tube (11200) is secured to an exterior surface of distal outer sheath (11033) of shaft assembly (11030) distally of articulation section (11130). The remainder of annular members (11202) of outer sheath (11200) are slidably disposed about shaft assembly (11030), including articulation section (11130), such that annular members (11202) are translatable along a length shaft assembly (11030) relative to one another. As shown in FIG. 104A, when in the expanded configuration, annular members (11202), although positioned about articulation section (11130), are spaced apart from one another. The space between consecutive annular members (11202) allows articulation section (11130) to flex to thereby deflect end effector (11040) relative to the longitudinal axis of outer sheath (11032). As shown in FIG. 104B, annular members (11202) may be translated distally toward distal-most ring-shaped member (11202A) into the collapsed configuration. In the collapsed configuration, annular members (11202) abut one another to form a substantially continuous and rigid tubular member. Because annular members (11202) abut one another in the collapsed configuration, annular members (11202) function to provide rigidity to articulation section (11130) and/or to prevent inadvertent deflection of end effector (11040) relative to outer sheath (11032). If a user then desires to deflect end effector (11040), annular members (11202) may be moved back to the expanded configuration to permit articulation section (11130) to flex.

It should be understood that annular members (11202) may be moved directly (e.g. by grasping one or more of annular members (11202) directly, etc.) or by providing instrument (11010) with additional actuation features. For example, handle assembly (11020) of instrument (11010) may be provided with a slidable actuator that is operable to cause independent or concurrent translation of annular members (11202). It should further be understood that tube (11200) may be provided with additional features that are configured to improve the structural integrity of tube (11200) when in the collapsed configuration. For example, annular members (11202) may be provided with mating projections and recesses or slots that are configured to allow annular members (11202) to further engage one another when in the collapsed configuration. Additionally, or alternatively, annular members (11202) may be provided with mating pins and pinholes that are configured to allow annular members (11202) to further engage one another when in the collapsed configuration.

It should also be understood that annular members (11202) may be tethered to each other by wires, cables, or other kinds of flexible members. In such versions, when the proximal-most annular member (11202) is pulled proximally from the position shown in FIG. 104B to the position shown in FIG. 104A, such tethers may communicate the proximal motion from the proximal-most annular member (11202) to the rest of the annular members (11202), thereby pulling the rest of the proximal members from the positions shown in FIG. 104B to the positions shown in FIG. 104A. Such tethers may have a length selected to provide the spacing shown in FIG. 104A; while also having the flexibility to allow annular members (11202) to reach the positions shown in FIG. 104B. Various suitable ways in which annular members (11202) may be configured, actuated, and coupled with each other will be apparent to those of ordinary skill in the art in view of the teachings herein.

B. Exemplary Inflatable and Deflatable Rigidizing member

FIGS. 105-106C show shaft assembly (11030) of instrument (11010) described above having an inflatable and deflatable balloon (11220) secured thereto. As will be described in more detail below, balloon (11220) may function to selectively provide rigidity to articulation section (11130) and/or to prevent inadvertent deflection of end effector (11040) relative to outer sheath (11032). Balloon (11220) of the present example comprises a tubular body (11222) disposed about shaft assembly (11030), including articulation section (11130). Fluid is provided to tubular body (11222) via a tube (11224) which extends along a length of shaft assembly (11030) adjacent an exterior surface of outer sheath (11030). As will be described in more detail below, tube (11224) functions to provide fluid to or to remove fluid from tubular body (11222) so as to transition balloon (11220) between a deflated state (FIGS. 106A and 106C) and an inflated state (FIG. 106B). Also as will be described in more detail below, when in the inflated state, balloon (11220) functions to provide rigidity to articulation section (11130) and/or to prevent inadvertent deflection of end effector (11040) relative to outer sheath (11032) when balloon (11220) is in an inflated state.

Tubular body (11222) is disposed about shaft assembly (11030), including articulation section (11130). In the present example, tubular body (11222) is formed of a flexible yet non-extensible material. Various suitable materials that may be used to form tubular body (11222) will be apparent to those of ordinary skill in the art in view for the teachings herein. A distal end (11222A) of tubular body (11222) is secured to an exterior surface of distal outer sheath (11033) of shaft assembly (11030) distally of articulation section (11130). A proximal end (11222B) of tubular body (11222) is secured to an exterior surface of outer sheath (11032) of shaft assembly (11030) proximally of articulation section (11130). Thus, as shown in FIG. 106A, tubular body (11222) completely encompasses articulation section (11130). As shown in FIGS. 106A and 106C, when in the deflated state, tubular body (11222), although positioned about articulation section (11130), remains flexible enough to allow articulation section (11130) to flex to thereby deflect end effector (11040) relative to outer sheath (11032). As shown in FIG. 106B, when in the inflated state, tubular body (11222) becomes more rigid and functions to provide rigidity to articulation section (11130) and/or to prevent inadvertent deflection of end effector (11040) relative to outer sheath (11032). If a user then desires to deflect end effector (11040), tubular body (11222) may be deflated to permit articulation section (11130) to flex.

In the present example, the fluid communicated to tubular body (11222) comprises saline, though it should be understood that any other suitable fluid may be used. There are various ways in such fluid (e.g., saline, etc.) may be provided to tubular body (11222). By way of example only, a fluid syringe (not shown) may be coupled with a proximal end of tube (11224) to thereby provide fluid to and to remove fluid from tubular body (11222). It should also be understood that, when fluid is communicated to tubular body (11222), the non-extensibility of tubular body may enable tubular body (11222) to be inflated to pressures that make tubular body (11222) substantially rigid, thereby effectively rigidizing articulation section (11130). Various suitable fluid pressures and volumes that may be used for balloon (11220) will be apparent to those of ordinary skill in the art in view of the teachings herein.

C. Exemplary Accordion-Like Rigidizing member

FIGS. 107-111B show shaft assembly (11030) of instrument (11010) described above having an accordion-like rigidizing member (11240) incorporated therein. As will be described in more detail below, rigidizing member (11240) may function to selectively provide rigidity to articulation section (11130) and/or to prevent inadvertent deflection of end effector (11040) relative to outer sheath (11032). As best seen in FIGS. 108A and 108B, rigidizing member (11240) of the present example comprises a plurality of bellows (11242) linked to one another along a length of rigidizing member (11240). As will be described in more detail below, rigidizing member (11240) is longitudinally translatable along a length of shaft assembly (11030) so as to transition bellows (11242) between a contracted configuration (FIG. 108A) and an expanded configuration (FIG. 108B). Also as will be described in more detail below, when in the contracted configuration, bellows (11242) of rigidizing member (11240) function to provide rigidity to articulation section (11130) and/or to prevent inadvertent deflection of end effector (11040) relative to outer sheath (11032). By way of example only, rigidizing member (11240) may be formed by a series of linkages that pivotably define bellows (11242). Use of the term "bellows" should therefore be understood to not necessarily require a vessel that defines a variable capacity. Various suitable ways in which rigidizing member (11240) may be configured will be apparent to those of ordinary skill in the art in view of the teachings herein.

As shown in FIG. 107, shaft assembly (11030) of the present example comprises a plurality of couplers (11230) pivotably linked to one another via a plurality of pins (11232). Couplers (11230) are disposed about shaft assembly (11030), including articulation section (11130). A distal-most coupler (11230A) of couplers (11230) is secured to an exterior surface of distal outer sheath (11033) of shaft assembly (11030) distally of articulation section (11130). A proximal-most coupler (11230B) of couplers (11230) is secured to an exterior surface of outer sheath (11032) of shaft assembly (11030) proximally of articulation section (11130). Thus, as shown in FIG. 107, couplers (11230), when linked to one another, completely encompass articulation section (11130). Each coupler (11230) includes a pair of angled surfaces (11234) which, when couplers (11230) are linked to one another, forms a plurality of V-shaped pockets (11236) in a side surface rigidizing member (11240). Pockets (11236) are configured to provide clearance between couplers (11230) to allow couplers (11230) to pivot relative to each other about pins (11232) as articulation section (11130) is articulated. Pockets (11236) are also configured to receive bellows (11242) as described in greater detail below. While pockets (11236) are shown on only one side of couplers (11230) in this example, it should be understood that pockets (11236) may be provided on both sides of couplers (11230) if desired. Such a configuration may permit or facilitate articulation of articulation sections in two opposite directions relative to the longitudinal axis of outer sheath (11032).

As shown in FIG. 110A, with bellows (11242) in the contracted configuration, bellows (11242) of rigidizing member (11240) are configured to extend through V-shaped pockets (11236) and bear against angled surfaces (11234) of couplers (11230) to thereby provide rigidity to articulation section (11130) and/or to prevent inadvertent deflection of end effector (11040) relative to outer sheath (11032). As shown in FIG. 110B, rigidizing member (11240) is drawn proximally so as to transition bellows (11242) to the expanded configuration. This transitioning of bellows (11242) draws bellows (11242) inwardly from V-shaped pockets (11236) such that bellows (11242) no longer bear against angled surfaces (11234) of couplers (11230) and such that articulation section (11130) may flex to thereby deflect end effector (11040) relative to outer sheath (11032).

In some versions of instrument (11010), rigidizing member (11240) may be coupled with rotation knob (11120) such that rotation of rotation knob (11120) causes concurrent articulation of articulation section (11130) and translation of rigidizing member (11240). For instance, as shown in FIGS. 111A and 111B, the proximal end of rigidizing member (11240) may be coupled with rotation knob (11120) via a slot (11117) formed in a side of first hollow cylindrical portion (11112) of housing (11110). The distal end of rigidizing member (11240) may be fixedly secured to distal outer sheath (11033) or some other structure that is distal to articulation section (11130). Thus, as rotation knob (11120) is rotated in a first direction from the position shown in FIG. 111A to the position shown in FIG. 111B to cause articulation of articulation section (11130), rigidizing member (11240) is concurrently drawn proximally so as to transition bellows (11242) from the configuration shown in FIG. 110A to the configuration shown in FIG. 110B. This causes bellows (11242) to disengage angled surfaces (11234), thus allowing articulation section (11130) to flex to thereby deflect end effector (11040) relative to outer sheath (11032).

As rotation knob (11120) is rotated in the opposite direction from the position shown in FIG. 111B to the position shown in FIG. 111A to return articulation section (11130) to back toward the straight configuration, rigidizing member (11240) is concurrently driven distally so as to transition bellows (11242) back from the configuration shown in FIG. 110B to the configuration shown in FIG. 110A. This causes bellows (11242) to re-engage angled surfaces (11234), thus providing rigidity to articulation section (11130) and/or preventing inadvertent deflection of end effector (11040) relative to outer sheath (11032). It should therefore be understood that articulation section (11130) may be automatically rigidized upon reaching a straight configuration.

D. Exemplary Pegged Rigidizing member

FIGS. 112-114B show a rigidizing member (11260) that may be used in lieu of rigidizing member (11240) discussed above. As best seen in FIGS. 112 and 113, rigidizing member (11260) of the present example comprises an elongate shaft (11262), having a rectangular cross-section, and a plurality of pegs (11264) extending transversely from a side surface of shaft (11262). As will be described in more detail below, rigidizing member (11260) is laterally translatable within an interior space of shaft assembly (11030) between a first position (FIG. 114A) and a second position (FIG. 114B). Also as will be described in more detail below, when in the first position, pegs (11264) of rigidizing member (11260) function to provide rigidity to articulation section (11130) and/or to prevent inadvertent deflection of end effector (11040) relative to outer sheath (11032).

As shown in FIGS. 114A and 114B, rigidizing member (11260) is configured to be positioned within an interior space of shaft assembly (11030), including articulation section (11130). As shown in FIG. 114A, with rigidizing member (11260) positioned within the interior space of shaft assembly (11030) in the first position, pegs (11264) are configured to extend through V-shaped pockets (11236) and bear against (or at least contact) angled surfaces (11234) of couplers (11230) to thereby provide rigidity to articulation section (11130) and/or to prevent inadvertent deflection of end effector (11040) relative to outer sheath (11032). As shown in FIG. 114B, rigidizing member (11260) is translated laterally inwardly into the second position to thereby draw pegs (11264) inwardly from V-shaped pockets (11236) such that pegs (11264) no longer bear against (or otherwise contact) angled surfaces (11234) of couplers (11230). With pegs (11264) moved out of V-shaped pockets (11236), articulation section (11130) is free to flex to thereby deflect end effector (11040) relative to outer sheath (11032). Various suitable ways in which rigidizing member (11260) may be actuated between the positions shown in FIGS. 114A and 114B will be apparent to those of ordinary skill in the art in view of the teachings herein.

E. Exemplary Variable-Thickness Rigidizing Member and Couplers

FIGS. 115-116C show a variable-thickness rigidizing member (11280) that may be incorporated into articulation section (11130) of shaft assembly (11030) of instrument (11010). As will be described in more detail below, rigidizing member (11280) may function to selectively provide rigidity to articulation section (11130) and/or to prevent inadvertent deflection of end effector (11040) relative to outer sheath (11032). As best seen in FIG. 115, rigidizing member (11280) of the present example comprises a plurality of flanges (11282) linked to one another by a plurality of flexible rods (11284), which are positioned between consecutive flanges (11282). It should be understood that rods (11284) may be substituted with wires, cables, or any other suitable kind of flexible member. As will be described in more detail below, rigidizing member (11280) is longitudinally translatable along a length of shaft assembly (11030) so as to transition flanges (11282) between a first position (FIG. 116A) and a second position (FIGS. 116B and 116C). Also as will be described in more detail below, when in the first position, flanges (11282) of rigidizing member (11280) function to provide rigidity to articulation section (11130) and/or to prevent inadvertent deflection of end effector (11040) relative to outer sheath (11032).

In the present example a modified version of shaft assembly (11030) comprises a plurality of couplers (11290) that are pivotably linked to one another via a plurality of pins (11292). Couplers (11290) are disposed about shaft assembly (11030), including articulation section (11130). A distal-most coupler (11290A) of couplers (11290) is secured to an exterior surface of distal outer sheath (11033) of shaft assembly (11030) distally of articulation section (11130). A proximal-most coupler (11290B) of couplers (11290) is secured to an exterior surface of outer sheath (11032) of shaft assembly (11030) proximally of articulation section (11130). Thus, when linked to one another via pins (11292), couplers (11290) completely encompass articulation section (11130). As mentioned above, couplers (11290) are pivotably linked to one another via a plurality of pins (11292) such that couplers (11290) pivot about a plurality of axes defined by pins (11292). Pins (11292), which pivotably link couplers (11290) to one another, are aligned such that articulation section (11130) may flex along a plane (P1) oriented perpendicular to the axes of rotation of pins (11292).

As shown in FIGS. 116A-116C, rigidizing member (11280) is configured to be positioned within an interior space of shaft assembly (11030), including articulation section (11130), inside the assembly formed by couplers (11290). Rigidizing member (11280) is oriented such that flanges (11282) are substantially parallel to plane (P1) and perpendicular to the axes of rotation of pins (11292). As shown in FIG. 116A, with flanges (11282) in the first position, flanges (11282) of rigidizing member (11280) are positioned such that each flange (11282) extends between a space defined by consecutive couplers (11290) and such that pins (11292) are positioned above and below an intermediate portion of flanges (11282). Because flanges (11282) are positioned at the joints of couplers (11290), flanges (11282) prevent couplers (11290) from flexing at those joints. This further prevents flexing at articulation section. Thus, when rigidizing member (11280) is in the position shown in FIG. 116A, the assembly formed by rigidizing member (11280) and couplers (11290) prevents bending of articulation section (11130) and effectively rigidizes articulation section (11130).

As shown in FIGS. 116B and 116C, rigidizing member (11280) is translated proximally so as to move flanges (11282) away from the joints of couplers (11290) and to position flexible rods (11284) at the joints of couplers (11290). This positioning enables couplers (11290) to pivot at the joints. With couplers (11290) being enabled to pivot, and with flexible rods (11284) being enabled to flex, articulation section (11130) is thereby enabled to articulate as shown in FIG. 116C. Various suitable ways in which rigidizing member (11280) may be actuated between the position shown in FIG. 116A and the positions shown in FIGS. 116B-116C will be apparent to those of ordinary skill in the art in view of the teachings herein.

F. Exemplary Variable-Thickness Rigidizing Member

FIGS. 117-122C show shaft assembly (11030) of instrument (11010) described above having a variable-thickness rigidizing member (11300) incorporated therein. As will be described in more detail below, rigidizing member (11300) may function to selectively provide rigidity to articulation section (11130) and/or to prevent inadvertent deflection of end effector (11040) relative to outer sheath (11032). As best seen in FIG. 118, rigidizing member (11300) of the present example comprises a plurality of flanges (11302) linked to one another by a plurality of flexible rods (11304) that are positioned between consecutive flanges (11302). It should be understood that rods (11304) may be substituted with wires, cables, or any other suitable kind of flexible member. As shown in FIG. 119, flanges (11302) of the present example have a rectangular cross-section. In some other versions, flanges (11302) have a circular segment cross-section as shown in FIG. 120. Alternatively, flanges (11302) may have any other suitable cross-section as will be appreciated by one of ordinary skill in the art in view of the teachings herein. As will be described in more detail below, rigidizing member (11300) is longitudinally translatable along a length of shaft assembly (11030) so as to transition flanges (11302) between a first position (FIG. 122A) and a second position (FIGS. 122B and 122C). As will also be described in more detail below, when rigidizing member (11300) is in the first position, flanges (11302) of rigidizing member (11300) function to provide rigidity to articulation section (11130) and/or to prevent inadvertent deflection of end effector (11040) relative to outer sheath (11032).

As shown in FIG. 121, shaft assembly (11030) of the present example, including articulation section (11130), defines a channel (11310) in a top portion of ribbed body portions (11132, 11134) of articulation section (11130). Channel (11310) is configured to slidably receive rigidizing member (11300) such that rigidizing member (11300) is longitudinally translatable within channel (11310) along a length of shaft assembly (1130).

As shown in FIGS. 122A-122C, rigidizing member (11300) is configured to be positioned within an interior space of shaft assembly (11030), including articulation section (11130). Rigidizing member (11300) is oriented such that flanges (11302) are substantially parallel to a plane (P2) along which articulation member (11130) is configured to flex. As shown in FIG. 122A, with flanges (11302) in the first position, flanges (11302) of rigidizing member (11300) are positioned such that each flange (11302) extends between the spaces between consecutive retention collars (11133). Because of the orientation and position of flanges (11302) in this state, and because of the width of flanges (11302), flanges (11302) block relative movement of retention collars (11133) along plane (P2). Rigidizing member (11300) thus prevents bending of articulation section (11130) and effectively rigidizes articulation section (11130).

As shown in FIGS. 122B and 122C, rigidizing member (11300) is translated proximally so as to position flanges (11302) away from the spaces between consecutive retention collars (11133) and to position flexible rods (11304) between the spaces between consecutive retention collars (11133). This positioning enables retention collars (11133) to move relative to each other along plane (P2). With such movement of collars (11133) enabled, and with flexible rods (11304) being enabled to flex, articulation section (11130) is thereby enabled to articulate as shown in FIG. 122C. Various suitable ways in which rigidizing member (11300) may be actuated between the position shown in FIG. 122A and the positions shown in FIGS. 122B-122C will be apparent to those of ordinary skill in the art in view of the teachings herein.

G. Exemplary Rigidizing Sleeve Member

FIGS. 123-125C show an exemplary rigidizing sleeve member (11320). As will be described in more detail below, rigidizing sleeve member (11320) may function to selectively provide rigidity to articulation section (11130) and/or to prevent inadvertent deflection of end effector (11040) relative to outer sheath (11032). As best seen in FIG. 123, rigidizing member (11320) of the present example comprises a proximal semi-circular-cylindrical portion (11322) and a distal semi-circular-cylindrical portion (11324). Portions (11322, 11324) are coupled together via a flexible rod (11326). Rod (11326) provides lateral flexibility yet has sufficient column strength to provide effective actuation of rigidizing sleeve member (11320) as described below. It should be understood that rod (11326) may be substituted with a band or any other suitable kind of flexible member. Cylindrical portions (11322, 11324) are sized to receive and selectively couple about shaft assembly (11030) in a snap-fit manner. As will be described in more detail, however, sleeve member (11320) remains able to translate longitudinally along a length of shaft assembly (11030) so as to transition distal cylindrical portion (11324) between a first position (FIG. 125A) and a second position (FIGS. 125B and 125C). Also as will be described in more detail below, when sleeve member (11320) is in the first position, distal cylindrical portion (11324) of sleeve member (11320) functions to provide rigidity to articulation section (11130) and/or to prevent inadvertent deflection of end effector (11040) relative to outer sheath (11032).

As best seen in FIG. 123, proximal cylindrical portion (11322) comprises a pair of flanges (11328) extending from opposing sides of an exterior surface of proximal cylindrical portion (11322). A user may engage flanges (11328) to assist the user in positioning proximal cylindrical portion (11322) about and removing proximal cylindrical portion (11322) from shaft assembly (11030). Alternatively, any other suitable features may be used to facilitate manipulation of proximal cylindrical portion (11322). As shown in FIG. 124, distal cylindrical portion (11324) comprises a plurality of rectangular projections (11327) extending inwardly from an interior surface of distal cylindrical portion (11324).

As shown in FIGS. 125A-125C, and as discussed above, distal cylindrical portion (11324) is configured to be positioned about shaft assembly (11030), in particular, about articulation section (11130). As shown in FIG. 125A, with distal cylindrical portion (11324) in the first position, projections (11327) of distal cylindrical portion (11324) are positioned such that each projection (11327) is positioned within a corresponding space defined between consecutive retention collars (11133) such that projections (11327) abut consecutive retention collars (11133). Because projections (11327) abut consecutive retention collars (11133) when sleeve member (11320) is in the first position, projections (11327) function to provide rigidity to articulation section (11130) and/or to prevent inadvertent deflection of end effector (11040) relative to outer sheath (11032) by preventing movement of retention collars (11133) relative to each other.

As shown in FIGS. 125B and 125C, rigidizing sleeve member (11320) is translated proximally so as to draw projections (11327) from the spaces defined by consecutive retention collars (11133) and so as to position projections (11327) adjacent an exterior surface of retention collars (11133). With sleeve member (11320) in this position, the space between consecutive retention collars (11133) allows articulation section (11130) to flex to thereby deflect end effector (11040) relative to outer sheath (11032) as shown in FIG. 125C.

Distal cylindrical portion (11324) is formed of a resilient material that enables projections (11327) to deflect outwardly from the position shown in FIG. 125A to the position shown in FIGS. 125B and 125C. The resilient properties of distal cylindrical portion (11324) also cause projections (11327) to snap back into the spaces defined between consecutive retention collars (11133) when sleeve member (11320) is advanced distally back to the position shown in FIG. 125A. In the present example, sleeve member (11320) may be returned to the position shown in FIG. 125A after articulation section (11130) has been returned to a straight, non-articulated configuration. Also in the present example, sleeve member (11320) is translated between the distal position (FIG. 125A) and the proximal position (FIGS. 125B and 125C) by an operator grasping proximal cylindrical portion (11322) and thereby sliding sleeve member (11320) along shaft assembly (11030). Other suitable ways in which sleeve member (11320) may be actuated will be apparent to those of ordinary skill in the art in view of the teachings herein.

H. Exemplary C-Channel Rigidizing member

FIGS. 126-130B show another exemplary rigidizing member (11340). As will be described in more detail below, rigidizing member (11340) may function to selectively provide rigidity to articulation section (11130) and/or to prevent inadvertent deflection of end effector (11040) relative to outer sheath (11032). As best seen in FIG. 126, rigidizing member (11340) of the present example comprises a plurality of C-channel members (11342) linked to one another by a plurality of flexible rods (11344), which are positioned between consecutive C-channel members (11342). It should be understood that rods (11344) may be substituted with wires, cables, or any other suitable kind of flexible member. As will be described in more detail below, rigidizing member (11340) is configured to translate longitudinally along a length of shaft assembly (11030) so as to transition C-channel members (11342) between a first position (FIG. 129A) and a second position (FIGS. 129B and 129C). Also as will be described in more detail below, when rigidizing member (11340) is in the first position, C-channel members (11342) of rigidizing member (11340) function to provide rigidity to articulation section (11130) and/or to prevent inadvertent deflection of end effector (11040) relative to outer sheath (11032).

As shown in FIGS. 129A-129C, C-channel members (11342) are configured to be positioned about shaft assembly (11030), in particular, about articulation section (11130). As shown in FIG. 129A, with rigidizing member (11340) in the first position, C-channel members (11342) are positioned such that each C-channel member (11342) is positioned within a corresponding space defined between consecutive retention collars (11133) such that C-channel members (11342) abut consecutive retention collars (11133). Because C-channel members (11342) abut consecutive retention collars (11133) when rigidizing member (11340) is in the first position, C-channel members (11342) function to provide rigidity to articulation section (11130) and/or to prevent inadvertent deflection of end effector (11040) relative to outer sheath (11032) by preventing movement of retention collars (11133) relative to each other.

As shown in FIGS. 129B and 129C, rigidizing member (11340) is translated proximally so as to draw C-channel members (11342) from the spaces defined between consecutive retention collars (11133) and so as to position C-channel members (11342) adjacent an exterior surface of retention collars (11133). With rigidizing member (11340) in this position, the space between consecutive retention collars (11133) allows articulation section (11130) to flex to thereby deflect end effector (11040) relative to outer sheath (11032) as shown in FIG. 129C.

Rigidizng member (11340) is formed of a resilient material that enables C-channel members (11342) to deform and deflect outwardly from the position shown in FIG. 129A to the position shown in FIGS. 129B and 129C. The resilient properties of C-channel members (11342) also cause C-channel members (11342) to snap back into the spaces defined between consecutive retention collars (11133) when rigidizing member (11340) is advanced distally back to the position shown in FIG. 129A. In the present example, rigidizing member (11340) may be returned to the position shown in FIG. 129A after articulation section (11130) has been returned to a straight, non-articulated configuration. Various suitable ways in which rigidizing member (11340) may be actuated will be apparent to those of ordinary skill in the art in view of the teachings herein.

Although the example discussed above is provides just a single rigidizing member (11340), on just one side of articulation section (11130), it should be understood that two or more rigidizing members (11340) may be used. For instance, as shown in FIGS. 130A and 130B, a pair of rigidizing members (11340) may be positioned on opposite lateral sides of articulation section (11130) to provide rigidity to articulation section (11130) and/or to prevent inadvertent deflection of end effector (11040) relative to outer sheath (11032) in multiple directions.

I. Exemplary Rigidizing Clip Member

FIGS. 131-132B show an exemplary rigidizing clip member (11360). As will be described in more detail below, rigidizing clip member (11360) may function to selectively provide rigidity to articulation section (11130) and/or to prevent inadvertent deflection of end effector (11040) relative to outer sheath (11032). As best seen in FIG. 131, rigidizing clip member (11360) of the present example comprises a semi-circular-cylindrical body (11362). A plurality of slots (11364) formed in opposing side surfaces of cylindrical body (11362) separate a plurality of tabs (11366). As shown in FIGS. 132A and 132B, rigidizing clip member (11360) is configured to be positioned about shaft assembly (11030), in particular, about articulation section (11130).

As shown in FIG. 132A, spaces defined between consecutive retention collars (11133) provide clearance allowing articulation section (11130) to flex to thereby deflect end effector (11040) relative to outer sheath (11032). As shown in FIG. 132B, with rigidizing clip member (11360) positioned about articulation section (11130), tabs (11366) are positioned such that each tab (11366) is positioned within the space defined by consecutive retention collars (11133). Tabs (11366) abut consecutive retention collars (11133) in this state. Because tabs (11366) abut consecutive retention collars (11133), tabs (11366) function to provide rigidity to articulation section (11130) and/or to prevent inadvertent deflection of end effector (11040) relative to outer sheath (11032) by preventing movement of retention collars (11133) toward one another. It should be understood that clip member (11360) may be formed of a resilient material such that clip member (11360) may be removably secured to articulation section (11130) through a snap fit. Alternatively, clip member (11360) may be removably secured to articulation section (11130) in any other suitable fashion.

J. Exemplary Dual Structural Bands

FIGS. 133A-136B show a modified version of shaft assembly (11030) of instrument (11010) described above having a pair of overlapping articulation bands (11380, 11390). As will be described in more detail below, articulation bands (11380, 11390) may function to provide rigidity to articulation section (11130) and/or to prevent inadvertent deflection of end effector (11040) relative to outer sheath (11032). As best seen in FIG. 134, articulation band (11380) comprises an elongate strip (11382) having a plurality of circular openings (11384) formed therein to provide "weak spots" along the length of strip (11382). Circular openings (11384) are spaced apart from one another, and provide flexibility to articulation band (11380) at circular openings (11384). As best seen in FIG. 135, articulation band (11390) comprises an elongate strip (11392) having a plurality of opposing rectangular recesses (11394) formed therein to provide "weak spots" along the length of strip (11392). Rectangular recesses (11394) are spaced apart from one another, and provide flexibility to articulation band (11390) at rectangular recesses (11394). The spacing of recesses (11394) corresponds to the spacing of openings (11384).

As shown in FIGS. 133A and 133B, articulation bands (11380, 11390) are positioned within an interior space of shaft assembly (11030), including articulation section (11130). One set of articulation bands (11380, 11390) is positioned on one side of waveguide (11180); while another set of articulation bands (11380, 11390) is positioned on the other side of waveguide (11180). Articulation bands (11380, 11390) are longitudinally translatable relative to one another between a first configuration (FIG. 136A) and a second configuration (FIG. 136B). As shown in FIG. 136A, in the first configuration, articulation bands (11380, 11390) overlap one another in an arrangement such that circular openings (11384) of articulation band (11380) are offset from rectangular recesses (11394) of articulation band (11390). With these "weak spots" of articulation bands (11380, 11390) offset from one another, the remaining "strong spots" of articulation bands (11380, 11390) accommodate for the "weak spots" and prevent articulation bands (11380, 11390) from flexing. Articulation bands (11380, 11390) thus cooperate to provide rigidity to articulation section (11130) and/or prevent inadvertent deflection of end effector (11040) relative to outer sheath (11032) when articulation bands (11380, 11390) are arranged as shown in FIG. 136A. In the present example, articulation bands (11380, 11390) are positioned in this arrangement when articulation section (11130) is in a straight, non-articulated configuration as shown in FIG. 133A.

As shown in FIG. 136B, in the second configuration, articulation bands (11380, 11390) overlap one another in an arrangement such that circular openings (11384) of articulation band (11380) align with rectangular recesses (11394) of articulation band (11390). With these "weak spots" of articulation bands (11380, 11390) aligned, articulation bands (11380, 11390) may flex to thereby allow articulation section (11130) to flex to thereby deflect end effector (11040) relative to outer sheath (11032). In other words, articulation bands (11380, 11390) cooperate to provide flexibility to articulation section (11130) when articulation bands (11380, 11390) are arranged as shown in FIG. 136B. While the "weak spots" of articulation bands (11380, 11390) are formed as circular openings (11384) and rectangular recesses (11394) in the present example, it should be understood that the "weak spots" may have any other suitable configurations. Various suitable alternative configurations for "weak spots" will be apparent to those of ordinary skill in the art in view of the teachings herein.

Articulation control assembly (11100) may be readily modified to provide coordinated movement of articulation bands (11380, 11390). For instance, in one merely illustrative example, articulation control assembly (11100) is configured such that knob (11120) is rotatable through two ranges of motion from a neutral position where articulation section (11130) is in a straight, non-articulated configuration as shown in FIG. 133A. With knob (11120) in the neutral position, articulation bands (11380, 11390) are in the arrangement shown in FIG. 136A, such that articulation bands (11380, 11390) rigidize articulation section (11130), with articulation section (11130) being in the straight, non-articulated configuration. When knob (11120) is rotated through a first range of motion from the neutral position, articulation control assembly (11100) drives a first articulation band (11380, 11390) in each pair of articulation bands (11380, 11390) relative to a second articulation band (11380, 11390) in that pair. The second articulation band (11380, 11390) remains stationary during this first range of motion of knob (11120).

When knob (11120) completes the first range of motion, each pair of articulation bands (11380) is transitioned to the configuration shown in FIG. 136B, such that articulation bands (11380, 11390) are arranged to provide flexibility. When the operator then rotates knob (11120) through a second range of motion after completing the first range of motion, articulation control assembly (11100) drives a both articulation bands (11380, 11390) of one pair together in a first longitudinal direction, while simultaneously driving both articulation bands (11380, 11390) of the other pair together in a second longitudinal direction. The pairs of articulation bands (11380, 11390) thus cooperate to drive articulation as knob (11120) is rotated through the second range of motion.

When the operator wishes to subsequently transition articulation section (11130) back to a straight, non-articulated state, the operator may simply reverse rotation of knob (11120). During this reversal, the pairs of articulation bands (11380, 11390) will again cooperate to drive articulation section (11130) back to the straight, non-articulated state. Once articulation section (11130) reaches the straight, non-articulated state, knob (11120) will transition from the second range of motion back to the first range of motion as knob (11120) is further rotated. As knob (11120) is rotated back through the first range of motion toward the neutral position, articulation control assembly (11100) again drives a first articulation band (11380, 11390) in each pair of articulation bands (11380, 11390) relative to a second articulation band (11380, 11390) in that pair. The second articulation band (11380, 11390) remains stationary during this first range of motion of knob (11120). Once knob (11120) reaches the neutral position again, articulation bands (11380, 11390) are again returned to the arrangement shown in FIG. 136A, such that articulation bands (11380, 11390) again rigidize articulation section (11130). Various structures and features that may be incorporated into articulation control assembly (11100) in order to provide the above described operation will be apparent to those of ordinary skill in the art in view of the teachings herein.

While knob (11120) is used in the present example, it should be understood that any other suitable kind of actuator may be used, including but not limited to a slider, a lever, a dial, etc. In addition, in the present example knob (11120) is operable to both selectively rigidize articulation section (11130) (as knob (11120) is rotated through the first range of motion) and to drive articulation of articulation section (11130) (as knob (11120) is rotated through the second range of motion). In some other versions, two separate actuators are used—one actuator to selectively rigidize articulation section (11130) and another actuator to drive articulation of articulation section (11130).

It should also be understood that any other example described herein for selectively rigidizing articulation section (11130) may also be coupled with a modified version of articulation control assembly (11100) as described above. In other words, any other example described herein for selectively rigidizing articulation section (11130) may be coupled with a knob (11120) that rotates through two ranges of motion—a first range of motion to selectively rigidize articulation section (11130) and a second range of motion to drive articulation of articulation section (11130). Similarly, any other kind of actuator may be used, including but not limited to a slider, a lever, a dial, etc. Such alternative actuators may also be moved through two different ranges of motion to selectively rigidize articulation section (11130) (during a first range of motion of the actuator) and to drive articulation of articulation section (during a second range of motion of the actuator). Furthermore, any other example described herein for selectively rigidizing articulation section (11130) may also be coupled with two separate actuators—one actuator to selectively rigidize articulation section (11130) and another actuator to drive articulation of articulation section (11130). Various suitable ways in which these exemplary alternatives may be incorporated into the various examples described herein will be apparent to those of ordinary skill in the art in view of the teachings herein.

K. Exemplary Rigidizing Tubular Member

FIG. 137 shows a modified version of shaft assembly (11030) of instrument (11010) having a tubular member (11400) that is configured to selectively rigidize. As will be described in more detail below, tubular member (11400) may function to selectively provide rigidity to articulation section (11130) and/or to prevent inadvertent deflection of end effector (11040) relative to outer sheath (11032). Tubular member (11400) comprises hollow-cylindrical body (11402) filled with magnetorheological fluid (MR fluid) (11404). Cylindrical body (11402) is positioned about shaft assembly (11030) and encompasses articulation section (11130). Cylindrical body (11402) is capped at a distal end and a proximal end by a pair of magnets (11406). In the present example, magnets (11406) comprise electromagnets, such that magnets (11406) may be selectively activated (and thereby be selectively magnetized) by application of an electric current to magnets (11406). A distal magnet (11406A) of magnets (11406) is secured to an exterior surface of distal outer sheath (11033) of shaft assembly (11030) distally of articulation section (11130). A proximal magnet (11406B) of magnets (11406) is secured to an exterior surface of outer sheath (11032) of shaft assembly (11030) proximally of articulation section (11130).

Magnets (11406) are in direct contact with MR fluid (11404) such that magnets (11406) may function to selectively magnetize MR fluid (11404) based on selective activation of magnets (11406). Prior to magnetizing MR fluid (11404), cylindrical body (11402) of tubular member (11400) is operable to flex to thereby allow articulation section (11130) to flex to thereby deflect end effector (11040) relative to outer sheath (11032). Once MR fluid (11404) is magnetized via activation of magnets (11406), however, MR fluid (11404) becomes substantially rigid within cylindrical body (11402) to thereby rigidize tubular member (11400). Once tubular member (11400) is rigidized, tubular member (11400) may function to provide rigidity to articulation section (11130) and/or to prevent inadvertent deflection of end effector (11040) relative to outer sheath (11032).

By way of example only, one or more wires, conductive traces, and/or other electrically conductive conduits may extend along the length of shaft assembly (11030) to enable electrical power to be selectively delivered to magnets (11406). In one merely illustrative example, articulation control assembly (11100) is modified such that knob (11120) causes closure of an electrical switch when knob (11120) is rotated to a neutral position that is associated with articulation section (11130) being in a straight, non-articulated configuration. This switch may be in communication with magnets (11406) and a source of electrical power such that magnets (11406) are activated when knob (11120) is in the neutral position. Articulation section (11130) will thus be rigidized when knob (11120) is in the neutral position, with articulation section (11130) in the straight, non-articulated configuration. As soon as knob (11120) is rotated away from the neutral position to articulate articulation section (11130), the switch will be transitioned to an open state, thereby deactivating magnets (11406), thereby de-rigidizing articulation section (11130) and allowing articulation section (11130) to be articulated. When knob (11120) is subsequently rotated back to the neutral position, the switch will again be closed, thereby re-activating magnets (11406), thereby rigidizing articulation section (11130) again as articulation section (11130) reaches the straight, non-articulated configuration. Various other suitable ways in which magnets (11406) may be selectively activated will be apparent to those of ordinary skill in the art in view of the teachings herein.

L. Exemplary Rigidizing Valve Assembly

FIG. 138 shows a modified version of shaft assembly (11030) of instrument (11010) described above having a valve assembly (11420). As will be described in more detail below, valve assembly (11420) is configured to selectively rigidize so as to provide rigidity to articulation section (11130) and/or to prevent inadvertent deflection of end effector (11040) relative to outer sheath (11032). Valve assembly (11420) comprises a pair of plungers (11422, 11424) that are slidably disposed within a pair of cylinders (11426, 11428). Plungers (11422, 11424) are coupled with articulation bands (11140, 11142) of shaft assembly (11030) such that translation of articulation bands (11140, 11142) caused by articulation of articulation section (11130) causes concurrent translation of plungers (11422, 11424) within cylinders (11426, 11428). Cylinders (11426, 11428) are filled with MR fluid (11430, 11432). One or more electromagnets (not shown) are in direct contact with MR fluid (11430, 11432) such that the electromagnets may selectively magnetize MR fluid (11430, 11432) when the electromagnets are activated. Prior to magnetizing MR fluid (11430, 11432), plungers (11422, 11424) are operable to translate within cylinders (11426, 11428) to thereby allow articulation section (11130) to flex to thereby deflect end effector (11040) relative to outer sheath (11032). Once MR fluid (11430, 11432) is magnetized, however, MR fluid (110430, 11432) becomes substantially rigid within cylinders (11426, 11428) to thereby prevent movement of plungers (11422, 11424) to thereby prevent movement of articulation bands (11140, 11142) so as to provide rigidity to articulation section (11130) and/or to prevent inadvertent deflection of end effector (11040) relative to outer sheath (11032). Various suitable ways in which MR fluid (11430, 11432) may be selectively magnetized will be apparent to those of ordinary skill in the art in view of the teachings herein.

M. Exemplary Stiffening Friction Features

FIG. 139 shows a modified version shaft assembly (11030) of instrument (11010) described above having a pair of exemplary alternative articulation bands (11440, 11442). As will be described in more detail below, articulation bands (11440, 11442) may function to provide rigidity to articulation section (11130) and/or to prevent inadvertent deflection of end effector (11040) relative to outer sheath (11032). Each articulation band (11440, 11442) comprises a plurality of teeth (11444, 11446) projecting outwardly from opposing side surfaces of articulation bands (11440, 11442). An interior surface of outer sheath (11032) comprises two sets of teeth (11450, 11452) projecting inwardly from opposing sides of an interior surface of outer sheath (11032). Teeth (11444, 11446) of articulation bands (11440, 11442) are configured to engage teeth (11450, 11452) of outer sheath (11032) to thereby limit longitudinal translation of articulation bands (11440, 11442). Limiting the longitudinal translation of articulation bands (11440, 11442) subsequently limits articulation of articulation section (11130). Thus, it should be understood that depending upon the amount of engagement between teeth (11444, 11446) of articulation bands (11440, 11442) and teeth (450, 11452) of outer sheath (32), teeth (444, 11446, 11450, 11452) may function to merely limit actuation of articulation section (11130) or to substantially limit actuation of articulation section (11130) by requiring a lesser or greater force to articulate articulation section (11130).

In some versions, articulation bands (11440, 11442) are configured to transition laterally between an inward configuration and an outward configuration. When articulation bands (11440, 11442) are in the inward configuration, teeth (11444, 11446) are disengaged from teeth (11450, 11452), allowing articulation bands (11440, 11442) to translate freely (e.g., to freely drive articulation of articulation section (11130)). When articulation bands (11440, 11442) are in the outward configuration, teeth (11444, 11446) are engaged with teeth (11450, 11452), with enough force to prevent articulation bands (11440, 11442) from translating. With articulation bands (11440, 11442) being rigidly prevented from translating, articulation section (11130) is effectively rigidized. Various suitable ways in which articulation bands (11440, 11442) may be selectively transitioned between the inward configuration and the outward configuration will be apparent to those of ordinary skill in the art in view of the teachings herein.

In some other versions, articulation bands (11440, 11442) are resiliently biased outwardly such that teeth (11444, 11446) are biased into engagement with teeth (11450, 11452). Teeth (11444, 11446) remain engaged with teeth (11450, 11452), yet teeth (11444, 11446) are permitted to slide along teeth (11450, 11452) in a ratcheting fashion as articulation bands (11440, 11442) are oppositely translated to drive articulation of articulation section (11130). When articulation bands (11440, 11442) are held longitudinally stationary, engagement between teeth (11444, 11446) and teeth (11450, 11452) will prevent articulation section (11130) from having any "play", such that teeth (11444, 11446) and teeth (11450, 11452) cooperate to effectively rigidize articulation section (11130). It should be noted that teeth (11444, 11446) and teeth (11450, 11452) are positioned proximate to articulation section (11130) in this example, thereby minimizing any tolerance stacking that might otherwise frustrate the rigidization functionality in cases where teeth (11444, 11446) and teeth (11450, 11452) would be positioned further remotely from articulation section (11130).

N. Exemplary "Smart Material" Articulation Bands

FIGS. 140A and 140B show a modified version of shaft assembly (11030) of instrument (11010) described above having a pair of exemplary alternative articulation bands (11460, 11462). Articulation bands (11460, 11462) are coupled with a power source (11464) that is operable to provide an electrical current to articulation bands (11460, 11462). Articulation bands (11460, 11462) of the present example comprise a "smart material" (e.g. "muscle wire" shape memory alloy, electroactive polymer, etc.). In the absence of a current being applied to it, such a "smart material" may be stretched by a small force. Thus, as shown in FIG. 140B, in the absence of a current applied to articulation bands (11460, 11462), articulation bands (11460, 11462) may easily flex to thereby allow articulation section (11130) to flex so as to deflect end effector (11040) relative to outer sheath (11032). Once a current is applied to such a "smart material," the material becomes substantially harder and returns to its original length (e.g., a length that is shorter than the length when the current is removed). Thus, as shown in FIG. 140A, once power source (11464) provides an electrical current to articulation bands (11460, 11462), articulation bands (11460, 11462) become substantially rigid and return to their original (e.g., shorter) lengths so as to provide rigidity to articulation section (11130) and/or to prevent inadvertent deflection of end effector (11040) relative to outer sheath (11032). Various suitable ways in which articulation bands (11460, 11462) may be selectively activated by power source (11464) will be apparent to those of ordinary skill in the art in view of the teachings herein.

XIII. ULTRASONIC SURGICAL INSTRUMENT WITH RIGIDIZING ARTICULATION DRIVE MEMBERS

As noted above, in some examples it may be desirable to include various features to selectively increase the rigidity of an articulation section, such as articulation section (130) described above. For instance, because of various factors such as manufacturing tolerances, design limitations, material limitations, and/or other factors, articulation sections of some examples may be susceptible to some "play" or other small movement of the articulation section despite being relatively fixed in a given position, such that the articulation section is not entirely rigid. It may be desirable to reduce or eliminate such play in the articulation section, particularly when the articulation section is in a straight, non-articulated configuration. In some examples, such play may be reduced or eliminated by including features for selectively increasing tension in one or two articulation bands similar to articulation bands (140, 142) described above. Such features may reduce or eliminate play in the articulation section because the increased tension in the articulation bands may cause the components of the articulation section to longitudinally compress, thereby increasing the rigidity of the articulation section. It may be desirable to provide control of such features via the handle assembly and/or via the shaft assembly because such positioning may provide enhanced usability, ergonomics, and/or functionality.

In some versions, one or more resilient members resiliently bias articulation bands (140, 142) proximally in order to increase tension in articulation bands (140, 142). Various suitable ways in which one or more resilient members may be used to resiliently bias articulation bands (140, 142) proximally will be apparent to those of ordinary skill in the art in view of the teachings herein. Various examples of features that are configured to selectively increase tension in articulation bands are described in greater detail below. In some examples, tension is selectively increased in one articulation band (140, 142) in order to effectively rigidize the articulation section. In some other examples, tension is selectively increased in both articulation bands (140, 142) simultaneously in order to effectively rigidize the articulation section. Various other examples will be apparent to those of ordinary skill in the art in view of to the teachings herein.

A. Exemplary Alternative Articulation Control Assembly with Rigidizing Cam Feature FIGS. 141-144 show an exemplary alternative articulation control assembly (12200) that may be readily incorporated into instrument (10). Except as otherwise noted herein, it should be understood that articulation control assembly (12200) is substantially the same as articulation control assembly (100) described above. In particular, as similarly described above, articulation control assembly (12200) comprises a housing (12210) and a rotatable knob (12220). Like with housing (110) described above, housing (12210) of the present example comprises a pair of perpendicularly intersecting cylindrical portions (12212, 12214). Similarly, like knob (120), knob (12220) is rotatably disposed within a first hollow cylindrical portion (12212) of housing (12210) such that knob (12220) is operable to rotate within cylindrical portion (12212) of housing (12210).

Shaft assembly (30) is similarly slidably and rotatably disposed within a second cylindrical portion (12214). Shaft assembly (30) comprises a pair of translatable members (12261, 12262), both of which extend slidably and longitudinally through the proximal portion of outer sheath (32). Translatable members (12261, 12262) are each longitudinally translatable within second cylindrical portion (12214) between a distal position and a proximal position. Like with translatable member (161, 162) described above, translatable members (12261, 12262) are mechanically coupled with respective articulation bands (140, 142) such that longitudinal translation of translatable member (12261) causes longitudinal translation of articulation band (140), and such that longitudinal translation of translatable member (12262) causes longitudinal translation of articulation band (142).

Knob (12220) comprises a pair of pins (12222, 12224) extending downwardly from a bottom surface of knob (12220). Pins (12222, 12224) extend into second cylindrical portion (12214) of housing (12210) and are rotatably and slidably disposed within a respective pair of channels (12263, 12264) formed in top surfaces of translatable members (12261, 12262). However, unlike pins (122, 124), pins (12222, 12224) of the present example each include a cam surface (12229) on the proximal side of each pin (12222, 12224), as best seen in FIGS. 142-144. As will be described in greater detail below, each cam surface (12229) is configured to engage channels (12263, 12264) of translatable members (12261, 12262) to selectively drive translatable members (12261, 12262) proximally.

Channels (12263, 12264), like channels (163, 164) described above, are positioned on opposite sides of an axis of rotation of knob (12220), such that rotation of knob (12220) about that axis causes opposing longitudinal translation of translatable members (12261, 12262). For instance, rotation of knob (12220) in a first direction causes distal longitudinal translation of translatable member (12261) and articulation band (140), while simultaneously causing proximal longitudinal translation of translatable member (12262) and articulation band (142). Rotation of knob (12220) in a second direction causes proximal longitudinal translation of translatable member (12261) and articulation band (140), while simultaneously causing distal longitudinal translation of translatable member (12262) and articulation band (142). Thus, it should be understood that rotation of knob (12220) causes articulation of articulation section (130) as previously described with respect to instrument (10).

Unlike housing (110) described above, housing (12210) of the present example comprises a pair of detent features (12211, 12213) extending inwardly from an interior surface of first cylindrical portion (12212). Although detent features (12211, 12213) of the present example are shown as ball and spring detents, it should be understood that any other suitable detent feature may be used. With knob (12220) rotatably disposed within first cylindrical portion (12212) of housing (12210), detent features (12211, 12213) are configured to permit knob (12220) to be selectively repositioned such that detent features (12211, 12213) may be disposed within a pair of first arcuate channels (12221, 12223) or a pair of second arcuate channels (12225, 12227) formed in knob (12220). Thus, it should be understood that rotation of knob (12220) will be limited by movement of detent features (12211, 12213) within channels (12221, 12223, 12225, 12227). Detent features (12211, 12213) also retain knob (12220) in housing (12210), while permitting knob (12220) to be selectively positioned between a first vertical position and a second vertical position within first cylindrical portion (12212) of housing (12210).

Like with first cylindrical portion (112) described above, an interior surface of first cylindrical portion (12212) of the present example further comprises a first angular array of teeth (12216) and a second angular array of teeth (12218) formed in an interior surface of first cylindrical portion (12212). Rotatable knob (12220) comprises a pair of outwardly extending engagement members (12226, 12228) that are configured to engage teeth (12216, 12218) of first cylindrical portion (12212) in a detent relationship to thereby selectively lock knob (12220) in a given rotational position. The engagement of engagement members (12226, 12228) with teeth (12216, 12218) may be overcome by a user applying sufficient rotational force to knob (12220); but absent such force, the engagement will suffice to maintain the straight or articulated configuration of articulation section (12230). It should therefore be understood that the ability to selectively lock knob (12220) in a particular rotational position will enable an operator to selectively lock articulation section (12230) in a particular deflected position relative to the longitudinal axis defined by outer sheath (32).

FIGS. 143 and 144 show an exemplary use of articulation control assembly (12200). As can be seen in FIG. 143, articulation control assembly (12200) may be initially configured such that knob (12220) is in the first vertical position. It should be understood that in the present example the first position of knob (12220) corresponds to articulation bands (140, 142) being in high tension to thereby increase the rigidity of articulation section (130). In particular, cam surface (12229) of each pin (12222, 12224) fully engages a corresponding cam surface (12265) of each channel (12263, 12264) in each translatable member (12261, 12262). Engagement bet between each cam surface (12229, 12265) causes translatable member (12261, 12262) to be driven proximally relative to knob (12220) thereby increasing articulation bands (140, 142). Such a tension in articulation bands (140, 142) may take up any slack that might otherwise exist in articulation section (130), thereby increasing rigidity in articulation section (130) because such tension places articulation section (130) in compression. It should be understood that it may be desirable to only move knob (12220) to the vertical position shown in FIG. 143 when articulation section (130) is in a straight, non-articulated configuration.

Detent features (12211, 12213) maintain knob (12220) in the first position because detent features (12211, 12213) resiliently engage arcuate channels (12221, 12223) of knob (12220). To articulate articulation section (130) an operator will first have to decrease the rigidity of articulation section (130). When an operator desires to decrease the rigidity of articulation section (130), an operator may transition knob (12220) to the second vertical position as seen in FIG. 144. To transition knob (12220) to the second position, an operator may apply an upward force to knob (12220) by pulling upwardly on knob (12220) while holding housing (12210) stationary. Such an upward force should be sufficient to overcome the resiliency of detent features (12211, 12213) to thereby disengage detent features from arcuate channels (12221, 12223). Once detent features (12211, 12213) are disengaged from arcuate channels (12221, 12223) further upward movement of knob (12220) will cause detent features to engage arcuate channels (12225, 12227) to thereby lock knob (12220) in the second vertical position as shown in FIG. 144.

Once knob (12220) is in the second vertical position, the tension in articulation bands (140, 142) is released and articulation section (130) is in a configuration for articulation. In particular, as can be seen in FIG. 144, knob (12220) is positioned relative to each translatable member (12261, 12262) such that cam surface (12229) of each pin (12222, 12224) only partially engages the corresponding cam surface (12265) defined by each translatable member (12261, 12262). Such engagement may permit each translatable member (12261, 12262) to translate distally thereby reducing the tension in articulation bands (140, 142).

When knob (12220) is in the second position, such a positioning may be visually indicated by an indicator (12219) on knob (12220). In the present example, indicator (12219) (as seen in FIG. 142) is shown as a red stripe around the exterior of knob (12220). When knob (12220) is in the first position, indicator (12219) is covered by cylindrical portion (12212) of housing (12210) and is thereby obscured from view. Yet in the second position, indicator (12219) is visible because knob (12220) is in a higher vertical position relative to housing (12210), such that indicator (12219) is exposed. Although indicator (12219) is shown as a red stripe in the present example, it should be understood in other examples, any other color or any other type of indicator may be used.

With rotation knob (12220) in the second position, an operator may articulate articulation section (130) by applying a rotational force to knob (12220) to thereby rotate knob (12220). As rotation knob (12220) is rotated, pins (12222, 12224) drive translatable members (12261, 12262) in opposing directions as described above thereby articulating articulation section (130). Once articulation section (130) is articulated to a desired position, an operator may cease rotation of knob (12220). In some versions, if an operator desires to increase the rigidity of articulation section (130) once articulation section (130) is in the desired position, an operator may force knob (12220) downwardly to the first position as described above in order to effectively ridigize articulation section (130). In some other versions, articulation section (130) may only be rigidized by forcing knob (12220) downwardly to the second vertical position when articulation section (130) is in a straight, non-articulated configuration.

B. Exemplary Alternative Articulation Control Assembly with Pivoting Rotatable Knob FIGS. 145-147 show an exemplary alternative articulation control assembly (12300) that may be readily incorporated into instrument (10). Except as otherwise noted herein, it should be understood that articulation control assembly (12300) is substantially the same as articulation control assembly (100) described above. In particular, as similarly described above, articulation control assembly (12300) comprises a housing (12310) and a rotatable knob (12320). Like with housing (110) described above, housing (12310) of the present example comprises a pair of perpendicularly intersecting cylindrical portions (12312, 12314). Similarly, like knob (120), knob (12320) is rotatably disposed within a first hollow cylindrical portion (12312) of housing (12310) such that knob (12320) is operable to rotate within cylindrical portion (12312) of housing (12310).

Shaft assembly (30) is similarly slidably and rotatably disposed within a second cylindrical portion (12314). As can best be seen in FIG. 146, shaft assembly (30) comprises a pair of translatable members (12361) (though only a single translatable member is shown), both of which extend slidably and longitudinally through the proximal portion of outer sheath (32). Translatable members (12361) are each longitudinally translatable within second cylindrical portion (12314) between a distal position and a proximal position. Like with translatable members (161, 162) described above, translatable members (12361) are mechanically coupled with respective articulation bands (140, 142) such that longitudinal translation of translatable member (12361) causes longitudinal translation of articulation band (140), and such that longitudinal translation of the other translatable member (not shown) causes longitudinal translation of articulation band (142).

Knob (12320) comprises a pair of pins (12324) (though only a single pin is shown) extending downwardly from a bottom surface of knob (12320). Pins (12324) extend into second cylindrical portion (12314) of housing (12310) and are rotatably and slidably disposed within a respective pair of channels (12363) (though only a single channel is shown) formed in top surfaces of translatable members (12361). Channels (12363), like channels (163, 164) described above, are positioned on opposite sides of an axis of rotation of knob (12320), such that rotation of knob (12320) about that axis causes opposing longitudinal translation of translatable members (12361). For instance, rotation of knob (12320) in a first direction causes distal longitudinal translation of translatable member (12361) and articulation band (140), while simultaneously causing proximal longitudinal translation of translatable member and articulation band (142). Rotation of knob (12320) in a second direction causes proximal longitudinal translation of translatable member (12361) and articulation band (140), while simultaneously causing distal longitudinal translation of translatable member and articulation band (142). Thus, it should be understood that rotation of knob (12320) causes articulation of articulation section (130) a previously described with respect to instrument (10).

Unlike housing (110) described above, housing (12310) of the present example comprises a single set screw (12313) extending inwardly from an interior surface of first cylindrical portion (12312). With knob (12320) rotatably disposed within first cylindrical portion (12312) of housing (12310), set screw (12313) is slidably disposed within an arcuate channel (12323) formed in knob (12320). Thus, it should be understood that rotation of knob (12320) will be limited by movement of set screws (12313) within channel (12323). Set screw (12313) also retain knob (12320) in housing (12310), preventing knob (12320) from traveling vertically within first cylindrical portion (12312) of housing (12310).

Housing (12310) further includes an open portion (12311). As can best be seen in FIG. 145, open portion (12311) is disposed on the distal face of housing (12310) and is formed as a vertically extending channel that interrupts the circumference of cylindrical portion (12312). Generally, open portion (12311) is configured to permit at least a portion of knob (12320) to pass distally through housing (12310). As will be described in greater detail below, open portion (12311) is configured to permit passage of at least a portion of knob (12320) because such a feature permits at least a portion of knob (12320) to be pivotable relative to housing (12310). A knob lock (12315) is disposed adjacent to open portion (12311). Knob lock (12315) is configured to selectively lock and unlock pivoting of knob (12320) by selectively closing at least a portion of open portion (12311) or otherwise engaging knob (12320) to prevent pivoting. By way of example only, knob lock (12315) may comprise a "C" shaped member that selectively rotates about cylindrical portion (12312) to selectively close off or open the open portion (12311) of cylindrical portion (12312). As another merely illustrative example, knob lock (12315) may comprise a protrusion that selectively extends into or over a portion of open portion (12311). Various suitable ways in which a knob lock (12315) may be configured and operable will be apparent to those of ordinary skill in the art in view of the teachings herein.

Like with first cylindrical portion (112) described above, an interior surface of first cylindrical portion (12312) of the present example comprises a first angular array of teeth (not shown) and a second angular array of teeth (not shown) formed in an interior surface of first cylindrical portion (12312). Likewise, knob (12320) comprises a pair of outwardly extending engagement members (not shown) that are configured to engage the teeth of first cylindrical portion (12312) in a detent relationship to thereby selectively lock knob (12320) in a given rotational position. The engagement of the engagement members with the teeth may be overcome by a user applying sufficient rotational force to knob (12320); but absent such force, the engagement will suffice to maintain the straight or articulated configuration of articulation section (12330). It should therefore be understood that the ability to selectively lock knob (12320) in a particular rotational position lock will enable an operator to selectively lock articulation section (12330) in a particular deflected position relative to the longitudinal axis defined by outer sheath (32).

FIGS. 146 and 147 show an exemplary use of articulation control assembly (12300) to selectively stiffen articulation section (130). It should be understood that in some examples it may be desirable to pivot articulation control assembly (12300) to selectively stiffen articulation section (130) because such a feature may improve usability and/or ergonomics. As can be seen in FIG. 146, articulation control assembly (12300) may be initially configured such that knob (12320) is in a first pivotal position. It should be understood that in the present example the first pivotal position of knob (12320) corresponds to articulation bands (140, 142) being relatively relaxed to such that articulation bands (140, 142) are in a configuration for articulating articulation section (130). Further, the first pivotal position corresponds to knob (12320) being seated within first cylindrical portion (12312) of housing (12310). Thus, knob (12320) is positioned to rotate within first cylindrical position (12312) about a rotation axis to opposingly drive translatable members (12361) via pins (12324). Accordingly, an operator may rotate knob (12320) about the rotation axis while knob (12320) is in the first pivotal position in order to articulate articulation section (130). Additionally, to maintain knob (12320) within first cylindrical portion (12312) while the articulation feature is in use, an operator may optionally engage knob lock (12315) in a locked position.

Once an operator desires to increase the rigidity of articulation section (130), an operator may first transition knob lock (12315) to an unlocked position to thereby permit pivotal motion of knob (12320) about a pivot axis. In this example, the pivot axis is perpendicular to the rotation axis of knob (12320) and offset from the rotation axis of knob (12320). The pivot axis is also perpendicular to the longitudinal axis of shaft assembly (30) and offset from the longitudinal axis of shaft assembly (30). In particular, in the views shown in FIGS. 146-147, the pivot axis runs into and out of the page, the rotation axis runs vertically between the top of the view and the bottom of the view, and the longitudinal axis runs horizontally between the sides of the view. Once knob lock (12315) is in the unlocked position, at least a portion of knob (12320) is permitted to pass through open portion (12311) of housing (12310). To increase the rigidity of articulation section (130) an operator may next apply a horizontal force to knob (12320) (e.g., to the left-hand side of the view shown in FIGS. 146-147) while holding housing (12310) stationary. Such a horizontal force acting on knob (12320) may begin to pivot knob (12320) about the pivot axis toward the position shown in FIG. 147.

The above described pivoting of knob (12320) may be provided and carried out in numerous different ways. For instance, in some examples knob (12320) is comprised of three separate components—a pivoting member, and two side members. In such an example, the pivoting member is be secured to each of the side members by a shaft suitable for pivoting the pivoting member relative to the two side members. In other examples, first cylindrical portion (12312) may be equipped with a hinge member or other feature that may be equipped to permit both knob (12320) and first cylindrical portion (12312) to pivot relative to second cylindrical portion (12314). Alternative, any other suitable mechanism for pivoting knob (12320) may be used as will be apparent to those of ordinary skill in the art in view of the teachings herein.

Regardless of the particular mechanism for pivoting knob (12320), it should be understood that as knob (12320) is pivoted, the pivoting action generally applies tension to articulation bands (140, 142) via pins (12324) and translatable members (12361), thereby increasing the rigidity of articulation section (130). In particular, the pivoting of knob (12320) causes pins (12324) to move about the pivot axis. As pins (12324) move, pins (12324) engage a proximal portion of each translatable member (12361) such that further movement of pins (12324) will simultaneously drive each translatable member (12361) proximally. As translatable members (12361) are driven proximally, tension is communicated to articulation bands (140, 142) to increase the rigidity of articulation section (130) by taking up any slack that might otherwise exist in articulation section (130). It should be understood that, in the present example, knob (12320) may be pivoted to the position shown in FIG. 147 only when articulation section (130) is in a straight, non-articulated configuration. Some other versions may permit knob (12320) to be pivoted to the position shown in FIG. 147 when articulation section (130) is in an articulated configuration.

With knob (12320) pivoted to a fully pivoted position shown in FIG. 147, articulation bands (140, 142) are in a tensioned configuration and articulation section (130) is correspondingly in a rigid configuration. Once knob (12320) is pivoted to the fully pivoted position, an operator may optionally lock knob (12320) in the fully pivoted position by transitioning knob lock (12315) back to the locked position. However, unlike the locking configuration described above, in this configuration knob lock (12315) engages at least a portion of knob (12320) to maintain knob (12320) in the fully pivoted position. It should be understood that in some examples, knob (12320) comprises openings, indentations, or other features that receive a portion of knob lock (12314), thereby permitting knob lock (12315) to engage knob (12320).

C. Exemplary Alternative Articulation Section with Asymmetrical Retention Collars FIGS. 148 and 149 show an exemplary alternative articulation section that may be readily incorporated into instrument (10). It should be understood that unless otherwise described herein, articulation section (12430) is substantially the same as articulation section (130) described above. For instance, like articulation section (130), articulation section (12430) comprises a pair of ribbed body portions (12432, 12434) surrounding flexible portion (166) of waveguide (180). Similarly, ribbed body portions (12432, 12434) are configured to flex with flexible portion (12466) of waveguide (180) when articulation section (12430) bends to achieve an articulated state.

Also like articulation section (130), articulation section (12430) includes a plurality of retention collars (12433). Although retention collars (12433) of the present example are configured to surround ribbed body portions (12432, 12434) and are configured to retain articulation bands (140, 142), retention collars (12433) are also generally configured for the purpose of providing rigidity to articulation section (12430). As can best be seen in FIG. 148, retention collars (12433) of the present example are generally wider compared to retention collars (133). With such a width, it should be understood that retention collars (12433) substantially abut each other. Each retention collar (12433) is asymmetrical and comprises an articulating portion (12435) and a locking portion (12437). Each articulating portion (12435) comprises a chamfered edge (12436) on each side of each articulating portion (12435). As will be described in greater detail below, each chamfered edge (12436) is generally at an oblique angle suitable to permit articulation of articulation section (12430). In some examples, each chamfered edge (12436) is at an angle of about 15° relative to the longitudinal axis of each retention collar (12433), although any other suitable angle may be used.

Each locking portion (12437) is generally square or rectangular in shape. Accordingly, each locking portion (12437) forms a generally straight edge (12438) positioned adjacent to each chamfered edge (12436) of each articulating portion (12435). As will be understood, each straight edge (12438) is generally configured to maintain rigidity of articulation section (12430) in a given direction when each retention collar (12433) is adjacent to the others.

FIGS. 148 and 149 show an exemplary operation of articulation section (12430). As can be seen in FIG. 148, articulation section (12430) is generally both unidirectionally rigid and unidirectionally articulable. For instance, if a transversely oriented force is applied to the distal portion of shaft assembly (30) in the direction of locking portions (12437) and perpendicular to the longitudinal axis of shaft assembly (30), articulation section (12430) resists articulation because each straight edge (12438) of each locking portion (12437) that is adjacent to another straight edge (12438) engages with the other straight edge (12438) and thus prevents lateral bending of articulation section (12430). Yet, if a transversely oriented force is applied to the distal portion of shaft assembly (12300) in the direction of articulating portions (12435) and perpendicular to the longitudinal axis of shaft assembly (30), articulation section (12430) may be articulated because chamfered edges (12436) of each articulating portion (12435) provide sufficient clearance to permit lateral bending of articulation section (12430).

Although articulating portions (12435) permit articulation, it should be understood that articulating portions (12435) only permit articulation to the extent that chamfered edges (12436) remain away from each other. Once articulation section (12430) is articulated to a point where each chamfered edge (12436) is adjacent to another, each chamfered edge (12436) will act as a physical stop to further articulation similarly to straight edges (12438) of each locking portion (12437). Thus, both chamfered edges (12436) and straight edges (12438) act as physical stops that prevent articulation of articulation section (12430), but straight edges (12438) permit very little to no articulation, while chamfered edges (12436) permit a certain predetermined range of articulation. Therefore, if articulation bands (140, 142) are neither in tension nor compression, an operator may apply an articulation force to articulate articulation section (12430) in only a single direction and only to a certain predetermined extent. By way of example only, chamfered edges (12436) may permit articulation section (12430) to achieve an articulation angle of up to approximately 30°. Alternatively, any other suitable maximum articulation angle may be provided. It should be understood that the "articulation angle" may be an angle defined between the longitudinal axis of distal outer sheath (33) and the longitudinal axis of proximal outer sheath (32).

When an operator desires to lock articulation section (12430) in a straight configuration as seen in FIG. 148, a user may place at least articulation band (141) in tension thereby compressing retention collars (12433) such that straight edges (12438) of locking portions (12437) are compressed against each other. While straight edges (12438) will prevent articulation in the direction of locking portions (12437), tension in articulation band (141) will also prevent articulation in the direction toward articulating portions (12435). This is because the tension in articulation band (140) will prevent straight edges (12438) from separating relative to each other.

Tension may be applied to articulation band (140) using the articulation control assemblies (110, 12210, 12310) described above, or any other suitable means. Articulation band (142) may also be placed in tension using the features of articulation assemblies (12210, 12310) described above, or any other suitable means. Alternatively, articulation band (142) may merely be passive in state with merely no force applied.

When an operator desires to articulate articulation section (12430), an operator may release tension from articulation band (140). Once tension is released from articulation band (140), articulation section (12430) will be in the passive state described above where articulation is permitted in the direction of articulating portions (12435) but not in the direction of locking portions (12437). To initiate articulation, an operator may place articulation band (142) in tension while maintaining articulation band (140) in a passive state or actively driving articulation band (140) distally. Tension may be applied to articulation band (140) using articulation control assemblies (110, 12210, 12310) as described above, or by using any other suitable means. As tension is applied, articulation band (142) generates a moment that bends articulation section (12430). Articulation section (12430) is then permitted to bend until chamfered edges (12436) of articulating portions (12435) are adjacent to each other. At such a point chamfered edges (12436) begin acting as physical stops as described above thereby preventing further articulation.

FIG. 150 shows an exemplary alternative housing (12510) that may be readily incorporated into instrument (10), particularly when instrument (10) is equipped with articulation section (12430) described above. Unless otherwise described herein, it should be understood that housing (12510) is substantially the same as housing (110) described above. Additionally, it should be understood that any of the features described herein with respect to housing (12510) may be readily incorporated into any housings (110, 12210, 12310) described above.

Like with housing (110), housing (12510) comprises a first cylindrical portion (12512) and a second cylindrical portion (12514). Second cylindrical portion (12514) is substantially the same as second cylindrical portion (114) described above such that further details will not be described herein.

First cylindrical portion (12512) is substantially the same as first cylindrical portion (112) described above. For instance, as can be seen in FIG. 150, first cylindrical portion (12512) comprises a first angular array of teeth (12516) and a second angular array of teeth (12518) formed in an interior surface of first cylindrical portion (12512). However, unlike teeth (116, 118) described above, teeth (12516, 12518) of the present example are configured for use with articulation section (12430) described above. In particular, each angular array of teeth (12516, 12518) comprises a respective plurality of articulation teeth (12520, 12522), a single lock tooth valley (12524, 12526), and an exaggerated tooth (12528, 12529) separating the articulation teeth (12520, 12522) from the lock tooth valley (12524, 12526).

Each set of articulation teeth (12520, 12522) functions similarly to teeth (116, 118) described above. For instance, articulation teeth (12520, 12522) are configured to engage engagement members (126, 128) of rotatable knob (120) such that knob (120) may be rotated to articulate articulation section (12430) to a desired position and remain in the same position once any rotational force is removed from knob (120). However, unlike teeth (116, 118), articulation teeth (12520, 12522) are disposed for movement of articulation section (12430) in only a single direction because, as described above, articulation section (12430) is only configured for articulation in a single direction.

Each lock tooth valley (12524, 12526) is configured to hold knob (120) in a position corresponding to a locked position of articulation section (12430). It should be understood that each lock tooth valley (12524, 12526) is disposed in a position corresponding to knob (120) being rotated slightly past a neutral position (e.g., the position aligned with the longitudinal axis of instrument (10)). This positioning ensures that some tension will be applied to actuation band (140) to achieve the locking configuration described above with respect to articulation section (12430) while articulation section (12430) is in a substantially straight, non-articulated configuration. Although each lock tooth valley (12524, 12526) of the present example is shown in a given position, it should be understood that the precise position of each lock tooth valley (12524, 12526) may be varied as desired to achieve a sufficient level of tension in actuation band (140).

Each exaggerated tooth (12528, 12529) is positioned between each set of actuation teeth (12520, 12522) and each lock tooth valley (12524, 12526). Each exaggerated tooth (12528, 12529) is configured to act as a detent feature that may provide additional support to hold knob (120) in the locked position described above. In particular, each exaggerated tooth (12528, 12529) is configured to engage engagement members (126, 128) to hold engagement members (126, 128) respective lock tooth valleys (12524, 12526). Additionally, each exaggerated tooth (12528, 12529) may act to provide tactile feedback to an operator as knob (120) is transitioned between each set of actuation teeth (12520, 12522) and each lock tooth valley (12524, 12526). Although each exaggerated tooth (12528, 12529) of the present example is shown as having a particular size, it should be understood that the configuration of exaggerated tooth (12528, 12529) may be varied as desired to achieve suitable detent and/or tactile feedback characteristics.

D. Exemplary Alternative Articulation Section with Articulation Segments

FIG. 151 shows another exemplary alternative articulation section (12630) that may be readily incorporated into instrument (10). Articulation section (12630) comprises three articulation segments (12632, 12642, 12652) disposed between a distal block (12660) and a proximal block (12664). Articulation segments (12632, 12642, 12652) are configured to operate cooperatively to act as physical stops for different amounts of articulation for a given side of each articulation segment (12632, 12642, 12652). Articulation segments (12632, 12642, 12652) consist of a first articulation segment (12632), a second articulation segment (12642), and a third articulation segment (12652). Although three total articulation segments are shown, it should be understood that in other examples, any suitable number of articulation segments (12632, 12642, 12652) may be used. For instance, in some examples a plurality of second articulation segments (12642) may be incorporated between first and third articulation segments (12632, 12652). In still other examples, second articulation segment (12642) may be omitted altogether with first and third articulation segments (12632, 12652) being adjacent to each other.

First articulation segment (12632) includes an articulation portion (12633) and a lock portion (12636). Articulation portion (12633) comprises a straight end (12634) disposed adjacent to distal block (12660) and a chamfered end (12635) disposed adjacent to second articulation segment (12642). Straight end (12634) is generally straight and is configured to rest squarely against distal block (12660). Chamfered end (12635) is configured with a chamfer disposed at an angle of approximately 15° relative to the longitudinal axis of first articulation segment (12632). As will be described in greater detail below, chamfered end (12635) is generally configured to permit articulation of articulation section (12630) for a certain amount of articulation (e.g., approximately 30°) before acting as a physical stop.

Lock portion (12636) comprises a straight end (12637) and a chamfered end (12638). Straight end (12637) is generally straight and is configured to rest squarely against distal block (12660). Chamfered end (12638) is configured with a chamfer disposed at an angle of approximately 1° to 5° relative to the longitudinal axis of first articulation segment (12632). While chamfered end (12638) is configured to permit some articulation of articulation section (12630), it should be understood that chamfered end (12638) is configured to permit only a limited amount of articulation prior to acting as a physical stop. This is because of the relatively shallow chamfer angle as compared to the chamfer angle of chamfered end (12635) described above. Accordingly, as will be described in greater detail below, lock portion (12636) generally acts a physical stop for articulation in articulation section (12630) despite allowing some relatively limited amount of articulation.

Second articulation segment (12642) includes an articulation portion (12643) and a lock portion (12646). Articulation portion (12643) comprises two chamfered ends (12644, 12645) with a distal chamfered end (12644) disposed adjacent to first articulation segment (12632) and a proximal chamfered end (12645) disposed adjacent to third articulation segment (12652). Chamfered ends (12644, 12645) are generally symmetrical and are both configured with a chamfer disposed at an angle of approximately 15° relative to the longitudinal axis of second articulation segment (12642). As will be described in greater detail below, chamfered ends (12644, 12645) are generally configured to permit articulation of articulation section (12630) for a certain amount of articulation (e.g., approximately 30°) before acting as a physical stop.

Lock portion (12646) comprises two chamfered ends (12647, 12648) with a distal chamfered end (12647) disposed adjacent to first articulation segment (12632) and a proximal chamfered end (12648) disposed adjacent to third articulation segment (12652). Chamfered ends (12637, 12638) are both configured with a chamfer disposed at an angle of approximately 1° to 5° relative to the longitudinal axis of second articulation segment (12642). While chamfered ends (12647, 12648) are configured to permit some articulation of articulation section (12630), it should be understood that chamfered ends (12647, 12648) are configured to permit only a limited amount of articulation prior to acting as a physical stop. This is because of the relatively shallow chamfer angle as compared to the chamfer angle of chamfered ends (12644, 12645) described above. Accordingly, as will be described in greater detail below, lock portion (12646) generally acts a physical stop for articulation in articulation section (12630) despite allowing some relatively limited amount of articulation.

Third articulation segment (12652) is similar to first articulation segment (12632) and includes an articulation portion (12653) and a lock portion (12656). Articulation portion (12653) comprises a chamfered end (12654) disposed adjacent to second articulation segment (12642) and a straight end (12655) disposed adjacent to proximal block (12664). Chamfered end (12654) is configured with a chamfer disposed at an angle of approximately 15° relative to the longitudinal axis of third articulation segment (12652). As will be described in greater detail below, chamfered end (12654) is generally configured to permit articulation of articulation section (12630) for a certain amount of articulation (e.g., approximately 30°) before acting as a physical stop. Straight end (12655) is generally straight and is configured to rest squarely against proximal block (12664).

Lock portion (12656) comprises a chamfered end (12657) and a straight end (12658). Chamfered end (12657) is configured with a chamfer disposed at an angle of approximately 1° to 5° relative to the longitudinal axis of third articulation segment (12652). While chamfered end (12657) is configured to permit some articulation of articulation section (12630), it should be understood that chamfered end (12657) is configured to permit only a limited amount of articulation prior to acting as a physical stop. This is because of the relatively shallow chamfer angle as compared to the chamfer angle of chamfered end (12654) described above. Accordingly, as will be described in greater detail below, lock portion (12656) generally acts a physical stop for articulation in articulation section (12630) despite allowing some relatively limited amount of articulation. Straight end (12658) is generally straight and is configured to rest squarely against proximal block (12664).

Each articulation segment (12632, 12642, 12652) includes a respective bore (12639, 12649, 12659) extending transversely therethough. Each bore (12639, 12649, 12659) is configured to surround but not contact waveguide (180). For instance, each bore (12639, 12649, 12659) is cut into a larger portion of each respective lock portion (12636, 12646, 12656) relative to each respective articulation portion (12633, 12643, 12653). Because each articulation portion (12633, 12643, 12653) is configured to articulate articulation section (12630) a larger amount relative to each lock portion (12636, 12646, 12656), each bore (12639, 12649, 12659) is configured to include additional space on the side of each lock portion (12636, 12646, 12656) to accommodate bending of waveguide (180).

Distal and proximal block (12660, 12664) each similarly include a respective bore (12662, 12666) that is configured to surround waveguide (180) without contacting waveguide (180). Additionally, blocks (12660, 12664) are configured to abut articulation segments (12632, 12642, 12652) and to provide a stable point of contact for segments (12632, 12642, 12652). Although not shown, it should be understood that blocks (12660, 12664) may also include channels or other features configured to provide a surface for articulation bands (140, 142) to move upon.

In an exemplary mode of operation, an operator may lock articulation section (12630) in a generally straight configuration by applying tension to articulation band (140). In particular, tension may be applied using articulation control assemblies (100, 12200, 12300) as described above. Once tension begins to be applied to articulation band (140), a moment will be created by such tension that will urge chamfered ends (12638, 12647) of first and second articulation segments (12632, 12642) toward each other and chamfered ends (12648, 12657) of second and third articulation segments (12642, 12652) toward each other until each chamfered end (12638, 12647, 12648, 12657) abuts another. Because of the limited chamfer of chamfered ends (12638, 12647, 12648, 12657) any articulation of articulation section (12630) will be limited at this stage.

Once chamfered ends (12638, 12647, 12648, 12657) are abutting, additional articulation will be prevented by physical contact between chamfered ends (12638, 12647, 12648, 12657). Thus, while tension is applied to articulation band (140), articulation section (130) will be held in a position of limited to no articulation. It should be understood that the particular amount of articulation of articulation section (630) will be determined by the particular chamfer angles of chamfered ends (12638, 12647, 12648, 12657).

When an operator desires to articulate articulation section (12630), an operator may first release any tension in articulation band (140). Once tension is released, an operator may apply tension to articulation band (142) using articulation control assembly (100, 12200, 12300) described above. One tension is applied to articulation band (142), a moment will be created by such tension that will urge chamfered ends (12635, 12644) of first and second articulation segments (12632, 12642) toward each other and chamfered ends (12645, 12654) of second and third articulation segments (12642, 12652) toward each other until each chamfered end (12635, 12644, 12645, 12654) abut another. It should be understood that because of the relatively large chamfer of chamfered ends (12635, 12644, 12645, 12654) (compared to chamfered ends (12638, 12647, 12648, 12657)), articulation of articulation section (12630) about articulation portions (12633, 12643, 12653) will be relatively large in comparison to articulation about lock portions (12636, 12646, 12656). In some examples, such an articulation of articulation section will be approximately 30°.

Once chamfered ends (12635, 12644, 12645, 12654) are abutting, additional articulation will be prevented by physical contact between chamfered ends (12635, 12644, 12645, 12654). Thus, while tension is applied to articulation band (140), articulation section (130) will be held in an articulated position. It should be understood that the particular amount of articulation of articulation section (12630) will be determined by the particular chamfer angles of chamfered ends (12635, 12644, 12645, 12654). Accordingly, chamfered ends (12635, 12644, 12645, 12654) may be configured to permit any suitable amount of articulation as may be desired.

In one merely illustrative example, a modified version of instrument (10) includes articulation section (12630) and housing (12510). It should therefore be understood that articulation section (12630) may be operated in a manner similar to that described above with respect to articulation section (12430). Alternatively, any other suitable control elements may be combined with articulation section (12630).

E Exemplary Alternative Instrument with Tensioning Lever

FIG. 152 shows an exemplary alternative instrument (121010). It should be understood that instrument (121010) of the present example is substantially the same as instrument (10) described above, except as otherwise noted herein. For instance, Instrument (121010) of the present example comprises a handle assembly (121020), a shaft assembly (121030), and an end effector (121040). Handle assembly (121020) comprises a body (121022) including a pistol grip (121024) and a pair of buttons (121026). Handle assembly (121020) also includes a trigger (121028) that is pivotable toward and away from pistol grip (121024). It should be understood, however, that various other suitable configurations may be used, including but not limited to a scissor grip configuration. End effector (121040) includes an ultrasonic blade (121160) and a pivoting clamp arm (121044). Clamp arm (121044) is coupled with trigger (121028) such that clamp arm (121044) is pivotable toward ultrasonic blade (121160) in response to pivoting of trigger (121028) toward pistol grip (121024); and such that clamp arm (121044) is pivotable away from ultrasonic blade (121160) in response to pivoting of trigger (121028) away from pistol grip (121024). Various suitable ways in which clamp arm (121044) may be coupled with trigger (121028) will be apparent to those of ordinary skill in the art in view of the teachings herein. In some versions, one or more resilient members are used to bias clamp arm (121044) and/or trigger (121028) to the open position shown in FIG. 152.

An ultrasonic transducer assembly (121012) extends proximally from body (121022) of handle assembly (121020). Transducer assembly (121012) is coupled with a generator (121016) via a cable (121014), such that transducer assembly (121012) receives electrical power from generator (121016). Piezoelectric elements in transducer assembly (121012) convert that electrical power into ultrasonic vibrations. Generator (121016) may include a power source and control module that is configured to provide a power profile to transducer assembly (121012) that is particularly suited for the generation of ultrasonic vibrations through transducer assembly (121012).

Blade (121160) of the present example is operable to vibrate at ultrasonic frequencies in order to effectively cut through and seal tissue. Blade (121160) is positioned at the distal end of an acoustic drivetrain. This acoustic drivetrain includes transducer assembly (121012) and an acoustic waveguide (not shown). The acoustic waveguide comprises a flexible portion (not shown) similar to flexible portion (166) described above with respect to instrument (10). Transducer assembly (121012) includes a set of piezoelectric discs (not shown) located proximal to a horn (not shown) of the waveguide. The piezoelectric discs are operable to convert electrical power into ultrasonic vibrations, which are then transmitted along the waveguide to blade (121160) in accordance with known configurations and techniques. By way of example only, this portion of the acoustic drivetrain may be configured in accordance with various teachings of various references that are cited herein.

Shaft assembly (121030) of the present example extends distally from handle assembly (121020). Unless otherwise noted herein, shaft assembly (121030) is substantially the same as shaft assembly (30) described above with respect to instrument. For instance, shaft assembly (121030) includes an articulation section (121130), which is located at a distal portion of shaft assembly (121030), with end effector (121040) being located distal to articulation section (121130). As shown in FIG. 152, a knob (121031) is secured to a proximal portion of shaft assembly (121030). Knob (121031) is rotatable relative to body (121022), such that shaft assembly (121030) is rotatable about the longitudinal axis defined by shaft assembly (121030), relative to handle assembly (121020). Such rotation may provide rotation of end effector (121040), articulation section (121130), and shaft assembly (121030) unitarily. Of course, rotatable features may simply be omitted if desired.

Articulation section (121130) is substantially the same as articulation section (130) described above with respect to instrument (10), unless otherwise note herein. For instance, articulation section (121130) is operable to selectively position end effector (121040) at various lateral deflection angles relative to a longitudinal axis defined by shaft assembly (121030). Like with articulation section (130), articulation section (121130) is driven by a pair of articulation bands (121140, 121142) disposed within articulation section (121130) and extending through shaft assembly (121030). When articulation bands (121140, 121142) translate longitudinally in an opposing fashion, this will cause articulation section (121130) to bend, thereby laterally deflecting end effector (121040) away from the longitudinal axis of shaft assembly (121030) from a straight configuration to an articulated configuration. In particular, end effector (121040) will be articulated toward the articulation band (121140, 121142) that is being pulled proximally. During such articulation, the other articulation band (121140, 121142) may be pulled or pushed distally Instrument further includes an articulation control assembly (121100) that is secured to a proximal portion of shaft assembly (121030). Articulation control assembly (121100) comprises a housing (121110) and a rotatable knob (121120). Like with articulation control assembly (100) described above, rotatable knob (121120) is configured to rotate relative to housing (121110) to drive articulation bands (121140, 121142) in opposing longitudinal directions. For instance, rotation of knob (121120) in a first direction causes distal longitudinal translation of articulation band (121140), while simultaneously causing proximal longitudinal translation of articulation band (121142). Rotation of knob (121120) in a second direction causes proximal longitudinal translation of articulation band (121140), while simultaneously causing distal longitudinal translation of articulation band (121142). Thus, it should be understood that rotation of rotation knob (121120) causes articulation of articulation section (121130).

Unlike instrument (10) described above, instrument (121010) of the present example further includes a tensioning assembly (121200). Tensioning assembly (121200) is generally operable to translate the entire articulation control assembly (121100) relative to shaft assembly (121030) to thereby simultaneously apply tension to articulation bands (121140, 121142). As can best be seen in FIG. 153, tensioning assembly (121200) comprises a lever arm (121210) and a link (121220). Lever arm (121210) is pivotably secured within handle assembly (121020) and is configured to pivot about a pivot point (121212) connecting lever arm (121210) to housing (121020).

Link (121220) is pivotably connected to lever arm (121210) at a pivot point (121222) connecting link (121220) to lever arm (121210). Link (121220) extends from lever arm (121210) through handle assembly (121020) and through knob (121031) where link (121220) pivotably connects to articulation control assembly (121100). Although not shown, it should be understood that link (121220) may connect to articulation control assembly (121100) by any suitable means. For instance, in some examples link (121220) is connected to articulation control assembly (121100) by a rotatable collar assembly that is configured to permit articulation control assembly (121100) to rotate relative to link (121220) while still permitting link (121220) to drive translation of articulation control assembly (121100). In other examples, link (121220) may simply be integral with articulation control assembly (121100) or connected with a pin or other securing feature. Of course any other suitable mechanisms for connecting link (121220) to articulation control assembly (121100) as will be apparent to those of ordinary skill in the art in view of the teachings herein.

As can best be seen in FIG. 154, articulation control assembly (121100) is configured to translate relative to knob (121031) and shaft assembly (121030). In particular, a proximal portion of housing (121110) is translatably received within knob (121031) to permit some translation of articulation control assembly (121100) relative to knob (121031). Additionally, a spring (121224) is disposed between articulation control assembly (121100) and knob (121031) to resiliently bias articulation control assembly (121100) toward a distal position. As will be described in greater detail below, the distal position of articulation control assembly (121100) corresponds to an articulation position, where articulation bands (121140, 121142) are subjected to low tension, such that articulation control assembly (121100) may cause articulation section (121130) to articulate.

FIGS. 153 and 155 show an exemplary mode of operation of tensioning assembly (1200). In particular, FIG. 153 shows tensioning assembly (121200) in an articulation position. Generally, the articulation position corresponds to articulation bands (121140, 121142) being in a low tension state such that knob (121120) of articulation control assembly (121100) may be used to drive articulation bands (121140, 121142) in opposing directions to articulate articulation section (121130). In the articulation position, lever arm (121210) is pivoted distally relative to handle assembly (121020). Because link (121220) is attached to lever arm (121210), link (121220) is also positioned distally to thereby permit spring (121224) to drive articulation control assembly (121100) distally.

An operator may desire to increase the rigidity of articulation section (121130) to thereby lock articulation section (121130) in a particular state of articulation (e.g., straight). To do so, it may be desirable to simultaneously apply tension to both articulation bands (121140, 121142) because such tension may provide opposing forces on articulation section (121130) that work to maintain articulation section (121130) in a given position. To simultaneously tension both articulation bands (121140, 121142), an operator may grasp lever arm (121210) and pull lever arm (121210) proximally relative to handle assembly (121020).

As can be seen in FIG. 155, pulling lever arm (121210) proximally causes link (121220) to act on articulation control assembly (121100) to thereby translate articulation control assembly (121100) proximally relative to knob (121031). Because articulation bands (121140, 121142) are both connected to articulation control assembly (121100), such translation will simultaneously increase tension each articulation band (121140, 121142). This tension will be transferred to the movable components within articulation section (121130), thereby taking up any slack that might otherwise exist within articulation section (121130). Once tension is applied to articulation bands (121140, 121142), the particular articulation state of articulation section (121130) (e.g., straight) will thus correspondingly be locked.

In some examples, tensioning assembly (121200) may include a lock feature or other mechanism to selectively maintain lever arm (121210) in the tensioned position. Where such features are included, an operator may actuate such features after lever arm (121210) is positioned to tension articulation bands (121140, 121142). As another merely illustrative example, lever arm (121210) and link (121220) may be configured to provide an over-center toggle mechanism, such as the over-center toggle described below. Alternatively, locking features may be omitted and lever arm (121210) may simply return to the articulation position once an operator releases lever arm (121210), due to the resilience of spring (121224).

F. Exemplary Alternative Instrument with Over-Center Toggle Tensioning Assembly

FIG. 156 shows an exemplary alternative instrument (121310). It should be understood that instrument (121310) of the present example is substantially the same as instrument (10) described above, except as otherwise noted herein. For instance, Instrument (121310) of the present example comprises a handle assembly (121320), a shaft assembly (121330), and an end effector (121340). Handle assembly (121320) comprises a body (121322) including a pistol grip (121324) and a pair of buttons (121326). Handle assembly (121320) also includes a trigger (121328) that is pivotable toward and away from pistol grip (121324). It should be understood, however, that various other suitable configurations may be used, including but not limited to a scissor grip configuration. End effector (121340) includes an ultrasonic blade (121460) and a pivoting clamp arm (121344). Clamp arm (121344) is coupled with trigger (121328) such that clamp arm (121344) is pivotable toward ultrasonic blade (121460) in response to pivoting of trigger (121328) toward pistol grip (121324); and such that clamp arm (121344) is pivotable away from ultrasonic blade (121460) in response to pivoting of trigger (121328) away from pistol grip (121324). Various suitable ways in which clamp arm (121344) may be coupled with trigger (121328) will be apparent to those of ordinary skill in the art in view of the teachings herein. In some versions, one or more resilient members are used to bias clamp arm (121344) and/or trigger (121328) to the open position shown in FIG. 156.

An ultrasonic transducer assembly (121312) extends proximally from body (121322) of handle assembly (121320). Transducer assembly (121312) is coupled with a generator (121316) via a cable (121314), such that transducer assembly (121312) receives electrical power from generator (121316). Piezoelectric elements in transducer assembly (121312) convert that electrical power into ultrasonic vibrations. Generator (121316) may include a power source and control module that is configured to provide a power profile to transducer assembly (121312) that is particularly suited for the generation of ultrasonic vibrations through transducer assembly (121312).

Blade (121460) of the present example is operable to vibrate at ultrasonic frequencies in order to effectively cut through and seal tissue. Blade (121460) is positioned at the distal end of an acoustic drivetrain. This acoustic drivetrain includes transducer assembly (121312) and an acoustic waveguide (not shown). The acoustic waveguide comprises a flexible portion (not shown) similar to flexible portion (166) described above with respect to instrument (10). Transducer assembly (121312) includes a set of piezoelectric discs (not shown) located proximal to a horn (not shown) of the waveguide. The piezoelectric discs are operable to convert electrical power into ultrasonic vibrations, which are then transmitted along the waveguide to blade (121460) in accordance with known configurations and techniques. By way of example only, this portion of the acoustic drivetrain may be configured in accordance with various teachings of various references that are cited herein.

Shaft assembly (121330) of the present example extends distally from handle assembly (121320). Unless otherwise noted herein, shaft assembly (121330) is substantially the same as shaft assembly (30) described above with respect to instrument. For instance, shaft assembly (121330) includes an articulation section (121430), which is located at a distal portion of shaft assembly (121330), with end effector (121340) being located distal to articulation section (121430). As shown in FIG. 156, a knob (121331) is secured to a proximal portion of shaft assembly (121330). Knob (121331) is rotatable relative to body (121322), such that shaft assembly (121330) is rotatable about the longitudinal axis defined by shaft assembly (121330), relative to handle assembly (121320). Such rotation may provide rotation of end effector (121340), articulation section (121430), and shaft assembly (121330) unitarily. Of course, rotatable features may simply be omitted if desired.

Articulation section (121430) is substantially the same as articulation section (130) described above with respect to instrument (10), unless otherwise note herein. For instance, articulation section (121430) is operable to selectively position end effector (121340) at various lateral deflection angles relative to a longitudinal axis defined by shaft assembly (121430). Like with articulation section (130), articulation section (121430) is driven by a pair of articulation bands (121440, 121442) disposed within articulation section (121430) and extending through shaft assembly (121330). When articulation bands (121440, 121142) translate longitudinally in an opposing fashion, this will cause articulation section (121430) to bend, thereby laterally deflecting end effector (121340) away from the longitudinal axis of shaft assembly (121330) from a straight configuration to an articulated configuration. In particular, end effector (121340) will be articulated toward the articulation band (121440, 121442) that is being pulled proximally. During such articulation, the other articulation band (121440, 121442) may be pulled or pushed distally.

Instrument further includes an articulation control assembly (121400) that is secured to a proximal portion of shaft assembly (121330). Articulation control assembly (121400) comprises a housing (121410) and a rotatable knob (121420). Like with articulation control assembly (100) described above, rotatable knob (121420) is configured to rotate relative to housing (121410) to drive articulation bands (121440, 121442) in opposing longitudinal directions. For instance, rotation of knob (121420) in a first direction causes distal longitudinal translation of articulation band (121440), while simultaneously causing proximal longitudinal translation of articulation band (121442). Rotation of knob (121420) in a second direction causes proximal longitudinal translation of articulation band (121440), while simultaneously causing distal longitudinal translation of articulation band (121442). Thus, it should be understood that rotation of rotation knob (121420) causes articulation of articulation section (121430).

Unlike instrument (10) described above, instrument (121310) of the present example further includes a tensioning assembly (121500). Tensioning assembly (121500) is generally operable as a over-center toggle mechanism to directly apply tension to articulation bands (121440, 121442) and to maintain such tension. In particular, as can best be seen in FIGS. 156 and 157, tensioning assembly (121500) comprises a lever arm (121510) and a collar (121520) disposed about shaft assembly (121330). Lever arm (121510) is attached to housing (121410) of actuation control assembly (121400) at an integral attachment yoke (121415) of housing (121410). Lever arm (121510) is connected to attachment yoke (121415) via a pin (121511) that is configured to permit lever arm (121510) to pivot relative to attachment yoke (121415). As will be described in greater detail below, lever arm (121510) is generally configured to pivot relative to attachment yoke (121415) as an over-center toggle mechanism to drive collar (121520) proximally or distally.

Lever arm (121510) is connected to collar (121520) by two links (121512, 121514) extending between lever arm (121510) and collar (121520). Each link (121512, 121514) is pivotably connected to lever arm at a pin (121515) disposed near the center of lever arm (121510). Each link (121512, 121514) also pivotably connects to collar (121520) at a respective pivotal coupling (121521, 121522). Both pin (121515) and pivotal couplings (121521, 121522) allow each link to pivot as lever arm (121510) and collar (121520) are moved.

As can best be seen in FIGS. 157 and 158, collar (121520) includes a pair of inwardly extending armatures (121524) (only a single armature is shown) that extend from collar (121520) and into shaft assembly (121330) through a pair of slots (121333) in shaft assembly (121330). Each armature (121524) connects to a respective articulation band (121440, 121442). In particular, each articulation band (121440, 121442) includes a slot that receives a corresponding armature (121524). The slots and armatures (121524) are configured such that articulation bands (121440, 121442) may move freely in opposing longitudinal directions when collar (121520) is in the distal position shown in FIG. 159. However, when collar (121520) is moved to the proximal position shown in FIG. 160 as described in greater detail below, the and armatures (121524) are configured such that armatures (121524) reach the proximal ends of those slots, thereby pulling proximally on articulation bands (121440, 121442) to provide tension in articulation bands (121440, 121442). The opposite end of each armature (121524) is integral or fixedly secured to an inner ring (121526) disposed within collar (121520). Inner ring (121526) is configured to freely rotate within collar (121520) while still transferring any translation of collar (121520) to each armature (121524). Such a feature may be desirable because when collar (121520) includes such a feature, collar (121520) may remain stationary while shaft assembly (121330) is rotated.

As another exemplary configuration, collar (121520) may include a cam feature that provides selective engagement between collar (121520) and articulation bands (121440, 121442). For instance, when such a cam feature is in a first position, collar (121520) may be disengaged from articulation bands (121440, 121442), such that articulation bands (121440, 121442) may move freely in opposing longitudinal directions when the cam feature is in the first position. When the cam feature is moved (e.g., rotated, slid, etc.) to a second position, the cam feature may provide engagement between collar (121520) and articulation bands (121440, 121442), such that longitudinal motion of collar (121520) provides corresponding, simultaneous longitudinal motion of articulation bands (121440, 121442). Other suitable structures and relationships that may be provided between collar (121520) and articulation bands (121440, 121442) will be apparent to those of ordinary skill in the art in view of the teachings herein.

An exemplary use of tensioning assembly (121500) is shown in FIGS. 159 and 160. In particular, tensioning assembly (121500) may initially be in a non-tensioning or relaxed position. In such a position, lever arm (121510) is pivotably disposed upwardly such that pin (121515) is disposed above pin (121511). With lever arm (121510) positioned upwardly, collar (121520) is pushed to a distal position relative to shaft assembly (121330) by each link (121512, 121514). Because collar (121520) is attached to articulation bands (121440, 121442) via armatures (121524), articulation bands (121440, 121442) are in a non-tensioned or relaxed state when collar (121520) is in the distal position. Accordingly, articulation bands (121440, 121442) may be used to articulate articulation section (121430) via articulation control assembly (121400) as described above when collar (121520) is in the distal position.

To transition tensioning assembly (121500) to a tensioning position, an operator may pivot lever arm (121510) downwardly to the position shown in FIG. 160. As can be seen, when lever arm (121510) is forced downwardly, each link (121512, 121514) pulls collar (121520) proximally relative to shaft assembly (121330). Because collar (121520) is attached to each articulation band (121440, 121442), collar (121520) will simultaneously pull each articulation band (121440, 121442) correspondingly proximally. Thus, collar (121520) will act to apply tension to each articulation band (121440, 121442) as it is pulled proximally by lever arm (121510).

With lever arm (121510) in the position shown in FIG. 160, tensioning assembly (121500) is in a tensioned position. In the tensioned position, collar (121520) is at its furthest proximal position relative to shaft assembly (121330) and articulation bands (121440, 121442) are correspondingly fully tensioned. Additionally, lever arm (121510) is positioned such that pin (121515) is disposed below pin (121511). Because of this and the tensioning force generated between lever arm (121510) and collar (121520), lever arm (121510) is generally fixed in the tensioned position, such that tensioning assembly (121500) provides an over-center toggle. Accordingly, should an operator desire to return tensioning assembly (121500) to the non-tensioning or relaxed position, the operator will need to pivot lever arm (121510) upwardly back to the position shown in FIG. 156. While the present example includes an over-center toggle feature to maintain lever arm (121510) in the tensioned position, any other suitable feature or mechanism may be used. Alternatively, in other examples such a feature may simply be omitted.

In one some alternative versions of instrument (121400), collar (121520) is omitted. In some such versions, yoke (121415) is an integral feature of body (121322) of handle assembly (121320), such that lever arm (121510) is pivotably coupled directly to handle assembly (121320). In addition, in some such versions, the distal ends of links (121512, 121514) are pivotably coupled directly with housing (121410) of articulation control assembly (121400). Such an example may operate similar to the example of instrument (121100) described above. Thus, when lever arm (121510) is pivoted to an upward position, articulation control assembly (121400) is in a distal position and articulation bands (121440, 121442) are free to translate in order to provide articulation of articulation section (121430). When lever arm (121510) is pivoted to a downward position, articulation control assembly (121400) is in a proximal assembly, pulling articulation bands (121440, 121442) such that articulation bands (121440, 121442) are in tension, thereby effectively rigidizing articulation section (121430) (e.g., when articulation section is in a straight or non-articulated state). Other suitable variations will be apparent to those of ordinary skill in the art in view of the teachings herein.

XIV. ULTRASONIC SURGICAL INSTRUMENT WITH MOVABLE RIGIDIZING MEMBER

As noted above, in some versions of instrument (10) it may be desirable to provide features that are configured to selectively provide rigidity to articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Features may thus be provided to selectively rigidize articulation section (130). Various examples of features that are configured to selectively provide rigidity to articulation section (130) and/or to limit or prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof such that the already existing rigidity of articulation section (130) may be increased. Thus, terms such as "rigidize," "provide rigidity," and "providing rigidity" shall be understood to include just increasing rigidity that is already present in some degree. The terms "rigidize," "provide rigidity," and "providing rigidity" should not be read as necessarily requiring articulation section (130) to completely lack rigidity before the rigidity is "provided."

It should also be understood that "rigidizing" articulation section (130) may be viewed as more than merely locking articulation section (130). For instance, while articulating sections in some conventional instruments may include a locking feature that selectively locks the articulation section, such instruments may still demonstrate some degree of play in the articulation section, even when the articulation section purports to be in a locked state. By further "rigidizing" the articulation section as described herein, that play would be removed from the locked articulation section. Thus, terms such as "rigidizing" and "locking" should not be read as being synonymous.

Various examples of features that are configured to selectively rigidize articulation section (130) are described in greater detail below. Various other examples will be apparent to those of ordinary skill in the art in view of to the teachings herein.

A. Articulation Section with Movable Sheath

FIGS. 161 and 162 show a version of shaft assembly (30) that is modified to include a movable sheath (13210), which is slidably disposed about proximal outer sheath (32). Sheath (13210) is generally cylindrical in shape and is configured to fit over outer sheath (32). In particular, sheath (13210) comprises a tapered open distal end (13212) and a tapered open proximal end (13214). Accordingly, sheath (13210) is a generally hollow tube that surrounds outer sheath (32). Each end (13212, 13214) defines an inner diameter that is closely matched to the outer diameter of outer sheath (32). Such a relationship between the inner diameter of sheath (13210) and outer sheath (32) may be desirable because such a relationship may prevent movement of articulation section (130) when sheath (13210) is disposed over articulation section (130). Although the inner diameter of sheath (13210) is similar to the outer diameter of outer sheath (32) it should be understood that the inner diameter of sheath (13210) may still be large enough relative to the outer diameter of outer sheath (32) to permit sheath (13210) to slide relative to outer sheath (32). As will be described in greater detail below, such slidability is desirable because it may permit sheath (13210) to be selectively positioned over articulation section (130).

Sheath (13210) is comprised of a generally rigid thin walled biocompatible material such as titanium, stainless steel, rigid plastic, and/or any other suitable material(s). Because distal and proximal ends (13212, 13214) of sheath (13210) are tapered, the wall thickness of sheath (13210) varies by length. Such a taper may prevent sheath (13210) from being snagged on a trocar or other surgical port as shaft assembly (30) is inserted into and withdrawn from the trocar or other port. It should be understood that such a taper is merely optional, and in some examples sheath (13210) may have a uniform thickness along the full length of sheath (13210).

FIGS. 161 and 162 show an exemplary use of sheath (13210). As can be seen in FIG. 161, sheath (13210) may initially be disposed in a first position. In the first position, sheath (13210) is disposed proximally of articulation section (130). In such a position, articulation section (130) is free to articulate as described above in response to an operator acting upon articulation control assembly (100).

When an operator desires to rigidize articulation section (130) in a fixed, straight position, an operator may do so by grasping sheath (13210) and translating sheath (13210) distally to the position shown in FIG. 162. The position shown in FIG. 162 corresponds to sheath (13210) being in a second position. In the second position, sheath (13210) is disposed over articulation section (130) with distal end (13212) disposed over at least a portion of distal outer sheath (33) and proximal end (13214) over at least a portion of proximal outer sheath (32). When in the second position, the inner diameter of sheath (13210) engages distal outer sheath (33), articulation section (130) and proximal outer sheath (32) to prevent substantially all articulation and/or other movement of articulation section (130). In other words, sheath (13210) rigidizes articulation section (130) when sheath (13210) is disposed in the second position.

Although sheath (13210) of the present example is described herein as being manually translatable by an operator, it should be understood that in other examples sheath (13210) may be translatable by other means. For instance, in some examples sheath (13210) may further comprise certain actuation components that are in communication with articulation bands (140, 142). In examples incorporating such actuation components, the actuation components are responsive to movement of articulation bands (140, 142) such that sheath (13210) is automatically transitioned between the first and second positions by movement of articulation bands (140, 142) through certain predetermined positions. Additionally or in the alternative, sheath (13210) may also be spring loaded to automatically transition sheath (13210) from the first position to the second position. As yet another merely illustrative alternative, sheath (13210) may be actuated by knob (120), some other user input feature at articulation control assembly (100), and/or some other feature of handle assembly (20). Still other suitable mechanisms for transitioning sheath (210) between the first and second positions will be apparent to those of ordinary skill in the art in view of the teachings herein.

B. Articulation Section with Movable Sheath and Sheath Securing Features

FIGS. 163-165 show a version of shaft assembly (30) that is modified to include another movable sheath (13310), which is slidably disposed about proximal outer sheath (32). Sheath (13310) is generally cylindrical in shape and is configured to fit over outer sheath (32). In particular, sheath (13310) comprises a tapered open distal end (13312), a tapered open proximal end (13314), and a grip portion (13316) disposed distally of proximal end (13314). Accordingly, sheath (13310) is a generally hollow tube that surrounds outer sheath (32). Each end (13312, 13314) defines an inner diameter of sheath (13310) that is closely matched to the outer diameter of outer sheath (32). Such a relationship between the inner diameter of sheath (13310) and outer sheath (32) may be desirable because such a relationship may prevent movement of articulation section (130) when sheath (13310) is disposed over articulation section (130). Although the inner diameter of sheath (13310) is similar to the outer diameter of outer sheath (32) it should be understood that the inner diameter of sheath (13310) may still be large enough relative to the outer diameter of outer sheath (32) to permit sheath (13310) to slide relative to outer sheath. As will be described in greater detail below, such slidability is desirable because it may permit sheath (13310) to be selectively positioned over articulation section (130).

Grip portion (13316) is generally configured to facilitate grasping of sheath (13310) by an operator. Grip portion (13316) of sheath comprises a plurality of grip features (13317). Grip features (13317) of the present example are shown as spaced-apart indentations in the outer diameter of sheath (13310). In other examples, grip features (13317) are formed by integral protrusions or separately secured protrusions. In examples utilizing protrusions, it should be understood that the protrusions protrude from sheath (13310) may be fixed by the inner diameter of a trocar or other port that instrument (10) may be used in conjunction with. It should also be understood that grip portion (13312) is merely optional, such that grip portion (13312) is omitted in some versions.

Sheath (13310) is comprised of a generally rigid thin walled biocompatible material such as titanium, stainless steel, rigid plastic, or etc. Because distal and proximal ends (13312, 13314) of sheath (13310) are tapered, the wall thickness of sheath (13310) varies by length. Such a taper may prevent sheath (13310) from being snagged on a trocar or other surgical port as shaft assembly (30) is inserted into and withdrawn from the trocar or other port. It should be understood that such a taper is merely optional, and in some examples sheath (13310) may have a uniform thickness along the full length of sheath (13310).

Distal outer sheath (33) and proximal outer sheath (32) in the present example each include a flared stop member (13320, 13326). In particular, a distal stop member is positioned on distal outer sheath (33) and a proximal stop member (13326) is positioned on proximal outer sheath (33). Each stop member (13320, 13326) is unitarily secured to the corresponding sheath (32, 33). Each stop member (13320, 13326) is generally frustoconical in shape, with a maximum outer diameter that is greater than the inner diameter of sheath (13310) such that stop members (13320, 13326) are configured to engage with sheath (13310) and thereby restrict longitudinal movement of sheath (13310). In the present example, each stop member (13320, 13326) is overmolded onto each respective sheath (32, 33) and comprises a resilient material such as a soft plastic or rubber. In some other examples, each stop members (13320, 13326) is unitarily formed with each respective sheath (32, 33).

As will be described in greater detail below, sheath (13310) is generally slidable and into engagement with either distal stop member (13320) or proximal stop member (13326). Thus, distal stop member (13320) is positioned such that an engagement end (13322) is positioned proximally, while proximal stop member (13326) is positioned such that an engagement end (13328) is positioned distally. Engagement end (13322) is sized for snug receipt within sheath (13310), such that distal stop member (13320) may releasably hold sheath (13310) in a distal position through friction between engagement end and the interior of sheath (13310). Similarly, engagement end (13328) is sized for snug receipt within sheath (13310), such that proximal stop member (13326) may releasably hold sheath (13310) in a proximal position through friction between engagement end and the interior of sheath (13310). The enlarged distal end of distal stop member (13320) will restrict distal movement of sheath (13310), while the enlarged proximal end of proximal stop member (13326) will restrict proximal movement of sheath (13310).

FIGS. 163-165 show an exemplary use of sheath (13310). As can be seen in FIG. 163, sheath (13310) may initially be disposed in a first position. In the first position, sheath (13310) is disposed proximally of articulation section (130) yet distally of proximal stop member (13326). In such a position, articulation section (130) is free to articulate as described above in response to an operator acting upon articulation control assembly (100). Further, sheath (13310) is free from both stop members (13320, 13326) such that sheath (13310) is freely movable between stop members (13320, 13326).

When sheath (13310) is in the first position, an operator may optionally lock sheath (13310) in a second position, or advance sheath (13310) to a third position. FIG. 164 shows sheath (13310) in the second position. As can be seen, the second position corresponds to sheath (13310) being disposed over proximal outer sheath (32) and engaged with proximal stop member (13326). It should be understood that the second position corresponds to the furthest proximal position of sheath (13310). In particular, stop member (13326) prevents further proximal movement of sheath (13310). Additionally, stop member (13326) resiliently locks sheath (13310) in position by resiliently engaging the inner diameter of sheath (13310). In other words, sheath (13310) compresses engagement end (13328) and thereby creates friction that releasably holds sheath (13310) in place.

When an operator desires to rigidize articulation section (130) in a fixed, straight position, the operator may do so by grasping sheath (13310) and translating sheath (13310) distally to the position shown in FIG. 165 from either the first position or the second position. The position shown in FIG. 165 corresponds to sheath (13310) being in the third position. In the third position, sheath (13310) is disposed over articulation section (130) with distal end (13312) disposed over at least a portion of distal outer sheath (33) and proximal end (13314) over at least a portion of proximal outer sheath (32). Additionally, distal end (13312) engages at least a portion of distal stop member (13320). Sheath (13310) compresses engagement end (13322) and thereby creates friction that releasably holds sheath (13310) in place. In addition, stop member (13320) prevents further distal movement of sheath (13310). When in the third position, the inner diameter of sheath (13310) engages distal outer sheath (33), articulation section (130), and proximal outer sheath (32) to prevent substantially all articulation and/or movement of articulation section (130). In other words, sheath (13310) rigidizes articulation section (130) when sheath (13310) is disposed in the third position.

Like with sheath (13210) described above, sheath (13310) of the present example may also be translatable by other non-manual means. For instance, in some examples sheath (13310) may further comprise certain actuation components that are in communication with articulation bands (140, 142). In examples incorporating such actuation components, the actuation components are responsive to movement of articulation bands (140, 142) such that sheath (13310) is automatically transitioned between the first and second positions by movement of articulation bands (140, 142) through certain predetermined positions. Additionally or in alternative, sheath (13310) may also be spring loaded to automatically transition sheath (13310) from the first position to the second position. As yet another merely illustrative alternative, sheath (13310) may be actuated by knob (120), some other user input feature at articulation control assembly (100), and/or some other feature of handle assembly (20). Still other suitable mechanisms for transitioning sheath (13310) between the first and second positions will be apparent to those of ordinary skill in the art in view of the teachings herein.

C. Articulation Section with Rotatable Locking Sheath

FIGS. 166-170 show a version of shaft assembly (30) that is modified to include a rotatable sheath (13410), which is rotatably disposed about articulation section (130). Rotatable sheath (13410) is generally tubular in structure and comprises two tab members (13420, 13430) of unitary construction with sheath (13410). Tab members (13420, 13430) are formed by slits (13420, 13430) cut (13421, 13431) within sheath (13410) to define a longitudinal portion (13424, 13434) and a transverse portion (13426, 13436) of each tab member (13420, 13430), such that each tab member (13420, 13430) has a "T" shape. As can be seen in FIG. 167, the thickness of each tab member (13420, 13430) expands from transverse portion (13426, 13436) to longitudinal portion (13424, 13434) such that at least a portion of each tab member (13420, 13430) extends into the inner diameter of sheath (13410). As will be described in greater detail below, the increased thickness of each longitudinal portion (13424, 13434) is configured to engage with retention collars (133) of articulation section (130) to prevent articulation of articulation section (130). In some versions, each tab member (13420, 13430) has a uniform thickness and tab members (13420, 13430) are simply resiliently biased to extend inwardly into the inner diameter of sheath (13410). For instance, transverse portions (13426, 13436) may be bent inwardly to resiliently position longitudinal portions (13424, 13434) into the inner diameter of sheath (13410).

Sheath (13410) further comprises a generally flexible material such that sheath (13410) is configured to bend as articulation section (130) is articulated. Although the material of sheath (13410) is generally flexible, it should also be understood that the material of sheath (13410) is somewhat rigid. As will be described in greater detail below, tab members (13420, 13430) are configured to engage retention collars (133) of articulation section (130) to selectively prevent articulation of articulation section (130). Accordingly, sheath (13410) is comprised of a material of sufficient column strength such that tab members (13420, 13430) resist buckling when compressed between retention collars (133). Sheath (13410) may comprise any suitable material such as biocompatible polymers and/or any other material(s) as will be apparent to those of ordinary skill in the art in view of the teachings herein.

FIGS. 166, 168, and 169-170 show an exemplary use of sheath (13410). In particular, as can be seen in FIGS. 166 and 168, sheath (13410) is initially in a first angular position. When sheath (13410) is in the first angular position, longitudinal portions (13424, 13434) of each tab member (13420, 13430) are aligned with an articulation plane through which the central longitudinal axis of shaft assembly (30) articulates. As can best be seen in FIG. 168, when sheath (13410) is in the first position, longitudinal portions (13424, 13434) of each tab member (13420, 13430) are positioned between each retention collar (133) along the articulation plane. Accordingly, longitudinal portions (13424, 13434) are positioned to block any articulation of articulation section (130) because longitudinal portions (13424, 13434) prevent retention collars (133) from moving closer to one another. Therefore, sheath (13410) acts as a locking member to increase the rigidity of articulation section (130) when sheath (13410) is in the first angular position.

To unlock articulation section (130) for articulation, an operator may rotate sheath (13410) 90° about the longitudinal axis of shaft assembly (30), relative to the rest of shaft assembly (30), to a second angular position. As can be seen in FIGS. 169 and 170, when sheath (13410) is in the second angular position, longitudinal portions (13424, 13434) are oriented perpendicularly from the articulation plane of articulation section (130). Thus, although longitudinal portions (13424, 13434) remain disposed between retention collars (133) of articulation section (130), articulation section (130) is permitted to articulate because longitudinal portions (13424, 13434) are not positioned to block movement of retention collars (133) along the articulation plane as articulation section (130) is articulated. Moreover, because sheath (13410) is relatively flexible, sheath (13410) itself does not prevent articulation of articulation section (130). Therefore, sheath (13410) acts to permit articulation of articulation section (130) when sheath (13410) is in the second angular position.

By way of example only, an operator may selectively transition sheath (13410) between the first and second angular positions by simply grasping sheath (13410) and rotating sheath (13410) about the longitudinal axis of shaft assembly (30) while holding the rest of shaft assembly (30) stationary. Alternatively, sheath (13410) may be actuated between the first and second angular positions via a user input feature that is incorporated into articulation control assembly (100) and/or some other feature of handle assembly (20). Various suitable ways in which sheath (13410) may be actuated will be apparent to those of ordinary skill in the art in view of the teachings herein.

FIG. 171 shows an exemplary alternative sheath (13510) that operates similarly to sheath (13410) and may be readily incorporated into shaft assembly (30) of instrument (10). In the present example, sheath (13510) is positioned over articulation section (130) as described above. In some versions, retention collars (133) are omitted when sheath (13510) is incorporated into shaft assembly (30). As can be seen, sheath (13510) is comprised of a plurality of segments (13512, 13518, 13524) that are disposed over articulation section (130). In particular, segments (13512, 13518, 13524) form a generally tubular structure that is configured to bend in a single lateral direction as indicated by arrow (13530), but resist bending in other directions that are generally oblique or perpendicular to arrow (13530).

Segments (13512, 13518, 13524) of the present example comprise two end segments (13512, 13524) and three intermediate segments (13518). Each end segment (13512, 13524) includes an end portion (13514, 13526) and a connecting portion (13516, 13528). End portions (13514, 13526) are generally circular in cross-section and are configured to receive distal outer sheath (33) and proximal outer sheath (32), respectively. Connecting portions (13516, 13528) are configured to abut a corresponding intermediate segment (13518). Each connecting portion (13516, 13528) defines an indentation (13517, 13529) therein. As will be described in greater detail below, each indentation (13517, 13529) is generally configured to cooperate with corresponding indentation (13523) of an adjacent intermediate segment (13518) to thereby permit articulation of sheath (13510) along the lateral direction indicated by arrow (13530).

Each intermediate segment (13518) of the present example is substantially the same. Although the present example is shown as comprising three intermediate segments (13518), it should be understood that any suitable number of intermediate segments (13518) may be used. Further, in some examples intermediate segments (13518) may be omitted and end segments (13512, 13524) may simply be adjacent to each other. Each intermediate segment (13518) is generally symmetrical with a distal portion (13520) and a proximal portion (13522). Each portion (13520, 13522) defines an indentation (13523) and abuts a corresponding adjacent segment (13512, 13518, 13524). Each indentation (13523) is aligned with either an adjacent indentation (13523) of another intermediate segment (13518) or an adjacent indentation (13517, 13529) of end segments (13512, 13524).

Segments (13512, 13518, 13524) are connected to each other sequentially to form the tubular structure of sheath (13510). Segments (13512, 13518, 13524) are connected to each other such that each segment (13512, 13518, 13524) is movable relative to an adjacent segment (13512, 13518, 13524). For instance, suitable connections may include wire connections, thin walled flexible integral members, hinge members, or any other suitable structures as will be apparent to those of ordinary skill in the art in view of the teachings herein. Regardless of the particular connection used, each segment (13512, 13518, 13524) is aligned with an adjacent segment (13512, 13518, 13524) such that all indentations (13517, 13523, 13529) are aligned with each other along a linear path that is generally parallel to the longitudinal axis of shaft assembly (30). It should be understood that the alignment of indentations (13517, 13523, 13529) may permit flexibility of sheath (13510) along the linear path of alignment because each indentation (13517, 13523, 13529) provides space for each segment to pivot relative to the other. In contrast, where each segment (13512, 13518, 13524) abuts another without the presence of indentation (13517, 13523, 13529), flexibility of sheath (13510) is blocked because each segment (13512, 13518, 13524) has little to no space to move relative to other segments (13512, 13518, 13524).

FIGS. 171 and 172 show an exemplary use of sheath (13510). In particular, FIG. 171 shows sheath (13510) in a first angular position. In the first angular position, indentations (13517, 13523, 13529) of each segment (13512, 13518, 13524) of sheath (13510) are aligned along the articulation plane of shaft assembly (30) as indicated by arrow (13530). Thus, when sheath (13510) is in the first position, sheath (13510) permits articulation of articulation section (130). To articulate articulation section (130), an operator may actuate articulation control assembly (100) as described above.

Once an operator desires to lock articulation section (130) in a straight position, the operator may first transition articulation section (130) to the straight configuration using articulation control assembly (100) as described above. Once articulation section (130) is in the straight configuration, the operator may rotate sheath (13510) 90° about the longitudinal axis of shaft assembly (30), relative to the rest of shaft assembly (30), to a second angular position as shown in FIG. 172. As can be seen, when sheath (13510) is rotated to the second angular position, indentations (13517, 13523, 13529) of each segment (13512, 13518, 13524) of sheath (13510) are aligned in a position that is normal to the articulation plane of shaft assembly (30). As described above, sheath (13510) is only bendable in the direction of indentations (13517, 13523, 13529). Accordingly, when indentations (13517, 13523, 13529) are positioned normal to the articulation plane of shaft assembly (30), sheath (13510) prevents articulation of articulation section (130) because segments (13512, 13518, 13524) are incapable of moving relative to each other along the articulation plane of articulation section (130) when sheath (13510) is in the second angular position. Therefore, when sheath (13510) is positioned in the second angular position, articulation section (130) is locked from articulation and/or increased in rigidity due to the angular positioning of sheath (13510).

By way of example only, an operator may selectively transition sheath (13510) between the first and second angular positions by simply grasping sheath (13510) and rotating sheath (13510) about the longitudinal axis of shaft assembly (30) while holding the rest of shaft assembly (30) stationary. Alternatively, sheath (13510) may be actuated between the first and second angular positions via a user input feature that is incorporated into articulation control assembly (100) and/or some other feature of handle assembly (20). Various suitable ways in which sheath (13510) may be actuated will be apparent to those of ordinary skill in the art in view of the teachings herein.

D. Articulation Section with Complementary Locking Shafts

FIGS. 173-175 show an exemplary alternative sheath assembly (13610) that may be readily incorporated into shaft assembly (30) described above. In examples where sheath assembly (13610) is incorporated into shaft assembly (30), sheath assembly (13610) may be disposed around articulation section (130) to thereby selectively rigidize articulation section (130). Sheath assembly (13610) is longitudinally fixed about articulation section (130). Sheath assembly (13610) comprises an inner sheath (13612) disposed coaxially within an outer sheath (13620). As will be described in greater detail below, sheaths (13612, 13620) are configured to cooperate to selectively rigidize articulation section (130). In the present example sheaths (13612, 13620) are each about 0.0075" thick, although any suitable thickness may be used. For instance, in some examples sheaths (13612, 13620) range from about 0.005" to about 0.010" in wall thickness.

As can be seen in FIG. 173 outer sheath (13620) comprises a plurality of openings (13622) on the exterior of outer sheath (13620). In particular, openings (13622) are all substantially the same and have an elongate ovular or elliptical shape. As will be described in greater detail below, openings (13622) are generally configured to locally increase the flexibility of outer sheath (13620) in the region of outer sheath (13620) where openings (13622) are positioned. Although not shown, it should be understood that openings (13622) extend laterally though outer sheath (13620) and thus are also disposed on the opposite outer wall of outer sheath (13620). Such a feature is configured to increase the local flexibility of outer sheath (13620) because openings (13622) on one side may expand while openings (13622) on another side may contract as outer sheath (13620) bends along an articulation plane. It should be understood that openings (13622) are configured to allow outer sheath (13620) to bend along just one plane.

As best seen in FIG. 174, inner sheath (13612) also comprises a plurality of openings (13614) on the exterior of inner sheath (13612). Openings (13614) are similar to openings (13622) described above. For instance, openings (13614) have a generally elongate ovular or elliptical shape. Furthermore, openings (13614) are likewise configured to locally increase the flexibility of inner sheath (13612) in the region of inner sheath (13612) where openings (13614) are positioned. However, in contrast to openings (13622), openings (13614) are smaller in scale proportionally to the smaller diameter of inner sheath (13612). Although smaller in scale, openings (13614) are positioned to align with openings (13622) of outer sheath (13620). Although the present example is shown as including five sets of openings (13614, 13622), it should be understood that in other examples any suitable number of openings (13614, 13622) may be used. Openings (13614) are configured to allow inner sheath (13612) to bend along a single plane, with openings (13614) on one side of inner sheath (13612) expanding while openings (13614) on the other side of inner sheath (13612) contracting as inner sheath (13612) bends along the plane. In the present example, inner sheath (13612) is fixedly secured about articulation section (130) such that inner sheath (13612) does not rotate about articulation section (130). However, outer sheath (13620) is rotatable about inner sheath (13612) and thus about articulation section (130).

FIGS. 173 and 175 show an exemplary use of sheath assembly (13610). Initially, sheath assembly (13610) may be in a first configuration as shown in FIG. 173. As can be seen, when sheath assembly (13610) is in the first configuration, inner and outer sheaths (13612, 13620) are angularly aligned such that openings (13614) of inner sheath (13612) are aligned with openings (13622) of outer sheath (13620). When openings (13614, 13622) are aligned, the respective bending planes of inner and outer sheaths (13612, 13620) are aligned such that inner and outer sheaths (13612, 13620) are together bendable along their common bending plane. Thus, in the first position sheath assembly (13610) permits articulation of articulation section (130) when incorporated into shaft assembly (30) described above.

If an operator desires to make sheath assembly (13610) rigid, such as when sheath assembly (13610) is incorporated into shaft assembly (30) described above, the operator may rotate outer sheath (13620) relative to inner sheath (13612) 90° about the longitudinal axis of sheath assembly (13610) to a second angular position shown in FIG. 175. As can be seen, in the second position, outer sheath (13620) has been rotated approximately 90° such that openings (13622) of outer sheath (13620) are angularly offset from openings (13614) of outer sheath (13612). When openings (13614, 13622) are angularly offset by 90°, any flexibility achieved by use of openings (13614, 13622) is lost because solid portions of sheath (13612) block flexibility of openings (13622) and solid portions of sheath (13620) block flexibility of openings (13614). Therefore, when outer sheath (13620) is in the second angular position, sheath assembly (13610) is used to lock and/or increase the rigidity of articulation section (130).

Although the second position is shown in FIG. 175 as outer sheath (13620) being rotated approximately 90° from the position of outer sheath (13620) in the first position, it should be understood that outer sheath (13620) may be rotated to other positions to achieve the same outcome of stiffening sheath assembly (13610). For instance, in some examples outer sheath (13620) may be rotated as little as 15° before causing stiffening of sheath assembly (13610). Of course, in other examples outer sheath (13620) may be rotated even further than 90°. Additionally, although outer sheath (13620) is described herein as being rotated, in other examples inner sheath (13612) may be rotated instead, or both sheaths (13612, 13620) may be rotated simultaneously at different rates to achieve the same result. In still other examples, sheaths (13612, 13620) may not be rotated at all. Instead, one sheaths (13612, 13620) may be translated longitudinally relative to the other sheaths (13612, 13620) in order to position openings (13622) of outer sheath (13620) at longitudinal positions that are offset from the longitudinal positions of openings (13614) of outer sheath (13612), such that sheaths (13612, 13620) are out of phase with each other.

Although sheath assembly (13610) of the present example is described herein as being manually actuated by an operator, it should be understood that in other examples sheath assembly (13610) may be actuated by other means. For instance, in some examples sheath assembly (13610) may further comprise certain actuation components that are in communication with articulation bands (140, 142). In examples incorporating such actuation components, the actuation components are responsive to movement of articulation bands (140, 142) such that outer sheath (13620) is automatically transitioned between the first and second angular positions by movement of articulation bands (140, 142) through certain predetermined positions. Additionally or in the alternative, sheath assembly (13610) may also be spring loaded to automatically transition outer sheath (13620) from the first position to the second position. As yet another merely illustrative alternative, sheath assembly (13610) may be actuated by knob (120), some other user input feature at articulation control assembly (100), and/or some other feature of handle assembly (20). Still other suitable mechanisms for transitioning outer sheath (13620) between the first and second angular positions will be apparent to those of ordinary skill in the art in view of the teachings herein.

E. Articulation Section with Interlocking Coil Sheath

FIGS. 176 and 177 show a version of shaft assembly (30) that is modified to include a sheath assembly (13710), which is generally configured to selectively rigidize articulation section (130). In the present example, at least a portion of sheath assembly (13710) is disposed around articulation section (130) to thereby permit sheath assembly 13(710) to selectively rigidize articulation section (130). Sheath assembly (13710) comprises a first coil member (13712) with a second coil member (13720) interlockingly engaged with first coil member (13712). As will be described in greater detail below, coil members (13712, 13720) are configured to cooperatively rigidize articulation section (130).

As can be seen in FIG. 176 first coil member (13712) comprises a first helical band (13714) that is wrapped around the exterior of articulation section (130). First helical band (13714) has a constant helix angle and a constant diameter along the length of articulation section (130). While first helical band (13714) is fixedly secured about articulation section (130), first helical band (13714) is configured to flex with articulation section (130) as articulation section (130) articulates. When articulation section (130) articulates, first helical band (13714) flexes such that the helix contracts on one side of the helix axis while the helix expands on the other side of the helix axis.

Second coil member (13720) is configured substantially similarly to comprises first coil member (13712). For instance, second coil member (13720) comprises a second helical band (13722) that is wrapped around the exterior of at least a portion of articulation section (130) and at least a portion of proximal outer shaft (32). Second helical band (13722) has a constant helix angle and a constant diameter along a length corresponding to the length of articulation section (130). The helix angle and diameter of second helical band (13722) is the same as the helix angle and diameter of first helical band (13714). Moreover, the longitudinal thickness of second helical band (13722) is approximately the same as the longitudinal spacing between helix segments of first helical band (13714). Likewise, the longitudinal thickness of first helical band (13714) is approximately the same as the longitudinal spacing between helix segments of second helical band (13722). It should therefore be understood that the complementary configuration of helical bands (13714, 13722) permits second helical band (13722) to nest with first helical band (13714). In particular, Therefore, coil members (13712, 13720) are configured such that one coil member (13712, 13720) is rotatable relative to the other coil member (13712, 13720) to interlock coils (13714, 13722) to thereby form a generally tubular structure.

Coil members (13712, 13720) comprise a material that is generally rigid when coil members (13712, 13720) are interlocked; but is generally bendable when coil members (13712, 13720) are separate. By way of example only, suitable materials may include stainless steel, aluminum, or certain polymers such as PTFE, polyethylene terephthalate (PET), high-density polyethylene (HDPE), etc. Of course, any other suitable material(s) may be used as will be apparent to those of ordinary skill in the art in view of the teachings herein.

FIGS. 176 and 177 show an exemplary use of sheath assembly (13710). Initially, sheath assembly (13710) may be in a first configuration as shown in FIG. 176. As can be seen, when sheath assembly (13710) is in the first configuration, coil members (13712, 13720) are longitudinally positioned such that there is little to no interlocking between each coil member (13712, 13720). When coil members (13712, 13720) are in this arrangement, coil members (13712, 13720) permit free articulation of articulation section (130). First coil member (13712) will flex with articulation section (130) as articulation section (130) articulates. Second coil member (13720) is positioned proximal to articulation section (130) in this state, such that second coil member (13720) is unaffected by articulation of articulation section (130); and second coil member (13720) does not impede articulation of articulation section (130).

If an operator wishes to rigidize actuation section (130), the operator may transition sheath assembly (13710) to a second configuration shown in FIG. 177. To transition sheath assembly (13710) to the second configuration, the operator may grasp either second coil member (13720) and rotate second coil member (13720) to advance second coil member (13720) distally into engagement with first coil member (13712). As second coil member (13720) is rotated, coils (13714, 13722) become interlocked with each other such that coils (13714, 13722) are placed in an alternating relationship. As can be seen in FIG. 177, once the second configuration is reached, coil members (13712, 13720) are fully interlocked such that coils (13714, 13722) alternatingly combine to form a rigid tubular structure. With the rigid tubular structure formed, the spacing between each coil (13714, 13722) is eliminated. With the spacing eliminated, the movement of each coil (13714, 13722) is correspondingly limited such that sheath assembly (13710) forms a rigid structure that encompasses articulation section (130). Because articulation section (130) is encompassed by the rigid structure of sheath assembly (13710), articulation of articulation section (130) is correspondingly limited. Thus, it should be understood that when sheath assembly (13710) is in the second position, articulation section (130) is generally locked and/or rigid.

Although sheath assembly (13710) of the present example is described herein as being manually actuated by an operator, it should be understood that in other examples sheath assembly (13710) may be actuated by other means. For instance, in some examples sheath assembly (13710) may further comprise certain actuation components that are in communication with articulation bands (140, 142). In examples incorporating such actuation components, the actuation components are responsive to movement of articulation bands (140, 142) second coil member (13720) is automatically transitioned between the first and second configurations by movement of articulation bands (140, 142) through certain predetermined positions. Additionally or in the alternative, sheath assembly (13710) may also be spring loaded to automatically transition second coil member (13720) from the first configuration to the second configuration. As yet another merely illustrative alternative, sheath assembly (13710) may be actuated by knob (120), some other user input feature at articulation control assembly (100), and/or some other feature of handle assembly (20). Still other suitable mechanisms for actuating sheath assembly (13710) will be apparent to those of ordinary skill in the art in view of the teachings herein.

F. Exemplary Alternative Articulation Section with Rigidizing Linkage

FIGS. 178-179 show a modified version of shaft assembly (30) having a linkage assembly (13810) incorporated therein. Linkage assembly (13810) is generally configured to engage with a portion of articulation section (130) to thereby rigidize articulation section (130). Linkage assembly (13810) comprises a first bar (13820), a second bar (13830), and a third bar (13840). As can be seen in FIG. 25 first bar (13820) has a distal end (13822) and a proximal end (13826). Distal end (13822) defines a slot (13824) that is configured to slidably receive a pin (13825). Pin (13825) is fixedly secured to distal outer sheath (33). Pin (13825) connects first bar (13820) to distal outer sheath (33) such that first bar (13820) is operable to slide a predetermined distance and pivot relative to distal outer sheath (33). As will be described in greater detail below, slot (13824) permits linkage assembly (13810) to slide relative to shaft assembly (30) to lock and unlock articulation section (130). Proximal end (13826) of first bar (13820) comprises a connector (13828), which pivotably connects first bar (13820) to second bar (13830) as will be described in greater detail below.

Second bar (13830) comprises a distal end (13832) and proximal end (13836). As noted above, second bar (13830) is pivotably secured to first bar (13820) via connector (13828). In particular, connector (13828) connects proximal end (13826) of first bar (13820) to distal end (13832) of second bar (13830) such that second bar (13830) is operable to pivot relative to first bar (13820). Proximal end (13836) of second bar (13830) is pivotably secured to third bar (13840), as will be described in greater detail below.

Third bar (13840) has a distal end (13842) and a proximal end (not shown). Distal end (13842) of third bar (13840) comprises a connector (13844). Connector (13844) is configured to pivotably connect proximal end (13836) of second bar (13830) to distal end of third bar (13840). Accordingly second bar (13830) is configured to pivot relative to third bar (13840). Although not shown, it should be understood that the proximal end of third bar (13840) may be connected to an actuator, handle, or other device to provide longitudinal translation of third bar (13840) relative to shaft assembly (30). As will be described in greater detail below, such an actuation device permits linkage assembly (13810) to be translated longitudinally relative to shaft assembly (30) to selectively rigidize articulation section (130).

Linkage assembly (13810) further comprises a first pair of ridges (13850) and a second pair of ridges (13852). Each set of ridges (13850, 13852) extends upwardly (i.e., out of the page in the views shown in FIGS. 17-179) and longitudinally. First ridges (13850) are fixed to at least one retention collar (133) (e.g., the middle retention collar (133) in the present example) and are configured to rigidly engage proximal end (13826) of first bar (13820) and distal end (13842) of second bar (13830). In particular, first ridges (13850) receive proximal end (13826) of first bar (13820) and distal end (13842) of second bar (13830) in a gap laterally defined between first ridges (13850). Second ridges (13852) are fixed on at least a portion of proximal outer sheath (32). Second ridges (13852) are configured to rigidly engage proximal end (13836) of second bar (13830) and distal end (13842) of third bar (13840). In particular, second ridges (13852) receive proximal end (13836) of second bar (13830) and distal end (13842) of third bar (13840) in a gap laterally defined between second ridges (13852). Generally, ridges (13850, 13852) are configured to selectively maintain linkage assembly (13810) in a rigid configuration, as will be described in greater detail below.

FIGS. 178-179 show an exemplary use of linkage assembly (13810). Initially, linkage assembly (13810) is in a first position as shown in FIG. 178. As can be seen, when linkage assembly (13810) is in the first position, bars (13820, 13830, 13840) are positioned such that proximal end (13826) of first bar (13820) and distal end (13832) of second bar (13830) are positioned in the gap laterally defined between first ridges (13850). Additionally, proximal end (13836) of second bar (13830) and distal end (13842) of third bar (13840) are positioned in the gap laterally defined between second ridges (13852). Because of this positioning, ridges (13850, 13852) maintain linkage assembly (13810) in a rigid position. Additionally, because first ridges (13850) are secured to at least one retention collar (133), articulation section (130) is also maintained in a rigid configuration. Therefore, when linkage assembly (13810) is in the first position, linkage assembly (13810) rigidizes articulation section (130).

If an operator desires to articulate articulation section (130), the operator may transition linkage assembly (13810) to a second position shown in FIG. 179. To transition linkage assembly (13810) to the second position, an operator may actuate third bar (13840) proximally to longitudinally translate linkage assembly (13810) proximally. Alternatively, if instrument (10) is so equipped, an operator may actuate articulation control assembly (100) or other device described above that may be connected to the proximal end of third bar (13840). Regardless of how linkage assembly (13810) is longitudinally translated proximally, it should be understood that such translation will lead to bars (13820, 13830, 13840) becoming disengaged from ridges (13850, 13852). In particular, as linkage assembly (13810) is translated proximally, bars (13820, 13830, 13840) may deflect upwardly (i.e., out of the page in the views shown in FIGS. 178-179) to exit the gaps laterally defined between ridges (13850, 13852) such that bars (13820, 13830, 13840) become free to move transversely relative to ridges (13850, 13852). With bars (13820, 13830, 13840) free from ridges (13850, 13852), bars (13820, 13830, 13840) are now operable to pivot about pin (13825) and connectors (13828, 13844). Thus, linkage assembly (13810) is no longer in a rigid state. Because linkage assembly (13810) is not in a rigid state and because linkage assembly is no longer engaged with slot (13850), linkage assembly (13810) no longer rigidizes articulation section (130).

G. Exemplary Alternative Articulation Section with Translatable Rigidizing Member FIGS. 180-182 show a modified version of shaft assembly (30) equipped with a rigidizing plate assembly (13910). Plate assembly (13910) comprises a rigidizing member (13920), an actuation assembly (13920), and a pair of plate tracks (13940) secured to each retention collar (133) of articulation section (130). Rigidizing member (13920) is generally configured to translate longitudinally across the upper portion of proximal outer sheath (32) and articulation section (130) to selectively rigidize articulation section (130). As can be seen in FIG. 28, rigidizing member (13920) is has a generally rectangular shape that is contoured to correspond to the outer radius of proximal outer sheath (32). Rigidizing member (13920) further comprises two L-shaped engagement members (13922, 13924). Rigidizing member (13920) is formed of a rigid material such as plastic, metal, and/or any other suitable rigid material(s). As will be described in greater detail below, engagement members (13922, 13924) are generally configured to engage and slide along plate tracks (13940) rigidize articulation section (130).

Actuation assembly (13920) further comprises a pair of distal wires (13932) and a pair of proximal wires (13934). Each pair of wires (13932, 13934) is secured to rigidizing member (13920) such that wires (13932, 13934) are configured to pull rigidizing member (13920) distally or proximally. Distal wires (13932) extend distally and are received in a pair of openings (936) in distal outer sheath (33). Openings (936) may be connected to a pair of passages extending through shaft assembly (30) to thereby permit distal wires (13932) to return to handle assembly (20) described above. Similarly, proximal wires (13934) extend proximally down the length of shaft assembly (30) until proximal wires (13934) may be received by handle assembly (20). Although not shown, it should be understood that actuation assembly (13920) may include features disposed in handle assembly (20) for actuating wires. By way of example only, such features may include a rotatable wheel, which may drive wires (13932, 13934) to thereby translate rigidizing member (13920) proximally or distally. Of course, any other suitable features for driving wires (13932, 13934) may be incorporated into instrument (10) as will be apparent to those of ordinary skill in the art in view of the teachings herein. Similarly, wires (13932, 13934) are just one merely illustrative example of how rigidizing member (13920) may be driven between a proximal position and a distal position. Other suitable features that may be used to drive rigidizing member (13920) between a proximal position and a distal position will be apparent to those of ordinary skill in the art in view of the teachings herein.

Tracks (13940) are fixedly secured to each retention collar (133). Tracks (13940) are generally shaped to slidably receive the L-shape of engagement members (13922, 13924). In other words, tracks (13940) are configured such that engagement members (13922, 13924) are permitted to slide longitudinally within tracks (13940), while limiting any lateral movement of engagement members (13922, 13924). Although tracks (13940) are described herein as being secured to each retention collar (133), it should be understood that in other examples, tracks (13940) may be unitarily formed features of retention collars (133).

An exemplary use of plate assembly (13910) can be seen in FIGS. 180 and 182. As can be seen in FIG. 180, plate assembly (13910) is initially in a first longitudinal position. In the first position, rigidizing member (13920) is disposed proximally of articulation section (130). Because rigidizing member (13920) is disposed proximally of articulation section (130), rigidizing member (13920) is not acting upon actuation section (130) and articulation section (130) is thus free to articulate. Therefore, when plate assembly (13910) is in the first position, articulation section (130) is unlocked and/or otherwise free to articulate via articulation control assembly (100) described above.

If an operator desires to rigidize articulation section (130), the operator may transition plate assembly (13910) to a second longitudinal position shown in FIG. 182. In the second position, rigidizing member (13920) is in a distal position such that rigidizing member (13920) is in engagement with articulation section (130). To transition rigidizing member (13920) to the second position, the operator may actuate wires (13932, 13934) of actuation assembly (13920) to pull rigidizing member (13920) distally using any of the above described mechanisms. As rigidizing member (13920) moves distally, engagement members (13922, 13924) of rigidizing member (13920) will be slidably received by tracks (13920) until rigidizing member (13920) is disposed at the distal position. In the distal position, engagement members (13922, 13924) of rigidizing member (13920) remain disposed within tracks (13940). Because engagement members (13922, 13924) are integral to rigidizing member (13920), the rigidity of rigidizing member (13920) is imparted onto engagement members (13922, 13924). Because engagement members (13922, 13924) engage tracks (13940) that are fixedly secured to retention collars (133), the rigidity of rigidizing member (13920) is imparted to retention collars (133) and articulation section (130). Therefore, plate assembly (13910) rigidizes articulation section (130) when plate assembly (13910) is in the second position. If the operator wishes to articulate articulation section (130), the operator may simply retract rigidizing member (13920) proximally back to the first position shown in FIG. 180, thereby de-rigidizing articulation section (130) and enabling articulation section (130) to flex in response to actuation of articulation control assembly (100).

H. Exemplary Alternative Instrument with Translatable Outer Sheath

FIG. 183 shows an exemplary alternative instrument (131010). Instrument (131010) of the present example is substantially the same as instrument (10) described above, except as otherwise noted herein. For instance, instrument (131010) of the present example comprises a handle assembly (131020), a shaft assembly (131030), and an end effector (131040). Handle assembly (131020) comprises a body (131022) including a pistol grip (131024) and a pair of buttons (131026). Handle assembly (131020) also includes a trigger (131028) that is pivotable toward and away from pistol grip (131024). It should be understood, however, that various other suitable configurations may be used, including but not limited to a scissor grip configuration. End effector (131040) includes an ultrasonic blade (131160) and a pivoting clamp arm (131044). Clamp arm (131044) is coupled with trigger (131028) such that clamp arm (131044) is pivotable toward ultrasonic blade (131160) in response to pivoting of trigger (131028) toward pistol grip (131024); and such that clamp arm (131044) is pivotable away from ultrasonic blade (131160) in response to pivoting of trigger (131028) away from pistol grip (131024). Various suitable ways in which clamp arm (131044) may be coupled with trigger (131028) will be apparent to those of ordinary skill in the art in view of the teachings herein. In some versions, one or more resilient members are used to bias clamp arm (131044) and/or trigger (131028) to the open position shown in FIG. 183.

An ultrasonic transducer assembly (131012) extends proximally from body (131022) of handle assembly (131020). Transducer assembly (131012) is coupled with a generator (131016) via a cable (131014), such that transducer assembly (131012) receives electrical power from generator (131016). Piezoelectric elements in transducer assembly (131012) convert that electrical power into ultrasonic vibrations. Generator (131016) may include a power source and control module that is configured to provide a power profile to transducer assembly (131012) that is particularly suited for the generation of ultrasonic vibrations through transducer assembly (131012).

Blade (131160) of the present example is operable to vibrate at ultrasonic frequencies in order to effectively cut through and seal tissue. Blade (131160) is positioned at the distal end of an acoustic drivetrain. This acoustic drivetrain includes transducer assembly (131012) and an acoustic waveguide (not shown). The acoustic waveguide comprises a flexible portion (not shown) similar to flexible portion (166) described above with respect to instrument (10). Transducer assembly (131012) includes a set of piezoelectric discs (not shown) located proximal to a horn (not shown) of the waveguide. The piezoelectric discs are operable to convert electrical power into ultrasonic vibrations, which are then transmitted along the waveguide to blade (131160) in accordance with known configurations and techniques. By way of example only, this portion of the acoustic drivetrain may be configured in accordance with various teachings of various references that are cited herein.

Shaft assembly (131030) of the present example extends distally from handle assembly (131020). Unless otherwise noted herein, shaft assembly (131030) is substantially the same as shaft assembly (30) described above with respect to instrument (10). For instance, shaft assembly (131030) includes an articulation section (131130), which is located at a distal portion of shaft assembly (131030), with end effector (131040) being located distal to articulation section (131130). As shown in FIG. 183, a knob (131031) is secured to a proximal portion of shaft assembly (131030). Knob (131031) is rotatable relative to body (131022), such that shaft assembly (131030) is rotatable about the longitudinal axis defined by shaft assembly (131030), relative to handle assembly (131020). Such rotation may provide rotation of end effector (131040), articulation section (131130), and shaft assembly (131030) unitarily. Of course, rotatable features may simply be omitted if desired.

Articulation section (131130) is substantially the same as articulation section (130) described above with respect to instrument (10), unless otherwise note herein. For instance, articulation section (131130) is operable to selectively position end effector (131040) at various lateral deflection angles relative to a longitudinal axis defined by shaft assembly (131030). Like with articulation section (130), articulation section (131130) is driven by a pair of articulation bands (not shown) disposed within articulation section (131130) and extending through shaft assembly (131030). When the articulation bands translate longitudinally in an opposing fashion, this will cause articulation section (131130) to bend, thereby laterally deflecting end effector (131040) away from the longitudinal axis of shaft assembly (131030) from a straight configuration to an articulated configuration. In particular, end effector (131040) will be articulated toward the articulation band that is being pulled proximally. During such articulation, the other articulation band may be pulled distally.

Instrument (131100) further includes an articulation control assembly (131100) that is secured to a proximal portion of shaft assembly (131030). Articulation control assembly (131100) comprises a housing (131110) and a rotatable knob (131120). Like with articulation control assembly (100) described above, rotatable knob (131120) is configured to rotate relative to housing (131110) to drive the articulation bands in opposing directions.

Unlike instrument (10) described above, instrument (131010) of the present example further includes a sheath drive assembly (131200). Sheath drive assembly (131200) is generally operable to translate a proximal outer sheath (131032) of shaft assembly (131030) to lock and/or increase the rigidity of articulation section (131130). Sheath drive assembly (131200) comprises an actuation driver (131210) extending through a slot (131220) disposed on the exterior of handle assembly (131020).

FIG. 31 shows an exploded view of outer sheath (131032) and actuation driver (131210). As can be seen, outer sheath (131032) comprises a pair of flanges (131034) and a slot (131036). Flange pair (131034) is disposed at the proximal end of outer sheath (131032) and is configured to receive a corresponding portion of actuation driver (131210), as will be described in greater detail below. Slot (131036) is disposed in outer sheath (131032) proximally of the distal end of outer sheath (131032). Slot (131036) is configured to permit components associated with rotatable knob (131031) to extend through outer sheath (131032) such that outer sheath (131032) and other components of shaft assembly (131030) may be rotated by rotatable knob (131031).

Actuation driver (131210) is shown in FIG. 185. As can be seen, actuation driver (131210) comprises an annular member (131212), two armatures (131214), and two tabs (131216) Annular member (131212) is configured to be rotatably received by flange pair (131034) of outer sheath (131032). When annular member (131212) is disposed between flanges (131034), outer sheath (131032) can freely rotate relative to annular member (131212). This feature may be desirable because free rotation of outer sheath (131032) relative to annular member (131212) may permit outer sheath (131032) to rotate while actuation driver (131210) may remain fixed. This feature may be further desirable because flange pair (131034) may still permit actuation driver (131210) to drive translation of outer sheath (131032) despite rotation of outer sheath (131032).

Armatures (131214) extend outwardly from annular member (131212). Armatures (131214) are configured to extend through corresponding slots (131220) in handle assembly (131020), with each tab (131216) disposed on the exterior of handle assembly (131020). Thus, armatures (131214) connect tabs (131216), which are disposed on the outside of handle assembly (131020), to annular member (131212), which is disposed on the inside of handle assembly (131020).

FIGS. 183 and 186 show an exemplary use of sheath drive assembly (131200). As can be seen in FIG. 183, sheath drive assembly (131200) is initially in a first longitudinal position. In the first position, outer sheath (131032) is disposed in a proximal position such that outer sheath (131032) is proximal of articulation section (131130). Correspondingly, actuation driver (131210) is in a proximal position relative to slot (131220). Thus, in the first position, articulation section (131130) is free to articulate via articulation control assembly (131100) as described above.

If an operator desires to rigidize articulation section (131130), the operator may actuate sheath drive assembly (131200) to a second longitudinal position shown in FIG. 186. In the second position, outer sheath (131032) is driven distally over articulation section (131130). To drive outer sheath (131032) distally to the distal position shown in FIG. 186, the operator may apply a force distally to tab (131216) of actuation driver (131210) thereby driving actuation driver (131210) distally. Actuation driver (131210) will then act on flange (131034) of outer sheath (131032) via annular member (131212) to drive outer sheath (131032) distally. Once outer sheath (131032) is disposed over articulation section (131130), the rigidity of outer sheath (131032) will rigidize articulation section (131130). Therefore, it should be understood that when sheath drive assembly (131200) is in the second position, articulation section (131130) is rigidized.

In some versions, one or more features in communication with actuation driver (131210) will also lock out rotatable knob (131120) such that knob (131120) cannot be rotated when actuation driver (131210) is in the distal position. In addition or in the alternative, one or more features in communication with knob (131120) may lock out actuation driver (131210) such that actuation driver (131210) cannot be slid from the proximal position to the distal position unless knob (131120) is at the neutral rotational position that is associated with articulation section (131130) being in a straight, non-articulated configuration. Various suitable ways in which such lockout features may be configured will be apparent to those of ordinary skill in the art in view of the teachings herein.

As yet another merely illustrative example, one or more features in communication with actuation driver (131210) may be configured to automatically de-articulate an otherwise articulated articulation section (131130) in response to distal movement of actuation driver (131210) from the proximal position toward the distal position. Various suitable ways in which such features may be configured will be apparent to those of ordinary skill in the art in view of the teachings herein.

I. Exemplary Alternative Instrument with Translatable Rigidizing Members

FIG. 187 shows an exemplary alternative instrument (131310). Instrument (131310) of the present example is substantially the same as instrument (10) described above, except as otherwise noted herein. For instance, instrument (131310) of the present example comprises a handle assembly (131320), a shaft assembly (131330), and an end effector (131340). Handle assembly (131320) comprises a body (131322) including a pistol grip (131324) and a pair of buttons (131326). Handle assembly (131320) also includes a trigger (131328) that is pivotable toward and away from pistol grip (131324). It should be understood, however, that various other suitable configurations may be used, including but not limited to a scissor grip configuration. End effector (131340) includes an ultrasonic blade (131460) and a pivoting clamp arm (131344). Clamp arm (131344) is coupled with trigger (131328) such that clamp arm (131344) is pivotable toward ultrasonic blade (131460) in response to pivoting of trigger (131328) toward pistol grip (131324); and such that clamp arm (131344) is pivotable away from ultrasonic blade (131460) in response to pivoting of trigger (131328) away from pistol grip (131324). Various suitable ways in which clamp arm (131344) may be coupled with trigger (131328) will be apparent to those of ordinary skill in the art in view of the teachings herein. In some versions, one or more resilient members are used to bias clamp arm (131344) and/or trigger (131328) to the open position shown in FIG. 187.

An ultrasonic transducer assembly (131312) extends proximally from body (131322) of handle assembly (131320). Transducer assembly (131312) is coupled with a generator (131316) via a cable (131314), such that transducer assembly (131312) receives electrical power from generator (131316). Piezoelectric elements in transducer assembly (131312) convert that electrical power into ultrasonic vibrations. Generator (131316) may include a power source and control module that is configured to provide a power profile to transducer assembly (131312) that is particularly suited for the generation of ultrasonic vibrations through transducer assembly (131312).

Blade (131460) of the present example is operable to vibrate at ultrasonic frequencies in order to effectively cut through and seal tissue. Blade (131460) is positioned at the distal end of an acoustic drivetrain. This acoustic drivetrain includes transducer assembly (131312) and an acoustic waveguide (131480) (as can be seen in FIG. 190). The acoustic waveguide (131480) comprises a flexible portion (not shown) similar to flexible portion (166) described above with respect to instrument (10). Transducer assembly (131312) includes a set of piezoelectric discs (not shown) located proximal to a horn (not shown) of waveguide (131480). The piezoelectric discs are operable to convert electrical power into ultrasonic vibrations, which are then transmitted along waveguide (131480) to blade (131460) in accordance with known configurations and techniques. By way of example only, this portion of the acoustic drivetrain may be configured in accordance with various teachings of various references that are cited herein.

Shaft assembly (131330) of the present example extends distally from handle assembly (131320). Unless otherwise noted herein, shaft assembly (131330) is substantially the same as shaft assembly (30) described above with respect to instrument (10). For instance, shaft assembly (131330) includes an articulation section (131430), which is located at a distal portion of shaft assembly (131330), with end effector (131340) being located distal to articulation section (131430). As shown in FIG. 187, a knob (131331) is secured to a proximal portion of shaft assembly (131330). Knob (131331) is rotatable relative to body (131322), such that shaft assembly (131330) is rotatable about the longitudinal axis defined by shaft assembly (131330), relative to handle assembly (131320). Such rotation may provide rotation of end effector (131340), articulation section (131430), and shaft assembly (131330) unitarily. Of course, rotatable features may simply be omitted if desired.

Articulation section (131430) is substantially the same as articulation section (130) described above with respect to instrument (10), unless otherwise note herein. For instance, articulation section (131430) is operable to selectively position end effector (131340) at various lateral deflection angles relative to a longitudinal axis defined by shaft assembly (131430). Like with articulation section (130), articulation section (131430) is driven by a pair of articulation bands (131440, 131442) (as shown in FIG. 190) disposed within articulation section (131430) and extending through shaft assembly (131330). When articulation bands (131440, 131442) translate longitudinally in an opposing fashion, this will cause articulation section (131430) to bend, thereby laterally deflecting end effector (131340) away from the longitudinal axis of shaft assembly (131330) from a straight configuration to an articulated configuration. In particular, end effector (131340) will be articulated toward the articulation band (131440, 131442) that is being pulled proximally. During such articulation, the other articulation band (131440, 131442) may be pulled distally Instrument (131310) further includes an articulation control assembly (131400) that is secured to a proximal portion of shaft assembly (131330). Articulation control assembly (131400) comprises a housing (131410) and a rotatable knob (131420). Like with articulation control assembly (100) described above, rotatable knob (131420) is configured to rotate relative to housing (131410) to drive articulation bands (131440, 131442) in opposing directions. For instance, rotation of knob (131420) in a first direction causes distal longitudinal translation of articulation band (131440), and proximal longitudinal translation of articulation band (131442); and rotation of knob (131420) in a second direction causes proximal longitudinal translation of articulation band (131440), and distal longitudinal translation of articulation band (131442). Thus, it should be understood that rotation of rotation knob (131420) causes articulation of articulation section (131430).

Unlike instrument (10) described above, instrument (131310) of the present example further includes a rigidizing member drive assembly (131500). Drive assembly (131500) is generally operable to advance a rigidizing member (131520) within shaft assembly (131330) selectively rigidize articulation section (131430). Drive assembly (131500) comprises drive member (131510) and a rigidizing member (131520). Drive member (131510) extends through a slot (131530) in handle assembly (131320) and is rotatably attachable to rigidizing member (131520) to drive rigidizing member (131520) while permitting rotation of rigidizing member (131520) with shaft assembly (131330).

As can be seen in FIG. 188, rigidizing member (131520) comprises two longitudinally extending posts (131522) and a generally tubular body (131524). As will be described in greater detail below, posts (131522) extend through shaft assembly (131330) and engage with articulation section (131430) to selectively ridigize articulation section (131430). Body (131524) comprises a flange pair (131526) and a slot (131528). Flange pair (131526) is disposed on the proximal end of body (131524) and is configured to receive drive member (131510), as will be described in greater detail below. Slot (131528) is disposed distally of flange pair (131526). Slot (131528) is configured to receive at least a portion of rotatable knob (131331) such that rotatable knob (131331) may engage with rigidizing member (131520) and various components of shaft assembly (131330) to rotate rigidizing member (131520) along with shaft assembly (131330).

Drive member (131510) is shown in FIG. 189. As can be seen, drive member (131510) comprises an annular member (131512), two armatures (131514), and two tabs (131516). Annular member (131512) is configured to be rotatably received by flanged portion (131526) of rigidizing member (131520). When annular member (131512) is between flanges (131526), rigidizing member (131520) can freely rotate relative to annular member (131512). This feature may be desirable because free rotation of rigidizing member (131520) relative to annular member (131512) may permit rigidizing member (131520) to rotate while drive member (131510) may remain fixed. This feature may be further desirable because flange pair (131526) may still permit drive member (131510) to drive translation of rigidizing member (131520) despite rotation of rigidizing member (131520).

Armatures (131514) extend outwardly from annular member (131512). Armatures (131514) are configured to extend through corresponding slots (131530) in handle assembly (131320), with each tab (131516) disposed on the exterior of handle assembly (131320). Thus, armatures (131514) connect tabs (131516), which are disposed on the outside of handle assembly (131320), to annular member (131512), which is disposed on the inside of handle assembly (131320).

FIG. 190 shows rigidizing member (131520) disposed within shaft assembly (131330). As can be seen, a body (131334) of shaft assembly (131330) includes channels (131336) that are configured to receive both articulation bands (131440, 131442) and posts (131522) of rigidizing member (131520) adjacent to articulation bands (131440, 131442). Although shaft assembly (131330) of the present example is shown as having a common channels (131336) for both articulation bands (131440, 131442) and posts (131522), it should be understood that in other examples, shaft assembly (131330) includes separate channels for articulation bands (131440, 131442) and posts (131522).

FIGS. 191-196 show an exemplary mode of operation for drive assembly (131500). As can be seen in FIGS. 191-192, drive assembly (131500) is initially in a first longitudinal position. In the first position, drive member (131510) is positioned in a proximal position relative to handle assembly (131320) such that rigidizing member (131520) is correspondingly in a proximal position relative to articulation section (131430). As can best be seen in FIG. 192, when rigidizing member (131520) is in the proximal position, posts (131522) of rigidizing member (131520) are disposed proximally of articulation section (131430). With posts (131522) of rigidizing member (131520) disposed proximally of articulation section (131430), articulation section (131430) is free to articulate via articulation control assembly (131400) as described above. Thus, when drive assembly (131500) is in the first position, articulation section (131430) is in an unlocked and/or non-rigid configuration.

If an operator desires to rigidize articulation section (131430), the operator may do so by advancing drive assembly (131500) to a second longitudinal position (as shown in FIGS. 195-196). To advance drive assembly (131500) to the second position, the operator will advance tabs (131516) of drive member (131510) distally as shown in FIG. 193. Distal advancement of drive member (131510) will cause corresponding advancement of posts (131522) of rigidizing member (131520) within shaft assembly (131330) as shown in FIG. 194. As posts (131522) are advanced distally, posts (131522) begin to engage articulation section (131430). FIGS. 195-196 show drive assembly (131500) fully advanced to the second position. As can be seen, in the second position, tabs (131516) of drive member (131510) are advanced to a fully distal position relative to handle assembly (131320). Correspondingly, posts (131522) of rigidizing member (131520) are advanced to a fully distal position. When posts (131522) are in the fully distal position, posts (131522) fully engage articulation section (131430) to rigidize articulation section (131430). In this state, the distal ends of posts (131522) are positioned distal to articulation section (131430), such that posts (131522) span along the full length of articulation section (131430) and are grounded relative to the distal portion of shaft assembly (131330).

In some examples, instrument (131310) described above may include a rigidizing member drive assembly similar to drive assembly (131600) described above having a rigidizing member (131620) with a single post (131622). Such a configuration may be desirable to improve the overall operation of instrument (131310), to improve the ease of use, or to improve the amount of rigidity provided by rigidizing member (131520). For instance, FIGS. 197-199 show an exemplary alternative rigidizing member drive assembly (131600). It should be understood that drive assembly (131600) is substantially the same as drive assembly (131500) described above, unless otherwise noted herein. Drive assembly (131600) of the present example is generally operable to advance a rigidizing member (131620) within shaft assembly (131330) to selectively rigidize articulation section (131430). Drive assembly (131600) comprises drive member (131610) and rigidizing member (131620). Drive member (131610) extends through a slot (131630) in handle assembly (131320) and is rotatably attached to rigidizing member (131620) to drive rigidizing member (131620) while permitting rotation of rigidizing member (131620) with shaft assembly (131330).

As can be seen in FIG. 197, rigidizing member (131620) comprises a single longitudinally extending post (131622) and a generally tubular body (131624). As will be described in greater detail below, post (131622) extends through shaft assembly (131330) and engages with articulation section (131430) to selectively rigidize articulation section (131430). Body (131624) comprises a flange pair (131626) and a slot (131628). Flange pair (131626) is disposed on the proximal end of body (131624) and is configured to receive drive member (131610), as will be described in greater detail below. Slot (131628) is disposed distally of flanged portion (131626). Slot (131628) is configured to receive at least a portion of rotatable knob (131331) such that rotatable knob (131331) may engage with rigidizing member (131620) and various components of shaft assembly (131330) to rotate rigidizing member (131620) along with shaft assembly (131330).

Drive member (131610) is shown in FIG. 198. As can be seen, drive member (131610) comprises an annular member (131612), two armatures (131614), and two tabs (131616) Annular member (131612) is configured to be rotatably received between flanges (131626) of rigidizing member (131620). When annular member (131612) is disposed between flanges (131626), rigidizing member (131620) can freely rotate relative to annular member (131612). This feature may be desirable because free rotation of rigidizing member (131620) relative to annular member (131612) may permit rigidizing member (131620) to rotate while drive member (131610) may remain fixed. This feature may be further desirable because flange pair (131626) may still permit drive member (131610) to drive translation of rigidizing member (131620) despite rotation of rigidizing member (131620).

Armatures (131614) extend outwardly from annular member (131612). Armatures (131614) are configured to extend through slot (131630) in handle assembly (131320) with each tab (131616) disposed on the exterior of handle assembly (131320). Thus, armatures (131614) connect tabs (131616), which are disposed on the outside of handle assembly (131320), to annular member (131612), which is disposed on the inside of handle assembly (131320).

FIG. 199 shows rigidizing member (131620) disposed within shaft assembly (131330). As can be seen, a body (131334) of shaft assembly includes channels (131336) that are configured to receive articulation bands (131440, 131442). Additionally body (131334) includes an additional channel (131338) to receive post (131622) of rigidizing member (131620).

FIGS. 200-205 show an exemplary mode of operation for drive assembly (131600). As can be seen in FIGS. 200-201, drive assembly (131600) is initially in a first longitudinal position. In the first position, drive member (131610) is positioned in a proximal position relative to handle assembly (131320) such that rigidizing member (131620) is correspondingly in a proximal position. As can best be seen in FIG. 201, when rigidizing member (131620) is in the proximal position, post (131622) of rigidizing member (131620) is disposed proximally of articulation section (131430). With post (131622) of rigidizing member (131620) disposed proximally of articulation section (131430), articulation section (131430) is free to articulate via articulation control assembly (131400) as described above. Thus, when drive assembly (131600) is in the first position, articulation section (131430) is in an unlocked and/or non-rigid configuration.

If an operator desires to rigidize articulation section (131430), the operator may do so by advancing drive assembly (131600) to a second longitudinal position (as shown in FIGS. 204-205). To advance drive assembly (131600) to the second position, the operator will advance tabs (131616) of drive member (131610) distally as shown in FIG. 202. Distal advancement of drive member (131610) will cause corresponding advancement of post (131622) of rigidizing member (131620) within shaft assembly (131330) as shown in FIG. 203. As post (131622) is advanced distally, post (131622) begins to engage articulation section (131430).

FIGS. 204-205 show drive assembly (131600) fully advanced to the second position. As can be seen, in the second position, tabs (131616) of drive member (131610) are advanced to a fully distal position relative to handle assembly (131320). Correspondingly, post (131622) of rigidizing member (131520) is advanced to a fully distal position. When post (131622) is in the fully distal position, post (131622) fully engages articulation section (131430) to rigidize articulation section (131430). In this state, the distal ends of post (131622) is positioned distal to articulation section (131430), such that post (131622) spans along the full length of articulation section (131430) and is grounded relative to the distal portion of shaft assembly (131330). In the present example, post (131622) extends along a path that is offset from the articulation plane of articulation section (131430). In particular, post (131622) is located above the articulation plane of articulation section (131430). This positioning of post (131622) may enhance the rigidization effect provided by post (131622) when post (131622) is in the distal position shown in FIG. 205. In some other versions, post (131622) is located in the articulation plane of articulation section (131430) (e.g., similar to the positioning of one of posts (131522)), on one side of articulation section (131430).

XV. ULTRASONIC SURGICAL INSTRUMENT WITH ARTICULATING END EFFECTOR HAVING A CURVED BLADE

FIGS. 206-208 show an exemplary alternative waveguide (14280) that may be readily incorporated into instrument (10), particularly, into an acoustic drivetrain of instrument (10). Waveguide (14280) of the present example includes a blade (14260), which is operable to vibrate at ultrasonic frequencies in order to effectively cut through and seal tissue, particularly when the tissue is being compressed between blade (14260) and another portion of an end effector, such as a curved version of clamp pad (46) of end effector (40). As best shown in FIG. 208, blade (14260) is curved at a bend angle "0" relative to a longitudinal axis of waveguide (14280).

In one example, the acoustic drivetrain includes transducer assembly (12) and acoustic waveguide (14280). Acoustic waveguide (14280) comprises a flexible portion (14266). Transducer assembly (12) includes a set of piezoelectric discs (not shown) located proximal to a horn (not shown) of waveguide (14280). The piezoelectric discs are operable to convert electrical power into ultrasonic vibrations, which are then transmitted along waveguide (14280), including flexible portion (14266) of waveguide (14280), to blade (14260) in accordance with known configurations and techniques. By way of example only, this portion of the acoustic drivetrain may be configured in accordance with various teachings of various references that are cited herein.

Flexible portion (14266) of waveguide (14280) includes a distal flange (14236), a proximal flange (14238), and a narrowed section (14264) located between flanges (14236, 14238). Waveguide (14280) includes longitudinally extending notches that are formed in the waveguide flanges to accommodate cable (14274), which is discussed in more detail below. Cable is received in the lower notches (not shown); and the upper notches (14237, 14239) are formed to provide balance (i.e., to compensate for the presence of the lower notches). Waveguide (14280) includes a tapered region (14239) between distal flange (14236) and blade (14260). In the present example, flanges (14236, 14238) are located at positions corresponding to nodes associated with resonant ultrasonic vibrations communicated through waveguide (14280). Narrowed section (14264) is configured to allow flexible portion (14266) of waveguide (14280) to flex without significantly affecting the ability of flexible portion (14266) of waveguide (14280) to transmit ultrasonic vibrations. By way of example only, narrowed section (14264) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein.

It should be understood that waveguide (14280) may be configured to amplify mechanical vibrations transmitted through waveguide (14280). Furthermore, waveguide (14280) may include features operable to control the gain of the longitudinal vibrations along waveguide (14280) and/or features to tune waveguide (14280) to the resonant frequency of the system. For example, as shown in FIG. 206, waveguide (14280) includes a plurality of opposing pairs of longitudinally spaced, laterally presented notches (14282a, 14282b). In the present example, each notch (14282a) of the three most proximal pairs of notches (14282a) has a longer length than each notch (14282b) of the two most distal pairs of notches (14282b). Notches (14282a, 282b) are provided, at least in part, to assist in controlling the vibratory properties of the waveguide (14280), which are different in waveguide (14280) than in waveguide (180) due in part to the curved configuration of blade (14260). Various suitable ways in which waveguide (14280) may be mechanically and acoustically coupled with transducer assembly (12) will be apparent to those of ordinary skill in the art in view of the teachings herein.

Each flange (14236, 14238) of waveguide (14280) includes a respective pair of opposing, laterally presented flats (14292, 14296). Flats (14292, 14296) are oriented along vertical planes that are parallel to a vertical plane extending through narrowed section (14264) of flexible portion (14266). Flats (14296) are configured to provide clearance for articulation bands (14212, 14214). In particular, flats (14296) of proximal flange (14238) accommodate articulation bands (14214) between proximal flange (14238) and the inner diameter of proximal outer sheath (14204). Notably, articulation bands (14212, 14214) are coupled to waveguide (14280) at a point proximal to distal flange (14236). Of course, flats (14292, 14296) could be substituted with a variety of features, including but not limited to slots, channels, etc., with any suitable kind of profile (e.g., square, flat, round, etc.). In the present example, flats (14292, 14296) are formed in a milling process, though it should be understood that any other suitable process(es) may be used. Various suitable alternative configurations and methods of forming flats (14292, 14296) will be apparent to those of ordinary skill in the art in view of the teachings herein. It should also be understood that waveguide (14280) may include flats formed in accordance with at least some of the teachings of U.S. Pub. No. 2013/0289592, entitled "Ultrasonic Device for Cutting and Coagulating," published Oct. 31, 2013, the disclosure of which is incorporated by reference herein.

In the present example, the distal end of blade (14260) is located at a position corresponding to an anti-node associated with resonant ultrasonic vibrations communicated through flexible portion (14266) of waveguide (14280), in order to tune the acoustic assembly to a preferred resonant frequency $f_o$ when the acoustic assembly is not loaded by tissue. When transducer assembly (12) is energized, the distal end of blade (14260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (14280) to reach blade (14260), thereby providing oscillation of blade (14260) at the resonant ultrasonic frequency. Thus, when tissue is secured between blade (14260) and a curved version of clamp pad (46), for example, the ultrasonic oscillation of blade (14260) may simultaneously sever the tissue and denature the proteins in adjacent tissue cells, thereby providing a coagulative effect with relatively little thermal spread. In some versions, an electrical current may also be provided through blade (14260) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, various suitable ways in which waveguide (14280) may be configured will be apparent to those of ordinary skill in the art in view of the teachings herein.

FIGS. 209-211 and 227A-228B show an exemplary alternative shaft assembly (14200) and end effector (14240) that may be readily incorporated into instrument (10). In the example shown, shaft assembly (14200) and end effector are configured to accommodate for the properties of curved blade (14260), as discussed in more detail below. Shaft assembly (14200) of this example comprises a distal outer sheath (14202), a proximal outer sheath (14204), and a plurality of flex rings (14206) that form a portion of an articulation section (14210). While articulation section (130) is configured to articulate in two lateral directions relative to the longitudinal axis of shaft assembly (30), articulation section (14210) of the present example is configured to articulate in only one direction relative to a longitudinal axis of shaft assembly (14200). Particularly, in the present example, articulation section (14210) is allowed to articulate in one lateral direction, but is substantially prevented from articulating in the opposite lateral direction.

Articulation section (14210) is operable to selectively position end effector (14240) at various lateral deflection angles, in one direction, relative to a longitudinal axis defined by proximal outer sheath (14204). In the present example, the direction in which articulation section (14210) is permitted to articulate is the same direction which curved blade (14260) bends away from the axis (at bend angle (A)). End effector (14240) includes blade (14260) and a pivoting clamp arm (14244) having a clamp pad (14245). In the present example, clamp arm (14244) and clamp pad (14245) are curved at a bend angle that is substantially similar to the bend angle (A) of blade (14260). End effector (14240) is configured to operate substantially similar to end effector (40) discussed above except for the differences discussed below. In particular, clamp arm (14244) of end effector (14240) is operable to compress tissue against blade (14260). When blade (14260) is activated while clamp arm (14244) compresses tissue against blade (14260), end effector (14240) simultaneously severs the tissue and denatures the proteins in adjacent tissue cells, thereby providing a coagulative effect.

Clamp arm (14244) is operable to selectively pivot toward and away from blade (14242) to selectively clamp tissue between clamp pad (14245) and blade (14260), in a manner substantially similar to clamp arm (44). Clamp arm (14244) is coupled to a trigger (e.g., trigger (28)) such that clamp arm (14244) is pivotable toward ultrasonic blade (14260) in response to pivoting of trigger (28) toward pistol grip (24); and such that clamp arm (14244) is pivotable away from ultrasonic blade (14260) in response to pivoting of trigger (28) away from pistol grip (24). As best seen in FIGS. 210-211, a cable (14274) is secured to a lower distal shaft element (14270). Cable (14274) is operable to translate longitudinally relative to an articulation section (14210) of shaft assembly (14200) to selectively pivot clamp arm (14244) toward and away from blade (14260). In particular, cable (14274) is coupled with trigger (28) such that cable (14274) translates proximally in response to pivoting of trigger (28) toward pistol grip (24), and such that clamp arm (14244) thereby pivots toward blade (14260) in response to pivoting of trigger (28) toward pistol grip (24). In addition, cable (14274) translates distally in response to pivoting of trigger (28) away from pistol grip (24), such that clamp arm (14244) pivots away from blade (14260) in response to pivoting of trigger (28) away from pistol grip (24). Clamp arm (14244) may be biased toward the open position, such that (at least in some instances) the operator may effectively open clamp arm (14244) by releasing a grip on trigger (28). Various suitable ways in which clamp arm (14244) may be coupled with trigger (28) will be apparent to those of ordinary skill in the art in view of the teachings herein.

In the example shown, cable (14274) is secured to a proximal end of a lower distal shaft element (14270), which is configured in a manner substantially similar to lower distal shaft element (170). In that regard, lower distal shaft element (14270) comprises a pair of distal flanges (not shown) extending from a semi-circular base. The flanges each comprise a respective opening (not shown). Clamp arm (14244) is rotatably coupled to lower distal shaft element (14270) via a pair of inwardly extending integral pins (not shown). The pins extend inwardly from arms (14256) of clamp arm (14244) and are rotatably disposed within respective openings of lower distal shaft element (14270). In a manner similar to that shown in FIGS. 205A-C, longitudinal translation of cable (14274) causes longitudinal translation of lower distal shaft element (14270) between a proximal position and a distal position. Longitudinal translation of lower distal shaft element (14270) causes rotation of clamp arm (14244) between a closed position and an open position.

Shaft assembly (14200) further comprises a pair of articulation bands (14212, 14214). Distal ends of articulation bands (14212, 14214) are secured to distal flex member (14302) of articulation section (14210). Articulation bands (14212, 14214) are configured to operate substantially similar to articulation bands (140, 142) discussed above except for the differences discussed below. In particular, as shown best in FIGS. 227A-228B, articulation bands (14212, 14214) are permitted to cause articulation of articulation section (14210) in only one direction, as discussed in more detailed below. When articulation bands (14212, 14214) are translated longitudinally in an opposing fashion, a moment is created and applied to distal flex member (14302) and also distal outer sheath (14202), and also to other components of the articulation section (14210) due to the operable coupling among the distal flex member (14302), distal outer sheath (14202), and other components of articulation section (14210). This causes articulation section (14210) and narrowed section (14249) of flexible portion (14248) of waveguide (14280) to articulate, without transferring axial forces in articulation bands (14212, 14214) to waveguide (14246).

As shown in FIGS. 209-211, articulation section (14210) comprises a distal flex member (14302), a proximal flex member (14304), and a plurality of flex base members (14306a-c). Articulation section (14210) further comprises distal outer sheath (14202), a proximal outer sheath (14204), and flex rings (14206a-c). Articulation section (14210) also includes a flexible collar (14300) that is configured to operably couple certain components of the articulation section (14210) to one another, as discussed in more detail below. Distal flex member (14302) is operably coupled to the distal ends of a respective articulation band (14212, 14214). Flex base members (14304a-c) are positioned proximally relative to the distal flex member (14302), and proximal flex member (14304) positioned proximal of flex base members (14306a-c). Distal flex member (14302), proximal flex member (14304), and flex base members (14306a-c) collectively define opposing channels (14308, 14310) for receiving articulation bands (14212, 14214), respectively.

FIGS. 212-213 show distal flex member (14302) of the present example in more detail. As shown, distal flex member (14302) includes a proximal end (14314), a distal end (14316), and a generally U-shaped body (14318) that defines a space (14319) configured for receiving at least a portion of waveguide (14280). A bottom portion of distal flex member (14302) includes a longitudinally extending recess (14320) that is configured to receive cable (14274). Each side of distal flex member (14302) includes a channel (14322) that is shaped and configured for receiving a distal end of a respective articulation band (14212, 214). Each channel (14322) includes an aperture (14324) that is configured to receive a portion of a fastener (14325) (FIG. 210) for coupling a respective articulation band (14212, 14214) to a side of the distal flex member (14302). By way of example only, fastener (14325) may comprise a pin, a rivet, and/or any other suitable kind of structure.

Space (14319) for receiving waveguide (14280) includes a first dimensioned portion (14326) that receives a distal portion of waveguide and a second dimensioned portion (14328), which includes a smaller dimension than first dimensioned portion (14326). Second dimensioned portion (14328) is configured to receive narrowed section (14264) of waveguide (14280). Notably, however, distal flex member (14302) does not contact waveguide (14280). Second dimensioned portion (14326) is defined by a pair of opposing angled flanges (14330) which extend radially inwardly toward a central longitudinal axis of distal flex member (14302). Angled flanges (14330) define a tapered transition portion between the first dimensioned portion (14326) and second dimensioned portion (14328). Second dimensioned portion (14328) is further defined by a pair of flanges (14332), which also extend radially inwardly toward the central longitudinal axis of distal flex member (14302), at the proximal end (14314) of distal flex member (14302). Flanges (14330, 14332) define a pair of opposing slots (14334) that extend along a plane that is parallel to the longitudinal axis of distal flex member. Each slot (14334) includes an aperture (14336). Various suitable ways in which distal flex member (14302) may be configured will be apparent to those of ordinary skill in the art in view of the teachings herein.

FIGS. 214-215 show proximal flex member (14304) of the present example in more detail. As shown, proximal flex member (14304) includes a proximal end (14338), a distal end (14340) and a generally U-shaped body (14342) that defines a space (14343) configured for receiving at least a portion of waveguide (14280). A bottom portion of proximal flex member (14302) includes a longitudinal recess (14344)

that is configured to receive cable (14274). Each side of proximal flex member (14304) includes a channel (14346) that is shaped and configured for receiving portion of a respective articulation band (14212, 14214) (and which forms a portion of channels (14308, 14310)). Each channel (14346) is defined in part by an upper, shelf (14348) and a lower shelf (14350).

The space (14343) of proximal flex member (14304) for receiving waveguide (14280) includes a first dimensioned portion (14352) that receives a portion of waveguide (14280) and a second dimensioned portion (14354), which includes a smaller dimension than first dimensioned portion (14326). Second dimensioned portion (14354) is configured to receive narrowed section (14264) of waveguide (14280), though proximal flex member (14304) does not contact waveguide (14280). Second dimensioned portion (14354) is defined by a pair of opposing angled flanges (14356) which extend radially inwardly toward a central longitudinal axis of proximal flex member (14304). Angled flanges (14356) define a tapered transition portion between the first dimensioned portion (14352) and second dimensioned portion (14354). Second dimensioned portion (14354) is further defined by a pair of flanges (14358), which also extend radially inwardly toward the central longitudinal axis of proximal flex member (14304), at the distal end (14340) of proximal flex member (14304). Flanges (14356, 14358) define a pair of opposing slots (14360). Each slot (14360) includes a generally rectangular aperture (14362). Various suitable ways in which proximal flex member (14304) may be configured will be apparent to those of ordinary skill in the art in view of the teachings herein.

Flex base members (14306a-c), as shown in more detail in FIGS. 216-218B, define a single, unitary body (14364) comprising three members (14306a-c), with living hinges (14366) between adjoining members (14306a-c). However, in other examples, flex base members (14306a-c) may be separate, individual members. In the example shown, body (14364) is generally U-shaped and defines a space (14368) configured for receiving at least a portion of waveguide (14280). However, body (14364) does not contact waveguide (14280). A bottom portion of each flex base member (14306a-c) includes a longitudinal recess (14370) configured to receive cable (14274). Each side of each base member (14306a-c) includes a radially outwardly extending shelf (14372), each of which defines a boundary on each side of the base members (14306a-c) for receiving a portion of a respective articulation band (14212, 14214). Each base member (14306a-c) includes a respective pair of opposing distal flanges (14374) and a respective pair of opposing proximal flanges (14376) extending radially inwardly toward a central longitudinal axis of body (14364). The distal and proximal flanges (14374, 14376) in each pair of flanges (14374, 14376) define a slot (14378) therebetween. Each slot (14378) includes a generally rectangular aperture (14380).

Each base member (14306a-c) includes a respective first distal face portion (14382a), a second distal face portion (14382b), a first proximal face portion (14384a), and a second proximal face portion (14384b). As shown best in FIG. 218B, base members (14306a-c) are configured to transition to a flexed position from an unflexed position (FIG. 218A) when, for example, articulation bands (14212, 14214) are moved longitudinally relative to one another. In the unflexed position, there is a gap between adjacent first proximal and distal faces (14384a, 14382a); and between second proximal and distal faces (14384b, 14382b). First distal faces (14382a) and second distal faces (14382b) are disposed at an oblique angle ($\theta_{218A-1}$) relative to an imaginary plane that is perpendicular to the longitudinal axis of base members (14306a-c). First proximal edges (14384a) and first proximal edges (14384b) are disposed at an oblique angle ($\theta_{218A-2}$) relative to an imaginary plane that is perpendicular to the longitudinal axis of base members (14306a-c). In the present example, angle ($\theta_{218A-1}$) and angle ($\theta_{218A-2}$) are substantially equal. Thus, the angle between adjacent first proximal and distal edges (14384a, 14382a) in an unflexed position; and between adjacent second proximal and distal edges (14384b, 14382b) in an unflexed position, is $\theta_{218A-1} + \theta_{218A-2}$.

As shown in FIG. 218B, base members (14306a-c) are in a flexed position after pivoting in one direction relative to a central longitudinal axis about living hinges (14366), such that first proximal faces (14384a) substantially abut respective first distal faces (14382a) of an adjoining base member (14306a-c). It will be understood that in some versions, base members (14306a-c) may pivot in an opposite direction, for example, such that second proximal faces (14382b) substantially abut respective second distal faces (14382b) of an adjoining base member (14306a-c). However, in the present example, as will be understood from the discussion below, other components of articulation section (14210) may effectively allow base members (14306a-c) to pivot in only one direction. Various suitable ways in which flex base members (14306a-c) may be configured will be apparent to those of ordinary skill in the art in view of the teachings herein.

Still referring to FIGS. 209-211, articulation section (14210) of the present example also includes a distal outer sheath (14202), a proximal outer sheath (14204), and flex rings (14206a-c) that at least partially surround other components of articulation section (14210). Referring also to FIGS. 219-220 and 227A-228B, distal outer sheath (14202) of the present example more particularly comprises a proximal end (14386), a distal end (14388), and a lumen (14390) extending therebetween. At least a first portion (14392) of a proximal edge of distal outer sheath (14202) extends along an imaginary plane (14393) that is perpendicular to the longitudinal axis of distal outer sheath (14202), while a second portion (14394) of proximal edge extends at angle ($\theta_{220}$) relative to plane (14393). Distal outer sheath (14202) of the present example further comprises a longitudinal channel (14396) extending from the proximal edge (14392) in a direction parallel to a longitudinal axis of distal outer sheath (14202). Longitudinal channel (14396) terminates at a transverse channel (14398). Transverse channel (14398) of the present example extends parallel to the plane (14393) but perpendicular to longitudinal channel (14396).

Distal outer sheath (14202) is coupled to waveguide (14280) via an elastomeric ring (14403), which is positioned about distal flange (14236) of waveguide (14280). Thus, as discussed in more detail below, when distal outer sheath (14202) is laterally deflected by the articulation of articulation section (14210), distal outer sheath (14202) transfers that lateral deflection to waveguide (14280), thereby articulating end effector (14240).

Distal outer sheath (14202) of the present example further comprises a pair of apertures (14400), which are generally rectangular in shape, and spaced laterally from one another and from longitudinal cutout (14396). Distal outer sheath (14202) further includes a plurality of circumferentially spaced obround apertures (14402). As shown, in the present example, there are six obround apertures (14402), but in other examples, there may be more or less than six obround apertures (14402). Longitudinally between obround apertures (14402) and proximal end (14386), distal tube member includes a pair of angularly spaced, generally rectangular apertures (14404). Various suitable ways in which distal outer sheath (14202) may be configured will be apparent to those of ordinary skill in the art in view of the teachings herein.

Proximal outer sheath (14204) of the present example, referring to FIGS. 209-211 and 221-222, is suitable for incorporation into instrument (10) in a manner substantially similar to outer sheath (32). Proximal outer sheath (14204) is substantially similar to outer sheath (32), except for the differences discussed herein. Particularly, proximal outer sheath (14204) includes a proximal end (not shown), a distal end (14406), and a lumen (14408) extending therebetween. As best seen in FIG. 222, a first portion (14410) of distal edge extends along an imaginary plane (14411) that is perpendicular to the longitudinal axis of proximal outer sheath (14204), while a second portion (14412) of distal edge (14410) extends at an oblique angle ($\theta_{222}$) relative to plane (14412). Proximal outer sheath (14204) further comprises a longitudinal channel (14414) extending from distal edge (14410) in a direction parallel to a longitudinal axis of proximal outer sheath (14204). Longitudinal channel (14414) terminates at a transverse channel (14416). Transverse channel (14416) of the present example extends parallel to plane (14412) but perpendicular relative to longitudinal channel (14414). Proximal outer sheath (14204) of the present example further comprises a pair of apertures (14419), which are generally rectangular in shape, and spaced laterally from one another and from longitudinal cutout (14414). Various suitable ways in which proximal outer sheath (14204) may be configured will be apparent to those of ordinary skill in the art in view of the teachings herein.

As shown in FIGS. 209-211, distal, middle, and proximal flex rings (14206a-c) are positioned between distal outer sheath (14202) and proximal outer sheath (14204) such that flex rings (14206a-c), distal outer sheath (14202), and proximal outer sheath (14204) define at least a portion of a radially outward boundary of shaft assembly (14200). Flex rings (14206a-c) define a single, unitary body (14364) comprising three members (14306a-c), with living hinges (14366) between adjoining flex rings (14206a-c). However, in other examples, flex rings (14206a-c) may be separate, individual members. Referring also to FIGS. 223-224B, three flex rings (14206a-c) are shown, but it will be understood that there may be more or less than three flex rings (14206a-c). In the present example, each flex ring (14206a-c) includes a first portion (14418) that is partially circular in cross-section and a pair of flanges (14420). The flanges (14420) of each pair of flanges (14420) extend radially inwardly from each end of the first portion (14418) toward one another, and along a plane extending parallel to a longitudinal axis of each flex ring (14206). Each flange (14420) includes a generally rectangular aperture (14421) extending therethrough.

Each flex ring (14206a-c) includes a first distal edge portion (14422a), second distal edge portion (14422b), first proximal edge portion (14424a), and second proximal edge portion (14424b). In the present example, first distal edge portion (14422a) extends at an oblique angle relative to second distal edge portion (14422b). Second distal edge portion (14422b) of each flex ring (14206a-c) extends along a first plane (14426) that is perpendicular to the longitudinal axis of each flex ring (14206a-c). Thus, the first distal edge portion (14422a) extends at an oblique angle ($\theta_{224A-1}$) relative to a first plane (14426) that is perpendicular to the longitudinal axis of each flex ring (14206). Similarly, first proximal edge portion (14424a) extends at an oblique angle relative to second proximal edge portion (14424b). Second proximal edge portion (14424b) extends along a second plane (14428) that is perpendicular to the longitudinal axis of each flex ring (14206a-c). Thus, the first proximal edge portion (14424a) of each flex ring (14206a-c) extends at an oblique angle ($\theta_{224A-2}$) relative to its second proximal edge portion (14424b).

When assembled as shown in FIGS. 209-210, the distal most flex ring (206a) is substantially abutted distally by distal outer sheath (14202) (force represented by arrow (14430) in FIG. 224A), while the proximal most flex ring (14206c) is substantially abutted proximally by proximal outer sheath (14204) (force represented by arrow (14432) in FIG. 224A). Flex rings (14206a-c) are configured to transition to a flexed position (FIG. 224B) from an unflexed position (FIG. 224A) when, for example, articulation bands (14212, 14214) are moved longitudinally relative to one another, as discussed in more detail below. However, second distal edge portions (14424a) and second proximal edge portions (14424b) interact with one another and with distal outer sheath (14202) and proximal outer sheath (14204) to act as positive stops to restrict pivoting of flex rings (14206a-c) to a single direction. As shown, longitudinal axis (14425) intersects the points of each flex ring (14206a-c) where the respective first and second distal portions (14422a, 14422b) meet, and where the respective first and second proximal portions (14424a, 14424b) meet. Because adjacent second distal and proximal portions (14422b, 14424b) act as a positive stop against one another (and also with adjacent distal and proximal tube members (14202a, 14202b)), flex rings are substantially prevented from pivoting along a path that is above axis (14425) ("above" direction represented by arrow (14435)). Therefore, in the present example, due to the operative coupling of flex rings (14206a-c) to other components of articulation mechanism (14210), articulation mechanism (14210) is permitted to articulate in only one direction (opposite to arrow (14435)) and may only pivot about axes (14427, 14429)).

Flex rings (14206a-c) are rigid in the present example such that any attempted articulation in the opposite direction does not substantially occur due to the material properties of flex rings (14206a-c). That is, where articulation bands (14212, 14214) are moved in a manner that causes a moment in the opposite direction, the material properties (rigidity, stiffness, etc.) of flex rings (14206a-c) are configured to prevent bending, buckling, compression, etc., of the flex rings (14206a-c) that may cause a certain amount of articulation in the direction of arrow (14435). Various suitable ways in which flex rings (14206a-c) may be configured will be apparent to those of ordinary skill in the art in view of the teachings herein.

FIGS. 209-211 and 225-228B show collar (14300) of the present example. As noted above, collar (14300) is configured to operably couple certain components of the articulation section (14210) to one another. Collar (14300) of the present example is further configured to couple distal outer sheath (14202) with proximal outer sheath (14204). As best shown in FIGS. 225-226, collar (14434) includes a proximal end (14436), and a distal end (14438), and a body (14440) extending therebetween. In the present example, collar (14300) includes a spine portion (14442) extending along a longitudinal axis and five pairs of opposing legs (14444a-e) extending from the spine portion (14442). Collar (14300) also includes an elongate rib (14443) extending along the axis of the collar (14300). Each of the five pairs of legs (14444a-e) are spaced apart equally along a longitudinal axis of the collar (14300). As shown, there are five pairs of opposing legs, but there may be more or less than five pairs of legs, and the pairs of opposing legs may or may not be equally spaced longitudinally. In the present example, each pair of legs includes a first leg that extends away from the spine (14442) in a first direction and a second leg extending away from the spine in second direction. Each of the first and second legs of each pair include curvilinear portions and are configured such that the first and second legs of each pair eventually extend parallel to one another. Each of the legs (14444*a-e*) includes a respective snap-fit feature (14446*a-e*) defining respective angled portions (14448*a-e*) and lip portions (14450*a-e*). In some examples, angled portions (14448*a-e*) are configured to act as cam members, in order to assist the collar (14300) to be coupled with other components of the articulation section. More particularly, angled portions (14448*a-e*) may act as cam members when being directed into respective slots and apertures, and legs (14444*a-e*) may flex inwardly temporarily as collar (14300) is being directed into engagement with certain components to provide a snap fit engagement. Various suitable ways in which collar (14300) may be configured will be apparent to those of ordinary skill in the art in view of the teachings herein The operable coupling of components of the articulation section (14210) allows the articulation section (14210) to articulate when a moment is applied directly to one or more components of the articulation section (14210). Referring to FIGS. 209-211, 227A and 228A, in the present example, in the unarticulated configuration, proximal end (14314) of distal flex member (14302) substantially abuts flex base member (14306*a*), particularly at the point where first distal portion (14382*a*) meets second distal portion (14382*b*). Distal end (14340) of proximal flex member (14304) substantially abuts flex base member (14306*c*), particularly where first proximal portion (14384*a*) meets second proximal portion (14384*b*). As discussed above, flex base member (14306*b*) is between flex base member (14306*a*) and flex base member (14306*c*).

In the present example, lumen (14390) of distal tube member (14302) coaxially receives distal flex member (14302) such that slots (14334) of distal flex member (14302) generally align with apertures (14400) of distal outer sheath (14202). Legs (14444*a*) extend into apertures (14400) and along slots (14334) such that lip portion (14450*a*) engages a portion of aperture (14336) and thereby secures collar (14300), distal flex member (14302), and distal outer sheath (14202) to one another. Lumen (14408) of proximal outer sheath (14204) receives proximal flex member (14304) such that slots (14360) of proximal flex member (14304) generally align with apertures (14419) of proximal tube member. Legs (14444*e*) extend into apertures (14419) and along slots (14360) such that lip portion (14450*e*) engages a portion of aperture (14362) and thereby secures collar (14300), proximal flex member (14304), and proximal outer sheath (14204) to one another.

Flex base members (14306*a-c*) of the present example are coaxially received in flex rings (14206*a-c*) such that flex base member (14306*a*) is coincident with flex ring (14206*a*), flex base member (14306*b*) is coincident with flex ring (14206*b*), and flex base member (14306*c*) is coincident with flex ring (14206*c*). Therefore, in such a configuration, apertures (14421) of each flex ring (14206*a-c*) generally align with slots (14378) of a respective flex base member (14306*a-c*). Legs (14444*b*) extend into apertures (14421) of flex ring (14206*a*) and along slots (14378) of flex base member (14306*a*) such that lip portions (14450*b*) engage a portion of a respective aperture (14380). Similarly, legs (14444*c*) extend into apertures (14421) of flex ring (14206*b*) and along slots (14378) of flex base member (14306*b*) such that lip portions (14450*c*) engage a portion of a respective aperture (14380). Similarly, legs (14444*d*) extend into apertures of flex ring (14206*b*) and along slots (14378) of flex base member (14306*c*) such that lip portions (14450*d*) engage a portion of a respective aperture (14380).

Still referring to FIGS. 209-211, 227A, and 228A, in the present example, in the unarticulated configuration, first portion (14392) of proximal edge of distal outer sheath (14202) substantially abuts second distal portion (14422*b*) of flex ring (14206*a*). Second proximal portion (14424*b*) of flex ring (14206*a*) substantially abuts second distal portion (14422*b*) of flex ring (14206*b*). Similarly, second proximal portion (14424*b*) of flex ring (14206*b*) substantially abuts second distal portion (14422*b*) of flex ring (14206*c*). Second proximal portion (14424*b*) of flex ring (14206*b*) substantially abuts first portion (14210) of distal edge of proximal outer sheath (14204). Various suitable ways in which articulation section (14210) may be configured will be apparent to those of ordinary skill in the art in view of the teachings herein.

In the present example, as articulation bands (14212, 14214) are moved longitudinally relative to one another, a moment is initially applied to distal flex member (14302). Due to the distal flex member (14302), flex base members (14306*a-c*), proximal flex member (14304), distal outer sheath (14202), flex rings (14206*a-c*), and proximal outer sheath (14304) being operably coupled via collar (14300) in the manner described herein, the moment applied to distal flex member (14302) is transferred to the collar (14300), distal flex member (14302), flex base members (14306*a-c*), proximal flex member (14304), distal outer sheath (14202), flex rings (14206*a-c*), and proximal outer sheath (14204). Thus, articulation section (14210) transitions to an articulated configuration, as best shown in FIGS. 227B, 228B. In the articulated configuration, articulation section (14210) articulates in the same direction away from the longitudinal axis of instrument (10) as the direction of the bend angle (A) of blade (14260).

As shown in FIGS. 227B and 228B, as a result of the moment applied onto the components of articulation section (14210), distal outer sheath (14202) is pivoted relative to flex ring (14206*a*) such that second portion (14394) of distal edge of distal outer sheath (14202) substantially abuts first distal portion (14422*a*) of flex ring (14206*a*). Flex ring (14206*a*) is shown to be pivoted relative to flex ring (14206*b*) such that first proximal portion (14424*a*) of flex ring (14206*b*) substantially abuts first distal portion (14422*a*) of flex ring (14206*b*). Flex ring (14206*b*) is shown pivoted relative to flex ring (14206*c*) such that first proximal portion (14424*a*) of flex ring (14206*b*) substantially abuts first distal portion (14422*a*) of flex ring (14206*c*). Flex ring (14206*c*) is shown to be pivoted such that first proximal portion (14424*a*) of flex ring (14206*c*) substantially abuts second portion (14412) of distal edge of proximal outer sheath (14204). Thus, in the present example, the maximum articulation angle (as measured between a central axis of distal outer sheath (14202) relative to a central axis of proximal outer sheath (14204)) due to the abutment of such structures is $\theta_A$, where $\theta_A = 3*(\theta_{2244\text{-}1} + \theta_{2244\text{-}2}) - \theta_{222} - \theta_{220}$.

Once the articulation bands (14212, 14214) move relative to one another in a manner opposite to that which caused the articulation, articulation section (14210) may return to the unarticulated configuration shown in FIGS. 227A and 228A. However, even if the operator somehow attempts to continue opposingly move articulation bands (14212, 14214) once articulation section (14210) reaches the unarticulated configuration shown in FIGS. 227A and 228A, engagement between adjacent edge portions (14422b, 14424b) will prevent articulation section (14210) from articulating past longitudinal axis (14425) in the direction of arrow (14435).

XVI. ULTRASONIC SURGICAL INSTRUMENT WITH OPPOSING THREAD DRIVE FOR END EFFECTOR ARTICULATION

A. Exemplary Alternative Articulation Control Configurations with Perpendicular Rotary Knob When an operator wishes to control articulation of articulation section (130) in instrument (10) as described above, the operator may need to use both hands. In particular, the operator may need to grasp pistol grip (24) with one hand and grasp knob (120) with the other hand, holding handle assembly (20) stationary via pistol grip (24) while the operator rotates knob (120). It may be desirable to provide control of articulation section (130) without requiring the operator to use both hands. This may enable the operator to have a free hand to grasp other instruments or otherwise use as they see fit. An exemplary alternative instrument (15200) is described below in which an operator may firmly grasp the instrument (15200) and control articulation of an articulation section using just one single hand. Various suitable ways in which the below teachings may be modified will be apparent to those of ordinary skill in the art in view of the teachings herein.

FIGS. 229-245C depict an exemplary electrosurgical instrument (15200) that includes a handle assembly (15220), a shaft assembly (15230) extending distally from handle assembly (15220), and an end effector (15240) disposed at a distal end of shaft assembly (15230). Handle assembly (15220) of the present example comprises a body (15222) including a pistol grip (15224) and a button (15226). Handle assembly (15220) also includes a trigger (15228) that is pivotable toward and away from pistol grip (15224) to selectively actuate end effector (15240) as described above and as described in one or more of the references cited herein. It should be understood, however, that various other suitable configurations may be used, including but not limited to a scissor grip configuration. End effector (15240) includes an ultrasonic blade (15260) and a pivoting clamp arm (15244). Clamp arm (15244) is coupled with trigger (15228) such that clamp arm (15244) is pivotable toward ultrasonic blade (15260) in response to pivoting of trigger (15228) toward pistol grip (15224); and such that clamp arm (15244) is pivotable away from ultrasonic blade (15260) in response to pivoting of trigger (15228) away from pistol grip (15224). Various suitable ways in which clamp arm (15244) may be coupled with trigger (15228) will be apparent to those of ordinary skill in the art in view of the teachings herein. In some versions, one or more resilient members are used to bias clamp arm (15244) and/or trigger (15228) to the open position shown in FIGS. 229 and 230.

An ultrasonic transducer assembly (15212) extends proximally from body (15222) of handle assembly (15220). Transducer assembly (15212) is coupled with a generator (15216) via a cable (15214), such that transducer assembly (15212) receives electrical power from generator (15216). Piezoelectric elements in transducer assembly (15212) convert that electrical power into ultrasonic vibrations. Generator (15216) may include a power source and control module that is configured to provide a power profile to transducer assembly (15212) that is particularly suited for the generation of ultrasonic vibrations through transducer assembly (15212). By way of example only, generator (15216) may comprise a GEN 300 sold by Ethicon Endo-Surgery, Inc. of Cincinnati, Ohio. In addition or in the alternative, generator (15216) may be constructed in accordance with at least some of the teachings of U.S. Pub. No. 2011/0087212, now issued as U.S. Pat. No. 8,986,302 on Mar. 24, 2015, entitled "Surgical Generator for Ultrasonic and Electrosurgical Devices," published Apr. 14, 2011, the disclosure of which is incorporated by reference herein. It should also be understood that at least some of the functionality of generator (15216) may be integrated into handle assembly (15220), and that handle assembly (15220) may even include a battery or other on-board power source such that cable (15214) is omitted. Still other suitable forms that generator (15216) may take, as well as various features and operabilities that generator (15216) may provide, will be apparent to those of ordinary skill in the art in view of the teachings herein.

An operator may activate button (15226) to selectively activate transducer assembly (15212) to thereby activate ultrasonic blade (15260). In the present example, a single button (15226) is provided. Button (15226) may be depressed to activate ultrasonic blade (15260) at a low power and to activate ultrasonic blade (15260) at a high power. For instance, button (15226) may be pressed through a first range of motion to activate ultrasonic blade (15260) at a low power; and through a second range of motion to activate ultrasonic blade (15260) at a high power. Of course, any other suitable number of buttons and/or otherwise selectable power levels may be provided. For instance, a foot pedal may be provided to selectively activate transducer assembly (15212). Button (15226) of the present example is positioned such that an operator may readily fully operate instrument (15200) with a single hand. For instance, the operator may position their thumb about pistol grip (15224), position their middle, ring, and/or little finger about trigger (15228), and manipulate button (15226) using their index finger. Alternatively, any other suitable techniques may be used to grip and operate instrument (15200); and button (15226) may be located at any other suitable positions.

In some versions, button (15226) also serves as a mechanical lockout against trigger (15224), such that trigger (15224) cannot be fully actuated unless button (15226) is being pressed simultaneously. Examples of how such a lockout may be provided are disclosed in one or more of the references cited herein. It should be understood that pistol grip (15222), trigger (15224), and button (15226) may be modified, substituted, supplemented, etc. in any suitable way, and that the descriptions of such components herein are merely illustrative.

1. Exemplary End Effector and Acoustic Drivetrain

As best seen in FIGS. 229 and 230, end effector (15240) of the present example comprises clamp arm (15244) and ultrasonic blade (15260). Clamp arm (15244) includes a clamp pad (15246) that is secured to the underside of clamp arm (15244), facing ultrasonic blade (15260). Clamp pad (15246) may comprise PTFE and/or any other suitable material(s). Clamp arm (15244) is operable to selectively pivot toward and away from ultrasonic blade (15260) to selectively clamp tissue between clamp arm (15244) and blade (15260).

As with clamp arm (15044) discussed above, clamp arm (15244) of the present example is pivotally secured to a cable (15274). Cable (15274) is slidably disposed within an outer sheath (15232) of shaft assembly (15230) as shown in FIGS. 233-234. Cable (15274) is operable to translate longitudinally relative to an articulation section (15330) of shaft assembly (15230) to selectively pivot clamp arm (15244) toward and away from blade (15260). In particular, cable (15274) is coupled with trigger (15228) such that cable (15274) translates proximally in response to pivoting of trigger (15228) toward pistol grip (15224), and such that clamp arm (15244) thereby pivots toward blade (15260) in response to pivoting of trigger (15228) toward pistol grip (15224). In addition, cable (15274) translates distally in response to pivoting of trigger (15228) away from pistol grip (15224), such that clamp arm (15244) pivots away from blade (15260) in response to pivoting of trigger (15228) away from pistol grip (15224). Clamp arm (15244) may be biased toward the open position, such that (at least in some instances) the operator may effectively open clamp arm (15244) by releasing a grip on trigger (15228). It should be understood that clamp arm (15244) is merely optional, such that clamp arm (15244) may be omitted if desired.

Blade (15260) of the present example is operable to vibrate at ultrasonic frequencies in order to effectively cut through and seal tissue, particularly when the tissue is being compressed between clamp pad (15246) and blade (15260). Blade (15260) is positioned at the distal end of an acoustic drivetrain. This acoustic drivetrain includes transducer assembly (15212) and an acoustic waveguide (15280). Acoustic waveguide (15280) comprises a flexible portion (15266). Transducer assembly (15212) includes a set of piezoelectric discs (not shown) located proximal to a horn (not shown) of waveguide (15280). The piezoelectric discs are operable to convert electrical power into ultrasonic vibrations, which are then transmitted along waveguide (15280), including flexible portion (15266) of waveguide (15280) to blade (15260) in accordance with known configurations and techniques. By way of example only, this portion of the acoustic drivetrain may be configured in accordance with various teachings of various references that are cited herein.

As with flexible portion (166) of waveguide (180) discussed above, flexible portion (15266) of waveguide (15280) includes a narrowed section (15264). Narrowed section (15264) is configured to allow flexible portion (15266) of waveguide (15280) to flex without significantly affecting the ability of flexible portion (15266) of waveguide (15280) to transmit ultrasonic vibrations. By way of example only, narrowed section (15264) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,045,367 on Aug. 4, 2015, the disclosures of which are incorporated by reference herein. It should be understood that waveguide (15280) may be configured to amplify mechanical vibrations transmitted through waveguide (15280). Furthermore, waveguide (15280) may include features operable to control the gain of the longitudinal vibrations along waveguide (15280) and/or features to tune waveguide (15280) to the resonant frequency of the system. Various suitable ways in which waveguide (15280) may be mechanically and acoustically coupled with transducer assembly (15212) will be apparent to those of ordinary skill in the art in view of the teachings herein.

In the present example, the distal end of blade (15260) is located at a position corresponding to an anti-node associated with resonant ultrasonic vibrations communicated through flexible portion (15266) of waveguide (15280), in order to tune the acoustic assembly to a preferred resonant frequency $f_o$ when the acoustic assembly is not loaded by tissue. When transducer assembly (15212) is energized, the distal end of blade (15260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (15212) of the present example is activated, these mechanical oscillations are transmitted through waveguide (15280) to reach blade (15260), thereby providing oscillation of blade (15260) at the resonant ultrasonic frequency. Thus, when tissue is secured between blade (15260) and clamp pad (15246), the ultrasonic oscillation of blade (15260) may simultaneously sever the tissue and denature the proteins in adjacent tissue cells, thereby providing a coagulative effect with relatively little thermal spread. In some versions, an electrical current may also be provided through blade (15260) and clamp arm (15244) to also cauterize the tissue. While some configurations for an acoustic transmission assembly and transducer assembly (15212) have been described, still other suitable configurations for an acoustic transmission assembly and transducer assembly (15212) will be apparent to one or ordinary skill in the art in view of the teachings herein. Similarly, other suitable configurations for end effector (15240) will be apparent to those of ordinary skill in the art in view of the teachings herein.

2. *Exemplary Shaft Assembly and Articulation Section*

Shaft assembly (15230) of the present example extends distally from handle assembly (15220). As best seen in FIGS. 229 and 230, shaft assembly (15230) includes distal outer sheath (15233) and a proximal outer sheath (15232) that enclose the drive features of clamp arm (15244) and the above-described acoustic transmission features. Shaft assembly (15230) further includes an articulation section (15330), which is located at a distal portion of shaft assembly (15230), with end effector (15240) being located distal to articulation section (15330).

Articulation section (15330) of the present example is configured and operable substantially similar to articulation section (130) discussed above except for the differences discussed below. In particular, articulation section (15330) is operable to selectively position end effector (15240) at various lateral deflection angles relative to a longitudinal axis defined by outer sheath (15232). Articulation section (15330) may take a variety of forms. By way of example only, articulation section (15330) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (15330) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. Various other suitable forms that articulation section (15330) may take will be apparent to those of ordinary skill in the art in view of the teachings herein.

As shown in FIGS. 233-234, shaft assembly (15230) further comprises a pair of articulation bands (15340, 15342) and a pair of translatable rods (15440, 15442). Articulation bands (15340, 15342) are configured to operate substantially similar to articulation bands (140, 142) discussed above, except for any differences discussed below. For instance, when articulation bands (15340, 15342) translate longitudinally in an opposing fashion, this will cause articulation section (15330) to bend, thereby laterally deflecting end effector (15240) away from the longitudinal axis of shaft assembly (15230) from a straight configuration as shown in FIG. 245A to an articulated configuration as shown in FIGS. 245B and 245C. In particular, end effector (15240) will be articulated toward the articulation band (15340, 15342) that is being pulled proximally. During such articulation, the other articulation band (15340, 15342) may be pulled distally. Alternatively, the other articulation band (15340, 15342) may be driven distally by articulation control assembly (15400), which is described in greater detail below. Flexible acoustic waveguide (15266) is configured to effectively communicate ultrasonic vibrations from waveguide (15280) to blade (15260) even when articulation section (15330) is in an articulated state as shown in FIGS. 245B and 245C.

Translatable members (15440, 15442) are slidably disposed within the proximal portion of outer sheath (15232). Translatable members (15440, 15442) extend longitudinally through the proximal portion of outer sheath (15232) along opposite sides of outer sheath (15232) and adjacent an interior surface of outer sheath (15232). As shown in FIG. 234, an elongate recess (15444) is formed in an exterior surface of a distal portion of each translatable member (15440, 15442). Elongate recesses (15444) are configured to receive a proximal portion of each articulation band (15340, 15342). Each translatable member (440, 15442) further includes a pin (15443) projecting outwardly from an interior surface of each elongate recess (15444). An opening (15341) formed in a proximal end of each articulation band (15340, 15342) is configured to receive a respective pin (15443) of translatable members (15440, 15442). Pins (15443) and openings (15341, 15343) thus function to mechanically couple translatable members (15440, 15442) with articulation bands (15340, 15342) such that longitudinal translation of translatable member (15440) causes concurrent longitudinal translation of articulation band (15340), and such that longitudinal translation of translatable member (15442) causes concurrent longitudinal translation of articulation band (15342).

When translatable members (15440, 15442) and articulation bands (15340, 15342) are translated longitudinally in an opposing fashion, a moment is created and applied to a distal end of distal outer sheath (15233) in the same manner as described above with respect to articulation section (130). This causes articulation section (15330) and narrowed section (15264) of flexible portion (15266) of waveguide (15280) to articulate, without transferring axial forces in articulation bands (15340, 15342) to waveguide (15280) as described above. It should be understood that one articulation band (15340, 15342) may be actively driven distally while the other articulation band (15340, 15342) is passively permitted to retract proximally. As another merely illustrative example, one articulation band (15340, 15342) may be actively driven proximally while the other articulation band (15340, 15342) is passively permitted to advance distally. As yet another merely illustrative example, one articulation band (15340, 15342) may be actively driven distally while the other articulation band (15340, 15342) is actively driven proximally. Various suitable ways in which articulation bands (15340, 15342) may be driven will be apparent to those of ordinary skill in the art in view of the teachings herein.

As shown in FIGS. 229-232, a rotation knob (15231) is secured to a proximal portion of proximal outer sheath (15232). Rotation knob (15231) is rotatable relative to body (15222), such that shaft assembly (15230) is rotatable about the longitudinal axis defined by outer sheath (15232), relative to handle assembly (15220). Such rotation may provide rotation of end effector (15240), articulation section (15330), and shaft assembly (15230) unitarily. Of course, rotatable features may simply be omitted if desired.

3. Exemplary Articulation Control Assembly

FIGS. 235-245C show the components and operation of an articulation control assembly (15400) that is configured to provide control for articulation of articulation section (15330). Articulation control assembly (15400) comprises an articulation control knob (15402) and a bevel gear (15404). Articulation control knob (15402) is rotatably disposed within a distal portion of body (15222) of handle assembly (15220). As best seen in FIG. 232, articulation control knob (15402) is oriented within body (15222) and relative to shaft assembly (15230) such that articulation control knob (15402) is configured to rotate about an axis that is perpendicular to the longitudinal axis defined by shaft assembly (15230). A portion of articulation control knob (15402) is exposed relative to body (15222) such that an operator may engage articulation control knob (15402) to thereby rotate articulation control knob (15402). For example, while gripping body (15222) via pistol grip (15224), an operator may use his or her index finger or thumb to rotate articulation control knob (15402). It should therefore be understood that the operator may rotate knob (15402) using the same hand that grasps pistol grip (15224). As will be described in more detail below, rotation of articulation control knob (15402) is configured to cause articulation of articulation section (15330). Since the operator may use the same hand to rotate knob (15402) and simultaneously grasp pistol grip (15224), articulation control assembly (15400) of this example provides full control of instrument (15200)—including pivoting of trigger (15228), actuation of button (15226), and actuation of knob (15402)—with just one single hand, such the operator's other hand may be completely free during the entire period when any and all functionality of instrument (15200) is being used.

Articulation control assembly (15400) further includes a structural frame (15370) secured within a proximal portion of an interior of body (15222) of handle assembly (15220) such that structural frame (15370) is configured to remain stationary within body (15222). As best seen in FIGS. 235 and 236, bevel gear (15404) is rotatably disposed about a cylindrical projection (15372) of structural frame (15370). As best seen in FIG. 232, bevel gear (15404) is mechanically coupled with articulation control knob (15402) via a slot (15406) formed in bevel gear (15404) and a mating key (15408) projecting from a top surface of articulation control knob (15402) such that rotation of articulation control knob (15402) causes concurrent rotation of bevel gear (15404) about cylindrical projection (15372) of structural frame (15370). Bevel gear (15404) includes a plurality of teeth (15410) and a detent feature (15412). As will be described in more detail below, teeth (15410) of bevel gear (15404) mesh with teeth (15439) of a bevel gear (15438) of a drive assembly (15420), such that rotation of bevel gear (15404) drives articulation of articulation section (15330).

Detent feature (15412) is configured to selectively engage a complementary, resiliently biased detent feature (15223) of handle assembly (15220) as best seen in FIG. 232. Detent feature (15412) is positioned to engage detent feature (15223) when control knob (15402) is rotated to a "neutral" position associated with articulation section (15330) being in a straight configuration. It should therefore be understood that detent features (15224, 15412) may cooperate to provide the operator with tactile feedback via control knob (15402) to indicate that articulation section (15330) is in the straight configuration. Detent features (15224, 15412) may also cooperate to provide some degree of mechanical resistance to rotation of knob (15402) from the neutral position, thereby resisting inadvertent articulation of articulation section (15330) that might otherwise result from incidental contact between knob (15402) and the operator's hand, etc.

In addition to or in lieu of including detent features (15224, 15412), knob (15402) may include a visual indicator that is associated with articulation section (15330) being in a substantially straight configuration. Such a visual indicator may align with a corresponding visual indicator on body (15222) of handle assembly (15220). Thus, when an operator has rotated knob (15402) to make articulation section (15330) approach a substantially straight configuration, the operator may observe such indicators to confirm whether articulation section (15330) has in fact reached a substantially straight configuration. By way of example only, this may be done right before instrument (15200) is withdrawn from a trocar to reduce the likelihood of articulation section (15330) snagging on a distal edge of the trocar. Of course, such indicators are merely optional.

As best seen in FIG. 235, articulation control assembly (15400) further comprises a drive assembly (15420). Drive assembly (15420) is secured to a proximal portion of proximal outer sheath (15232). Drive assembly (15420) is further rotatably disposed within rotation knob (15231) such that rotation knob (15231) is configured to rotate independently about drive assembly (15420) to thereby cause rotation of shaft assembly (15230) without causing rotation of drive assembly (15420).

Drive assembly (15420) comprises a housing (15430), a pair of lead screws (15450, 15460), and a cylindrical guide (15470). Housing (15430) comprises a pair of mating semi-cylindrical shrouding halves (15432, 15434) and a bevel gear (15438). When coupled to one another, shrouding halves (15432, 15434) form a cylindrical shroud (15431). A proximal end of shroud (15431) is coupled with and closed-off by bevel gear (15438). Shroud (15431), together with bevel gear (15438), form housing (15430) which substantially encompasses the internal components of drive assembly (15420) as will be described in more detail below.

Bevel gear (15438) includes a plurality of teeth (15439). Teeth (15439) of bevel gear (15438) are configured to engage teeth (15410) of bevel gear (15404) such that rotation of bevel gear (15404) causes concurrent rotation of bevel gear (15438). It should therefore be understood that rotation of articulation control knob (15402) is configured to cause concurrent rotation of housing (15430) via bevel gears (15404, 15438).

As best seen in FIG. 236, shrouding halves (15432, 15434) each include proximal internal threading (15433A) formed in an interior surface of each shrouding half (15432, 15434). Internal threadings (15433A) are configured to align with one another when shrouding halves (15432, 15434) are coupled together to form a continuous internal proximal threading (15433) within housing (15430). Shrouding halves (15432, 15434) each further include distal internal threading (15435A) formed in an interior surface of each shrouding half (15432, 15434). Internal threadings (15435A) are configured to align with one another when shrouding halves (15432, 15434) are coupled together to form a continuous internal distal threading (15435) within housing (15430). Threadings (15433, 15435) have opposing pitch angles or orientations in this example, such that the pitch orientation of threading (15433) is opposite the pitch orientation of threading (15435).

As shown in FIGS. 238-239, a first lead screw (15450) includes exterior threading (15452) that is configured to engage with threading (15433) of housing (15430). As shown in FIGS. 240-241 a second lead screw (15460) includes exterior threading (15462) that is configured to engage with threading (15435) of housing (15430). The pitch angle of threading (15452) complements the pitch angle of threading (15433); while the pitch angle of threading (15462) complements the pitch angle of threading (15435). As described in greater detail below, both lead screws (15450, 15460) are permitted to translate within drive assembly (15420) but are prevented from rotating within drive assembly (15420). It should therefore be understood that, due to the opposing pitch angles, rotation of housing (15430) in a first direction will drive lead screw (15450) distally while simultaneously driving lead screw (15460) proximally; and rotation of housing (15430) in a second direction will drive lead screw (15450) proximally while simultaneously driving lead screw (15460) distally.

As best seen in FIGS. 239 and 241, a through-bore (15454, 15464) formed in each lead screw (15450, 15460) includes a pair of recesses (15456, 15466) formed in radially opposing sides of an interior surface of through-bores (15454, 15464). Cylindrical guide (15470) is positioned within housing (15430) about the proximal portion of outer sheath (15232). As shown in FIGS. 242A and 242B, cylindrical guide (15470) is secured to a distal end of structural frame (15370) via a pair of semi-circular recesses (15374) formed in the distal end of structural frame (15370) and a pair of semi-circular projections (15476) extending proximally from cylindrical guide (15470). Thus, with structural frame (15370) secured within the proximal portion of the interior of body (15222) of handle assembly (15220) as described above, cylindrical guide (15470) is configured to remain stationary within housing (15430). A bearing member (15436) is coupled to a distal end of cylindrical guide (15470) via a pair of semi-circular recesses (15437) formed in bearing member (15436) and a pair of semi-circular projections (15478) extending distally from cylindrical guide (15470). A circular flange (15441) of bearing member (15436) is rotatable disposed within a pair of mating circular recesses (15451A) formed in a distal end of shroud halves (15432, 15434) such that housing (15430) is operable to rotate about bearing member (15436).

As best seen in FIGS. 242A and 242B, cylindrical guide (15470) comprises a proximal pair of longitudinal tracks (15472) and a distal pair of longitudinal tracks (15474) formed in opposing sides of a sidewall of cylindrical guide (15470). As shown in FIG. 243, proximal longitudinal tracks (15472) are configured to be received within recesses (15456) of first lead screw (15450) such that first lead screw (15450) is slidably disposed along proximal longitudinal tracks (15472). As shown in FIG. 244, distal longitudinal tracks (15474) are configured to be received within recesses (15466) of second lead screw (15460) such that second lead screw (15460) is slidably disposed along distal longitudinal tracks (15474). Thus, lead screws (15450, 15460) are operable to translate within housing (15430) but are prevented from rotating within housing (15430).

As shown in FIG. 243, first lead screw (15450) is secured to a proximal end of translatable member (15440) via a coupler (15458). An exterior surface of coupler (15458) is secured to an interior surface of through-bore (15454) of first lead screw (15450). A key (15459) of coupler (15458) is positioned within a mating slot (15447) formed in the proximal end of translatable member (15440) such that longitudinal translation of first lead screw (15450) causes concurrent translation of translatable member (15440) and articulation band (15340). Thus, in the present version, first lead screw (15450) is operable to both push articulation band (15340) distally and pull articulation band (15340) proximally, depending on which direction housing (15430) is rotated. Other suitable relationships will be apparent to those of ordinary skill in the art in view of the teachings herein.

As shown in FIG. 244, second lead screw (15460) is secured to a proximal end of translatable member (15442) via a coupler (15468). An exterior surface of coupler (15468) is secured to an interior surface of through-bore (15464) of second lead screw (15460). A key (15469) of coupler (15468) is positioned within a mating slot (15449) formed in the proximal end of translatable member (15442) such that longitudinal translation of second lead screw (15460) causes concurrent translation of translatable member (15422) and articulation band (15342). Thus, in the present version, second lead screw (15460) is operable to both push articulation band (15342) distally and pull articulation band (15342) proximally, depending on which direction housing (15430) is rotated. Other suitable relationships will be apparent to those of ordinary skill in the art in view of the teachings herein.

FIGS. 245A-245C show several of the above described components interacting to bend articulation section (15330) to articulate end effector (15240) in response to rotation of knob (15402) relative to handle assembly (15220). It should be understood that in FIGS. 245A-245C depicts a side elevational view of handle assembly (15220) and a top plan view of shaft assembly (15230), including articulation section (15330). In FIG. 245A, articulation section (15330) is in a substantially straight configuration. Then, housing (15430) is rotated by rotation of articulation knob (15402). In particular, rotation of articulation knob (15402) is communicated to housing (15430) via meshing bevel gears (15410, 15438). The resulting rotation of housing (15430) which causes first lead screw (15450) to translate proximally and second lead screw (15460) to advance distally. This proximal translation of first lead screw (15450) pulls articulation band (15340) proximally via translatable member (15440), which causes articulation section (15330) to start bending as shown in FIG. 245B. This bending of articulation section (15330) pulls articulation band (15342) distally. The distal advancement of second lead screw (15460) in response to rotation of housing (15430) enables articulation band (15342) and translatable member (15442) to advance distally. In some other versions, the distal advancement of second lead screw (15460) actively drives translatable member (15442) and articulation band (15342) distally. As the operator continues rotating housing (15430) by rotating articulation knob (15402), the above described interactions continue in the same fashion, resulting in further bending of articulation section (15330) as shown in FIG. 245C.

It should be understood that, after reaching the articulation state in FIG. 245C by rotating knob (15402) in a first direction, rotation of knob (15402) in a second (opposite) direction will cause articulation section (15330) to return to the straight configuration shown in FIG. 245A. As noted above, detent features (15224, 15412) may cooperate to provide tactile feedback via knob (15402) to indicate that articulation section (15330) has reached the straight configuration. Still further rotation of knob (15402) in that second direction will eventually result in articulation section (15330) deflecting in a direction opposite to that shown in FIGS. 245B-245C.

The angles of threading (15433, 15435, 15452, 15462) are configured such that articulation section (15330) will be effectively locked in any given articulated position, such that transverse loads on end effector (15240) will generally not bend articulation section (15330), due to friction between threading (15433, 15435, 15452, 41562). In other words, articulation section (15330) will only change its configuration when housing (15430) is rotated via knob (15402). While the angles of threading may substantially prevent bending of articulation section (15330) in response to transverse loads on end effector (15240), the angles may still provide ready rotation of housing (15430) to translate lead screws (15450, 15460). By way of example only, the angles of threading (15433, 15435, 15452, 15462) may be approximately +/−2 degrees or approximately +/−3 degrees. Other suitable angles will be apparent to those of ordinary skill in the art in view of the teachings herein. It should also be understood that threading (15433, 15435, 15452, 15462) may have a square or rectangular cross-section or any other suitable configuration.

In some instances, manufacturing inconsistencies may result in articulation bands (15340, 15342) and/or translatable members (15440, 15442) having slightly different lengths. In addition or in the alternative, there may be inherent manufacturing related inconsistencies in the initial positioning of lead screws (15450, 15460) relative to housing (15430) and/or other inconsistencies that might result in undesirable positioning/relationships of articulation bands (15340, 15342) and/or translatable members (15440, 15442). Such inconsistencies may result in lost motion or slop in the operation of the articulation features of instrument (15200). To address such issues, tensioner gears (not shown) may be incorporated into drive assembly (15420) to adjust the longitudinal position of translatable members (15440, 15442) relative to lead screws (15450, 15460). Lead screws (15450, 15460) may remain substantially stationary during such adjustments. Articulation section (15330) may remain substantially straight during such adjustments and may even be held substantially straight during such adjustments.

In addition to or in lieu of the foregoing, drive assembly (15420) may be configured and operable in accordance with at least some of the teachings of U.S. Pub. No. 2013/0023868, issued as U.S. Pat. No. 9,545,253 on Jan. 17, 2017, entitled "Surgical Instrument with Contained Dual Helix Actuator Assembly," published Jan. 24, 2013, the disclosure of which is incorporated by reference herein; in U.S. Pub. No. 2012/0078243, issued as U.S. Pat. No. 9,877,720 on Jan. 30, 2018, entitled "Control Features for Articulating Surgical Device," published Mar. 29, 2012, the disclosure of which is incorporated by reference herein; and in U.S. Pub. No. 2012/0078244, entitled "Control Features for Articulating Surgical Device," published Mar. 29, 2012, the disclosure of which is incorporated by reference herein.

B. Exemplary Motorized Articulation Control Assembly and Rigidizing Member

In some versions of instruments (10, 15200) it may be desirable to provide motorized control of articulation section (130, 15330). This may further promote single-handed use of the instrument, such that two hands are not required in order to control articulation section (130, 15300).

It may also be desirable to provide features that are configured to selectively provide rigidity to articulation sections (130, 15330). For instance, because of various factors such as manufacturing tolerances, design limitations, material limitations, and/or other factors, some versions of articulation sections (130, 15330) may be susceptible to some "play" or other small movement of the articulation section despite being relatively fixed in a given position, such that articulation sections (130, 15330) are not entirely rigid. It may be desirable to reduce or eliminate such play in articulation sections (130, 15330), particularly when articulation sections (130, 15330) are in a straight, non-articulated configuration. Features may thus be provided to selectively rigidize articulation sections (130, 15330). Various examples of features that are configured to selectively provide rigidity to articulation sections (130, 15330) and/or to limit or prevent inadvertent deflection of end effectors (15040, 15240) will be described in greater detail below. Other examples will be apparent to those of ordinary skill in the art according to the teachings herein. It should be understood that the examples of shaft assemblies and/or articulation sections described below may function substantially similar to shaft assemblies (15030, 15230) discussed above.

It should also be understood that articulation sections (130, 15330) may still be at least somewhat rigid before being modified to include the rigidizing features described below, such that the rigidizing features described below actually just increase the rigidity of articulation sections (130, 15330) rather than introducing rigidity to otherwise non-rigid articulation sections (130, 15330). For instance, articulation sections (130, 15330) in the absence of features as described below may be rigid enough to substantially maintain a straight or articulated configuration; yet may still provide "play" of about 1 mm or a fraction thereof such that the already existing rigidity of articulation sections (130, 15330) may be increased. Thus, terms such as "provide rigidity," "providing rigidity," "rigidize," and "rigidizing," etc. shall be understood to include just increasing rigidity that is already present in some degree. The terms "provide rigidity," "providing rigidity," "rigidize," and "rigidizing," etc. should not be read as necessarily requiring articulation sections (130, 330) to completely lack rigidity before the rigidity is "provided."

1. Overview

FIGS. 246-248 show an exemplary ultrasonic surgical instrument (15500) that is configured to be used in minimally invasive surgical procedures (e.g., via a trocar or other small diameter access port, etc.). As will be described in greater detail below, instrument (15500) is operable to cut tissue and seal or weld tissue (e.g., a blood vessel, etc.) substantially simultaneously. Instrument (15500) of this example comprises a disposable assembly (15501) and a reusable assembly (15502). The distal portion of reusable assembly (15502) is configured to removably receive the proximal portion of disposable assembly (15501), as seen in FIGS. 247-248, to form instrument (15500). By way of example only, instrument (15500) may be configured and operable in accordance with at least some of the teachings of U.S. patent application Ser. No. 14/623,812, Published as U.S. Pub. No. 2015/0245850 on Sep. 3, 2015, entitled "Ultrasonic Surgical Instrument with Removable Handle Assembly," filed Feb. 17, 2015, the disclosure of which is incorporated by reference herein.

In an exemplary use, assemblies (15501, 15502) are coupled together to form instrument (15500) before a surgical procedure, the assembled instrument (15500) is used to perform the surgical procedure, and then assemblies (15501, 15502) are decoupled from each other for further processing. In some instances, after the surgical procedure is complete, disposable assembly (15501) is immediately disposed of while reusable assembly (15502) is sterilized and otherwise processed for re-use. By way of example only, reusable assembly (15502) may be sterilized in a conventional relatively low temperature, relatively low pressure, hydrogen peroxide sterilization process. Alternatively, reusable assembly (15502) may be sterilized using any other suitable systems and techniques (e.g., autoclave, etc.). In some versions, reusable assembly (15502) may be sterilized and reused approximately 100 times. Alternatively, reusable assembly (15502) may be subject to any other suitable life cycle. For instance, reusable assembly (15502) may be disposed of after a single use, if desired. While disposable assembly (15501) is referred to herein as being "disposable," it should be understood that, in some instances, disposable assembly (15501) may also be sterilized and otherwise processed for re-use. By way of example only, disposable assembly (15501) may be sterilized and reused approximately 2-30 times, using any suitable systems and techniques. Alternatively, disposable assembly (15501) may be subject to any other suitable life cycle.

In some versions, disposable assembly (15501) and/or reusable assembly (15502) includes one or more features that are operable to track usage of the corresponding assembly (15501, 15502), and selectively restrict operability of the corresponding assembly (15501, 15502) based on use. For instance, disposable assembly (15501) and/or reusable assembly (15502) may include one or more counting sensors and a control logic (e.g., microprocessor, etc.) that is in communication with the counting sensor(s). The counting sensor(s) may be able to detect the number of times the ultrasonic transducer of instrument (15500) is activated, the number of surgical procedures the corresponding assembly (15501, 15502) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (15501, 15502). In instances where the control logic stores two or more threshold values (e.g., a first threshold for number of activations and a second threshold for number of surgical procedures, etc.), the control logic may disable operability of one or more components in the corresponding assembly (15501, 15502) the first time one of those thresholds is exceeded, or on some other basis.

In versions where a control logic is operable to disable instrument (15500) based on the amount of use, the control logic may also determine whether instrument (15500) is currently being used in a surgical procedure, and refrain from disabling instrument (15500) until that particular surgical procedure is complete. In other words, the control logic may allow the operator to complete the current surgical procedure but prevent instrument (15500) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (15500) will be apparent to those of ordinary skill in the art in view of the teachings herein. Of course, some versions of instrument (15500) may simply omit features that track and/or restrict the amount of usage of instrument (15500).

As shown in FIGS. 249-293C, disposable assembly (15501) of the present example comprises a body portion (15520), a shaft assembly (15530) extending distally from body portion (15520), and an end effector (15540) disposed at a distal end of shaft assembly (15530). Body portion (15520) of the present example comprises a housing (15522) which includes a button (15526). Button (15526) is operable just like button (15226) described above. Body portion (15520) also includes a trigger (15528) that is pivotable toward and away from a pistol grip (15524) of reusable assembly (15502) to selectively actuate end effector (15540) as described above and as described in one or more of the references cited herein. It should be understood, however, that various other suitable configurations may be used, including but not limited to a scissor grip configuration. End effector (15540) includes an ultrasonic blade (15560) and a pivoting clamp arm (15544). Clamp arm (15544) is coupled with trigger (15528) such that clamp arm (15544) is pivotable toward ultrasonic blade (15560) in response to pivoting of trigger (15528) toward pistol grip (15524); and such that clamp arm (15544) is pivotable away from ultrasonic blade (15560) in response to pivoting of trigger (15528) away from pistol grip (15524). Various suitable ways in which clamp arm (15544) may be coupled with trigger (15528) will be apparent to those of ordinary skill in the art in view of the teachings herein. In some versions, one or more resilient members are used to bias clamp arm (15544) and/or trigger (15528) to the open position shown in FIGS. 246-248. It should also be understood that clamp arm (15544) may be omitted if desired.

2. Exemplary End Effector and Acoustic Drivetrain

As discussed above, end effector (15540) of the present example comprises clamp arm (15544) and ultrasonic blade (15560). Clamp arm (15544) includes a clamp pad (15546) that is secured to the underside of clamp arm (15544), facing ultrasonic blade (15560). Clamp pad (15546) may comprise PTFE and/or any other suitable material(s). Clamp arm (15544) is operable to selectively pivot toward and away from ultrasonic blade (15560) to selectively clamp tissue between clamp arm (15544) and blade (15560).

As with clamp arms (15044, 15244) discussed above, clamp arm (15544) of the present example is pivotally secured to a cable (15574). Cable (15574) is slidably disposed within an outer sheath (15532) of shaft assembly (15530) as shown in FIG. 252. Cable (15574) is operable to translate longitudinally relative to an articulation section (15630) of shaft assembly (15530) to selectively pivot clamp arm (15544) toward and away from blade (15560). In particular, cable (15574) is coupled with trigger (15528) such that cable (15574) translates proximally in response to pivoting of trigger (15528) toward pistol grip (15524), and such that clamp arm (15544) thereby pivots toward blade (15560) in response to pivoting of trigger (15528) toward pistol grip (15524). In addition, cable (15574) translates distally in response to pivoting of trigger (15528) away from pistol grip (15524), such that clamp arm (15544) pivots away from blade (15560) in response to pivoting of trigger (15528) away from pistol grip (15524). Clamp arm (15544) may be biased toward the open position, such that (at least in some instances) the operator may effectively open clamp arm (15544) by releasing a grip on trigger (15528).

Blade (15560) of the present example is operable to vibrate at ultrasonic frequencies in order to effectively cut through and seal tissue, particularly when the tissue is being compressed between clamp pad (15546) and blade (15560). Blade (15560) is positioned at the distal end of an acoustic drivetrain. Acoustic waveguide (15580) comprises a flexible portion (15266). As with flexible portions (166, 15266) of waveguides (180, 15280) discussed above, flexible portion (15566) of waveguide (15580) includes a narrowed section (15564). Narrowed section (15564) is configured to allow flexible portion (15566) of waveguide (15580) to flex without significantly affecting the ability of flexible portion (15566) of waveguide (15580) to transmit ultrasonic vibrations. By way of example only, narrowed section (15564) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (15580) may be configured to amplify mechanical vibrations transmitted through waveguide (15580). Furthermore, waveguide (15580) may include features operable to control the gain of the longitudinal vibrations along waveguide (15580) and/or features to tune waveguide (15580) to the resonant frequency of the system.

In the present example, the distal end of blade (15560) is located at a position corresponding to an anti-node associated with resonant ultrasonic vibrations communicated through flexible portion (15566) of waveguide (15580), in order to tune the acoustic assembly to a preferred resonant frequency $f_o$ when the acoustic assembly is not loaded by tissue. When tissue is secured between blade (15560) and clamp pad (15546), the ultrasonic oscillation of blade (15560) may simultaneously sever the tissue and denature the proteins in adjacent tissue cells, thereby providing a coagulative effect with relatively little thermal spread. In some versions, an electrical current may also be provided through blade (15560) and clamp arm (15544) to also cauterize the tissue.

3. Exemplary Shaft Assembly, Articulation Section, and Rigidizing Features

Shaft assembly (15530) of the present example extends distally from body portion (15520). As best seen in FIGS. 251-252, shaft assembly (15530) includes distal outer sheath (15533) and a proximal outer sheath (15532) that enclose the drive features of clamp arm (15544) and the above-described acoustic transmission features. Shaft assembly (15530) further includes an articulation section (15530), which is located at a distal portion of shaft assembly (15530), with end effector (15540) being located distal to articulation section (15630).

Articulation section (15630) of the present example is configured to operate substantially similar to articulation sections (130, 15330) discussed above except for any differences discussed below. In particular, articulation section (15630) is operable to selectively position end effector (15540) at various lateral deflection angles relative to a longitudinal axis defined by outer sheath (15532). Articulation section (15630) may take a variety of forms. By way of example only, articulation section (15630) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (15630) may be configured in accordance with one or more teachings of U. S. Pub. No. 2014/0005701, issued as U.S. Pat. No. 9,393,037 on Jul. 19, 2016, and/or U. S. Pub. No. 2014/0114334, issued as U.S. Pat. No. 9,045,367 on Aug. 4, 2015, the disclosures of which are incorporated by reference herein. Various other suitable forms that articulation section (15630) may take will be apparent to those of ordinary skill in the art in view of the teachings herein.

As shown in FIGS. 251-253, shaft assembly (15530) further comprises a pair of articulation bands (15540, 15542) and a pair of translatable rods (15640, 15642). Articulation bands (15540, 15542) are configured to operate substantially similar to articulation bands (140, 142, 15340, 15342) discussed above, except for any differences discussed below. For instance, when articulation bands (15540, 15542) translate longitudinally in an opposing fashion, this will cause articulation section (15530) to bend, thereby laterally deflecting end effector (15540) away from the longitudinal axis of shaft assembly (15530) from a straight configuration as shown in FIG. 293A to an articulated configuration as shown in FIGS. 293B and 293C. In particular, end effector (15540) will be articulated toward the articulation band (15540, 15542) that is being pulled proximally. During such articulation, the other articulation band (15540, 15542) may be pulled distally. Alternatively, the other articulation band (15540, 15542) may be driven distally by an articulation control. Flexible acoustic waveguide (15566) is configured to effectively communicate ultrasonic vibrations from waveguide (15580) to blade (15560) even when articulation section (15630) is in an articulated state as shown in FIGS. 293B and 293C.

Translatable members (15640, 15642) are slidably disposed within the proximal portion of outer sheath (15532). Translatable members (15640, 15642) extend longitudinally through the proximal portion of outer sheath (15532) along opposite sides of outer sheath (15532) and adjacent an interior surface of outer sheath (15532). As best seen in FIG. 253, an elongate recess (15644) is formed in an exterior surface of a distal portion of each translatable member (15640, 15642). Elongate recesses (15644) are configured to receive a proximal portion of each articulation band (15540, 15542). Each translatable member (15640, 15642) further includes a pin (15643) projecting outwardly from an interior surface of each elongate recess (15644). An opening (15641) formed in a proximal end of each articulation band (15640, 15642) is configured to receive a respective pin (15643) of translatable members (15640, 15642). Pins (15643) and openings (15641) thus function to mechanically couple translatable members (15640, 15642) with articulation bands (15540, 542) such that longitudinal translation of translatable member (15640) causes concurrent longitudinal translation of articulation band (15540), and such that longitudinal translation of translatable member (15642) causes concurrent longitudinal translation of articulation band (15542).

When translatable members (15640, 15642) and articulation bands (15540, 15542) are translated longitudinally in an opposing fashion, a moment is created and applied to a distal end of distal outer sheath (15533) in a manner similar to that described above with respect to articulation section (130). This causes articulation section (15630) and narrowed section (15564) of flexible portion (15566) of waveguide (15580) to articulate, without transferring axial forces in articulation bands (15540, 15542) to waveguide (15580) as described above. It should be understood that one articulation band (15540, 15542) may be actively driven distally while the other articulation band (15540, 15542) is passively permitted to retract proximally. As another merely illustrative example, one articulation band (15340, 15342) may be actively driven proximally while the other articulation band (15540, 15542) is passively permitted to advance distally. As yet another merely illustrative example, one articulation band (15540, 15542) may be actively driven distally while the other articulation band (15540, 15542) is actively driven proximally. Various suitable ways in which articulation bands (15540, 15542) may be driven will be apparent to those of ordinary skill in the art in view of the teachings herein.

As shown in FIGS. 251-252, 269-271, 288-290, and 292A-292B, shaft assembly (15530) further comprises a rod member (15740) slidably disposed within the proximal portion of outer sheath (15532). As will be described in more detail below, rod member (15740) is operable to translate between a proximal longitudinal position (FIG. 292B) in which rod member (15740) is positioned proximally of articulation section (15630), and a distal longitudinal position (FIG. 292A) in which rod member (15740) extends through articulation section (15630) and thereby prevents rigidizes articulation section (15740).

As shown in FIGS. 249-250, a rotation knob (15531) is secured to a proximal portion of proximal outer sheath (15532). Rotation knob (15531) is rotatable relative to housing (15522), such that shaft assembly (15530) is rotatable about the longitudinal axis defined by outer sheath (15532), relative to body portion (15520). Such rotation may provide rotation of end effector (15540), articulation section (15630), and shaft assembly (15530) unitarily. Of course, rotatable features may simply be omitted if desired.

4. Exemplary Articulation Control Assembly

FIGS. 254-293C show the components and operation of an articulation control assembly (15700) that is configured to provide control for articulation of articulation section (15630). Articulation control assembly (15700) of this example comprises a motor (15702) and a bevel gear (15704). Motor (15702) is secured within an upper portion of housing (15522) of body portion (15520). As best seen in FIG. 256, motor (15702) is oriented obliquely relative to shaft assembly (15530) such that an axle (15703) of motor (15702) is configured to rotate about an axis that is oblique to the longitudinal axis defined by shaft assembly (15530). Motor (15702) comprises a button (15706) that is configured to selectively cause motor (15702) to rotate axle (15703) is a first direction and in a second direction. As best seen in FIG. 256, bevel gear (15704) is mechanically coupled with axle (15703) of motor (15702) such that rotation of axle (15703) causes concurrent rotation of bevel gear (15704). Bevel gear (15704) includes a plurality of teeth (15710). As will be described in more detail below, rotation of bevel gear (15704) by motor (15702) will cause articulation of articulation section (15630). In some alternative versions, motor (15702) and bevel gear (15704) are replaced with a manually rotatable knob and bevel gear similar to knob (15402) and bevel gear (15404) described above.

As best seen in FIG. 259, articulation control assembly (15700) further comprises a drive assembly (15720). Drive assembly (15720) is secured to a proximal portion of proximal outer sheath (15532). Drive assembly (15720) is further rotatably disposed within rotation knob (15531) such that rotation knob (15531) is configured to rotate independently about drive assembly (15720) to thereby cause rotation of shaft assembly (15530) without causing rotation of drive assembly (15720).

As shown in FIGS. 259A-260, drive assembly (15720) comprises a proximal housing (15730), a distal housing (15735), a plurality of lead screws (15750, 15760, 15770), and a cylindrical guide (15780). Distal housing (15735) and proximal housing (15730) are coupled to one another via a plurality of interlocking tabs (15769) and slots (15767) such that rotation of proximal housing (15730) causes concurrent rotation of distal housing (15735). Proximal housing (15730) is also coupled with an output flange (15936) of a gear reduction assembly (15900) through engagement between tabs (15769) and slots (15938), as will be described in greater detail below, such that rotation of output flange (15936) causes concurrent rotation of proximal housing (15730). Distal housing (15735), proximal housing (15730), and gear reduction assembly (15900) substantially encompass the internal components of drive assembly (15720) as will be described in more detail below.

FIGS. 259B-259J show gear reduction assembly (15900) in greater detail. Gear reduction (15900) assembly of the present example comprises a bevel gear (15910), a fixed spline member (15920), and a flex spline member (15930). As best seen in FIG. 259C, bevel gear (15910), fixed spline member (15920), and flex spline member (15930) are all coaxially aligned with each other and provide clearance for waveguide (15580) and the proximal portions of the rest of shaft assembly (15530) to be coaxially disposed therethrough. As best seen in FIGS. 259D-259E, bevel gear (15910) comprises an array of bevel gear teeth (15912) and an output shaft (15914). Bevel gear teeth (15912) are configured and positioned to mesh with teeth (15710) of bevel gear (15704) such that rotation of bevel gear (15704) causes concurrent rotation of bevel gear (15910). In other words, activation of motor (15702) will cause rotation of bevel gear (15910). As best seen in FIG. 259E, output shaft (15914) has an outer surface with an elliptical profile. This allows output shaft (15914) to act as a wave generator within gear reduction assembly (15900) as will be described in greater detail below.

FIGS. 259F-259G show fixed spline member (15920) in greater detail. Fixed spline member (15920) comprises a rigid cylindraceous body (15922) with an array of internal teeth (15924) and an outwardly extending annular flange (15926). Flange (15926) is fixedly secured to housing (15522) of body portion (15520) such that fixed spline member (15920) is configured to remain stationary within body portion (15520). FIGS. 259H-259I show flex spline member (15930) in greater detail. Flex spline member (15930) comprises a set external teeth (15932) positioned at a proximal end of a cylindraceous body (15934). Body (15934) is configured to deform radially outwardly yet is also configured to rigidly transfer rotation along the length of body (15934). Various suitable materials and configurations that may be used to provide such radial flexing combined with rigid torque transfer will be apparent to those of ordinary skill in the art in view of the teachings herein. Output flange (15936) is positioned at the distal end of body (15934). As noted above, output flange (15936) includes an array of slots (15938) that receive tabs (15769) of proximal housing (15730), such that rotation of flex spline member (15930) causes concurrent rotation of proximal housing (15730).

As best seen in FIG. 259J, teeth (15932) of flex spline member (15930) are configured and positioned to mesh with teeth (15924) of rigid spline member (15920). At any given moment, only some of teeth (15932) are engaged with teeth (15924). By way of example only, rigid spline member (15930) may be configured to have at least two more teeth (15924) than flex spline member (15930). As also best seen in FIG. 259J, the elliptical outer surface of output shaft (15914) of bevel gear (15910) bears against the inner surface (15935) of body (15934) of flex spline member (15930). In particular, the elliptical outer surface of output shaft (15914) bears against inner surface (15935) at the antipodal points of the major axis of the elliptical outer surface of output shaft (15914). Thus, as bevel gear (15910) is rotated, the points of contact between bevel gear (15910) and flex spline member (15930) orbit about the central longitudinal axis of gear reduction assembly (15900). This causes teeth (15932) to engage teeth (15924) in orbital paths about the central longitudinal axis of gear reduction assembly (15900), with body (15934) flexibly deforming to provide this engagement between teeth (15924, 15932). Rigid spline member (15920) remains stationary while flex spline member (15930) rotates during such engagement. The rotation of flex spline member (15930) provides rotation of proximal housing (15730) as noted above. Proximal housing (15730) thus rotates in response to rotation of bevel gear (15910).

It should be understood from the foregoing that activation of motor (15702) will cause rotation of housings (15730, 15735) via gear reduction assembly (15900). It should also be understood that gear reduction assembly (15900) provides a strain wave gearing system or harmonic drive system. By way of example only, gear reduction assembly (15900) may be further configured and operable in accordance with at least some of the teachings of U.S. Pat. No. 2,906,143, entitled "Strain Wave Gearing," issued Sep. 29, 1959, the disclosure of which is incorporated by reference herein. In the present example, gear reduction assembly (15900) provides a gear reduction of approximately 25:1. Alternatively, any other suitable gear reduction may be provided.

As shown in FIGS. 262-265, proximal housing (15730) includes internal threading (15733) formed in an interior surface of proximal housing (15730). As shown in FIGS. 272-276, distal housing (15735) includes proximal internal threading (15910) formed in an interior surface of distal housing (15735); and distal internal threading (15737) formed in the interior surface of distal housing (15735). Threadings (15736, 15737) have opposing pitch angles or orientations in this example. In other words, the pitch orientation of threading (15910) is opposite to the pitch orientation of threading (15737). As should be understood by comparing FIGS. 264, 265, 275, and 276, a proximal portion (15733A) of threading (15733) of proximal housing (15730) has a greater pitch angle than a distal portion (15733B) of threading (15733) as well as threadings (15736, 15737) of distal housing (15735). As will be described in more detail below, this difference in pitch angles is causes a variance in the speed of longitudinal translation of rod member (15740).

As shown in FIGS. 266-268, a first lead screw (15750) includes a pair of wedge-shaped projections (15751) extending outwardly from radially opposing sides of first lead screw (15750). First lead screw (15750) further includes a discrete exterior thread (15754) projecting outwardly from an exterior surface of projection (15751). Thread (15754) is configured to engage with threading (15733) of proximal housing (15730). The pitch angle of thread (15754) complements the pitch angle of threading (15733). As will be described in greater detail below, articulation control assembly (15700) is configured to permit lead screw (15750) to slide longitudinally within drive assembly (15720) yet prevent lead screw (15750) from rotating within drive assembly (15720). It should therefore be understood that rotation of proximal housing (15730) in a first direction will drive lead screw (15750) proximally; and rotation of proximal housing (15730) in a second direction will drive lead screw (15750) distally.

As shown in FIGS. 277-279, a second lead screw (15760) includes a pair of semi-cylindrical flanges (15761) extending from radially opposing sides of an annular body (15763). Second lead screw (15760) further includes a discrete exterior thread (15762) projecting outwardly from an exterior surface of flange (15761). Thread (15762) is configured to engage with proximal internal threading (15910) of distal housing (15735). As shown in FIGS. 280-282, a third lead screw (15770) includes a pair of semi-cylindrical flanges (15771) extending from radially opposing sides of an annular body (15773). Second lead screw (15770) further includes a discrete exterior thread (15772) projecting outwardly from an exterior surface of flange (15771). Thread (15772) is configured to engage with distal internal threading (15737) of distal housing (15735). The pitch angle of thread (15762) complements the pitch angle of threading (15910); while the pitch angle of thread (15772) complements the pitch angle of threading (15737). As will be described in greater detail below, articulation control assembly (15700) is configured to permit lead screws (15760, 15770) to slide longitudinally within drive assembly (15720) yet prevent lead screws (15760, 15770) from rotating within drive assembly (15720). It should therefore be understood that, due to the opposing pitch angles of threading (15736, 15737), rotation of distal housing (15735) in a first direction will drive lead screw (15760) distally while simultaneously driving lead screw (15770) proximally; and rotation of distal housing (15735) in a second direction will drive lead screw (15760) proximally while simultaneously driving lead screw (15770) distally.

As best seen in FIG. 278, a pair of semi-circular gaps (15765) are defined between an interior surface of each flange (15761) and an exterior surface of annular body (15763) of second lead screw (15760). As best seen in FIG. 281, a pair of semi-circular gaps (15775) are defined between an interior surface of each flange (15771) and an exterior surface of annular body (15773) of second lead screw (15770). As best seen in FIG. 260, cylindrical guide (15780) is positioned within housings (15730, 15735) about the proximal portion of outer sheath (15532). As shown in FIG. 261, a proximal end of cylindrical guide (15780) comprises a structural frame (15782). Structural frame (15782) of cylindrical guide (15780) is configured to be fixedly secured within the interior of housing (15522) of body portion (15520) such that cylindrical guide (15780) is configured to remain stationary within body portion (15520).

Cylindrical guide (15780) comprises a plurality of longitudinal slots (15784) formed by a plurality of elongate sidewalls (15786) of cylindrical guide (15780). In particular, a first pair of longitudinal slots (15784A) is formed in radially opposing sides of a sidewall of cylindrical guide (15780), and a second pair of longitudinal slots (15784B) is formed in radially opposing sides of a sidewall of cylindrical guide (15780). As shown in FIG. 243, projections (15751) of first lead screw (15750) are configured to be received within longitudinal slots (15784A) of cylindrical guide (15780) such that first lead screw (15750) is slidably disposed along longitudinal slots (15784A). Thus, lead screw (15750) is operable to translate within proximal housing (15730) but is prevented from rotating within proximal housing (15730).

As best seen in FIGS. 288 and 289, longitudinal sidewalls (15786) of cylindrical guide (15780) are configured to be received within gaps (15765) of second lead screw (15760) such that lead screw (15760) is slidably disposed along cylindrical guide (15780) within distal housing (15735). As best seen in FIG. 290, longitudinal sidewalls (15786) of cylindrical guide (15780) are configured to be received within gaps (15775) of third lead screw (15770) such that lead screw (15770) is slidably disposed along cylindrical guide (15780) within distal housing (15735). Thus, lead screws (15760, 15770) are operable to translate within distal housing (15735) but are prevented from rotating within distal housing (15735).

As shown in FIGS. 269 and 270, first lead screw (15750) is secured to a proximal end of rod member (15740) via a tensioner (15756). As shown in FIGS. 283-286, tensioner (15756) includes a first threaded member (15756A) and a second threaded member (15756B). Threaded members (15756A, 15756B) threadably engage one another such that a longitudinal position of threaded members (15756A, 15756B) relative to one another may be changed by rotation of first threaded member (15756A) and/or second threaded member (15756B). An exterior surface of first threaded member (15756A) of tensioner (15756) is secured to an interior surface of a through-bore (15755) of first lead screw (15750) such that longitudinal translation of first lead screw (15750) causes concurrent longitudinal translation of tensioner (15756). As best seen in FIG. 270, a key (15757) of second threaded member (15756B) of tensioner (15756) is positioned within a mating slot (15747) formed in the proximal end of rod member (15740) such that longitudinal translation of first lead screw (15750) causes current longitudinal translation of rod member (15740). Thus, in the present version, first lead screw (15750) is operable to both push rod member (15740) distally and pull rod member (15740) proximally, depending on which direction proximal housing (15730) is rotated. Other suitable relationships will be apparent to those of ordinary skill in the art in view of the teachings herein.

As shown in FIG. 287, a proximal end of each translatable rod (15640, 15642) includes a slot (15648, 15649) formed therein. As shown in FIG. 288, second lead screw (15760) is secured to a proximal end of translatable rod (15642) via a tensioner (15756). An exterior surface of a first threaded member (15756A) of tensioner (15756) is secured to an interior surface of annular body (15763) of second lead screw (15760) such that longitudinal translation of second lead screw (15760) causes concurrent longitudinal translation of tensioner (15756). A key (15757) of second threaded member (15756B) of tensioner (15756) is positioned within mating slot (15648) of translatable rod (15642) such that longitudinal translation of second lead screw (15760) causes current translation of translatable rod (15642). Thus, in the present version, second lead screw (15760) is operable to both push translatable rod (15642) distally and pull translatable rod (15642) proximally, depending on which direction distal housing (15735) is rotated. Because translatable member (15642) is mechanically coupled with articulation band (15542), it should be understood that second lead screw (15760) is operable to both push articulation band (15542) distally and pull articulation band (15542) proximally, depending on which direction distal housing (15735) is rotated. Other suitable relationships will be apparent to those of ordinary skill in the art in view of the teachings herein.

As shown in FIG. 290, third lead screw (15770) is secured to a proximal end of translatable rod (15640) via a tensioner (15756). An exterior surface of a first threaded member (15756A) of tensioner (15756) is secured to an interior surface of annular body (15773) of third lead screw (15770) such that longitudinal translation of third lead screw (15770) causes concurrent longitudinal translation of tensioner (15756). A key (15757) of second threaded member (15756B) of tensioner (15756) is positioned within mating slot (15649) of translatable rod (15640) such that longitudinal translation of third lead screw (15770) causes current translation of translatable rod (15640). Thus, in the present version, third lead screw (15770) is operable to both push translatable rod (15640) distally and pull translatable rod (15640) proximally, depending on which direction distal housing (15735) is rotated. Because translatable member (15640) are mechanically coupled with articulation band (15540), it should be understood that second lead screw (15760) is operable to both push articulation band (15540) distally and pull articulation band (15540) proximally, depending on which direction distal housing (15735) is rotated. Other suitable relationships will be apparent to those of ordinary skill in the art in view of the teachings herein.

FIGS. 291A-293C show several of the above described components interacting to bend articulation section (15630) to articulate end effector (15540). FIGS. 291A, 292A, and 293A correspond to one another. In FIG. 292A, rod member (15740) is in the distal longitudinal position and thereby rigidizes articulation section (15730). In FIG. 293A, articulation section (15630) is in a substantially straight configuration. Then, housings (15730, 15735) are rotated by motor (15702) via gear reduction assembly (15900). The rotation of housings (15730, 15735) causes first lead screw (15750) to translate proximally within proximal housing (15730), second lead screw (15760) to translate distally within distal housing (15735), and third lead screw (15770) to advance proximally within distal housing (15735). This proximal translation of first lead screw (15750) is caused by rotation of first lead screw (15750) within proximal portion (15733A) of threading (15733). As discussed above, the greater pitch angle of proximal portion (15733A) causes a greater rate of translation of first lead screw (15750) as compared with the translation rate of lead screws (15760, 15770), as will be understood by comparing FIGS. 291A-291C. The proximal translation of first lead screw (15750) pulls rod member (15740) proximally in to the proximal longitudinal position as shown in FIG. 292B.

The proximal translation of third lead screw (15770) pulls articulation band (15540) proximally via translatable rod (15640), which causes articulation section (15630) to start bending as shown in FIG. 293B. This bending of articulation section (15630) pulls articulation band (15542) distally. The distal advancement of second lead screw (15760) in response to rotation of distal housing (15735) enables articulation band (15542) and translatable rod (15642) to advance distally. In some other versions, the distal advancement of second lead screw (15760) actively drives translatable rod (15642) and articulation band (15542) distally. As the operator continues rotating housings (15730, 15735) via motor (15702) and gear reduction assembly (15900), the above described interactions continue in the same fashion, resulting in further bending of articulation section (15630) as shown in FIG. 293C. It should be understood that rotating housings (15730, 15735) in the opposite direction will cause articulation section (15630) return to the straight configuration shown in FIG. 293A; and rod member (15740) to return to the distal longitudinal position to thereby rigidize the straightened articulation section (15730).

The angles of threading (15733, 15736, 15737, 15754, 15762, 15772) are configured such that articulation section (15630) will be effectively locked in any given articulated position, such that transverse loads on end effector (15540) will generally not bend articulation section (15630), due to friction between threading (15733, 15736, 15737, 15754, 15762, 15772). In other words, articulation section (15630) will only change its configuration when housings (15730, 15735) are rotated. While the angles of threading may substantially prevent bending of articulation section (15630) in response to transverse loads on end effector (15540), the angles may still provide ready rotation of housings (15730, 15735) to translate lead screws (15750, 15760, 15770). By way of example only, the angles of threading (15733, 15736, 15737, 15754, 15762, 15772) may be approximately +/−2 degrees or approximately +/−3 degrees. Other suitable angles will be apparent to those of ordinary skill in the art in view of the teachings herein. It should also be understood that threading (15733, 15736, 15737, 15754, 15762, 15772) may have a square or rectangular cross-section or any other suitable configuration.

In some versions, housings (15730, 15735) include a visual indicator that is associated with articulation section (15630) being in a substantially straight configuration. Such a visual indicator may align with a corresponding visual indicator on rotation knob (15531) and/or body (15822) of body portion (15520). Thus, when an operator has rotated housings (15730, 15735) to make articulation section (15630) approach a substantially straight configuration, the operator may observe such indicators to confirm whether articulation section (15630) has in fact reached a substantially straight configuration. By way of example only, this may be done right before instrument (15500) is withdrawn from a trocar to reduce the likelihood of articulation section (15630) snagging on a distal edge of the trocar. Of course, such indicators are merely optional.

FIGS. 294-298A show components of an exemplary alternative shaft assembly (15830) comprising an elongate tube member (15850) and a tubular guide member (15860) that may be readily incorporated into instrument (10, 15200) in order to selectively rigidize articulation section (130, 15330) when articulation section (130, 15330) is in a straight, non-articulated configuration. Tube member (15850) and guide member (15860) may also be incorporated into instrument (15500) as a substitute for rod member (15740) and associated components to selectively rigidize articulation section (15630) when articulation section (15630) is in a straight, non-articulated configuration. In the present example, tube member (15850) and guide member (15860) are shown as selectively rigidizing an articulation section (15831), which may otherwise be configured and operable just like articulation sections (130, 15330, 15630) described above.

Elongate tube member (15850) of the present example comprises a semi-circular tongue (15852) extending proximally from a proximal end of elongate tube member (15850). As best seen in FIG. 295, tongue (15852) includes a pawl (15854) projecting inwardly and downwardly from an interior surface of tongue (15852). As will be described in more detail below, elongate tube member (15850) is longitudinally translatable along a length of shaft assembly (15830) between a distal longitudinal position (FIGS. 297A and 298A) and a proximal longitudinal position (FIGS. 297C and 298C). In the distal position, elongate tube member (15850) is positioned about articulation section (15831) to thereby rigidize articulation section (15831). In the proximal position, elongate tube member (15850) is located proximally of articulation section (15831) and thereby permits articulation of articulation section (15831). Elongate tube member (15850) of the present example is resiliently biased distally toward the distal longitudinal position. Various suitable ways in which elongate tube member (15850) may be biased distally toward the distal longitudinal position will be apparent to those of ordinary skill in the art in view of the teachings herein.

Elongate tube member (15850) is configured to slidably and rotatably receive tubular guide member (15860) such that elongate tube member (15850) is operable to translate along a length of tubular guide member (15860) and such that tubular guide member (15860) is operable to rotate within elongate tube member (15850). However, while elongate tube member (15850) is configured to translate along a length of tubular guide member (15860), elongate tube member (15850) is not configured to rotate about tubular guide member (15860). In other words, elongate tube member (15850) is configured to remain in a single rotational position. As shown in FIG. 296, tubular guide member (15860) includes an oval-shaped cam channel (15862) that is formed in a sidewall of tubular guide member (15860). Cam channel (15862) is oriented obliquely relative to the longitudinal axis of tubular guide member (15860). Cam channel (15862) is configured to slidably receive pawl (15854) of elongate tube member (15850). As will be described in more detail below, pawl (15854) serves as a cam follower such that rotation of tubular guide member (15860) within elongate tube member (15850) causes translation of elongate tube member (15850) as pawl (15854) translates within cam channel (15862) of tubular guide member (15860). As best seen in FIG. 296, a proximal portion (15862A) of cam channel (15862) comprises a detent (15864) formed in distal interior surface of cam channel (15862). As will be described in more detail below, detent (15864) is configured to receive pawl (15854) to selectively maintain the position of pawl (15854) within oval-shaped cam channel (15862).

FIGS. 297A-298C show several of the above described components interacting to provide rigidity to articulation section (15831) and/or to prevent inadvertent deflection of end effector (15840) relative to outer sheath (15832). In FIGS. 297A and 298A, articulation section (15831) is in a substantially straight configuration and elongate tube member (15850) covers articulation section (15831), thereby rigidizing articulation section (15831). Then, tubular guide member (15860) is rotated about the longitudinal axis of shaft assembly (15830), which causes elongate tube member (15850) to translate proximally as pawl (15854) travels along cam channel (15862) as shown in FIG. 297B. This proximal translation of elongate tube member (15850) exposes a portion of articulation section (15831) as shown in FIG. 298B. As the operator continues rotating tubular guide member (15860) about the longitudinal axis of shaft assembly (15830) as shown in FIG. 297C, the above described interactions continue in the same fashion, resulting in further proximal translation of elongate tube member (15850) due to engagement of pawl (15854) in cam channel (15862) until pawl (15854) engages detent (15864). As shown in FIG. 298C, this further proximal translation of elongate tube member (15850) completely exposes articulation section (15831) such that articulation section (15831) may be articulated. It should be understood that further rotation of tubular guide member (15860) in the same direction (15 or reversal of rotation of tubular guide member (15860)) will cause distal translation of elongate tube member (15850) back to the distal longitudinal position shown in FIGS. 297A and 298A due to engagement of pawl (15854) in cam channel (15862).

It should also be understood that the receipt of pawl (15854) in detent (15864) may provide the operator with tactile feedback indicating that elongate tube member (15850) has reached the fully proximal position. Cooperation between pawl (15854) and detent (15864) may also provide some degree of resistance to inadvertent rotation of tubular guide member (15860), thereby providing some degree of resistance to distal translation of elongate tube member (15850). Such resistance may be particularly desirable in versions where elongate tube member (15850) is resiliently biased toward the distal position.

Tubular guide member (15860) may be actuated in various ways. For instance, at least a portion of tubular guide member (15860) may be exposed such that the operator may directly grasp tubular guide member (15860) to rotate tubular guide member (15860). As another merely illustrative example, tubular guide member (15860) may include a knob or other user input feature that the operator may grasp or otherwise manipulate to rotate tubular guide member (15860). As yet another merely illustrative example, tubular guide member (15860) may be operatively coupled with an articulation control assembly such as articulation control assembly (100, 15400, 15700). In some such versions, the articulation control assembly may automatically actuate tubular guide member (15860) to drive elongate tube member (15850) to the distal position when articulation section (15830) reaches the straight, non-articulated configuration. The articulation control assembly may also automatically actuate tubular guide member (15860) to drive elongate tube member (15850) to the proximal position when the operator actuates the articulation control assembly to drive articulation section (15830) toward an articulated configuration. Elongate tube member (15850) may thus be actuated in a manner similar to rod member (15740) described above. Still other suitable ways in which elongate tube member (15850) and/or tubular guide member (15860) may be actuated will be apparent to those of ordinary skill in the art in view of the teachings herein.

XVII. MISCELLANEOUS

The above teachings may be readily combined with the teachings of each of the following: U.S. patent application Ser. No. 14/688,692, entitled "Ultrasonic Surgical Instrument with End Effector Having Restricted Articulation," filed on Apr. 16, 2015, published as Pub. No. 2015/0320438 on Nov. 12, 2015, the disclosure of which is incorporated by reference herein; U.S. patent application Ser. No. 14/688,234, entitled "Ultrasonic Surgical Instrument with Articulation Joint Having Plurality of Locking Positions," filed on Apr. 16, 2015, published as Pub. No. 2016/0302817 on Oct. 20, 2016, the disclosure of which is incorporated by reference herein; U.S. patent application Ser. No. 14/688,005 entitled "Ultrasonic Surgical Instrument with Rotatable Shaft Having Plurality of Locking Positions," filed on Apr. 16, 2015, issued as U.S. Pat. No. 10,111,698 on Oct. 30, 2018, the disclosure of which is incorporated by reference herein; U.S. patent application Ser. No. 14/688,424, entitled "Ultrasonic Surgical Instrument with Articulation Joint Having Integral Stiffening Members," filed on Apr. 16, 2015, issued as U.S. Pat. No. 10,029,125 Jul. 24, 2018, the disclosure of which is incorporated by reference herein; U.S. patent application Ser. No. 14/688,458, entitled "Ultrasonic Surgical Instrument with Rigidizing Articulation Drive Members," filed on Apr. 16, 2015, issued as U.S. Pat. No. 10,034,683 on Jul. 31, 2018, the disclosure of which is incorporated by reference herein; U.S. patent application Ser. No. 14/688,497, entitled "Ultrasonic Surgical Instrument with Movable Rigidizing Member," filed on Apr. 16, 2015, published as U.S. Pub. No. 2016/0302818 on Oct. 20, 2016, the disclosure of which is incorporated by reference herein; U.S. patent application Ser. No. 14/688,542 entitled "Ultrasonic Surgical Instrument with Articulating End Effector having a Curved Blade," filed on Apr. 16, 2015, published as Pub. No. 2016/0302819 on Oct. 20, 2016, the disclosure of which is incorporated by reference herein; and U.S. patent application Ser. No. 14/688,633 entitled "Ultrasonic Surgical Instrument with Opposing Thread Drive for End Effector Articulation," filed on Apr. 16, 2015, published as Pub. No. 2016/0302820 on Oct. 20, 2016, the disclosure of which is incorporated by reference herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of operating an apparatus, the apparatus comprising:
   (a) a shaft, wherein the shaft defines a longitudinal axis;
   (b) an acoustic waveguide, wherein the waveguide comprises a flexible portion, wherein the flexible portion comprises a narrowed section longitudinally interposed between a pair of enlarged portions, wherein the narrowed section of the acoustic waveguide comprises a single piece of material that is configured to bend and communicate ultrasonic vibrations while bent, wherein the enlarged portions are longitudinally spaced apart from each other;
   (c) an articulation section coupled with the shaft, wherein the articulation section is associated with the flexible portion of the waveguide, wherein the articulation section further comprises:
      (i) a first member, and
      (ii) a second member, wherein the second member is longitudinally translatable relative to the first member, wherein the first and second members are laterally offset from the narrowed section by the enlarged portions;
   (d) an end effector comprising:
      (i) an ultrasonic blade in acoustic communication with the waveguide, and
      (ii) a clamp arm, wherein the clamp arm is coupled with the first member and the second member; and
   (e) an articulation drive assembly operable to drive articulation of the articulation section to thereby deflect the end effector from the longitudinal axis;
   wherein the method comprises:
   (a) inserting the end effector into a patient;
   (b) actuating the articulation section by translating the first and second members along the enlarged portions, wherein the act of actuating the articulation section results in bending of the flexible portion of the acoustic waveguide, wherein the act of bending the flexible portion of the acoustic waveguide comprises flexing along the length of the single piece of material forming the narrowed section of the acoustic waveguide to define a curve between the pair of enlarged portions; and (c) actuating the end effector on tissue in the patient, wherein the act of actuating the end effector comprises communicating ultrasonic vibrations along the bent single piece of material forming the narrowed section of the acoustic waveguide.

2. The method of claim 1, wherein the articulation section includes a collar, wherein an upper portion of the collar is defined by the first member, wherein a lower portion of the collar is defined by the second member.

3. The method of claim 1, further comprising at least one translatable member secured to the first member.

4. The method of claim 3, wherein the at least one translatable member is operable to translate to thereby drive articulation of the articulation section.

5. The method of claim 3, wherein the at least one translatable member comprises a band.

6. The method of claim 1, further comprising at least one translatable member secured to the second member.

7. The method of claim 6, wherein the at least one translatable member is operable to translate to thereby drive the clamp arm toward and away from the ultrasonic blade.

8. The method of claim 1, wherein the articulation section further comprises an outer tube engaged with the first member.

9. The method of claim 1, wherein the articulation section comprises a set of ribs separated by gaps configured to promote flexing of the articulation section.

10. The method of claim 1, wherein the articulation drive assembly comprises a pair of translating members, wherein the pair of translating members are operable to translate simultaneously in opposite directions to thereby deflect the end effector from the longitudinal axis.

11. The method of claim 10, wherein the pair of translating members are further operable to translate simultaneously in the same direction to thereby drive the clamp arm toward and away from the ultrasonic blade.

12. The method of claim 10, wherein the waveguide includes at least one flange defining a pair of flats, wherein the pair of translating members are positioned at respective flats of the pair of flats.

13. The method of claim 1, wherein the clamp arm engages the first member in a ball-and-socket configuration.

14. A method of operating an apparatus, the apparatus comprising:
(a) a body assembly;
(b) a shaft extending distally from the body assembly, wherein the shaft defines a longitudinal axis;
(c) an articulation section coupled with the shaft;
(d) an end effector coupled with the articulation section, wherein the end effector comprises:
 (i) a working element configured to engage tissue, and
 (ii) a clamp arm operable to pivot toward and away from the working element; and
(e) an articulation drive assembly operable to drive articulation of the articulation section to thereby deflect the end effector from the longitudinal axis, wherein the articulation drive assembly comprises:
 (i) a first translating driver, and
 (ii) a second translating driver,
 wherein the first and second translating drivers are operable to translate simultaneously in opposite directions to thereby deflect the end effector from the longitudinal axis,
 wherein the first and second translating drivers are operable to translate simultaneously in the same direction to thereby drive the clamp arm toward and away from the working element;
wherein the method comprises:
(a) inserting the end effector into a patient;
(b) actuating the articulation section; and
(c) actuating the end effector on tissue in the patient.

15. A method of operating an apparatus, the apparatus comprising:
(a) a body assembly;
(b) a shaft extending distally from the body assembly, wherein the shaft defines a longitudinal axis;
(c) an acoustic waveguide, wherein the waveguide comprises a flexible portion;
(d) an articulation section coupled with the shaft, wherein a portion of the articulation section encompasses the flexible portion of the waveguide, wherein the articulation section further comprises:
 (i) a first member, and
 (ii) a second member, wherein the second member is longitudinally translatable relative to the first member;
(e) an end effector comprising:
 (i) an ultrasonic blade in acoustic communication with the waveguide, and
 (ii) a clamp arm, wherein the clamp arm is coupled with the first member and the second member, wherein the clamp arm engages the first member in a ball-and-socket configuration; and
(f) an articulation drive assembly operable to drive articulation of the articulation section to thereby deflect the end effector from the longitudinal axis;
wherein the method comprises:
(a) inserting the end effector into a patient;
(b) actuating the articulation section; and
(c) actuating the end effector on tissue in the patient.

16. The method of claim 15, further comprising a first translatable member secured to the first member, wherein the first translatable member is operable to translate to thereby translate the first member and deflect the first member laterally.

17. The method of claim 16, further comprising a second translatable member secured to the second member, wherein the second translatable member is operable to translate to thereby translate the second member and deflect the second member laterally.

18. The method of claim 17, wherein at least one of the first and second translatable members is operable to translate to thereby drive the clamp arm toward and away from the ultrasonic blade.

19. The method of claim 15, wherein the acoustic waveguide is interposed between the first and second members.

* * * * *